US011739325B2

(12) United States Patent
Vargeese et al.

(10) Patent No.: US 11,739,325 B2
(45) Date of Patent: Aug. 29, 2023

(54) OLIGONUCLEOTIDE COMPOSITIONS AND METHODS THEREOF

(71) Applicant: WAVE LIFE SCIENCES LTD., Singapore (SG)

(72) Inventors: Chandra Vargeese, Schwenksville, PA (US); Zhong Zhong, Hingham, MA (US); Naoki Iwamoto, Brighton, MA (US); Jason Jingxin Zhang, Walpole, MA (US); Jean-Cosme Dodart, Boston, MA (US); Yuanjing Liu, Arlington, MA (US); Pachamuthu Kandasamy, Belmont, MA (US); Sethumadhavan Divakaramenon, Lexington, MA (US); Genliang Lu, Winchester, MA (US); Subramanian Marappan, Acton, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 79 days.

(21) Appl. No.: 16/636,902

(22) PCT Filed: Aug. 7, 2018

(86) PCT No.: PCT/US2018/045659
§ 371 (c)(1),
(2) Date: Feb. 5, 2020

(87) PCT Pub. No.: WO2019/032612
PCT Pub. Date: Feb. 14, 2019

(65) Prior Publication Data
US 2021/0032620 A1    Feb. 4, 2021

Related U.S. Application Data

(60) Provisional application No. 62/542,778, filed on Aug. 8, 2017.

(51) Int. Cl.
C12N 15/113    (2010.01)
C12N 15/11     (2006.01)
C12Q 1/68      (2018.01)

(52) U.S. Cl.
CPC ............ *C12N 15/113* (2013.01); *C12N 15/11* (2013.01); *C12N 2310/11* (2013.01); *C12N 2310/12* (2013.01); *C12N 2310/315* (2013.01); *C12N 2310/321* (2013.01); *C12N 2310/33* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| 6,440,943 B1 * | 8/2002 | Cook ..................... C07H 19/04 435/7.2 |
| 6,867,295 B2 * | 3/2005 | Woodruff ................. B01J 45/00 536/103 |
| 8,470,987 B2 | 6/2013 | Wada et al. |
| 8,729,036 B2 | 5/2014 | Zamore et al. |
| 8,822,671 B2 | 9/2014 | Shimizu et al. |
| 8,859,755 B2 | 10/2014 | Wada et al. |
| 9,394,333 B2 | 7/2016 | Wada et al. |
| 9,476,044 B2 | 10/2016 | Tuschl et al. |
| 9,598,458 B2 | 3/2017 | Shimizu et al. |
| 9,605,019 B2 | 3/2017 | Verdine et al. |
| 9,617,547 B2 | 4/2017 | Gemba |
| 9,695,211 B2 | 7/2017 | Wada et al. |
| 9,744,183 B2 | 8/2017 | Verdine et al. |
| 9,896,729 B2 | 2/2018 | Pickering-Brown et al. |
| 9,982,257 B2 | 5/2018 | Butler et al. |

(Continued)

FOREIGN PATENT DOCUMENTS

| JP | 2003-238586 A | 8/2003 |
| WO | WO-2004/007718 A2 | 1/2004 |

(Continued)

OTHER PUBLICATIONS

U.S. Appl. No. 16/624,896, filed Dec. 19, 2019, Butler et al.
U.S. Appl. No. 16/869,126, filed May 7, 2020, Vargeese et al.
U.S. Appl. No. 17/046,752, filed Oct. 9, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/465,238, filed Feb. 9, 2021, Shimizu et al.
U.S. Appl. No. 17/605,997, filed Oct. 22, 2021, Byrne et al.
U.S. Appl. No. 17/605,998, filed Oct. 22, 2021, Byrne et al.

(Continued)

Primary Examiner — Sean Mcgarry
(74) Attorney, Agent, or Firm — Choate, Hall & Stewart LLP; Xiaodong Li; Dustin K. Goncharoff

(57) ABSTRACT

Among other things, the present disclosure provides oligonucleotides, compositions, and methods thereof. Among other things, the present disclosure encompasses the recognition that structural elements of oligonucleotides, such as base sequence, chemical modifications (e.g., modifications of sugar, base, and/or internucleotidic linkages) or patterns thereof, conjugation with additional chemical moieties, and/ or stereochemistry [e.g., stereochemistry of backbone chiral centers (chiral internucleotidic linkages)], and/or patterns thereof, can have significant impact on oligonucleotide properties and activities, e.g., knockdown ability, stability, delivery, etc. In some embodiments, the oligonucleotides decrease the expression, activity and/or level of a C9orf72 gene, including but not limited to, one comprising a repeat expansion, or a gene product thereof. In some embodiments, the present disclosure provides methods for treatment of diseases using provided oligonucleotide compositions, for example, in treatment of C9orf72-related disorders.

23 Claims, 7 Drawing Sheets

Specification includes a Sequence Listing.

(56) References Cited

U.S. PATENT DOCUMENTS

| | | | |
|---|---|---|---|
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 10,590,413 B2 | 3/2020 | Butler et al. | |
| 10,696,711 B2 | 6/2020 | Shimizu et al. | |
| 10,724,035 B2 | 7/2020 | Vargeese et al. | |
| 10,815,482 B2 | 10/2020 | Meena et al. | |
| 11,013,757 B2 | 5/2021 | Zhang et al. | |
| 11,136,346 B2 | 10/2021 | Shimizu et al. | |
| 2010/0197762 A1 | 8/2010 | Swayze | |
| 2014/0011860 A1* | 1/2014 | Liang | C12N 15/113 514/44 A |
| 2015/0267197 A1 | 9/2015 | Bennett et al. | |
| 2019/0077817 A1 | 3/2019 | Butler et al. | |
| 2019/0106696 A1* | 4/2019 | Meena | C12N 15/113 |
| 2019/0127733 A1 | 5/2019 | Butler et al. | |
| 2019/0249173 A1 | 8/2019 | Vargeese et al. | |
| 2019/0264267 A1 | 8/2019 | Yang et al. | |
| 2019/0375774 A1 | 12/2019 | Butler et al. | |
| 2019/0390197 A1 | 12/2019 | Butler et al. | |
| 2020/0056173 A1* | 2/2020 | Vargeese | C12N 15/113 |
| 2020/0157545 A1 | 5/2020 | Vargeese et al. | |
| 2020/0190515 A1 | 6/2020 | Vargeese et al. | |
| 2020/0231620 A1 | 7/2020 | Bowman et al. | |
| 2020/0299692 A1 | 9/2020 | Frank-Kamenetsky et al. | |
| 2020/0362337 A1 | 11/2020 | Dodart et al. | |
| 2020/0377946 A1* | 12/2020 | Bennett | C12Q 1/6897 |
| 2021/0115444 A1 | 4/2021 | Meena et al. | |
| 2021/0130821 A1* | 5/2021 | Butler | A61P 35/00 |
| 2021/0198305 A1 | 7/2021 | Vargeese et al. | |
| 2021/0228615 A1 | 7/2021 | Zhang et al. | |
| 2021/0254062 A1 | 8/2021 | Zhang et al. | |
| 2022/0098585 A1 | 3/2022 | Brown et al. | |
| 2022/0127301 A1 | 4/2022 | Shimizu et al. | |
| 2022/0145300 A1 | 5/2022 | Liu et al. | |
| 2022/0162598 A1 | 5/2022 | Vargeese et al. | |
| 2022/0186217 A1 | 6/2022 | Zhang et al. | |
| 2022/0195429 A1 | 6/2022 | Vargeese et al. | |

FOREIGN PATENT DOCUMENTS

| | | |
|---|---|---|
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2013/119979 A1 | 8/2013 |
| WO | WO-2013/159108 A2 | 10/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/054676 A1 | 4/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2016/024205 A1 | 2/2016 |
| WO | WO-2016/138353 A1 | 9/2016 |
| WO | WO-2016/168592 A2 | 10/2016 |
| WO | WO-2017/015555 A1 | 1/2017 |
| WO | WO-2017/015575 A1 | 1/2017 |
| WO | WO-2017/062862 A2 | 4/2017 |
| WO | WO-2017/079291 A1 | 5/2017 |
| WO | WO-2017/160741 A1 | 9/2017 |
| WO | WO-2017/180835 A1 | 10/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/002237 A1 | 1/2019 |
| WO | WO-2019/032607 A1 | 2/2019 |
| WO | WO-2019/055951 A1 | 3/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/099159 A1 | 5/2022 |

OTHER PUBLICATIONS

U.S. Appl. No. 17/609,330, filed Nov. 5, 2021, Liu et al.

Dejesus-Hernandez, M. et al., Expanded GGGGCC hexanucleotide repeat in non-coding region of C9ORF72 causes chromosome 9p-linked frontotemporal dementia and amyotrophic lateral sclerosis, Neuron, 72(2): 245-256 (2011).

International Search Report for PCT/US2018/045653, 5 pages (dated Dec. 17, 2018).

International Search Report for PCT/US2018/045659, 5 pages (dated Oct. 25, 2018).

Jiang, J. et al., Gain of Toxicity from ALS/FTD-Linked Repeat Expansions in C9ORF72 Is Alleviated by Antisense Oligonucleotides Targeting GGGGCC-Containing RNAs, Neuron, 1-16 (2016).

Koch, T., LNA Therapeutics—update, Navigate the phosphorothioate diastereoisomer space, Roche pRED RNA Therapeutics Research, EuroTIDES, PostillionConventionCenter, Amsterdam, Netherlands (Nov. 6-9, 2018).

Liu, Y. et al., Variant-selective stereopure oligonucleotides protect against pathologies associated with C9orf72-repeat expansion in preclinical models, Nat. Comm., 12:847, 15 pages (2021). Reporting Summary (4 pages) and Supplementary Information (22 pages).

Wan, W.B. et al., Synthesis, biophysical properties and biological activity of second generation antisense oligonucleotides containing chiral phosphorothioate linkages, Nucleic Acid Research, 42: 13456-13468 (2014). Supplementary Information, 14 pages.

Written Opinion for PCT/US2018/045653, 14 pages (dated Dec. 17, 2018).

Written Opinion for PCT/US2018/045659, 11 pages (dated Oct. 25, 2018).

U.S. Appl. No. 17/442,663, filed Sep. 24, 2021, Yokota et al.

U.S. Appl. No. 17/766,677, filed Apr. 5, 2022, Monlan et al.

U.S. Appl. No. 17/766,680, filed Apr. 5, 2022, Liu et al.

ClinicalTrials.gov Identifier: NCT03626012, A Study to Assess the Safety, Tolerability, and Pharmacokinetics of BIIB078 in Adults With C9ORF72-Associated Amyotrophic Lateral Sclerosis, First

(56) References Cited

OTHER PUBLICATIONS

Posted Aug. 10, 2018, Last Update Posted Jan. 14, 2022, <https://clinicaltrials.gov/ct2/show/NCT03626012?term=BIIB078&draw=2&rank=2>.

ClinicalTrials.gov Identifier: NCT04288856, A Study to Assess the Safety, Tolerability, and Pharmacokinetics, and Effect on Disease Progression of BIIB078 Administered to Previously Treated Adults C9ORF72-Associated Amyotrophic Lateral Sclerosis (ALS), First Posted Feb. 28, 2020, Last Update Posted Feb. 22, 2022, <https://clinicaltrials.gov/ct2/show/NCT04288856?term=BIIB078&draw=2&rank=1>.

ClinicalTrials.gov Identifier: NCT04931862, Study of WVE-004 in Patients With C9orf72-associated Amyotrophic Lateral Sclerosis (ALS) or Frontotemporal Dementia (FTD) (Focus-C9), First Posted Jun. 18, 2021, Last Update Posted Dec. 14, 2021, <https://www.clinicaltrials.gov/ct2/show/NCT04931862?term=wave+life+sciences&draw=2&rank=3>.

Liu, Y. et al., Preclinical evaluation of WVE-004, an investigational stereopure oligonucleotide for the treatment of C9orf72-associated ALS or FTD, Molecular Therapy: Nucleic Acids, 28:558-570 and Supplemental Information (2022).

Wave Life Sciences Press Release, Wave Life Sciences Announces Positive Update to Ongoing Phase 1b/2a Focus-C9 Study Driven by Potent, Durable Reductions of Poly(GP) with Low, Single Doses of WVE-004, 3 pages (Apr. 4, 2022).

Wave Life Sciences, Focus-C9 clinical trial update, Presentation (Apr. 2022), 25 pages.

Wilson, K. et al., Development of a sensitive trial-ready poly(GP) CSF biomarker assay for C9orf72-associated frontotemporal dementia and amyotrophic lateral sclerosis, J. Neurol. Neurosurg Psychiatry, 0:1-11 (2022).

Dale, E., Enhancing the pharmacologic profiles of CNS targeting therapeutic oligonucleotides, Wave Life Sciences, presented at Tides USA, on Sep. 23, 2021.

Ejebe, K. et al., Design of an Adaptive Phase 1b/2a Randomized Controlled Trial of WVE-004 in Patients with C9orf72-ALS/FTD, Wave Life Sciences, presented at European Network to Cure ALS (ENCALS) Virtual Meeting on May 10-12, 2021.

Kandasamy, P. et al., Impact of guanidine-containing backbone linkages on stereopure antisense oligonucleotides in the CNS, Nucleic Acids Research, 50(10):5401-5423 (2022).

Liu, Y. et al., Impact of Nitrogen-containing Backbone Linkages on Stereopure Antisense Oligonucleotides in the CNS, Wave Life Sciences, Presented at Tides USA: Oligonucleotide & Peptide Therapeutics on Sep. 20-23, 2021 in Boston, Massachusetts.

Liu, Y. et al., Variant-selective Stereopure Oligonucleotides Protect Against Pathologies Associated with C9orf72-repeat Expansion in Preclinical Models, Wave Life Sciences, presented at Neurodegenerative Diseases: Genes, Mechanisms and Therapeutics (Keystone eSymposia) on Jun. 7-9, 2021.

Panzara, M. A. P., Targeting pathological transcriptional variants in C9orf72-associated amyotrophic lateral sclerosis (ALS) and frontotemporal dementia (FTD): Initial results from the ongoing Focus-C9 clinical trial, Wave Life Sciences, presented at the ENCALS Meeting, on Friday 3, 2022.

Panzara, M. A. Stereopure Oligonucleotides in Development for the Treatment of Genetically Defined Diseases, Wave Life Sciences, presented at Tides Boston Virtual Conference on Sep. 15-18, 2020.

Vargeese, C., Exploring new oligonucleotide backbone chemistries and their deployment to improve the properties of stereopure oligonucleotides, Wave Life Sciences, presented at Tides USA on Sep. 22, 2021.

Viglietta, V., A Ph1b/2a study of WVE-003, an investigational allele-selective, mHTT-lowering oligonucleotide for the treatment of early manifest Huntington's disease, and review of Precision-HD results, Wave Life Sciences, presented at CHDI on Apr. 27, 2021.

Wave Life Sciences, Second Quarter 2022 Earnings Presentation, 27 pages, (2022).

Wave Life Sciences, Third Quarter 2022 Earnings Presentation, 24 pages, (2022).

Wave Life Sciences, Wave Life Sciences Corporate Presentation, 63 pages, May 12, 2022.

\* cited by examiner

FIG. 1D

↕ Phosphorothioate internucleotidic linkage

– Natural phosphate internucleotidic linkage

⊡ Non-negatively charged internucleotidic linkage

● 2'-MOE

⊖ 2'-OMe

○ Sugar or modified sugar in a core (Figs. 1A and 1B

Ⓓ 2'-deoxy (2'-deoxyribose)

Ⓕ 2'-F

Ⓛ LNA or other bicyclic sugar

⦀ Sugar or modified sugar in a core (Fig. 1C)

⦸ Sugar or modified sugar in a wing

FIG. 2

OLIGONUCLEOTIDE COMPOSITIONS AND METHODS THEREOF

CROSS-REFERENCE TO RELATED APPLICATIONS

This application is a National Stage Application of PCT International Application No. PCT/2018/045659, filed on Aug. 7, 2018, which claims priority to U.S. Provisional Application No. 62/542,778, filed Aug. 8, 2017, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Dec. 23, 2020, is named SL.txt and is 194,369 bytes in size.

BACKGROUND

Oligonucleotides are useful in various applications, e.g., therapeutic, diagnostic, and/or research applications, including but not limited to treatment of various conditions, disorders, and/or diseases.

SUMMARY

Among other things, the present disclosure encompasses the recognition that structural elements of oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have a significant impact on activities and properties, e.g., stability, toxicity, delivery, etc., of oligonucleotides. In some embodiments, the present disclosure demonstrates that oligonucleotides and compositions comprising oligonucleotides with controlled structural elements, e.g., controlled chemical modification and/or controlled backbone stereochemistry patterns, provide unexpected activities and properties including but not limited to those described herein. In some embodiments, the present disclosure demonstrates that combinations of chemical modifications and stereochemistry can provide unexpected, greatly improved activities and properties. In some embodiments, the present disclosure provides oligonucleotides and compositions comprising oligonucleotides that have a particular sequence of bases, and/or pattern of sugar modifications (e.g., 2'-OMe, 2'-F, 2'-MOE, etc.), and/or pattern or base modifications (e.g., 5-methylcytosine), and/or pattern of backbone modifications (e.g., natural phosphate linkages, modified internucleotidic linkages, etc.), and/or pattern of backbone chiral centers (e.g., Rp or Sp, and/or stereorandom, and/or non-chiral, backbone linkage phosphorus atoms).

In some embodiments, the present disclosure provides novel oligonucleotides, and compositions thereof (e.g., chirally controlled oligonucleotide compositions), wherein the oligonucleotides comprise a format of wing-core-wing, wherein the first and the second wing differ from the core and from each other chemically, e.g., in sugars or sugar modifications or combinations or patterns thereof, backbone internucleotidic linkages or combinations or patterns thereof, and/or combination or pattern of stereochemistry of the backbone internucleotidic linkages. Particularly, in some embodiments, the present disclosure provides oligonucleotides comprising a wing-core-wing structure, wherein each wing independently comprises one or more sugar modifications, wherein the pattern of sugar modifications of one wing is different from the other wing. In some embodiments, one wing comprises a sugar modification which is not in the other wing. In some embodiments, each sugar moiety of the core independently comprises no substituents at the 2'-position (two —H at the 2'-position). In some embodiments, each sugar moiety of the core is independently a natural DNA sugar moiety (a D-2-deoxyribose moiety) which is optionally substituted at the 5'-position. In some embodiments, each sugar moiety of the core is independently a natural DNA sugar moiety (a D-2-deoxyribose moiety). In some embodiments, such oligonucleotides comprise one or more chiral internucleotidic linkages (e.g., phosphorothioate linkage [—O—P(O)(SH)—O— which may exist as anion form —O—P(O)(S—)—O— at certain pH], neutral internucleotidic linkages as described herein, etc.). In some embodiments, such oligonucleotides comprise one or more (e.g., at least 5, 6, 7, 8, 9 or 10) chiral neutral internucleotidic linkages. In some embodiments, the present disclosure provides chirally controlled oligonucleotide compositions of such oligonucleotides. In some embodiments, provided oligonucleotides comprise a pattern of backbone chiral centers (linkage phosphorus) of (Np)t[(Op/Rp)n(Sp)m]y, wherein each variable is independently as described in the present disclosure. Unless otherwise specified, as appreciated by those skilled in the art, a stereochemistry pattern is from the 5' to the 3' direction.

In some embodiments, the present disclosure demonstrates that oligonucleotides comprising certain stereochemistry patterns, such as (Np)t[(Op/Rp)n(Sp)m]y, and chirally controlled oligonucleotide compositions thereof can provide highly improved activities (e.g., when used for cleavage of target nucleic acids), specificity (e.g., when used for cleavage of target nucleic acids wherein nucleic acids of similar sequences exist [e.g., transcripts of wild-type and mutant alleles, transcripts from alleles comprising single nucleotide polymorphisms (SNPs), etc.) and/or other properties (e.g., stability, delivery, etc.) compared to suitable control oligonucleotides and/or compositions thereof (e.g., unmodified oligonucleotides of the same base sequence; stereorandom oligonucleotides optionally of the same constitution; chirally controlled oligonucleotides optionally of the same constitution; or stereorandom and/or chirally controlled compositions thereof). In some embodiments, provided oligonucleotides comprises a stereochemistry pattern of (Np)t[(Op/Rp)n(Sp)m]y, wherein each variable is independently as described in the present disclosure. In some embodiments, each Np is Sp. In some embodiments, a pattern comprises at least one Op. In some embodiments, n is 1. In some embodiments, m is at least 2, 3, 4, or 5. In some embodiments, y is 1. In some embodiments, y is 2, 3, 4, or 5. In some embodiments, (Np)t[(Op/Rp)n(Sp)m]y is (Sp)t[(Op/Rp)(Sp)m]y. In some embodiments, (Np)t[(Op/Rp)n(Sp)m]y is (Sp)t[Op(Sp)m]y. In some embodiments, each Np, Rp, and/or Sp linkage phosphorus is independent a linkage phosphorus of phosphorothioate linkage. In some embodiments, each Op is independently a linkage phosphorus of a natural internucleotidic linkage (—O—P(O)(OH)—O— which may exist as anion form —O—P(O)(O⁻)—O— at certain pH. In some embodiments, each sugar moiety that connects to a linkage phosphorus of a stereochemistry pattern, e.g., (Np)t[(Op/Rp)n(Sp)m]y, contains no 2'-modifications. In some embodiments, each sugar moiety that connects at its 3'-position to a linkage phosphorus of a stereochemistry pattern, e.g., (Np)t[(Op/Rp)n(Sp)m]y, contains no 2'-modifications. In some embodiments, each sugar moiety that connects at its 5'-position to a linkage phosphorus of a stereochemistry pattern, e.g., (Np)t[(Op/Rp)n(Sp)m]y, contains no 2'-modifications. In some embodiments, each sugar moiety that connects to a linkage phosphorus of a stereochemistry pattern, e.g., (Np)t[(Op/Rp)n(Sp)m]y, is independently a natural DNA sugar moiety (a D-2-deoxyribose moiety), wherein the 5'-position is optionally substituted. In some embodiments, the 5'-position is not substituted. In some embodiments, a 5'-position is substituted, e.g., wherein the 5'-position is connected to a linkage phosphorus of Op.

In some embodiments, as demonstrated in the present disclosure, oligonucleotides that comprise a stereochemistry pattern comprising NpNpOp(Sp)m can cleave target sequences at an internucleotidic linkage position wise corresponding to the second internucleotidic linkage of the oligonucleotides upstream of the internucleotidic linkage comprising Op (at an internucleotidic linkage of the target that corresponds to the internucleotidic linkage comprising the underlined Np of NpNpOp(Sp)m).

In some embodiments, the present disclosure provides methods for controlled cleavage of a target nucleic acid, comprising providing an oligonucleotide or a chirally controlled oligonucleotide composition thereof, wherein the stereochemistry pattern of the oligonucleotide comprises (Np)t[(Op/Rp)n(Sp)m]y as described in the present disclosure.

In some embodiments, the present disclosure provides methods for controlled cleavage of a nucleic acid target, comprising contacting the target with a provided an oligonucleotide or composition thereof. In some embodiments, the present disclosure provides methods for selective cleavage of a nucleic acid target, comprising contacting the target with a provided an oligonucleotide or composition thereof. In some embodiments, the present disclosure provides methods for allele-specific cleavage of a transcript of a specific allele, comprising contacting the target with a provided an oligonucleotide or composition thereof. In some embodiments, such a provided oligonucleotide has a pattern of backbone chiral centers comprising Op(Sp)m. In some embodiments, a composition is a chirally controlled oligonucleotide composition of a plurality of oligonucleotides, whose pattern of backbone chiral centers comprises Op(Sp)m. In some embodiments, m is 2. In some embodiments, such a provided oligonucleotide has a pattern of backbone chiral centers comprising (Np)t[(Op/Rp)n(Sp)m]y, wherein each variable is as described in the present disclosure, n is 1, m is 2 or greater, and t is 2 or greater. In some embodiments, a composition is a chirally controlled oligonucleotide composition of a plurality of oligonucleotides, whose pattern of backbone chiral centers comprises (Np)t[(Op/Rp)n(Sp)m]y, wherein each variable is as described in the present disclosure, n is 1, m is 2 or greater, and t is 2 or greater. In some embodiments, Np is Sp.

In some embodiments, oligonucleotides that comprise an asymmetrical format and/or a stereochemistry pattern described in the present disclosure are capable of decreasing the level, expression and/or activity of a gene target or a gene product thereof.

Oligonucleotides of the present disclosure may function through various mechanisms. In some embodiments, provided oligonucleotides are capable of decreasing the level, expression and/or activity of a gene target or a gene product thereof via a mechanism involving RNase H, which recognizes a DNA/RNA duplex. In some embodiments, the core of an oligonucleotide comprises multiple deoxyribose (e.g., 2'-deoxyribose or 2'-DNA sugars as found in naturally-occurring DNA) moieties and is capable of annealing to a RNA (e.g., a target mRNA) to form a substrate for RNase H, allowing RNase H to cleave the RNA.

In some embodiments, provided oligonucleotides are capable of decreasing the level, expression and/or activity of a gene target or a gene product thereof via a mechanism involving steric hindrance. In some embodiments, provided oligonucleotides block or decrease translation of a target mRNA.

The present disclosure pertains to any oligonucleotide which has an asymmetrical format and operates through any mechanism, and which comprises any structure or format (or portion thereof) described herein, wherein the oligonucleotide comprises at least one non-naturally-occurring modification of a base, sugar and/or internucleotidic linkage.

In some embodiments, a provided oligonucleotide comprises at least one stereorandom internucleotidic linkage (non-chirally controlled internucleotidic linkage) (e.g., a stereorandom phosphorothioate linkage, a stereorandom neutral internucleotidic linkage, etc.). In some embodiments, a provided oligonucleotide comprises at least one stereocontrolled internucleotidic linkage (chirally controlled internucleotidic linkage) (e.g., a Rp or Sp phosphorothioate linkage, a Rp or Sp neutral internucleotidic linkage, etc.).

In some embodiments, the present disclosure encompasses the recognition that various optional additional chemical moieties, such as carbohydrate moieties, sugar moieties, targeting moieties, etc., when incorporated into oligonucleotides, can improve one or more properties. In some embodiments, an additional chemical moiety is selected from: glucose, GluNAc (N-acetyl amine glucosamine) and anisamide moieties. In some embodiments, an oligonucleotide can comprise two or more additional chemical moieties, wherein the additional chemical moieties are identical or non-identical, or are of the same or different categories (e.g., carbohydrate moiety, sugar moiety, targeting moiety, etc.). In some embodiments, certain additional chemical moieties facilitate delivery of oligonucleotides to desired cells, tissues and/or organs, facilitate internalization of oligonucleotides, and/or increase oligonucleotide stability.

In some embodiments, the present disclosure demonstrates that surprisingly high target specificity can be achieved with oligonucleotides which have an asymmetrical format. In some embodiments, an oligonucleotide which has an asymmetrical format is allele-specific, e.g., the oligonucleotide can preferential knockdown disease-associated transcript(s) of a gene target relative to wild-type (e.g., non-disease-associated) transcript(s). In some embodiments, a disease-associated transcript can comprise a disease-associated mutation or repeat expansion.

In some embodiments, the present disclosure provides an oligonucleotide which has an asymmetrical format and comprises any structure or format (or portion thereof) described herein, an optional additional chemical moiety (including but not limited to a carbohydrate moiety, and a targeting moiety), stereochemistry or patterns of stereochemistry, internucleotidic linkage or pattern of internucleotidic linkages; modification of sugar(s) or pattern of modifications of sugars; modification of base(s) or patterns of modifications of bases.

In some embodiments, the present disclosure provides methods for reducing levels of a nucleic acid or a product encoded thereby, comprising contacting the nucleic acid with a provided oligonucleotide or a composition thereof, wherein the base sequence of the oligonucleotide is complementary to the base sequence of the nucleic acid or a portion thereof. In some embodiments, the present disclosure provides a method for treating and/or preventing and/or treating various related conditions, disorders and/or diseases in a subject, wherein the method comprises the step of administering to the subject a provided oligonucleotide or a composition thereof.

BRIEF DESCRIPTION OF THE DRAWINGS

FIG. 1. presents certain provided formats of oligonucleotides having an asymmetric format as non-limiting examples. FIG. 1D provides a legend to FIG. 1A, FIG. 1B and FIG. 1C.

FIG. 2. Example cleavage data of oligonucleotides comprising certain stereochemistry patterns. Arrows indicate observed cleavage sites. As demonstrated, oligonucleotides comprising certain stereochemistry patterns can direct cleavage to selected sites. In some embodiments, as shown herein, cleavage occurs predominately at one site when chirally controlled oligonucleotide compositions of oligonucleotides comprising certain stereochemistry patterns were utilized. FIG. 2 discloses SEQ ID NOS 613, 9, 613, 38, 613, 39, 613, 104, 613, and 105, respectively, in order of appearance.

DETAILED DESCRIPTION OF CERTAIN EMBODIMENTS

Definitions

Figure 1A:
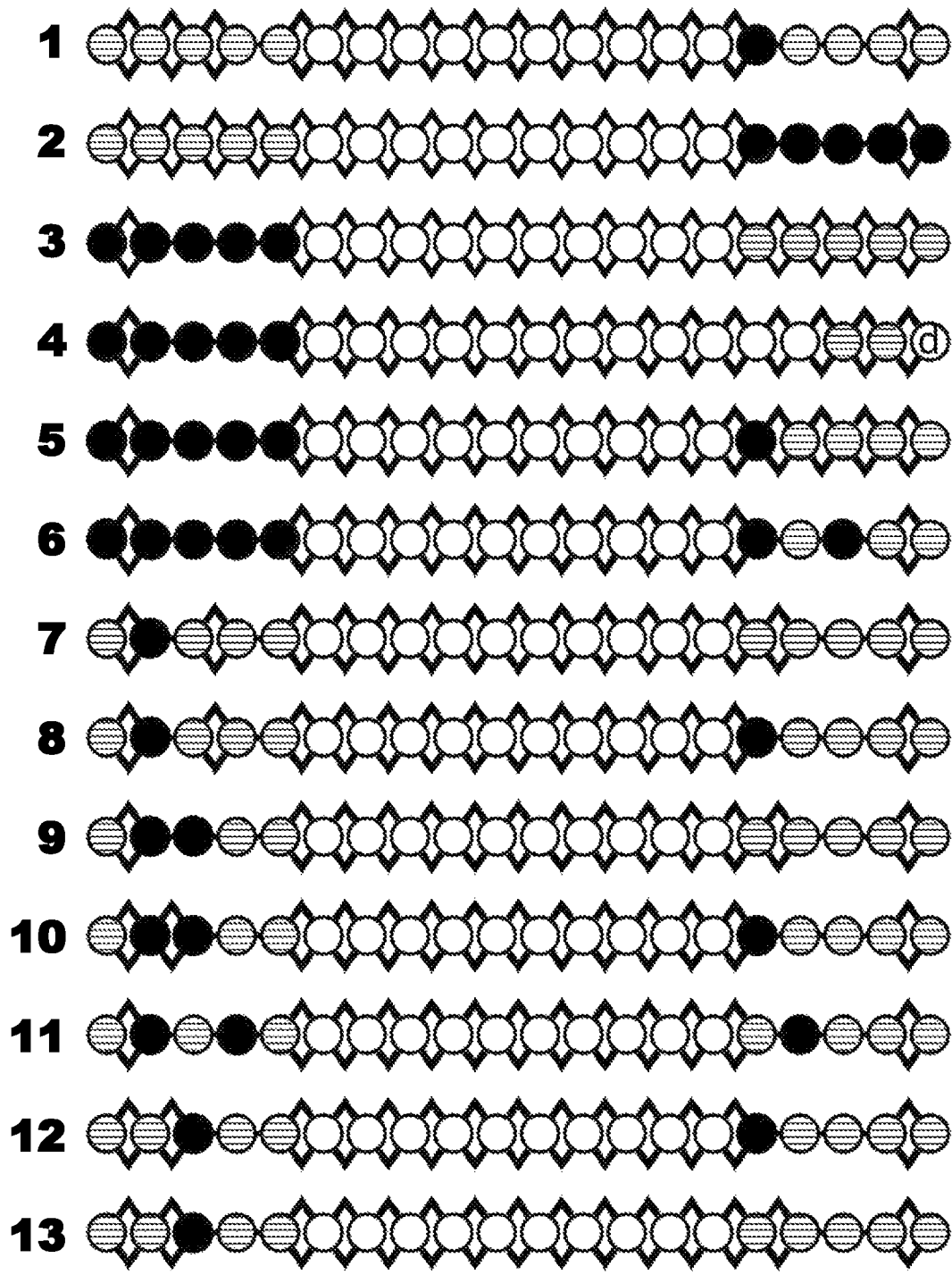
FIG. 1A and FIG. 1B present non-limiting examples of sugar modifications and/or patterns thereof in the first and second wing of an oligonucleotide having an asymmetric format.

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an alkyl group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an alkyl group, as defined herein, having one or more triple bonds.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted form thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is boron, oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.).

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

In vitro: As used herein, the term "in vitro" refers to events that occur in an artificial environment, e.g., in a test tube or reaction vessel, in cell culture, etc., rather than within an organism (e.g., animal, plant and/or microbe).

In vivo: As used herein, the term "in vivo" refers to events that occur within an organism (e.g., animal, plant and/or microbe).

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable atom, e.g., a suitable carbon atom, are independently halogen; —$(CH_2)_{0-4}R°$; —$(CH_2)_{0-4}OR°$; —$O(CH_2)_{0-4}R°$, —$O$—$(CH_2)_{0-4}C(O)OR°$; —$(CH_2)_{0-4}CH(OR°)_2$; —$(CH_2)_{0-4}Ph$, which may be substituted with $R°$; —$(CH_2)_{0-4}O(CH_2)_{0-1}Ph$ which may be substituted with $R°$; —$CH=CHPh$, which may be substituted with $R°$; —$(CH_2)_{0-4}O(CH_2)_{0-1}$-pyridyl which may be substituted with $R°$; —$NO_2$; —$CN$; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$Si(R°)_3$; —$OSi(R°)_3$; —$B(R°)_2$; —$OB(R°)_2$; —$OB(OR°)_2$; —$P(R°)_2$; —$P(OR°)_2$; —$OP(R°)_2$; —$OP(OR°)_2$; —$P(O)(R°)_2$; —$P(O)(OR°)_2$; —$OP(O)(R°)_2$; —$OP(O)(OR°)_2$; —$OP(OR°)(SR°)$; —$SP(O)(R°)_2$; —$SP(O)(OR°)_2$; —$N(R°)P(O)(R°)_2$; —$N(R°)P(O)(OR°)_2$; —$P(R°)_2[B(R°)_3]$; —$P(OR°)_2[B(R°)_3]$; —$OP(R°)_2[B(R°)_3]$; —$OP(OR°)_2[B(R°)_3]$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, —$CH_2$—$(C_{6-14}$ aryl), —$O(CH_2)_{0-1}(C_{6-14}$ aryl), —$CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R°$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R°$ (or the ring formed by taking two independent occurrences of $R°$ together with their intervening atoms), are independently halogen, —$(CH_2)_{0-2}R^●$, -(haloR^●), —$(CH_2)_{0-2}OH$, —$(CH_2)_{0-2}OR^●$, —$(CH_2)_{0-2}CH(OR^●)_2$; —$O(haloR^●)$, —$CN$, —$N_3$, —$(CH_2)_{0-2}C(O)R^●$, —$(CH_2)_{0-2}C(O)OH$, —$(CH_2)_{0-2}C(O)OR^●$, —$(CH_2)_{0-2}SR^●$, —$(CH_2)_{0-2}SH$, —$(CH_2)_{0-2}NH_2$, —$(CH_2)_{0-2}NHR^●$, —$(CH_2)_{0-2}NR^●_2$, —$NO_2$, —$SiR^●_3$, —$OSiR^●_3$, —$C(O)SR^●$, —$(C_{1-4}$ straight or branched alkylene)C(O)OR^●, or —$SSR^●$ wherein each $R^●$ is unsubstituted or where preceded by "halo" is substituted only with one or more halogens, and is independently selected from $C_{1-4}$ aliphatic, —$CH_2Ph$, —$O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R°$ include =O and =S.

Suitable divalent substituents, e.g., on a suitable carbon atom, are independently the following: =O, =S, =NNR*_2, =NNHC(O)R*, =NNHC(O)OR*, =NNHS(O)_2R*, =NR*, =NOR*, —$O(C(R*_2))_{2-3}O$—, or —$S(C(R*_2))_{2-3}S$—, wherein each independent occurrence of R* is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR*_2)_{2-3}O$—, wherein each independent occurrence of R* is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur.

Suitable substituents on the aliphatic group of R* are independently halogen, —$R^●$, -(haloR^●), —OH, —$OR^●$, —$O(haloR^●)$, —CN, —C(O)OH, —$C(O)OR^●$, —$NH_2$, —$NHR^●$, —$NR^●_2$, or —$NO_2$, wherein each $R^●$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, a provided oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen in the acidic groups are replaced with cations. In some embodiments, a pharmaceutically acceptable salt is a sodium salt of a provided oligonucleotide. In some embodiments, a pharmaceutically acceptable salt is a sodium salt of a provided oligonucleotide, wherein each acidic phosphate group exists as a salt form (all sodium salt).

In some embodiments, a pharmaceutically acceptable salt is a calcium salt of a provided oligonucleotide.

Protecting group: The term "protecting group," as used herein, is well known in the art and includes those described in detail in Protecting Groups in Organic Synthesis, T. W. Greene and P. G. M. Wuts, $3^{rd}$ edition, John Wiley & Sons, 1999, the entirety of which is incorporated herein by reference. Also included are those protecting groups specially adapted for nucleoside and nucleotide chemistry described in *Current Protocols in Nucleic Acid Chemistry*, edited by Serge L. Beaucage et al. 06/2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N' dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxycarbonyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4''-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4''-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group.

In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N-(2,2,2-trifluoroacetyl)amino]butyl.

Sample: A "sample" as used herein is a specific organism or material obtained therefrom. In some embodiments, a sample is a biological sample obtained or derived from a source of interest, as described herein. In some embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. In some embodiments, a sample is an organism. In some embodiments, a sample is a plant. In some embodiments, a sample is an animal. In some embodiments, a sample is a human. In some embodiments, a sample is an organism other than a human.

Subject: As used herein, the term "subject" or "test subject" refers to any organism to which a provided compound or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder and/or condition has been diagnosed with and/or displays one or more symptoms of a disease, disorder and/or condition.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotide linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleotide: The term "nucleotide" as used herein refers to a monomeric unit of a polynucleotide that consists of a nucleobase, a sugar, and one or more internucleotidic linkages. The naturally occurring bases (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Nucleoside: The term "nucleoside" refers to a moiety wherein a nucleobase or a modified nucleobase is covalently bound to a sugar or a modified sugar.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars.

Modified sugar: The term "modified sugar" refers to a moiety that can replace a sugar. A modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. A sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, "identity" means the percentage of identical nucleotide residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well-known Smith Waterman algorithm can also be used to determine identity.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, U1 adaptors, triplex-forming oligonucleotides, G-quadruplex oligonucleotides, RNA activators, immuno-stimulatory oligonucleotides, and decoy oligonucleotides.

Oligonucleotides of the present disclosure can be of any of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, or from about 20 to about 30 nucleotides in length. In some embodiments, an oligonucleotide is from about 10 to about 40 nucleotides in length. In some embodiments, an oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length. In some embodiments, each nucleotide counted in a length independently comprises an optionally substituted nucleobase selected from adenine, cytosine, guanosine, thymine, and uracil.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as found in naturally occurring DNA and RNA molecules (natural phosphate linkage). In some embodiments, an internucleotidic linkage includes a modified internucleotidic linkage. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to $=S$, $=Se$, $=NR'$, $-SR'$, $-SeR'$, $-N(R')_2$, $B(R')_3$, $-S-$, $-Se-$, and $-N(R')-$, wherein each R' is independently as defined and described in the present disclosure. In some embodiments, an internucleotidic linkage is a phosphotriester linkage, phosphorothioate diester linkage

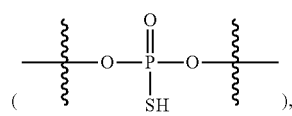 [SMILES: *OP(=O)(S)O*]

or modified phosphorothioate triester linkage. In some embodiments, an internucleotidic linkage is one of, e.g., PNA (peptide nucleic acid) or PMO (phosphorodiamidate Morpholino oligomer) linkage. It is understood by a person of ordinary skill in the art that an internucleotidic linkage may exist as an anion or cation at a given pH due to the existence of acid or base moieties in the linkage.

Non-limiting examples of modified internucleotidic linkages are modified internucleotidic linkages designated s, s1, s2, s3, s4, s5, s6, s7, s8, s9, s10, s11, s12, s13, s14, s15, s16, s17 and s18 as described in WO 2017/210647.

For instance, (Rp, Sp)-ATsCs1GA has 1) a phosphorothioate internucleotidic linkage (

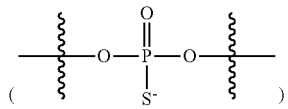 [SMILES: *OP(=O)([S-])O*]

) between T and C; and 2) a phosphorothioate triester internucleotidic linkage having the structure of

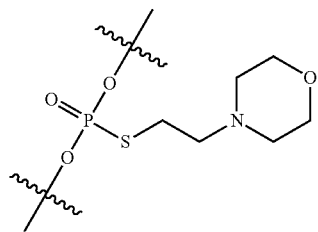 [SMILES: *OP(=O)(O*)SCCN1CCOCC1]

between C and G. Unless otherwise specified, the Rp/Sp designations preceding an oligonucleotide sequence describe the configurations of chiral linkage phosphorus atoms in the internucleotidic linkages sequentially from 5' to 3' of the oligonucleotide sequence. For instance, in (Rp, Sp)-ATsCs1GA, the phosphorus in the "s" linkage between T and C has Rp configuration and the phosphorus in "s1" linkage between C and G has Sp configuration. In some embodiments, "All-(Rp)" or "All-(Sp)" is used to indicate that all chiral linkage phosphorus atoms in oligonucleotide have the same Rp or Sp configuration, respectively.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—XLR$^1$" groups in formula I). In some embodiments, oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in pre-determined relative amounts.

Chiral control: As used herein, "chiral control" refers to control of the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same stereochemistry at one or more chiral internucleotidic linkages (chirally controlled internucleotidic linkages, whose chiral linkage phosphorus is Rp or Sp in the composition, not a random Rp and Sp mixture as non-chirally controlled internucleotidic linkage). Level of the plurality of oligonucleotides (or nucleic acids) in a chirally controlled oligonucleotide composition is pre-determined/controlled (e.g., through chirally controlled oligonucleotide preparation to stereoselectively form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a predetermined level is be about 1%-100%, (e.g., about 5%-100%, 10%-100%, 20%-100%, 30%-100%, 40%-100%, 50%-100%, 60%-100%, 70%-100%, 80%-100%, 90%-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications are oligonucleotides of the plurality, or of all oligonucleotides in a composition that share a common base sequence, a common patter of base modifications, a common pattern of sugar modifications, a common pattern of internucleotidic linkage types, and/or a common pattern of internucleotidic linkage modifications. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 1%-100% (e.g., about 5%-100%, 10%-100%, 20%-100%, 30%-100%, 40%-100%, 50%-100%, 60%-100%, 70%-100%, 80%-100%, 90%-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises non-random or controlled levels of individual oligonucleotide or nucleic acids types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of an oligonucleotide type, which composition comprises a non-random or controlled level of a plurality of oligonucleotides of the oligonucleotide type.

Chirally pure: as used herein, the phrase "chirally pure" is used to describe an oligonucleotide or compositions thereof, in which all are nearly all (the rest are impurities) of the oligonucleotide molecules exist in a single diastereomeric form with respect to the linkage phosphorus atoms.

Predetermined: By predetermined (or pre-determined) is meant deliberately selected or non-random or controlled, for example as opposed to randomly occurring, random, or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that are not controlled to intentionally generate the particular chemistry and/or stereochemistry features are not "predetermined" compositions. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the P of Formula I. In some embodiments, a linkage phosphorus atom is chiral. In some embodiments, a linkage phosphorus atom is achiral.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-R$^1$ wherein each of X, L and R$^1$ is independently as defined and described in the present disclosure.

Blockmer: the term "blockmer," as used herein, refers to an oligonucleotide strand whose pattern of structural features characterizing each individual nucleotide unit is characterized by the presence of at least two consecutive nucleotide units sharing a common structural feature at the internucleotidic phosphorus linkage. By common structural feature is meant common stereochemistry at the linkage phosphorus or a common modification at the linkage phosphorus. In some embodiments, the at least two consecutive nucleotide units sharing a common structure feature at the internucleotidic phosphorus linkage are referred to as a "block". In some embodiments, a provided oligonucleotide is a blockmer.

In some embodiments, a blockmer is a "stereoblockmer," e.g., at least two consecutive nucleotide units have the same stereochemistry at the linkage phosphorus. Such at least two consecutive nucleotide units form a "stereoblock."

In some embodiments, a blockmer is a "P-modification blockmer," e.g., at least two consecutive nucleotide units have the same modification at the linkage phosphorus. Such at least two consecutive nucleotide units form a "P-modification block". For instance, (Rp, Sp)-ATsCsGA is a P-modification blockmer because at least two consecutive nucleotide units, the Ts and the Cs, have the same P-modification (i.e., both are a phosphorothioate diester). In the same oligonucleotide of (Rp, Sp)-ATsCsGA, TsCs forms a block, and it is a P-modification block.

In some embodiments, a blockmer is a "linkage blockmer," e.g., at least two consecutive nucleotide units have identical stereochemistry and identical modifications at the linkage phosphorus. At least two consecutive nucleotide units form a "linkage block". For instance, (Rp, Rp)-ATsCsGA is a linkage blockmer because at least two consecutive nucleotide units, the Ts and the Cs, have the same stereochemistry (both Rp) and P-modification (both phosphorothioate). In the same oligonucleotide of (Rp, Rp)-ATsCsGA, TsCs forms a block, and it is a linkage block.

In some embodiments, a blockmer comprises one or more blocks independently selected from a stereoblock, a P-modification block and a linkage block. In some embodiments, a blockmer is a stereoblockmer with respect to one block, and/or a P-modification blockmer with respect to another block, and/or a linkage blockmer with respect to yet another block.

Altmer: the term "altmer," as used herein, refers to an oligonucleotide strand whose pattern of structural features characterizing each individual nucleotide unit is characterized in that no two consecutive nucleotide units of the oligonucleotide strand share a particular structural feature at the internucleotidic phosphorus linkage. In some embodiments, an altmer is designed such that it comprises a repeating pattern. In some embodiments, an altmer is designed such that it does not comprise a repeating pattern. In some embodiments, a provided oligonucleotide is a altmer.

In some embodiments, an altmer is a "stereoaltmer," e.g., no two consecutive nucleotide units have the same stereochemistry at the linkage phosphorus.

In some embodiments, an altmer is a "P-modification altmer" e.g., no two consecutive nucleotide units have the same modification at the linkage phosphorus. For instance, All-(Sp)-CAs1GsT, in which each linkage phosphorus has a different P-modification than the others.

In some embodiments, an altmer is a "linkage altmer," e.g., no two consecutive nucleotide units have identical stereochemistry or identical modifications at the linkage phosphorus.

Unimer: the term "unimer," as used herein, refers to an oligonucleotide strand whose pattern of structural features characterizing each individual nucleotide unit is such that all nucleotide units within the strand share at least one common structural feature at the internucleotidic phosphorus linkage. By common structural feature is meant common stereochemistry at the linkage phosphorus or a common modification at the linkage phosphorus. In some embodiments, a provided oligonucleotide is a unimer.

In some embodiments, a unimer is a "stereounimer," e.g., all nucleotide units have the same stereochemistry at the linkage phosphorus.

In some embodiments, a unimer is a "P-modification unimer", e.g., all nucleotide units have the same modification at the linkage phosphorus.

In some embodiments, a unimer is a "linkage unimer," e.g., all nucleotide units have the same stereochemistry and the same modifications at the linkage phosphorus.

Gapmer: as used herein, the term "gapmer" refers to an oligonucleotide strand characterized in that at least one internucleotidic phosphorus linkage of the oligonucleotide strand is a phosphate diester linkage, for example such as those found in naturally occurring DNA or RNA. In some embodiments, more than one internucleotidic phosphorus linkage of the oligonucleotide strand is a phosphate diester linkage such as those found in naturally occurring DNA or RNA. In some embodiments, a provided oligonucleotide is a gapmer.

Skipmer: as used herein, the term "skipmer" refers to a type of gapmer in which every other internucleotidic phosphorus linkage of the oligonucleotide strand is a phosphate diester linkage, for example such as those found in naturally occurring DNA or RNA, and every other internucleotidic phosphorus linkage of the oligonucleotide strand is a modified internucleotidic linkage. In some embodiments, a provided oligonucleotide is a skipmer.

For purposes of this disclosure, the chemical elements are identified in accordance with the Periodic Table of the Elements, CAS version, *Handbook of Chemistry and Physics*, 67th Ed., 1986-87, inside cover.

The methods and structures described herein relating to compounds and compositions of the disclosure also apply to the pharmaceutically acceptable acid or base addition salts and all stereoisomeric forms of these compounds and compositions.

DESCRIPTION OF CERTAIN EMBODIMENTS

Among other things, the present disclosure provides oligonucleotides of particular structural designs comprising base, sugar and/or internucleotidic linkage modifications and/or patterns thereof as described in the present disclosure. In some embodiments, the present disclosure provides compositions, e.g., chirally controlled oligonucleotide compositions, of such oligonucleotides. As demonstrated here, provided oligonucleotides and compositions thereof provide many advantages, e.g., greatly improved stability, activity, selectivity, etc. In some embodiments, the present disclosure provides technologies for assessing and/or using provided oligonucleotides and compositions thereof. For example, in some embodiments, the present disclosure provides methods for reducing levels of a nucleic acid (e.g., a transcript) and/or a product encoded thereby (e.g., a protein) using provided oligonucleotides and/or compositions thereof. In some embodiments, as demonstrated in the present disclosure, provided technologies (e.g., oligonucleotides, compositions, methods, etc.) provides high efficacy and/or specificity.

Certain Oligonucleotides and Compositions

In some embodiments, the present disclosure provides an oligonucleotide comprising a region of consecutive nucleotidic units:

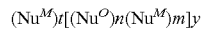

wherein:
each $Nu^M$ is independently a nucleotidic unit comprising a modified internucleotidic linkage;
each $Nu^O$ is independently a nucleotidic unit comprising a natural phosphate linkage;
each of t, n, and m is independently 1-20; and
y is 1-10.

In some embodiments, as demonstrated in the present disclosure, such oligonucleotides provide improved properties, e.g., improved stability, and/or activities.

In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10.

As defined herein, each $Nu^M$ independently comprises a modified internucleotidic linkage. In some embodiments, a modified internucleotidic linkage is a chiral internucleotidic linkage. In some embodiments, a modified internucleotidic linkage is of formula I or a salt form thereof. In some embodiments, a modified internucleotidic linkage is chiral and is of formula I or a salt form thereof. In some embodiments, a modified internucleotidic linkage is a phosphorothioate diester linkage. In some embodiments, a modified internucleotidic linkage is chiral and is chirally controlled. In some embodiments, each modified internucleotidic linkage is chirally controlled. In some embodiments, internucleotidic linkage of $Nu^M$ is a chirally controlled phosphorothioate diester linkage. In some embodiments, $Nu^M$ of a provided oligonucleotides comprises different types of modified internucleotidic linkages. In some embodiments, $Nu^M$ of a provided oligonucleotides comprises chiral internucleotidic linkages having linkage phosphorus atoms of different configuration. In some embodiments, $Nu^M$ of a provided oligonucleotides comprises different types of modified internucleotidic linkages. In some embodiments, $Nu^M$ of a provided oligonucleotides comprises chiral internucleotidic linkages having linkage phosphorus atoms of different configuration. In some embodiments, at least one chiral internucleotidic linkage of $Nu^M$ is Sp at its linkage phosphorus. In some embodiments, at least 2, 3, 4, 5, 6, 7, 8, 9, or 10 $Nu^M$ each independently comprise a chiral internucleotidic linkage of Sp at its linkage phosphorus. In some embodiments, each chiral internucleotidic linkage of $Nu^M$ is Sp at its linkage phosphorus. In some embodiments, at least one chiral internucleotidic linkage of $Nu^M$ is Rp at its linkage phosphorus. In some embodiments, at least one chiral internucleotidic linkage of $Nu^M$ is Rp at its linkage phosphorus, and at least one chiral internucleotidic linkage of $Nu^M$ is Sp at its linkage phosphorus. Additional nucleotidic unit comprising modified internucleotidic linkages suitable for $Nu^M$ are known in the art and/or described in the present disclosure and can be utilized in accordance with the present disclosure.

As defined herein, each $Nu^O$ is independently a nucleotidic unit comprising a natural phosphate linkage. In some embodiments, at least one $Nu^O$ is a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms. In some embodiments, each $Nu^O$ is independently a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms. In some embodiments, at least one $Nu^O$ comprises a structure of —$C(R^{5s})_2$—, which structure is directly boned to the natural phosphate linkage of $Nu^O$ and a ring moiety of the sugar unit of $Nu^O$. In some embodiments, each $Nu^O$ independently comprises a structure of —$C(R^{5s})_2$—, which structure is directly boned to the natural phosphate linkage of $Nu^O$ and a ring moiety of the sugar unit of $Nu^O$.

In some embodiments, each $Nu^O$ independently has the structure of formula N-I:

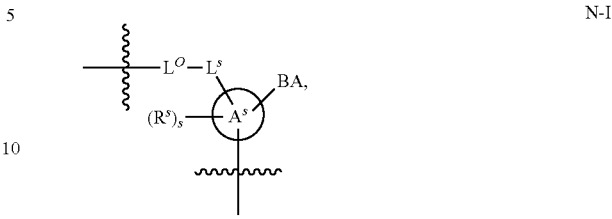

or a salt form thereof, wherein:

BA is an optionally substituted group selected from $C_{1-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

$L^O$ is a natural phosphate linkage;

$L^s$ is —$C(R^{5s})$—, or L;

each $R^{5s}$ and $R^s$ is independently —F, —Cl, —Br, —I, —CN, —$N_3$, —NO, —$NO_2$, -L-R', -L-OR', -L-SR', -L-N(R')$_2$, —O-L-OR', —O-L-SR', or —O-L-N(R')$_2$;

each L is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

Ring $A^s$ is an optionally substituted 3-20 membered monocyclic, bicyclic or polycyclic ring having 0-10 heteroatoms;

s is 0-20;

each R' is independently —R, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments,

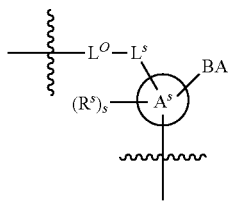

has the structure of

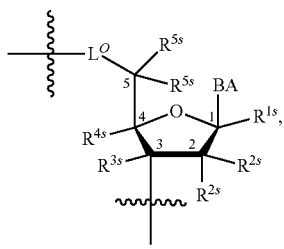

wherein each of $R^{1s}$, $R^{2s}$, $R^{3s}$, and $R^{4s}$ is independently $R^s$ and as described in the present disclosure. In some embodiments

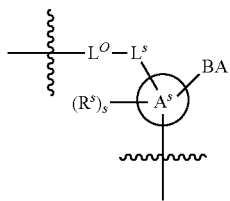

has the structure of

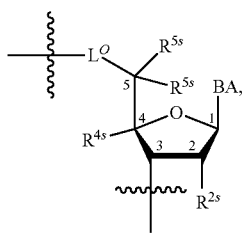

wherein each of $R^{1s}$, $R^{2s}$, $R^{3s}$, and $R^{4s}$ is independently as described in the present disclosure. In some embodiments,

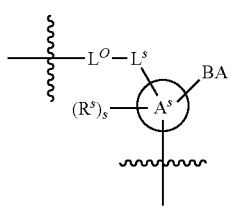

has the structure of

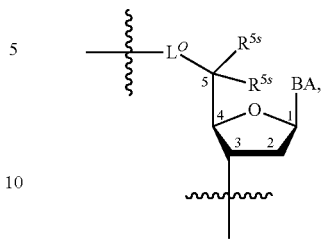

wherein each of $R^{1s}$, $R^{2s}$, $R^{3s}$, and $R^{4s}$ is independently as described in the present disclosure.

In some embodiments, $L^s$ is $-C(R^{5s})_2-$. In some embodiments, one $R^{5s}$ is $-H$ and $L^s$ is $-CHR^{5s}-$. In some embodiments, each $R^{5s}$ is independently R. In some embodiments, $-C(R^5)_2-$ is $-C(R)_2-$. In some embodiments, one $R^{5s}$ is $-H$ and $-C(R^5)_2-$ is $-CHR-$. In some embodiments, R is not hydrogen. In some embodiments, R is optionally substituted $C_{1-6}$ aliphatic. In some embodiments, R is optionally substituted $C_{1-6}$ alkyl. In some embodiments, R is substituted. In some embodiments, R is unsubstituted. In some embodiments, R is methyl. Additional example R groups are widely described in the present disclosure. In some embodiments, the C of $-C(R^{5s})_2-$ is chiral and is R. In some embodiments, the C of $-C(R^{5s})_2-$ is chiral and is S. In some embodiments, $-C(R^{5s})_2-$ is $-(R)-CHMe-$. In some embodiments, $-C(R^{5s})_2-$ is $-(S)-CHMe-$.

Certain Oligonucleotide Formats

In some embodiments, the present disclosure provides oligonucleotides that have an asymmetric format.

In some embodiments, an oligonucleotide having an asymmetric format is capable of mediating a decrease in the level, expression and/or activity of a target gene or a gene product thereof. In some embodiments, an oligonucleotide having an asymmetric format is capable of mediating a decrease in the level, expression and/or activity of a target gene or a gene product thereof in a cell in vitro.

In some embodiments, an oligonucleotide having an asymmetric format is capable of operating via any mechanism, including but not limited to: steric hindrance or an RNaseH-based mechanism. In some embodiments, in steric hindrance, an oligonucleotide having an asymmetric format blocks or decreases translation of a target mRNA. In some embodiments, in an RNaseH-based mechanism, an oligonucleotide having an asymmetric format comprises a core which comprises multiple deoxyribose sugars and is capable of annealing to a target RNA (including but not limited to a target gene mRNA), thus creating a DNA-RNA duplex, which acts as a substrate for RNaseH, which is capable of cleaving the target RNA. In some embodiments, an oligonucleotide having an asymmetric format comprises a core which is flanked on either side by a wing, each which also anneal to the target RNA. In some embodiments, one or both wings of an oligonucleotide having an asymmetric format are capable of improving the target specificity, target binding, stability, deliverability, efficacy, and/or other useful characteristic of an oligonucleotide having an asymmetric format.

In some embodiments, provided oligonucleotides comprise or are of a wing-core-wing, core-wing, or wing-core structure. In some embodiments, one wing differs chemically from the core and from the other wing. In some embodiments, a wing or a core is a block, and a wing-core-wing structure is a blockmer comprising three blocks. In some embodiments, a core is also designated a gap. In some embodiments, a wing-core-wing format is also designated a wing-gap-wing format. In some embodiments, a core is a gap wherein each sugar moiety of the core comprises no sugar modification of the wing(s). In some embodiments, an oligonucleotide having a wing-core-wing structure is also designated an oligonucleotide having a wing-gap-wing structure. In some embodiments, an oligonucleotide having a wing-core-wing structure is also designated a gapmer.

In some embodiments, a first wing, a second wing and a core can differ in sugar modifications or patterns thereof, and/or internucleotidic linkages or patterns thereof, and/or stereochemistry of internucleotidic linkages or patterns thereof.

In some embodiments, a wing-core-wing motif is described as "X-Y-Z", where "X" represents the length of the 5' wing, "Y" represents the length of the core, and "Z" represents the length of the 3' wing. In some embodiments, the core is positioned immediately adjacent to each of the 5' wing and the 3' wing. In some embodiments, X and Z are the same or different lengths and/or have the same or different modifications or patterns of modifications. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. In some embodiments, an oligonucleotide described herein has or comprises a wing-core-wing structure of, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In some embodiments, a core comprises at least 5 contiguous deoxyribose sugars. In some embodiments, a core comprises at least 5 contiguous deoxyribose sugars, and a first wing comprises a first type of sugar modification not in the core, and a second wing comprises a different type of sugar modification not in the core. In some embodiments, a core comprises at least 10 contiguous deoxyribose sugars, and a first wing comprises a first type of sugar modification not in the core, and a second wing comprises a different type of sugar modification not in the core. In some embodiments, a core comprises at least 10 contiguous deoxyribose sugars, and a first wing has a length of at least 5 bases and a first type of sugar modification not in the core, and a second wing has a length of at least 5 bases and comprises a different type of sugar modification not in the core. In some embodiments, a core comprises at least 10 contiguous deoxyribose sugars, and a first wing has a length of at least 5 bases and a first type of sugar modification not in the core, and a second wing has a length of at least 5 bases and comprises a second type of sugar modification not in the core, wherein the first and second type of sugar modification are not the same. In some embodiments, a core comprises at least 10 contiguous deoxyribose sugars, and a first wing has a length of at least 5 bases and a first and a second type of sugar modification not in the core, and a second wing has a length of at least 5 bases and comprises the first but not the second type of sugar modification.

In some embodiments of an oligonucleotide having an asymmetric format, the length of the first wing and the second wing are different. In some embodiments of an oligonucleotide having an asymmetric format, the length of the first wing and the second wing are the same.

In some embodiments, an oligonucleotide has a wing-core-wing-structure, wherein the length (in bases) of the first wing is represented by X, the length of the core is represented by Y and the length of the second wing is represented by Z, wherein X-Y-Z is any of: 1-5-1, 1-6-1, 1-7-1, 1-8-1, 1-9-1, 1-10-1, 1-11-1, 1-12-1, 1-13-1, 1-14-1, 1-15-1, 1-16-1, 1-17-1, 1-18-1, 1-19-1, 1-20-1, 1-5-2, 1-6-2, 1-7-2, 1-8-2, 1-9-2, 1-10-2, 1-11-2, 1-12-2, 1-13-2, 1-14-2, 1-15-2, 1-16-2, 1-17-2, 1-18-2, 1-19-2, 1-20-2, 1-5-3, 1-6-3, 1-7-3, 1-8-3, 1-9-3, 1-10-3, 1-11-3, 1-12-3, 1-13-3, 1-14-3, 1-15-3, 1-16-3, 1-17-3, 1-18-3, 1-19-3, 1-20-3, 1-5-4, 1-6-4, 1-7-4, 1-8-4, 1-9-4, 1-10-4, 1-11-4, 1-12-4, 1-13-4, 1-14-4, 1-15-4, 1-16-4, 1-17-4, 1-18-4, 1-19-4, 1-20-4, 1-5-5, 1-6-5, 1-7-5, 1-8-5, 1-9-5, 1-10-5, 1-11-5, 1-12-5, 1-13-5, 1-14-5, 1-15-5, 1-16-5, 1-17-5, 1-18-5, 1-19-5, 1-20-5, 2-5-1, 2-6-1, 2-7-1, 2-8-1, 2-9-1, 2-10-1, 2-12-1, 2-12-1, 2-13-1, 2-14-1, 2-15-1, 2-16-1, 2-17-1, 2-18-1, 2-19-1, 2-20-1, 2-5-2, 2-6-2, 2-7-2, 2-8-2, 2-9-2, 2-10-2, 2-12-2, 2-12-2, 2-13-2, 2-14-2, 2-15-2, 2-16-2, 2-17-2, 2-18-2, 2-19-2, 2-20-2, 2-5-3, 2-6-3, 2-7-3, 2-8-3, 2-9-3, 2-10-3, 2-12-3, 2-12-3, 2-13-3, 2-14-3, 2-15-3, 2-16-3, 2-17-3, 2-18-3, 2-19-3, 2-20-3, 2-5-4, 2-6-4, 2-7-4, 2-8-4, 2-9-4, 2-10-4, 2-12-4, 2-12-4, 2-13-4, 2-14-4, 2-15-4, 2-16-4, 2-17-4, 2-18-4, 2-19-4, 2-20-4, 2-5-5, 2-6-5, 2-7-5, 2-8-5, 2-9-5, 2-10-5, 2-12-5, 2-12-5, 2-13-5, 2-14-5, 2-15-5, 2-16-5, 2-17-5, 2-18-5, 2-19-5, 2-20-5, 3-5-1, 3-6-1, 3-7-1, 3-8-1, 3-9-1, 3-10-1, 3-13-1, 3-14-1, 3-13-1, 3-14-1, 3-15-1, 3-16-1, 3-17-1, 3-18-1, 3-19-1, 3-20-1, 3-5-2, 3-6-2, 3-7-2, 3-8-2, 3-9-2, 3-10-2, 3-13-2, 3-14-2, 3-13-2, 3-14-2, 3-15-2, 3-16-2, 3-17-2, 3-18-2, 3-19-2, 3-20-2, 3-5-3, 3-6-3, 3-7-3, 3-8-3, 3-9-3, 3-10-3, 3-13-3, 3-14-3, 3-13-3, 3-14-3, 3-15-3, 3-16-3, 3-17-3, 3-18-3, 3-19-3, 3-20-3, 3-5-4, 3-6-4, 3-7-4, 3-8-4, 3-9-4, 3-10-4, 3-13-4, 3-14-4, 3-13-4, 3-14-4, 3-15-4, 3-16-4, 3-17-4, 3-18-4, 3-19-4, 3-20-4, 3-5-5, 3-6-5, 3-7-5, 3-8-5, 3-9-5, 3-10-5, 3-13-5, 3-14-5, 3-13-5, 3-14-5, 3-15-5, 3-16-5, 3-17-5, 3-18-5, 3-19-5, 3-20-5, 4-5-1, 4-6-1, 4-7-1, 4-8-1, 4-9-1, 4-10-1, 4-14-1, 4-14-1, 4-13-1, 4-14-1, 4-15-1, 4-16-1, 4-17-1, 4-18-1, 4-19-1, 4-20-1, 4-5-2, 4-6-2, 4-7-2, 4-8-2, 4-9-2, 4-10-2, 4-14-2, 4-14-2, 4-13-2, 4-14-2, 4-15-2, 4-16-2, 4-17-2, 4-18-2, 4-19-2, 4-20-2, 4-5-3, 4-6-3, 4-7-3, 4-8-3, 4-9-3, 4-10-3, 4-14-3, 4-14-3, 4-13-3, 4-14-3, 4-15-3, 4-16-3, 4-17-3, 4-18-3, 4-19-3, 4-20-3, 4-5-4, 4-6-4, 4-7-4, 4-8-4, 4-9-4, 4-10-4, 4-14-4, 4-14-4, 4-13-4, 4-14-4, 4-15-4, 4-16-4, 4-17-4, 4-18-4, 4-19-4, 4-20-4, 4-5-5, 4-6-5, 4-7-5, 4-8-5, 4-9-5, 4-10-5, 4-14-5, 4-14-5, 4-13-5, 4-14-5, 4-15-5, 4-16-5, 4-17-5, 4-18-5, 4-19-5, 4-20-5, 5-5-1, 5-6-1, 5-7-1, 5-8-1, 5-9-1, 5-10-1, 5-15-1, 5-12-1, 5-13-1, 5-14-1, 5-15-1, 5-16-1, 5-17-1, 5-18-1, 5-19-1, 5-20-1, 5-5-2, 5-6-2, 5-7-2, 5-8-2, 5-9-2, 5-10-2, 5-15-2, 5-12-2, 5-13-2, 5-14-2, 5-15-2, 5-16-2, 5-17-2, 5-18-2, 5-19-2, 5-20-2, 5-5-3, 5-6-3, 5-7-3, 5-8-3, 5-9-3, 5-10-3, 5-15-3, 5-12-3, 5-13-3, 5-14-3, 5-15-3, 5-16-3, 5-17-3, 5-18-3, 5-19-3, 5-20-3, 5-5-4, 5-6-4, 5-7-4, 5-8-4, 5-9-4, 5-10-4, 5-15-4, 5-12-4, 5-13-4, 5-14-4, 5-15-4, 5-16-4, 5-17-4, 5-18-4, 5-19-4, 5-20-4, 5-5-5, 5-6-5, 5-7-5, 5-8-5, 5-9-5, 5-10-5, 5-15-5, 5-12-5, 5-13-5, 5-14-5, 5-15-5, 5-16-5, 5-17-5, 5-18-5, 5-19-5, 5-20-5, 1-5-6, 1-6-6, 1-7-6, 1-8-6, 1-9-6, 1-10-6, 1-11-6, 1-12-6, 1-13-6, 1-14-6, 1-15-6, 1-16-6, 1-17-6, 1-18-6, 1-19-6, 1-20-6, 2-5-6, 2-6-6, 2-7-6, 2-8-6, 2-9-6, 2-10-6, 2-11-6, 2-12-6, 2-13-6, 2-14-6, 2-15-6, 2-16-6, 2-17-6, 2-18-6, 2-19-6, 2-20-6, 3-5-6, 3-6-6, 3-7-6, 3-8-6, 3-9-6, 3-10-6, 3-11-6, 3-12-6, 3-13-6, 3-14-6, 3-15-6, 3-16-6, 3-17-6, 3-18-6, 3-19-6, 3-20-6, 4- 5-6, 4-6-6, 4-7-6, 4-8-6, 4-9-6, 4-10-6, 4-11-6, 4-12-6, 4-13-6, 4-14-6, 4-15-6, 4-16-6, 4-17-6, 4-18-6, 4-19-6, 4-20-6, 5-5-6, 5-6-6, 5-7-6, 5-8-6, 5-9-6, 5-10-6, 5-11-6, 5-12-6, 5-13-6, 5-14-6, 5-15-6, 5-16-6, 5-17-6, 5-18-6, 5-19-6, 5-20-6, 6-5-6, 6-6-6, 6-7-6, 6-8-6, 6-9-6, 6-10-6, 6-11-6, 6-12-6, 6-13-6, 6-14- 6, 6-15-6, 6-16-6, 6-17-6, 6-18-6, 6-19-6, 6-20-6, 7-5-6, 7-6-6, 7-7-6, 7-8-6, 7-9-6, 7-10-6, 7-11-6, 7-12- 6, 7-13-6, 7-14-6, 7-15-6, 7-16-6, 7-17-6, 7-18-6, 7-19-6, 7-20-6, 1-5-7, 1-6-7, 1-7-7, 1-8-7, 1-9-7, 1-10- 7, 1-11-7, 1-12-7, 1-13-7, 1-14-7, 1-15-7, 1-16-7, 1-17-7, 1-18-7, 1-19-7, 1-20-7, 2-5-7, 2-6-7, 2-7-7, 2-8-7, 2-9-7, 2-10-7, 2-11-7, 2-12-7, 2-13-7, 2-14-7, 2-15-7, 2-16-7, 2-17-7, 2-18-7, 2-19-7, 2-20-7, 3-5-7, 3-6-7, 3-7-7, 3-8-7, 3-9-7, 3-10-7, 3-11-7, 3-12-7, 3-13-7, 3-14-7, 3-15-7, 3-16-7, 3-17-7, 3-18-7, 3-19-7, 3-20-7, 4-5-7, 4-6-7, 4-7-7, 4-8-7, 4-9-7, 4-10-7, 4-11-7, 4-12-7, 4-13-7, 4-14-7, 4-15-7, 4-16-7, 4-17-7, 4-18-7, 4-19-7, 4-20-7, 5-5-7, 5-6-7, 5-7-7, 5-8-7, 5-9-7, 5-10-7, 5-11-7, 5-12-7, 5-13-7, 5-14-7, 5-15-7, 5-16-7, 5-17-7, 5-18-7, 5-19-7, 5-20-7, 6-5-7, 6-6-7, 6-7-7, 6-8-7, 6-9-7, 6-10-7, 6-11-7, 6-12-7, 6-13-7, 6-14-7, 6-15-7, 6-16-7, 6-17-7, 6-18-7, 6-19-7, 6-20-7, 7-5-7, 7-6-7, 7-7-7, 7-8-7, 7-9-7, 7-10-7, 7-11-7, 7-12-7, 7-13-7, 7-14-7, 7-15-7, 7-16-7, 7-17-7, 7-18-7, 7-19-7, or 7-20-7.

As described in the present disclosure, cores and wings can be of various lengths. In some embodiments, a core comprises no less than 5, 6, 7, 8, 9, 10, 11, 12, 13, 14, 15, 16, 17, 18, 19, or 20 nucleobases. In some embodiments, a wing comprises no less than 1, 2, 3, 4, 5, 6, 7, 8, 9, or 10 nucleobases. In some embodiments, a wing comprises no more than 2, 3, 4, 5, 6, 7, 8, 9, or 10 nucleobases. In some embodiments, for a wing-core-wing structure, both wings are of the same length, for example, of 5 nucleobases. In some embodiments, the two wings are of different lengths. In some embodiments, a core is no less than 40%, 45%, 50%, 60%, 70%, 80%, or 90% of total oligonucleotide length as measured by percentage of nucleoside units within the core. In some embodiments, a core is no less than 50% of total oligonucleotide length.

In some embodiments of an oligonucleotide having an asymmetric format, a wing has a length of 6 bases. A non-limiting example of such an oligonucleotide is WV-12485. In some embodiments of an oligonucleotide having an asymmetric format, a wing has a length of 7 bases. A non-limiting example of such an oligonucleotide is WV-12107.

In some embodiments, an oligonucleotide having an asymmetric format has a wing-core-wing structure, wherein one wing differs from the other wing. In some embodiments, a wing comprises one or more sugar modifications. In some embodiments, the two wings of a wing-core-wing structure comprise different sugar modifications. In some embodiments, sugar modifications provide improved stability compared to absence of sugar modifications.

In some embodiments, a core comprises no 2'-substitution. In some embodiments, each sugar unit of a core is a natural sugar unit found in natural unmodified DNA. In some embodiments, a core comprises one or more 2'-halogen modification. In some embodiments, a core comprises one or more 2'-F modification.

In some embodiments, certain sugar modifications, e.g., 2'-MOE increase stability against nucleases. In some embodiments, a wing comprises 2'-MOE modifications. In some embodiments, each nucleoside unit of a wing comprising a pyrimidine base (e.g., C, U, T, etc.) comprises a 2'-MOE modification. In some embodiments, each sugar unit of a wing comprises a 2'-MOE modification. In some embodiments, each nucleoside unit of a wing comprising a purine base (e.g., A, G, etc.) comprises no 2'-MOE modification (e.g., 2'-OMe, no 2'-modification, etc.). In some embodiments, each nucleoside unit of a wing comprising a purine base comprises a 2'-OMe modification. In some embodiments, each internucleotidic linkage at the 3'-position of a sugar unit comprising a 2'-MOE modification is a natural phosphate linkage. In some embodiments, each internucleotidic linkage at the 3'-position of a sugar unit comprising a 2'-MOE modification is a natural phosphate linkage, except that if the wing is a 5'-wing to the core, the first internucleotidic linkage of the wing is a modified internucleotidic linkage, e.g., a phosphorothioate diester linkage, and the internucleotidic linkage linking the 3'-end nucleoside unit of the wing and the 5'-end nucleoside unit of the core is a modified internucleotidic linkage, e.g., a phosphorothioate diester linkage; and if the wing is a 3'-wing to the core, the last internucleotidic linkage of the wing is a modified internucleotidic linkage, e.g., a phosphorothioate diester linkage, and the internucleotidic linkage linking the 3'-end nucleoside unit of the core and the 5'-end nucleoside unit of the wing is a modified internucleotidic linkage, e.g., a phosphorothioate diester linkage. In some embodiments, such a wing is a 5'-wing. In some embodiments, such a wing is a 3'-wing.

In some embodiments, a wing comprises no 2'-MOE modifications. In some embodiments, a wing comprises 2'-OMe modifications. In some embodiments, each nucleoside unit of a wing independently comprises a 2'-OMe modifications. Among other things, the present disclosure encompasses the recognition that oligonucleotides with 2'-OMe modifications are less stable than comparable oligonucleotides with 2'-MOE modifications under certain conditions. In some embodiments, modified non-natural internucleotidic linkages, such as phosphorothioate diester linkages, in some instances particularly Sp phosphorothioate diester linkages, can be utilized to improve properties, e.g., stability, of oligonucleotides. In some embodiments, a wing comprises no 2'-MOE modifications, and each internucleotidic linkage between nucleoside units of the wing is a modified internucleotidic linkage. In some embodiments, a wing comprises no 2'-MOE modifications, each nucleoside unit of the wing comprise a 2'-OMe modification, and each internucleotidic linkage between nucleoside units of the wing is a modified internucleotidic linkage. In some embodiments, a modified internucleotidic linkage is a phosphorothioate diester linage. In some embodiments, a modified internucleotidic linkage is a chirally controlled internucleotidic linkage. In some embodiments, a modified internucleotidic linkage is a chirally controlled internucleotidic linkage wherein the linkage phosphorus is of Sp configuration. In some embodiments, a modified internucleotidic linkage is a chirally controlled internucleotidic linkage wherein the linkage phosphorus is of Rp configuration. In some embodiments, a modified internucleotidic linkage is a Sp phosphorothioate diester linkage. In some embodiments, a modified internucleotidic linkage is a Rp phosphorothioate diester linkage. In some embodiments, such a wing is a 5'-wing. In some embodiments, such a wing is a 3'-wing.

In some embodiments, 2'-modifications and/or modified internucleotidic linkages can be utilized either individually or in combination to fine-tune properties, e.g., stability, and/or activities of oligonucleotides.

In some embodiments, a wing comprises one or more natural phosphate linkages. In some embodiments, a wing comprises one or more consecutive natural phosphate linkages. In some embodiments, a wing comprises one or more natural phosphate linkages and one or more modified internucleotidic linkages. In some embodiments, a modified internucleotidic linkage is a phosphorothioate diester linkage. In some embodiments, a modified internucleotidic linkage is a Sp phosphorothioate diester linkage.

In some embodiments, a wing comprises no natural phosphate linkages, and each internucleotidic linkage of the wing is independently a modified internucleotidic linkage. In some embodiments, a modified internucleotidic linkage is chiral and chirally controlled. In some embodiments, a modified internucleotidic linkage is a phosphorothioate diester linkage. In some embodiments, a modified internucleotidic linkage is a Sp phosphorothioate diester linkage.

In some embodiments, for an oligonucleotide comprising or is a wing-core-wing structure, the two wings are different in that they contain different levels and/or types of chemical modifications, backbone chiral center stereochemistry, and/or patterns thereof. In some embodiments, the two wings are different in that they contain different levels and/or types of sugar modifications, and/or internucleotidic linkages, and/or internucleotidic linkage stereochemistry, and/or patterns thereof. For example, in some embodiments, one wing comprises 2'-OR modifications wherein R is optionally substituted $C_{1-6}$ alkyl (e.g., 2-MOE), while the other wing comprises no such modifications, or lower level (e.g., by number and/or percentage) of such modifications; additionally and alternatively, one wing comprises natural phosphate linkages while the other wing comprises no natural phosphate linkages or lower level (e.g., by number and/or percentage) of natural phosphate linkages; additionally and alternatively, one wing may comprise a certain type of modified internucleotidic linkages (e.g., phosphorothioate diester internucleotidic linkage) while the other wing comprises no natural phosphate linkages or lower level (e.g., by number and/or percentage) of the type of modified internucleotidic linkages; additionally and alternatively, one wing may comprise chiral modified internucleotidic linkages comprising linkage phosphorus atoms of a particular configuration (e.g., Rp or Sp), while the other wing comprises no or lower level of chiral modified internucleotidic linkages comprising linkage phosphorus atoms of the particular configuration; alternatively or additionally, each wing may comprise a different pattern of sugar modification, internucleotidic linkages, and/or backbone chiral centers. In some embodiments, one wing comprises one or more natural phosphate linkages and one or more 2'-OR modifications wherein R is not —H or -Me, and the other wing comprises no natural phosphate linkages and no 2'-OR modifications wherein R is not —H or -Me. In some embodiments, one wing comprises one or more natural phosphate linkages and one or more 2'-MOE modifications, and each internucleotidic linkage in the other wing is a phosphorothioate linkage and each sugar unit of the other wing comprises a 2'-OMe modification. In some embodiments, one wing comprises one or more natural phosphate linkages and one or more 2'-MOE modifications, and each internucleotidic linkage in the other wing is a Sp phosphorothioate linkage and each sugar unit of the other wing comprises a 2'-OMe modification.

In some embodiments, an oligonucleotide comprises a wing-core-wing structure, wherein one wing comprises a 2'-OMe and the other wing comprises a bicyclic sugar. In some embodiments, an oligonucleotide comprises a wing-core-wing structure, wherein one wing comprises a 2'-OMe and the other wing comprises a bicyclic sugar, and the majority of the sugars in the core comprise a 2'-deoxy.

In some embodiments, an oligonucleotide comprises a wing-core-wing structure, wherein the majority of the sugars in one wing comprise a 2'-OMe and the majority of the sugars in the other wing are a bicyclic sugar. In some embodiments, an oligonucleotide comprises a wing-core-wing structure, wherein the majority of the sugars in one wing comprise a 2'-OMe and the majority of the sugars in the other wing are a bicyclic sugar, and the majority of the sugars in the core comprise a 2'-deoxy.

In some embodiments, an oligonucleotide comprises a wing-core-wing structure, wherein the majority of the sugars in one wing comprise a 2'-OMe and, in the other wing, at least one sugar is a bicyclic sugar and at least one sugar comprises a 2'-OMe. In some embodiments, an oligonucleotide comprises a wing-core-wing structure, wherein the majority of the sugars in one wing comprise a 2'-OMe and, in the other wing, at least one sugar is a bicyclic sugar and at least one sugar comprises a 2'-OMe, and the majority of the sugars in the core comprise a 2'-deoxy.

In some embodiments, an oligonucleotide comprises a wing-core-wing structure, wherein the majority of the sugars in one wing are a bicyclic sugar and, in the other wing, at least one sugar is a bicyclic sugar and at least one sugar comprises a 2'-OMe. In some embodiments, an oligonucleotide comprises a wing-core-wing structure, wherein the majority of the sugars in one wing are a bicyclic sugar and, in the other wing, at least one sugar is a bicyclic sugar and at least one sugar comprises a 2'-OMe, and the majority of the sugars in the core comprise a 2'-deoxy.

In some embodiments, an oligonucleotide comprises a wing-core-wing structure, wherein the majority of the sugars in one wing comprise a 2'-OMe and, in the other wing, at least two sugars are a bicyclic sugar and at least two sugars comprise a 2'-OMe. In some embodiments, an oligonucleotide comprises a wing-core-wing structure, wherein the majority of the sugars in one wing comprise a 2'-OMe and, in the other wing, at least two sugars are a bicyclic sugar and at least two sugars comprise a 2'-OMe, and the majority of the sugars in the core comprise a 2'-deoxy.

In some embodiments, an oligonucleotide comprises a wing-core-wing structure, wherein the majority of the sugars in one wing are a bicyclic sugar and, in the other wing, at least two sugars are a bicyclic sugar and at least two sugars comprise a 2'-OMe. In some embodiments, an oligonucleotide comprises a wing-core-wing structure, wherein the majority of the sugars in one wing are a bicyclic sugar and, in the other wing, at least two sugars are a bicyclic sugar and at least two sugars comprise a 2'-OMe, and the majority of the sugars in the core comprise a 2'-deoxy.

In some embodiments, an oligonucleotide comprises a wing-core-wing structure, wherein each sugar in one wing comprises a 2'-OMe and each sugar in the other wing comprises a bicyclic sugar. In some embodiments, an oligonucleotide comprises a wing-core-wing structure, wherein each sugar in one wing comprises a 2'-OMe and each sugar in the other wing comprises a bicyclic sugar, and the majority of the sugars in the core comprise a 2'-deoxy.

In some embodiments, an oligonucleotide comprises a wing-core-wing structure, wherein each sugar in one wing comprises a bicyclic sugar, each sugar in the other wing comprises a 2'-OMe, and each sugar in the core comprises a 2'-deoxy.

In some embodiments, an oligonucleotide comprises a wing-core-wing structure, wherein one wing comprises a bicyclic sugar and the other wing comprises a 2'-MOE. In some embodiments, an oligonucleotide comprises a wing-core-wing structure, wherein one wing comprises a bicyclic sugar and the other wing comprises a 2'-MOE, and the majority of the sugars in the core comprise a 2'-deoxy.

In some embodiments, an oligonucleotide comprises a wing-core-wing structure, wherein the majority of the sugars in one wing comprise a bicyclic sugar and the majority of the sugars in the other wing comprise a 2'-MOE. In some embodiments, an oligonucleotide comprises a wing-core-wing structure, wherein the majority of the sugars in one wing comprise a bicyclic sugar and the majority of the sugars in the other wing comprise a 2'-MOE, and the majority of the sugars in the core comprise a 2'-deoxy.

In some embodiments, an oligonucleotide comprises a wing-core-wing structure, wherein the majority of the sugars in one wing comprise a bicyclic sugar and, in the other wing, at least one sugar comprises a 2'-MOE and at least one sugar is a bicyclic sugar. In some embodiments, an oligonucleotide comprises a wing-core-wing structure, wherein the majority of the sugars in one wing comprise a bicyclic sugar and, in the other wing, at least one sugar comprises a 2'-MOE and at least one sugar is a bicyclic sugar, and the majority of the sugars in the core comprise a 2'-deoxy.

In some embodiments, an oligonucleotide comprises a wing-core-wing structure, wherein the majority of the sugars in one wing comprise a 2'-MOE and, in the other wing, at least one sugar comprises a 2'-MOE and at least one sugar is a bicyclic sugar. In some embodiments, an oligonucleotide comprises a wing-core-wing structure, wherein the majority of the sugars in one wing comprise a 2'-MOE and, in the other wing, at least one sugar comprises a 2'-MOE and at least one sugar is a bicyclic sugar, and the majority of the sugars in the core comprise a 2'-deoxy.

In some embodiments, an oligonucleotide comprises a wing-core-wing structure, wherein the majority of the sugars in one wing comprise a bicyclic sugar and, in the other wing, at least two sugars comprise a 2'-MOE and at least two sugars is a bicyclic sugar. In some embodiments, an oligonucleotide comprises a wing-core-wing structure, wherein the majority of the sugars in one wing comprise a bicyclic sugar and, in the other wing, at least two sugars comprise a 2'-MOE and at least two sugars is a bicyclic sugar, and the majority of the sugars in the core comprise a 2'-deoxy.

In some embodiments, an oligonucleotide comprises a wing-core-wing structure, wherein the majority of the sugars in one wing comprise a 2'-MOE and, in the other wing, at least two sugars comprise a 2'-MOE and at least two sugars is a bicyclic sugar. In some embodiments, an oligonucleotide comprises a wing-core-wing structure, wherein the majority of the sugars in one wing comprise a 2'-MOE and, in the other wing, at least two sugars comprise a 2'-MOE and at least two sugars is a bicyclic sugar, and the majority of the sugars in the core comprise a 2'-deoxy.

In some embodiments, an oligonucleotide comprises a wing-core-wing structure, wherein each sugar in one wing are a bicyclic sugar and each sugar in the other wing comprises a 2'-MOE. In some embodiments, an oligonucleotide comprises a wing-core-wing structure, wherein each sugar in one wing are a bicyclic sugar and each sugar in the other wing comprises a 2'-MOE, and the majority of the sugars in the core comprise a 2'-deoxy.

In some embodiments, an oligonucleotide comprises a wing-core-wing structure, wherein each sugar in one wing comprises a 2'-MOE, each sugar in the other wing are a bicyclic sugar, and each sugar in the core comprises a 2'-deoxy.

In some embodiments, a bicyclic sugar is a LNA, a cEt or BNA.

In some embodiments, an oligonucleotide comprises a wing-core-wing structure, wherein one wing comprises a 2'-OMe and the other wing comprises 2'-F. In some embodiments, an oligonucleotide comprises a wing-core-wing structure, wherein one wing comprises a 2'-OMe and the other wing comprises 2'-F, and the majority of the sugars in the core comprise a 2'-deoxy.

In some embodiments, an oligonucleotide comprises a wing-core-wing structure, wherein the majority of the sugars in one wing comprise a 2'-OMe and the majority of the sugars in the other wing are 2'-F. In some embodiments, an oligonucleotide comprises a wing-core-wing structure, wherein the majority of the sugars in one wing comprise a 2'-OMe and the majority of the sugars in the other wing are 2'-F, and the majority of the sugars in the core comprise a 2'-deoxy.

In some embodiments, an oligonucleotide comprises a wing-core-wing structure, wherein the majority of the sugars in one wing comprise a 2'-OMe and, in the other wing, at least one sugar is 2'-F and at least one sugar comprises a 2'-OMe. In some embodiments, an oligonucleotide comprises a wing-core-wing structure, wherein the majority of the sugars in one wing comprise a 2'-OMe and, in the other wing, at least one sugar is 2'-F and at least one sugar comprises a 2'-OMe, and the majority of the sugars in the core comprise a 2'-deoxy.

In some embodiments, an oligonucleotide comprises a wing-core-wing structure, wherein the majority of the sugars in one wing are 2'-F and, in the other wing, at least one sugar is 2'-F and at least one sugar comprises a 2'-OMe. In some embodiments, an oligonucleotide comprises a wing-core-wing structure, wherein the majority of the sugars in one wing are 2'-F and, in the other wing, at least one sugar is 2'-F and at least one sugar comprises a 2'-OMe, and the majority of the sugars in the core comprise a 2'-deoxy.

In some embodiments, an oligonucleotide comprises a wing-core-wing structure, wherein the majority of the sugars in one wing comprise a 2'-OMe and, in the other wing, at least two sugars are 2'-F and at least two sugars comprise a 2'-OMe. In some embodiments, an oligonucleotide comprises a wing-core-wing structure, wherein the majority of the sugars in one wing comprise a 2'-OMe and, in the other wing, at least two sugars are 2'-F and at least two sugars comprise a 2'-OMe, and the majority of the sugars in the core comprise a 2'-deoxy.

In some embodiments, an oligonucleotide comprises a wing-core-wing structure, wherein the majority of the sugars in one wing are 2'-F and, in the other wing, at least two sugars are 2'-F and at least two sugars comprise a 2'-OMe. In some embodiments, an oligonucleotide comprises a wing-core-wing structure, wherein the majority of the sugars in one wing are 2'-F and, in the other wing, at least two sugars are 2'-F and at least two sugars comprise a 2'-OMe, and the majority of the sugars in the core comprise a 2'-deoxy.

In some embodiments, an oligonucleotide comprises a wing-core-wing structure, wherein each sugar in one wing comprises a 2'-OMe and each sugar in the other wing comprises 2'-F. In some embodiments, an oligonucleotide comprises a wing-core-wing structure, wherein each sugar in one wing comprises a 2'-OMe and each sugar in the other wing comprises 2'-F, and the majority of the sugars in the core comprise a 2'-deoxy.

In some embodiments, an oligonucleotide comprises a wing-core-wing structure, wherein each sugar in one wing comprises 2'-F, each sugar in the other wing comprises a 2'-OMe, and each sugar in the core comprises a 2'-deoxy.

In some embodiments, an oligonucleotide comprises a wing-core-wing structure, wherein one wing comprises 2'-F and the other wing comprises a 2'-MOE. In some embodiments, an oligonucleotide comprises a wing-core-wing structure, wherein one wing comprises 2'-F and the other wing comprises a 2'-MOE, and the majority of the sugars in the core comprise a 2'-deoxy.

In some embodiments, an oligonucleotide comprises a wing-core-wing structure, wherein the majority of the sugars in one wing comprise a 2'-F and the majority of the sugars in the other wing comprise a 2'-MOE. In some embodiments, an oligonucleotide comprises a wing-core-wing structure, wherein the majority of the sugars in one wing comprise 2'-F and the majority of the sugars in the other wing comprise a 2'-MOE, and the majority of the sugars in the core comprise a 2'-deoxy.

In some embodiments, an oligonucleotide comprises a wing-core-wing structure, wherein the majority of the sugars in one wing comprise 2'-F and, in the other wing, at least one sugar comprises a 2'-MOE and at least one sugar is 2'-F. In some embodiments, an oligonucleotide comprises a wing-core-wing structure, wherein the majority of the sugars in one wing comprise 2'-F and, in the other wing, at least one sugar comprises a 2'-MOE and at least one sugar is 2'-F, and the majority of the sugars in the core comprise a 2'-deoxy.

In some embodiments, an oligonucleotide comprises a wing-core-wing structure, wherein the majority of the sugars in one wing comprise a 2'-MOE and, in the other wing, at least one sugar comprises a 2'-MOE and at least one sugar is 2'-F. In some embodiments, an oligonucleotide comprises a wing-core-wing structure, wherein the majority of the sugars in one wing comprise a 2'-MOE and, in the other wing, at least one sugar comprises a 2'-MOE and at least one sugar is 2'-F, and the majority of the sugars in the core comprise a 2'-deoxy.

In some embodiments, an oligonucleotide comprises a wing-core-wing structure, wherein the majority of the sugars in one wing comprise 2'-F and, in the other wing, at least two sugars comprise a 2'-MOE and at least two sugars is 2'-F. In some embodiments, an oligonucleotide comprises a wing-core-wing structure, wherein the majority of the sugars in one wing comprise 2'-F and, in the other wing, at least two sugars comprise a 2'-MOE and at least two sugars is 2'-F, and the majority of the sugars in the core comprise a 2'-deoxy.

In some embodiments, an oligonucleotide comprises a wing-core-wing structure, wherein the majority of the sugars in one wing comprise a 2'-MOE and, in the other wing, at least two sugars comprise a 2'-MOE and at least two sugars is 2'-F. In some embodiments, an oligonucleotide comprises a wing-core-wing structure, wherein the majority of the sugars in one wing comprise a 2'-MOE and, in the other wing, at least two sugars comprise a 2'-MOE and at least two sugars is 2'-F, and the majority of the sugars in the core comprise a 2'-deoxy.

In some embodiments, an oligonucleotide comprises a wing-core-wing structure, wherein each sugar in one wing is 2'-F and each sugar in the other wing comprises a 2'-MOE. In some embodiments, an oligonucleotide comprises a wing-core-wing structure, wherein each sugar in one wing is 2'-F and each sugar in the other wing comprises a 2'-MOE, and the majority of the sugars in the core comprise a 2'-deoxy.

In some embodiments, an oligonucleotide comprises a wing-core-wing structure, wherein each sugar in one wing comprises a 2'-MOE, each sugar in the other wing are 2'-F, and each sugar in the core comprises a 2'-deoxy.

In some embodiments, 5%, 10%, 20%, 30%, 40%, 50%, 60%, 70%, 80%, 90% or more of the sugar moieties of provided oligonucleotides are modified. In some embodiments, each sugar moiety of provided oligonucleotides is modified. In some embodiments, a modified sugar moiety comprises a 2'-modification. In some embodiments, a modified sugar moiety comprises a 2'-modification. In some embodiments, a 2'-modification is 2'-OR$^1$. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-OR$^1$ or 2'-F. In some embodiments, each sugar modification is independently 2'-OR$^1$ or 2'-F, wherein R$^1$ is optionally substituted C$_{1-6}$ alkyl. In some embodiments, each sugar modification is independently 2'-OR$^1$ or 2'-F, wherein at least one is 2'-F. In some embodiments, each sugar modification is independently 2'-OR$^1$ or 2'-F, wherein R$^1$ is optionally substituted C$_{1-6}$ alkyl, and wherein at least one is 2'-OR$^1$. In some embodiments, each sugar modification is independently 2'-OR$^1$ or 2'-F, wherein at least one is 2'-F, and at least one is 2'-OR$^1$. In some embodiments, each sugar modification is independently 2'-OR$^1$ or 2'-F, wherein R$^1$ is optionally substituted C$_{1-6}$ alkyl, and wherein at least one is 2'-F, and at least one is 2'-OR$^1$.

In some embodiments, a nucleoside comprising a 2'-modification is followed by a modified internucleotidic linkage. In some embodiments, a nucleoside comprising a 2'-modification is preceded by a modified internucleotidic linkage. In some embodiments, a modified internucleotidic linkage is a chiral internucleotidic linkage. In some embodiments, a modified internucleotidic linkage is a phosphorothioate. In some embodiments, a chiral internucleotidic linkage is Sp. In some embodiments, a nucleoside comprising a 2'-modification is followed by a Sp chiral internucleotidic linkage. In some embodiments, a nucleoside comprising a 2'-F is followed by a Sp chiral internucleotidic linkage. In some embodiments, a nucleoside comprising a 2'-modification is preceded by a Sp chiral internucleotidic linkage. In some embodiments, a nucleoside comprising a 2'-F is preceded by a Sp chiral internucleotidic linkage. In some embodiments, a chiral internucleotidic linkage is Rp. In some embodiments, a nucleoside comprising a 2'-modification is followed by an Rp chiral internucleotidic linkage. In some embodiments, a nucleoside comprising a 2'-F is followed by an Rp chiral internucleotidic linkage. In some embodiments, a nucleoside comprising a 2'-modification is preceded by an Rp chiral internucleotidic linkage. In some embodiments, a nucleoside comprising a 2'-F is preceded by an Rp chiral internucleotidic linkage.

In some embodiments, a provided oligonucleotide having an asymmetric formats has a wing-core-wing structure. In some embodiments of an oligonucleotide having an asymmetric format having an asymmetrical format, one wing differs from another. In some embodiments of an oligonucleotide having an asymmetric format having an asymmetrical format, one wing differs from another in the sugar modifications or combination or pattern thereof, or the backbone internucleotidic linkages or combination or pattern thereof, or the backbone chiral centers or combination or pattern thereof. In some embodiments of an oligonucleotide having an asymmetrical format, the core comprises 1 or more 2'-deoxy sugars. In some embodiments of an oligonucleotide having an asymmetrical format, the core comprises 5 or more consecutive 2'-deoxy sugars. In some embodiments of an oligonucleotide having an asymmetrical format, the core comprises 5, 6, 7, 8, 9, 10, 11, 12, 13, 14, 15 or more consecutive 2'-deoxy sugars. Some non-limiting examples of oligonucleotides having an asymmetrical format are shown herein. In some embodiments of an oligonucleotide having an asymmetric format having an asymmetrical format, a first wing and a second wing independently has a pattern of 2'-modifications of sugars which is or comprises F, FF, FFF, FFFF, FFFFF, FMMMF, FMMMF, LMMMm, m, M, mm, MM, mmm, mMm, MMm, MMM, mmm, mmmm, mMMm, MMMm, MMMM, mmmm, mmmmm, MMMMM, mMMMm, MMMMM, mmmmm, or any pattern of 2'-modifications of any wing of any oligonucleotide described herein, wherein the pattern of 2'-modifications of the first and second wing are different, and wherein m=2'-OMe; M=2'-MOE; F=2'-F; and L=LNA.

In some embodiments, an oligonucleotide having an asymmetric format (e.g., wherein one wing differs chemically from another wing) has an improved biological activity compared to an oligonucleotide having the same base sequence but a different structure (e.g., a symmetric format wherein both wings have the same pattern of chemical modifications; or a different asymmetric format). In some embodiments, improved biological activity includes improved decrease of the expression, activity, and/or level or a gene or gene product. In some embodiments, improved biological activity is improved delivery to a cellular nucleus. In some embodiments, improved biological activity is improved delivery to a cellular nucleus and one wing in an oligonucleotide having an asymmetric format comprises a 2'-F or two or more 2'-F. In some embodiments, improved biological activity is improved delivery to a cellular nucleus and one wing in an oligonucleotide having an asymmetric format comprises a 2'-MOE or two or more 2'-MOE. In some embodiments, improved biological activity is improved delivery to a cellular nucleus and one wing in an oligonucleotide having an asymmetric format comprises a 2'-OMe or two or more 2'-OMe. In some embodiments, improved biological activity is improved delivery to a cellular nucleus and one wing in an oligonucleotide having an asymmetric format comprises a bicyclic sugar or two or more bicyclic sugars.

In some embodiments, an oligonucleotide having an asymmetric format comprises a first wing having a particular sugar modification(s) or combination or pattern thereof, and a second wing having a different particular sugar modification(s) or combination or pattern thereof.

In some embodiments, an oligonucleotide having an asymmetric format comprises a first wing having a particular 2'-sugar modification(s) or combination or pattern thereof, and a second wing having a different particular 2'-sugar modification(s) or combination or pattern thereof.

In some embodiments, a pattern of sugar modifications of an oligonucleotide having an asymmetric format comprises any one or more of: S1-S1-S1-S1, S1-S1-S1-S2, S1-S1-S2-S1, S1-S1-S2-S2, S1-S2-S1-S1, S1-S2-S1-S2, S1-S2-S1-S2, S1-S2-S2-S1, S1-S2-S2-S2, S2-S1-S1-S1, S2-S1-S1-S2, S2-S1-S1-S2, S2-S1-S1-S2, S2-S1-S2-S2, S2-S2-S1-S1, S2-S2-S1-S2, S2-S2-S2-S1, S2-S2-S2-S2, S1-S1-S1-S1, S1-S1-S1-S3, S1-S1-S3-S1, S1-S1-S3-S3, S1-S3-S1-S1, S1-S3-S1-S3, S1-S3-S3-S1, S1-S3-S3-S3, S3-S1-S1-S1, S3-S1-S1-S3, S3-S1-S1-S3, S3-S1-S3-S1, S3-S1-S3-S1, S3-S1-S3-S3, S3-S1-S3-S3, S3-S3-S1-S1, S3-S3-S1-S1, S3-S3-S1-S3, S3-S3-S1-S3, S3-S3-S3-S1, S3-S3-S3-S1, S3-S3-S3-S3, S3-S3-S3-S3, S1-S1-S1-S1, S1-S1-S1-S4, S1-S1-S1-S4, S1-S1-S4-S1, S1-S1-S4-S1, S1-S1-S4-S4, S1-S1-S4-S4, S1-S4-S1-S1, S1-S4-S1-S1, S1-S4-S1-S4, S1-S4-S1-S4, S1-S4-S4-S1, S1-S4-S4-S1, S1-S4-S4-S4, S1-S4-S4-S4, S4-S1-S1-S1, S4-S1-S1-S1, S4-S1-S1-S4, S4-S1-S1-S4, S4-S1-S4-S1, S4-S1-S4-S1, S4-S1-S4-S4, S4-S4-S1-S1, S4-S4-S1-S1, S4-S4-S1-S4, S4-S4-S1-S4, S4-S4-S4-S1, S4-S4-S4-S4, S1-S1-S1-S2, S1-S1-S1-S3, S1-S1-S1-S3, S1-S1-S1-S3, S1-S1-S2-S1, S1-S1-S2-S1, S1-S1-S2-S1, S1-S1-S2-S2, S1-S1-S2-S2, S1-S1-S2-S2, S1-S1-S2-S3, S1-S1-S2-S3, S1-S1-S2-S3, S1-S1-S3-S1, S1-S1-S3-S1, S1-S1-S3-S1, S1-S1-S3-S2, S1-S1-S3-S2, S1-S1-S3-S2, S1-S1-S3-S3, S1-S1-S3-S3, S1-S2-S1-S1, S1-S2-S1-S1, S1-S2-S1-S1, S1-S2-S1-S2, S1-S2-S1-S2, S1-S2-S1-S2, S1-S2-S1-S2, S1-S2-S1-S3, S1-S2-S1-S3, S1-S2-S1-S3, S1-S2-S2-S1, S1-S2-S2-S1, S1-S2-S2-S1, S1-S2-S2-S2, S1-S2-S2-S2, S1-S2-S2-S2, S1-S2-S2-S3, S1-S2-S2-S3, S1-S2-S2-S3, S1-S2-S3-S1, S1-S2-S3-S1, S1-S2-S3-S1, S1-S2-S3-S1, S1-S2-S3-S2, S1-S2-S3-S2, S1-S2-S3-S2, S1-S2-S3-S3, S1-S2-S3-S3, S1-S3-S1-S1, S1-S3-S1-S1, S1-S3-S1-S1, S1-S3-S1-S1, S1-S3-S1-S2, S1-S3-S1-S2, S1-S3-S1-S2, S1-S3-S1-S3, S1-S3-S1-S3, S1-S3-S1-S3, S1-S3-S2-S1, S1-S3-S2-S1, S1-S3-S2-S1, S1-S3-S2-S2, S1-S3-S2-S2, S1-S3-S2-S3, S1-S3-S2-S3, S1-S3-S2-S3, S1-S3-S3-S1, S1-S3-S3-S1, S1-S3-S3-S1, S1-S3-S3-S2, S1-S3-S3-S2, S1-S3-S3-S2, S1-S3-S3-S3, S1-S3-S3-S3, S2-S1-S1-S1, S2-S1-S1-S1, S2-S1-S1-S1, S2-S1-S1-S2, S2-S1-S1-S2, S2-S1-S1-S2, S2-S1-S1-S3, S2-S1-S1-S3, S2-S1-S1-S3, S2-S1-S2-S1, S2-S1-S2-S1, S2-S1-S2-S1, S2-S1-S2-S2, S2-S1-S2-S2, S2-S1-S2-S2, S2-S1-S2-S2, S2-S1-S2-S3, S2-S1-S2-S3, S2-S1-S2-S3, S2-S1-S3-S1, S2-S1-S3-S1, S2-S1-S3-S1, S2-S1-S3-S2, S2-S1-S3-S2, S2-S1-S3-S2, S2-S1-S3-S3, S2-S1-S3-S3, S2-S1-S3-S3, S2-S2-S1-S1, S2-S2-S1-S1, S2-S2-S1-S1, S2-S2-S1-S2, S2-S2-S1-S2, S2-S2-S1-S2, S2-S2-S1-S3, S2-S2-S1-S3, S2-S2-S1-S3, S2-S2-S2-S1, S2-S2-S2-S1, S2-S2-S2-S1, S2-S2-S2-S2, S2-S2-S2-S2, S2-S2-S2-S2, S2-S2-S2-S3, S2-S2-S2-S3, S2-S2-S3-S1, S2-S2-S3-S1, S2-S2-S3-S1, S2-S2-S3-S2, S2-S2-S3-S2, S2-S2-S3-S2, S2-S2-S3-S3, S2-S2-S3-S3, S2-S3-S1-S1, S2-S3-S1-S1, S2-S3-S1-S2, S2-S3-S1-S2, S2-S3-S1-S2, S2-S3-S1-S3, S2-S3-S1-S3, S2-S3-S1-S3, S2-S3-S2-S1, S2-S3-S2-S1, S2-S3-S2-S1, S2-S3-S2-S2, S2-S3-S2-S2, S2-S3-S2-S2, S2-S3-S2-S3, S2-S3-S2-S3, S2-S3-S3-S1, S2-S3-S3-S1, S2-S3-S3-S1, S2-S3-S3-S2, S2-S3-S3-S2, S2-S3-S3-S2, S2-S3-S3-S3, S2-S3-S3-S3, S2-S3-S3-S3, S3-S1-S1-S1, S3-S1-S1-S1, S3-S1-S1-S1, S3-S1-S1-S2, S3-S1-S1-S2, S3-S1-S1-S2, S3-S1-S1-S3, S3-S1-S1-S3, S3-S1-S1-S3, S3-S1-S2-S1, S3-S1-S2-S1, S3-S1-S2-S1, S3-S1-S2-S2, S3-S1-S2-S2, S3-S1-S2-S2, S3-S1-S2-S2, S3-S1-S2-S3, S3-S1-S2-S3, S3-S1-S2-S3, S3-S1-S3-S1, S3-S1-S3-S1, S3-S1-S3-S1, S3-S1-S3-S2, S3-S1-S3-S2, S3-S1-S3-S2, S3-S1-S3-S3, S3-S1-S3-S3, S3-S1-S3-S3, S3-S2-S1-S1, S3-S2-S1-S1, S3-S2-S1-S1, S3-S2-S1-S2, S3-S2-S1-S2, S3-S2-S1-S2, S3-S2-S1-S3, S3-S2-S1-S3, S3-S2-S1-S3, S3-S2-S2-S1, S3-S2-S2-S1, S3-S2-S2-S1, S3-S2-S2-S2, S3-S2-S2-S2, S3-S2-S2-S2, S3-S2-S2-S3, S3-S2-S2-S3, S3-S2-S2-S3, S3-S2-S3-S1, S3-S2-S3-S1, S3-S2-S3-S2, S3-S2-S3-S2, S3-S2-S3-S3, S3-S2-S3-S3, S3-S2-S3-S3, S3-S3-S1-S1, S3-S3-S1-S1, S3-S3-S1-S1, S3-S3-S1-S2, S3-S3-S1-S2, S3-S3-S1-S2, S3-S3-S1-S3, S3-S3-S1-S3, S3-S3-S1-S3, S3-S3-S1-S3, S3-S3-S2-S1, S3-S3-S2-S1, S3-S3-S2-S1, S3-S3-S2-S2, S3-S3-S2-S2, S3-S3-S2-S2, S3-S3-S2-S3, S3-S3-S2-S3, S3-S3-S2-S3, S3-S3-S3-S1, S3-S3-S3-S1, S3-S3-S3-S1, S3-S3-S3-S2, S3-S3-S3-S2, S3-S3-S3-S2, S3-S3-S3-S3, S3-S3-S3-S3, S3-S3-S3-S3, S3-S3-S3-S3, S1-S1-S1-S2, S1-S1-S1-S4, S1-S1-S1-S4, S1-S1-S1-S4, S1-S1-S2-S1, S1-S1-S2-S1, S1-S1-S2-S1, S1-S1-S2-S2, S1-S1-S2-S2, S1-S1-S2-S2, S1-S1-S2-S4, S1-S1-S2-S4, S1-S1-S2-S4, S1-S1-S4-S1, S1-S1-S4-S1, S1-S1-S4-S1, S1-S1-S4-S2, S1-S1-S4-S2, S1-S1-S4-S2, S1-S1-S4-S4, S1-S1-S4-S4, S1-S2-S1-S1, S1-S2-S1-S1, S1-S2-S1-S1, S1-S2-S1-S1, S1-S2-S1-S2, S1-S2-S1-S2, S1-S2-S1-S2, S1-S2-S1-S4, S1-S2-S1-S4, S1-S2-S1-S4, S1-S2-S2-S1, S1-S2-S2-S1, S1-S2-S2-S1, S1-S2-S2-S2, S1-S2-S2-S2, S1-S2-S2-S2, S1-S2-S2-S2, S1-S2-S2-S4, S1-S2-S2-S4, S1-S2-S2-S4, S1-S2-S4-S1, S1-S2-S4-S1, S1-S2-S4-S1, S1-S2-S4-S2, S1-S2-S4-S2, S1-S2-S4-S2, S1-S2-S4-S4, S1-S2-S4-S4, S1-S2-S4-S4, S1-S4-S1-S1, S1-S4-S1-S1, S1-S4-S1-S1, S1-S4-S1-S2, S1-S4-S1-S2, S1-S4-S1-S2, S1-S4-S1-S4, S1-S4-S1-S4, S1-S4-S2-S1, S1-S4-S2-S1, S1-S4-S2-S1, S1-S4-S2-S1, S1-S4-S2-S2, S1-S4-S2-S4, S1-S4-S2-S4, S1-S4-S2-S4, S1-S4-S4-S1, S1-S4-S4-S1, S1-S4-S4-S1, S1-S4-S4-S2, S1-S4-S4-S2, S1-S4-S4-S2, S1-S4-S4-S4, S1-S4-S4-S4, S1-S4-S4-S4, S2-S1-S1-S1, S2-S1-S1-S1, S2-S1-S1-S1, S2-S1-S1-S2, S2-S1-S1-S2, S2-S1-S1-S2, S2-S1-S1-S4, S2-S1-S1-S4, S2-S1-S1-S4, S2-S1-S1-S4, S2-S1-S2-S1, S2-S1-S2-S1, S2-S1-S2-S1, S2-S1-S2-S2, S2-S1-S2-S2, S2-S1-S2-S2, S2-S1-S2-S4, S2-S1-S2-S4, S2-S1-S2-S4, S2-S1-S4-S1, S2-S1-S4-S1, S2-S1-S4-S1, S2-S1-S4-S2, S2-S1-S4-S2, S2-S1-S4-S2, S2-S1-S4-S4, S2-S1-S4-S4, S2-S1-S4-S4, S2-S2-S1-S1, S2-S2-S1-S1, S2-S2-S1-S1, S2-S2-S1-S2, S2-S2-S1-S2, S2-S2-S1-S2, S2-S2-S1-S2, S2-S2-S1-S4, S2-S2-S1-S4, S2-S2-S1-S4, S2-S2-S2-S1, S2-S2-S2-S1, S2-S2-S2-S1, S2-S2-S2-S2, S2-S2-S2-S2, S2-S2-S2-S2, S2-S2-S2-S4, S2-S2-S2-S4, S2-S2-S2-S4, S2-S2-S4-S1, S2-S2-S4-S1, S2-S2-S4-S1, S2-S2-S4-S2, S2-S2-S4-S2, S2-S2-S4-S2, S2-S2-S4-S4, S2-S2-S4-S4, S2-S2-S4-S4, S2-S2-S4-S4, S2-S4-S1-S1, S2-S4-S1-S1, S2-S4-S1-S1, S2-S4-S1-S2, S2-S4-S1-S2, S2-S4-S1-S2, S2-S4-S1-S4, S2-S4-S1-S4, S2-S4-S1-S4, S2-S4-S2-S1, S2-S4-S2-S1, S2-S4-S2-S1, S2-S4-S2-S2, S2-S4-S2-S2, S2-S4-S2-S2, S2-S4-S2-S4, S2-S4-S2-S4, S2-S4-S2-S4, S2-S4-S4-S1, S2-S4-S4-S1, S2-S4-S4-S1, S2-S4-S4-S2, S2-S4-S4-S2, S2-S4-S4-S2, S2-S4-S4-S4, S2-S4-S4-S4, S4-S1-S1-S1, S4-S1-S1-S1, S4-S1-S1-S1, S4-S1-S1-S2, S4-S1-S1-S2, S4-S1-S1-S2, S4-S1-S1-S4, S4-S1-S1-S4, S4-S1-S1-S4, S4-S1-S2-S1, S4-S1-S2-S1, S4-S1-S2-S1, S4-S1-S2-S2, S4-S1-S2-S2, S4-S1-S2-S2, S4-S1-S2-S4, S4-S1-S2-S4, S4-S1-S2-S4, S4-S1-S4-S1, S4-S1-S4-S1, S4-S1-S4-S1, S4-S1-S4-S2, S4-S1-S4-S2, S4-S1-S4-S2, S4-S1-S4-S4, S4-S1-S4-S4, S4-S1-S4-S4, S4-S2-S1-S1, S4-S2-S1-S1, S4-S2-S1-S1, S4-S2-S1-S2, S4-S2-S1-S2, S4-S2-S1-S2, S4-S2-S1-S4, S4-S2-S1-S4, S4-S2-S1-S4, S4-S2-S2-S1, S4-S2-S2-S1, S4-S2-S2-S1, S4-S2-S2-S2, S4-S2-S2-S2, S4-S2-S2-S2, S4-S2-S2-S4, S4-S2-S2-S4, S4-S2-S2-S4, S4-S2-S4-S1, S4-S2-S4-S1, S4-S2-S4-S1, S4-S2-S4-S2, S4-S2-S4-S2, S4-S2-S4-S2, S4-S2-S4-S4, S4-S2-S4-S4, S4-S2-S4-S4, S4-S4-S1-S1, S4-S4-S1-S1, S4-S4-S1-S1, S4-S4-S1-S2, S4-S4-S1-S2, S4-S4-S1-S2, S4-S4-S1-S4, S4-S4-S1-S4, S4-S4-S1-S4, S4-S4-S2-S1, S4-S4-S2-S1, S4-S4-S2-S1, S4-S4-S2-S2, S4-S4-S2-S2, S4-S4-S2-S2, S4-S4-S2-S4, S4-S4-S2-S4, S4-S4-S4-S1, S4-S4-S4-S1, S4-S4-S4-S1, S4-S4-S4-S2, S4-S4-S4-S2, S4-S4-S4-S2, S4-S4-S4-S4, S4-S4-S4-S4, or S4-S4-S4-S4, wherein S1, S2, S3 and S4 are different types of sugar modifications. In some embodiments, S1, S2, S3 and S4 are different types of 2'-sugar modifications. In some embodiments, such a pattern of sugar modifications is in a first wing, a second wing, and/or a core of an oligonucleotide having an asymmetric format.

In some embodiments, a pattern of sugar modifications of an oligonucleotide having an asymmetric format comprises any one or more of: S1-S1-S1-S1-S1, S1-S1-S1-S1-S2, S1-S1-S1-S2-S1, S1-S1-S1-S2-S2, S1-S1-S2-S1-S1, S1-S1-S2-S1-S2, S1-S1-S2-S2-S1, S1-S1-S2-S2-S2, S1-S2-S1-S1-S1, S1-S2-S1-S1-S2, S1-S2-S1-S2-S1, S1-S2-S1-S2-S2, S1-S2-S2-S1-S1, S1-S2-S2-S1-S2, S1-S2-S2-S2-S1, S1-S2-S2-S2-S2, S2-S1-S1-S1-S1, S2-S1-S1-S1-S2, S2-S1-S1-S2-S1, S2-S1-S1-S2-S2, S2-S1-S2-S1-S1, S2-S1-S2-S1-S2, S2-S1-S2-S2-S1, S2-S1-S2-S2-S2, S2-S2-S1-S1-S1, S2-S2-S1-S1-S2, S2-S2-S1-S2-S1, S2-S2-S1-S2-S2, S2-S2-S2-S1-S1, S2-S2-S2-S1-S2, S2-S2-S2-S2-S1, S2-S2-S2-S2-S2, S1-S1-S1-S1-S1, S1-S1-S1-S1-S3, S1-S1-S1-S3-S1, S1-S1-S1-S3-S3, S1-S1-S3-S1-S1, S1-S1-S3-S1-S3, S1-S1-S3-S3-S1, S1-S1-S3-S3-S3, S1-S3-S1-S1-S1, S1-S3-S1-S1-S3, S1-S3-S1-S3-S1, S1-S3-S1-S3-S3, S1-S3-S3-S1-S1, S1-S3-S3-S1-S3, S1-S3-S3-S3-S1, S1-S3-S3-S3-S3, S3-S1-S1-S1-S1,
S1, S3-S1-S1-S1-S3, S3-S1-S1-S3-S1, S3-S1-S1-S3-S3, S3-S1-S3-S1-S1, S3-S1-S3-S1-S3, S3-S1-S3-S3-S1, S3-S1-S3-S3-S3, S3-S3-S1-S1-S1, S3-S3-S1-S1-S3, S3-S3-S1-S3-S1, S3-S3-S1-S3-S3, S3-S3-S3-S1-S1, S3-S3-S3-S1-S3, S3-S3-S3-S3-S1, S3-S3-S3-S3-S3, S1-S1-S1-S1-S4, S1-S1-S1-S4-S1, S1-S1-S1-S4-S4, S1-S1-S4-S1-S1, S1-S1-S4-S1-S4, S1-S1-S4-S4-S1, S1-S1-S4-S4-S4, S1-S4-S1-S1-S1, S1-S4-S1-S1-S4, S1-S4-S1-S4-S1, S1-S4-S1-S4-S4, S1-S4-S4-S1-S1, S1-S4-S4-S1-S4, S1-S4-S4-S4-S1, Si-S4-S4-S4-S4, S4-S1-S1-S1-S1, S4-S1-S1-S1-S4, S4-S1-S1-S4-S1, S4-S1-S1-S4-S4, S4-S1-S4-S1-S1, S4-S1-S4-S1-S4, S4-S1-S4-S4-S1, S4-S1-S4-S4-S4, S4-S4-S1-S1-S1, S4-S4-S1-S1-S4, S4-S4-S1-S4-S1, S4-S4-S1-S4-S4, S4-S4-S4-S1-S1, S4-S4-S4-S1-S4, S4-S4-S4-S4-S1, S4-S4-S4-S4-S4, S1-S1-S1-S2-S3, S1-S1-S1-S3-S1, S1-S1-S1-S3-S2, S1-S1-S1-S3-S3, S1-S1-S2-S1-S1, S1-S1-S2-S1-S2, S1-S1-S2-S1-S3, S1-S1-S2-S2-S1, S1-S1-S2-S2-S2, S1-S1-S2-S2-S3, S1-S1-S2-S3-S1, S1-S1-S2-S3-S2, S1-S1-S2-S3-S3, S1-S1-S3-S1-S1, S1-S1-S3-S1-S2, S1-S1-S3-S1-S3, S1-S1-S3-S2-S1, S1-S1-S3-S2-S2, S1-S1-S3-S2-S3, S1-S1-S3-S3-S1, S1-S1-S3-S3-S2, S1-S1-S3-S3-S3, S1-S2-S1-S1-S1, S1-S2-S1-S1-S2, S1-S2-S1-S1-S3, S1-S2-S1-S2-S1, S1-S2-S1-S2-S2, S1-S2-S1-S2-S3, S1-S2-S1-S3-S1, S1-S2-S1-S3-S2, S1-S2-S1-S3-S3, S1-S2-S2-S1-S1, S1-S2-S2-S1-S2, S1-S2-S2-S1-S3, S1-S2-S2-S2-S1, S1-S2-S2-S2-S2, S1-S2-S2-S2-S3, S1-S2-S2-S3-S1, S1-S2-S2-S3-S2, S1-S2-S2-S3-S3, S1-S2-S3-S1-S1, S1-S2-S3-S1-S2, S1-S2-S3-S1-S3, S1-S2-S3-S2-S1, S1-S2-S3-S2-S2, S1-S2-S3-S2-S3, S1-S2-S3-S3-S1, S1-S2-S3-S3-S2, S1-S2-S3-S3-S3, S1-S3-S1-S1-S1, S1-S3-S1-S1-S2, S1-S3-S1-S1-S3, S1-S3-S1-S2-S1, S1-S3-S1-S2-S2, S1-S3-S1-S2-S3, S1-S3-S1-S3-S1, S1-S3-S1-S3-S2, S1-S3-S1-S3-S3, S1-S3-S2-S1-S1, S1-S3-S2-S1-S2, S1-S3-S2-S1-S3, S1-S3-S2-S2-S1, S1-S3-S2-S2-S2, S1-S3-S2-S2-S3, S1-S3-S2-S3-S1, S1-S3-S2-S3-S2, S1-S3-S2-S3-S3, S1-S3-S3-S1-S1, S1-S3-S3-S1-S2, S1-S3-S3-S1-S3, S1-S3-S3-S2-S1, S1-S3-S3-S2-S2, S1-S3-S3-S2-S3, S1-S3-S3-S3-S1, S1-S3-S3-S3-S2, S1-S3-S3-S3-S3, S2-S1-S1-S1-S1, S2-S1-S1-S1-S2, S2-S1-S1-S1-S3, S2-S1-S1-S2-S1, S2-S1-S1-S2-S2, S2-S1-S1-S2-S3, S2-S1-S1-S3-S1, S2-S1-S1-S3-S2, S2-S1-S1-S3-S3, S2-S1-S2-S1-S1, S2-S1-S2-S1-S2, S2-S1-S2-S1-S3, S2-S1-S2-S2-S1, S2-S1-S2-S2-S2, S2-S1-S2-S2-S3, S2-S1-S2-S3-S1, S2-S1-S2-S3-S2, S2-S1-S2-S3-S3, S2-S1-S3-S1-S1, S2-S1-S3-S1-S2, S2-S1-S3-S1-S3, S2-S1-S3-S2-S1, S2-S1-S3-S2-S2, S2-S1-S3-S2-S3, S2-S1-S3-S3-S1, S2-S1-S3-S3-S2, S2-S1-S3-S3-S3, S2-S2-S1-S1-S1, S2-S2-S1-S1-S2, S2-S2-S1-S1-S3, S2-S2-S1-S2-S1, S2-S2-S1-S2-S2, S2-S2-S1-S2-S3, S2-S2-S1-S3-S1, S2-S2-S1-S3-S2, S2-S2-S1-S3-S3, S2-S2-S2-S1-S1, S2-S2-S2-S1-S2, S2-S2-S2-S1-S3, S2-S2-S2-S2-S1, S2-S2-S2-S2-S2, S2-S2-S2-S2-S3, S2-S2-S2-S3-S1, S2-S2-S2-S3-S2, S2-S2-S2-S3-S3, S2-S2-S3-S1-S1, S2-S2-S3-S1-S2, S2-S2-S3-S1-S3, S2-S2-S3-S2-S1, S2-S2-S3-S2-S2, S2-S2-S3-S2-S3, S2-S2-S3-S3-S1, S2-S2-S3-S3-S2, S2-S2-S3-S3-S3, S2-S3-S1-S1-S1, S2-S3-S1-S1-S2, S2-S3-S1-S1-S3, S2-S3-S1-S2-S1, S2-S3-S1-S2-S2, S2-S3-S1-S2-S3, S2-S3-S1-S3-S1, S2-S3-S1-S3-S2, S2-S3-S1-S3-S3, S2-S3-S2-S1-S1, S2-S3-S2-S1-S2, S2-S3-S2-S1-S3, S2-S3-S2-S2-S1, S2-S3-S2-S2-S2, S2-S3-S2-S2-S3, S2-S3-S2-S3-S1, S2-S3-S2-S3-S2, S2-S3-S2-S3-S3, S2-S3-S3-S1-S1, S2-S3-S3-S1-S2, S2-S3-S3-S1-S3, S2-S3-S3-S2-S1, S2-S3-S3-S2-S2, S2-S3-S3-S2-S3, S2-S3-S3-S3-S1, S2-S3-S3-S3-S2, S2-S3-S3-S3-S3, S3-S1-S1-S1-S1, S3-S1-S1-S1-S2, S3-S1-S1-S1-S3, S3-S1-S1-S2-S1, S3-S1-S1-S2-S2, S3-S1-S1-S2-S3, S3-S1-S1-S3-S1, S3-S1-S1-S3-S2, S3-S1-S1-S3-S3, S3-S1-S2-S1-S1, S3-S1-S2-S1-S2, S3-S1-S2-S1-S3, S3-S1-S2-S2-S1, S3-S1-S2-S2-S2, S3-S1-S2-S2-S3, S3-S1-S2-S3-S1, S3-S1-S2-S3-S2, S3-S1-S2-S3-S3, S3-S1-S3-S1-S1, S3-S1-S3-S1-S2, S3-S1-S3-S1-S3, S3-S1-S3-S2-S1, S3-S1-S3-S2-S2, S3-S1-S3-S2-S3, S3-S1-S3-S3-S1, S3-S1-S3-S3-S2, S3-S1-S3-S3-S3, S3-S2-S1-S1-S1, S3-S2-S1-S1-S2, S3-S2-S1-S1-S3, S3-S2-S1-S2-S1, S3-S2-S1-S2-S2, S3-S2-S1-S2-S3, S3-S2-S1-S3-S1, S3-S2-S1-S3-S2, S3-S2-S1-S3-S3, S3-S2-S2-S1-S1, S3-S2-S2-S1-S2, S3-S2-S2-S1-S3, S3-S2-S2-S2-S1, S3-S2-S2-S2-S2, S3-S2-S2-S2-S3, S3-S2-S2-S3-S1, S3-S2-S2-S3-S2, S3-S2-S2-S3-S3, S3-S2-S3-S1-S1, S3-S2-S3-S1-S2, S3-S2-S3-S1-S3, S3-S2-S3-S2-S1, S3-S2-S3-S2-S2, S3-S2-S3-S2-S3, S3-S2-S3-S3-S1, S3-S2-S3-S3-S2, S3-S2-S3-S3-S3, S3-S3-S1-S1-S1, S3-S3-S1-S1-S2, S3-S3-S1-S1-S3, S3-S3-S1-S2-S1, S3-S3-S1-S2-S2, S3-S3-S1-S2-S3, S3-S3-S1-S3-S1, S3-S3-S1-S3-S2, S3-S3-S1-S3-S3, S3-S3-S2-S1-S1, S3-S3-S2-S1-S2, S3-S3-S2-S1-S3, S3-S3-S2-S2-S1, S3-S3-S2-S2-S2, S3-S3-S2-S2-S3, S3-S3-S2-S3-S1, S3-S3-S2-S3-S2, S3-S3-S2-S3-S3, S3-S3-S3-S1-S1, S3-S3-S3-S1-S2, S3-S3-S3-S1-S3, S3-S3-S3-S2-S1, S3-S3-S3-S2-S2, S3-S3-S3-S2-S3, S3-S3-S3-S3-S1, S3-S3-S3-S3-S2, S3-S3-S3-S3-S3, S1-S1-S1-S2-S4, S1-S1-S1-S4-S1, S1-S1-S1-S4-S2, S1-S1-S1-S4-S4, S1-S1-S2-S1-S1, S1-S1-S2-S1-S2, S1-S1-S2-S1-S4, S1-S1-S2-S2-S1, S1-S1-S2-S2-S2, S1-S1-S2-S2-S4, S1-S1-S2-S4-S1, S1-S1-S2-S4-S2, S1-S1-S2-S4-S4, S1-S1-S4-S1-S1, S1-S1-S4-S1-S2, S1-S1-S4-S1-S4, S1-S1-S4-S2-S1, S1-S1-S4-S2-S2, S1-S1-S4-S2-S4, S1-S1-S4-S4-S1, S1-S1-S4-S4-S2, S1-S1-S4-S4-S4, S1-S2-S1-S1-S1, S1-S2-S1-S1-S2, S1-S2-S1-S1-S4, S1-S2-S1-S2-S1, S1-S2-S1-S2-S2, S1-S2-S1-S2-S4, S1-S2-S1-S4-S1, S1-S2-S1-S4-S2, S1-S2-S1-S4-S4, S1-S2-S2-S1-S1, S1-S2-S2-S1-S2, S1-S2-S2-S1-S4, S1-S2-S2-S2-S1, S1-S2-S2-S2-S2, S1-S2-S2-S2-S4, S1-S2-S2-S4-S1, S1-S2-S2-S4-S2, S1-S2-S2-S4-S4, S1-S2-S4-S1-S1, S1-S2-S4-S1-S2, S1-S2-S4-S1-S4, S1-S2-S4-S2-S1, S1-S2-S4-S2-S2, S1-S2-S4-S2-S4, S1-S2-S4-S4-S1, S1-S2-S4-S4-S2, S1-S2-S4-S4-S4, S1-S4-S1-S1-S1, S1-S4-S1-S1-S2, S1-S4-S1-S1-S4, S1-S4-S1-S2-S1, S1-S4-S1-S2-S2, S1-S4-S1-S2-S4, S1-S4-S1-S4-S1, S1-S4-S1-S4-S2, S1-S4-S1-S4-S4, S1-S4-S2-S1-S1, S1-S4-S2-S1-S2, S1-S4-S2-S1-S4, S1-S4-S2-S2-S1, S1-S4-S2-S2-S2, S1-S4-S2-S2-S4, S1-S4-S2-S4-S1, S1-S4-S2-S4-S2, S1-S4-S2-S4-S4, S1-S4-S4-S1-S1, S1-S4-S4-S1-S2, S1-S4-S4-S1-S4, S1-S4-S4-S2-S1, S1-S4-S4-S2-S2, S1-S4-S4-S2-S4, S1-S4-S4-S4-S1, S1-S4-S4-S4-S2, S1-S4-S4-S4-S4, S2-S1-S1-S1-S1, S2-S1-S1-S1-S2, S2-S1-S1-S1-S4, S2-S1-S1-S2-S1, S2-S1-S1-S2-S2, S2-S1-S1-S2-S4, S2-S1-S1-S4-S1, S2-S1-S1-S4-S2, S2-S1-S1-S4-S4, S2-S1-S2-S1-S1, S2-S1-S2-S1-S2, S2-S1-S2-S1-S4, S2-S1-S2-S2-S1, S2-S1-S2-S2-S2, S2-S1-S2-S2-S4, S2-S1-S2-S4-S1, S2-S1-S2-S4-S2, S2-S1-S2-S4-S4, S2-S1-S4-S1-S1, S2-S1-S4-S1-S2, S2-S1-S4-S1-S4, S2-S1-S4-S2-S1, S2-S1-S4-S2-S2, S2-S1-S4-S2-S4, S2-S1-S4-S4-S1, S2-S1-S4-S4-S2, S2-S1-S4-S4-S4, S2-S2-S1-S1-S1, S2-S2-S1-S1-S2, S2-S2-S1-S1-S4, S2-S2-S1-S2-S1, S2-S2-S1-S2-S2, S2-S2-S1-S2-S4, S2-S2-S1-S4-S1, S2-S2-S1-S4-S2, S2-S2-S1-S4-S4, S2-S2-S2-S1-S1, S2-S2-S2-S1-S2, S2-S2-S2-S2-S1, S2-S2-S2-S2-S2, S2-S2-S2-S2-S4, S2-S2-S2-S4-S1, S2-S2-S2-S4-S2, S2-S2-S2-S4-S4, S2-S2-S4-S1-S1, S2-S2-S4-S1-S2, S2-S2-S4-S1-S4, S2-S2-S4-S2-S1, S2-S2-S4-S2-S2, S2-S2-S4-S2-S4, S2-S2-S4-S4-S1, S2-S2-S4-S4-S2, S2-S2-S4-S4-S4, S2-S4-S1-S1-S1, S2-S4-S1-S1-S2, S2-S4-S1-S1-S4, S2-S4-S1-S2-S1, S2-S4-S1-S2-S2, S2-S4-S1-S2-S4, S2-S4-S1-S4-S1, S2-S4-S1-S4-S2, S2-S4-S1-S4-S4, S2-S4-S2-S1-S1, S2-S4-S2-S1-S2, S2-S4-S2-S1-S4, S2-S4-S2-S2-S1, S2-S4-S2-S2-S2, S2-S4-S2-S2-S4, S2-S4-S2-S4-S1, S2-S4-S2-S4-S2, S2-S4-S2-S4-S4, S2-S4-S4-S1-S1, S2-S4-S4-S1-S2, S2-S4-S4-S1-S4, S2-S4-S4-S2-S1, S2-S4-S4-S2-S2, S2-S4-S4-S2-S4, S2-S4-S4-S4-S1, S2-S4-S4-S4-S2, S2-S4-S4-S4-S4, S4-S1-S1-S1-S1, S4-S1-S1-S1-S2, S4-S1-S1-S1-S4, S4-S1-S1-S2-S1, S4-S1-S1-S2-S2, S4-S1-S1-S2-S4, S4-S1-S1-S4-S1, S4-S1-S1-S4-S2, S4-S1-S1-S4-S4, S4-S1-S2-S1-S1, S4-S1-S2-S1-S2, S4-S1-S2-S1-S4, S4-S1-S2-S2-S1, S4-S1-S2-S2-S2, S4-S1-S2-S2-S4, S4-S1-S2-S4-S1, S4-S1-S2-S4-S2, S4-S1-S2-S4-S4, S4-S1-S4-S1-S1, S4-S1-S4-S1-S2, S4-S1-S4-S1-S4, S4-S1-S4-S2-S1, S4-S1-S4-S2-S2, S4-S1-S4-S2-S4, S4-S1-S4-S4-S1, S4-S1-S4-S4-S2, S4-S1-S4-S4-S4, S4-S2-S1-S1-S1, S4-S2-S1-S1-S2, S4-S2-S1-S1-S4, S4-S2-S1-S2-S1, S4-S2-S1-S2-S2, S4-S2-S1-S2-S4, S4-S2-S1-S4-S1, S4-S2-S1-S4-S2, S4-S2-S1-S4-S4, S4-S2-S2-S1-S1, S4-S2-S2-S1-S2, S4-S2-S2-S1-S4, S4-S2-S2-S2-S1, S4-S2-S2-S2-S2, S4-S2-S2-S2-S4, S4-S2-S2-S4-S1, S4-S2-S2-S4-S2, S4-S2-S2-S4-S4, S4-S2-S4-S1-S1, S4-S2-S4-S1-S2, S4-S2-S4-S1-S4, S4-S2-S4-S2-S1, S4-S2-S4-S2-S2, S4-S2-S4-S2-S4, S4-S2-S4-S4-S1, S4-S2-S4-S4-S2, S4-S2-S4-S4-S4, S4-S4-S1-S1-S1, S4-S4-S1-S1-S2, S4-S4-S1-S1-S4, S4-S4-S1-S2-S1, S4-S4-S1-S2-S2, S4-S4-S1-S2-S4, S4-S4-S1-S4-S1, S4-S4-S1-S4-S2, S4-S4-S1-S4-S4, S4-S4-S2-S1-S1, S4-S4-S2-S1-S2, S4-S4-S2-S1-S4, S4-S4-S2-S2-S1, S4-S4-S2-S2-S2, S4-S4-S2-S2-S4, S4-S4-S2-S4-S1, S4-S4-S2-S4-S2, S4-S4-S2-S4-S4, S4-S4-S4-S1-S1, S4-S4-S4-S1-S2, S4-S4-S4-S1-S4, S4-S4-S4-S2-S1, S4-S4-S4-S2-S2, S4-S4-S4-S2-S4, S4-S4-S4-S4-S1, S4-S4-S4-S4-S2, S4-S4-S4-S4-S4, or S4-S4-S4-S4-S4, wherein S1, S2, S3 and S4 are different types of sugar modifications. In some embodiments, S1, S2, S3 and S4 are different types of 2'-sugar modifications. In some embodiments, such a pattern of sugar modifications is in a first wing, a second wing, and/or a core of an oligonucleotide having an asymmetric format.

In some embodiments, a pattern of sugar modifications of an oligonucleotide having an asymmetric format comprises any one or more of: LLLLL, LLLLD, LLLDL, LLLDD, LLDLL, LLDLD, LLDDL, LLDDD, LDLLL, LDLLD, LDLDL, LDLDD, LDDLL, LDDLD, LDDDL, LDDDD, DLLLL, DLLLD, DLLDL, DLLDD, DLDLL, DLDLD, DLDDL, DLDDD, DDLLL, DDLLD, DDLDL, DDLDD, DDDLL, DDDLD, DDDDL, DDDDD, LLLLL, LLLLM, LLLML, LLLMM, LLMLL, LLMLM, LLMML, LLMMM, LMLLL, LMLLM, LMLML, LMLMM, LMMLL, LMMLM, LMMML, LMMMM, MLLLL, MLLLM, MLLML, MLLMM, MLMLL, MLMLM, MLMML, MLMMM, MMLLL, MMLLM, MMLML, MMLMM, MMMLL, MMMLM, MMMML, MMMMM, LLLLm, LLLLmL, LLLmmm, LLmLL, LLmLm, LLmmL, LLmmm, LmLLL, LmLLm, LmLmL, LmLmm, LmmLL, LmmLm, LmmmL, Lmmmm, mLLLL, mLLLm, mLLmL, mLLmm, mLmLL, mLmLm, mLmmL, mLmmm, mmLLL, mmLLm, mmLmL, mmLmm, mmmLL, mmmLm, mmmmL, mmmmm, LLLDM, LLLML, LLLMD, LLLMM, LLDLL, LLDLD, LLDLM, LLDDL, LLDDD, LLDDM, LLDML, LLDMD, LLDMM, LLMLL, LLMLD, LLMLM, LLMDL, LLMDD, LLMDM, LLMML, LLMMD, LLMMM, LDLLL, LDLLD, LDLLM, LDLDL, LDLDD, LDLDM, LDLML, LDLMD, LDLMM, LDDLL, LDDLD, LDDLM, LDDDL, LDDDD, LDDDM, LDDML, LDDMD, LDDMM, LDMLL, LDMLD, LDMLM, LDMDL, LDMDD, LDMDM, LDMML, LDMMD, LDMMM, LMLLL, LMLLD, LMLLM, LMLDL, LMLDD, LMLDM, LMLML, LMLMD, LMLMM, LMDLL, LMDLD, LMDLM, LMDDL, LMDDD, LMDDM, LMDML, LMDMD, LMDMM, LMMLL, LMMLD, LMMLM, LMMDL, LMMDD, LMMDM, LMMML, LMMMD, LMMMM, DLLLL, DLLLD, DLLLM, DLLDL, DLLDD, DLLDM, DLLML, DLLMD, DLLMM, DLDLL, DLDLD, DLDLM, DLDDL, DLDDD, DLDDM, DLDML, DLDMD, DLDMM, DLMLL, DLMLD, DLMLM, DLMDL, DLMDD, DLMDM, DLMML, DLMMD, DLMMM, DDLLL, DDLLD, DDLLM, DDLDL, DDLDD, DDLDM, DDLML, DDLMD, DDLMM, DDDLL, DDDLD, DDDLM, DDDDL, DDDDD, DDDDM, DDDML, DDDMD, DDDMM, DDMLL, DDMLD, DDMLM, DDMDL, DDMDD, DDMDM, DDMML, DDMMD, DDMMM, DMLLL, DMLLD, DMLLM, DMLDL, DMLDD, DMLDM, DMLML, DMLMD, DMLMM, DMDLL, DMDLD, DMDLM, DMDDL, DMDDD, DMDDM, DMDML, DMDMD, DMDMM, DMMLL, DMMLD, DMMLM, DMMDL, DMMDD, DMMDM, DMMML, DMMMD, DMMMM, MLLLL, MLLLD, MLLLM, MLLDL, MLLDD, MLLDM, MLLML, MLLMD, MLLMM, MLDLL, MLDLD, MLDLM, MLDDL, MLDDD, MLDDM, MLDML, MLDMD, MLDMM, MLMLL, MLMLD, MLMLM, MLMDL, MLMDD, MLMDM, MLMML, MLMMD, MLMMM, MDLLL, MDLLD, MDLLM, MDLDL, MDLDD, MDLDM, MDLML, MDLMD, MDLMM, MDDLL, MDDLD, MDDLM, MDDDL, MDDDD, MDDDM, MDDML, MDDMD, MDDMM, MDMLL, MDMLD, MDMLM, MDMDL, MDMDD, MDMDM, MDMML, MDMMD, MDMMM, MMLLL, MMLLD, MMLLM, MMLDL, MMLDD, MMLDM, MMLML, MMLMD, MMLMM, MMDLL, MMDLD, MMDLM, MMDDL, MMDDD, MMDDM, MMDML, MMDMD, MMDMM, MMMLL, MMMLD, MMMLM, MMMDL, MMMDD, MMMDM, MMMML, MMMMD, MMMMM, MMMMM, LLLDm, LLLmL, LLLmD, LLLmm, LLDLL, LLDLD, LLDLm, LLDDL, LLDDD, LLDDm, LLDmL, LLDmD, LLDmm, LLmLL, LLmLD, LLmLm, LLmDL, LLmDD, LLmDm, LLmmL, LLmmD, LLmmm, LDLLL, LDLLD, LDLLm, LDLDL, LDLDD, LDLDm, LDLmL, LDLmD, LDLmm, LDDLL, LDDLD, LDDLm, LDDDL, LDDDD, LDDDm, LDDmL, LDDmD, LDDmm, LDmLL, LDmLD, LDmLm, LDmDL, LDmDD, LDmDm, LDmmL, LDmmD, LDmmm, LmLLL, LmLLD, LmLLm, LmLDL, LmLDD, LmLDm, LmLmL, LmLmD, LmLmm, LmDLL, LmDLD, LmDLm, LmDDL, LmDDD, LmDDm, LmDmL, LmDmD, LmDmm, LmmLL, LmmLD, LmmLm, LmmDL, LmmDD, LmmDm, LmmmL, LmmmD, Lmmmm, DLLLL, DLLLD, DLLLm, DLLDL, DLLDD, DLLDm, DLLmL, DLLmD, DLLmm, DLDLL, DLDLD, DLDLm, DLDDL, DLDDD, DLDDm, DLDmL, DLDmD, DLDmm, DLmLL, DLmLD, DLmLm, DLmDL, DLmDD, DLmDm, DLmmL, DLmmD, DLmmm, DDLLL, DDLLD, DDLLm, DDLDL, DDLDD, DDLDm, DDLmL, DDLmD, DDLmm, DDDLL, DDDLD, DDDLm, DDDDL, DDDDD, DDDDm, DDDmL, DDDmD, DDDmm, DDmLL, DDmLD, DDmLm, DDmDL, DDmDD, DDmDm, DDmmL, DDmmD, DDmmm, DmLLL, DmLLD, DmLLm, DmLDL, DmLDD, DmLDm, DmLmL, DmLmD, DmLmm, DmDLL, DmDLD, DmDLm, DmDDL, DmDDD, DmDDm, DmDmL, DmDmD, DmDmm, DmmLL, DmmLD, DmmLm, DmmDL, DmmDD, DmmDm, DmmmL, DmmmD, Dmmmm, mLLLL, mLLLD, mLLLm, mLLDL, mLLDD, mLLDm, mLLmL, mLLmD, mLLmm, mLDLL, mLDLD, mLDLm, mLDDL, mLDDD, mLDDm, mLDmL, mLDmD, mLDmm, mLmLL, mLmLD, mLmLm, mLmDL, mLmDD, mLmDm, mLmmL, mLmmD, mLmmm, mDLLL, mDLLD, mDLLm, mDLDL, mDLDD, mDLDm, mDLmL, mDLmD, mDLmm, mDDLL, mDDLD, mDDLm, mDDDL, mDDDD, mDDDm, mDDmL, mDDmD, mDDmm, mDmLL, mDmLD, mDmLm, mDmDL, mDmDD, mDmDm, mDmmL, mDmmD, mDmmm, mmLLL, mmLLD, mmLLm, mmLDL, mmLDD, mmLDm, mmLmL, mmLmD, mmLmm, mmDLL, mmDLD, mmDLm, mmDDL, mmDDD, mmDDm, mmDmL, mmDmD, mmDmm, mmmLL, mmmLD, mmmLm, mmmDL, mmmDD, mmmDm, mmmmL, mmmmD, mmmmm, or mmmmm, wherein L=LNA, D=deoxy, M=2'-MOE, and m=2'-OMe. In some embodiments, such a pattern of sugar modifications is in a first wing, a second wing, and/or a core of an oligonucleotide having an asymmetric format.

Various non-limiting examples of asymmetric formats for oligonucleotides are described herein. Also described herein are various non-limiting examples of oligonucleotides having such formats.

In some embodiments of an oligonucleotide having an asymmetric format, a core comprises any sugar or sugar modification described herein or known in the art, or any pattern or combination of two or more different sugars and/or sugar modifications.

In some embodiments of an oligonucleotide having an asymmetric format: a core comprises: D. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDDDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: DDDDDDDDDD. Non-limiting example(s) of such an oligonucleotide include: WV-8645, WV-8646, WV-8647, WV-8648, WV-8661, WV-8662, WV-8663, WV-8664.

In some embodiments of an oligonucleotide having an asymmetric format: a core comprises: 5'BrdU.

In some embodiments of an oligonucleotide having an asymmetric format: a core comprises: 5'BrdU and D.

In some embodiments of an oligonucleotide having an asymmetric format: a core comprises: 5'BrdU and two or more D.

In some embodiments of an oligonucleotide having an asymmetric format: a core comprises: 5'BrdU and two or more consecutive D.

In some embodiments, an oligonucleotide having an asymmetric format can comprise a first wing; and a second wing, wherein the first and second wing differ chemically from each other and from the core.

Figure 1B:
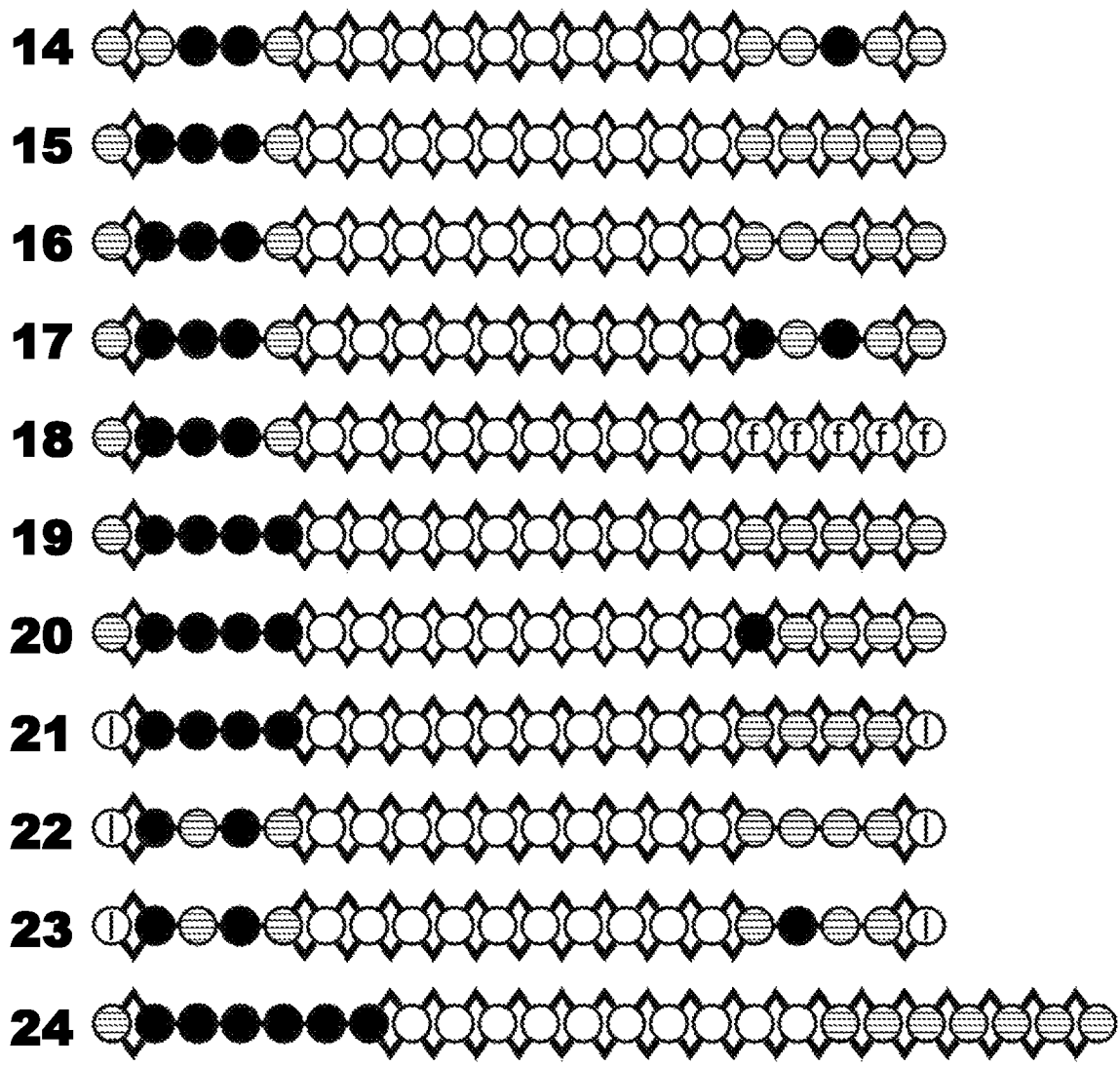
Figure 1C:
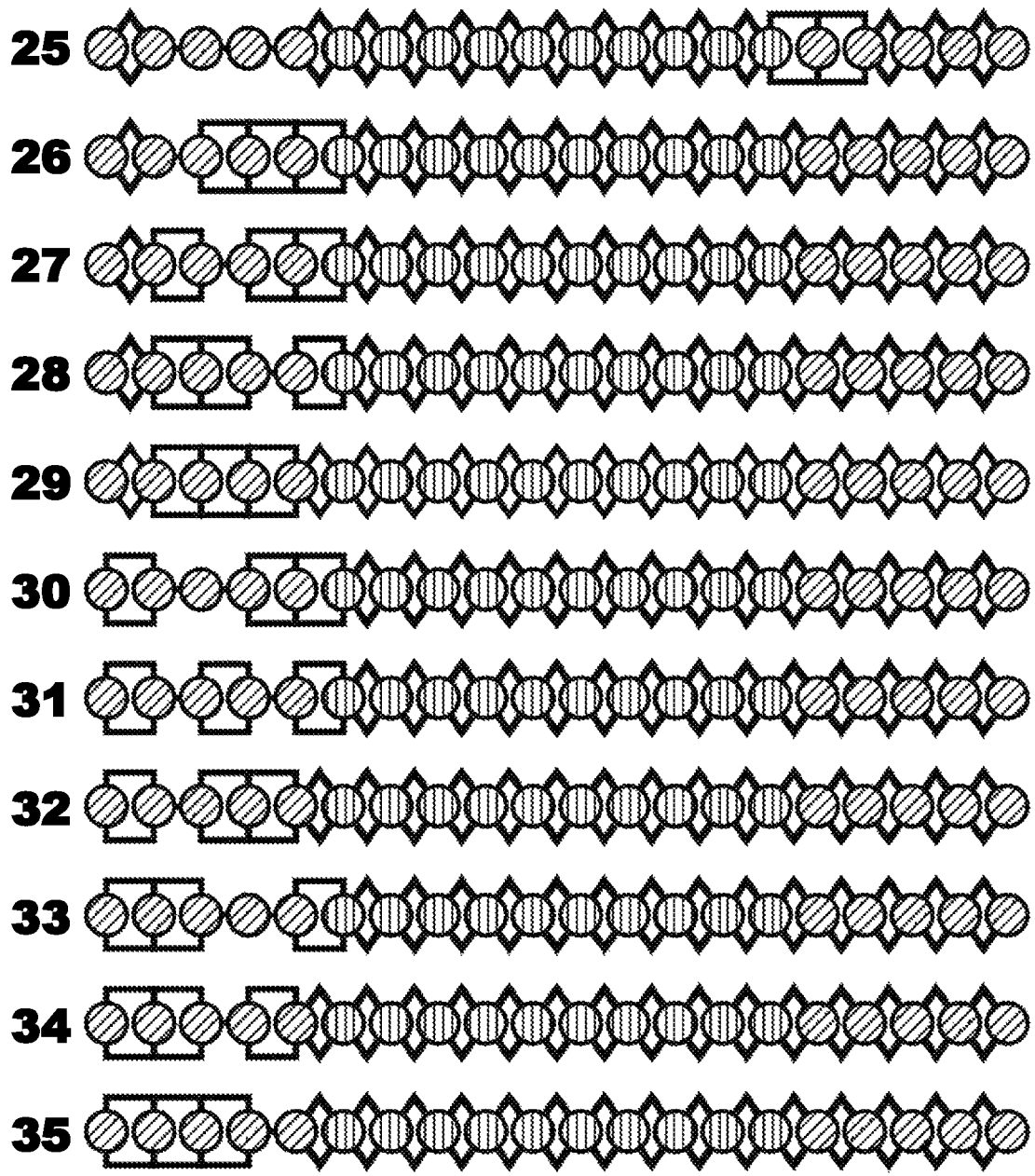
FIG. 1C presents non-limiting examples of internucleotidic linkages in the first and second wing of an oligonucleotide having an asymmetric format.

Non-limiting examples of formats of an oligonucleotide having an asymmetric format, wherein the first and second wing differ chemically from each other and from the core are illustrated in FIG. 1A and FIG. 1B, with a legend to FIG. 1A and FIG. 1B provided in FIG. 1D.

In some embodiments, an oligonucleotide having an asymmetric format can comprise a first wing; and a second wing, wherein the first and second wing differ chemically from each other and from the core, wherein the first and/or second wing can comprise M, m and/or L, wherein M is (at least one) 2'-MOE (or, if the base is C, optionally methyl-C 2'-MOE); m is (at least one) 2'-OMe, and L is (at least one) LNA, and wherein either the first or second wing can be at the 5' end, and the other wing is at the 3' end of the wing-core-wing format.

In some embodiments of an oligonucleotide having an asymmetric format: a first wing comprises: 2 or more consecutive M; and a second wing comprises: 2 or more consecutive m. Non-limiting example(s) of such an oligonucleotide include: WV-8852, and WV-8856.

In some embodiments of an oligonucleotide having an asymmetric format: a first wing comprises: 2 or more consecutive m; and a second wing comprises: 2 or more consecutive M. Non-limiting example(s) of such an oligonucleotide include: WV-8043-8048.

In some embodiments of an oligonucleotide having an asymmetric format: a first wing comprises: mmmmm; and a second wing comprises: MMMMM. Non-limiting example(s) of such an oligonucleotide include: WV-8043-8048.

In some embodiments of an oligonucleotide having an asymmetric format: a first wing comprises: MMMMM; and a second wing comprises: mmmmm. Non-limiting example(s) of such an oligonucleotide include: WV-8852, and WV-8856.

In some embodiments of an oligonucleotide having an asymmetric format: a first wing comprises: m and M in a particular order and number; and a second wing comprises: m and M in a different order and/or different number. Non-limiting example(s) of such an oligonucleotide include: WV-8248.

In some embodiments of an oligonucleotide having an asymmetric format: a first wing comprises: mMmMm; and a second wing comprises: mMmmm. Non-limiting example(s) of such an oligonucleotide include: WV-8248.

In some embodiments of an oligonucleotide having an asymmetric format: a first wing comprises: m and 2 or more consecutive M; and a second wing comprises: M and 2 or more consecutive m. Non-limiting example(s) of such an oligonucleotide include: WV-9894-9896.

In some embodiments of an oligonucleotide having an asymmetric format: a first wing comprises: mMMMM; and a second wing comprises: Mmmmm. Non-limiting example(s) of such an oligonucleotide include: WV-9894-9896, and WV-10253 to 10254.

In some embodiments of an oligonucleotide having an asymmetric format: a first wing comprises: m and M in a particular order and number; and a second wing comprises: 2 or more consecutive M.

In some embodiments of an oligonucleotide having an asymmetric format: a first wing comprises: mMMMMMM; and a second wing comprises: MMMMMMM. Non-limiting example(s) of such an oligonucleotide include: WV-12099, WV-12101, WV-12103, WV-12105, WV-12107, and WV-12109.

In some embodiments of an oligonucleotide having an asymmetric format: a first wing comprises: mMMMM; and a second wing comprises: MMMMM. Non-limiting example(s) of such an oligonucleotide include: WV-10250, and WV-9869 to WV-9870.

In some embodiments of an oligonucleotide having an asymmetric format: a first wing comprises: mMMMm; and a second wing comprises: all M. Non-limiting example(s) of such an oligonucleotide include: WV-9441-9445.

In some embodiments of an oligonucleotide having an asymmetric format: a first wing comprises: mMMMm; and a second wing comprises: MMMMM. Non-limiting example(s) of such an oligonucleotide include: WV-9441-9445.

In some embodiments of an oligonucleotide having an asymmetric format: a first wing comprises: m and M in a particular order and number; and a second wing comprises: 2 or more consecutive m.

In some embodiments of an oligonucleotide having an asymmetric format: a first wing comprises: 2 or more consecutive m; and a second wing comprises: m and M in a particular order and number.

In some embodiments of an oligonucleotide having an asymmetric format: a first wing comprises: 2 or more consecutive M; and a second wing comprises: m and M in a particular order and number.

In some embodiments of an oligonucleotide having an asymmetric format: a first wing comprises: L, m and M in a particular order and number; and a second wing comprises: L, m and M in a different order and/or different number. Non-limiting example(s) of such an oligonucleotide include: WV-8250.

In some embodiments of an oligonucleotide having an asymmetric format: a first wing comprises: LMmMm; and a second wing comprises: mMmmL. Non-limiting example(s) of such an oligonucleotide include: WV-8250.

In some embodiments of an oligonucleotide having an asymmetric format: a first wing comprises: L, m and M; and a second wing comprises: m and L. Non-limiting example(s) of such an oligonucleotide include: WV-8246.

In some embodiments of an oligonucleotide having an asymmetric format: a first wing comprises: LMmMm; and a second wing comprises: mmmmL. Non-limiting example(s) of such an oligonucleotide include: WV-8246.

In some embodiments of an oligonucleotide having an asymmetric format: a first wing comprises: L and M; and a second wing comprises: m and L. Non-limiting example(s) of such an oligonucleotide include: WV-11958, and WV-11960, and WV-11962.

In some embodiments of an oligonucleotide having an asymmetric format: a first wing comprises: L and 2 or more consecutive M; and a second wing comprises: 2 or more consecutive m and L. Non-limiting example(s) of such an oligonucleotide include: WV-11958, WV-11960, and WV-11962.

In some embodiments of an oligonucleotide having an asymmetric format: a first wing comprises: LMMMM; and a second wing comprises: mmmmL. Non-limiting example(s) of such an oligonucleotide include: WV-11958, WV-11960, and WV-11962.

In some embodiments of an oligonucleotide having an asymmetric format: a first wing comprises: two different types of sugar modifications; and a second wing comprises: only one type of sugar modification. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: a pattern of m and M; and a second wing comprises: two or more consecutive m. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: mMMMm; and a second wing comprises: two or more consecutive m. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: a pattern of two different types of sugar modifications; and a second wing comprises: a different pattern of the same two different types of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: a pattern of m and M; and a second wing comprises: a different pattern of m and M. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: mmMMm; and a second wing comprises: mmMmm. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: m and two or more consecutive M; and a second wing comprises: two or more consecutive m. Non-limiting example(s) of such an oligonucleotide include: WV-12110, WV-12111, WV-12112, WV-12113, and WV-12114.

In some embodiments of an oligonucleotide having an asymmetric format: a first wing comprises: mMMMM; and a second wing comprises: two or more consecutive m. Non-limiting example(s) of such an oligonucleotide include: WV-12110, WV-12111, WV-12112, WV-12113, and WV-12114.

In some embodiments of an oligonucleotide having an asymmetric format: a first wing comprises: mMMMm; and a second wing comprises: two or more consecutive m. Non-limiting example(s) of such an oligonucleotide include: WV-13303, WV-13304, WV-13809, WV-14087, WV-14349, WV-14556, WV-14557, WV-14558, WV-14559, WV-14560, WV-14561, WV-14562, WV-14563, WV-14564, WV-14733, WV-14734, WV-14735, WV-14736, WV-14737, WV-14771, WV-15310, WV-15311, WV-15312, WV-15313, WV-15314, WV-15315, WV-15316, WV-15317, WV-15318, WV-15319, WV-15320, WV-15321, WV-15351, WV-15352, WV-15353, WV-15354, WV-15355, WV-15356, WV-15357, WV-15358, WV-15359, WV-15360, WV-15361, WV-15362, WV-15363, WV-15364, WV-15365, WV-15562, WV-15563, WV-15863, WV-15864, and WV-15887.

In some embodiments of an oligonucleotide having an asymmetric format: a first wing comprises: two or more consecutive M; and a second wing comprises: two or more consecutive m. Non-limiting example(s) of such an oligonucleotide include: WV-8552, WV-8554, WV-8570, WV-8571, WV-8572, WV-8573, WV-8574, WV-8575, WV-8576, WV-8577, WV-8578, WV-8579, WV-8580, and WV-8581.

In some embodiments of an oligonucleotide having an asymmetric format: a first wing comprises: two or more consecutive M; and a second wing comprises: two different types of sugar modifications. Non-limiting example(s) of such an oligonucleotide include: WV-14552, WV-14553, WV-14554, and WV-14555.

In some embodiments of an oligonucleotide having an asymmetric format: a first wing comprises: two or more consecutive M; and a second wing comprises: two different types of sugar modifications. Non-limiting example(s) of such an oligonucleotide include: WV-8456.

In some embodiments of an oligonucleotide having an asymmetric format: a first wing comprises: two or more consecutive M; and a second wing comprises: two or more consecutive m. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: two or more consecutive m; and a second wing comprises: two different types of sugar modifications. Non-limiting example(s) of such an oligonucleotide include: WV-8125.

In some embodiments of an oligonucleotide having an asymmetric format: a first wing comprises: two or more consecutive m; and a second wing comprises: two or more consecutive M. Non-limiting example(s) of such an oligonucleotide include: WV-8314.

In some embodiments of an oligonucleotide having an asymmetric format: a first wing comprises: two different types of sugar modifications; and a second wing comprises: a third type of sugar modification. Non-limiting example(s) of such an oligonucleotide include: WV-9508, WV-9509, and WV-9510.

In some embodiments of an oligonucleotide having an asymmetric format: a first wing comprises: two different types of sugar modifications; and a second wing comprises: two or more consecutive F. Non-limiting example(s) of such an oligonucleotide include: WV-9508, WV-9509, and WV-9510.

In some embodiments of an oligonucleotide having an asymmetric format: a first wing comprises: two different types of sugar modifications; and a second wing comprises: two or more consecutive m. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: two different types of sugar modifications; and a second wing comprises: two or more consecutive m. Non-limiting example(s) of such an oligonucleotide include: WV-9488, WV-9489, WV-9490, WV-9491, WV-9492, WV-9494, WV-9505, WV-9506, WV-9507, WV-8452, WV-8453, WV-8009, WV-8010, WV-8011, WV-8012, WV-8454, and WV-8455.

In some embodiments of an oligonucleotide having an asymmetric format: a first wing comprises: two different types of sugar modifications; and a second wing comprises: two or more consecutive m. Non-limiting example(s) of such an oligonucleotide include: WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: a particular pattern of two different types of sugar modifications; and a second wing comprises: a different pattern of two different types of sugar modifications. Non-limiting example(s) of such an oligonucleotide include: WV-8121, WV-8129, WV-8118, WV-8126, WV-8472, WV-8473, WV-8474, WV-8475, and WV-8476.

In some embodiments of an oligonucleotide having an asymmetric format: a first wing comprises: a particular pattern of two different types of sugar modifications; and a second wing comprises: a different pattern of two different types of sugar modifications. Non-limiting example(s) of such an oligonucleotide include: WV-8119 and WV-8127.

In some embodiments of an oligonucleotide having an asymmetric format: a first wing comprises: two different types of sugar modifications; and a second wing comprises: a only one type of sugar modifications. Non-limiting example(s) of such an oligonucleotide include: WV-8115 and WV-8123.

In some embodiments of an oligonucleotide having an asymmetric format: a first wing comprises: a particular pattern of two different types of sugar modifications; and a second wing comprises: a different pattern of two different types of sugar modifications. Non-limiting example(s) of such an oligonucleotide include: WV-8120 and WV-8128.

In some embodiments of an oligonucleotide having an asymmetric format: a first wing comprises: two different types of sugar modifications; and a second wing comprises: one type of sugar modifications. Non-limiting example(s) of such an oligonucleotide include: WV-8116 and WV-8124.

In some embodiments of an oligonucleotide having an asymmetric format: a first wing comprises: two or more consecutive M; and a second wing comprises: M and two or more consecutive m. Non-limiting example(s) of such an oligonucleotide include: WV-14552, WV-14553, WV-14554, and WV-14555.

In some embodiments of an oligonucleotide having an asymmetric format: a first wing comprises: two or more consecutive M; and a second wing comprises: MmMmm. Non-limiting example(s) of such an oligonucleotide include: WV-8456.

In some embodiments of an oligonucleotide having an asymmetric format: a first wing comprises: two or more consecutive M; and a second wing comprises: two or more consecutive m. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: two or more consecutive m; and a second wing comprises: M and two or more consecutive m. Non-limiting example(s) of such an oligonucleotide include: WV-8125.

In some embodiments of an oligonucleotide having an asymmetric format: a first wing comprises: two or more consecutive m; and a second wing comprises: two or more consecutive M. Non-limiting example(s) of such an oligonucleotide include: WV-8314.

In some embodiments of an oligonucleotide having an asymmetric format: a first wing comprises: two different types of sugar modification; and a second wing comprises: a third type of sugar modification. Non-limiting example(s) of such an oligonucleotide include: WV-9508, WV-9509, WV-9510.

In some embodiments of an oligonucleotide having an asymmetric format: a first wing comprises: mMMMm; and a second wing comprises: two or more consecutive F. Non-limiting example(s) of such an oligonucleotide include: WV-9508, WV-9509, WV-9510.

In some embodiments of an oligonucleotide having an asymmetric format: a first wing comprises: mMMMm; and a second wing comprises: two or more consecutive m. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: mMMMm; and a second wing comprises: two or more consecutive m. Non-limiting example(s) of such an oligonucleotide include: WV-9488, WV-9489, WV-9490, WV-9491, WV-9492, WV-9494, WV-9505, WV-9506, and WV-9507.

In some embodiments of an oligonucleotide having an asymmetric format: a first wing comprises: a particular pattern of two different types of sugar modification; and a second wing comprises: a different pattern of two different types of sugar modification. Non-limiting example(s) of such an oligonucleotide include: WV-8452 and WV-8453.

In some embodiments of an oligonucleotide having an asymmetric format: a first wing comprises: mMMMm; and a second wing comprises: MmMmm. Non-limiting example(s) of such an oligonucleotide include: WV-8452 and WV-8453.

In some embodiments of an oligonucleotide having an asymmetric format: a first wing comprises: mMMMm; and a second wing comprises: two or more consecutive m. Non-limiting example(s) of such an oligonucleotide include: WV-8009, WV-8010, WV-8011, WV-8012, WV-8454, and WV-8455.

In some embodiments of an oligonucleotide having an asymmetric format: a first wing comprises: mMMMm; and a second wing comprises: two or more consecutive m. Non-limiting example(s) of such an oligonucleotide include:

WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: mMMmm; and a second wing comprises: M and two or more consecutive m. Non-limiting example(s) of such an oligonucleotide include: WV-8121 and WV-8129.

In some embodiments of an oligonucleotide having an asymmetric format: a first wing comprises: two different types of sugar modifications; and a second wing comprises: only one type of sugar modification. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: mMMmm; and a second wing comprises: two or more consecutive m. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: mMmmm; and a second wing comprises: M and two or more consecutive m. Non-limiting example(s) of such an oligonucleotide include: WV-8119 and WV-8127.

In some embodiments of an oligonucleotide having an asymmetric format: a first wing comprises: mMmmm; and a second wing comprises: two or more consecutive m. Non-limiting example(s) of such an oligonucleotide include: WV-8115 and WV-8123.

In some embodiments of an oligonucleotide having an asymmetric format: a first wing comprises: mmMmm; and a second wing comprises: M and two or more consecutive m. Non-limiting example(s) of such an oligonucleotide include: WV-8120 and WV-8128.

In some embodiments of an oligonucleotide having an asymmetric format: a first wing comprises: mmMmm; and a second wing comprises: two or more consecutive m. Non-limiting example(s) of such an oligonucleotide include: WV-8116 and WV-8124.

In some embodiments of an oligonucleotide having an asymmetric format: a first wing comprises: two or more consecutive M; and a second wing comprises: DMMD. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: MMD. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: DDMMD. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: two or more consecutive m. Non-limiting example(s) of such an oligonucleotide include: WV-8637, WV-8638, WV-8639, WV-8640, WV-8653, WV-8654, WV-8655, WV-8656, WV-8665, WV-8666, WV-8667, WV-8668, WV-8669, WV-8670, WV-8671, WV-8672, WV-12947, WV-12948, WV-12949, WV-12950, WV-12951, WV-12952, WV-12953, WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, and WV-12976.

In some embodiments of an oligonucleotide having an asymmetric format: a first wing comprises: two or more consecutive m; and a second wing comprises: two or more consecutive M. Non-limiting example(s) of such an oligonucleotide include: WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000, WV-13001, WV-13002, WV-13003, WV-13004, WV-13005, WV-13006, WV-13007, and WV-13008.

In some embodiments of an oligonucleotide having an asymmetric format: a first wing comprises: mMMMM; and a second wing comprises: M and two or more consecutive m. Non-limiting example(s) of such an oligonucleotide include: WV-9887, WV-9888, WV-10245, and WV-10246.

In some embodiments of an oligonucleotide having an asymmetric format: a first wing comprises: mMMMM; and a second wing comprises: two or more consecutive m. Non-limiting example(s) of such an oligonucleotide include: WV-9871 and WV-9872.

In some embodiments of an oligonucleotide having an asymmetric format: a first wing comprises: mMMMMM; and a second wing comprises: mmmmmmm. Non-limiting example(s) of such an oligonucleotide include: WV-12101.

In some embodiments of an oligonucleotide having an asymmetric format: a first wing comprises: mMMMM; and a second wing comprises: M and two or more consecutive m. Non-limiting example(s) of such an oligonucleotide include: WV-9873 and WV-9874.

In some embodiments of an oligonucleotide having an asymmetric format: a first wing comprises: mMMMM; and a second wing comprises: two or more consecutive m. Non-limiting example(s) of such an oligonucleotide include: WV-9885, WV-9886, WV-10243, and WV-10244.

In some embodiments of an oligonucleotide having an asymmetric format: a first wing comprises: mMMMm; and a second wing comprises: two or more consecutive F. Non-limiting example(s) of such an oligonucleotide include: WV-9526, WV-9527, WV-9528, WV-9529, WV-9530, WV-9531, WV-9532, WV-9533, WV-9590, WV-9591, WV-9592, and WV-9593.

In some embodiments of an oligonucleotide having an asymmetric format: a first wing comprises: mMMMm; and a second wing comprises: two or more consecutive m. Non-limiting example(s) of such an oligonucleotide include: WV-8610, WV-8611, WV-8612, WV-8613, WV-8614, WV-8615, WV-8616, WV-8617, WV-8618, WV-8619, WV-8629, WV-8632, WV-8673, WV-8674, WV-8675, WV-8676, WV-8677, WV-8678, WV-8679, WV-8680, WV-8681, WV-8682, WV-8683, WV-8684, WV-8685, WV-8686, WV-8687, and WV-8688.

In some embodiments of an oligonucleotide having an asymmetric format: a first wing comprises: 2 or more consecutive m; and a second wing comprises: a different sugar modification or a different combination or pattern of sugar modifications. Non-limiting example(s) of such an oligonucleotide include: WV-8852, and WV-8856.

In some embodiments of an oligonucleotide having an asymmetric format: a first wing comprises: 2 or more consecutive M; and a second wing comprises: a different sugar modification or a different combination or pattern of sugar modifications. Non-limiting example(s) of such an oligonucleotide include: WV-8043-8048.

In some embodiments of an oligonucleotide having an asymmetric format: a first wing comprises: MMMMM; and a second wing comprises: a different sugar modification or a different combination or pattern of sugar modifications. Non-limiting example(s) of such an oligonucleotide include: WV-8043-8048.

In some embodiments of an oligonucleotide having an asymmetric format: a first wing comprises: mmmmm; and a second wing comprises: a different sugar modification or a different combination or pattern of sugar modifications. Non-limiting example(s) of such an oligonucleotide include: WV-8852, and WV-8856.

In some embodiments of an oligonucleotide having an asymmetric format: a first wing comprises: m and M in a different order and/or different number; and a second wing comprises: a different sugar modification or a different combination or pattern of sugar modifications. Non-limiting example(s) of such an oligonucleotide include: WV-8248.

In some embodiments of an oligonucleotide having an asymmetric format: a first wing comprises: mMmmm; and a second wing comprises: a different sugar modification or a different combination or pattern of sugar modifications. Non-limiting example(s) of such an oligonucleotide include: WV-8248.

In some embodiments of an oligonucleotide having an asymmetric format: a first wing comprises: M and 2 or more consecutive m; and a second wing comprises: a different sugar modification or a different combination or pattern of sugar modifications. Non-limiting example(s) of such an oligonucleotide include: WV-9894-9896.

In some embodiments of an oligonucleotide having an asymmetric format: a first wing comprises: Mmmmm; and a second wing comprises: a different sugar modification or a different combination or pattern of sugar modifications. Non-limiting example(s) of such an oligonucleotide include: WV-9894-9896, and WV-10253 to 10254.

In some embodiments of an oligonucleotide having an asymmetric format: a first wing comprises: 2 or more consecutive M; and a second wing comprises: a different sugar modification or a different combination or pattern of sugar modifications.

In some embodiments of an oligonucleotide having an asymmetric format: a first wing comprises: MMMMMMM; and a second wing comprises: a different sugar modification or a different combination or pattern of sugar modifications. Non-limiting example(s) of such an oligonucleotide include: WV-12099, WV-12101, WV-12103, WV-12105, WV-12107, and WV-12109.

In some embodiments of an oligonucleotide having an asymmetric format: a first wing comprises: MMMMM; and a second wing comprises: a different sugar modification or a different combination or pattern of sugar modifications. Non-limiting example(s) of such an oligonucleotide include: WV-10250, and WV-9869 to WV-9870.

In some embodiments of an oligonucleotide having an asymmetric format: a first wing comprises: all M; and a second wing comprises: a different sugar modification or a different combination or pattern of sugar modifications. Non-limiting example(s) of such an oligonucleotide include: WV-9441-9445.

In some embodiments of an oligonucleotide having an asymmetric format: a first wing comprises: MMMMM; and a second wing comprises: a different sugar modification or a different combination or pattern of sugar modifications. Non-limiting example(s) of such an oligonucleotide include: WV-9441-9445.

In some embodiments of an oligonucleotide having an asymmetric format: a first wing comprises: 2 or more consecutive m; and a second wing comprises: a different sugar modification or a different combination or pattern of sugar modifications.

In some embodiments of an oligonucleotide having an asymmetric format: a first wing comprises: m and M in a particular order and number; and a second wing comprises: a different sugar modification or a different combination or pattern of sugar modifications.

In some embodiments of an oligonucleotide having an asymmetric format: a first wing comprises: m and M in a particular order and number; and a second wing comprises: a different sugar modification or a different combination or pattern of sugar modifications.

In some embodiments of an oligonucleotide having an asymmetric format: a first wing comprises: L, m and M in a different order and/or different number; and a second wing comprises: a different sugar modification or a different combination or pattern of sugar modifications. Non-limiting example(s) of such an oligonucleotide include: WV-8250.

In some embodiments of an oligonucleotide having an asymmetric format: a first wing comprises: mMmmL; and a second wing comprises: a different sugar modification or a different combination or pattern of sugar modifications. Non-limiting example(s) of such an oligonucleotide include: WV-8250.

In some embodiments of an oligonucleotide having an asymmetric format: a first wing comprises: m and L; and a second wing comprises: a different sugar modification or a different combination or pattern of sugar modifications. Non-limiting example(s) of such an oligonucleotide include: WV-8246.

In some embodiments of an oligonucleotide having an asymmetric format: a first wing comprises: mmmmL; and a second wing comprises: a different sugar modification or a different combination or pattern of sugar modifications. Non-limiting example(s) of such an oligonucleotide include: WV-8246.

In some embodiments of an oligonucleotide having an asymmetric format: a first wing comprises: m and L; and a second wing comprises: a different sugar modification or a different combination or pattern of sugar modifications. Non-limiting example(s) of such an oligonucleotide include: WV-11958, and WV-11960, and WV-11962.

In some embodiments of an oligonucleotide having an asymmetric format: a first wing comprises: 2 or more consecutive m and L; and a second wing comprises: a different sugar modification or a different combination or pattern of sugar modifications. Non-limiting example(s) of such an oligonucleotide include: WV-11958, WV-11960, and WV-11962.

In some embodiments of an oligonucleotide having an asymmetric format: a first wing comprises: mmmmL; and a second wing comprises: a different sugar modification or a different combination or pattern of sugar modifications. Non-limiting example(s) of such an oligonucleotide include: WV-11958, WV-11960, and WV-11962.

In some embodiments of an oligonucleotide having an asymmetric format: a first wing comprises: only one type of sugar modification; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: a different pattern of the same two different types of sugar modifications; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: a different pattern of m and M; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: mmMmm; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-12110, WV-12111, WV-12112, WV-12113, and WV-12114.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-12110, WV-12111, WV-12112, WV-12113, and WV-12114.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-13303, WV-13304, WV-13809, WV-14087, WV-14349, WV-14556, WV-14557, WV-14558, WV-14559, WV-14560, WV-14561, WV-14562, WV-14563, WV-14564, WV-14733, WV-14734, WV-14735, WV-14736, WV-14737, WV-14771, WV-15310, WV-15311, WV-15312, WV-15313, WV-15314, WV-15315, WV-15316, WV-15317, WV-15318, WV-15319, WV-15320, WV-15321, WV-15351, WV-15352, WV-15353, WV-15354, WV-15355, WV-15356, WV-15357, WV-15358, WV-15359, WV-15360, WV-15361, WV-15362, WV-15363, WV-15364, WV-15365, WV-15562, WV-15563, WV-15863, WV-15864, and WV-15887.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8552, WV-8554, WV-8570, WV-8571, WV-8572, WV-8573, WV-8574, WV-8575, WV-8576, WV-8577, WV-8578, WV-8579, WV-8580, and WV-8581.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-14552, WV-14553, WV-14554, and WV-14555.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8456.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8125.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8314.

In some embodiments of an oligonucleotide having an asymmetric format: a first wing comprises: a third type of sugar modification; and a second wing comprises: a different sugar modification or a different combination or pattern of sugar modifications. Non-limiting example(s) of such an oligonucleotide include: WV-9508, WV-9509, and WV-9510.

In some embodiments of an oligonucleotide having an asymmetric format: a first wing comprises: two or more consecutive F; and a second wing comprises: a different sugar modification or a different combination or pattern of sugar modifications. Non-limiting example(s) of such an oligonucleotide include: WV-9508, WV-9509, and WV-9510.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-9488, WV-9489, WV-9490, WV-9491, WV-9492, WV-9494, WV-9505, WV-9506, WV-9507, WV-8452, WV-8453, WV-8009, WV-8010, WV-8011, WV-8012, WV-8454, and WV-8455.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: a different pattern of two different types of sugar modifications; and a second wing comprises: a different sugar modification or a different combination or pattern of sugar modifications. Non-limiting example(s) of such an oligonucleotide include: WV-8121, WV-8129, WV-8118, WV-8126, WV-8472, WV-8473, WV-8474, WV-8475, and WV-8476.

In some embodiments of an oligonucleotide having an asymmetric format: a first wing comprises: a different pattern of two different types of sugar modifications; and a second wing comprises: a different sugar modification or a different combination or pattern of sugar modifications. Non-limiting example(s) of such an oligonucleotide include: WV-8119 and WV-8127.

In some embodiments of an oligonucleotide having an asymmetric format: a first wing comprises: a only one type of sugar modifications; and a second wing comprises: a different sugar modification or a different combination or pattern of sugar modifications. Non-limiting example(s) of such an oligonucleotide include: WV-8115 and WV-8123.

In some embodiments of an oligonucleotide having an asymmetric format: a first wing comprises: a different pattern of two different types of sugar modifications; and a second wing comprises: a different sugar modification or a different combination or pattern of sugar modifications. Non-limiting example(s) of such an oligonucleotide include: WV-8120 and WV-8128.

In some embodiments of an oligonucleotide having an asymmetric format: a first wing comprises: one type of sugar modifications; and a second wing comprises: a different sugar modification or a different combination or pattern of sugar modifications. Non-limiting example(s) of such an oligonucleotide include: WV-8116 and WV-8124.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-14552, WV-14553, WV-14554, and WV-14555.

In some embodiments of an oligonucleotide having an asymmetric format: a first wing comprises: MmMmm; and a second wing comprises: a different sugar modification or a different combination or pattern of sugar modifications. Non-limiting example(s) of such an oligonucleotide include: WV-8456.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-8125.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8314.

In some embodiments of an oligonucleotide having an asymmetric format: a first wing comprises: a third type of sugar modification; and a second wing comprises: a different sugar modification or a different combination or pattern of sugar modifications. Non-limiting example(s) of such an oligonucleotide include: WV-9508, WV-9509, WV-9510.

In some embodiments of an oligonucleotide having an asymmetric format: a first wing comprises: two or more consecutive F; and a second wing comprises: a different sugar modification or a different combination or pattern of sugar modifications. Non-limiting example(s) of such an oligonucleotide include: WV-9508, WV-9509, WV-9510.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-9488, WV-9489, WV-9490, WV-9491, WV-9492, WV-9494, WV-9505, WV-9506, and WV-9507.

In some embodiments of an oligonucleotide having an asymmetric format: a first wing comprises: a different pattern of two different types of sugar modification; and a second wing comprises: a different sugar modification or a different combination or pattern of sugar modifications. Non-limiting example(s) of such an oligonucleotide include: WV-8452 and WV-8453.

In some embodiments of an oligonucleotide having an asymmetric format: a first wing comprises: MmMmm; and a second wing comprises: a different sugar modification or a different combination or pattern of sugar modifications. Non-limiting example(s) of such an oligonucleotide include: WV-8452 and WV-8453.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8009, WV-8010, WV-8011, WV-8012, WV-8454, and WV-8455.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-8121 and WV-8129.

In some embodiments of an oligonucleotide having an asymmetric format: a first wing comprises: only one type of sugar modification; and a second wing comprises: a different sugar modification or a different combination or pattern of sugar modifications. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-8119 and WV-8127.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8115 and WV-8123.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-8120 and WV-8128.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8116 and WV-8124.

In some embodiments of an oligonucleotide having an asymmetric format: a first wing comprises: DMMD; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: MMD; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: DDMMD; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8637, WV-8638, WV-8639, WV-8640, WV-8653, WV-8654, WV-8655, WV-8656, WV-8665, WV-8666, WV-8667, WV-8668, WV-8669, WV-8670, WV-8671, WV-8672, WV-12947, WV-12948, WV-12949, WV-12950, WV-12951, WV-12952, WV-12953, WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, and WV-12976.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000, WV-13001, WV-13002, WV-13003, WV-13004, WV-13005, WV-13006, WV-13007, and WV-13008.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-9887, WV-9888, WV-10245, and WV-10246.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-9871 and WV-9872.

In some embodiments of an oligonucleotide having an asymmetric format: a first wing comprises: mmmmmmm; and a second wing comprises: a different sugar modification or a different combination or pattern of sugar modifications. Non-limiting example(s) of such an oligonucleotide include: WV-12101.

In some embodiments of an oligonucleotide having an asymmetric format: a first wing comprises: M and two or more consecutive m; and a second wing comprises: a different sugar modification or a different combination or pattern of sugar modifications. Non-limiting example(s) of such an oligonucleotide include: WV-9873 and WV-9874.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-9885, WV-9886, WV-10243, and WV-10244.

In some embodiments of an oligonucleotide having an asymmetric format: a first wing comprises: two or more consecutive F; and a second wing comprises: a different sugar modification or a different combination or pattern of sugar modifications. Non-limiting example(s) of such an oligonucleotide include: WV-9526, WV-9527, WV-9528, WV-9529, WV-9530, WV-9531, WV-9532, WV-9533, WV-9590, WV-9591, WV-9592, and WV-9593.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8610, WV-8611, WV-8612, WV-8613, WV-8614, WV-8615, WV-8616, WV-8617, WV-8618, WV-8619, WV-8629, WV-8632, WV-8673, WV-8674, WV-8675, WV-8676, WV-8677, WV-8678, WV-8679, WV-8680, WV-8681, WV-8682, WV-8683, WV-8684, WV-8685, WV-8686, WV-8687, and WV-8688.

In some embodiments of an oligonucleotide having an asymmetric format: a first wing comprises: 2 or more consecutive M; and a second wing comprises: a different sugar modification or a different combination or pattern of sugar modifications. Non-limiting example(s) of such an oligonucleotide include: WV-8852, and WV-8856.

In some embodiments of an oligonucleotide having an asymmetric format: a first wing comprises: 2 or more consecutive m; and a second wing comprises: a different sugar modification or a different combination or pattern of sugar modifications. Non-limiting example(s) of such an oligonucleotide include: WV-8043-8048.

In some embodiments of an oligonucleotide having an asymmetric format: a first wing comprises: mmmmm; and a second wing comprises: a different sugar modification or a different combination or pattern of sugar modifications. Non-limiting example(s) of such an oligonucleotide include: WV-8043-8048.

In some embodiments of an oligonucleotide having an asymmetric format: a first wing comprises: MMMMM; and a second wing comprises: a different sugar modification or a different combination or pattern of sugar modifications. Non-limiting example(s) of such an oligonucleotide include: WV-8852, and WV-8856.

In some embodiments of an oligonucleotide having an asymmetric format: a first wing comprises: m and M in a particular order and number; and a second wing comprises: a different sugar modification or a different combination or pattern of sugar modifications. Non-limiting example(s) of such an oligonucleotide include: WV-8248.

In some embodiments of an oligonucleotide having an asymmetric format: a first wing comprises: mMmMm; and a second wing comprises: a different sugar modification or a different combination or pattern of sugar modifications. Non-limiting example(s) of such an oligonucleotide include: WV-8248.

In some embodiments of an oligonucleotide having an asymmetric format: a first wing comprises: m and 2 or more consecutive M; and a second wing comprises: a different sugar modification or a different combination or pattern of sugar modifications. Non-limiting example(s) of such an oligonucleotide include: WV-9894-9896.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-9894-9896, and WV-10253 to 10254.

In some embodiments of an oligonucleotide having an asymmetric format: a first wing comprises: m and M in a particular order and number; and a second wing comprises: a different sugar modification or a different combination or pattern of sugar modifications.

In some embodiments of an oligonucleotide having an asymmetric format: a first wing comprises: mMMMMMM; and a second wing comprises: a different sugar modification or a different combination or pattern of sugar modifications. Non-limiting example(s) of such an oligonucleotide include: WV-12099, WV-12101, WV-12103, WV-12105, WV-12107, and WV-12109.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-10250, and WV-9869 to WV-9870.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-9441-9445.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-9441-9445.

In some embodiments of an oligonucleotide having an asymmetric format: a first wing comprises: m and M in a particular order and number; and a second wing comprises: a different sugar modification or a different combination or pattern of sugar modifications.

In some embodiments of an oligonucleotide having an asymmetric format: a first wing comprises: 2 or more consecutive m; and a second wing comprises: a different sugar modification or a different combination or pattern of sugar modifications.

In some embodiments of an oligonucleotide having an asymmetric format: a first wing comprises: 2 or more consecutive M; and a second wing comprises: a different sugar modification or a different combination or pattern of sugar modifications.

In some embodiments of an oligonucleotide having an asymmetric format: a first wing comprises: L, m and M in a particular order and number; and a second wing comprises: a different sugar modification or a different combination or pattern of sugar modifications. Non-limiting example(s) of such an oligonucleotide include: WV-8250.

In some embodiments of an oligonucleotide having an asymmetric format: a first wing comprises: LMmMm; and a second wing comprises: a different sugar modification or a different combination or pattern of sugar modifications. Non-limiting example(s) of such an oligonucleotide include: WV-8250.

In some embodiments of an oligonucleotide having an asymmetric format: a first wing comprises: L, m and M; and a second wing comprises: a different sugar modification or a different combination or pattern of sugar modifications. Non-limiting example(s) of such an oligonucleotide include: WV-8246.

In some embodiments of an oligonucleotide having an asymmetric format: a first wing comprises: LMmMm; and a second wing comprises: a different sugar modification or a different combination or pattern of sugar modifications. Non-limiting example(s) of such an oligonucleotide include: WV-8246.

In some embodiments of an oligonucleotide having an asymmetric format: a first wing comprises: L and M; and a second wing comprises: a different sugar modification or a different combination or pattern of sugar modifications. Non-limiting example(s) of such an oligonucleotide include: WV-11958, and WV-11960, and WV-11962.

In some embodiments of an oligonucleotide having an asymmetric format: a first wing comprises: L and 2 or more consecutive M; and a second wing comprises: a different sugar modification or a different combination or pattern of sugar modifications. Non-limiting example(s) of such an oligonucleotide include: WV-11958, WV-11960, and WV-11962.

In some embodiments of an oligonucleotide having an asymmetric format: a first wing comprises: LMMMM; and a second wing comprises: a different sugar modification or a different combination or pattern of sugar modifications. Non-limiting example(s) of such an oligonucleotide include: WV-11958, WV-11960, and WV-11962.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: a pattern of m and M; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-11114, WV-11533, WV-12503, WV-12504, WV-12505, WV-8553, WV-8555, WV-8556, WV-8557, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, and WV-9698.

In some embodiments of an oligonucleotide having an asymmetric format: a first wing comprises: a pattern of two different types of sugar modifications; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: a pattern of m and M; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: mmMMm; and a second wing comprises: a different sugar modification or a different combination or pattern of sugar modifications. Non-limiting example(s) of such an oligonucleotide include: WV-8097, WV-8098, WV-8099, WV-8100, WV-8101, WV-8102, and WV-8109.

In some embodiments of an oligonucleotide having an asymmetric format: a first wing comprises: m and two or more consecutive M; and a second wing comprises: a different sugar modification or a different combination or pattern of sugar modifications. Non-limiting example(s) of such an oligonucleotide include: WV-12110, WV-12111, WV-12112, WV-12113, and WV-12114.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-12110, WV-12111, WV-12112, WV-12113, and WV-12114.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-13303, WV-13304, WV-13809, WV-14087, WV-14349, WV-14556, WV-14557, WV-14558, WV-14559, WV-14560, WV-14561, WV-14562, WV-14563, WV-14564, WV-14733, WV-14734, WV-14735, WV-14736, WV-14737, WV-14771, WV-15310, WV-15311, WV-15312, WV-15313, WV-15314, WV-15315, WV-15316, WV-15317, WV-15318, WV-15319, WV-15320, WV-15321, WV-15351, WV-15352, WV-15353, WV-15354, WV-15355, WV-15356, WV-15357, WV-15358, WV-15359, WV-15360, WV-15361, WV-15362, WV-15363, WV-15364, WV-15365, WV-15562, WV-15563, WV-15863, WV-15864, and WV-15887.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8552, WV-8554, WV-8570, WV-8571, WV-8572, WV-8573, WV-8574, WV-8575, WV-8576, WV-8577, WV-8578, WV-8579, WV-8580, and WV-8581.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-14552, WV-14553, WV-14554, and WV-14555.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8456.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8125.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8314.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-9508, WV-9509, and WV-9510.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-9508, WV-9509, and WV-9510.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-9488, WV-9489, WV-9490, WV-9491, WV-9492, WV-9494, WV-9505, WV-9506, WV-9507, WV-8452, WV-8453, WV-8009, WV-8010, WV-8011, WV-8012, WV-8454, and WV-8455.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: a particular pattern of two different types of sugar modifications; and a second wing comprises: a different sugar modification or a different combination or pattern of sugar modifications. Non-limiting example(s) of such an oligonucleotide include: WV-8121, WV-8129, WV-8118, WV-8126, WV-8472, WV-8473, WV-8474, WV-8475, and WV-8476.

In some embodiments of an oligonucleotide having an asymmetric format: a first wing comprises: a particular pattern of two different types of sugar modifications; and a second wing comprises: a different sugar modification or a different combination or pattern of sugar modifications. Non-limiting example(s) of such an oligonucleotide include: WV-8119 and WV-8127.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8115 and WV-8123.

In some embodiments of an oligonucleotide having an asymmetric format: a first wing comprises: a particular pattern of two different types of sugar modifications; and a second wing comprises: a different sugar modification or a different combination or pattern of sugar modifications. Non-limiting example(s) of such an oligonucleotide include: WV-8120 and WV-8128.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8116 and WV-8124.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-14552, WV-14553, WV-14554, and WV-14555.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8456.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8005, WV-8006, WV-8007, WV-8008, WV-8466, WV-8467, WV-8468, WV-8469, WV-8470, WV-8471, WV-8547, WV-8548, WV-8594, WV-13305, WV-13306, WV-13307, WV-13308, WV-13309, WV-13310, WV-13311, WV-13313, WV-13803, WV-13804, and WV-13805.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8125.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-8314.

In some embodiments of an oligonucleotide having an asymmetric format: a first wing comprises: two different types of sugar modification; and a second wing comprises: a different sugar modification or a different combination or pattern of sugar modifications. Non-limiting example(s) of such an oligonucleotide include: WV-9508, WV-9509, WV-9510.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-9508, WV-9509, WV-9510.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, and WV-9487.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-9488, WV-9489, WV-9490, WV-9491, WV-9492, WV-9494, WV-9505, WV-9506, and WV-9507.

In some embodiments of an oligonucleotide having an asymmetric format: a first wing comprises: a particular pattern of two different types of sugar modification; and a second wing comprises: a different sugar modification or a different combination or pattern of sugar modifications. Non-limiting example(s) of such an oligonucleotide include: WV-8452 and WV-8453.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-8452 and WV-8453.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-8009, WV-8010, WV-8011, WV-8012, WV-8454, and WV-8455.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-8549, WV-8550, WV-8551, WV-8568, WV-8569, WV-13312, WV-14758, WV-14772, WV-15049, WV-15050, and WV-15051.

In some embodiments of an oligonucleotide having an asymmetric format: a first wing comprises: mMMmm; and a second wing comprises: a different sugar modification or a different combination or pattern of sugar modifications. Non-limiting example(s) of such an oligonucleotide include: WV-8121 and WV-8129.

In some embodiments of an oligonucleotide having an asymmetric format: a first wing comprises: two different types of sugar modifications; and a second wing comprises: a different sugar modification or a different combination or pattern of sugar modifications. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: mMMmm; and a second wing comprises: a different sugar modification or a different combination or pattern of sugar modifications. Non-limiting example(s) of such an oligonucleotide include: WV-8118, WV-8126, WV-8472, WV-8473, WV-8474, WV-8475, and WV-8476.

In some embodiments of an oligonucleotide having an asymmetric format: a first wing comprises: mMmmm; and a second wing comprises: a different sugar modification or a different combination or pattern of sugar modifications. Non-limiting example(s) of such an oligonucleotide include: WV-8119 and WV-8127.

In some embodiments of an oligonucleotide having an asymmetric format: a first wing comprises: mMmmm; and a second wing comprises: a different sugar modification or a different combination or pattern of sugar modifications. Non-limiting example(s) of such an oligonucleotide include: WV-8115 and WV-8123.

In some embodiments of an oligonucleotide having an asymmetric format: a first wing comprises: mmMmm; and a second wing comprises: a different sugar modification or a different combination or pattern of sugar modifications. Non-limiting example(s) of such an oligonucleotide include: WV-8120 and WV-8128.

In some embodiments of an oligonucleotide having an asymmetric format: a first wing comprises: mmMmm; and a second wing comprises: a different sugar modification or a different combination or pattern of sugar modifications. Non-limiting example(s) of such an oligonucleotide include: WV-8116 and WV-8124.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8645, WV-8646, WV-8647, WV-8648, WV-8661, WV-8662, WV-8663, and WV-8664.

In some embodiments of an oligonucleotide having an asymmetric format: a first wing comprises: two or more consecutive M; and a second wing comprises: a different sugar modification or a different combination or pattern of sugar modifications. Non-limiting example(s) of such an oligonucleotide include: WV-8637, WV-8638, WV-8639, WV-8640, WV-8653, WV-8654, WV-8655, WV-8656, WV-8665, WV-8666, WV-8667, WV-8668, WV-8669, WV-8670, WV-8671, WV-8672, WV-12947, WV-12948, WV-12949, WV-12950, WV-12951, WV-12952, WV-12953, WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, and WV-12976.

In some embodiments of an oligonucleotide having an asymmetric format: a first wing comprises: two or more consecutive m; and a second wing comprises: a different sugar modification or a different combination or pattern of sugar modifications. Non-limiting example(s) of such an oligonucleotide include: WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000, WV-13001, WV-13002, WV-13003, WV-13004, WV-13005, WV-13006, WV-13007, and WV-13008.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-9887, WV-9888, WV-10245, and WV-10246.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-9871 and WV-9872.

In some embodiments of an oligonucleotide having an asymmetric format: a first wing comprises: mMMMMMM; and a second wing comprises: a different sugar modification or a different combination or pattern of sugar modifications. Non-limiting example(s) of such an oligonucleotide include: WV-12101.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-9873 and WV-9874.

In some embodiments of an oligonucleotide having an asymmetric format: a first wing comprises: mMMMM; and a second wing comprises: a different sugar modification or a different combination or pattern of sugar modifications. Non-limiting example(s) of such an oligonucleotide include: WV-9885, WV-9886, WV-10243, and WV-10244.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-9526, WV-9527, WV-9528, WV-9529, WV-9530, WV-9531, WV-9532, WV-9533, WV-9590, WV-9591, WV-9592, and WV-9593.

In some embodiments of an oligonucleotide having an asymmetric format: a first wing comprises: mMMMm; and a second wing comprises: a different sugar modification or a different combination or pattern of sugar modifications. Non-limiting example(s) of such an oligonucleotide include: WV-8610, WV-8611, WV-8612, WV-8613, WV-8614, WV-8615, WV-8616, WV-8617, WV-8618, WV-8619, WV-8629, WV-8632, WV-8673, WV-8674, WV-8675, WV-8676, WV-8677, WV-8678, WV-8679, WV-8680, WV-8681, WV-8682, WV-8683, WV-8684, WV-8685, WV-8686, WV-8687, and WV-8688.

In some embodiments, two or more consecutive m is mm. In some embodiments, two or more consecutive m is mmm. In some embodiments, two or more consecutive m is mmmm. In some embodiments, two or more consecutive m is mmmmm. In some embodiments, two or more consecutive m is mmmmmm. In some embodiments, two or more consecutive m is mmmmmmm.

In some embodiments, two or more consecutive M is MM. In some embodiments, two or more consecutive M is MMM. In some embodiments, two or more consecutive M is MMMM. In some embodiments, two or more consecutive M is MMMMM. In some embodiments, two or more consecutive M is MMMMMM. In some embodiments, two or more consecutive M is MMMMMMM.

In some embodiments, two or more consecutive F is FF. In some embodiments, two or more consecutive F is FFF. In some embodiments, two or more consecutive F is FFFF. In some embodiments, two or more consecutive F is FFFFF. In some embodiments, two or more consecutive F is FFFFFF. In some embodiments, two or more consecutive F is FFFFFFF.

In some embodiments, oligonucleotides of the present disclosure comprise sugar modifications. In some embodiments, oligonucleotides can comprise any sugar described herein or known in the art. In some embodiments, a first wing of an oligonucleotide having an asymmetric format can comprise any sugar described herein or known in the art, and a second wing of the oligonucleotide does not comprise the sugar. In some embodiments, a first wing of an oligonucleotide having an asymmetric format can comprise any sugar described herein or known in the art, and a second wing of the oligonucleotide comprises a different sugar.

In some embodiments, a sugar has a structure of:

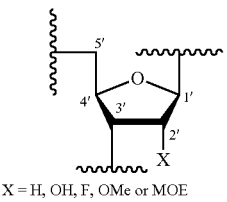

X = H, OH, F, OMe or MOE

Modified sugars can be incorporated into a provided oligonucleotide. In some embodiments, a modified sugar contains one or more substituents at the 2' position including one of the following: —F; —CF$_3$, —CN, —N$_3$, —NO, —NO$_2$, —OR', —SR', or —N(R')$_2$, wherein each R' is independently described in the present disclosure; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. Examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the 2', 3', 4', 5', or 6' positions of the sugar or modified sugar, including the 3' position of the sugar on the 3'-terminal nucleotide or in the 5' position of the 5'-terminal nucleotide.

In some embodiments, a 2'-modification is 2'-F.

In some embodiments, the 2'-OH of a ribose is replaced with a substituent including one of the following: —H, —F; —CF$_3$, —CN, —N$_3$, —NO, —NO$_2$, —OR', —SR', or —N(R')$_2$, wherein each R' is independently described in the present disclosure; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —OCH$_2$CH$_2$OMe.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, -L- is —O—CH$_2$—, wherein —CH$_2$— is optionally substituted. In some embodiments, -L- is —O—CH$_2$—. In some embodiments, -L- is —O—CH(Et)-. In some embodiments, -L- is between C2 and C4 of a sugar moiety. In some embodiments, a locked nucleic acid has the structure indicated below. A locked nucleic acid of the structure below is indicated, wherein B represents a nucleobase or modified nucleobase as described herein, and wherein, e.g., R$^{2s}$ and R$^{4s}$ are R taken together with their intervening atoms to form a ring. In some embodiments, a modified nucleoside has a structure of:

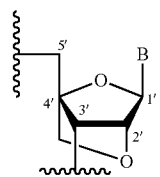

wherein B is a base.

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xenonucleic acid), for instance, arabinose, anhydrohexitol, threose, 2'fluoroarabinose, or cyclohexene.

Modified sugars include cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

Non-limiting examples of modified sugars include glycerol, which form glycerol nucleic acid (GNA). One example of a GNA is shown below and is described in Zhang, R et al., *J. Am. Chem. Soc.,* 2008, 130, 5846-5847; Zhang L, et al., *J. Am. Chem. Soc.,* 2005, 127, 4174-4175 and Tsai C H et al., *PNAS,* 2007, 14598-14603. In some embodiments, a nucleoside has a structure of:

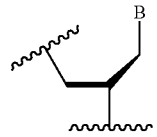

Wherein B is a base.

A flexible nucleic acid (FNA) based on the mixed acetal aminal of formyl glycerol, is described in Joyce G F et al., *PNAS,* 1987, 84, 4398-4402 and Heuberger B D and Switzer C, *J. Am. Chem. Soc.,* 2008, 130, 412-413. In some embodiments, a nucleoside has a structure of:

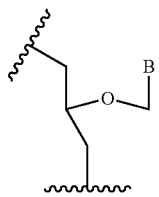

Wherein B is a base.

Additional non-limiting examples of modified sugars and/or modified nucleosides and/or modified nucleotides include hexopyranosyl (6' to 4'), pentopyranosyl (4' to 2'), pentopyranosyl (4' to 3'), 5'-deoxy-5'-C-malonyl, squaryldiamide, and tetrofuranosyl (3' to 2') sugars. In some embodiments, a modified nucleoside comprises a hexopyranosyl (6' to 4') sugar and has the structure of any one in the following formulae:

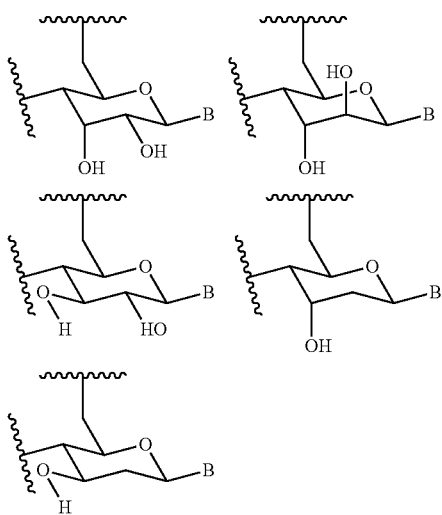

wherein $X^s$ corresponds to the P-modification group "—XLR$^1$" described herein wherein XLR$^1$ is equivalent to X-L-R$^1$ and X, L, and R$^1$ are as defined in Formula I, disclosed herein, and B is a base.

In some embodiments, a modified nucleotide comprises a pentopyranosyl (4' to 2') sugar and has a structure of any one in the following formulae:

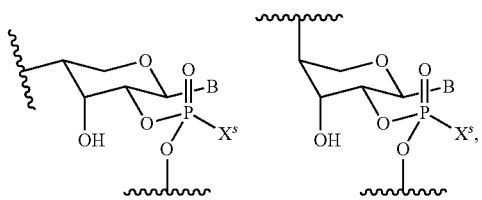

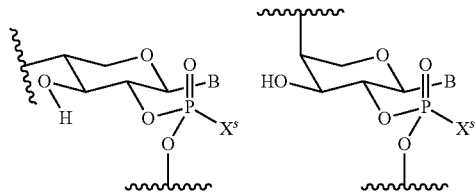

wherein $X^s$ corresponds to the P-modification group "—XLR$^1$" described herein, wherein XLR$^1$ is equivalent to X-L-R$^1$ and X, L, and R$^1$ are as defined in Formula I, disclosed herein, and B is a base.

In some embodiments, a modified nucleotide comprises a pentopyranosyl (4' to 3') sugar and is of any one in the following formulae:

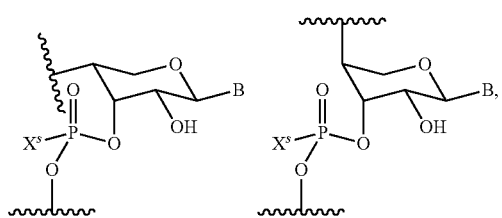

wherein $X^s$ corresponds to the P-modification group "—XLR$^1$" described herein, wherein XLR$^1$ is equivalent to X-L-R$^1$ and X, L, and R' are as defined in Formula I, disclosed herein, and B is a base.

In some embodiments, a modified nucleotide comprises a tetrofuranosyl (3' to 2') sugar and is of either in the following formulae:

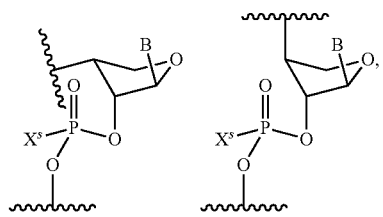

wherein $X^s$ corresponds to the P-modification group "—XLR$^1$" described herein, wherein XLR$^1$ is equivalent to X-L-R$^1$ and X, L, and R$^1$ are as defined in Formula I, disclosed herein, and B is a base.

In some embodiments, a modified nucleotide comprises a modified sugar and is of any one in the following formulae:

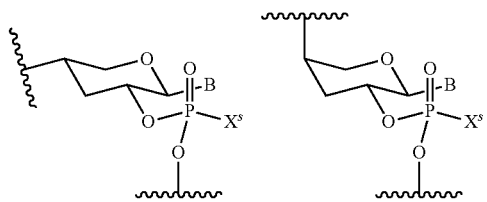

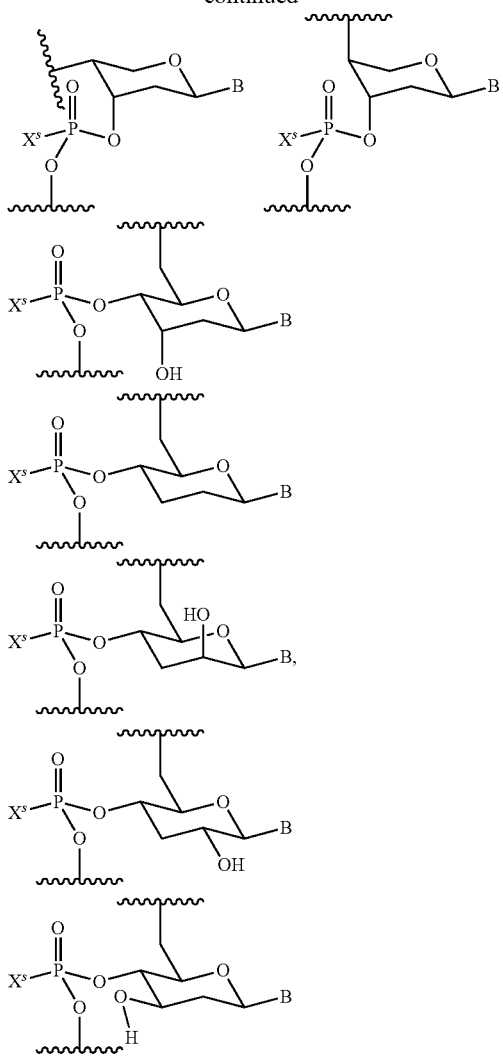

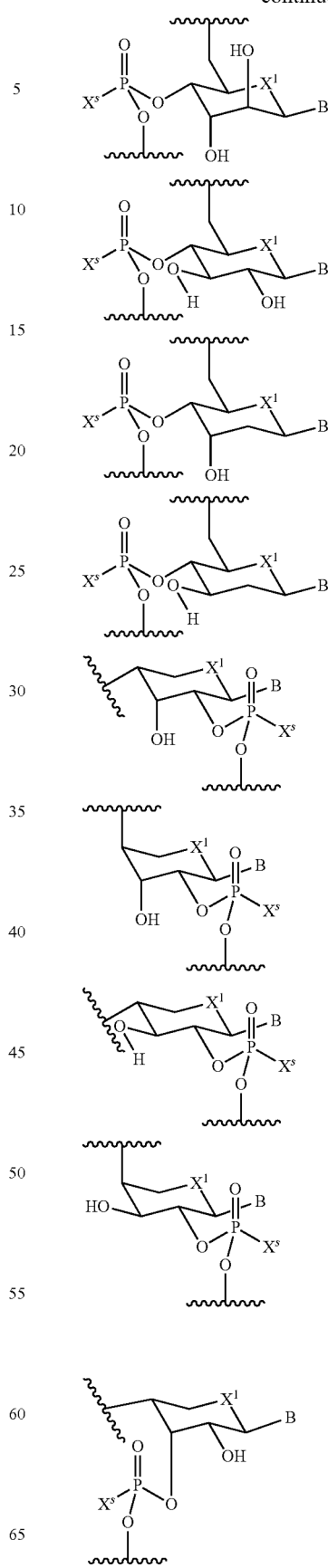

wherein $X^s$ corresponds to the P-modification group "—$XLR^1$" described herein, wherein $XLR^1$ is equivalent to X-L-$R^1$ and X, L, and $R^1$ are as defined in Formula I, disclosed herein, and B is a base.

In some embodiments, one or more hydroxyl group in a sugar moiety is optionally and independently replaced with halogen, R' —N(R')$_2$, —OR', or —SR', wherein each R' is independently described in the present disclosure.

In some embodiments, a modified nucleotide is as illustrated below, wherein $X^s$ corresponds to the P-modification group "—$XLR^1$" described herein, wherein $XLR^1$ is equivalent to X-L-$R^1$ and X, L, and $R^1$ are as defined in Formula I, disclosed herein, B is a base, and $X^1$ is selected from —S—, —Se—, —$CH_2$—, —NMe-, —NEt- and —NiPr—

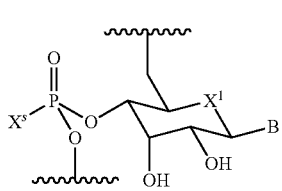

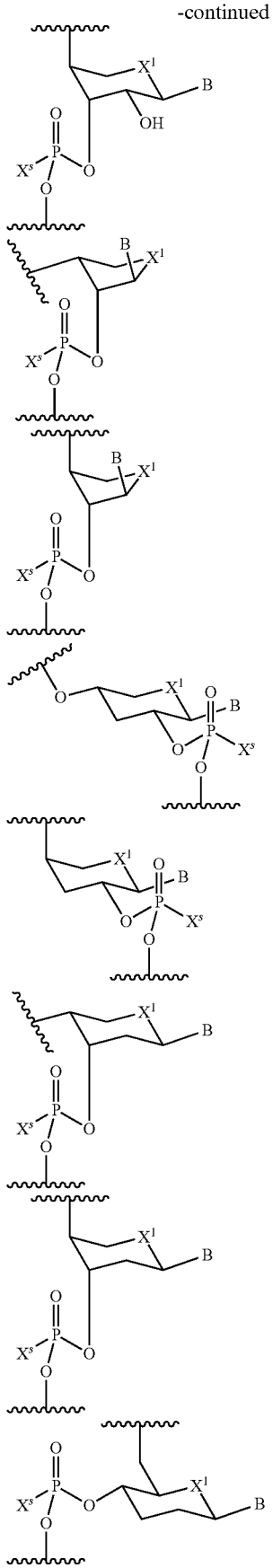
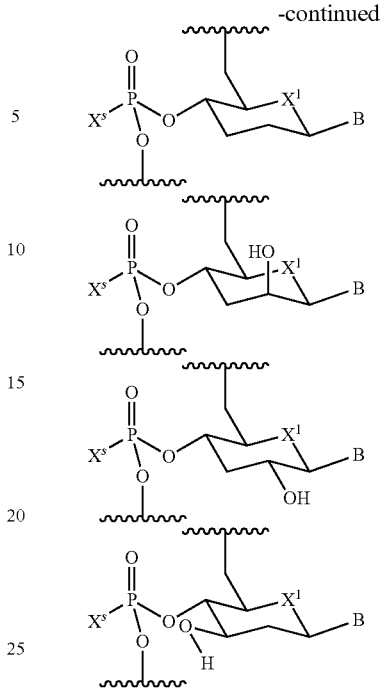

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in an oligonucleotide having an asymmetric format are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 3²%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars can be prepared by methods known in the art, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in Chemical Synthesis: Gnosis to Prognosis, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310). In some embodiments, a modified sugar is any of those described in PCT Publication No. WO2012/030683, incorporated herein by reference, and/or depicted herein. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified nucleotide is selected from:

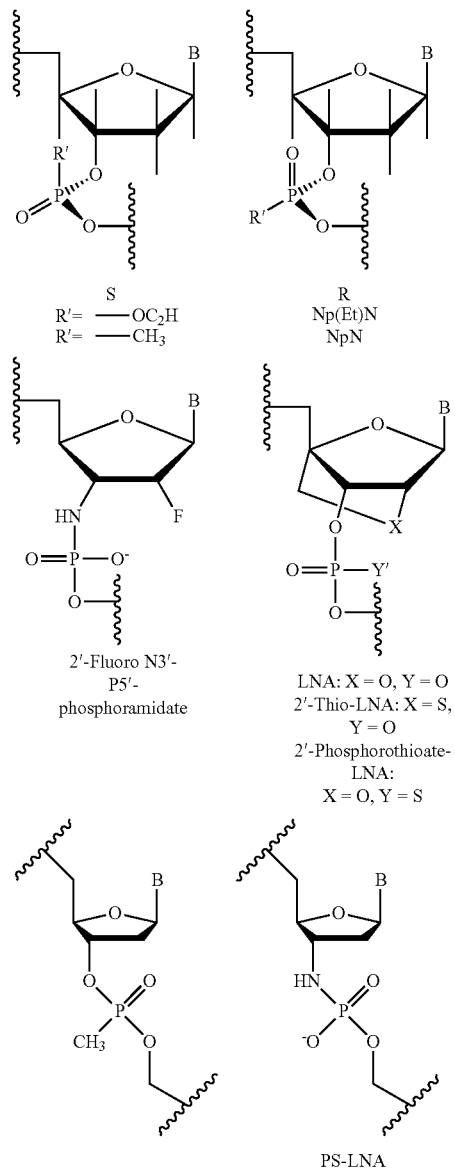

In some embodiments, a nucleotide has a structure selected from any of

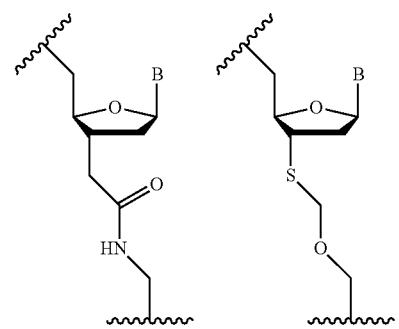

-continued
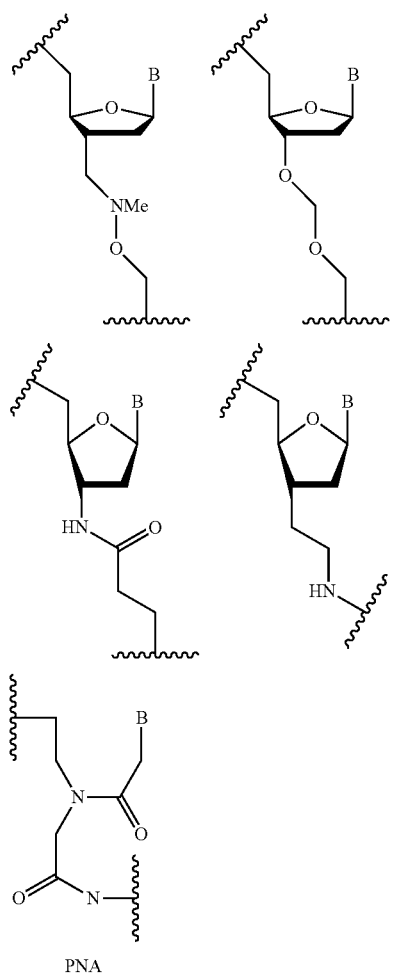
In some embodiments, a modified nucleoside has a structure selected from:
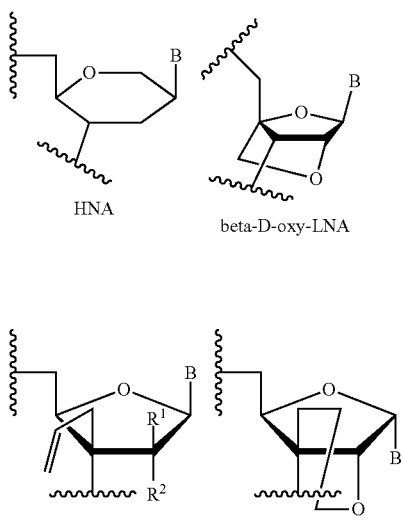
$R^1$ and $R^2$ are independently —H, —F, —OMe, -MOE or substituted or unsubstituted $C_{1-6}$ alkyl;
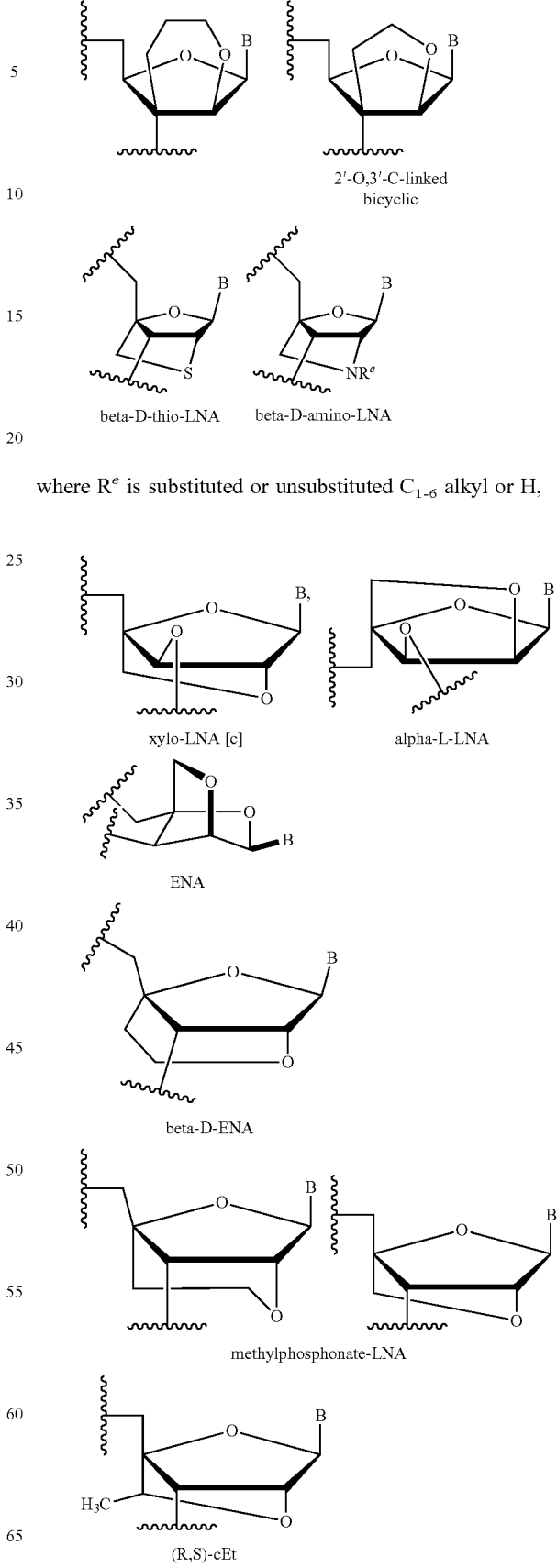
where $R^e$ is substituted or unsubstituted $C_{1-6}$ alkyl or H,

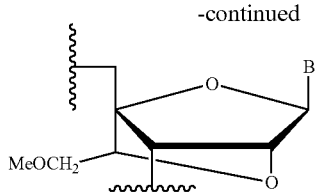

(R,S)-cMOE
(R,S)-cMOE

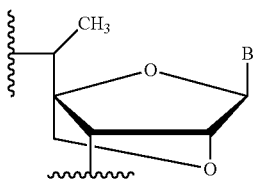

(R,S)-5'-Me-LNA

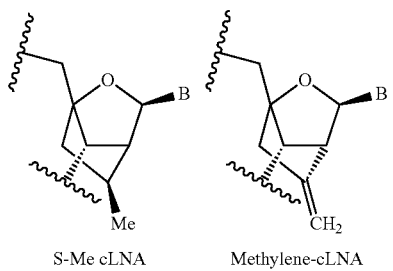

S-Me cLNA   Methylene-cLNA

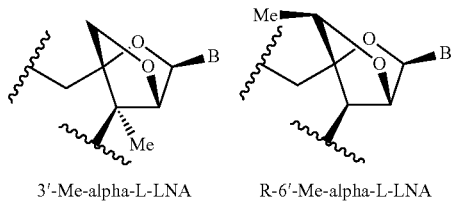

3'-Me-alpha-L-LNA   R-6'-Me-alpha-L-LNA

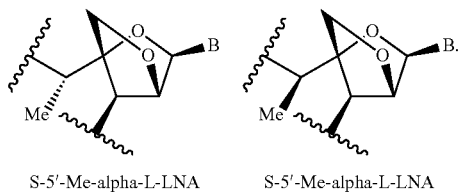

S-5'-Me-alpha-L-LNA   S-5'-Me-alpha-L-LNA

R-5'-Me-alpha-L-LNA. Additional chemically modified sugars are described in WO 2008/101157, WO 2007/134181, WO 2016/167780, and published US Patent Application US2005-0130923. In some embodiments, a nucleotide and adjacent nucleoside have the structure of:

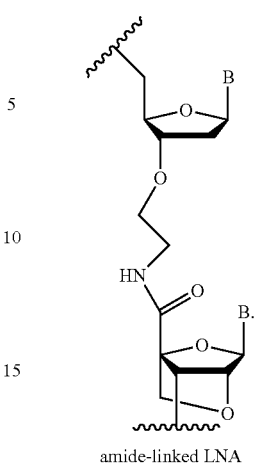

amide-linked LNA

In some embodiments, a locked nucleic acid or LNA or LNA nucleoside or LNA nucleotide is or comprises a nucleic acid monomer having a bridge connecting two carbon atoms between the 4' and 2' position of the nucleoside sugar unit, thereby forming a bicyclic sugar. Examples of such a bicyclic sugar include but are not limited to alpha-L-Methyleneoxy (4'-CH$_2$—O-2') LNA, beta-D-Methyleneoxy (4'-CH$_2$—O-2') LNA, Ethyleneoxy (4'-(CH$_2$)$_2$—O-2') LNA, Aminooxy (4'-CH$_2$—O—N(R)-2') LNA, and Oxyamino (4'-CH$_2$—N(R)—O-2') LNA. In some embodiments, R is R$_1$ or R$_2$.

Examples of nucleosides having modified sugar moieties include without limitation nucleosides comprising 5'-vinyl, 5'-methyl group (R or S), 4'-S, 2'-F, 2'-OCH$_3$, 2'-OCH$_2$CH$_3$, 2'-OCH$_2$CH$_2$F and 2'-O(CH$_2$)$_{20}$CH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_1$)—(CH$_2$)$_2$—N(R$_m$)(R$_n$), where each R$_1$, R$_m$ and R$_n$ is, independently, H or substituted or unsubstituted C$_1$-C$_{10}$ alkyl.

In some embodiments, a bicyclic nucleoside includes any modified nucleoside comprising a bicyclic sugar moiety. Examples of bicyclic nucleic acids (BNAs) include without limitation nucleosides comprising a bridge between the 4' and the 2' ribosyl ring atoms. In some embodiments, antisense compounds provided herein include one or more BNA nucleosides wherein the bridge comprises one of the formulas: 4'-(CH$_2$)—O-2' (LNA); 4'-(CH$_2$)—S-2'; 4,- CH$_2$)$_2$—O-2' (ENA); 4'-CH(CH$_3$)—O-2' and 4'-CH(CH$_2$OCH$_3$)—O-2' (and analogs thereof, see U.S. Pat. No. 7,399,845); 4'-C(CH$_3$)(CH$_3$)—O-2' (and analogs thereof, see PCT/US2008/068922 published as WO/2009/006478); 4'-CH$_2$—N(OCH$_3$)-2' (and analogs thereof, see PCT/US2008/064591 published as WO/2008/150729); 4'-CH$_2$—O—N(CH$_3$)-2' (see published U.S. Patent Application US2004-0171570); 4'-CH$_2$—N(R)—O-2', wherein R is H, C$_1$-C$_{12}$ alkyl, or a protecting group (see U.S. Pat. No. 7,427,672); 4'-CH$_2$—C(H)(CH$_3$)-2' (see Chattopadhyaya et al, J. Org. Chem., 2009, 74, 118-134); and 4,—CH$_2$—C(=CH$_2$)-2' (and analogs thereof, see PCT/US2008/066154 published as WO 2008/154401).

Further bicyclic nucleosides have been reported in the literature (see for example: Srivastava et al, J. Am. Chem. Soc., 2007, 129(26) 8362-8379; Frieden et al, Nucleic Acids Research, 2003, 21, 6365-6372; Elayadi et al, Curr. Opinion Inverts. Drugs, 2001, 2, 558-561; Braasch et al, Chem. Biol, 2001, 8, 1-7; Oram et al, Curr. Opinion Mol Ther., 2001, 3, 239-243; Wahlestedt et al, Proc. Natl Acad. Sci. U.S.A, 2000, 97, 5633-5638; Singh et al, Chem. Commun., 1998, 4, 455-456; Koshkin et al, Tetrahedron, 1998, 54, 3607-3630; Kumar et al, Bioorg. Med. Chem. Lett., 1998, 8, 2219-2222; Singh et al, J. Org. Chem., 1998, 63, 10035-10039; U.S. Pat. Nos. 7,399,845; 7,053,207; 7,034,133; 6,794,499; 6,770, 748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026, 998; 61/026,995; 60/989,574; International applications WO 2007/134181; WO 2005/021570; WO 2004/106356; and PCT International Applications Nos.: PCT/US2008/068922; PCT/US2008/066154; and PCT/US2008/064591).

In some embodiments, a bicyclic nucleoside can be prepared having one or more stereochemical sugar configurations including for example alpha-L-ribofuranose and beta-D-ribofuranose (see PCT international application PCT/DK98/00393, published as WO 99/14226). In some embodiments, a monocyclic nucleosides is a nucleoside comprising a modified sugar moiety that is not a bicyclic sugar moiety. In some embodiments, the sugar moiety, or sugar moiety analogue, of a nucleoside may be modified or substituted at any position. In some embodiments, a 4'-2' bicyclic nucleoside or 4' to 2' bicyclic nucleoside is a bicyclic nucleoside comprising a furanose ring comprising a bridge connecting two carbon atoms of the furanose ring connects the 2' carbon atom and the 4' carbon atom of the sugar ring. In some embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C($R_a$)($R_b$)]$_n$—, —C($R_a$)=C($R_b$)—, —C($R_a$)=N—, —C(=N$R_a$)—, —C(=O)—, —C(=S)—, —O—, —Si($R_a$)$_2$—, —S(=O)x-, and —N($R_a$)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In some embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In some embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2' wherein each R is, independently, H, a protecting group or $C_1$-$C_{12}$ alkyl.

In some embodiments, bicyclic nucleosides are further defined by isomeric configuration. For example, a nucleoside comprising a 4'-(CH$_2$)—O-2' bridge, may be in the alpha-L configuration or in the beta-D configuration. alpha-L-methyleneoxy (4'-CH$_2$—O-2') BNA's have been incorporated into antisense oligonucleotides that showed antisense activity (Frieden et al., Nucleic Acids Research, 2003, 21, 6365-6372).

In some embodiments, bicyclic nucleosides include those having a 4' to 2' bridge wherein such bridges include without limitation, a-L-4'-(CH$_2$)—O-2', P-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or $C_1$-$C_{12}$ alkyl.

Analogs of various bicyclic nucleosides that have 4' to 2' bridging groups such as 4'-CH$_2$-0-2' and 4'-CH$_2$—S-2', have also been prepared (Kumar et al, Bioorg. Med. Chem. Lett., 1998, 8, 2219-2222). Preparation of oligodeoxyribonucleotide duplexes comprising bicyclic nucleosides for use as substrates for nucleic acid polymerases has also been described (Wengel et al, WO 99/14226). Furthermore, synthesis of 2'-amino-BNA, a novel conformationally restricted high-affinity oligonucleotide analog has been described in the art (Singh et al, J. Org. Chem., 1998, 63, 10035-10039). In addition, 2'-amino- and 2'-methylamino-BNA's have been prepared and the thermal stability of their duplexes with complementary RNA and DNA strands has been previously reported.

One carbocyclic bicyclic nucleoside having a 4'-(CH$_2$)$_3$-2' bridge and the alkenyl analog bridge 4'-CH=CH—CH$_2$-2' have been described (Frier et al., Nucleic Acids Research, 1997, 25(22), 4429-4443 and Albaek et al., J. Org. Chem., 2006, 71, 7731-7740). The synthesis and preparation of carbocyclic bicyclic nucleosides along with their oligomerization and biochemical studies have also been described (Srivastava et al, J. Am. Chem. Soc. 2007, 129(26), 8362-8379).

In some embodiments, bicyclic nucleosides include, but are not limited to, alpha-L-methyleneoxy (4'-CH$_2$—O-2') BNA, beta-D-methyleneoxy (4'-CH$_2$—O-2') BNA, ethyleneoxy (4'-(CH$_2$)$_2$—O-2') BNA, aminooxy (4'-CH$_2$—O—N(R)-2') BNA, oxyamino (4'-CH$_2$—N(R)—O-2') BNA, methyl(methyleneoxy) (4'-CH(CH$_3$)—O-2') BNA (also referred to as constrained ethyl or cEt), methylene-thio (4'-CH$_2$—S-2') BNA, methylene-amino (4'-CH$_2$—N(R)-2') BNA, methyl carbocyclic (4'-CH$_2$—CH(CH$_3$)-2') BNA, propylene carbocyclic (4'-(CH$_2$)$_3$-2') BNA, and vinyl BNA.

In some embodiments, LNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group. Non-limiting examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_{2-O}$-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl. Also included within the definition of LNA are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. In some embodiments, in the case of the bicylic sugar moiety having an ethylene bridging group in this position, the term ethyleneoxy (4'-CH$_2$CH$_2$—O-2') LNA is used. alpha-L-methyleneoxy (4'-CH$_2$—O-2'), an isomer of methyleneoxy (4'-CH$_2$—O-2') LNA, is also encompassed within the definition of LNA, as used herein.

In some embodiments, a 2'-modification is —F. In some embodiments, a 2'-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, a modified tetrahydropyran nucleoside or modified THP nucleoside is a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, Bioorg. Med. Chem., 2002, 10, 841-854) or fluoro HNA (F-HNA) having a tetrahydropyranyl ring system as illustrated below.

In some embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506).

Combinations of modifications are also provided without limitation, such as 2'-F-5'-methyl substituted nucleosides (see PCT International Application WO 2008/101157 for other disclosed 5', 2'-bis substituted nucleosides) and replacement of the ribosyl ring oxygen atom with S and further substitution at the 2'-position (see published U.S. Patent Application US2005-0130923) or alternatively 5'-substitution of a bicyclic nucleic acid (see PCT International Application WO 2007/134181, wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al, J. Am. Chem. Soc. 2007, 129(26), 8362-8379).

In some embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, Robeyns et al, J. Am. Chem. Soc., 2008, 130(6), 1979-1984; Horvath et al, Tetrahedron Letters, 2007, 48, 3621-3623; Nauwelaerts et al, J. Am. Chem. Soc., 2007, 129(30), 9340-9348; Gu et al., Nucleosides, Nucleotides & Nucleic Acids, 2005, 24(5-7), 993-998; Nauwelaerts et al, Nucleic Acids Research, 2005, 33(8), 2452-2463; Robeyns et al., Acta Crystallographica, Section F: Structural Biology and Crystallization Communications, 2005, F61(6), 585-586; Gu et al, Tetrahedron, 2004, 60(9), 2111-2123; Gu et al, Oligonucleotides, 2003, 13(6), 479-489; Wang et al, J. Org. Chem., 2003, 68, 4499-4505; Verbeure et al, Nucleic Acids Research, 2001, 29(24), 4941-4947; Wang et al, J. Org. Chem., 2001, 66, 8478-82; Wang et al, Nucleosides, Nucleotides & Nucleic Acids, 2001, 20(4-7), 785-788; Wang et al, J. Am. Chem., 2000, 122, 8595-8602; Published PCT application, WO 06/047842; and Published PCT Application WO 01/049687.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. Bioorg. & Med. Chem., 2002, 10, 841-854). Such ring systems can undergo various additional substitutions to further enhance their activity. In some embodiments, a 2'-modified sugar is a furanosyl sugar modified at the 2' position. In some embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In some embodiments, 2' modifications are selected from substituents including, but not limited to: O[(CH$_2$)$_n$O]$_m$CH, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an R A cleaving group, a reporter group, an intercalator, a group for improving pharmacokinetic properties, or a group for improving the pharmacodynamic properties of an antisense compound, and other substituents having similar properties. In some embodiments, modified nucleosides comprise a 2'-MOE side chain (Baker et al, J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, Helv. Chim. Acta, 1995, 78, 486-504; Altmann et al., Chimia, 1996, 50, 168-176; Altmann et al., Biochem. Soc.

Trans., 1996, 24, 630-637; and Altmann et al., Nucleosides Nucleotides, 1997, 16, 917-926).

In some embodiments, a 2'-modified" or 2'-substituted nucleoside is a nucleoside comprising a sugar comprising a substituent at the 2' position other than H or OH. In some embodiments, 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$O—$CH_3$, 2'-O$(CH_2)_2$S$CH_3$, O—$(CH_2)_2$—O—N$(R_m)(R_n)$, or O—$CH_2$—C(=O)—N$(R_m)(R_n)$, where each $R_m$ and $R_n$ is, independently, H or substituted or unsubstituted $C_1$-$C_{10}$ alkyl.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219 published as WO 2005/121371.

In some embodiments, $R^1$ is R as defined and described. In some embodiments, $R^2$ is R. In some embodiments, $R^e$ is R. In some embodiments, $R^e$ is H, $CH_3$, Bn, $COCF_3$, benzoyl, benzyl, pyren-1-ylcarbonyl, pyren-1-ylmethyl, 2-aminoethyl. In some embodiments, a non-limiting example internucleotidic linkage or sugar is or comprises a component of any of: N-methanocarba, C3-amide, Formacetal, Thioformacetal, MMI, PMO (phosphorodiamidate linked morpholino), PNA (peptide nucleic acid), LNA, cMOE BNA, cEt BNA, a-L-NA or a related analog, HNA, Me-ANA, MOE-ANA, Ara-FHNA, FHNA, R-6'-Me-FHNA, S-6'-Me-FHNA, ENA, or c-ANA. In some embodiments, a non-limiting example internucleotidic linkage or sugar is or comprises a component of any of those described in Allerson et al. 2005 J. Med. Chem. 48: 901-4; BMCL 2011 21: 1122; BMCL 2011 21: 588; BMCL 2012 22: 296; Chattopadhyaya et al. 2007 J. Am. Chem. Soc. 129: 8362; Chem. Bio. Chem. 2013 14: 58; Curr. Prot. Nucl. Acids Chem. 2011 1.24.1; Egli et al. 2011 J. Am. Chem. Soc. 133: 16642; Hendrix et al. 1997 Chem. Eur. J. 3: 110; Hyrup et al. 1996 Bioorg. Med. Chem. 4: 5; Imanishi 1997 Tet. Lett. 38: 8735; J. Am. Chem. Soc. 1994, 116, 3143; J. Med. Chem. 2009 52: 10; J. Org. Chem. 2010 75: 1589; Jepsen et al. 2004 Oligo. 14: 130-146; Jones et al. J. Org. Chem. 1993, 58, 2983; Jung et al. 2014 ACIEE 53: 9893; Kodama et al. 2014 AGDS; Koizumi 2003 BMC 11: 2211; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Lima et al. 2012 Cell 150: 883-894; Mesmaeker et al. Angew. Chem., Int. Ed. Engl. 1994, 33, 226; Migawa et al. 2013 Org. Lett. 15: 4316; Mol. Ther. Nucl. Acids 2012 1: e47; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Murray et al. 2012 Nucl. Acids Res. 40: 6135; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Obika et al. 2008 J. Am. Chem. Soc. 130: 4886; Obika et al. 2011 Org. Lett. 13: 6050; Oestergaard et al. 2014 JOC 79: 8877; Pallan et al. 2012 Biochem. 51: 7; Pallan et al. 2012 Chem. Comm. 48: 8195-8197; Petersen et al. 2003 TRENDS Biotech. 21: 74-81; Prakash et al. 2010 J. Med. Chem. 53: 1636; Prakash et al. 2015 Nucl. Acids Res. 43: 2993-3011; Prakash et al. 2016 Bioorg. Med. Chem. Lett. 26: 2817-2820; Rajwanshi et al. 1999 Chem. Commun. 1395-1396; Schultz et al. 1996 Nucleic Acids Res. 24: 2966; Seth et al. 2008 Nucl. Acid Sym. Ser. 52: 553; Seth et al. 2009 J. Med. Chem. 52: 10-13; Seth et al. 2010 J. Am. Chem. Soc. 132: 14942; Seth et al. 2010 J. Med. Chem. 53: 8309-8318; Seth et al. 2010 J. Org. Chem. 75: 1569-1581; Seth et al. 2011 BMCL 21: 4690; Seth et al. 2012 Bioo. Med. Chem. Lett. 22: 296-299; Seth et al. 2012 Mol. Ther-Nuc. Acids. 1, e47; Seth et al., Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Starrup et al. 2010 Nucl. Acids Res. 38: 7100; Swayze et al. 2007 Nucl. Acids Res. 35: 687; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 2016/079181; U.S. Pat. Nos. 6,326,199; 6,066,500; and 6,440,739, the base and sugar modifications of each of which is herein incorporated by reference.

In some embodiments, oligonucleotides of the present disclosure comprise one or more modified sugar moieties. In some embodiments, oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198, WO2014/012081 and WO/2015/107425, the sugar and base modifications of each of which are incorporated herein by reference.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, an oligonucleotide having an asymmetric format can comprise any sugar described herein or known in the art. In some embodiments, an oligonucleotide can comprise any sugar described herein or known in the art in combination with any other structural element or modification described herein, including but not limited to, base sequence or portion thereof, base; internucleotidic linkage; stereochemistry or combination or pattern thereof, additional chemical moiety, including but not limited to, a targeting moiety, etc.; pattern of modifications of sugars, bases or internucleotidic linkages; format or any structural element thereof, and/or any other structural element or modification described herein; and in some embodiments, the present disclosure pertains to multimers of any such oligonucleotides.

Certain Internucleotidic Linkages, Stereochemistry of Linkage Phosphorus, and Patterns Thereof In some embodiments, provided oligonucleotides comprise one or more modified internucleotidic linkages. In some embodiments, a modified internucleotidic linkage is a chiral internucleotidic linkage. In some embodiments, a chiral internucleotidic linkage is a chirally controlled internucleotidic linkage. Various internucleotidic linkages including modified internucleotidic linkages can be utilized in accordance with the present disclosure, for example, those described in WO2017/062862, US20180216108, US20170037399, and U.S. Pat. No. 9,982,257, the internucleotidic linkages of each of which is incorporated herein by reference.

In some embodiments, an oligonucleotide having an asymmetric format comprises a first wing having a particular internucleotidic linkage(s) or combination or pattern thereof, and a second wing having a different particular internucleotidic linkage(s) or combination or pattern thereof.

In some embodiments, an oligonucleotide having an asymmetric format comprises a first wing having a particular stereochemistry of internucleotidic linkage(s) or combination or pattern thereof, and a second wing having a different particular stereochemistry of internucleotidic linkage(s) or combination or pattern thereof.

In some embodiments, an oligonucleotide having an asymmetrical format comprises a first and a second wing which each independently comprise R, S, O, X, and/or nX, wherein R=PS (phosphorothioate) in the Rp configuration, S=PS in the Sp configuration, 0=PO (phosphodiester), and X is a stereorandom (not chirally controlled) PS, and nX=a non-negatively charged (e.g., neutral) internucleotidic linkage. In some embodiments, such a pattern of internucleotidic linkages is in a first wing, a second wing, and/or a core of an oligonucleotide having an asymmetric format.

In some embodiments, an oligonucleotide having an asymmetric format comprises one or more internucleotidic linkages which comprise an asymmetric P atom.

In some embodiments, an oligonucleotide having an asymmetric format comprises one or more internucleotidic linkages which comprise an asymmetric P atom, including but not limited to a phosphorothioate.

In some embodiments, the present disclosure pertains to a composition of an oligonucleotide having an asymmetric format and comprising one or more internucleotidic linkages which comprise an asymmetric P atom, including but not limited to a phosphorothioate, wherein the composition is stereorandom. In some embodiments, the present disclosure pertains to a composition of an oligonucleotide having an asymmetric format and comprising one or more phosphorothioates, wherein the composition is stereorandom. In some embodiments, the present disclosure pertains to a composition of an oligonucleotide having an asymmetric format, wherein every internucleotidic linkage is a phosphorothioate and wherein the composition is stereorandom.

In some embodiments, the present disclosure pertains to a composition of an oligonucleotide having an asymmetric format and comprising two or more internucleotidic linkages which comprise an asymmetric P atom, including but not limited to a phosphorothioate, wherein the composition is stereorandom at at least one said internucleotidic linkage and the composition is stereocontrolled (e.g., chirally controlled) at at least one other said internucleotidic linkage. In some embodiments, the present disclosure pertains to a composition of an oligonucleotide having an asymmetric format and comprising two or more phosphorothioates, wherein the composition is stereorandom at at least one phosphorothioate and stereocontrolled (e.g., chirally controlled) at at least one other phosphorothioate. In some embodiments, the present disclosure pertains to a composition of an oligonucleotide having an asymmetric format, wherein all of the internucleotidic linkages are a phosphorothioate and wherein the composition is stereorandom at at least one phosphorothioate and stereocontrolled (e.g., chirally controlled) at at least one other phosphorothioate.

In some embodiments, the present disclosure pertains to a composition of an oligonucleotide having an asymmetric format and comprising one or more internucleotidic linkages which comprise an asymmetric P atom, including but not limited to a phosphorothioate, wherein the composition is stereocontrolled (e.g., chirally controlled). In some embodiments, the present disclosure pertains to a composition of an oligonucleotide having an asymmetric format and comprising one or more phosphorothioates, wherein the composition is stereocontrolled (e.g., chirally controlled). In some embodiments, the present disclosure pertains to a composition of an oligonucleotide having an asymmetric format, wherein every internucleotidic linkage is a phosphorothioate and wherein the composition is stereocontrolled (e.g., chirally controlled).

In some embodiments, a wing comprises one or more natural phosphate linkages. In some embodiments, a wing comprises one or more consecutive natural phosphate linkages. In some embodiments, a wing comprises one or more natural phosphate linkages and one or more modified internucleotidic linkages. In some embodiments, a modified internucleotidic linkage is a phosphorothioate diester linkage. In some embodiments, a modified internucleotidic linkage is a Sp phosphorothioate diester linkage.

In some embodiments, a wing comprises no natural phosphate linkages, and each internucleotidic linkage of the wing is independently a modified internucleotidic linkage. In some embodiments, a modified internucleotidic linkage is chiral and chirally controlled. In some embodiments, a modified internucleotidic linkage is a phosphorothioate diester linkage. In some embodiments, a modified internucleotidic linkage is a Sp phosphorothioate diester linkage.

In some embodiments, for an oligonucleotide comprising or is a wing-core-wing structure, the two wings are different in that they contain different levels and/or types of chemical modifications, backbone chiral center stereochemistry, and/or patterns thereof.

In some embodiments of an oligonucleotide having an asymmetrical format, a first wing and a second wing independently has a pattern of internucleotidic linkages which is or comprises PS, PO, PS-PS, PS-PO, PO-PS, PO-PO, PO-PS-PS, PS-PO-PO-PO-PS, PS-PO-PO-PS, PS-PS-PS-PS, PS-PS-PS-PS-PS, PS-Xn-Xn-Xn-PS, or any pattern of internucleotidic linkages of any wing of any oligonucleotide described herein, wherein the pattern of internucleotidic linkages of the first and second wing are different, and wherein PS=Phosphorothioate; PO=phosphodiester; Xn=any neutral internucleotidic linkage. In some embodiments of an oligonucleotide having an asymmetrical format, a first wing and a second wing independently has a pattern of stereochemistry of internucleotidic linkages which is or comprises PO, SR, Sp, Rp, Sp-PO, Rp-PO, PO-Sp, PO-Rp, PO-PO-PO, Sp-PO-PO, Rp-PO-PO, Rp-PO-PO-PO-Rp, Rp-PO-PO-Rp-Rp, Rp-PO-Rp-PO-Rp, Rp-Rp-PO-PO-Rp, Sp-PO-PO-PO-Sp, Sp-Sp-Sp-Sp, Sp-Sp-Sp-Sp, Sp-Sp-Sp-Sp-Sp, Sp-Xn-Xn-Xn-Sp, SR-PO-PO-PO-SR, SR-SR-SR-SR, SR-SR-SR-SR-SR, SR-Xn-Xn-Xn-SR, or any pattern of stereochemistry of internucleotidic linkages of any wing of any oligonucleotide described herein, wherein the pattern of stereochemistry of internucleotidic linkages of the first and second wing are different, and wherein SR=internucleotidic linkage which is stereorandom (e.g., not chirally controlled); PO=phosphodiester (which lacks a chiral center);

Sp=internucleotidic linkage in the Sp configuration; Rp=internucleotidic linkage in the Rp configuration; Xn=a neutral internucleotidic linkage, which can be independently stereocontrolled (in the Rp or Sp configuration) or stereorandom. In some embodiments of an oligonucleotide having an asymmetrical format, the first wing is the 5' wing (the wing closer to the 5'-end of the oligonucleotide) and the second wing is the 3'-wing (the wing closer to the 3'-end of the oligonucleotide). In some embodiments of an oligonucleotide having an asymmetrical format, the first wing is the 3' wing (the wing closer to the 3'-end of the oligonucleotide) and the second wing is the 5'-wing (the wing closer to the 5'-end of the oligonucleotide). In some embodiments, the first and second wings are the same or different lengths.

In some embodiments, no less than 70%, 80%, 90% or 100% of internucleotidic linkages in a core is a modified internucleotidic linkage. In some embodiments, no less than 70%, 80%, or 90% of internucleotidic linkages in a core is independently a modified internucleotidic linkage of Sp configuration, and the core also contains 1, 2, 3, 4, or 5 internucleotidic linkages selected from modified internucleotidic linkages of Rp configuration and natural phosphate linkages. In some embodiments, the core also contains 1 or 2 internucleotidic linkages selected from modified internucleotidic linkages of Rp configuration and natural phosphate linkages. In some embodiments, the core also contains 1 and no more than 1 internucleotidic linkage selected from a modified internucleotidic linkage of Rp configuration and a natural phosphate linkage, and the rest internucleotidic linkages are independently modified internucleotidic linkages of Sp configuration. In some embodiments, the core also contains 2 and no more than 2 internucleotidic linkage each independently selected from a modified internucleotidic linkage of Rp configuration and a natural phosphate linkage, and the rest internucleotidic linkages are independently modified internucleotidic linkages of Sp configuration. In some embodiments, the core also contains 1 and no more than 1 natural phosphate linkage, and the rest internucleotidic linkages are independently modified internucleotidic linkages of Sp configuration. In some embodiments, the core also contains 2 and no more than 2 natural phosphate linkages, and the rest internucleotidic linkages are independently modified internucleotidic linkages of Sp configuration. In some embodiments, the core also contains 1 and no more than 1 modified internucleotidic linkage of Rp configuration, and the rest internucleotidic linkages are independently modified internucleotidic linkages of Sp configuration. In some embodiments, the core also contains 2 and no more than 2 modified internucleotidic linkages of Rp configuration, and the rest internucleotidic linkages are independently modified internucleotidic linkages of Sp configuration. In some embodiments, the two natural phosphate linkages, or the two modified internucleotidic linkages of Rp configuration, are separated by two or more modified internucleotidic linkages of Sp configuration. In some embodiments, a modified internucleotidic linkage is of Formula I, disclosed herein. In some embodiments, a modified internucleotidic linkage is a phosphorothioate diester linkage.

In some embodiments, an oligonucleotide composition or an internucleotidic linkage in an oligonucleotide composition has a particular diastereomeric purity.

In some embodiments, a provided oligonucleotide composition has a diastereomeric purity of 60%-100%. In some embodiments, a diastereomeric purity is at least 60%, 65%, 70%, 75%, 80%, 85%, 90%, 91%, 92%, 93%, 94%, 95%, 96%, 97%, 98%, or 99%. In some embodiments, a chiral element, e.g., a chiral center (carbon, phosphorus, etc.) of a provided compound, e.g. a provided oligonucleotide, has a diastereomeric purity of 60%-100%. In some embodiments, a chiral element, e.g., a chiral center (carbon, phosphorus, etc.) has a diastereomeric purity of at least 60%, 65%, 70%, 75%, 80%, 85%, 90%, 91%, 92%, 93%, 94%, 95%, 96%, 97%, 98%, or 99%. In some embodiments, a diastereomeric purity is at least 60%. In some embodiments, a diastereomeric purity is at least 70%. In some embodiments, a diastereomeric purity is at least 80%. In some embodiments, a diastereomeric purity is at least 85%. In some embodiments, a diastereomeric purity is at least 90%. In some embodiments, a diastereomeric purity is at least 91%. In some embodiments, a diastereomeric purity is at least 92%. In some embodiments, a diastereomeric purity is at least 93%. In some embodiments, a diastereomeric purity is at least 94%. In some embodiments, a diastereomeric purity is at least 95%. In some embodiments, a diastereomeric purity is at least 96%. In some embodiments, a diastereomeric purity is at least 97%. In some embodiments, a diastereomeric purity is at least 98%. In some embodiments, a diastereomeric purity is at least 99%. In some embodiments, a diastereomeric purity is at least 99.5%.

In some embodiments, at least 1, 2, 3, 4, 5, 6, 7, 8, 9 or more chiral elements of a provided compound each independently have a diastereomeric purity as described herein. In some embodiments, at least 1, 2, 3, 4, 5, 6, 7, 8, 9 or more chiral carbon centers of a provided compound each independently have a diastereomeric purity as described herein. In some embodiments, at least 1, 2, 3, 4, 5, 6, 7, 8, 9 or more chiral phosphorus centers of a provided compound each independently have a diastereomeric purity as described herein.

In some embodiments, at least 5%-100% of all chiral elements of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral elements of a provided compound each independently have a diastereomeric purity as described herein. In some embodiments, at least 5%-100% of all chiral phosphorus centers of a provided compound each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral phosphorus centers of a provided compound each independently have a diastereomeric purity as described herein.

In some embodiments, each chiral element independently has a diastereomeric purity as described herein. In some embodiments, each chiral center independently has a diastereomeric purity as described herein. In some embodiments, each chiral carbon center independently has a diastereomeric purity as described herein. In some embodiments, each chiral phosphorus center independently has a diastereomeric purity as described herein.

The present disclosure provides chirally controlled oligonucleotides, and chirally controlled oligonucleotide compositions which are of high crude purity and of high diastereomeric purity. In some embodiments, the present disclosure provides chirally controlled oligonucleotides, and chirally controlled oligonucleotide compositions which are of high crude purity. In some embodiments, the present disclosure provides chirally controlled oligonucleotides, and chirally controlled oligonucleotide compositions which are of high diastereomeric purity.

In some embodiments, an oligonucleotide having an asymmetric format is a substantially pure preparation of an oligonucleotide type in that oligonucleotides in the composition that are not of the oligonucleotide type are impurities form the preparation process of said oligonucleotide type, in some case, after certain purification procedures.

In some embodiments, a single oligonucleotide having an asymmetric format in a provided composition has at least about 25% of its internucleotidic linkages in Sp configuration. In some embodiments, a single oligonucleotide in a provided composition has at least about 30% of its internucleotidic linkages in Sp configuration. In some embodiments, a single oligonucleotide in a provided composition has at least about 35% of its internucleotidic linkages in Sp configuration. In some embodiments, a single oligonucleotide in a provided composition has at least about 40% of its internucleotidic linkages in Sp configuration. In some embodiments, a single oligonucleotide in a provided composition has at least about 45% of its internucleotidic linkages in Sp configuration. In some embodiments, a single oligonucleotide in a provided composition has at least about 50% of its internucleotidic linkages in Sp configuration. In some embodiments, a single oligonucleotide in a provided composition has at least about 55% of its internucleotidic linkages in Sp configuration. In some embodiments, a single oligonucleotide in a provided composition has at least about 60% of its internucleotidic linkages in Sp configuration. In some embodiments, a single oligonucleotide in a provided composition has at least about 65% of its internucleotidic linkages in Sp configuration. In some embodiments, a single oligonucleotide in a provided composition has at least about 70% of its internucleotidic linkages in Sp configuration. In some embodiments, a single oligonucleotide in a provided composition has at least about 75% of its internucleotidic linkages in Sp configuration. In some embodiments, a single oligonucleotide in a provided composition has at least about 80% of its internucleotidic linkages in Sp configuration. In some embodiments, a single oligonucleotide in a provided composition has at least about 85% of its internucleotidic linkages in Sp configuration. In some embodiments, a single oligonucleotide in a provided composition has at least about 90% of its internucleotidic linkages in Sp configuration.

In some embodiments, the present disclosure provides oligonucleotides having an asymmetric format and comprising one or more diastereomerically pure internucleotidic linkages with respect to the chiral linkage phosphorus. In some embodiments, the present disclosure provides oligonucleotides comprising one or more diastereomerically pure internucleotidic linkages having the structure of Formula I, disclosed herein. In some embodiments, the present disclosure provides oligonucleotides comprising one or more diastereomerically pure internucleotidic linkages with respect to the chiral linkage phosphorus, and one or more phosphate diester linkages. In some embodiments, the present disclosure provides oligonucleotides comprising one or more diastereomerically pure internucleotidic linkages having the structure of Formula I, and one or more phosphate diester linkages. In some embodiments, the present disclosure provides oligonucleotides comprising one or more diastereomerically pure internucleotidic linkages having the structure of Formula I-c, and one or more phosphate diester linkages. In some embodiments, such oligonucleotides are prepared by using stereoselective oligonucleotide synthesis, as described in this application, to form pre-designed diastereomerically pure internucleotidic linkages with respect to the chiral linkage phosphorus. Example internucleotidic linkages, including those having structures of Formula I, are further described herein.

In some embodiments, the present disclosure provides oligonucleotides and oligonucleotide compositions that are chirally controlled. For instance, in some embodiments, a provided composition contains non-random or controlled levels of one or more individual oligonucleotide types, wherein an oligonucleotide type is defined by: 1) base sequence; 2) pattern of backbone linkages; 3) pattern of backbone chiral centers; and 4) pattern of backbone P-modifications. In some embodiments, a particular oligonucleotide type may be defined by 1A) base identity; 1B) pattern of base modification; 1C) pattern of sugar modification; 2) pattern of backbone linkages; 3) pattern of backbone chiral centers; and 4) pattern of backbone P-modifications, wherein the oligonucleotide has an asymmetrical format. In some embodiments, oligonucleotides of the same oligonucleotide type are identical. In some embodiments, the present disclosure provides chirally controlled oligonucleotide compositions of oligonucleotides, wherein the composition comprises a non-random or controlled level of a plurality of oligonucleotides, wherein oligonucleotides of the plurality share a common base sequence, and comprise the same configuration of linkage phosphorus at at least 1, 2, 3, 4, 5, 6, 7, 8, 9, 10, 11, 12, 13, 14, 15, 16, 17, 18, 19, 20, 21, 22, 23, 24, or 25 chiral internucleotidic linkages (chirally controlled internucleotidic linkages). In some embodiments, oligonucleotides of a predetermined level and/or a provided plurality, e.g., those of formula O-I, $A^c$-[-$L^M$-($R^D$)$_a$]$_b$, [($A^c$)$_a$-$L^M$]$_b$-$R^D$, ($A^c$)$_a$-$L^M$-($A^c$)$_b$, or ($A^c$)$_a$-$L^M$-($R^D$)$_b$, comprise 1-30 chirally controlled internucleotidic linkages. In some embodiments, provided oligonucleotides having an asymmetric format comprise 2-30 chirally controlled internucleotidic linkages. In some embodiments, provided oligonucleotides comprise 5-30 chirally controlled internucleotidic linkages. In some embodiments, provided oligonucleotides comprise 10-30 chirally controlled internucleotidic linkages. In some embodiments, provided oligonucleotides comprise 1 chirally controlled internucleotidic linkage. In some embodiments, provided oligonucleotides comprise 2 chirally controlled internucleotidic linkages. In some embodiments, provided oligonucleotides comprise 3 chirally controlled internucleotidic linkages. In some embodiments, provided oligonucleotides comprise 4 chirally controlled internucleotidic linkages. In some embodiments, provided oligonucleotides comprise 5 chirally controlled internucleotidic linkages. In some embodiments, provided oligonucleotides comprise 6 chirally controlled internucleotidic linkages. In some embodiments, provided oligonucleotides comprise 7 chirally controlled internucleotidic linkages. In some embodiments, provided oligonucleotides comprise 8 chirally controlled internucleotidic linkages. In some embodiments, provided oligonucleotides comprise 9 chirally controlled internucleotidic linkages. In some embodiments, provided oligonucleotides comprise 10 chirally controlled internucleotidic linkages. In some embodiments, provided oligonucleotides comprise 11 chirally controlled internucleotidic linkages. In some embodiments, provided oligonucleotides comprise 12 chirally controlled internucleotidic linkages. In some embodiments, provided oligonucleotides comprise 13 chirally controlled internucleotidic linkages. In some embodiments, provided oligonucleotides comprise 14 chirally controlled internucleotidic linkages. In some embodiments, provided oligonucleotides have 15 chirally controlled internucleotidic linkages. In some embodiments, provided oligonucleotides have 16 chirally controlled internucleotidic linkages. In some embodiments, provided oligonucleotides have 17 chirally controlled internucleotidic linkages. In some embodiments, provided oligonucleotides have 18 chirally controlled internucleotidic linkages. In some embodiments, provided oligonucleotides have 19 chirally controlled internucleotidic linkages. In some embodiments, provided oligonucleotides have 20 chirally controlled internucleotidic linkages. In some embodiments, about 1-100% of all internucleotidic linkages are chirally controlled internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 965, 96%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 965, 96%, 98%, or 99%.

In some embodiments, a provided oligonucleotide is a unimer. In some embodiments, a provided oligonucleotide is a P-modification unimer. In some embodiments, a provided oligonucleotide is a stereounimer. In some embodiments, a provided oligonucleotide is a stereounimer where each chiral linkage phosphorus is Rp. In some embodiments, a provided oligonucleotide is a stereounimer where each chiral linkage phosphorus is Sp.

In some embodiments, a pattern of internucleotidic linkages comprises any one or more of IL1-IL1-IL1-IL1, IL1-IL1-IL1-IL2, IL1-IL1-IL2-IL1, IL1-IL1-IL2-IL2, IL1-IL2-IL1-IL1, IL1-IL2-IL1-IL2, IL1-IL2-IL1-IL2, IL1-IL2-IL2-IL1, IL1-IL2-IL2-IL2, IL2-IL1-IL1-IL1, IL2-IL1-IL1-IL2, IL2-IL1-IL1-IL2, IL2-IL1-IL2-IL1, IL2-IL1-IL2-IL2, IL2-IL2-IL1-IL1, IL2-IL2-IL1-IL2, IL2-IL2-IL2-IL1, IL2-IL2-IL2-IL2, IL1-IL1-IL1-IL1, IL1-IL1-IL1-IL3, IL1-IL1-IL3-IL1, IL1-IL1-IL3-IL3, IL1-IL3-IL1-IL1, IL1-IL3-IL1-IL3, IL1-IL3-IL3-IL1, IL1-IL3-IL3-IL3, IL3-IL1-IL1-IL1, IL3-IL1-IL1-IL3, IL3-IL1-IL1-IL3, IL3-IL1-IL3-IL1, IL3-IL1-IL3-IL1, IL3-IL1-IL3-IL3, IL3-IL1-IL3-IL3, IL3-IL3-IL1-IL1, IL3-IL3-IL1-IL1, IL3-IL3-IL1-IL3, IL3-IL3-IL1-IL3, IL3-IL3-IL3-IL1, IL3-IL3-IL3-IL1, IL3-IL3-IL3-IL3, IL3-IL3-IL3-IL3, IL1-IL1-IL1-IL1, IL1-IL1-IL1-IL4, IL1-IL1-IL1-IL4, IL1-IL1-IL4-IL1, IL1-IL1-IL4-IL1, IL1-IL1-IL4-IL4, IL1-IL1-IL4-IL4, IL1-IL4-IL1-IL1, IL1-IL4-IL1-IL1, IL1-IL4-IL1-IL4, IL1-IL4-IL4-IL1, IL1-IL4-IL4-IL1, IL4-IL1-IL1-IL1, IL4-IL1-IL1-IL1, IL4-IL1-IL1-IL4, IL4-IL1-IL1-IL4, IL4-IL1-IL4-IL1, IL4-IL1-IL4-IL1, IL4-IL1-IL4-IL4, IL4-IL1-IL4-IL4, IL4-IL4-IL1-IL1, IL4-IL4-IL1-IL1, IL4-IL1-IL1-IL4, IL4-IL4-IL1-IL4, IL4-IL4-IL4-IL1, IL4-IL4-IL1, IL4-IL4-IL4-IL4, IL4-IL4-IL4-IL4, IL1-IL1-IL1-IL2, IL1-IL1-IL1-IL3, IL1-IL1-IL1-IL3, IL1-IL1-IL1-IL3, IL1-IL1-IL2-IL1, IL1-IL1-IL2-IL1, IL1-IL1-IL2-IL1, IL1-IL1-IL2-IL2, IL1-IL1-IL2-IL2, IL1-IL1-IL2-IL2, IL1-IL1-IL2-IL3, IL1-IL1-IL2-IL3, IL1-IL1-IL2-IL3, IL1-IL1-IL3-IL1, IL1-IL1-IL3-IL1, IL1-IL1-IL3-IL1, IL1-IL1-IL3-IL2, IL1-IL1-IL3-IL2, IL1-IL1-IL3-IL2, IL1-IL1-IL3-IL3, IL1-IL1-IL3-IL3, IL1-IL1-IL3-IL3, IL1-IL2-IL1-IL1, IL1-IL2-IL1-IL1, IL1-IL2-IL1-IL1, IL1-IL2-IL1-IL2, IL1-IL2-IL1-IL2, IL1-IL2-IL1-IL2, IL1-IL2-IL1-IL3, IL1-IL2-IL1-IL3, IL1-IL2-IL2-IL1, IL1-IL2-IL2-IL1, IL1-IL2-IL2-IL1, IL1-IL2-IL2-IL2, IL1-IL2-IL2-IL2, IL1-IL2-IL2-IL2, IL1-IL2-IL2-IL3, IL1-IL2-IL2-IL3, IL1-IL2-IL2-IL3, IL1-IL2-IL3-IL1, IL1-IL2-IL3-IL1, IL1-IL2-IL3-IL1, IL1-IL2-IL3-IL2, IL1-IL2-IL3-IL2, IL1-IL2-IL3-IL2, IL1-IL2-IL3-IL3, IL1-IL2-IL3-IL3, IL1-IL2-IL3-IL3, IL1-IL3-IL1-IL1, IL1-IL3-IL1-IL1, IL1-IL3-IL1-IL1, IL1-IL3-IL1-IL2, IL1-IL3-IL1-IL2, IL1-IL3-IL1-IL2, IL1-IL3-IL1-IL3, IL1-IL3-IL1-IL3, IL1-IL3-IL2-IL1, IL1-IL3-IL2-IL1, IL1-IL3-IL2-IL1, IL1-IL3-IL2-IL2, IL1-IL3-IL2-IL2, IL1-IL3-IL2-IL2, IL1-IL3-IL2-IL3, IL1-IL3-IL3-IL1, IL1-IL3-IL3-IL1, IL1-IL3-IL3-IL1, IL1-IL3-IL3-IL2, IL1-IL3-IL3-IL2, IL1-IL3-IL3-IL2, IL1-IL3-IL3-IL3, IL1-IL3-IL3-IL3, IL1-IL3-IL3-IL3, IL2-IL1-IL1-IL1, IL2-IL1-IL1-IL1, IL2-IL1-IL1-IL1, IL2-IL1-IL1-IL2, IL2-IL1-IL1-IL2, IL2-IL1-IL1-IL2, IL2-IL1-IL1-IL3, IL2-IL1-IL1-IL3, IL2-IL1-IL1-IL3, IL2-IL1-IL2-IL1, IL2-IL1-IL2-IL1, IL2-IL1-IL2-IL1, IL2-IL1-IL2-IL2, IL2-IL1-IL2-IL2, IL2-IL1-IL2-IL2, IL2-IL1-IL2-IL3, IL2-IL1-IL2-IL3, IL2-IL1-IL2-IL3, IL2-IL1-IL3-IL1, IL2-IL1-IL3-IL1, IL2-IL1-IL3-IL1, IL2-IL1-IL3-IL2, IL2-IL1-IL3-IL2, IL2-IL1-IL3-IL2, IL2-IL1-IL3-IL3, IL2-IL1-IL3-IL3, IL2-IL1-IL3-IL3, IL2-IL2-IL1-IL1, IL2-IL2-IL1-IL1, IL2-IL2-IL1-IL1, IL2-IL2-IL1-IL2, IL2-IL2-IL1-IL2, IL2-IL2-IL1-IL2, IL2-IL2-IL1-IL3, IL2-IL2-IL1-IL3, IL2-IL2-IL1-IL3, IL2-IL2-IL2-IL1, IL2-IL2-IL2-IL1, IL2-IL2-IL2-IL1, IL2-IL2-IL2-IL2, IL2-IL2-IL2-IL2, IL2-IL2-IL2-IL2, IL2-IL2-IL2-IL3, IL2-IL2-IL2-IL3, IL2-IL2-IL2-IL3, IL2-IL2-IL3-IL1, IL2-IL2-IL3-IL1, IL2-IL2-IL3-IL1, IL2-IL2-IL3-IL2, IL2-IL2-IL3-IL2, IL2-IL2-IL3-IL2, IL2-IL2-IL3-IL3, IL2-IL2-IL3-IL3, IL2-IL2-IL3-IL3, IL2-IL3-IL1-IL1, IL2-IL3-IL1-IL1, IL2-IL3-IL1-IL1, IL2-IL3-IL1-IL2, IL2-IL3-IL1-IL2, IL2-IL3-IL1-IL3, IL2-IL3-IL1-IL3, IL2-IL3-IL1-IL3, IL2-IL3-IL2-IL1, IL2-IL3-IL2-IL1, IL2-IL3-IL2-IL1, IL2-IL3-IL2-IL2, IL2-IL3-IL2-IL2, IL2-IL3-IL2-IL2, IL2-IL3-IL2-IL3, IL2-IL3-IL2-IL3, IL2-IL3-IL2-IL3, IL2-IL3-IL3-IL1, IL2-IL3-IL3-IL1, IL2-IL3-IL3-IL1, IL2-IL3-IL3-IL2, IL2-IL3-IL3-IL2, IL2-IL3-IL3-IL2, IL2-IL3-IL3-IL3, IL2-IL3-IL3-IL3, IL3-IL1-IL1-IL1, IL3-IL1-IL1-IL1, IL3-IL1-IL1-IL1, IL3-IL1-IL1-IL2, IL3-IL1-IL1-IL2, IL3-IL1-IL1-IL2, IL3-IL1-IL1-IL3, IL3-IL1-IL1-IL3, IL3-IL1-IL1-IL3, IL3-IL1-IL2-IL1, IL3-IL1-IL2-IL1, IL3-IL1-IL2-IL1, IL3-IL1-IL2-IL2, IL3-IL1-IL2-IL2, IL3-IL1-IL2-IL2, IL3-IL1-IL2-IL3, IL3-IL1-IL2-IL3, IL3-IL1-IL2-IL3, IL3-IL1-IL3-IL1, IL3-IL1-IL3-IL1, IL3-IL1-IL3-IL1, IL3-IL1-IL3-IL2, IL3-IL1-IL3-IL2, IL3-IL1-IL3-IL2, IL3-IL1-IL3-IL3, IL3-IL1-IL3-IL3, IL3-IL2-IL1-IL1, IL3-IL2-IL1-IL1, IL3-IL2-IL1-IL1, IL3-IL2-IL1-IL2, IL3-IL2-IL1-IL2, IL3-IL2-IL1-IL2, IL3-IL2-IL1-IL3, IL3-IL2-IL1-IL3, IL3-IL2-IL1-IL3, IL3-IL2-IL2-IL1, IL3-IL2-IL2-IL1, IL3-IL2-IL2-IL1, IL3-IL2-IL2-IL2, IL3-IL2-IL2-IL2, IL3-IL2-IL2-IL2, IL3-IL2-IL2-IL3, IL3-IL2-IL2-IL3, IL3-IL2-IL2-IL3, IL3-IL2-IL3-IL1, IL3-IL2-IL3-IL1, IL3-IL2-IL3-IL1, IL3-IL2-IL3-IL2, IL3-IL2-IL3-IL2, IL3-IL2-IL3-IL2, IL3-IL2-IL3-IL3, IL3-IL2-IL3-IL3, IL3-IL2-IL3-IL3, IL3-IL3-IL1-IL1, IL3-IL3-IL1-IL1, IL3-IL3-IL1-IL1, IL3-IL3-IL1-IL2, IL3-IL3-IL1-IL2, IL3-IL3-IL1-IL2, IL3-IL3-IL1-IL3, IL3-IL3-IL1-IL3, IL3-IL3-IL1-IL3, IL3-IL3-IL2-IL1, IL3-IL3-IL2-IL1, IL3-IL3-IL2-IL2, IL3-IL3-IL2-IL2, IL3-IL3-IL2-IL2, IL3-IL3-IL2-IL3, IL3-IL3-IL2-IL3, IL3-IL3-IL2-IL3, IL3-IL3-IL3-IL1, IL3-IL3-IL3-IL1, IL3-IL3-IL3-IL1, IL3-IL3-IL3-IL2, IL3-IL3-IL3-IL2, IL3-IL3-IL3-IL2, IL3-IL3-IL3-IL2, IL3-IL3-IL3-IL3, IL3-IL3-IL3-IL3, IL3-IL3-IL3-IL3, IL1-IL1-IL1-IL2, IL1-IL1-IL1-IL4, IL1-IL1-IL1-IL4, IL1-IL1-IL1-IL4, IL1-IL1-IL2-IL1, IL1-IL1-IL2-IL1, IL1-IL1-IL2-IL1, IL1-IL1-IL2-IL1, IL1-IL1-IL2-IL2, IL1-IL1-IL2-IL2, IL1-IL1-IL2-IL2, IL1-IL1-IL2-IL4, IL1-IL1-IL2-IL4, IL1-IL1-IL2-IL4, IL1-IL1-IL4-IL1, IL1-IL1-IL4-IL1, IL1-IL4-IL1, IL1-IL1-IL4-IL2, IL1-IL1-IL4-IL2, IL1-IL1-IL4-IL2, IL1-IL1-IL4-IL4, IL1-IL1-IL4-IL4, IL1-IL1-IL4-IL4, IL1-IL2-IL1-IL1, IL1-IL2-IL1-IL1, IL1-IL2-IL1-IL1, IL1-IL2-IL1-IL2, IL1-IL2-IL1-IL2, IL1-IL2-IL1-IL4, IL1-IL2-IL1-IL4, IL1-IL2-IL1-IL4, IL1-IL2-IL1-IL1, IL1-IL2-IL2-IL1, IL1-IL2-IL2-IL1, IL1-IL2-IL2-IL2-

IL2, IL1-IL2-IL2-IL2, IL1-IL2-IL2-IL2, IL1-IL2-IL2-IL4, IL1-IL2-IL2-IL4, IL1-IL2-IL2-IL4, IL1-IL2-IL4-IL1, IL1-IL2-IL4-IL1, IL1-IL2-IL4-IL1, IL1-IL2-IL4-IL1, IL1-IL2-IL4-IL2, IL1-IL2-IL4-IL2, IL1-IL2-IL4-IL2, IL1-IL2-IL4-IL2, IL1-IL2-IL4-IL4, IL1-IL2-IL4-IL4, IL1-IL2-IL4-IL4, IL1-IL4-IL1-IL1, IL1-IL4-IL1-IL1, IL1-IL4-IL1-IL1, IL1-IL4-IL1-IL2, IL1-IL4-IL1-IL2, IL1-IL4-IL1-IL2, IL1-IL4-IL1-IL4, IL1-IL4-IL1-IL4, IL1-IL4-IL2-IL1, IL1-IL4-IL2-IL1, IL1-IL4-IL2-IL1, IL1-IL4-IL2-IL2, IL1-IL4-IL2-IL2, IL1-IL4-IL2-IL2, IL1-IL4-IL2-IL4, IL1-IL4-IL2-IL4, IL1-IL4-IL2-IL4, IL1-IL4-IL4-IL1, IL1-IL4-IL4-IL1, IL1-IL4-IL4-IL1, IL1-IL4-IL4-IL2, IL1-IL4-IL4-IL2, IL1-IL4-IL4-IL2, IL1-IL4-IL4-IL4, IL1-IL4-IL4-IL4, IL1-IL4-IL4-IL4, IL2-IL1-IL1-IL1, IL2-IL1-IL1-IL1, IL2-IL1-IL1-IL1, IL2-IL1-IL1-IL2, IL2-IL1-IL1-IL2, IL2-IL1-IL1-IL2, IL2-IL1-IL1-IL4, IL2-IL1-IL1-IL4, IL2-IL1-IL1-IL4, IL2-IL1-IL2-IL1, IL2-IL1-IL2-IL1, IL2-IL1-IL2-IL1, IL2-IL1-IL2-IL2, IL2-IL1-IL2-IL2, IL2-IL1-IL2- IL2, IL2-IL1-IL2-IL4, IL2-IL1-IL2-IL4, IL2-IL1-IL2-IL4, IL2-IL1-IL4-IL1, IL2-IL1-IL4-IL1, IL2-IL1-IL4-IL1, IL2-IL1-IL4-IL2, IL2-IL1-IL4-IL2, IL2-IL1-IL4-IL2, IL2-IL1-IL4-IL4, IL2-IL1-IL4-IL4, IL2- IL1-IL4-IL4, IL2-IL2-IL1-IL1, IL2-IL2-IL1-IL1, IL2-IL2-IL1-IL1, IL2-IL2-IL1-IL2, IL2-IL2-IL1-IL2, IL2-IL2-IL1-IL2, IL2-IL2-IL1-IL4, IL2-IL2-IL1-IL4, IL2-IL2-IL1-IL4, IL2-IL2-IL2-IL1, IL2-IL2-IL2- IL1, IL2-IL2-IL2-IL1, IL2-IL2-IL2-IL2, IL2-IL2-IL2-IL2, IL2-IL2-IL2-IL2, IL2-IL2-IL2-IL4, IL2-IL2-IL2-IL4, IL2-IL2-IL2-IL4, IL2-IL2-IL4-IL1, IL2-IL2-IL4-IL1, IL2-IL2-IL4-IL1, IL2-IL2-IL4-IL2, IL2- IL2-IL4-IL2, IL2-IL2-IL4-IL2, IL2-IL2-IL4-IL4, IL2-IL2-IL4-IL4, IL2-IL2-IL4-IL4, IL2-IL4-IL1-IL1, IL2-IL4-IL1-IL1, IL2-IL4-IL1-IL1, IL2-IL4-IL1-IL2, IL2-IL4-IL1-IL2, IL2-IL4-IL1-IL2, IL2-IL4-IL1- IL4, IL2-IL4-IL1-IL4, IL2-IL4-IL1-IL4, IL2-IL4-IL2-IL1, IL2-IL4-IL2-IL1, IL2-IL4-IL2-IL1, IL2-IL4-IL2-IL2, IL2-IL4-IL2-IL2, IL2-IL4-IL2-IL2, IL2-IL4-IL2-IL4, IL2-IL4-IL2-IL4, IL2-IL4-IL2-IL4, IL2- IL4-IL4-IL1, IL2-IL4-IL4-IL1, IL2-IL4-IL4-IL1, IL2-IL4-IL4-IL2, IL2-IL4-IL4-IL2, IL2-IL4-IL4-IL2, IL2-IL4-IL4-IL4, IL2-IL4-IL4-IL4, IL2-IL4-IL4-IL4, IL4-IL1-IL1-IL1, IL4-IL1-IL1-IL1, IL4-IL1-IL1- IL1, IL4-IL1-IL1-IL2, IL4-IL1-IL1-IL2, IL4-IL1-IL1-IL2, IL4-IL1-IL1-IL4, IL4-IL1-IL1-IL4, IL4-IL1-IL1-IL4, IL4-IL1-IL2-IL1, IL4-IL1-IL2-IL1, IL4-IL1-IL2-IL1, IL4-IL1-IL2-IL2, IL4-IL1-IL2-IL2, IL4-IL1-IL2-IL2, IL4-IL1-IL2-IL4, IL4-IL1-IL2-IL4, IL4-IL1-IL2-IL4, IL4-IL1-IL4-IL1, IL4-IL1-IL4-IL1, IL4-IL1-IL4-IL1, IL4-IL1-IL4-IL2, IL4-IL1-IL4-IL2, IL4-IL1-IL4-IL2, IL4-IL1-IL4-IL4, IL4-IL1-IL4- IL4, IL4-IL1-IL4-IL4, IL4-IL2-IL1-IL1, IL4-IL2-IL1-IL1, IL4-IL2-IL1-IL1, IL4-IL2-IL1-IL2, IL4-IL2-IL1-IL2, IL4-IL2-IL1-IL2, IL4-IL2-IL1-IL4, IL4-IL2-IL1-IL4, IL4-IL2-IL1-IL4, IL4-IL2-IL2-IL1, IL4- IL2-IL2-IL1, IL4-IL2-IL2-IL1, IL4-IL2-IL2-IL2, IL4-IL2-IL2-IL2, IL4-IL2-IL2-IL2, IL4-IL2-IL2-IL4, IL4-IL2-IL2-IL4, IL4-IL2-IL2-IL4, IL4-IL2-IL4-IL1, IL4-IL2-IL4-IL1, IL4-IL2-IL4-IL1, IL4-IL2-IL4- IL2, IL4-IL2-IL4-IL2, IL4-IL2-IL4-IL2, IL4-IL2-IL4-IL4, IL4-IL2-IL4-IL4, IL4-IL2-IL4-IL4, IL4-IL4-IL1-IL1, IL4-IL4-IL1-IL1, IL4-IL4-IL1-IL1, IL4-IL4-IL1-IL2, IL4-IL4-IL1-IL2, IL4-IL4-IL1-IL2, IL4- IL4-IL1-IL4, IL4-IL4-IL1-IL4, IL4-IL4-IL1-IL4, IL4-IL4-IL2-IL1, IL4-IL4-IL2-IL1, IL4-IL4-IL2-IL1, IL4-IL4-IL2-IL2, IL4-IL4-IL2-IL2, IL4-IL4-IL2-IL2, IL4-IL4-IL2-IL4, IL4-IL4-IL2-IL4, IL4-IL4-IL2- IL4, IL4-IL4-IL4-IL1, IL4-IL4-IL4-IL1, IL4-IL4-IL4-IL1, IL4-IL4-IL4-IL2, IL4-IL4-IL4-IL2, IL4-IL4-IL4-IL2, IL4-IL4-IL4-IL4, IL4-IL4-IL4-IL4, IL4-IL4-IL4-IL4, or IL4-IL4-IL4-IL4, wherein IL1, IL2, IL3 and IL4 are different types of internucleotidic linkages. In some embodiments, IL1, IL2, IL3 and IL4 are different types of internucleotidic linkages that differ in chemistry and/or stereochemistry. In some embodiments, such a pattern of internucleotidic linkages is in a first wing, a second wing, and/or a core of an oligonucleotide having an asymmetric format.

In some embodiments, a pattern of internucleotidic linkages of an oligonucleotide comprises any one or more of IL1-IL1-IL1-IL1-IL1, IL1-IL1-IL1-IL1-IL2, IL1-IL1-IL1-IL2-IL1, IL1-IL1-IL1-IL2-IL2, IL1-IL1-IL2-IL1-IL1, IL1-IL1-IL2-IL1-IL2, IL1-IL1-IL2-IL2-IL1, IL1-IL1-IL2-IL2-IL2, IL1-IL2-IL1-IL1-IL1, IL1-IL2-IL1-IL1-IL2, IL1-IL2-IL1-IL2-IL1, IL1-IL2-IL1-IL2-IL2, IL1- IL2-IL2-IL1-IL1, IL1-IL2-IL2-IL1-IL2, IL1-IL2-IL2-IL2-IL1, IL1-IL2-IL2-IL2-IL2, IL2-IL1-IL1-IL1-IL1, IL2-IL1-IL1-IL1-IL2, IL2-IL1-IL1-IL2-IL1, IL2-IL1-IL1-IL2-IL2, IL2-IL1-IL2-IL1-IL1, IL2-IL1-IL2-IL1-IL2, IL2-IL1-IL2-IL2-IL1, IL2-IL1-IL2-IL2-IL2, IL2-IL2-IL1-IL1-IL1, IL2-IL2-IL1-IL1-IL2, IL2-IL2-IL1-IL2-IL1, IL2-IL2-IL1-IL2-IL2, IL2-IL2-IL2-IL1-IL1, IL2-IL2-IL2-IL1-IL2, IL2-IL2-IL2-IL2-IL1, IL2-IL2-IL2-IL2-IL2, IL1-IL1-IL1-IL1-IL1, IL1-IL1-IL1-IL1-IL3, IL1-IL1-IL1-IL3-IL1, IL1- IL1-IL1-IL3-IL3, IL1-IL1-IL3-IL1-IL1, IL1-IL1-IL3-IL1-IL3, IL1-IL1-IL3-IL3-IL1, IL1-IL1-IL3-IL3-IL3, IL1-IL3-IL1-IL1-IL1, IL1-IL3-IL1-IL1-IL3, IL1-IL3-IL1-IL3-IL1, IL1-IL3-IL1-IL3-IL3, IL1-IL3-IL3-IL1-IL1, IL1-IL3-IL3-IL1-IL3, IL1-IL3-IL3-IL3-IL1, IL1-IL3-IL3-IL3-IL3, IL3-IL1-IL1-IL1-IL1, IL3-IL1-IL1-IL1-IL3, IL3-IL1-IL1-IL3-IL1, IL3-IL1-IL1-IL3-IL3, IL3-IL1-IL3-IL1-IL1, IL3-IL1-IL3-IL1-IL3, IL3-IL1-IL3-IL3-IL1, IL3-IL1-IL3-IL3-IL3, IL3-IL3-IL1-IL1-IL1, IL3-IL3-IL1-IL1-IL3, IL3- IL3-IL1-IL3-IL1, IL3-IL3-IL1-IL3-IL3, IL3-IL3-IL3-IL1-IL1, IL3-IL3-IL3-IL1-IL3, IL3-IL3-IL3-IL3-IL1, IL3-IL3-IL3-IL3-IL3, IL1-IL1-IL1-IL1-IL4, IL1-IL1-IL1-IL4-IL1, IL1-IL1-IL1-IL4-IL4, IL1-IL1-IL4-IL1-IL1, IL1-IL1-IL4-IL1-IL4, IL1-IL1-IL4-IL4-IL1, IL1-IL1-IL4-IL4-IL4, IL1-IL4-IL1-IL1-IL1, IL1-IL4-IL1-IL1-IL4, IL1-IL4-IL1-IL4-IL1, IL1-IL4-IL1-IL4-IL4, IL1-IL4-IL4-IL1-IL1, IL1-IL4-IL4-IL1-IL4, IL1-IL4-IL4-IL4-IL1, IL1-IL4-IL4-IL4-IL4, IL4-IL1-IL1-IL1-IL1, IL4-IL1-IL1-IL1-IL4, IL4- IL1-IL1-IL4-IL1, IL4-IL1-IL1-IL4-IL4, IL4-IL1-IL4-IL1-IL1, IL4-IL1-IL4-IL1-IL4, IL4-IL1-IL4-IL4-IL1, IL4-IL1-IL4-IL4-IL4, IL4-IL4-IL1-IL1-IL1, IL4-IL4-IL1-IL1-IL4, IL4-IL4-IL1-IL4-IL1, IL4-IL4-IL1-IL4-IL4, IL4-IL4-IL4-IL1-IL1, IL4-IL4-IL4-IL1-IL4, IL4-IL4-IL4-IL4-IL1, IL4-IL4-IL4-IL4-IL4, IL1-IL1-IL1-IL2-IL3, IL1-IL1-IL1-IL3-IL1, IL1-IL1-IL1-IL3-IL2, IL1-IL1-IL1-IL3-IL3, IL1-IL1-IL2-IL1-IL1, IL1-IL1-IL2-IL1-IL2, IL1-IL1-IL2-IL1-IL3, IL1-IL1-IL2-IL2-IL1, IL1-IL1-IL2-IL2-IL2, IL1- IL1-IL2-IL2-IL3, IL1-IL1-IL2-IL3-IL1, IL1-IL1-IL2-IL3-IL2, IL1-IL1-IL2-IL3-IL3, IL1-IL1-IL3-IL1-IL1, IL1-IL1-IL3-IL1-IL2, IL1-IL1-IL3-IL1-IL3, IL1-IL1-IL3-IL2-IL1, IL1-IL1-IL3-IL2-IL2, IL1-IL1-IL3-IL2-IL3, IL1-IL1-IL3-IL3-IL1, IL1-IL1-IL3-IL3-IL2, IL1-IL1-IL3-IL3-IL3, IL1-IL2-IL1-IL1-IL1, IL1-IL2-IL1-IL1-IL2, IL1-IL2-IL1-IL1-IL3, IL1-IL2-IL1-IL2-IL1, IL1-IL2-IL1-IL2-IL2, IL1-IL2-IL1-IL2-IL3, IL1-IL2-IL1-IL3-IL1, IL1-IL2-IL1-IL3-IL2, IL1-IL2-IL1-IL3-IL3, IL1-IL2-IL2-IL1-IL1, IL1- IL2-IL2-IL1-IL2, IL1-IL2-IL2-IL1-IL3, IL1-IL2-IL2-IL2-IL1, IL1-IL2-IL2-IL2-IL2, IL1-IL2-IL2-IL2-IL3, IL1-IL2-IL2-IL3-IL1, IL1-IL2-IL2-IL3-IL2, IL1-IL2-IL2-IL3-IL3, IL1-IL2-IL3-IL1-IL1, IL1-IL2-IL3-IL1-IL2, IL1-IL2-IL3-IL1-IL3, IL1-IL2-IL3-IL2-IL1, IL1-IL2-IL3-IL2-IL2, IL1-IL2-IL3-IL2-IL3, IL1-IL2-IL3-IL3-IL1, IL1-IL2-IL3-IL3-IL2, IL1-IL2-IL3-IL3-IL3, IL1-IL3-IL1-IL1-IL1, IL1-IL3-IL1-IL1-IL2, IL1-IL3-IL1-IL1-IL3, IL1-IL3-IL1-IL2-IL1, IL1-IL3-IL1-IL2-IL2, IL1-IL3-IL1-IL2-IL3, IL1- IL3-IL1-IL3-IL1, IL1-IL3-IL1-IL3-IL2, IL1-IL3-IL1-IL3-IL3, IL1-IL3-IL2-IL1-IL1, IL1-IL3-IL2-IL1-IL2, IL1-IL3-IL2-IL1-IL3, IL1-IL3-IL2-IL2-IL1, IL1-IL3-IL2-IL2-IL2, IL1-IL3-IL2-IL2-IL3, IL1-IL3-IL2-IL3-IL1, IL1-IL3-IL2-IL3-IL2, IL1-

IL3-IL2-IL3-IL3, IL1-IL3-IL3-IL1-IL1, IL1-IL3-IL3-IL1-IL2, IL1-IL3-IL3-IL1-IL3, IL1-IL3-IL3-IL2-IL1, IL1-IL3-IL3-IL2-IL2, IL1-IL3-IL3-IL2-IL3, IL1-IL3-IL3-IL3-IL1, IL1-IL3-IL3-IL3-IL2, IL1-IL3-IL3-IL3-IL3, IL2-IL1-IL1-IL1-IL1, IL2-IL1-IL1-IL1-IL2, IL2- IL1-IL1-IL1-IL3, IL2-IL1-IL1-IL2-IL1, IL2-IL1-IL1-IL2-IL2, IL2-IL1-IL1-IL2-IL3, IL2-IL1-IL1-IL3-IL1, IL2-IL1-IL1-IL3-IL2, IL2-IL1-IL1-IL3-IL3, IL2-IL1-IL2-IL1-IL1, IL2-IL1-IL2-IL1-IL2, IL2-IL1-IL2-IL1-IL3, IL2-IL1-IL2-IL2-IL1, IL2-IL1-IL2-IL2-IL2, IL2-IL1-IL2-IL2-IL3, IL2-IL1-IL2-IL3-IL1, IL2-IL1-IL2-IL3-IL2, IL2-IL1-IL2-IL3-IL3, IL2-IL1-IL3-IL1-IL1, IL2-IL1-IL3-IL1-IL2, IL2-IL1-IL3-IL1-IL3, IL2-IL1-IL3-IL2-IL1, IL2-IL1-IL3-IL2-IL2, IL2-IL1-IL3-IL2-IL3, IL2-IL1-IL3-IL3-IL1, IL2- IL1-IL3-IL3-IL2, IL2-IL1-IL3-IL3-IL3, IL2-IL2-IL1-IL1-IL1, IL2-IL2-IL1-IL1-IL2, IL2-IL2-IL1-IL1-IL3, IL2-IL2-IL1-IL2-IL1, IL2-IL2-IL1-IL2-IL2, IL2-IL2-IL1-IL2-IL3, IL2-IL2-IL1-IL3-IL1, IL2-IL2-IL1-IL3-IL2, IL2-IL2-IL1-IL3-IL3, IL2-IL2-IL2-IL1-IL1, IL2-IL2-IL2-IL1-IL2, IL2-IL2-IL2-IL1-IL3, IL2-IL2-IL2-IL2-IL1, IL2-IL2-IL2-IL2-IL2, IL2-IL2-IL2-IL2-IL3, IL2-IL2-IL2-IL3-IL1, IL2-IL2-IL2-IL3-IL2, IL2-IL2-IL2-IL3-IL3, IL2-IL2-IL3-IL1-IL1, IL2-IL2-IL3-IL1-IL2, IL2-IL2-IL3-IL1-IL3, IL2- IL2-IL3-IL2-IL1, IL2-IL2-IL3-IL2-IL2, IL2-IL2-IL3-IL2-IL3, IL2-IL2-IL3-IL3-IL1, IL2-IL2-IL3-IL3-IL2, IL2-IL2-IL3-IL3-IL3, IL2-IL3-IL1-IL1-IL1, IL2-IL3-IL1-IL1-IL2, IL2-IL3-IL1-IL1-IL3, IL2-IL3-IL1-IL2-IL1, IL2-IL3-IL1-IL2-IL2, IL2-IL3-IL1-IL2-IL3, IL2-IL3-IL1-IL3-IL1, IL2-IL3-IL1-IL3-IL2, IL2-IL3-IL1-IL3-IL3, IL2-IL3-IL2-IL1-IL1, IL2-IL3-IL2-IL1-IL2, IL2-IL3-IL2-IL1-IL3, IL2-IL3-IL2-IL2-IL1, IL2-IL3-IL2-IL2-IL2, IL2-IL3-IL2-IL2-IL3, IL2-IL3-IL2-IL3-IL1, IL2- IL3-IL2-IL3-IL3, IL2-IL3-IL3-IL1-IL1, IL2-IL3-IL3-IL1-IL2, IL2-IL3-IL3-IL1-IL3, IL2-IL3-IL3-IL2-IL1, IL2-IL3-IL3-IL2-IL2, IL2-IL3-IL3-IL2-IL3, IL2-IL3-IL3-IL3-IL1, IL2-IL3-IL3-IL3-IL2, IL2-IL3-IL3-IL3-IL3, IL3-IL1-IL1-IL1-IL1, IL3-IL1-IL1-IL1-IL2, IL3-IL1-IL1-IL1-IL3, IL3-IL1-IL1-IL2-IL1, IL3-IL1-IL1-IL2-IL2, IL3-IL1-IL1-IL2-IL3, IL3-IL1-IL1-IL3-IL1, IL3-IL1-IL1-IL3-IL2, IL3-IL1-IL1-IL3-IL3, IL3-IL1-IL2-IL1-IL1, IL3-IL1-IL2-IL1-IL2, IL3-IL1-IL2-IL1-IL3, IL3-IL1-IL2-IL2-IL1, IL3-IL1-IL2-IL2-IL2, IL3-IL1-IL2-IL2-IL3, IL3-IL1-IL2-IL3-IL1, IL3-IL1-IL2-IL3-IL2, IL3-IL1-IL2-IL3-IL3, IL3-IL1-IL3-IL1-IL1, IL3-IL1-IL3-IL1-IL2, IL3-IL1-IL3-IL1-IL3, IL3-IL1-IL3-IL2-IL1, IL3-IL1-IL3-IL2-IL2, IL3-IL1-IL3-IL2-IL3, IL3-IL1-IL3-IL3-IL1, IL3-IL1-IL3-IL3-IL2, IL3- IL1-IL3-IL3-IL3, IL3-IL2-IL1-IL1-IL1, IL3-IL2-IL1-IL1-IL2, IL3-IL2-IL1-IL1-IL3, IL3-IL2-IL1-IL2-IL1, IL3-IL2-IL1-IL2-IL2, IL3-IL2-IL1-IL2-IL3, IL3-IL2-IL1-IL3-IL1, IL3-IL2-IL1-IL3-IL2, IL3-IL2-IL1-IL3-IL3, IL3- IL2-IL2-IL1-IL1, IL3-IL2-IL2-IL1-IL2, IL3-IL2-IL2-IL1-IL3, IL3-IL2-IL2-IL2-IL1, IL3-IL2-IL2-IL2-IL2, IL3-IL2-IL2-IL2-IL3, IL3-IL2-IL2-IL3-IL1, IL3-IL2-IL2-IL3-IL2, IL3-IL2-IL2-IL3-IL3, IL3-IL2-IL3-IL1-IL1, IL3-IL2-IL3-IL1-IL2, IL3-IL2-IL3-IL1-IL3, IL3-IL2-IL3-IL2-IL1, IL3-IL2-IL3-IL2-IL2, IL3-IL2-IL3-IL2-IL3, IL3-IL2-IL3-IL3-IL1, IL3-IL2-IL3-IL3-IL2, IL3-IL2-IL3-IL3-IL3, IL3-IL3-IL1-IL1-IL1, IL3-IL3-IL1-IL1-IL2, IL3-IL3-IL1-IL1-IL3, IL3-IL3-IL1-IL2-IL1, IL3-IL3-IL1-IL2-IL2, IL3- IL3-IL1-IL2-IL3, IL3-IL3-IL1-IL3-IL1, IL3-IL3-IL1-IL3-IL2, IL3-IL3-IL1-IL3-IL3, IL3-IL3-IL2-IL1-IL1, IL3-IL3-IL2-IL1-IL2, IL3- IL3-IL2-IL1-IL3, IL3-IL3-IL2-IL2-IL1, IL3-IL3-IL2-IL2-IL2, IL3-IL3-IL2-IL2-IL3, IL3-IL3-IL2-IL3-IL1, IL3-IL3-IL2-IL3-IL2, IL3-IL3-IL2-IL3-IL3, IL3-IL3-IL3-IL1-IL1, IL3-IL3-IL3-IL1-IL2, IL3-IL3-IL3-IL1-IL3, IL3-IL3-IL3-IL2-IL1, IL3-IL3-IL3-IL2-IL2, IL3-IL3-IL3-IL2-IL3, IL3-IL3-IL3-IL3-IL1, IL3-IL3-IL3-IL3-IL2, IL3-IL3-IL3-IL3-IL3, IL1- IL1-IL1-IL1-IL4, IL1-IL1-IL1-IL4-IL1, IL1-IL1-IL1-IL4-IL2, IL1-IL1-IL1-IL4-IL4, IL1-IL1-IL2-IL1-IL1, IL1-IL1-IL2-IL1-IL2, IL1-IL1-IL2-IL1-IL4, IL1-IL1-IL2-IL2-IL1, IL1-IL1-IL2-IL2-IL2, IL1-IL1-IL2-IL2-IL4, IL1-IL1-IL2-IL4-IL1, IL1-IL1-IL2-IL4-IL2, IL1-IL1-IL2-IL4-IL4, IL1-IL1-IL4-IL1-IL1, IL1-IL1-IL4-IL1-IL2, IL1-IL1-IL4-IL1-IL4, IL1-IL1-IL4-IL2-IL1, IL1-IL1-IL4-IL2-IL2, IL1-IL1-IL4-IL2-IL4, IL1-IL1-IL4-IL4-IL1, IL1-IL1-IL4-IL4-IL2, IL1-IL1-IL4-IL4-IL4, IL1-IL2-IL1-IL1-IL1, IL1- IL2-IL1-IL1-IL2, IL1-IL2-IL1-IL1-IL4, IL1-IL2-IL1-IL2-IL1, IL1-IL2-IL1-IL2-IL2, IL1-IL2-IL1-IL2-IL4, IL1-IL2-IL1-IL4-IL1, IL1-IL2-IL1-IL4-IL2, IL1-IL2-IL1-IL4-IL4, IL1-IL2-IL2-IL1-IL1, IL1-IL2-IL2-IL1-IL2, IL1-IL2-IL2-IL1-IL4, IL1-IL2-IL2-IL2-IL1, IL1-IL2-IL2-IL2-IL2, IL1-IL2-IL2-IL2-IL4, IL1-IL2-IL2-IL4-IL1, IL1-IL2-IL2-IL4-IL2, IL1-IL2-IL2-IL4-IL4, IL1-IL2-IL4-IL1-IL1, IL1-IL2-IL4-IL1-IL2, IL1-IL2-IL4-IL1-IL4, IL1-IL2-IL4-IL2-IL1, IL1-IL2-IL4-IL2-IL2, IL1-IL2-IL4-IL2-IL4, IL1- IL2-IL4-IL4-IL1, IL1-IL2-IL4-IL4-IL2, IL1-IL2-IL4-IL4-IL4, IL1-IL4-IL1-IL1-IL1, IL1-IL4-IL1-IL1-IL2, IL1-IL4-IL1-IL1-IL4, IL1-IL4-IL1-IL2-IL1, IL1-IL4-IL1-IL2-IL2, IL1-IL4-IL1-IL2-IL4, IL1-IL4-IL1-IL4-IL1, IL1-IL4-IL1-IL4-IL2, IL1-IL4-IL1-IL4-IL4, IL1-IL4-IL2-IL1-IL1, IL1-IL4-IL2-IL1-IL2, IL1-IL4-IL2-IL1-IL4, IL1-IL4-IL2-IL2-IL1, IL1-IL4-IL2-IL2-IL2, IL1-IL4-IL2-IL2-IL4, IL1-IL4-IL2-IL4-IL1, IL1-IL4-IL2-IL4-IL2, IL1-IL4-IL2-IL4-IL4, IL1-IL4-IL4-IL1-IL1, IL1-IL4-IL4-IL1-IL2, IL1- IL4-IL4-IL1-IL4, IL1-IL4-IL4-IL2-IL1, IL1-IL4-IL4-IL2-IL2, IL1-IL4-IL4-IL2-IL4, IL1-IL4-IL4-IL4-IL1, IL1-IL4-IL4-IL4-IL2, IL1-IL4-IL4-IL4-IL4, IL2-IL1-IL1-IL1-IL1, IL2-IL1-IL1-IL1-IL2, IL2-IL1-IL1-IL1-IL4, IL2-IL1-IL1-IL2-IL1, IL2-IL1-IL1-IL2-IL2, IL2-IL1-IL1-IL2-IL4, IL2-IL1-IL1-IL4-IL1, IL2-IL1-IL1-IL4-IL2, IL2-IL1-IL1-IL4-IL4, IL2-IL1-IL2-IL1-IL1, IL2-IL1-IL2-IL1-IL2, IL2-IL1-IL2-IL1-IL4, IL2-IL1-IL2-IL2-IL1, IL2-IL1-IL2-IL2-IL2, IL2-IL1-IL2-IL2-IL4, IL2-IL1-IL2-IL4-IL1, IL2- IL1-IL2-IL4-IL2, IL2-IL1-IL2-IL4-IL4, IL2-IL1-IL4-IL1-IL1, IL2-IL1-IL4-IL1-IL2, IL2-IL1-IL4-IL1-IL4, IL2-IL1-IL4-IL2-IL1, IL2-IL1-IL4-IL2-IL2, IL2-IL1-IL4-IL2-IL4, IL2-IL1-IL4-IL4-IL1, IL2-IL1-IL4-IL4-IL2, IL2-IL1-IL4-IL4-IL4, IL2-IL2-IL1-IL1-IL1, IL2-IL2-IL1-IL1-IL2, IL2-IL2-IL1-IL1-IL4, IL2-IL2-IL1-IL2-IL1, IL2-IL2-IL1-IL2-IL2, IL2-IL2-IL1-IL2-IL4, IL2-IL2-IL1-IL4-IL1, IL2-IL2-IL1-IL4-IL2, IL2-IL2-IL1-IL4-IL4, IL2-IL2-IL2-IL1-IL1, IL2- IL2-IL2-IL1-IL2, IL2-IL2-IL2-IL1-IL4, IL2-IL2-IL2-IL2-IL1, IL2-IL2-IL2-IL2-IL2, IL2-IL2-IL2-IL2-IL4, IL2-IL2-IL2-IL4-IL1, IL2-IL2-IL2-IL4-IL2, IL2-IL2-IL2-IL4-IL4, IL2-IL2-IL4-IL1-IL1, IL2-IL2-IL4-IL1-IL2, IL2-IL2-IL4-IL1-IL4, IL2-IL2-IL4-IL2-IL1, IL2-IL2-IL4-IL2-IL2, IL2-IL2-IL4-IL2-IL4, IL2-IL2-IL4-IL4-IL1, IL2-IL2-IL4-IL4-IL2, IL2-IL2-IL4-IL4-IL4, IL2-IL4-IL1-IL1-IL1, IL2-IL4-IL1-IL1-IL2, IL2-IL4-IL1-IL1-IL4, IL2-IL4-IL1-IL2-IL1, IL2-IL4-IL1-IL2-IL2, IL2-IL4-IL1-IL2-IL4, IL2-IL4-IL1-IL4-IL1, IL2-IL4-IL1-IL4-IL2, IL2- IL4-IL1-IL4-IL4, IL2-IL4-IL2-IL1-IL1, IL2-IL4-IL2-IL1-IL2, IL2-IL4-IL2-IL1-IL4, IL2-IL4-IL2-IL2-IL1, IL2-IL4-IL2-IL2-IL2, IL2-IL4-IL2-IL2-IL4, IL2-IL4-IL2-IL4-IL1, IL2-IL4-IL2-IL4-IL2, IL2-IL4-IL2-IL4-IL4, IL2-IL4-IL4-IL1-IL1, IL2-IL4-IL4-IL1-IL2, IL2-IL4-IL4-IL1-IL4, IL2-IL4-IL4-IL2-IL1, IL2-IL4-IL4-IL2-IL2, IL2-IL4-IL4-IL2-IL4, IL2-IL4-IL4-IL4-IL1, IL2-IL4-IL4-IL4-IL2, IL2-IL4-IL4-IL4-IL4, IL4-IL1-IL1-IL1-IL1, IL4-IL1-IL1-IL1-IL2, IL4-IL1-IL1-IL1-IL4, IL4-IL1-IL1-IL2-IL1, IL4- IL1-IL1-IL2-IL2, IL4-IL1-IL1-IL2-IL4, IL4-IL1-IL1-IL4-IL1, IL4-IL1-IL1-IL4-IL2, IL4-IL1-IL1-IL4-IL4, IL4-IL1-IL2-IL1-IL1, IL4-IL1-IL2-IL1-IL2, IL4-IL1-IL2-IL1-IL4, IL4-IL1-IL2-IL2-IL1, IL4-IL1-IL2-IL2-IL2, IL4-IL1-IL2-IL2-IL4, IL4-IL1-IL2-IL4-IL1, IL4-IL1-IL2-IL4-IL2, IL4-IL1-IL2-IL4-IL4, IL4-IL1-IL4-

IL1-IL1, IL4-IL1-IL4-IL1-IL2, IL4-IL1-IL4-IL1-IL4, IL4-IL1-IL4-IL2-IL1, IL4-IL1-IL4-IL2-IL2, IL4-IL1-IL4-IL2-IL4, IL4-IL1-IL4-IL4-IL1, IL4-IL1-IL4-IL4-IL2, IL4-IL1-IL4-IL4-IL4, IL4- IL2-IL1-IL1-IL1, IL4-IL2-IL1-IL1-IL2, IL4-IL2-IL1-IL1-IL4, IL4-IL2-IL1-IL2-IL1, IL4-IL2-IL1-IL2-IL2, IL4-IL2-IL1-IL2-IL4, IL4-IL2-IL1-IL4-IL1, IL4-IL2-IL1-IL4-IL2, IL4-IL2-IL1-IL4-IL4, IL4-IL2-IL2-IL1-IL1, IL4-IL2-IL2-IL1-IL2, IL4-IL2-IL2-IL1-IL4, IL4-IL2-IL2-IL2-IL1, IL4-IL2-IL2-IL2-IL2, IL4-IL2-IL2-IL2-IL4, IL4-IL2-IL2-IL4-IL1, IL4-IL2-IL2-IL4-IL2, IL4-IL2-IL2-IL4-IL4, IL4-IL2-IL4-IL1-IL1, IL4-IL2-IL4-IL1-IL2, IL4-IL2-IL4-IL1-IL4, IL4-IL2-IL4-IL2-IL1, IL4-IL2-IL4-IL2-IL2, IL4- IL2-IL4-IL2-IL4, IL4-IL2-IL4-IL4-IL1, IL4-IL2-IL4-IL4-IL2, IL4-IL2-IL4-IL4-IL4, IL4-IL4-IL1-IL1-IL1, IL4-IL4-IL1-IL1-IL2, IL4-IL4-IL1-IL1-IL4, IL4-IL4-IL1-IL2-IL1, IL4-IL4-IL1-IL2-IL2, IL4-IL4-IL1-IL2-IL4, IL4-IL4-IL1-IL4-IL1, IL4-IL4-IL1-IL4-IL2, IL4-IL4-IL1-IL4-IL4, IL4-IL4-IL2-IL1-IL1, IL4-IL4-IL2-IL1-IL2, IL4-IL4-IL2-IL1-IL4, IL4-IL4-IL2-IL2-IL1, IL4-IL4-IL2-IL2-IL2, IL4-IL4-IL2-IL2-IL4, IL4-IL4-IL2-IL4-IL1, IL4-IL4-IL2-IL4-IL2, IL4-IL4-IL2-IL4-IL4, IL4-IL4-IL4-IL1-IL1, IL4-IL4-IL4-IL1-IL2, IL4-IL4-IL4-IL1-IL4, IL4-IL4-IL4-IL2-IL1, IL4-IL4-IL4-IL2-IL2, IL4-IL4-IL4-IL2-IL4, IL4-IL4-IL4-IL4-IL1, IL4-IL4-IL4-IL4-IL2, or IL4-IL4-IL4-IL4-IL4, wherein IL1, IL2, IL3 and IL4 are different types of internucleotidic linkages. In some embodiments, IL1, IL2, IL3 and IL4 are different types of internucleotidic linkages that differ in chemistry and/or stereochemistry. In some embodiments, such a pattern of internucleotidic linkages is in a first wing, a second wing, and/or a core of an oligonucleotide having an asymmetric format.

In some embodiments, a pattern of chiral centers of the backbone of an oligonucleotide (linkage phosphorus) comprises any one or more of the following patterns of stereochemistry: RRRRR, RRRRS, RRRSR, RRRSS, RRSRR, RRSRS, RRSSR, RRSSS, RSRRR, RSRRS, RSRSR, RSRSS, RSSRR, RSSRS, RSSSR, RSSSS, SRRRR, SRRRS, SRRSR, SRRSS, SRSRR, SRSRS, SRSSR, SRSSS, SSRRR, SSRRS, SSRSR, SSRSS, SSSRR SSSRS, SSSSR, SSSSS, RRRRR, RRRRO, RRROR, RRROO, RRORR, RRORO, RROOR, RROOO, RORRR, RORRO, ROROR, ROROO, ROORR, ROORO, ROOOR, ROOOO, ORRRR, ORRRO, ORROR, ORROO, ORORR, ORORO, OROOR, OROOO, OORRR, OORRO, OOROR, OOROO, OOORR, OOORO, OOOOR, OOOOO, OOOOS, OOOSO, OOOSS, OOSOO, OOSOS, OOSSO, OOSSS, OSOOO, OSOOS, OSOSO, OSOSS, OSSOO, OSSOS, OSSSO, OSSSS, SOOOO, SOOOS, SOOSO, SOOSS, SOSOO, SOSOS, SOSSO, SOSSS, SSOOO, SSOOS, SSOSO, SSOSS, SSSOO, SSSOS, SSSSO, SSSSS, RRRRR, RRRRS, RRRRO, RRRSR, RRRSS, RRRSO, RRROR, RRROS, RRROO, RRSRR, RRSRS, RRSRO, RRSSR, RRSSS, RRSSO, RRSOR, RRSOS, RRSOO, RRORR, RRORS, RRORO, RROSR, RROSS, RROSO, RROOR, RROOS, RROOO, RSRRR, RSRRS, RSRRO, RSRSR, RSRSS, RSRSO, RSROR, RSROS, RSROO, RSSRR, RSSRS, RSSRO, RSSSR, RSSSS, RSSSO, RSSOR, RSSOS, RSSOO, RSORR, RSORS, RSORO, RSOSR, RSOSS, RSOSO, RSOOR, RSOOS, RSOOO, RORRR, RORRS, RORRO, RORSR, RORSS, RORSO, ROROR, ROROS, ROROO, ROSRR, ROSRS, ROSRO, ROSSR, ROSSS, ROSSO, ROSOR, ROSOS, ROSOO, ROORR, ROORS, ROORO, ROOSR, ROOSS, ROOSO, ROOOR, ROOOS, ROOOO, SRRRR, SRRRS, SRRRO, SRRSR, SRRSS, SRRSO, SRROR, SRROS, SRROO, SRSRR, SRSRS, SRSRO, SRSSR, SRSSS, SRSSO, SRSOR, SRSOS, SRSOO, SRORR, SRORS, SRORO, SROSR, SROSS, SROSO, SROOR, SROOS, SROOO, SSRRR, SSRRS, SSRRO, SSRSR, SSRSS, SSRSO, SSROR, SSROS, SSROO, SSSRR, SSSRS, SSSRO, SSSSR, SSSSS, SSSSO, SSSOR, SSSOS, SSSOO, SSORR, SSORS, SSORO, SSOSR, SSOSS, SSOSO, SSOOR, SSOOS, SSOOO, SORRR, SORRS, SORRO, SORSR, SORSS, SORSO, SOROR, SOROS, SOROO, SOSRR, SOSRS, SOSRO, SOSSR, SOSSS, SOSSO, SOSOR, SOSOS, SOSOO, SOORR, SOORS, SOORO, SOOSR, SOOSS, SOOSO, SOOOR, SOOOS, SOOOO, ORRRR, ORRRS, ORRRO, ORRSR, ORRSS, ORRSO, ORROR, ORROS, ORROO, ORSRR, ORSRS, ORSRO, ORSSR, ORSSS, ORSSO, ORSOR, ORSOS, ORSOO, ORORR, ORORS, ORORO, OROSR, OROSS, OROSO, OROOR, OROOS, OROOO, OSRRR, OSRRS, OSRRO, OSRSR, OSRSS, OSRSO, OSROR, OSROS, OSROO, OSSRR, OSSRS, OSSRO, OSSSR, OSSSS, OSSSO, OSSOR, OSSOS, OSSOO, OSORR, OSORS, OSORO, OSOSR, OSOSS, OSOSO, OSOOR, OSOOS, OSOOO, OORRR, OORRS, OORRO, OORSR, OORSS, OORSO, OOROR, OOROS, OOROO, OOSRR, OOSRS, OOSRO, OOSSR, OOSSS, OOSSO, OOSOR, OOSOS, OOSOO, OOORR, OOORS, OOORO, OOOSR, OOOSS, OOOSO, OOOOR, OOOOS, OOOOO, OOOOX, OOOXO, OOOXX, OOXOO, OOXOX, OOXXO, OOXXX, OXOOO, OXOOX, OXOXO, OXOXX, OXXOO, OXXOX, OXXXO, OXXXX, XOOOO, XOOOX, XOOXO, XOOXX, XOXOO, XOXOX, XOXXO, XOXXX, XXOOO, XXOOX, XXOXO, XXOXX, XXXOO, XXXOX, XXXXO, or XXXXX, wherein R is a phosphorothioate diester in the Rp configuration, S is a phosphorothioate diester in the Sp configuration, O is a phosphodiester linkage, and X is a stereorandom phosphorothioate. In some embodiments, such a pattern of stereochemistry is in a first wing, a second wing, and/or the core.

In some embodiments, a common pattern of backbone chiral centers (e.g., a pattern of backbone chiral centers in an oligonucleotide or in a core or a wing or in two wings thereof) comprises a pattern of OSOSO, OSSSO, OSSSOS, SOSO, SOSO, SOSOS, SOSOSO, SOSOSOSO, SOSSSO, SSOSSSOSS, SSSOSOSS, SSSSOSOSSS, SSSSS, SSSSSS, SSSSSSS, SSSSSSSS, SSSSSSSSS, or RRR, wherein S represents a phosphorothioate diester (PS) in the Sp configuration, O represents a phosphodiester, and R represents a phosphorothioate diester (PS) in the Rp configuration.

In some embodiments of an oligonucleotide, a core comprises any internucleotidic linkage described herein or known in the art, or any pattern or combination of two or more different internucleotidic linkages, wherein R=PS (phosphorothioate) in the Rp configuration, S=PS in the Sp configuration, O=PO (phosphodiester), and X is a stereorandom (not chirally controlled) PS, and nX=a non-negatively charged (e.g., neutral) internucleotidic linkage.

In some embodiments, a provided oligonucleotide or a core or a wing or both wings thereof comprises a pattern of backbone linkages. In some embodiments, a pattern of backbone linkages is or comprises a sequence of any of: OOO, OOOO, OOOOO, OOOOOO, OOOOOOO, OOOOOOOO, OOOOOOOOO, OOOOOOOOOO, OɵO ɵ, OɵOɵ, Oɵ ɵO, ɵ ɵOOɵ ɵ, ɵOɵOɵO ɵ ɵ, OɵOɵOɵOO, ɵ ɵ ɵ, ɵ ɵ ɵ ɵ, ɵɵ ɵɵɵ, ɵɵɵɵɵɵ, ɵɵɵɵɵɵɵ, ɵɵ ɵɵɵɵɵɵɵ, ɵɵɵ ɵɵɵɵɵɵɵɵ, ɵɵɵ ɵɵɵɵɵɵɵ, OOOOOOOOOOOOOOOO, OOOOOOOOOOOOOOOO, ӨӨӨ Ө ӨО Ө ООООООООӨ Ө,    Ө Ө Ө ӨО
ӨОӨ Ө ӨО Ө ОООООО Ө Ө, Ө Ө Ө ӨОӨО
Ө ӨО ӨООООО Ө Ө Ө,    Ө Ө Ө ӨОӨО Ө
ӨОО Ө ООООООО Ө Ө,    Ө Ө Ө ӨОӨО Ө
Ө ОӨО ӨОООО Ө Ө,   Ө Ө Ө ӨОӨО Ө ӨО
Ө ОӨ Ө Ө Ө Ө Ө,    Ө Ө Ө ӨОӨО Ө ӨО
ӨОӨ Ө Ө Ө Ө ӨО,    Ө Ө Ө ӨОӨО Ө ӨО
ӨОӨ Ө Ө Ө Ө Ө,    Ө Ө Ө ӨОӨО Ө ӨО
ӨОӨ Ө Ө Ө Ө Ө Ө ӨО,   Ө Ө Ө ӨОӨО
Ө Ө ӨОӨОӨ Ө Ө Ө Ө Ө Ө Ө Ө,   Ө Ө
Ө ӨОӨОӨ Ө Ө Ө ӨОООООООӨ Ө, Ө Ө Ө
ӨОӨОӨ Ө Ө Ө ӨОООООО Ө Ө,    Ө Ө Ө
ӨОӨ Ө Ө Ө ӨОООООО Ө Ө Ө,   Ө Ө ӨОӨО
Ө Ө Ө Ө ӨО ӨОООООО Ө Ө,    Ө Ө Ө ӨОӨО
Ө Ө Ө Ө ӨО ӨОООО Ө Ө,    Ө Ө Ө ӨОӨО Ө
Ө Ө Ө ӨО Ө Ө Ө Ө Ө, Ө Ө Ө ӨОӨО Ө
Ө Ө ӨОӨ Ө Ө Ө Ө ӨО,   Ө Ө Ө ӨОӨО Ө
Ө Ө ӨОӨ Ө Ө Ө Ө Ө,   Ө Ө Ө ӨОӨО Ө
Ө Ө ӨОӨ Ө Ө Ө Ө Ө Ө Ө ӨО, Ө Ө Ө ӨО
ӨОӨ Ө Ө Ө ӨОӨ Ө Ө Ө Ө Ө Ө Ө Ө Ө,
Ө Ө Ө Ө ӨО Ө Ө ӨОО Ө ОО Ө Ө Ө Ө Ө ӨО,    Ө
Ө Ө Ө ӨО Ө Ө ӨОО Ө ОО Ө Ө Ө Ө ӨО,   Ө Ө
Ө Ө ӨОӨ Ө ӨО ӨОӨ Ө ОООООООӨ Ө, Ө Ө Ө
ӨОӨ Ө Ө ӨОӨОӨ Ө ООООООӨ Ө,    Ө Ө Ө ӨО
Ө Ө Ө ӨОӨОӨ Ө Ө ӨОООО Ө Ө Ө,   Ө Ө ӨОӨ Ө
Ө Ө ӨОӨОӨ Ө ӨОООООООӨ Ө,    Ө Ө Ө ӨОӨ
Ө Ө ӨОӨОӨ Ө Ө ОООО Ө Ө,   Ө Ө Ө ӨОӨ Ө
ӨОӨОӨ Ө Ө Ө Ө Ө Ө,   Ө Ө Ө ӨОӨ Ө
ӨОӨОӨ Ө Ө Ө Ө Ө ӨО, Ө Ө Ө ӨОӨ Ө
ӨОӨОӨ Ө Ө Ө Ө Ө Ө Ө, Ө Ө Ө ӨОӨ Ө
ӨОӨОӨ Ө Ө Ө Ө Ө Ө Ө Ө ӨО, Ө Ө Ө
ӨОӨ Ө ӨОӨОӨ Ө Ө Ө Ө Ө Ө Ө Ө
Ө,    Ө Ө Ө ӨОӨ Ө ӨОӨ Ө ӨОООООООӨ Ө
Ө,    Ө Ө Ө ӨОӨ Ө ӨОӨ Ө ӨОООООО Ө Ө,
Ө Ө Ө Ө ӨОӨ Ө ӨОӨ Ө ӨОООООӨ Ө Ө,    Ө
Ө Ө Ө ӨОӨ Ө ӨОӨ Ө ӨОӨОООООӨ Ө,    Ө
Ө Ө Ө ӨОӨ Ө ӨОӨ Ө ӨОӨОООО Ө Ө,   Ө Ө
Ө Ө ӨОӨ Ө ӨОӨ Ө ӨОӨ Ө Ө Ө Ө,   Ө Ө Ө
ӨОӨ Ө ӨОӨ Ө ӨОӨ Ө Ө Ө Ө Ө ӨО,   Ө Ө Ө
ӨОӨ Ө ӨОӨ Ө ӨОӨ Ө Ө Ө Ө Ө Ө, Ө Ө Ө
ӨОӨ Ө ӨОӨ Ө ӨОӨ Ө Ө Ө Ө Ө Ө Ө
ӨО,    Ө Ө Ө ӨОӨ Ө ӨОӨ Ө Ө Ө Ө Ө Ө Ө
Ө Ө Ө Ө Ө Ө,   Ө Ө Ө Ө Ө ӨОӨООО Ө ОО Ө
Ө Ө Ө ӨО,   Ө Ө Ө Ө Ө ӨОӨООО Ө Ө Ө
Ө Ө Ө ӨО,    Ө Ө Ө Ө Ө ӨОӨОӨО
ӨОООООООӨ Ө,    Ө Ө Ө Ө Ө ӨОӨОӨО
ӨОООООООӨ Ө, In some embodiments of an oligonucleotide, e.g., an oligonucleotide having an asymmetric format: a core comprises: XXX. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: XX. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: X. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: OORSSSSRS. Non-limiting example(s) of such an oligonucleotide include: WV-12099.

In some embodiments of an oligonucleotide, e.g., an oligonucleotide having an asymmetric format: a core comprises: OORSSSSRS. Non-limiting example(s) of such an oligonucleotide include: WV-12103.

In some embodiments of an oligonucleotide, e.g., an oligonucleotide having an asymmetric format: a core comprises: OORSSSSRSS. Non-limiting example(s) of such an oligonucleotide include: WV-12099.

In some embodiments of an oligonucleotide, e.g., an oligonucleotide having an asymmetric format: a core comprises: OORSSSSRSS. Non-limiting example(s) of such an oligonucleotide include: WV-12103.

In some embodiments of an oligonucleotide, e.g., an oligonucleotide having an asymmetric format: a core comprises: OORSSSSRSSS. Non-limiting example(s) of such an oligonucleotide include: WV-12099.

In some embodiments of an oligonucleotide, e.g., an oligonucleotide having an asymmetric format: a core comprises: OORSSSSRSSS. Non-limiting example(s) of such an oligonucleotide include: WV-12103.

In some embodiments of an oligonucleotide, e.g., an oligonucleotide having an asymmetric format: a core comprises: OORSSSSRSSSS. Non-limiting example(s) of such an oligonucleotide include: WV-12099.

In some embodiments of an oligonucleotide, e.g., an oligonucleotide having an asymmetric format: a core comprises: OORSSSSRSSSS. Non-limiting example(s) of such an oligonucleotide include: WV-12103.

In some embodiments of an oligonucleotide, e.g., an oligonucleotide having an asymmetric format: a core comprises: OORSSSSRSSSSS. Non-limiting example(s) of such an oligonucleotide include: WV-12099.

In some embodiments of an oligonucleotide, e.g., an oligonucleotide having an asymmetric format: a core comprises: OORSSSSRSSSSS. Non-limiting example(s) of such an oligonucleotide include: WV-12103.

In some embodiments of an oligonucleotide, e.g., an oligonucleotide having an asymmetric format: a core comprises: OORSSSSRSSSSSS. Non-limiting example(s) of such an oligonucleotide include: WV-12099.

In some embodiments of an oligonucleotide, e.g., an oligonucleotide having an asymmetric format: a core comprises: OORSSSSRSSSSSS. Non-limiting example(s) of such an oligonucleotide include: WV-12103.

In some embodiments of an oligonucleotide, e.g., an oligonucleotide having an asymmetric format: a core comprises: ORSSSSRS. Non-limiting example(s) of such an oligonucleotide include: WV-12100.

In some embodiments of an oligonucleotide, e.g., an oligonucleotide having an asymmetric format: a core comprises: ORSSSSRS. Non-limiting example(s) of such an oligonucleotide include: WV-12101.

In some embodiments of an oligonucleotide, e.g., an oligonucleotide having an asymmetric format: a core comprises: ORSSSSRSS. Non-limiting example(s) of such an oligonucleotide include: WV-12100.

In some embodiments of an oligonucleotide, e.g., an oligonucleotide having an asymmetric format: a core comprises: ORSSSSRSS. Non-limiting example(s) of such an oligonucleotide include: WV-12101.

In some embodiments of an oligonucleotide, e.g., an oligonucleotide having an asymmetric format: a core comprises: ORSSSSRSSS. Non-limiting example(s) of such an oligonucleotide include: WV-12100.

In some embodiments of an oligonucleotide, e.g., an oligonucleotide having an asymmetric format: a core comprises: ORSSSSRSSS. Non-limiting example(s) of such an oligonucleotide include: WV-12101.

In some embodiments of an oligonucleotide, e.g., an oligonucleotide having an asymmetric format: a core comprises: ORSSSSRSSSS. Non-limiting example(s) of such an oligonucleotide include: WV-12100.

In some embodiments of an oligonucleotide, e.g., an oligonucleotide having an asymmetric format: a core comprises: ORSSSSRSSSS. Non-limiting example(s) of such an oligonucleotide include: WV-12101.

In some embodiments of an oligonucleotide, e.g., an oligonucleotide having an asymmetric format: a core comprises: ORSSSSRSSSSR. Non-limiting example(s) of such an oligonucleotide include: WV-12100.

In some embodiments of an oligonucleotide, e.g., an oligonucleotide having an asymmetric format: a core comprises: ORSSSSRSSSSRO. Non-limiting example(s) of such an oligonucleotide include: WV-12100.

In some embodiments of an oligonucleotide, e.g., an oligonucleotide having an asymmetric format: a core comprises: ORSSSSRSSSSS. Non-limiting example(s) of such an oligonucleotide include: WV-12101.

In some embodiments of an oligonucleotide, e.g., an oligonucleotide having an asymmetric format: a core comprises: ORSSSSRSSSSSS. Non-limiting example(s) of such an oligonucleotide include: WV-12099.

In some embodiments of an oligonucleotide, e.g., an oligonucleotide having an asymmetric format: a core comprises: ORSSSSRSSSSSS. Non-limiting example(s) of such an oligonucleotide include: WV-12101.

In some embodiments of an oligonucleotide, e.g., an oligonucleotide having an asymmetric format: a core comprises: ORSSSSRSSSSSS. Non-limiting example(s) of such an oligonucleotide include: WV-12103.

In some embodiments of an oligonucleotide, e.g., an oligonucleotide having an asymmetric format: a core comprises: RSSSSRSSSSRO. Non-limiting example(s) of such an oligonucleotide include: WV-12100.

In some embodiments of an oligonucleotide, e.g., an oligonucleotide having an asymmetric format: a core comprises: RSSSSRSSSSSS. Non-limiting example(s) of such an oligonucleotide include: WV-12099.

In some embodiments of an oligonucleotide, e.g., an oligonucleotide having an asymmetric format: a core comprises: RSSSSRSSSSSS. Non-limiting example(s) of such an oligonucleotide include: WV-12099.

In some embodiments of an oligonucleotide, e.g., an oligonucleotide having an asymmetric format: a core comprises: RSSSSRSSSSSS. Non-limiting example(s) of such an oligonucleotide include: WV-12101.

In some embodiments of an oligonucleotide, e.g., an oligonucleotide having an asymmetric format: a core comprises: RSSSSRSSSSSS. Non-limiting example(s) of such an oligonucleotide include: WV-12103.

In some embodiments of an oligonucleotide, e.g., an oligonucleotide having an asymmetric format: a core comprises: RSSSSRSSSSSS. Non-limiting example(s) of such an oligonucleotide include: WV-12103.

In some embodiments of an oligonucleotide, e.g., an oligonucleotide having an asymmetric format: a core comprises: SSRSSSSRO. Non-limiting example(s) of such an oligonucleotide include: WV-12100.

In some embodiments of an oligonucleotide, e.g., an oligonucleotide having an asymmetric format: a core comprises: SSRSSSSSS. Non-limiting example(s) of such an oligonucleotide include: WV-12101.

In some embodiments of an oligonucleotide, e.g., an oligonucleotide having an asymmetric format: a core comprises: SSSRSSSSRO. Non-limiting example(s) of such an oligonucleotide include: WV-12100.

In some embodiments of an oligonucleotide, e.g., an oligonucleotide having an asymmetric format: a core comprises: SSSRSSSSRO. Non-limiting example(s) of such an oligonucleotide include: WV-12100.

In some embodiments of an oligonucleotide, e.g., an oligonucleotide having an asymmetric format: a core comprises: SSSRSSSSSS. Non-limiting example(s) of such an oligonucleotide include: WV-12099.

In some embodiments of an oligonucleotide, e.g., an oligonucleotide having an asymmetric format: a core comprises: SSSRSSSSSS. Non-limiting example(s) of such an oligonucleotide include: WV-12101.

In some embodiments of an oligonucleotide, e.g., an oligonucleotide having an asymmetric format: a core comprises: SSSRSSSSSS. Non-limiting example(s) of such an oligonucleotide include: WV-12101.

In some embodiments of an oligonucleotide, e.g., an oligonucleotide having an asymmetric format: a core comprises: SSSRSSSSSS. Non-limiting example(s) of such an oligonucleotide include: WV-12103.

In some embodiments of an oligonucleotide, e.g., an oligonucleotide having an asymmetric format: a core comprises: SSSSRSSSSRO. Non-limiting example(s) of such an oligonucleotide include: WV-12100.

In some embodiments of an oligonucleotide, e.g., an oligonucleotide having an asymmetric format: a core comprises: SSSSRSSSSRO. Non-limiting example(s) of such an oligonucleotide include: WV-12100.

In some embodiments of an oligonucleotide, e.g., an oligonucleotide having an asymmetric format: a core comprises: SSSSRSSSSSS. Non-limiting example(s) of such an oligonucleotide include: WV-12099.

In some embodiments of an oligonucleotide, e.g., an oligonucleotide having an asymmetric format: a core comprises: SSSSRSSSSSS. Non-limiting example(s) of such an oligonucleotide include: WV-12099.

In some embodiments of an oligonucleotide, e.g., an oligonucleotide having an asymmetric format: a core comprises: SSSSRSSSSSS. Non-limiting example(s) of such an oligonucleotide include: WV-12101.

In some embodiments of an oligonucleotide, e.g., an oligonucleotide having an asymmetric format: a core comprises: SSSSRSSSSSS. Non-limiting example(s) of such an oligonucleotide include: WV-12101.

In some embodiments of an oligonucleotide, e.g., an oligonucleotide having an asymmetric format: a core comprises: SSSSRSSSSSS. Non-limiting example(s) of such an oligonucleotide include: WV-12103.

In some embodiments of an oligonucleotide, e.g., an oligonucleotide having an asymmetric format: a core comprises: SSSSRSSSSSS. Non-limiting example(s) of such an oligonucleotide include: WV-12103.

In some embodiments of an oligonucleotide, e.g., an oligonucleotide having an asymmetric format: a core comprises: O and X. Non-limiting example(s) of such an oligonucleotide include: WV-10252, WV-8600, WV-8613, WV-8628, WV-8632, WV-8640, WV-8648.

In some embodiments of an oligonucleotide, e.g., an oligonucleotide having an asymmetric format: a core comprises: two or more O and two or more X. Non-limiting example(s) of such an oligonucleotide include: WV-10252, WV-8600, WV-8613, WV-8628, WV-8632, WV-8640, WV-8648.

In some embodiments of an oligonucleotide, e.g., an oligonucleotide having an asymmetric format: a core comprises: nXnX. Non-limiting example(s) of such an oligonucleotide include: WV-15355.

In some embodiments of an oligonucleotide, e.g., an oligonucleotide having an asymmetric format: a core comprises: nXS. Non-limiting example(s) of such an oligonucleotide include: WV-15354.

In some embodiments of an oligonucleotide, e.g., an oligonucleotide having an asymmetric format: a core comprises: nXSSnX. Non-limiting example(s) of such an oligonucleotide include: WV-15351.

In some embodiments of an oligonucleotide, e.g., an oligonucleotide having an asymmetric format: a core comprises: nXSSnXSSnXS. Non-limiting example(s) of such an oligonucleotide include: WV-15351.

In some embodiments of an oligonucleotide, e.g., an oligonucleotide having an asymmetric format: a core comprises: nXSSRSSRS. Non-limiting example(s) of such an oligonucleotide include: WV-15352.

In some embodiments of an oligonucleotide, e.g., an oligonucleotide having an asymmetric format: a core comprises: RnXnX. Non-limiting example(s) of such an oligonucleotide include: WV-15357.

In some embodiments of an oligonucleotide, e.g., an oligonucleotide having an asymmetric format: a core comprises: RnXnXRnXnXRnX. Non-limiting example(s) of such an oligonucleotide include: WV-15355.

In some embodiments of an oligonucleotide, e.g., an oligonucleotide having an asymmetric format: a core comprises: RnXnXRSSRS. Non-limiting example(s) of such an oligonucleotide include: WV-15356.

In some embodiments of an oligonucleotide, e.g., an oligonucleotide having an asymmetric format: a core comprises: RSnX. Non-limiting example(s) of such an oligonucleotide include: WV-15361.

In some embodiments of an oligonucleotide, e.g., an oligonucleotide having an asymmetric format: a core comprises: RSSnXSSRS. Non-limiting example(s) of such an oligonucleotide include: WV-15353.

In some embodiments of an oligonucleotide, e.g., an oligonucleotide having an asymmetric format: a core comprises: RSSRnXnXRS. Non-limiting example(s) of such an oligonucleotide include: WV-15357.

In some embodiments of an oligonucleotide, e.g., an oligonucleotide having an asymmetric format: a core comprises: RSSRSSnXS. Non-limiting example(s) of such an oligonucleotide include: WV-15354.

In some embodiments of an oligonucleotide, e.g., an oligonucleotide having an asymmetric format: a core comprises: RSSRSSRnX. Non-limiting example(s) of such an oligonucleotide include: WV-15358.

In some embodiments of an oligonucleotide, e.g., an oligonucleotide having an asymmetric format: a core comprises: SHORTENED: Non-limiting example(s) of such an oligonucleotide include:

In some embodiments of an oligonucleotide, e.g., an oligonucleotide having an asymmetric format: a core comprises: SnX. Non-limiting example(s) of such an oligonucleotide include: WV-15353.

In some embodiments of an oligonucleotide, e.g., an oligonucleotide having an asymmetric format: a core comprises: SnXnX. Non-limiting example(s) of such an oligonucleotide include: WV-15359.

In some embodiments of an oligonucleotide, e.g., an oligonucleotide having an asymmetric format: a core comprises: SnXS. Non-limiting example(s) of such an oligonucleotide include: WV-15352.

In some embodiments of an oligonucleotide, e.g., an oligonucleotide having an asymmetric format: a core comprises: SnXSSnXSSnX. Non-limiting example(s) of such an oligonucleotide include: WV-15351.

In some embodiments of an oligonucleotide, e.g., an oligonucleotide having an asymmetric format: a core comprises: SnXSSnXSSnXS. Non-limiting example(s) of such an oligonucleotide include: WV-15351.

In some embodiments of an oligonucleotide, e.g., an oligonucleotide having an asymmetric format: a core comprises: SnXSSRSSR. Non-limiting example(s) of such an oligonucleotide include: WV-15352.

In some embodiments of an oligonucleotide, e.g., an oligonucleotide having an asymmetric format: a core comprises: SnXSSRSSRS. Non-limiting example(s) of such an oligonucleotide include: WV-15352.

In some embodiments of an oligonucleotide, e.g., an oligonucleotide having an asymmetric format: a core comprises: SRnX. Non-limiting example(s) of such an oligonucleotide include: WV-15358.

In some embodiments of an oligonucleotide, e.g., an oligonucleotide having an asymmetric format: a core comprises: SRnXnXRnXnXR. Non-limiting example(s) of such an oligonucleotide include: WV-15355.

In some embodiments of an oligonucleotide, e.g., an oligonucleotide having an asymmetric format: a core comprises: SRnXnXRnXnXRnX. Non-limiting example(s) of such an oligonucleotide include: WV-15355.

In some embodiments of an oligonucleotide, e.g., an oligonucleotide having an asymmetric format: a core comprises: SRnXnXRSSR. Non-limiting example(s) of such an oligonucleotide include: WV-15356.

In some embodiments of an oligonucleotide, e.g., an oligonucleotide having an asymmetric format: a core comprises: SRnXnXRSSRS. Non-limiting example(s) of such an oligonucleotide include: WV-15356.

In some embodiments of an oligonucleotide, e.g., an oligonucleotide having an asymmetric format: a core comprises: SRSSnXSSR. Non-limiting example(s) of such an oligonucleotide include: WV-15353.

In some embodiments of an oligonucleotide, e.g., an oligonucleotide having an asymmetric format: a core comprises: SRSSnXSSRS. Non-limiting example(s) of such an oligonucleotide include: WV-15353.

In some embodiments of an oligonucleotide, e.g., an oligonucleotide having an asymmetric format: a core comprises: SRSSRnXnXR. Non-limiting example(s) of such an oligonucleotide include: WV-15357.

In some embodiments of an oligonucleotide, e.g., an oligonucleotide having an asymmetric format: a core comprises: SRSSRnXnXRS. Non-limiting example(s) of such an oligonucleotide include: WV-15357.

In some embodiments of an oligonucleotide, e.g., an oligonucleotide having an asymmetric format: a core comprises: SRSSRSSnX. Non-limiting example(s) of such an oligonucleotide include: WV-15354.

In some embodiments of an oligonucleotide, e.g., an oligonucleotide having an asymmetric format: a core comprises: SRSSRSSnXS. Non-limiting example(s) of such an oligonucleotide include: WV-15354.

In some embodiments of an oligonucleotide, e.g., an oligonucleotide having an asymmetric format: a core comprises: SRSSRSSRnX. Non-limiting example(s) of such an oligonucleotide include: WV-15358.

In some embodiments of an oligonucleotide, e.g., an oligonucleotide having an asymmetric format: a core comprises: SSnXS. Non-limiting example(s) of such an oligonucleotide include: WV-15360.

In some embodiments of an oligonucleotide, e.g., an oligonucleotide having an asymmetric format: a core comprises: SSRnX. Non-limiting example(s) of such an oligonucleotide include: WV-15362.

In some embodiments of an oligonucleotide, e.g., an oligonucleotide having an asymmetric format: a core comprises: SSRnX. Non-limiting example(s) of such an oligonucleotide include: WV-15364.

In some embodiments of an oligonucleotide, e.g., an oligonucleotide having an asymmetric format: a core comprises: SSSRnX. Non-limiting example(s) of such an oligonucleotide include: WV-15365.

In some embodiments of an oligonucleotide, e.g., an oligonucleotide having an asymmetric format: a core comprises: SSSSSSnXnX. Non-limiting example(s) of such an oligonucleotide include: WV-15359.

In some embodiments of an oligonucleotide, e.g., an oligonucleotide having an asymmetric format: a core comprises: SSSSSSnXS. Non-limiting example(s) of such an oligonucleotide include: WV-15360.

In some embodiments of an oligonucleotide, e.g., an oligonucleotide having an asymmetric format: a core comprises: SSSSSSRnX. Non-limiting example(s) of such an oligonucleotide include: WV-15362.

In some embodiments of an oligonucleotide, e.g., an oligonucleotide having an asymmetric format: a core comprises: SSSSSSRnX. Non-limiting example(s) of such an oligonucleotide include: WV-15364.

In some embodiments of an oligonucleotide, e.g., an oligonucleotide having an asymmetric format: a core comprises: SSSSSSRnX. Non-limiting example(s) of such an oligonucleotide include: WV-15365.

In some embodiments of an oligonucleotide, e.g., an oligonucleotide having an asymmetric format: a core comprises: SSSSSSRS. Non-limiting example(s) of such an oligonucleotide include: WV-15363.

In some embodiments of an oligonucleotide, e.g., an oligonucleotide having an asymmetric format: a core comprises: SSSSSSRSnX. Non-limiting example(s) of such an oligonucleotide include: WV-15361.

In some embodiments of an oligonucleotide, e.g., an oligonucleotide having an asymmetric format: a core comprises: SSSSSSSnX. Non-limiting example(s) of such an oligonucleotide include: WV-15359.

In some embodiments of an oligonucleotide, e.g., an oligonucleotide having an asymmetric format: a core comprises: SSSSSSSnX. Non-limiting example(s) of such an oligonucleotide include: WV-15360.

In some embodiments of an oligonucleotide, e.g., an oligonucleotide having an asymmetric format: a core comprises: SSSSSSSnXnX. Non-limiting example(s) of such an oligonucleotide include: WV-15359.

In some embodiments of an oligonucleotide, e.g., an oligonucleotide having an asymmetric format: a core comprises: SSSSSSSnXS. Non-limiting example(s) of such an oligonucleotide include: WV-15360.

In some embodiments of an oligonucleotide, e.g., an oligonucleotide having an asymmetric format: a core comprises: SSSSSSSRnX. Non-limiting example(s) of such an oligonucleotide include: WV-15362.

In some embodiments of an oligonucleotide, e.g., an oligonucleotide having an asymmetric format: a core comprises: SSSSSSSRnX. Non-limiting example(s) of such an oligonucleotide include: WV-15364.

In some embodiments of an oligonucleotide, e.g., an oligonucleotide having an asymmetric format: a core comprises: SSSSSSSRnX. Non-limiting example(s) of such an oligonucleotide include: WV-15365.

In some embodiments of an oligonucleotide, e.g., an oligonucleotide having an asymmetric format: a core comprises: SSSSSSSRS. Non-limiting example(s) of such an oligonucleotide include: WV-15363.

In some embodiments of an oligonucleotide, e.g., an oligonucleotide having an asymmetric format: a core comprises: SSSSSSSRSnX. Non-limiting example(s) of such an oligonucleotide include: WV-15361.

In some embodiments of an oligonucleotide, e.g., an oligonucleotide having an asymmetric format: a core comprises: XnXR. Non-limiting example(s) of such an oligonucleotide include: WV-15356.

In some embodiments of an oligonucleotide, e.g., an oligonucleotide having an asymmetric format: a core comprises: 5MSd. Non-limiting example(s) of such an oligonucleotide include: WV-9396, WV-9397.

In some embodiments of an oligonucleotide, e.g., an oligonucleotide having an asymmetric format: a core comprises: 5MRd. Non-limiting example(s) of such an oligonucleotide include: WV-9398, WV-9399.

In some embodiments of an oligonucleotide, e.g., an oligonucleotide having an asymmetric format: a core comprises: SRS. Non-limiting example(s) of such an oligonucleotide include: WV-10244, WV-10246, WV-9872.

In some embodiments of an oligonucleotide, e.g., an oligonucleotide having an asymmetric format: a core comprises: RSS. Non-limiting example(s) of such an oligonucleotide include: WV-10244, WV-10246, WV-9872.

In some embodiments of an oligonucleotide, e.g., an oligonucleotide having an asymmetric format: a core comprises: RSSR. Non-limiting example(s) of such an oligonucleotide include: WV-10244, WV-10246, WV-9872.

In some embodiments of an oligonucleotide, e.g., an oligonucleotide having an asymmetric format: a core comprises: SSRSS. Non-limiting example(s) of such an oligonucleotide include: WV-10244, WV-10246, WV-9872.

In some embodiments of an oligonucleotide, e.g., an oligonucleotide having an asymmetric format: a core comprises: XXXXXXXXX. Non-limiting example(s) of such an oligonucleotide include: WV-10243, WV-10245, WV-10249, WV-10252, WV-11963, WV-11964, WV-12445, WV-12446, WV-12447, WV-12448, WV-12449, WV-12450, WV-12451, WV-12480, WV-12481, WV-12482, WV-12483, WV-12484, WV-12486.

In some embodiments of an oligonucleotide, e.g., an oligonucleotide having an asymmetric format: a core comprises: XXXXXXX. Non-limiting example(s) of such an oligonucleotide include: WV-10243.

In some embodiments of an oligonucleotide, e.g., an oligonucleotide having an asymmetric format: a core comprises: SSSRSSRS. Non-limiting example(s) of such an oligonucleotide include: WV-10244, WV-10246, WV-8610, WV-8629, WV-9526.

In some embodiments of an oligonucleotide, e.g., an oligonucleotide having an asymmetric format: a core comprises: RSSSRSSRSS. Non-limiting example(s) of such an oligonucleotide include: WV-10244, WV-10246, WV-9872.

In some embodiments of an oligonucleotide, e.g., an oligonucleotide having an asymmetric format: a core comprises: XXXXXXX. Non-limiting example(s) of such an oligonucleotide include: WV-10245, WV-10249, WV-10252, WV-11963, WV-11964, WV-12445, WV-12446, WV-12447, WV-12448, WV-12449, WV-12450, WV-12451, WV-12480, WV-12481, WV-12482, WV-12483.

In some embodiments of an oligonucleotide, e.g., an oligonucleotide having an asymmetric format: a core comprises: SSSSRSSR. Non-limiting example(s) of such an oligonucleotide include: WV-10250, WV-10253, WV-8560, WV-8562, WV-8564, WV-8566, WV-8620, WV-8637, WV-8645, WV-8665, WV-8673, WV-8677, WV-9859, WV-9861.

In some embodiments of an oligonucleotide, e.g., an oligonucleotide having an asymmetric format: a core comprises: RSSSSRSSRS. Non-limiting example(s) of such an oligonucleotide include: WV-10250, WV-10253, WV-8560, WV-9859, WV-9861.

In some embodiments of an oligonucleotide, e.g., an oligonucleotide having an asymmetric format: a core comprises: RSSSSRSSSS. Non-limiting example(s) of such an oligonucleotide include: WV-10251, WV-10254, WV-11958, WV-11962, WV-12100, WV-9670, WV-9862.

In some embodiments of an oligonucleotide, e.g., an oligonucleotide having an asymmetric format: a core comprises: SSSSRSSS. Non-limiting example(s) of such an oligonucleotide include: WV-10251, WV-10254, WV-11958, WV-11962, WV-8597, WV-8599, WV-8625, WV-8638, WV-8646, WV-8666, WV-8674, WV-8678, WV-9670, WV-9862.

In some embodiments of an oligonucleotide, e.g., an oligonucleotide having an asymmetric format: a core comprises: XXXXXXXXX. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: XXXXXX. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417.

In some embodiments of an oligonucleotide, e.g., an oligonucleotide having an asymmetric format: a core comprises: XXXXXX. Non-limiting example(s) of such an oligonucleotide include: WV-10418, WV-10419, WV-10420, WV-10421, WV-10422, WV-10423, WV-10424, WV-10425, WV-10426.

In some embodiments of an oligonucleotide, e.g., an oligonucleotide having an asymmetric format: a core comprises: XXXXXXXX. Non-limiting example(s) of such an oligonucleotide include: WV-10423.

In some embodiments of an oligonucleotide, e.g., an oligonucleotide having an asymmetric format: a core comprises: XXXXXXXX. Non-limiting example(s) of such an oligonucleotide include: WV-10424, WV-10425, WV-10426, WV-10427, WV-11966, WV-12113, WV-12114, WV-12439, WV-12440, WV-12441, WV-12442, WV-12443, WV-12444, WV-12485, WV-12582, WV-12583, WV-12947, WV-12948, WV-12949, WV-12950, WV-12951, WV-12952.

In some embodiments of an oligonucleotide, e.g., an oligonucleotide having an asymmetric format: a core comprises: XXXXXX. Non-limiting example(s) of such an oligonucleotide include: WV-10427.

In some embodiments of an oligonucleotide, e.g., an oligonucleotide having an asymmetric format: a core comprises: SSRSSRSSRS. Non-limiting example(s) of such an oligonucleotide include: WV-11114, WV-12503, WV-12504, WV-12505, WV-13809, WV-14349, WV-8043, WV-8044, WV-8045, WV-8046, WV-8047, WV-8048, WV-8257, WV-9696, WV-9697.

In some embodiments of an oligonucleotide, e.g., an oligonucleotide having an asymmetric format: a core comprises: SRSSRSSR. Non-limiting example(s) of such an oligonucleotide include: WV-11114, WV-12503, WV-12504, WV-12505, WV-13809, WV-14349, WV-8043, WV-8044, WV-8045, WV-8046, WV-8047, WV-8048, WV-8257.

In some embodiments of an oligonucleotide, e.g., an oligonucleotide having an asymmetric format: a core comprises: two or more R and two or more S. Non-limiting example(s) of such an oligonucleotide include: WV-11532, WV-11965, WV-11967, WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592, WV-9508, WV-11114, WV-12503, WV-12504, WV-12505, WV-13809, WV-14349, WV-8043, WV-8044, WV-8045, WV-8046, WV-8047, WV-8048, WV-8257, WV-9696, WV-9697, WV-9698, WV-11533, WV-12110, WV-12112, WV-13303, WV-13304, WV-8083, WV-8102, WV-8108, WV-8575, WV-8581, WV-8587, WV-8593

In some embodiments of an oligonucleotide, e.g., an oligonucleotide having an asymmetric format: a core comprises: SRSSRSS. Non-limiting example(s) of such an oligonucleotide include: WV-11532, WV-11965, WV-11967, WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592.

In some embodiments of an oligonucleotide, e.g., an oligonucleotide having an asymmetric format: a core comprises: R and S. Non-limiting example(s) of such an oligonucleotide include: WV-11532, WV-11965, WV-11967, WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592, WV-9508, WV-11114, WV-12503, WV-12504, WV-12505, WV-13809, WV-14349, WV-8043, WV-8044, WV-8045, WV-8046, WV-8047, WV-8048, WV-8257, WV-9696, WV-9697, WV-9698, WV-11533, WV-12110, WV-12112, WV-13303, WV-13304, WV-8083, WV-8102, WV-8108, WV-8575, WV-8581, WV-8587, WV-8593.

In some embodiments of an oligonucleotide, e.g., an oligonucleotide having an asymmetric format: a core comprises: SSRSSRSSS. Non-limiting example(s) of such an oligonucleotide include: WV-11532.

In some embodiments of an oligonucleotide, e.g., an oligonucleotide having an asymmetric format: a core comprises: SRSSRSSRS. Non-limiting example(s) of such an oligonucleotide include: WV-11533, WV-12110, WV-12112, WV-13303, WV-13304, WV-8083, WV-8102, WV-8108, WV-8575, WV-8581, WV-8587, WV-8593.

In some embodiments of an oligonucleotide, e.g., an oligonucleotide having an asymmetric format: a core comprises: RSSRSSR. Non-limiting example(s) of such an oligonucleotide include: WV-11533, WV-12110, WV-12112, WV-13303, WV-13304, WV-8083, WV-8102, WV-8108, WV-8575, WV-8581, WV-8587, WV-8593, WV-9058.

In some embodiments of an oligonucleotide, e.g., an oligonucleotide having an asymmetric format: a core comprises: SSSSRSSSS. Non-limiting example(s) of such an oligonucleotide include: WV-11960, WV-8606, WV-8608, WV-8654, WV-8662, WV-8670, WV-8682, WV-8686, WV-9890, WV-9893, WV-9896, WV-8611, WV-9527.

In some embodiments of an oligonucleotide, e.g., an oligonucleotide having an asymmetric format: a core comprises: SSSRSSS. Non-limiting example(s) of such an oligonucleotide include: WV-11960, WV-8606, WV-8608, WV-8654, WV-8662, WV-8670, WV-8682, WV-8686, WV-9890, WV-9893.

In some embodiments of an oligonucleotide, e.g., an oligonucleotide having an asymmetric format: a core comprises: SSRSSRSSS. Non-limiting example(s) of such an oligonucleotide include: WV-11965.

In some embodiments of an oligonucleotide, e.g., an oligonucleotide having an asymmetric format: a core comprises: XXXXXX. Non-limiting example(s) of such an oligonucleotide include: WV-11966, WV-12113, WV-12114, WV-12439, WV-12440, WV-12441, WV-12442, WV-12443, WV-12444, WV-12582, WV-12583, WV-12947, WV-12948, WV-12949.

In some embodiments of an oligonucleotide, e.g., an oligonucleotide having an asymmetric format: a core comprises: SSRSSRSSS. Non-limiting example(s) of such an oligonucleotide include: WV-11967.

In some embodiments of an oligonucleotide, e.g., an oligonucleotide having an asymmetric format: a core comprises: ORSSSSRSSSSS. Non-limiting example(s) of such an oligonucleotide include: WV-12099.

In some embodiments of an oligonucleotide, e.g., an oligonucleotide having an asymmetric format: a core comprises: OORSSSSRSSSSSS. Non-limiting example(s) of such an oligonucleotide include: WV-12099.

In some embodiments of an oligonucleotide, e.g., an oligonucleotide having an asymmetric format: a core comprises: ORSSSSRSSSSRO. Non-limiting example(s) of such an oligonucleotide include: WV-12100.

In some embodiments of an oligonucleotide, e.g., an oligonucleotide having an asymmetric format: a core comprises: RSSSSRSSSSS. Non-limiting example(s) of such an oligonucleotide include: WV-12101.

In some embodiments of an oligonucleotide, e.g., an oligonucleotide having an asymmetric format: a core comprises: ORSSSSRSSSSSS. Non-limiting example(s) of such an oligonucleotide include: WV-12101.

In some embodiments of an oligonucleotide, e.g., an oligonucleotide having an asymmetric format: a core comprises: ORSSSSRSSSSS. Non-limiting example(s) of such an oligonucleotide include: WV-12103.

In some embodiments of an oligonucleotide, e.g., an oligonucleotide having an asymmetric format: a core comprises: OORSSSSRSSSSSS. Non-limiting example(s) of such an oligonucleotide include: WV-12103.

In some embodiments of an oligonucleotide, e.g., an oligonucleotide having an asymmetric format: a core comprises: OXXXXXXXXXX. Non-limiting example(s) of such an oligonucleotide include: WV-12105.

In some embodiments of an oligonucleotide, e.g., an oligonucleotide having an asymmetric format: a core comprises: OOXXXXXXXXXXX. Non-limiting example(s) of such an oligonucleotide include: WV-12105.

In some embodiments of an oligonucleotide, e.g., an oligonucleotide having an asymmetric format: a core comprises: XXXXXXXXXX. Non-limiting example(s) of such an oligonucleotide include: WV-12107, WV-12485, WV-8132.

In some embodiments of an oligonucleotide, e.g., an oligonucleotide having an asymmetric format: a core comprises: OXXXXXXXXXXX. Non-limiting example(s) of such an oligonucleotide include: WV-12107.

In some embodiments of an oligonucleotide, e.g., an oligonucleotide having an asymmetric format: a core comprises: OXXXXXXXXXXX. Non-limiting example(s) of such an oligonucleotide include: WV-12109.

In some embodiments of an oligonucleotide, e.g., an oligonucleotide having an asymmetric format: a core comprises: OOXXXXXXXXXXX. Non-limiting example(s) of such an oligonucleotide include: WV-12109.

In some embodiments of an oligonucleotide, e.g., an oligonucleotide having an asymmetric format: a core comprises: SRSSRSSSS. Non-limiting example(s) of such an oligonucleotide include: WV-12111.

In some embodiments of an oligonucleotide, e.g., an oligonucleotide having an asymmetric format: a core comprises: RSSRSSS. Non-limiting example(s) of such an oligonucleotide include: WV-12111.

In some embodiments of an oligonucleotide, e.g., an oligonucleotide having an asymmetric format: a core comprises: XXXXXXX. Non-limiting example(s) of such an oligonucleotide include: WV-12484, WV-12486, WV-12977, WV-12978, WV-12979, WV-12980, WV-12981, WV-12982, WV-12983, WV-12984, WV-12985, WV-12986, WV-12987, WV-12988, WV-12989, WV-12990.

In some embodiments of an oligonucleotide, e.g., an oligonucleotide having an asymmetric format: a core comprises: SSRSSSSS. Non-limiting example(s) of such an oligonucleotide include: WV-12893, WV-13312, WV-13313, WV-14087, WV-7603, WV-7605, WV-7659, WV-8005, WV-8007, WV-8009, WV-8011.

In some embodiments of an oligonucleotide, e.g., an oligonucleotide having an asymmetric format: a core comprises: SRSSSS. Non-limiting example(s) of such an oligonucleotide include: WV-12893.

In some embodiments of an oligonucleotide, e.g., an oligonucleotide having an asymmetric format: a core comprises: XXXXXX. Non-limiting example(s) of such an oligonucleotide include: WV-12950.

In some embodiments of an oligonucleotide, e.g., an oligonucleotide having an asymmetric format: a core comprises: XXXXXXXX. Non-limiting example(s) of such an oligonucleotide include: WV-12953.

In some embodiments of an oligonucleotide, e.g., an oligonucleotide having an asymmetric format: a core comprises: XXXXXXXXX. Non-limiting example(s) of such an oligonucleotide include: WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997.

In some embodiments of an oligonucleotide, e.g., an oligonucleotide having an asymmetric format: a core comprises: XXXXXXX. Non-limiting example(s) of such an oligonucleotide include: WV-12991.

In some embodiments of an oligonucleotide, e.g., an oligonucleotide having an asymmetric format: a core comprises: XXXXXXXXX. Non-limiting example(s) of such an oligonucleotide include: WV-12998.

In some embodiments of an oligonucleotide, e.g., an oligonucleotide having an asymmetric format: a core comprises: XXXXXXXXX. Non-limiting example(s) of such an oligonucleotide include: WV-12999, WV-13000, WV-13001, WV-13002, WV-13003, WV-13004, WV-13005, WV-13006, WV-13007, WV-13008, WV-13804, WV-13805, WV-3421, WV-3662, WV-3688, WV-3690, WV-6408, WV-6474.

In some embodiments of an oligonucleotide, e.g., an oligonucleotide having an asymmetric format: a core comprises: XXXXXXX. Non-limiting example(s) of such an oligonucleotide include: WV-13005, WV-13006, WV-13007, WV-13008, WV-13804, WV-13805, WV-3421, WV-3662, WV-3688, WV-3690, WV-6408, WV-6474, WV-6936.

In some embodiments of an oligonucleotide, e.g., an oligonucleotide having an asymmetric format: a core comprises: SSRSSRSSS. Non-limiting example(s) of such an oligonucleotide include: WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592.

In some embodiments of an oligonucleotide, e.g., an oligonucleotide having an asymmetric format: a core comprises: SRSSSRS. Non-limiting example(s) of such an oligonucleotide include: WV-13308, WV-13309, WV-13310, WV-13311, WV-9505.

In some embodiments of an oligonucleotide, e.g., an oligonucleotide having an asymmetric format: a core comprises: SRSSSS. Non-limiting example(s) of such an oligonucleotide include: WV-13312, WV-13313, WV-14087, WV-7603, WV-7605, WV-7659, WV-8005, WV-8007, WV-8009, WV-8011, WV-8452, WV-8454.

In some embodiments of an oligonucleotide, e.g., an oligonucleotide having an asymmetric format: a core comprises: XXXXXXX. Non-limiting example(s) of such an oligonucleotide include: WV-13803, WV-3174, WV-3536, WV-3542, WV-8132, WV-8548, WV-8550, WV-8552, WV-8553, WV-8556, WV-8594, WV-8595, WV-8609, WV-8617, WV-8656, WV-8664, WV-8672, WV-8684, WV-8688.

In some embodiments of an oligonucleotide, e.g., an oligonucleotide having an asymmetric format: a core comprises: XXXXXXXXX. Non-limiting example(s) of such an oligonucleotide include: WV-6936.

In some embodiments of an oligonucleotide, e.g., an oligonucleotide having an asymmetric format: a core comprises: XXXXXXX. Non-limiting example(s) of such an oligonucleotide include: WV-6951.

In some embodiments of an oligonucleotide, e.g., an oligonucleotide having an asymmetric format: a core comprises: SSSSRSS. Non-limiting example(s) of such an oligonucleotide include: WV-7657, WV-8099, WV-8105, WV-8322, WV-8329, WV-8572, WV-8578, WV-8584, WV-8590.

In some embodiments of an oligonucleotide, e.g., an oligonucleotide having an asymmetric format: a core comprises: SSSSSRSSS. Non-limiting example(s) of such an oligonucleotide include: WV-7657.

In some embodiments of an oligonucleotide, e.g., an oligonucleotide having an asymmetric format: a core comprises: SSSSSSSRS. Non-limiting example(s) of such an oligonucleotide include: WV-8097, WV-8103, WV-8248, WV-8250, WV-8570, WV-8576, WV-8582, WV-8588.

In some embodiments of an oligonucleotide, e.g., an oligonucleotide having an asymmetric format: a core comprises: SSSSSSR. Non-limiting example(s) of such an oligonucleotide include: WV-8097, WV-8103, WV-8248, WV-8250, WV-8570, WV-8576, WV-8582, WV-8588, WV-8602, WV-8605, WV-8616, WV-8655, WV-8663, WV-8671.

In some embodiments of an oligonucleotide, e.g., an oligonucleotide having an asymmetric format: a core comprises: SSSSSSRSS. Non-limiting example(s) of such an oligonucleotide include: WV-8098, WV-8104, WV-8571, WV-8577, WV-8583, WV-8589, WV-8619, WV-9506.

In some embodiments of an oligonucleotide, e.g., an oligonucleotide having an asymmetric format: a core comprises: SSSSSRS. Non-limiting example(s) of such an oligonucleotide include: WV-8098, WV-8104, WV-8571, WV-8577, WV-8583, WV-8589, WV-8619, WV-9506.

In some embodiments of an oligonucleotide, e.g., an oligonucleotide having an asymmetric format: a core comprises: SSSSSRSSS. Non-limiting example(s) of such an oligonucleotide include: WV-8099, WV-8105, WV-8322, WV-8329, WV-8572, WV-8578, WV-8584, WV-8590.

In some embodiments of an oligonucleotide, e.g., an oligonucleotide having an asymmetric format: a core comprises: SSSSRSSRS. Non-limiting example(s) of such an oligonucleotide include: WV-8100, WV-8106, WV-8114, WV-8115, WV-8116, WV-8117, WV-8118, WV-8119, WV-8120, WV-8121.

In some embodiments of an oligonucleotide, e.g., an oligonucleotide having an asymmetric format: a core comprises: SSSRSSR. Non-limiting example(s) of such an oligonucleotide include: WV-8100, WV-8106, WV-8114, WV-8115, WV-8116, WV-8117, WV-8118, WV-8119, WV-8120, WV-8121, WV-8246, WV-8311, WV-8312, WV-8313, WV-8314, WV-8466, WV-8468, WV-8470, WV-8472, WV-8474, WV-8476.

In some embodiments of an oligonucleotide, e.g., an oligonucleotide having an asymmetric format: a core comprises: SSSRSSRSS. Non-limiting example(s) of such an oligonucleotide include: WV-8122, WV-8123, WV-8124, WV-8125, WV-8126, WV-8127, WV-8128, WV-8129, WV-8315, WV-8316, WV-8317, WV-8318, WV-8467, WV-8469, WV-8471, WV-8473, WV-8475, WV-8569, WV-8614, WV-8692, WV-8695, WV-9530, WV-9886.

In some embodiments of an oligonucleotide, e.g., an oligonucleotide having an asymmetric format: a core comprises: SSRSSRS. Non-limiting example(s) of such an oligonucleotide include: WV-8122.

In some embodiments of an oligonucleotide, e.g., an oligonucleotide having an asymmetric format: a core comprises: SSRSSRS. Non-limiting example(s) of such an oligonucleotide include: WV-8123.

In some embodiments of an oligonucleotide, e.g., an oligonucleotide having an asymmetric format: a core comprises: SSRSSRS. Non-limiting example(s) of such an oligonucleotide include: WV-8124, WV-8125, WV-8126, WV-8127, WV-8128, WV-8129, WV-8315, WV-8316, WV-8317, WV-8318, WV-8467, WV-8469.

In some embodiments of an oligonucleotide, e.g., an oligonucleotide having an asymmetric format: a core comprises: SSSSRSSRS. Non-limiting example(s) of such an oligonucleotide include: WV-8246, WV-8311, WV-8312, WV-8313, WV-8314, WV-8466, WV-8468.

In some embodiments of an oligonucleotide, e.g., an oligonucleotide having an asymmetric format: a core comprises: SSRSSSSRS. Non-limiting example(s) of such an oligonucleotide include: WV-8259.

In some embodiments of an oligonucleotide, e.g., an oligonucleotide having an asymmetric format: a core comprises: SRSSSSSR. Non-limiting example(s) of such an oligonucleotide include: WV-8259.

In some embodiments of an oligonucleotide, e.g., an oligonucleotide having an asymmetric format: a core comprises: SSRSSSSS. Non-limiting example(s) of such an oligonucleotide include: WV-8452.

In some embodiments of an oligonucleotide, e.g., an oligonucleotide having an asymmetric format: a core comprises: SSRSSSSS. Non-limiting example(s) of such an oligonucleotide include: WV-8454.

In some embodiments of an oligonucleotide, e.g., an oligonucleotide having an asymmetric format: a core comprises: SSRSSSSS. Non-limiting example(s) of such an oligonucleotide include: WV-8456.

In some embodiments of an oligonucleotide, e.g., an oligonucleotide having an asymmetric format: a core comprises: SRSSSSS. Non-limiting example(s) of such an oligonucleotide include: WV-8456.

In some embodiments of an oligonucleotide, e.g., an oligonucleotide having an asymmetric format: a core comprises: SSSSRSSRS. Non-limiting example(s) of such an oligonucleotide include: WV-8470.

In some embodiments of an oligonucleotide, e.g., an oligonucleotide having an asymmetric format: a core comprises: SSRSSRS. Non-limiting example(s) of such an oligonucleotide include: WV-8471.

In some embodiments of an oligonucleotide, e.g., an oligonucleotide having an asymmetric format: a core comprises: SSSSRSSRS. Non-limiting example(s) of such an oligonucleotide include: WV-8472, WV-8474, WV-8476, WV-8568, WV-8573, WV-8579, WV-8585, WV-8591, WV-8601, WV-8603, WV-8653, WV-8661, WV-8669, WV-8681, WV-8685, WV-8691, WV-8694, WV-9889, WV-9892.

In some embodiments of an oligonucleotide, e.g., an oligonucleotide having an asymmetric format: a core comprises: SSRSSRS. Non-limiting example(s) of such an oligonucleotide include: WV-8473.

In some embodiments of an oligonucleotide, e.g., an oligonucleotide having an asymmetric format: a core comprises: SSRSSRS. Non-limiting example(s) of such an oligonucleotide include: WV-8475.

In some embodiments of an oligonucleotide, e.g., an oligonucleotide having an asymmetric format: a core comprises: SSSSSRSSRS. Non-limiting example(s) of such an oligonucleotide include: WV-8562, WV-8564, WV-8566, WV-8620, WV-8637, WV-8645, WV-8665, WV-8673.

In some embodiments of an oligonucleotide, e.g., an oligonucleotide having an asymmetric format: a core comprises: SSSSSSSSRS. Non-limiting example(s) of such an oligonucleotide include: WV-8563, WV-8565, WV-8567, WV-8596, WV-8612, WV-8621, WV-8624, WV-8639, WV-8647, WV-8667, WV-8675.

In some embodiments of an oligonucleotide, e.g., an oligonucleotide having an asymmetric format: a core comprises: SSSSSSSR. Non-limiting example(s) of such an oligonucleotide include: WV-8563, WV-8565, WV-8567, WV-8596, WV-8612, WV-8621, WV-8624, WV-8639, WV-8647, WV-8667, WV-8675.

In some embodiments of an oligonucleotide, e.g., an oligonucleotide having an asymmetric format: a core comprises: SSSRSSR. Non-limiting example(s) of such an oligonucleotide include: WV-8568.

In some embodiments of an oligonucleotide, e.g., an oligonucleotide having an asymmetric format: a core comprises: SSSSRSSSS. Non-limiting example(s) of such an oligonucleotide include: WV-8597.

In some embodiments of an oligonucleotide, e.g., an oligonucleotide having an asymmetric format: a core comprises: SSSSSRSSSS. Non-limiting example(s) of such an oligonucleotide include: WV-8599, WV-8625, WV-8638, WV-8646, WV-8666, WV-8674.

In some embodiments of an oligonucleotide, e.g., an oligonucleotide having an asymmetric format: a core comprises: SSSSSSSRS. Non-limiting example(s) of such an oligonucleotide include: WV-8602.

In some embodiments of an oligonucleotide, e.g., an oligonucleotide having an asymmetric format: a core comprises: SSSSSSSRS. Non-limiting example(s) of such an oligonucleotide include: WV-8605, WV-8616, WV-8655, WV-8663, WV-8671, WV-8683.

In some embodiments of an oligonucleotide, e.g., an oligonucleotide having an asymmetric format: a core comprises: SSSSRSSRSS. Non-limiting example(s) of such an oligonucleotide include: WV-8610.

In some embodiments of an oligonucleotide, e.g., an oligonucleotide having an asymmetric format: a core comprises: SSSRSSSS. Non-limiting example(s) of such an oligonucleotide include: WV-8611.

In some embodiments of an oligonucleotide, e.g., an oligonucleotide having an asymmetric format: a core comprises: SSSRSSSSS. Non-limiting example(s) of such an oligonucleotide include: WV-8615.

In some embodiments of an oligonucleotide, e.g., an oligonucleotide having an asymmetric format: a core comprises: SSRSSSS. Non-limiting example(s) of such an oligonucleotide include: WV-8615.

In some embodiments of an oligonucleotide, e.g., an oligonucleotide having an asymmetric format: a core comprises: SSSSSSSRSS. Non-limiting example(s) of such an oligonucleotide include: WV-8618.

In some embodiments of an oligonucleotide, e.g., an oligonucleotide having an asymmetric format: a core comprises: SSSSSSRS. Non-limiting example(s) of such an oligonucleotide include: WV-8618.

In some embodiments of an oligonucleotide, e.g., an oligonucleotide having an asymmetric format: a core comprises: SSSSRSSRSS. Non-limiting example(s) of such an oligonucleotide include: WV-8629.

In some embodiments of an oligonucleotide, e.g., an oligonucleotide having an asymmetric format: a core comprises: XXXXXXXXX. Non-limiting example(s) of such an oligonucleotide include: WV-8676, WV-8680, WV-8689, WV-8693, WV-8696, WV-8697, WV-8809, WV-8844, WV-8846, WV-8847, WV-8849, WV-8851, WV-8853, WV-8855, WV-8857, WV-8858, WV-8860.

In some embodiments of an oligonucleotide, e.g., an oligonucleotide having an asymmetric format: a core comprises: SSSSSRSSRS. Non-limiting example(s) of such an oligonucleotide include: WV-8677.

In some embodiments of an oligonucleotide, e.g., an oligonucleotide having an asymmetric format: a core comprises: SSSSSRSSSS. Non-limiting example(s) of such an oligonucleotide include: WV-8678.

In some embodiments of an oligonucleotide, e.g., an oligonucleotide having an asymmetric format: a core comprises: SSSSSSSSRS. Non-limiting example(s) of such an oligonucleotide include: WV-8679.

In some embodiments of an oligonucleotide, e.g., an oligonucleotide having an asymmetric format: a core comprises: SSSSSSSR. Non-limiting example(s) of such an oligonucleotide include: WV-8679.

In some embodiments of an oligonucleotide, e.g., an oligonucleotide having an asymmetric format: a core comprises: SSSSSSR. Non-limiting example(s) of such an oligonucleotide include: WV-8683.

In some embodiments of an oligonucleotide, e.g., an oligonucleotide having an asymmetric format: a core comprises: SSSSSSSRS. Non-limiting example(s) of such an oligonucleotide include: WV-8687.

In some embodiments of an oligonucleotide, e.g., an oligonucleotide having an asymmetric format: a core comprises: SSSSSSR. Non-limiting example(s) of such an oligonucleotide include: WV-8687.

In some embodiments of an oligonucleotide, e.g., an oligonucleotide having an asymmetric format: a core comprises: XXXXXXXX. Non-limiting example(s) of such an oligonucleotide include: WV-8690, WV-8845, WV-8848, WV-8850, WV-8852, WV-8854, WV-8856, WV-8859, WV-9431, WV-9432, WV-9433, WV-9434, WV-9435, WV-9441, WV-9442, WV-9443, WV-9444, WV-9445, WV-9486.

In some embodiments of an oligonucleotide, e.g., an oligonucleotide having an asymmetric format: a core comprises: XXXXX. Non-limiting example(s) of such an oligonucleotide include: WV-8810.

In some embodiments of an oligonucleotide, e.g., an oligonucleotide having an asymmetric format: a core comprises: SRSSRSSRS. Non-limiting example(s) of such an oligonucleotide include: WV-9058.

In some embodiments of an oligonucleotide, e.g., an oligonucleotide having an asymmetric format: a core comprises: SRSSRSSRS. Non-limiting example(s) of such an oligonucleotide include: WV-9059.

In some embodiments of an oligonucleotide, e.g., an oligonucleotide having an asymmetric format: a core comprises: RSSRSSR. Non-limiting example(s) of such an oligonucleotide include: WV-9059.

In some embodiments of an oligonucleotide, e.g., an oligonucleotide having an asymmetric format: a core comprises: XXXXXXXXX. Non-limiting example(s) of such an oligonucleotide include: WV-9060.

In some embodiments of an oligonucleotide, e.g., an oligonucleotide having an asymmetric format: a core comprises: SSSRSSSSSS. Non-limiting example(s) of such an oligonucleotide include: WV-9062.

In some embodiments of an oligonucleotide, e.g., an oligonucleotide having an asymmetric format: a core comprises: SSRSSSSS. Non-limiting example(s) of such an oligonucleotide include: WV-9062.

In some embodiments of an oligonucleotide, e.g., an oligonucleotide having an asymmetric format: a core comprises: SSSRSSSSSS. Non-limiting example(s) of such an oligonucleotide include: WV-9063.

In some embodiments of an oligonucleotide, e.g., an oligonucleotide having an asymmetric format: a core comprises: SSRSSSSS. Non-limiting example(s) of such an oligonucleotide include: WV-9063.

In some embodiments of an oligonucleotide, e.g., an oligonucleotide having an asymmetric format: a core comprises: SSSRSSRSSS. Non-limiting example(s) of such an oligonucleotide include: WV-9285, WV-9286, WV-9380, WV-9381.

In some embodiments of an oligonucleotide, e.g., an oligonucleotide having an asymmetric format: a core comprises: SSRSSRSS. Non-limiting example(s) of such an oligonucleotide include: WV-9285, WV-9286, WV-9380, WV-9381.

In some embodiments of an oligonucleotide, e.g., an oligonucleotide having an asymmetric format: a core comprises: SSOSSSSSS. Non-limiting example(s) of such an oligonucleotide include: WV-9394.

In some embodiments of an oligonucleotide, e.g., an oligonucleotide having an asymmetric format: a core comprises: SOSSSSS. Non-limiting example(s) of such an oligonucleotide include: WV-9394.

In some embodiments of an oligonucleotide, e.g., an oligonucleotide having an asymmetric format: a core comprises: SOSSOSS. Non-limiting example(s) of such an oligonucleotide include: WV-9395, WV-9397.

In some embodiments of an oligonucleotide, e.g., an oligonucleotide having an asymmetric format: a core comprises: SSOSSOSSS. Non-limiting example(s) of such an oligonucleotide include: WV-9395.

In some embodiments of an oligonucleotide, e.g., an oligonucleotide having an asymmetric format: a core comprises: SSOSSSSSS. Non-limiting example(s) of such an oligonucleotide include: WV-9396.

In some embodiments of an oligonucleotide, e.g., an oligonucleotide having an asymmetric format: a core comprises: SOSSSSS. Non-limiting example(s) of such an oligonucleotide include: WV-9396.

In some embodiments of an oligonucleotide, e.g., an oligonucleotide having an asymmetric format: a core comprises: SSOSSOSSS. Non-limiting example(s) of such an oligonucleotide include: WV-9397.

In some embodiments of an oligonucleotide, e.g., an oligonucleotide having an asymmetric format: a core comprises: SSOSSSSSS. Non-limiting example(s) of such an oligonucleotide include: WV-9398.

In some embodiments of an oligonucleotide, e.g., an oligonucleotide having an asymmetric format: a core comprises: SOSSSSS. Non-limiting example(s) of such an oligonucleotide include: WV-9398.

In some embodiments of an oligonucleotide, e.g., an oligonucleotide having an asymmetric format: a core comprises: SSOSSOSSS. Non-limiting example(s) of such an oligonucleotide include: WV-9399.

In some embodiments of an oligonucleotide, e.g., an oligonucleotide having an asymmetric format: a core comprises: SOSSOSS. Non-limiting example(s) of such an oligonucleotide include: WV-9399.

In some embodiments of an oligonucleotide, e.g., an oligonucleotide having an asymmetric format: a core comprises: SSSRSSRSSS. Non-limiting example(s) of such an oligonucleotide include: WV-9421.

In some embodiments of an oligonucleotide, e.g., an oligonucleotide having an asymmetric format: a core comprises: SSRSSRSS. Non-limiting example(s) of such an oligonucleotide include: WV-9421.

In some embodiments of an oligonucleotide, e.g., an oligonucleotide having an asymmetric format: a core comprises: XXXXXXXX. Non-limiting example(s) of such an oligonucleotide include: WV-9487.

In some embodiments of an oligonucleotide, e.g., an oligonucleotide having an asymmetric format: a core comprises: SSSSSRSSS. Non-limiting example(s) of such an oligonucleotide include: WV-9507.

In some embodiments of an oligonucleotide, e.g., an oligonucleotide having an asymmetric format: a core comprises: SSSSRSS. Non-limiting example(s) of such an oligonucleotide include: WV-9507.

In some embodiments of an oligonucleotide, e.g., an oligonucleotide having an asymmetric format: a core comprises: SSRSSRSSS. Non-limiting example(s) of such an oligonucleotide include: WV-9508, WV-13308, WV-13309, WV-13310, WV-13311, WV-9505.

In some embodiments of an oligonucleotide, e.g., an oligonucleotide having an asymmetric format: a core comprises: SRSSRSS. Non-limiting example(s) of such an oligonucleotide include: WV-9508.

In some embodiments of an oligonucleotide, e.g., an oligonucleotide having an asymmetric format: a core comprises: SSRSSSRSS. Non-limiting example(s) of such an oligonucleotide include: WV-9509.

In some embodiments of an oligonucleotide, e.g., an oligonucleotide having an asymmetric format: a core comprises: SRSSSRS. Non-limiting example(s) of such an oligonucleotide include: WV-9509.

In some embodiments of an oligonucleotide, e.g., an oligonucleotide having an asymmetric format: a core comprises: SSSSRSSRSS. Non-limiting example(s) of such an oligonucleotide include: WV-9526.

In some embodiments of an oligonucleotide, e.g., an oligonucleotide having an asymmetric format: a core comprises: SSSRSSSS. Non-limiting example(s) of such an oligonucleotide include: WV-9527.

In some embodiments of an oligonucleotide, e.g., an oligonucleotide having an asymmetric format: a core comprises: SSSSSSRSS. Non-limiting example(s) of such an oligonucleotide include: WV-9528.

In some embodiments of an oligonucleotide, e.g., an oligonucleotide having an asymmetric format: a core comprises: SSSSSSRS. Non-limiting example(s) of such an oligonucleotide include: WV-9528.

In some embodiments of an oligonucleotide, e.g., an oligonucleotide having an asymmetric format: a core comprises: SSSRSSSSS. Non-limiting example(s) of such an oligonucleotide include: WV-9531.

In some embodiments of an oligonucleotide, e.g., an oligonucleotide having an asymmetric format: a core comprises: SSRSSSS. Non-limiting example(s) of such an oligonucleotide include: WV-9531.

In some embodiments of an oligonucleotide, e.g., an oligonucleotide having an asymmetric format: a core comprises: SSSSSSRSS. Non-limiting example(s) of such an oligonucleotide include: WV-9532.

In some embodiments of an oligonucleotide, e.g., an oligonucleotide having an asymmetric format: a core comprises: SSSSSRS. Non-limiting example(s) of such an oligonucleotide include: WV-9532.

In some embodiments of an oligonucleotide, e.g., an oligonucleotide having an asymmetric format: a core comprises: XXXXXXXX. Non-limiting example(s) of such an oligonucleotide include: WV-9533, WV-9885, WV-9887, WV-9891, WV-9894.

In some embodiments of an oligonucleotide, e.g., an oligonucleotide having an asymmetric format: a core comprises: SSSSRSSRSS. Non-limiting example(s) of such an oligonucleotide include: WV-9590.

In some embodiments of an oligonucleotide, e.g., an oligonucleotide having an asymmetric format: a core comprises: SSSRSSRS. Non-limiting example(s) of such an oligonucleotide include: WV-9590.

In some embodiments of an oligonucleotide, e.g., an oligonucleotide having an asymmetric format: a core comprises: SSSSRSSSSS. Non-limiting example(s) of such an oligonucleotide include: WV-9591.

In some embodiments of an oligonucleotide, e.g., an oligonucleotide having an asymmetric format: a core comprises: SSSRSSSS. Non-limiting example(s) of such an oligonucleotide include: WV-9591.

In some embodiments of an oligonucleotide, e.g., an oligonucleotide having an asymmetric format: a core comprises: SSSSSSSRSS. Non-limiting example(s) of such an oligonucleotide include: WV-9592.

In some embodiments of an oligonucleotide, e.g., an oligonucleotide having an asymmetric format: a core comprises: SSSSSSRS. Non-limiting example(s) of such an oligonucleotide include: WV-9592.

In some embodiments of an oligonucleotide, e.g., an oligonucleotide having an asymmetric format: a core comprises: SRSSRSSR. Non-limiting example(s) of such an oligonucleotide include: WV-9696.

In some embodiments of an oligonucleotide, e.g., an oligonucleotide having an asymmetric format: a core comprises: SRSSRSSR. Non-limiting example(s) of such an oligonucleotide include: WV-9697.

In some embodiments of an oligonucleotide, e.g., an oligonucleotide having an asymmetric format: a core comprises: SSRSSRSSRS. Non-limiting example(s) of such an oligonucleotide include: WV-9698.

In some embodiments of an oligonucleotide, e.g., an oligonucleotide having an asymmetric format: a core comprises: SRSSRSSR. Non-limiting example(s) of such an oligonucleotide include: WV-9698.

In some embodiments of an oligonucleotide, e.g., an oligonucleotide having an asymmetric format: a core comprises: XXXXX. Non-limiting example(s) of such an oligonucleotide include: WV-980.

In some embodiments of an oligonucleotide, e.g., an oligonucleotide having an asymmetric format: a core comprises: SSSSRSSR. Non-limiting example(s) of such an oligonucleotide include: WV-9869.

In some embodiments of an oligonucleotide, e.g., an oligonucleotide having an asymmetric format: a core comprises: RSSSSRSSRS. Non-limiting example(s) of such an oligonucleotide include: WV-9869.

In some embodiments of an oligonucleotide, e.g., an oligonucleotide having an asymmetric format: a core comprises: SSSSRSSS. Non-limiting example(s) of such an oligonucleotide include: WV-9870.

In some embodiments of an oligonucleotide, e.g., an oligonucleotide having an asymmetric format: a core comprises: RSSSSRSSSS. Non-limiting example(s) of such an oligonucleotide include: WV-9870.

In some embodiments of an oligonucleotide, e.g., an oligonucleotide having an asymmetric format: a core comprises: SSSRSSRS. Non-limiting example(s) of such an oligonucleotide include: WV-9872.

In some embodiments of an oligonucleotide, e.g., an oligonucleotide having an asymmetric format: a core comprises: SSSRSSRS. Non-limiting example(s) of such an oligonucleotide include: WV-9874.

In some embodiments of an oligonucleotide, e.g., an oligonucleotide having an asymmetric format: a core comprises: RSSSRSSRSS. Non-limiting example(s) of such an oligonucleotide include: WV-9874.

In some embodiments of an oligonucleotide, e.g., an oligonucleotide having an asymmetric format: a core comprises: SSSRSSRSS. Non-limiting example(s) of such an oligonucleotide include: WV-9888.

In some embodiments of an oligonucleotide, e.g., an oligonucleotide having an asymmetric format: a core comprises: SSSSRSSRS. Non-limiting example(s) of such an oligonucleotide include: WV-9895.

In some embodiments of an oligonucleotide, e.g., an oligonucleotide having an asymmetric format: a core comprises: SSSRSSS. Non-limiting example(s) of such an oligonucleotide include: WV-9896.

In some embodiments of an oligonucleotide, e.g., an oligonucleotide having an asymmetric format: a core comprises: 4 or more consecutive X. Non-limiting example(s) of such an oligonucleotide include: WV-10424, WV-10425, WV-10426, WV-10427, WV-11966, WV-12113, WV-12114, WV-12439, WV-12440, WV-12441, WV-12442, WV-12443, WV-12444, WV-12485, WV-12582, WV-12583, WV-12947, WV-12948, WV-12949, WV-12950, WV-12951, WV-12952.

In some embodiments of an oligonucleotide, e.g., an oligonucleotide having an asymmetric format: a core comprises: two or more consecutive O, and two or more consecutive X. Non-limiting example(s) of such an oligonucleotide include: WV-12105.

In some embodiments of an oligonucleotide, e.g., an oligonucleotide having an asymmetric format: a core comprises: two or more consecutive O, and two or more consecutive X. Non-limiting example(s) of such an oligonucleotide include: WV-12109.

In some embodiments of an oligonucleotide, e.g., an oligonucleotide having an asymmetric format: a core comprises: two or more consecutive O, and R, and two or more consecutive S, and R, and two or more consecutive S. Non-limiting example(s) of such an oligonucleotide include: WV-12099.

In some embodiments of an oligonucleotide, e.g., an oligonucleotide having an asymmetric format: a core comprises: two or more consecutive O, and R, and two or more consecutive S, and R, and two or more consecutive S. Non-limiting example(s) of such an oligonucleotide include: WV-12103.

In some embodiments of an oligonucleotide, e.g., an oligonucleotide having an asymmetric format: a core comprises: two or more consecutive S, and O, and two or more consecutive S, and O, and two or more consecutive S. Non-limiting example(s) of such an oligonucleotide include: WV-9395.

In some embodiments of an oligonucleotide, e.g., an oligonucleotide having an asymmetric format: a core comprises: two or more consecutive S, and O, and two or more consecutive S, and O, and two or more consecutive S. Non-limiting example(s) of such an oligonucleotide include: WV-9397.

In some embodiments of an oligonucleotide, e.g., an oligonucleotide having an asymmetric format: a core comprises: two or more consecutive S, and O, and two or more consecutive S, and O, and two or more consecutive S. Non-limiting example(s) of such an oligonucleotide include: WV-9399.

In some embodiments of an oligonucleotide, e.g., an oligonucleotide having an asymmetric format: a core comprises: two or more consecutive S, and O, and two or more consecutive S. Non-limiting example(s) of such an oligonucleotide include: WV-9394.

In some embodiments of an oligonucleotide, e.g., an oligonucleotide having an asymmetric format: a core comprises: two or more consecutive S, and O, and two or more consecutive S. Non-limiting example(s) of such an oligonucleotide include: WV-9396.

In some embodiments of an oligonucleotide, e.g., an oligonucleotide having an asymmetric format: a core comprises: two or more consecutive S, and O, and two or more consecutive S. Non-limiting example(s) of such an oligonucleotide include: WV-9398.

In some embodiments of an oligonucleotide, e.g., an oligonucleotide having an asymmetric format: a core comprises: two or more consecutive S, and R. Non-limiting example(s) of such an oligonucleotide include: WV-8097, WV-8103, WV-8248, WV-8250, WV-8570, WV-8576, WV-8582, WV-8588, WV-8602, WV-8605, WV-8616, WV-8655, WV-8663, WV-8671.

In some embodiments of an oligonucleotide, e.g., an oligonucleotide having an asymmetric format: a core comprises: two or more consecutive S, and R. Non-limiting example(s) of such an oligonucleotide include: WV-8683.

In some embodiments of an oligonucleotide, e.g., an oligonucleotide having an asymmetric format: a core comprises: two or more consecutive S, and R. Non-limiting example(s) of such an oligonucleotide include: WV-8687.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8122.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8123.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8124, WV-8125, WV-8126, WV-8127, WV-8128, WV-8129, WV-8315, WV-8316, WV-8317, WV-8318, WV-8467, WV-8469.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8471.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8473.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8475.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9285, WV-9286, WV-9380, WV-9381.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9421.

In some embodiments of an oligonucleotide, e.g., an oligonucleotide having an asymmetric format: a core comprises: two or more consecutive S, and R, and two or more consecutive S, and R, and two or more consecutive S, and RS. Non-limiting example(s) of such an oligonucleotide include: WV-11114, WV-12503, WV-12504, WV-12505, WV-13809, WV-14349, WV-8043, WV-8044, WV-8045, WV-8046, WV-8047, WV-8048, WV-8257, WV-9696, WV-9697.

In some embodiments of an oligonucleotide, e.g., an oligonucleotide having an asymmetric format: a core comprises: two or more consecutive S, and R, and two or more consecutive S, and R, and two or more consecutive S, and RS. Non-limiting example(s) of such an oligonucleotide include: WV-9698.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-11532.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-11965.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-11967.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9508, WV-13308, WV-13309, WV-13310, WV-13311, WV-9505.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9509.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8615.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9531.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9062.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9063.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8259.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-12893, WV-13312, WV-13313, WV-14087, WV-7603, WV-7605, WV-7659, WV-8005, WV-8007, WV-8009, WV-8011.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8452.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8454.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8456.

In some embodiments of an oligonucleotide, e.g., an oligonucleotide having an asymmetric format: a core comprises: two or more consecutive S, and R, and two or more consecutive S, and R. Non-limiting example(s) of such an oligonucleotide include: WV-8100, WV-8106, WV-8114, WV-8115, WV-8116, WV-8117, WV-8118, WV-8119, WV-8120, WV-8121, WV-8246, WV-8311, WV-8312, WV-8313, WV-8314, WV-8466, WV-8468, WV-8470, WV-8472, WV-8474, WV-8476.

In some embodiments of an oligonucleotide, e.g., an oligonucleotide having an asymmetric format: a core comprises: two or more consecutive S, and R, and two or more consecutive S, and R. Non-limiting example(s) of such an oligonucleotide include: WV-8568.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-10244, WV-10246, WV-8610, WV-8629, WV-9526.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-9590.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-9872.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-9874.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-8122, WV-8123, WV-8124, WV-8125, WV-8126, WV-8127, WV-8128, WV-8129, WV-8315, WV-8316, WV-8317, WV-8318, WV-8467, WV-8469, WV-8471, WV-8473, WV-8475, WV-8569, WV-8614, WV-8692, WV-8695, WV-9530, WV-9886.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9888.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9285, WV-9286, WV-9380, WV-9381.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9421.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-11960, WV-8606, WV-8608, WV-8654, WV-8662, WV-8670, WV-8682, WV-8686, WV-9890, WV-9893.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9896.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8611.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9527.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9591.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8615.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9531.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9062.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9063.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-7657, WV-8099, WV-8105, WV-8322, WV-8329, WV-8572, WV-8578, WV-8584, WV-8590.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9507.

In some embodiments of an oligonucleotide, e.g., an oligonucleotide having an asymmetric format: a core comprises: two or more consecutive S, and R, and two or more consecutive S, and R. Non-limiting example(s) of such an oligonucleotide include: WV-10250, WV-10253, WV-8560, WV-8562, WV-8564, WV-8566, WV-8620, WV-8637, WV-8645, WV-8665, WV-8673, WV-8677, WV-8859, WV-9861.

In some embodiments of an oligonucleotide, e.g., an oligonucleotide having an asymmetric format: a core comprises: two or more consecutive S, and R, and two or more consecutive S, and R. Non-limiting example(s) of such an oligonucleotide include: WV-9869.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8100, WV-8106, WV-8114, WV-8115, WV-8116, WV-8117, WV-8118, WV-8119, WV-8120, WV-8121.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8246, WV-8311, WV-8312, WV-8313, WV-8314, WV-8466, WV-8468.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8470.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8472, WV-8474, WV-8476, WV-8568, WV-8573, WV-8579, WV-8585, WV-8591, WV-8601, WV-8603, WV-8653, WV-8661, WV-8669, WV-8681, WV-8685, WV-8691, WV-8694, WV-9889, WV-9892.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-9895.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8610.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-8629.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9526.

In some embodiments of an oligonucleotide, e.g., an oligonucleotide having an asymmetric format: a core comprises: two or more consecutive S, and R, and two or more consecutive S, and R, and two or more consecutive S. Non-limiting example(s) of such an oligonucleotide include: WV-9590.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-10251, WV-10254, WV-11958, WV-11962, WV-8597, WV-8599, WV-8625, WV-8638, WV-8646, WV-8666, WV-8674, WV-8678, WV-9670, WV-9862.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9870.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-11960, WV-8606, WV-8608, WV-8654, WV-8662, WV-8670, WV-8682, WV-8686, WV-9890, WV-9893, WV-9896, WV-8611, WV-9527.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9591.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8562, WV-8564, WV-8566, WV-8620, WV-8637, WV-8645, WV-8665, WV-8673.

In some embodiments of an oligonucleotide, e.g., an oligonucleotide having an asymmetric format: a core comprises: two or more consecutive S, and R, and two or more consecutive S, and RS. Non-limiting example(s) of such an oligonucleotide include: WV-8677.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-7657.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8099, WV-8105, WV-8322, WV-8329, WV-8572, WV-8578, WV-8584, WV-8590.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9507.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8597.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8599, WV-8625, WV-8638, WV-8646, WV-8666, WV-8674.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8678.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-8098, WV-8104, WV-8571, WV-8577, WV-8583, WV-8589, WV-8619, WV-9506.

In some embodiments of an oligonucleotide, e.g., an oligonucleotide having an asymmetric format: a core comprises: two or more consecutive S, and R, and two or more consecutive S. Non-limiting example(s) of such an oligonucleotide include: WV-9532.

In some embodiments of an oligonucleotide, e.g., an oligonucleotide having an asymmetric format: a core comprises: two or more consecutive S, and RS. Non-limiting example(s) of such an oligonucleotide include: WV-8098, WV-8104, WV-8571, WV-8577, WV-8583, WV-8589, WV-8619, WV-9506.

In some embodiments of an oligonucleotide, e.g., an oligonucleotide having an asymmetric format: a core comprises: two or more consecutive S, and RS. Non-limiting example(s) of such an oligonucleotide include: WV-9532.

In some embodiments of an oligonucleotide, e.g., an oligonucleotide having an asymmetric format: a core comprises: two or more consecutive S, and RS. Non-limiting example(s) of such an oligonucleotide include: WV-8618.

In some embodiments of an oligonucleotide, e.g., an oligonucleotide having an asymmetric format: a core comprises: two or more consecutive S, and RS. Non-limiting example(s) of such an oligonucleotide include: WV-9528.

In some embodiments of an oligonucleotide, e.g., an oligonucleotide having an asymmetric format: a core comprises: two or more consecutive S, and RS. Non-limiting example(s) of such an oligonucleotide include: WV-9592.

In some embodiments of an oligonucleotide, e.g., an oligonucleotide having an asymmetric format: a core comprises: 5 or more consecutive X. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: 6 or more consecutive X. Non-limiting example(s) of such an oligonucleotide include: WV-10243, WV-10245, WV-10249, WV-10252, WV-11963, WV-11964, WV-12445, WV-12446, WV-12447, WV-12448, WV-12449, WV-12450, WV-12451, WV-12480, WV-12481, WV-12482, WV-12483, WV-12484, WV-12486.

In some embodiments of an oligonucleotide, e.g., an oligonucleotide having an asymmetric format: a core comprises: 7 or more consecutive X. Non-limiting example(s) of such an oligonucleotide include: WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997.

In some embodiments of an oligonucleotide, e.g., an oligonucleotide having an asymmetric format: a core comprises: 8 or more consecutive X. Non-limiting example(s) of such an oligonucleotide include: WV-12999, WV-13000, WV-13001, WV-13002, WV-13003, WV-13004, WV-13005, WV-13006, WV-13007, WV-13008, WV-13804, WV-13805, WV-3421, WV-3662, WV-3688, WV-3690, WV-6408, WV-6474.

In some embodiments of an oligonucleotide, e.g., an oligonucleotide having an asymmetric format: a core comprises: 9 or more consecutive X. Non-limiting example(s) of such an oligonucleotide include: WV-8676, WV-8680, WV-8689, WV-8693, WV-8696, WV-8697, WV-8809, WV-8844, WV-8846, WV-8847, WV-8849, WV-8851, WV-8853, WV-8855, WV-8857, WV-8858, WV-8860.

In some embodiments of an oligonucleotide, e.g., an oligonucleotide having an asymmetric format: a core comprises: and two or more consecutive S and R. Non-limiting example(s) of such an oligonucleotide include: WV-8563, WV-8565, WV-8567, WV-8596, WV-8612, WV-8621, WV-8624, WV-8639, WV-8647, WV-8667, WV-8675.

In some embodiments of an oligonucleotide, e.g., an oligonucleotide having an asymmetric format: a core comprises: and two or more consecutive S and R. Non-limiting example(s) of such an oligonucleotide include: WV-8679.

In some embodiments of an oligonucleotide, e.g., an oligonucleotide having an asymmetric format: a core comprises: and two or more consecutive S and R, and two or more consecutive S. Non-limiting example(s) of such an oligonucleotide include: WV-8618.

In some embodiments of an oligonucleotide, e.g., an oligonucleotide having an asymmetric format: a core comprises: and two or more consecutive S and R, and two or more consecutive S. Non-limiting example(s) of such an oligonucleotide include: WV-9528.

In some embodiments of an oligonucleotide, e.g., an oligonucleotide having an asymmetric format: a core comprises: and two or more consecutive S and R, and two or more consecutive S. Non-limiting example(s) of such an oligonucleotide include: WV-9592.

In some embodiments of an oligonucleotide, e.g., an oligonucleotide having an asymmetric format: a core comprises: and two or more consecutive S and RS. Non-limiting example(s) of such an oligonucleotide include: WV-8097, WV-8103, WV-8248, WV-8250, WV-8570, WV-8576, WV-8582, WV-8588.

In some embodiments of an oligonucleotide, e.g., an oligonucleotide having an asymmetric format: a core comprises: and two or more consecutive S and RS. Non-limiting example(s) of such an oligonucleotide include: WV-8602.

In some embodiments of an oligonucleotide, e.g., an oligonucleotide having an asymmetric format: a core comprises: and two or more consecutive S and RS. Non-limiting example(s) of such an oligonucleotide include: WV-8605, WV-8616, WV-8655, WV-8663, WV-8671, WV-8683.

In some embodiments of an oligonucleotide, e.g., an oligonucleotide having an asymmetric format: a core comprises: and two or more consecutive S and RS. Non-limiting example(s) of such an oligonucleotide include: WV-8687.

In some embodiments of an oligonucleotide, e.g., an oligonucleotide having an asymmetric format: a core comprises: and two or more consecutive S and RS. Non-limiting example(s) of such an oligonucleotide include: WV-8563, WV-8565, WV-8567, WV-8596, WV-8612, WV-8621, WV-8624, WV-8639, WV-8647, WV-8667, WV-8675.

In some embodiments of an oligonucleotide, e.g., an oligonucleotide having an asymmetric format: a core comprises: and two or more consecutive S and RS. Non-limiting example(s) of such an oligonucleotide include: WV-8679.

In some embodiments of an oligonucleotide, e.g., an oligonucleotide having an asymmetric format: a core comprises: 0, and 4 or more consecutive S. Non-limiting example(s) of such an oligonucleotide include: WV-12101, WV-9394, WV-9396, WV-9398.

In some embodiments of an oligonucleotide, e.g., an oligonucleotide having an asymmetric format: a core comprises: O, and 5 or more consecutive S. Non-limiting example(s) of such an oligonucleotide include: WV-12101, WV-9394, WV-9396, WV-9398.

In some embodiments of an oligonucleotide, e.g., an oligonucleotide having an asymmetric format: a core comprises: 0, and 6 or more consecutive S. Non-limiting example(s) of such an oligonucleotide include: WV-12101, WV-9394, WV-9396, WV-9398.

In some embodiments of an oligonucleotide, e.g., an oligonucleotide having an asymmetric format: a core comprises: 0, and two or more consecutive X. Non-limiting example(s) of such an oligonucleotide include: WV-12105.

In some embodiments of an oligonucleotide, e.g., an oligonucleotide having an asymmetric format: a core comprises: 0, and two or more consecutive X. Non-limiting example(s) of such an oligonucleotide include: WV-12109.

In some embodiments of an oligonucleotide, e.g., an oligonucleotide having an asymmetric format: a core comprises: 0, and two or more consecutive X. Non-limiting example(s) of such an oligonucleotide include: WV-12107.

In some embodiments of an oligonucleotide, e.g., an oligonucleotide having an asymmetric format: a core comprises: 0, R and S. Non-limiting example(s) of such an oligonucleotide include: WV-12100, WV-12099, WV-12103, WV-12101.

In some embodiments of an oligonucleotide, e.g., an oligonucleotide having an asymmetric format: a core comprises: 0, R, and 4 or more consecutive S. Non-limiting example(s) of such an oligonucleotide include: WV-12099, WV-12103.

In some embodiments of an oligonucleotide, e.g., an oligonucleotide having an asymmetric format: a core comprises: OR, and two or more consecutive S, and R, and two or more consecutive S, and RO. Non-limiting example(s) of such an oligonucleotide include: WV-12100.

In some embodiments of an oligonucleotide, e.g., an oligonucleotide having an asymmetric format: a core comprises: OR, and two or more consecutive S, and R, and two or more consecutive S. Non-limiting example(s) of such an oligonucleotide include: WV-12099.

In some embodiments of an oligonucleotide, e.g., an oligonucleotide having an asymmetric format: a core comprises: OR, and two or more consecutive S, and R, and two or more consecutive S. Non-limiting example(s) of such an oligonucleotide include: WV-12103.

In some embodiments of an oligonucleotide, e.g., an oligonucleotide having an asymmetric format: a core comprises: OR, and two or more consecutive S, and R, and two or more consecutive S. Non-limiting example(s) of such an oligonucleotide include: WV-12101.

In some embodiments of an oligonucleotide, e.g., an oligonucleotide having an asymmetric format: a core comprises: R, and two or more consecutive S, and R, and two or more consecutive S, and R. Non-limiting example(s) of such an oligonucleotide include: WV-11533, WV-12110, WV-12112, WV-13303, WV-13304, WV-8083, WV-8102, WV-8108, WV-8575, WV-8581, WV-8587, WV-8593, WV-9058.

In some embodiments of an oligonucleotide, e.g., an oligonucleotide having an asymmetric format: a core comprises: R, and two or more consecutive S, and R, and two or more consecutive S, and R. Non-limiting example(s) of such an oligonucleotide include: WV-9059.

In some embodiments of an oligonucleotide, e.g., an oligonucleotide having an asymmetric format: a core comprises: R, and two or more consecutive S, and R, and two or more consecutive S. Non-limiting example(s) of such an oligonucleotide include: WV-12111.

In some embodiments of an oligonucleotide, e.g., an oligonucleotide having an asymmetric format: a core comprises: R, and two or more consecutive S, and R, and two or more consecutive S, and R, and two or more consecutive S. Non-limiting example(s) of such an oligonucleotide include: WV-10244, WV-10246, WV-9872.

In some embodiments of an oligonucleotide, e.g., an oligonucleotide having an asymmetric format: a core comprises: R, and two or more consecutive S, and R, and two or more consecutive S, and R, and two or more consecutive S. Non-limiting example(s) of such an oligonucleotide include: WV-9874.

In some embodiments of an oligonucleotide, e.g., an oligonucleotide having an asymmetric format: a core comprises: R, and two or more consecutive S, and R, and two or more consecutive S, and RS. Non-limiting example(s) of such an oligonucleotide include: WV-10250, WV-10253, WV-8560, WV-9859, WV-9861.

In some embodiments of an oligonucleotide, e.g., an oligonucleotide having an asymmetric format: a core comprises: R, and two or more consecutive S, and R, and two or more consecutive S, and RS. Non-limiting example(s) of such an oligonucleotide include: WV-9869.

In some embodiments of an oligonucleotide, e.g., an oligonucleotide having an asymmetric format: a core comprises: R, and two or more consecutive S, and R, and two or more consecutive S. Non-limiting example(s) of such an oligonucleotide include: WV-10251, WV-10254, WV-11958, WV-11962, WV-12100, WV-9670, WV-9862.

In some embodiments of an oligonucleotide, e.g., an oligonucleotide having an asymmetric format: a core comprises: R, and two or more consecutive S, and R, and two or more consecutive S. Non-limiting example(s) of such an oligonucleotide include: WV-9870.

In some embodiments of an oligonucleotide, e.g., an oligonucleotide having an asymmetric format: a core comprises: R, and two or more consecutive S, and R, and two or more consecutive S. Non-limiting example(s) of such an oligonucleotide include: WV-12101.

In some embodiments of an oligonucleotide, e.g., an oligonucleotide having an asymmetric format: a core comprises: SO, and two or more consecutive S. Non-limiting example(s) of such an oligonucleotide include: WV-9394.

In some embodiments of an oligonucleotide, e.g., an oligonucleotide having an asymmetric format: a core comprises: SO, and two or more consecutive S. Non-limiting example(s) of such an oligonucleotide include: WV-9396.

In some embodiments of an oligonucleotide, e.g., an oligonucleotide having an asymmetric format: a core comprises: SO, and two or more consecutive S. Non-limiting example(s) of such an oligonucleotide include: WV-9398.

In some embodiments of an oligonucleotide, e.g., an oligonucleotide having an asymmetric format: a core comprises: SO, and two or more consecutive S, and O, and two or more consecutive S. Non-limiting example(s) of such an oligonucleotide include: WV-9395, WV-9397.

In some embodiments of an oligonucleotide, e.g., an oligonucleotide having an asymmetric format: a core comprises: SO, and two or more consecutive S, and O, and two or more consecutive S. Non-limiting example(s) of such an oligonucleotide include: WV-9399.

In some embodiments of an oligonucleotide, e.g., an oligonucleotide having an asymmetric format: a core comprises: SR, and two or more consecutive S. Non-limiting example(s) of such an oligonucleotide include: WV-12893.

In some embodiments of an oligonucleotide, e.g., an oligonucleotide having an asymmetric format: a core comprises: SR, and two or more consecutive S. Non-limiting example(s) of such an oligonucleotide include: WV-13312, WV-13313, WV-14087, WV-7603, WV-7605, WV-7659, WV-8005, WV-8007, WV-8009, WV-8011, WV-8452, WV-8454.

In some embodiments of an oligonucleotide, e.g., an oligonucleotide having an asymmetric format: a core comprises: SR, and two or more consecutive S. Non-limiting example(s) of such an oligonucleotide include: WV-8456.

In some embodiments of an oligonucleotide, e.g., an oligonucleotide having an asymmetric format: a core comprises: SR, and two or more consecutive S, and R. Non-limiting example(s) of such an oligonucleotide include: WV-8259.

In some embodiments of an oligonucleotide, e.g., an oligonucleotide having an asymmetric format: a core comprises: SR, and two or more consecutive S, and R, and two or more consecutive S. Non-limiting example(s) of such an oligonucleotide include: WV-11532, WV-11965, WV-11967, WV-13305, WV-13306, WV-13307, WV-14552, WV-7124, WV-7130, WV-7601, WV-7604, WV-7606, WV-7658, WV-8006, WV-8008, WV-8010, WV-8012, WV-8101, WV-8107, WV-8321, WV-8453, WV-8455, WV-8580, WV-8586, WV-8592.

In some embodiments of an oligonucleotide, e.g., an oligonucleotide having an asymmetric format: a core comprises: SR, and two or more consecutive S, and R, and two or more consecutive S. Non-limiting example(s) of such an oligonucleotide include: WV-9508.

In some embodiments of an oligonucleotide, e.g., an oligonucleotide having an asymmetric format: a core comprises: SR, and two or more consecutive S, and R, and two or more consecutive S, and R. Non-limiting example(s) of such an oligonucleotide include: WV-11114, WV-12503, WV-12504, WV-12505, WV-13809, WV-14349, WV-8043, WV-8044, WV-8045, WV-8046, WV-8047, WV-8048, WV-8257.

In some embodiments of an oligonucleotide, e.g., an oligonucleotide having an asymmetric format: a core comprises: SR, and two or more consecutive S, and R, and two or more consecutive S, and R. Non-limiting example(s) of such an oligonucleotide include: WV-9696.

In some embodiments of an oligonucleotide, e.g., an oligonucleotide having an asymmetric format: a core comprises: SR, and two or more consecutive S, and R. Non-limiting example(s) of such an oligonucleotide include: WV-9697.

In some embodiments of an oligonucleotide, e.g., an oligonucleotide having an asymmetric format: a core comprises: SR, and two or more consecutive S, and R. Non-limiting example(s) of such an oligonucleotide include: WV-9698.

In some embodiments of an oligonucleotide, e.g., an oligonucleotide having an asymmetric format: a core comprises: SR, and two or more consecutive S, and R, and two or more consecutive S, and RS. Non-limiting example(s) of such an oligonucleotide include: WV-11533, WV-12110, WV-12112, WV-13303, WV-13304, WV-8083, WV-8102, WV-8108, WV-8575, WV-8581, WV-8587, WV-8593.

In some embodiments of an oligonucleotide, e.g., an oligonucleotide having an asymmetric format: a core comprises: SR, and two or more consecutive S, and R, and two or more consecutive S, and RS. Non-limiting example(s) of such an oligonucleotide include: WV-9058.

In some embodiments of an oligonucleotide, e.g., an oligonucleotide having an asymmetric format: a core comprises: SR, and two or more consecutive S, and R, and two or more consecutive S, and RS. Non-limiting example(s) of such an oligonucleotide include: WV-9059.

In some embodiments of an oligonucleotide, e.g., an oligonucleotide having an asymmetric format: a core comprises: SR, and two or more consecutive S, and R, and two or more consecutive S. Non-limiting example(s) of such an oligonucleotide include: WV-12111.

In some embodiments of an oligonucleotide, e.g., an oligonucleotide having an asymmetric format: a core comprises: SR, and two or more consecutive S, and RS. Non-limiting example(s) of such an oligonucleotide include: WV-13308, WV-13309, WV-13310, WV-13311, WV-9505.

In some embodiments of an oligonucleotide, e.g., an oligonucleotide having an asymmetric format: a core comprises: SR, and two or more consecutive S, and RS. Non-limiting example(s) of such an oligonucleotide include: WV-9509.

In some embodiments of an oligonucleotide, e.g., an oligonucleotide having an asymmetric format: a core comprises: two or more consecutive X. Non-limiting example(s) of such an oligonucleotide include: WV-8810.

In some embodiments of an oligonucleotide, e.g., an oligonucleotide having an asymmetric format: a core comprises: two or more consecutive X. Non-limiting example(s) of such an oligonucleotide include: WV-980.

In some embodiments of an oligonucleotide, e.g., an oligonucleotide having an asymmetric format: a core comprises: two or more consecutive X. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417.

In some embodiments of an oligonucleotide, e.g., an oligonucleotide having an asymmetric format: a core comprises: two or more consecutive X. Non-limiting example(s) of such an oligonucleotide include: WV-10418, WV-10419, WV-10420, WV-10421, WV-10422, WV-10423, WV-10424, WV-10425, WV-10426.

In some embodiments of an oligonucleotide, e.g., an oligonucleotide having an asymmetric format: a core comprises: two or more consecutive X. Non-limiting example(s) of such an oligonucleotide include: WV-10427.

In some embodiments of an oligonucleotide, e.g., an oligonucleotide having an asymmetric format: a core comprises: two or more consecutive X. Non-limiting example(s) of such an oligonucleotide include: WV-12484, WV-12486, WV-12977, WV-12978, WV-12979, WV-12980, WV-12981, WV-12982, WV-12983, WV-12984, WV-12985, WV-12986, WV-12987, WV-12988, WV-12989, WV-12990.

In some embodiments of an oligonucleotide, e.g., an oligonucleotide having an asymmetric format: a core comprises: two or more consecutive X. Non-limiting example(s) of such an oligonucleotide include: WV-12991.

In some embodiments of an oligonucleotide, e.g., an oligonucleotide having an asymmetric format: a core comprises: two or more consecutive X. Non-limiting example(s) of such an oligonucleotide include: WV-13005, WV-13006, WV-13007, WV-13008, WV-13804, WV-13805, WV-3421, WV-3662, WV-3688, WV-3690, WV-6408, WV-6474, WV-6936.

In some embodiments of an oligonucleotide, e.g., an oligonucleotide having an asymmetric format: a core comprises: two or more consecutive X. Non-limiting example(s) of such an oligonucleotide include: WV-6951.

In some embodiments of an oligonucleotide, e.g., an oligonucleotide having an asymmetric format: a core comprises: two or more consecutive X. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a core comprises: two or more consecutive X. Non-limiting example(s) of such an oligonucleotide include: WV-10423.

In some embodiments of an oligonucleotide, e.g., an oligonucleotide having an asymmetric format: a core comprises: two or more consecutive X. Non-limiting example(s) of such an oligonucleotide include: WV-10424, WV-10425, WV-10426, WV-10427, WV-11966, WV-12113, WV-12114, WV-12439, WV-12440, WV-12441, WV-12442, WV-12443, WV-12444, WV-12485, WV-12582, WV-12583, WV-12947, WV-12948, WV-12949, WV-12950, WV-12951, WV-12952.

In some embodiments of an oligonucleotide, e.g., an oligonucleotide having an asymmetric format: a core comprises: two or more consecutive X. Non-limiting example(s) of such an oligonucleotide include: WV-12953.

In some embodiments of an oligonucleotide, e.g., an oligonucleotide having an asymmetric format: a core comprises: two or more O, two or more R, and two or more S. Non-limiting example(s) of such an oligonucleotide include: WV-12100, WV-12099, WV-12103, WV-12101.

In some embodiments of an oligonucleotide, e.g., an oligonucleotide having an asymmetric format, a first and/or a second wing can comprise any internucleotidic linkage described herein or known in the art, or any pattern or combination of two or more different internucleotidic linkages, wherein R=PS (phosphorothioate) in the Rp configuration, S=PS in the Sp configuration, O=PO (phosphodiester), and X is a stereorandom (not chirally controlled) PS, and nX=a non-negatively charged (e.g., neutral) internucleotidic linkage.

In some embodiments of an oligonucleotide, e.g., an oligonucleotide having an asymmetric format: a first wing comprises: S and nX; and a second wing comprises: S and no nX. Non-limiting example(s) of such an oligonucleotide include: WV-15361.

In some embodiments of an oligonucleotide, e.g., an oligonucleotide having an asymmetric format: a first wing comprises: S and nX; and a second wing comprises: S and O. Non-limiting example(s) of such an oligonucleotide include: WV-15361.

In some embodiments of an oligonucleotide, e.g., an oligonucleotide having an asymmetric format: a first wing comprises: S and nX; and a second wing comprises: S and O and no nX. Non-limiting example(s) of such an oligonucleotide include: WV-15361.

In some embodiments of an oligonucleotide, e.g., an oligonucleotide having an asymmetric format: a first wing comprises: nX; and a second wing comprises: no nX. Non-limiting example(s) of such an oligonucleotide include: WV-11533, WV-14556, WV-14557, WV-14558, WV-14559, WV-14560, WV-14561, WV-14562, WV-14563, WV-14564.

In some embodiments of an oligonucleotide, e.g., an oligonucleotide having an asymmetric format: a first wing comprises: nX and O; and a second wing comprises: S. Non-limiting example(s) of such an oligonucleotide include: WV-14556, WV-14557, WV-14558, WV-14559, WV-14560, WV-14561, WV-14562, WV-14563, WV-14564.

In some embodiments of an oligonucleotide, e.g., an oligonucleotide having an asymmetric format: a first wing comprises: nX and O; and a second wing comprises: two or more S. Non-limiting example(s) of such an oligonucleotide include: WV-14556, WV-14557, WV-14558, WV-14559, WV-14560, WV-14561, WV-14562, WV-14563, WV-14564.

In some embodiments of an oligonucleotide, e.g., an oligonucleotide having an asymmetric format: a first wing comprises: X and 2 or more consecutive O; and a second wing comprises: 2 or more consecutive X. Non-limiting example(s) of such an oligonucleotide include: WV-10249, and WV-10252.

In some embodiments of an oligonucleotide, e.g., an oligonucleotide having an asymmetric format: a first wing comprises: XOOOOO; and a second wing comprises: XXXXXX. Non-limiting example(s) of such an oligonucleotide include: WV-12109.

In some embodiments of an oligonucleotide, e.g., an oligonucleotide having an asymmetric format: a first wing comprises: XOOO; and a second wing comprises: XXXX. Non-limiting example(s) of such an oligonucleotide include: WV-10249, and WV-10252.

In some embodiments of an oligonucleotide, e.g., an oligonucleotide having an asymmetric format: a first wing comprises: S and 2 or more consecutive O; and a second wing comprises: 2 or more consecutive S. Non-limiting example(s) of such an oligonucleotide include: WV-10250, and WV-10251.

In some embodiments of an oligonucleotide, e.g., an oligonucleotide having an asymmetric format: a first wing comprises: SOOO; and a second wing comprises: SSSS. Non-limiting example(s) of such an oligonucleotide include: WV-10250, and WV-10251.

In some embodiments of an oligonucleotide, e.g., an oligonucleotide having an asymmetric format: a first wing comprises: SOOOOO; and a second wing comprises: SSSSSS. Non-limiting example(s) of such an oligonucleotide include: WV-11962.

In some embodiments of an oligonucleotide, e.g., an oligonucleotide having an asymmetric format: a first wing comprises: 2 or more consecutive S; and a second wing comprises: 2 or more consecutive R. Non-limiting example(s) of such an oligonucleotide include: WV-8044.

In some embodiments of an oligonucleotide, e.g., an oligonucleotide having an asymmetric format: a first wing comprises: SSSS; and a second wing comprises: RRRR. Non-limiting example(s) of such an oligonucleotide include: WV-8044.

In some embodiments of an oligonucleotide, e.g., an oligonucleotide having an asymmetric format: a first wing comprises: 2 or more consecutive S; and a second wing comprises: 2 or more consecutive O and S. Non-limiting example(s) of such an oligonucleotide include: WV-8045.

In some embodiments of an oligonucleotide, e.g., an oligonucleotide having an asymmetric format: a first wing comprises: SSSS; and a second wing comprises: OOOS. Non-limiting example(s) of such an oligonucleotide include: WV-8045.

In some embodiments of an oligonucleotide, e.g., an oligonucleotide having an asymmetric format: a first wing comprises: 2 or more consecutive S; and a second wing comprises: 2 or more consecutive O R. Non-limiting example(s) of such an oligonucleotide include: WV-8047.

In some embodiments of an oligonucleotide, e.g., an oligonucleotide having an asymmetric format: a first wing comprises: SSSS; and a second wing comprises: OOOR. Non-limiting example(s) of such an oligonucleotide include: WV-8047.

In some embodiments of an oligonucleotide, e.g., an oligonucleotide having an asymmetric format: a first wing comprises: two or more consecutive X; and/or a second wing comprises: two or more consecutive X. Non-limiting example(s) of such an oligonucleotide include: WV-10426, WV-10427, WV-3174, WV-3536, WV-3542, WV-9431, WV-9432, WV-9433, WV-9434, WV-9435.

In some embodiments of an oligonucleotide, e.g., an oligonucleotide having an asymmetric format: a first wing comprises: two or more consecutive X; and/or a second wing comprises: XX, and two or more consecutive O, and X. Non-limiting example(s) of such an oligonucleotide include: WV-12445, WV-12446, WV-12447, WV-12448, WV-12449, WV-12450, WV-12451, WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000, WV-13001, WV-13002, WV-13003, WV-13004, WV-13005, WV-13006, WV-13007, WV-13008, WV-8844, WV-8846, WV-8847, WV-8849, WV-8851, WV-8853, WV-8855, WV-8857, WV-8858, WV-8860.

In some embodiments of an oligonucleotide, e.g., an oligonucleotide having an asymmetric format: a first wing comprises: XO, and two or more consecutive X; and/or a second wing comprises: XX, and two or more consecutive O, and XX. Non-limiting example(s) of such an oligonucleotide include: WV-8110.

In some embodiments of an oligonucleotide, e.g., an oligonucleotide having an asymmetric format: a first wing comprises: X, and two or more consecutive O, and XXX; and/or a second wing comprises: two or more consecutive X. Non-limiting example(s) of such an oligonucleotide include: WV-8553.

In some embodiments of an oligonucleotide, e.g., an oligonucleotide having an asymmetric format: a first wing comprises: X, and two or more consecutive O, and XXX; and/or a second wing comprises: XX, and two or more consecutive O, and XX. Non-limiting example(s) of such an oligonucleotide include: WV-8555.

In some embodiments of an oligonucleotide, e.g., an oligonucleotide having an asymmetric format: a first wing comprises: X, and two or more consecutive O, and XX; and/or a second wing comprises: two or more consecutive X. Non-limiting example(s) of such an oligonucleotide include: WV-10406, WV-10407, WV-10408, WV-10409, WV-10410, WV-10411, WV-10412, WV-10413, WV-10414, WV-10415, WV-10416, WV-10417, WV-10418, WV-10419, WV-10420, WV-10421, WV-10422.

In some embodiments of an oligonucleotide, e.g., an oligonucleotide having an asymmetric format: a first wing comprises: X, and two or more consecutive O, and XX; and/or a second wing comprises: two or more consecutive X. Non-limiting example(s) of such an oligonucleotide include: WV-10423, WV-10424, WV-10425, WV-11966, WV-12113, WV-12439, WV-12440, WV-12441, WV-12442, WV-12443, WV-12444, WV-12582, WV-12583, WV-12947, WV-12948, WV-12949, WV-12950, WV-12951, WV-12952, WV-12953.

In some embodiments of an oligonucleotide, e.g., an oligonucleotide having an asymmetric format: a first wing comprises: X, and two or more consecutive O, and XX; and/or a second wing comprises: two or more consecutive X. Non-limiting example(s) of such an oligonucleotide include: WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, WV-12976, WV-8548, WV-8550, WV-8552, WV-8556, WV-8594, WV-8595, WV-8609, WV-8617, WV-8656, WV-8664, WV-8672, WV-8684, WV-8688.

In some embodiments of an oligonucleotide, e.g., an oligonucleotide having an asymmetric format: a first wing comprises: X, and two or more consecutive O, and XX; and/or a second wing comprises: two or more consecutive X. Non-limiting example(s) of such an oligonucleotide include:

WV-8690, WV-8845, WV-8848, WV-8850, WV-8852, WV-8854, WV-8856, WV-8859, WV-9441, WV-9442, WV-9443, WV-9444, WV-9445, WV-9486, WV-9487, WV-9488, WV-9489, WV-9490, WV-9491, WV-9492, WV-9494, WV-9510, WV-9533, WV-9885, WV-9887, WV-9891, WV-9894.

In some embodiments of an oligonucleotide, e.g., an oligonucleotide having an asymmetric format: a first wing comprises: X, and two or more consecutive O, and XX; and/or a second wing comprises: XXXOXX. Non-limiting example(s) of such an oligonucleotide include: WV-8551, WV-8693, WV-9061.

In some embodiments of an oligonucleotide, e.g., an oligonucleotide having an asymmetric format: a first wing comprises: X, and two or more consecutive O, and XX; and/or a second wing comprises: XXOXXX. Non-limiting example(s) of such an oligonucleotide include: WV-9060, WV-8547, WV-8549, WV-8554, WV-8557, WV-8696.

In some embodiments of an oligonucleotide, e.g., an oligonucleotide having an asymmetric format: a first wing comprises: X, and two or more consecutive O, and XX; and/or a second wing comprises: XX, and two or more consecutive O, and X. Non-limiting example(s) of such an oligonucleotide include: WV-11963, WV-11964, WV-12480, WV-12481, WV-12482, WV-12483, WV-12484, WV-12486, WV-3421, WV-3662, WV-3688, WV-3690, WV-6408, WV-6474, WV-6936, WV-6951, WV-6952, WV-6969, WV-6976, WV-6981, WV-6982, WV-6989, WV-7002, WV-7027, WV-7118, WV-7805, WV-8109, WV-9436, WV-9437, WV-9438, WV-9439, WV-9440, WV-9493, WV-9694, WV-9695, WV-12485.

In some embodiments of an oligonucleotide, e.g., an oligonucleotide having an asymmetric format: a first wing comprises: X, and two or more consecutive O, and XX; and/or a second wing comprises: XX, and two or more consecutive Xn, and X. Non-limiting example(s) of such an oligonucleotide include: WV-13804.

In some embodiments of an oligonucleotide, e.g., an oligonucleotide having an asymmetric format: a first wing comprises: X, and two or more consecutive O X; and/or a second wing comprises: two or more consecutive X. Non-limiting example(s) of such an oligonucleotide include: WV-12114.

In some embodiments of an oligonucleotide, e.g., an oligonucleotide having an asymmetric format: a first wing comprises: X, and two or more consecutive O; and/or a second wing comprises: two or more consecutive X. Non-limiting example(s) of such an oligonucleotide include: WV-12107.

In some embodiments of an oligonucleotide, e.g., an oligonucleotide having an asymmetric format: a first wing comprises: X, and two or more consecutive Xn, and XX; and/or a second wing comprises: two or more consecutive X. Non-limiting example(s) of such an oligonucleotide include: WV-13803.

In some embodiments of an oligonucleotide, e.g., an oligonucleotide having an asymmetric format: a first wing comprises: X, and two or more consecutive Xn, and XX; and/or a second wing comprises: XX, and two or more consecutive Xn, and X. Non-limiting example(s) of such an oligonucleotide include: WV-13805.

In some embodiments of an oligonucleotide, e.g., an oligonucleotide having an asymmetric format: a first wing comprises: two or more consecutive S; and/or a second wing comprises: two or more consecutive S. Non-limiting example(s) of such an oligonucleotide include: WV-8315, WV-8311.

In some embodiments of an oligonucleotide, e.g., an oligonucleotide having an asymmetric format: a first wing comprises: two or more consecutive S; and/or a second wing comprises: SR, and two or more consecutive O, and R. Non-limiting example(s) of such an oligonucleotide include: WV-8318.

In some embodiments of an oligonucleotide, e.g., an oligonucleotide having an asymmetric format: a first wing comprises: two or more consecutive S O, and two or more consecutive S, and; and/or a second wing comprises: two or more consecutive S, and two or more consecutive O, and S. Non-limiting example(s) of such an oligonucleotide include: WV-8122.

In some embodiments of an oligonucleotide, e.g., an oligonucleotide having an asymmetric format: a first wing comprises: two or more consecutive S O, and two or more consecutive S, and; and/or a second wing comprises: two or more consecutive S, and two or more consecutive O, and S. Non-limiting example(s) of such an oligonucleotide include: WV-8114.

In some embodiments of an oligonucleotide, e.g., an oligonucleotide having an asymmetric format: a first wing comprises: two or more consecutive S O, and two or more consecutive S, and; and/or a second wing comprises: two or more consecutive S, and, and two or more consecutive O, and S. Non-limiting example(s) of such an oligonucleotide include: WV-8125.

In some embodiments of an oligonucleotide, e.g., an oligonucleotide having an asymmetric format: a first wing comprises: two or more consecutive S O, and two or more consecutive S, and; and/or a second wing comprises: two or more consecutive S, and, and two or more consecutive O, and S. Non-limiting example(s) of such an oligonucleotide include: WV-8117.

In some embodiments of an oligonucleotide, e.g., an oligonucleotide having an asymmetric format: a first wing comprises: two or more consecutive S O, and two or more consecutive S, and; and/or a second wing comprises: two or more consecutive S, and, and two or more consecutive O, and R. Non-limiting example(s) of such an oligonucleotide include: WV-8314.

In some embodiments of an oligonucleotide, e.g., an oligonucleotide having an asymmetric format: a first wing comprises: two or more consecutive S, and, and two or more consecutive O, and, and two or more consecutive S, and; and/or a second wing comprises: two or more consecutive S, and two or more consecutive O, and S. Non-limiting example(s) of such an oligonucleotide include: WV-8124, WV-8116.

In some embodiments of an oligonucleotide, e.g., an oligonucleotide having an asymmetric format: a first wing comprises: two or more consecutive S, and, and two or more consecutive O, and, and two or more consecutive S, and; and/or a second wing comprises: two or more consecutive S, and, and two or more consecutive O, and S. Non-limiting example(s) of such an oligonucleotide include: WV-8128, WV-8129, WV-8120, WV-8121.

In some embodiments of an oligonucleotide, e.g., an oligonucleotide having an asymmetric format: a first wing comprises: SO, and two or more consecutive S; and/or a second wing comprises: two or more consecutive S, and, and two or more consecutive O, and, and two or more consecutive S. Non-limiting example(s) of such an oligonucleotide include: WV-8108, WV-8107, WV-8106, WV-8105, WV-8104, WV-8103.

In some embodiments of an oligonucleotide, e.g., an oligonucleotide having an asymmetric format: a first wing comprises: SOSO, and two or more consecutive S, and; and/or a second wing comprises: two or more consecutive S, and two or more consecutive O, and S. Non-limiting example(s) of such an oligonucleotide include: WV-8123.

In some embodiments of an oligonucleotide, e.g., an oligonucleotide having an asymmetric format: a first wing comprises: SOSO, and two or more consecutive S, and; and/or a second wing comprises: two or more consecutive S, and two or more consecutive O, and S. Non-limiting example(s) of such an oligonucleotide include: WV-8115.

In some embodiments of an oligonucleotide, e.g., an oligonucleotide having an asymmetric format: a first wing comprises: SOSO, and two or more consecutive S, and; and/or a second wing comprises: two or more consecutive S, and, and two or more consecutive O, and S. Non-limiting example(s) of such an oligonucleotide include: WV-8127.

In some embodiments of an oligonucleotide, e.g., an oligonucleotide having an asymmetric format: a first wing comprises: SOSO, and two or more consecutive S, and; and/or a second wing comprises: two or more consecutive S, and, and two or more consecutive O, and S. Non-limiting example(s) of such an oligonucleotide include: WV-8119.

In some embodiments of an oligonucleotide, e.g., an oligonucleotide having an asymmetric format: a first wing comprises: S, and two or more consecutive O, and, and two or more consecutive S; and/or a second wing comprises: two or more consecutive S. Non-limiting example(s) of such an oligonucleotide include: WV-8476.

In some embodiments of an oligonucleotide, e.g., an oligonucleotide having an asymmetric format: a first wing comprises: S, and two or more consecutive O, and, and two or more consecutive S; and/or a second wing comprises: two or more consecutive S, and two or more consecutive O, and S. Non-limiting example(s) of such an oligonucleotide include: WV-8475.

In some embodiments of an oligonucleotide, e.g., an oligonucleotide having an asymmetric format: a first wing comprises: S, and two or more consecutive O, and, and two or more consecutive S; and/or a second wing comprises: two or more consecutive S, and two or more consecutive O, and S. Non-limiting example(s) of such an oligonucleotide include: WV-8474.

In some embodiments of an oligonucleotide, e.g., an oligonucleotide having an asymmetric format: a first wing comprises: S, and two or more consecutive O, and, and two or more consecutive S; and/or a second wing comprises: two or more consecutive S, and, and two or more consecutive O, and S. Non-limiting example(s) of such an oligonucleotide include: WV-8473.

In some embodiments of an oligonucleotide, e.g., an oligonucleotide having an asymmetric format: a first wing comprises: S, and two or more consecutive O, and, and two or more consecutive S; and/or a second wing comprises: two or more consecutive S, and, and two or more consecutive O, and S. Non-limiting example(s) of such an oligonucleotide include: WV-8472.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S. Non-limiting example(s) of such an oligonucleotide include: WV-8587, WV-9395, WV-9397, WV-9399, WV-9394, WV-9396, WV-9398, WV-11967, WV-7606, WV-8012, WV-8586, WV-9508, WV-9505, WV-9509, WV-12893, WV-14087, WV-7605, WV-8011, WV-8569, WV-8614, WV-9530, WV-8615, WV-9531, WV-8568, WV-8585, WV-8601, WV-8653, WV-8661, WV-8669, WV-8681, WV-8685, WV-8606.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S. Non-limiting example(s) of such an oligonucleotide include: WV-8654, WV-8662, WV-8670, WV-8682, WV-8686, WV-8584, WV-9507, WV-8583, WV-8619, WV-9506, WV-9532, WV-8582, WV-8602, WV-8605, WV-8616, WV-8655, WV-8663, WV-8671, WV-8683.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S. Non-limiting example(s) of such an oligonucleotide include: WV-8687.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S O, and two or more consecutive S. Non-limiting example(s) of such an oligonucleotide include: WV-9059, WV-8455, WV-8454, WV-8692, WV-8691.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and two or more consecutive O, and S. Non-limiting example(s) of such an oligonucleotide include: WV-8126.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and two or more consecutive O, and S. Non-limiting example(s) of such an oligonucleotide include: WV-8118.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and O, and two or more consecutive S. Non-limiting example(s) of such an oligonucleotide include: WV-9058.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive O, and, and two or more consecutive S. Non-limiting example(s) of such an oligonucleotide include: WV-8593, WV-7604, WV-8010, WV-8592, WV-7603, WV-8009, WV-8695, WV-8591, WV-8694, WV-8590, WV-8589.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive O, and, and two or more consecutive S. Non-limiting example(s) of such an oligonucleotide include: WV-8588, WV-8083, WV-8102, WV-11965, WV-7124, WV-7130, WV-8101, WV-8453, WV-8452, WV-8100, WV-8246, WV-8603, WV-8608, WV-8099, WV-8098, WV-8097, WV-8248.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive O, and S. Non-limiting example(s) of such an oligonucleotide include: WV-8250.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive Xn, and S. Non-limiting example(s) of such an oligonucleotide include: WV-13303.

In some embodiments of an oligonucleotide, e.g., an oligonucleotide having an asymmetric format: a first wing comprises: S, and two or more consecutive O, and RS; and/or a second wing comprises: two or more consecutive S. Non-limiting example(s) of such an oligonucleotide include: WV-12110, WV-12111, WV-13306, WV-13310, WV-9886, WV-9892, WV-11960.

In some embodiments of an oligonucleotide, e.g., an oligonucleotide having an asymmetric format: a first wing comprises: S, and two or more consecutive O, and RS; and/or a second wing comprises: two or more consecutive S. Non-limiting example(s) of such an oligonucleotide include: WV-9893.

In some embodiments of an oligonucleotide, e.g., an oligonucleotide having an asymmetric format: a first wing comprises: S, and two or more consecutive O, and RS; and/or a second wing comprises: SR, and two or more consecutive S. Non-limiting example(s) of such an oligonucleotide include: WV-9888, WV-9895, WV-9896.

In some embodiments of an oligonucleotide, e.g., an oligonucleotide having an asymmetric format: a first wing comprises: S, and two or more consecutive O, and RS; and/or a second wing comprises: SR, and two or more consecutive O, and S. Non-limiting example(s) of such an oligonucleotide include: WV-9889.

In some embodiments of an oligonucleotide, e.g., an oligonucleotide having an asymmetric format: a first wing comprises: S, and two or more consecutive O, and RS; and/or a second wing comprises: SR, and two or more consecutive O, and S. Non-limiting example(s) of such an oligonucleotide include: WV-9890.

In some embodiments of an oligonucleotide, e.g., an oligonucleotide having an asymmetric format: a first wing comprises: S, and two or more consecutive O, and S; and/or a second wing comprises: two or more consecutive S. Non-limiting example(s) of such an oligonucleotide include: WV-12112.

In some embodiments of an oligonucleotide, e.g., an oligonucleotide having an asymmetric format: a first wing comprises: S, and two or more consecutive O; and/or a second wing comprises: two or more consecutive S. Non-limiting example(s) of such an oligonucleotide include: WV-12101.

In some embodiments of an oligonucleotide, e.g., an oligonucleotide having an asymmetric format: a first wing comprises: S, and two or more consecutive O; and/or a second wing comprises: R, and two or more consecutive O, and S. Non-limiting example(s) of such an oligonucleotide include: WV-12100.

In some embodiments of an oligonucleotide, e.g., an oligonucleotide having an asymmetric format: a first wing comprises: S, and two or more consecutive Xn, and, and two or more consecutive S, and; and/or a second wing comprises: two or more consecutive S. Non-limiting example(s) of such an oligonucleotide include: WV-11533.

In some embodiments of an oligonucleotide, e.g., an oligonucleotide having an asymmetric format: a first wing comprises: S, and two or more consecutive Xn, and, and two or more consecutive S, and; and/or a second wing comprises: two or more consecutive S. Non-limiting example(s) of such an oligonucleotide include: WV-11532.

In some embodiments of an oligonucleotide, e.g., an oligonucleotide having an asymmetric format: a first wing comprises: S, and two or more consecutive Xn, and, and two or more consecutive S, and; and/or a second wing comprises: two or more consecutive S. Non-limiting example(s) of such an oligonucleotide include: WV-13312.

In some embodiments of an oligonucleotide, e.g., an oligonucleotide having an asymmetric format: a first wing comprises: S, and two or more consecutive Xn, and, and two or more consecutive S, and; and/or a second wing comprises: two or more consecutive S, and, and two or more consecutive Xn, and S. Non-limiting example(s) of such an oligonucleotide include: WV-13304.

In some embodiments of an oligonucleotide, e.g., an oligonucleotide having an asymmetric format: a first wing comprises: S, and two or more consecutive Xn, and RS; and/or a second wing comprises: two or more consecutive S. Non-limiting example(s) of such an oligonucleotide include: WV-13307.

In some embodiments of an oligonucleotide, e.g., an oligonucleotide having an asymmetric format: a first wing comprises: S, and two or more consecutive Xn, and RS; and/or a second wing comprises: two or more consecutive S. Non-limiting example(s) of such an oligonucleotide include: WV-13311.

In some embodiments of an oligonucleotide, e.g., an oligonucleotide having an asymmetric format: a first wing comprises: two or more consecutive R, and S; and/or a second wing comprises: two or more consecutive S, and, and two or more consecutive R. Non-limiting example(s) of such an oligonucleotide include: WV-8313.

In some embodiments of an oligonucleotide, e.g., an oligonucleotide having an asymmetric format: a first wing comprises: two or more consecutive R, and S; and/or a second wing comprises: S, and two or more consecutive R. Non-limiting example(s) of such an oligonucleotide include: WV-7601, WV-8317.

In some embodiments of an oligonucleotide, e.g., an oligonucleotide having an asymmetric format: a first wing comprises: two or more consecutive R, and S; and/or a second wing comprises: S, and two or more consecutive R. Non-limiting example(s) of such an oligonucleotide include: WV-7657.

In some embodiments of an oligonucleotide, e.g., an oligonucleotide having an asymmetric format: a first wing comprises: R, and two or more consecutive R, and ORS; and/or a second wing comprises: SR, and two or more consecutive O, and, and two or more consecutive R. Non-limiting example(s) of such an oligonucleotide include: WV-8322.

In some embodiments of an oligonucleotide, e.g., an oligonucleotide having an asymmetric format: a first wing comprises: two or more consecutive R, and, and two or more consecutive O, and RS; and/or a second wing comprises: SR, and two or more consecutive O, and, and two or more consecutive R. Non-limiting example(s) of such an oligonucleotide include: WV-8321.

In some embodiments of an oligonucleotide, e.g., an oligonucleotide having an asymmetric format: a first wing comprises: two or more consecutive R, and, and two or more consecutive O, and RS; and/or a second wing comprises: SR, and two or more consecutive O, and, and two or more consecutive R. Non-limiting example(s) of such an oligonucleotide include: WV-8329.

In some embodiments of an oligonucleotide, e.g., an oligonucleotide having an asymmetric format: a first wing comprises: R, and two or more consecutive O, and RS; and/or a second wing comprises: two or more consecutive S. Non-limiting example(s) of such an oligonucleotide include: WV-8575, WV-8008, WV-13308, WV-8007, WV-8471, WV-8470, WV-8573.

In some embodiments of an oligonucleotide, e.g., an oligonucleotide having an asymmetric format: a first wing comprises: R, and two or more consecutive O, and RS; and/or a second wing comprises: two or more consecutive S. Non-limiting example(s) of such an oligonucleotide include: WV-8572, WV-8571.

In some embodiments of an oligonucleotide, e.g., an oligonucleotide having an asymmetric format: a first wing comprises: R, and two or more consecutive O, and RS; and/or a second wing comprises: two or more consecutive S. Non-limiting example(s) of such an oligonucleotide include: WV-8570.

In some embodiments of an oligonucleotide, e.g., an oligonucleotide having an asymmetric format: a first wing comprises: R, and two or more consecutive O, and RS; and/or a second wing comprises: two or more consecutive S, and two or more consecutive O, and S. Non-limiting example(s) of such an oligonucleotide include: WV-8469.

In some embodiments of an oligonucleotide, e.g., an oligonucleotide having an asymmetric format: a first wing comprises: R, and two or more consecutive O, and RS; and/or a second wing comprises: two or more consecutive S, and two or more consecutive O, and S. Non-limiting example(s) of such an oligonucleotide include: WV-8468.

In some embodiments of an oligonucleotide, e.g., an oligonucleotide having an asymmetric format: a first wing comprises: R, and two or more consecutive O, and RS; and/or a second wing comprises: two or more consecutive S, and, and two or more consecutive O, and, and two or more consecutive S. Non-limiting example(s) of such an oligonucleotide include: WV-8581, WV-8006, WV-8580, WV-8005, WV-8579, WV-8578, WV-8577.

In some embodiments of an oligonucleotide, e.g., an oligonucleotide having an asymmetric format: a first wing comprises: R, and two or more consecutive O, and RS; and/or a second wing comprises: two or more consecutive S, and, and two or more consecutive O, and, and two or more consecutive S. Non-limiting example(s) of such an oligonucleotide include: WV-8576.

In some embodiments of an oligonucleotide, e.g., an oligonucleotide having an asymmetric format: a first wing comprises: R, and two or more consecutive O, and RS; and/or a second wing comprises: two or more consecutive S, and, and two or more consecutive O, and S. Non-limiting example(s) of such an oligonucleotide include: WV-8456, WV-8467, WV-8466.

In some embodiments of an oligonucleotide, e.g., an oligonucleotide having an asymmetric format: a first wing comprises: R, and two or more consecutive O, and RS; and/or a second wing comprises: two or more consecutive S, and, and two or more consecutive O, and R. Non-limiting example(s) of such an oligonucleotide include: WV-8312.

In some embodiments of an oligonucleotide, e.g., an oligonucleotide having an asymmetric format: a first wing comprises: R, and two or more consecutive O, and RS; and/or a second wing comprises: SR, and two or more consecutive S. Non-limiting example(s) of such an oligonucleotide include: WV-14552.

In some embodiments of an oligonucleotide, e.g., an oligonucleotide having an asymmetric format: a first wing comprises: R, and two or more consecutive O, and RS; and/or a second wing comprises: SR, and two or more consecutive O, and R. Non-limiting example(s) of such an oligonucleotide include: WV-7658.

In some embodiments of an oligonucleotide, e.g., an oligonucleotide having an asymmetric format: a first wing comprises: R, and two or more consecutive O, and RS; and/or a second wing comprises: SR, and two or more consecutive O, and R. Non-limiting example(s) of such an oligonucleotide include: WV-7659.

In some embodiments of an oligonucleotide, e.g., an oligonucleotide having an asymmetric format: a first wing comprises: R, and two or more consecutive O, and RS; and/or a second wing comprises: SR, and two or more consecutive O, and R. Non-limiting example(s) of such an oligonucleotide include: WV-8316.

In some embodiments of an oligonucleotide, e.g., an oligonucleotide having an asymmetric format: a first wing comprises: R, and two or more consecutive Xn, and RS; and/or a second wing comprises: two or more consecutive S. Non-limiting example(s) of such an oligonucleotide include: WV-13305.

In some embodiments of an oligonucleotide, e.g., an oligonucleotide having an asymmetric format: a first wing comprises: R, and two or more consecutive Xn, and RS; and/or a second wing comprises: two or more consecutive S. Non-limiting example(s) of such an oligonucleotide include: WV-13309.

In some embodiments of an oligonucleotide, e.g., an oligonucleotide having an asymmetric format: a first wing comprises: R, and two or more consecutive Xn, and RS; and/or a second wing comprises: two or more consecutive S. Non-limiting example(s) of such an oligonucleotide include: WV-13313.

In some embodiments of an oligonucleotide, e.g., an oligonucleotide having an asymmetric format: a first wing comprises: O, and two or more consecutive X; and/or a second wing comprises: two or more consecutive X. Non-limiting example(s) of such an oligonucleotide include: WV-8448.

In some embodiments of an oligonucleotide, e.g., an oligonucleotide having an asymmetric format: a first wing comprises: O, and two or more consecutive X; and/or a second wing comprises: two or more consecutive X. Non-limiting example(s) of such an oligonucleotide include: WV-8809.

In some embodiments of an oligonucleotide, e.g., an oligonucleotide having an asymmetric format: a first wing comprises: OX, and two or more consecutive O, and X; and/or a second wing comprises: two or more consecutive X. Non-limiting example(s) of such an oligonucleotide include: WV-10243, WV-10245, WV-10249, WV-10252, WV-8600, WV-8613, WV-8628, WV-8632, WV-8640, WV-8648, WV-8668, WV-8676, WV-8680, WV-8689, WV-8697, WV-9529, WV-9593, WV-9860, WV-9868, WV-9871.

In some embodiments of an oligonucleotide, e.g., an oligonucleotide having an asymmetric format: a first wing comprises: OX, and two or more consecutive O, and X; and/or a second wing comprises: two or more consecutive X. Non-limiting example(s) of such an oligonucleotide include: WV-9873.

In some embodiments of an oligonucleotide, e.g., an oligonucleotide having an asymmetric format: a first wing comprises: OX, and two or more consecutive O, and X; and/or a second wing comprises: XX, and two or more consecutive O, and X. Non-limiting example(s) of such an oligonucleotide include: WV-8132.

In some embodiments of an oligonucleotide, e.g., an oligonucleotide having an asymmetric format: a first wing comprises: OX, and two or more consecutive O; and/or a second wing comprises: two or more consecutive X. Non-limiting example(s) of such an oligonucleotide include: WV-12105.

In some embodiments of an oligonucleotide, e.g., an oligonucleotide having an asymmetric format: a first wing comprises: OX, and two or more consecutive O; and/or a second wing comprises: two or more consecutive X. Non-limiting example(s) of such an oligonucleotide include: WV-12109.

In some embodiments of an oligonucleotide, e.g., an oligonucleotide having an asymmetric format: a first wing comprises: O, and two or more consecutive S; and/or a second wing comprises: two or more consecutive S. Non-limiting example(s) of such an oligonucleotide include: WV-8043.

In some embodiments of an oligonucleotide, e.g., an oligonucleotide having an asymmetric format: a first wing comprises: O, and two or more consecutive S; and/or a second wing comprises: two or more consecutive S, and, and two or more consecutive R. Non-limiting example(s) of such an oligonucleotide include: WV-8044.

In some embodiments of an oligonucleotide, e.g., an oligonucleotide having an asymmetric format: a first wing comprises: O, and two or more consecutive S; and/or a second wing comprises: two or more consecutive S, and, and two or more consecutive R. Non-limiting example(s) of such an oligonucleotide include: WV-8257.

In some embodiments of an oligonucleotide, e.g., an oligonucleotide having an asymmetric format: a first wing comprises: O, and two or more consecutive S; and/or a second wing comprises: two or more consecutive S, and, and two or more consecutive R. Non-limiting example(s) of such an oligonucleotide include: WV-8259.

In some embodiments of an oligonucleotide, e.g., an oligonucleotide having an asymmetric format: a first wing comprises: O, and two or more consecutive S; and/or a second wing comprises: two or more consecutive S, and, and two or more consecutive O, and S. Non-limiting example(s) of such an oligonucleotide include: WV-8045.

In some embodiments of an oligonucleotide, e.g., an oligonucleotide having an asymmetric format: a first wing comprises: O, and two or more consecutive S; and/or a second wing comprises: two or more consecutive S, and, and two or more consecutive O, and S. Non-limiting example(s) of such an oligonucleotide include: WV-8046.

In some embodiments of an oligonucleotide, e.g., an oligonucleotide having an asymmetric format: a first wing comprises: O, and two or more consecutive S; and/or a second wing comprises: two or more consecutive S, and, and two or more consecutive O, and R. Non-limiting example(s) of such an oligonucleotide include: WV-8047.

In some embodiments of an oligonucleotide, e.g., an oligonucleotide having an asymmetric format: a first wing comprises: 0, and two or more consecutive S; and/or a second wing comprises: two or more consecutive S, and, and two or more consecutive O, and R. Non-limiting example(s) of such an oligonucleotide include: WV-8048.

In some embodiments of an oligonucleotide, e.g., an oligonucleotide having an asymmetric format: a first wing comprises: OS, and two or more consecutive O, and S; and/or a second wing comprises: two or more consecutive S. Non-limiting example(s) of such an oligonucleotide include: WV-11114, WV-12503, WV-13809, WV-14349, WV-9696, WV-9697, WV-9698, WV-9380, WV-9381, WV-9421, WV-9062, WV-9063, WV-8610, WV-8629, WV-9526, WV-9590, WV-8611, WV-9527, WV-9591, WV-8562, WV-8564, WV-8620, WV-8637, WV-8645, WV-8665, WV-8673, WV-8677, WV-8597, WV-8625, WV-8638, WV-8646, WV-8666, WV-8674, WV-8678, WV-8618, WV-9528, WV-9592, WV-8563.

In some embodiments of an oligonucleotide, e.g., an oligonucleotide having an asymmetric format: a first wing comprises: OS, and two or more consecutive O, and S; and/or a second wing comprises: two or more consecutive S. Non-limiting example(s) of such an oligonucleotide include: WV-8565, WV-8596, WV-8612, WV-8621, WV-8624, WV-8639, WV-8647, WV-8667, WV-8675.

In some embodiments of an oligonucleotide, e.g., an oligonucleotide having an asymmetric format: a first wing comprises: OS, and two or more consecutive O, and S; and/or a second wing comprises: two or more consecutive S. Non-limiting example(s) of such an oligonucleotide include: WV-8679.

In some embodiments of an oligonucleotide, e.g., an oligonucleotide having an asymmetric format: a first wing comprises: OS, and two or more consecutive O, and S; and/or a second wing comprises: two or more consecutive S O, and two or more consecutive S. Non-limiting example(s) of such an oligonucleotide include: WV-9285.

In some embodiments of an oligonucleotide, e.g., an oligonucleotide having an asymmetric format: a first wing comprises: OS, and two or more consecutive O, and S; and/or a second wing comprises: two or more consecutive S O, and two or more consecutive S. Non-limiting example(s) of such an oligonucleotide include: WV-9286.

In some embodiments of an oligonucleotide, e.g., an oligonucleotide having an asymmetric format: a first wing comprises: OS, and two or more consecutive O, and S; and/or a second wing comprises: two or more consecutive S, and, and two or more consecutive O, and S. Non-limiting example(s) of such an oligonucleotide include: WV-8566.

In some embodiments of an oligonucleotide, e.g., an oligonucleotide having an asymmetric format: a first wing comprises: OS, and two or more consecutive O, and S; and/or a second wing comprises: two or more consecutive S, and, and two or more consecutive O, and S. Non-limiting example(s) of such an oligonucleotide include: WV-8599.

In some embodiments of an oligonucleotide, e.g., an oligonucleotide having an asymmetric format: a first wing comprises: OS, and two or more consecutive O, and S; and/or a second wing comprises: two or more consecutive S, and, and two or more consecutive O, and S. Non-limiting example(s) of such an oligonucleotide include: WV-8567.

In some embodiments of an oligonucleotide, e.g., an oligonucleotide having an asymmetric format: a first wing comprises: OS, and two or more consecutive O, and R; and/or a second wing comprises: two or more consecutive S. Non-limiting example(s) of such an oligonucleotide include: WV-10244, WV-9872, WV-10250, WV-9869, WV-10251, WV-11958.

In some embodiments of an oligonucleotide, e.g., an oligonucleotide having an asymmetric format: a first wing comprises: OS, and two or more consecutive O, and R; and/or a second wing comprises: two or more consecutive S. Non-limiting example(s) of such an oligonucleotide include: WV-11962.

In some embodiments of an oligonucleotide, e.g., an oligonucleotide having an asymmetric format: a first wing comprises: OS, and two or more consecutive O, and R; and/or a second wing comprises: two or more consecutive S. Non-limiting example(s) of such an oligonucleotide include: WV-9870.

In some embodiments of an oligonucleotide, e.g., an oligonucleotide having an asymmetric format: a first wing comprises: OS, and two or more consecutive O, and R; and/or a second wing comprises: SR, and two or more consecutive S. Non-limiting example(s) of such an oligonucleotide include: WV-10246, WV-9874, WV-10253, WV-9861, WV-10254.

In some embodiments of an oligonucleotide, e.g., an oligonucleotide having an asymmetric format: a first wing comprises: OS, and two or more consecutive O, and R; and/or a second wing comprises: SR, and two or more consecutive S. Non-limiting example(s) of such an oligonucleotide include: WV-9862.

In some embodiments of an oligonucleotide, e.g., an oligonucleotide having an asymmetric format: a first wing comprises: OS, and two or more consecutive O, and R; and/or a second wing comprises: SR, and two or more consecutive O, and S. Non-limiting example(s) of such an oligonucleotide include: WV-9859.

In some embodiments of an oligonucleotide, e.g., an oligonucleotide having an asymmetric format: a first wing comprises: OS, and two or more consecutive O, and R; and/or a second wing comprises: SR, and two or more consecutive O, and S. Non-limiting example(s) of such an oligonucleotide include: WV-9670.

In some embodiments of an oligonucleotide, e.g., an oligonucleotide having an asymmetric format: a first wing comprises: OS, and two or more consecutive O; and/or a second wing comprises: two or more consecutive S. Non-limiting example(s) of such an oligonucleotide include: WV-12099.

In some embodiments of an oligonucleotide, e.g., an oligonucleotide having an asymmetric format: a first wing comprises: OS, and two or more consecutive O; and/or a second wing comprises: two or more consecutive S. Non-limiting example(s) of such an oligonucleotide include: WV-12103.

In some embodiments of an oligonucleotide, e.g., an oligonucleotide having an asymmetric format: a first wing comprises: OS, and two or more consecutive $X_n$, and S; and/or a second wing comprises: two or more consecutive S. Non-limiting example(s) of such an oligonucleotide include: WV-12504.

In some embodiments of an oligonucleotide, e.g., an oligonucleotide having an asymmetric format: a first wing comprises: OS, and two or more consecutive $X_n$, and S; and/or a second wing comprises: two or more consecutive S. Non-limiting example(s) of such an oligonucleotide include: WV-12505.

In some embodiments of an oligonucleotide, e.g., an oligonucleotide having an asymmetric format: a first wing comprises: OR, and two or more consecutive O, and R; and/or a second wing comprises: two or more consecutive S. Non-limiting example(s) of such an oligonucleotide include: WV-8560.

In some embodiments of an oligonucleotide, e.g., an oligonucleotide having an asymmetric format: a first wing comprises: two or more consecutive O, and XX; and/or a second wing comprises: XXX, and two or more consecutive O. Non-limiting example(s) of such an oligonucleotide include: WV-980.

In some embodiments of an oligonucleotide, e.g., an oligonucleotide having an asymmetric format: a first wing comprises: two or more consecutive X; and/or a second wing comprises: two or more consecutive X. Non-limiting example(s) of such an oligonucleotide include: WV-10426, WV-10427, WV-3174, WV-3536, WV-3542, WV-9431, WV-9432, WV-9433, WV-9434.

In some embodiments of an oligonucleotide, e.g., an oligonucleotide having an asymmetric format: a first wing comprises: two or more consecutive X; and/or a second wing comprises: two or more consecutive X. Non-limiting example(s) of such an oligonucleotide include: WV-9435.

In some embodiments of an oligonucleotide, e.g., an oligonucleotide having an asymmetric format: a first wing comprises: two or more consecutive X; and/or a second wing comprises: X, and two or more consecutive O, and X. Non-limiting example(s) of such an oligonucleotide include: WV-12445, WV-12446, WV-12447, WV-12448, WV-12449, WV-12450, WV-12451, WV-12977, WV-12978, WV-12979, WV-12980, WV-12981.

In some embodiments of an oligonucleotide, e.g., an oligonucleotide having an asymmetric format: a first wing comprises: two or more consecutive X; and/or a second wing comprises: X, and two or more consecutive O, and X. Non-limiting example(s) of such an oligonucleotide include: WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000.

In some embodiments of an oligonucleotide, e.g., an oligonucleotide having an asymmetric format: a first wing comprises: two or more consecutive X; and/or a second wing comprises: X, and two or more consecutive O, and X. Non-limiting example(s) of such an oligonucleotide include: WV-13001, WV-13002, WV-13003, WV-13004, WV-13005, WV-13006, WV-13007, WV-13008, WV-8844, WV-8846, WV-8847, WV-8849, WV-8851, WV-8853, WV-8855, WV-8857, WV-8858.

In some embodiments of an oligonucleotide, e.g., an oligonucleotide having an asymmetric format: a first wing comprises: two or more consecutive X; and/or a second wing comprises: X, and two or more consecutive O, and X. Non-limiting example(s) of such an oligonucleotide include: WV-8860.

In some embodiments of an oligonucleotide, e.g., an oligonucleotide having an asymmetric format: a first wing comprises: XOXXX; and/or a second wing comprises: X, and two or more consecutive O, and XX. Non-limiting example(s) of such an oligonucleotide include: WV-8110.

In some embodiments of an oligonucleotide, e.g., an oligonucleotide having an asymmetric format: a first wing comprises: X, and two or more consecutive O, and XX; and/or a second wing comprises: two or more consecutive X. Non-limiting example(s) of such an oligonucleotide include: WV-8553.

In some embodiments of an oligonucleotide, e.g., an oligonucleotide having an asymmetric format: a first wing comprises: X, and two or more consecutive O, and XX; and/or a second wing comprises: X, and two or more consecutive O, and XX. Non-limiting example(s) of such an oligonucleotide include: WV-8555.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-10406, WV-10407, WV-10408.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-10409, WV-10410, WV-10411, WV-10412, WV-10413, WV-10414, WV-10415, WV-10416, WV-10417, WV-10418, WV-10419.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-10420, WV-10421, WV-10422, WV-10423, WV-10424, WV-10425, WV-11966, WV-12113, WV-12439, WV-12440, WV-12441, WV-12442, WV-12443, WV-12444, WV-12582, WV-12583, WV-12947, WV-12948, WV-12949, WV-12950, WV-12951, WV-12952, WV-12953.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, WV-12976, WV-8548.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-8550, WV-8552, WV-8556, WV-8594, WV-8595, WV-8609, WV-8617, WV-8656, WV-8664, WV-8672, WV-8684, WV-8688, WV-8690, WV-8845, WV-8848, WV-8850, WV-8852, WV-8854, WV-8856, WV-8859, WV-9441, WV-9442, WV-9443, WV-9444.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-9445, WV-9486, WV-9487, WV-9488, WV-9489, WV-9490, WV-9491, WV-9492, WV-9494, WV-9510, WV-9533, WV-9885, WV-9887, WV-9891.

In some embodiments of an oligonucleotide, e.g., an oligonucleotide having an asymmetric format: a first wing comprises: X, and two or more consecutive O, and X; and/or a second wing comprises: two or more consecutive X. Non-limiting example(s) of such an oligonucleotide include: WV-9894.

In some embodiments of an oligonucleotide, e.g., an oligonucleotide having an asymmetric format: a first wing comprises: X, and two or more consecutive O, and X; and/or a second wing comprises: XXOXX. Non-limiting example(s) of such an oligonucleotide include: WV-8551, WV-8693.

In some embodiments of an oligonucleotide, e.g., an oligonucleotide having an asymmetric format: a first wing comprises: X, and two or more consecutive O, and X; and/or a second wing comprises: XXOXX. Non-limiting example(s) of such an oligonucleotide include: WV-9061.

In some embodiments of an oligonucleotide, e.g., an oligonucleotide having an asymmetric format: a first wing comprises: X, and two or more consecutive O, and X; and/or a second wing comprises: XOXXX. Non-limiting example(s) of such an oligonucleotide include: WV-9060.

In some embodiments of an oligonucleotide, e.g., an oligonucleotide having an asymmetric format: a first wing comprises: X, and two or more consecutive O, and X; and/or a second wing comprises: X, and two or more consecutive O, and XX. Non-limiting example(s) of such an oligonucleotide include: WV-8547, WV-8549, WV-8554, WV-8557.

In some embodiments of an oligonucleotide, e.g., an oligonucleotide having an asymmetric format: a first wing comprises: X, and two or more consecutive O, and X; and/or a second wing comprises: X, and two or more consecutive O, and XX. Non-limiting example(s) of such an oligonucleotide include: WV-8696.

In some embodiments of an oligonucleotide, e.g., an oligonucleotide having an asymmetric format: a first wing comprises: X, and two or more consecutive O, and X; and/or a second wing comprises: X, and two or more consecutive O, and X. Non-limiting example(s) of such an oligonucleotide include: WV-11963, WV-11964, WV-12480, WV-12481, WV-12482, WV-12483, WV-12484, WV-12486, WV-3421, WV-3662, WV-3688, WV-3690, WV-6408, WV-6474, WV-6936, WV-6951, WV-6952, WV-6969, WV-6976, WV-6981, WV-6982, WV-6989, WV-7002, WV-7027, WV-7118, WV-7805, WV-8109, WV-9436, WV-9437, WV-9438, WV-9439, WV-9440, WV-9493, WV-9694.

In some embodiments of an oligonucleotide, e.g., an oligonucleotide having an asymmetric format: a first wing comprises: X, and two or more consecutive O, and X; and/or a second wing comprises: X, and two or more consecutive O, and X. Non-limiting example(s) of such an oligonucleotide include: WV-9695.

In some embodiments of an oligonucleotide, e.g., an oligonucleotide having an asymmetric format: a first wing comprises: X, and two or more consecutive O, and X; and/or a second wing comprises: X, and two or more consecutive O, and X. Non-limiting example(s) of such an oligonucleotide include: WV-12485.

In some embodiments of an oligonucleotide, e.g., an oligonucleotide having an asymmetric format: a first wing comprises: X, and two or more consecutive O, and X; and/or a second wing comprises: X, and two or more consecutive Xn, and X. Non-limiting example(s) of such an oligonucleotide include: WV-13804.

In some embodiments of an oligonucleotide, e.g., an oligonucleotide having an asymmetric format: a first wing comprises: X, and two or more consecutive O; and/or a second wing comprises: two or more consecutive X. Non-limiting example(s) of such an oligonucleotide include: WV-12107.

In some embodiments of an oligonucleotide, e.g., an oligonucleotide having an asymmetric format: a first wing comprises: X, and two or more consecutive O; and/or a second wing comprises: two or more consecutive X. Non-limiting example(s) of such an oligonucleotide include: WV-12114.

In some embodiments of an oligonucleotide, e.g., an oligonucleotide having an asymmetric format: a first wing comprises: XnXnXnXX; and/or a second wing comprises: two or more consecutive X. Non-limiting example(s) of such an oligonucleotide include: WV-13803.

In some embodiments of an oligonucleotide, e.g., an oligonucleotide having an asymmetric format: a first wing comprises: X, and two or more consecutive Xn, and X; and/or a second wing comprises: X, and two or more consecutive Xn, and X. Non-limiting example(s) of such an oligonucleotide include: WV-13805.

In some embodiments of an oligonucleotide, e.g., an oligonucleotide having an asymmetric format: a first wing comprises: two or more consecutive S; and/or a second wing comprises: two or more consecutive S. Non-limiting example(s) of such an oligonucleotide include: WV-8315.

In some embodiments of an oligonucleotide, e.g., an oligonucleotide having an asymmetric format: a first wing comprises: two or more consecutive S; and/or a second wing comprises: two or more consecutive S. Non-limiting example(s) of such an oligonucleotide include: WV-8311.

In some embodiments of an oligonucleotide, e.g., an oligonucleotide having an asymmetric format: a first wing comprises: two or more consecutive S; and/or a second wing comprises: R, and two or more consecutive O, and R. Non-limiting example(s) of such an oligonucleotide include: WV-8318.

In some embodiments of an oligonucleotide, e.g., an oligonucleotide having an asymmetric format: a first wing comprises: two or more consecutive S OS; and/or a second wing comprises: two or more consecutive S, and, and two or more consecutive O, and S. Non-limiting example(s) of such an oligonucleotide include: WV-8122.

In some embodiments of an oligonucleotide, e.g., an oligonucleotide having an asymmetric format: a first wing comprises: two or more consecutive S OS; and/or a second wing comprises: two or more consecutive S, and, and two or more consecutive O, and S. Non-limiting example(s) of such an oligonucleotide include: WV-8114.

In some embodiments of an oligonucleotide, e.g., an oligonucleotide having an asymmetric format: a first wing comprises: two or more consecutive S OS; and/or a second wing comprises: S, and two or more consecutive O, and S. Non-limiting example(s) of such an oligonucleotide include: WV-8125.

In some embodiments of an oligonucleotide, e.g., an oligonucleotide having an asymmetric format: a first wing comprises: two or more consecutive S OS; and/or a second wing comprises: S, and two or more consecutive O, and S. Non-limiting example(s) of such an oligonucleotide include: WV-8117.

In some embodiments of an oligonucleotide, e.g., an oligonucleotide having an asymmetric format: a first wing comprises: two or more consecutive S OS; and/or a second wing comprises: S, and two or more consecutive O, and R. Non-limiting example(s) of such an oligonucleotide include: WV-8314.

In some embodiments of an oligonucleotide, e.g., an oligonucleotide having an asymmetric format: a first wing comprises: two or more consecutive S, and, and two or more consecutive O, and S; and/or a second wing comprises: two or more consecutive S, and, and two or more consecutive O, and S. Non-limiting example(s) of such an oligonucleotide include: WV-8124.

In some embodiments of an oligonucleotide, e.g., an oligonucleotide having an asymmetric format: a first wing comprises: two or more consecutive S, and, and two or more consecutive O, and S; and/or a second wing comprises: two or more consecutive S, and, and two or more consecutive O, and S. Non-limiting example(s) of such an oligonucleotide include: WV-8116.

In some embodiments of an oligonucleotide, e.g., an oligonucleotide having an asymmetric format: a first wing comprises: two or more consecutive S, and, and two or more consecutive O, and S; and/or a second wing comprises: S, and two or more consecutive O, and S. Non-limiting example(s) of such an oligonucleotide include: WV-8128, WV-8129, WV-8120.

In some embodiments of an oligonucleotide, e.g., an oligonucleotide having an asymmetric format: a first wing comprises: two or more consecutive S, and, and two or more consecutive O, and S; and/or a second wing comprises: S, and two or more consecutive O, and S. Non-limiting example(s) of such an oligonucleotide include: WV-8121.

In some embodiments of an oligonucleotide, e.g., an oligonucleotide having an asymmetric format: a first wing comprises: SO, and two or more consecutive S; and/or a second wing comprises: S, and two or more consecutive O, and, and two or more consecutive S, and. Non-limiting example(s) of such an oligonucleotide include: WV-8108, WV-8107, WV-8106, WV-8105, WV-8104.

In some embodiments of an oligonucleotide, e.g., an oligonucleotide having an asymmetric format: a first wing comprises: SO, and two or more consecutive S; and/or a second wing comprises: S, and two or more consecutive O, and, and two or more consecutive S, and. Non-limiting example(s) of such an oligonucleotide include: WV-8103.

In some embodiments of an oligonucleotide, e.g., an oligonucleotide having an asymmetric format: a first wing comprises: SOSOS; and/or a second wing comprises: two or more consecutive S, and, and two or more consecutive O, and S. Non-limiting example(s) of such an oligonucleotide include: WV-8123.

In some embodiments of an oligonucleotide, e.g., an oligonucleotide having an asymmetric format: a first wing comprises: SOSOS; and/or a second wing comprises: two or more consecutive S, and, and two or more consecutive O, and S. Non-limiting example(s) of such an oligonucleotide include: WV-8115.

In some embodiments of an oligonucleotide, e.g., an oligonucleotide having an asymmetric format: a first wing comprises: SOSOS; and/or a second wing comprises: S, and two or more consecutive O, and S. Non-limiting example(s) of such an oligonucleotide include: WV-8127.

In some embodiments of an oligonucleotide, e.g., an oligonucleotide having an asymmetric format: a first wing comprises: SOSOS; and/or a second wing comprises: S, and two or more consecutive O, and S. Non-limiting example(s) of such an oligonucleotide include: WV-8119.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S. Non-limiting example(s) of such an oligonucleotide include: WV-8476.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive O, and S. Non-limiting example(s) of such an oligonucleotide include: WV-8475.

In some embodiments of an oligonucleotide, e.g., an oligonucleotide having an asymmetric format: a first wing comprises: S, and two or more consecutive O, and, and two or more consecutive S, and; and/or a second wing comprises: two or more consecutive S, and, and two or more consecutive O, and S. Non-limiting example(s) of such an oligonucleotide include: WV-8474.

In some embodiments of an oligonucleotide, e.g., an oligonucleotide having an asymmetric format: a first wing comprises: S, and two or more consecutive O, and, and two or more consecutive S, and; and/or a second wing comprises: S, and two or more consecutive O, and S. Non-limiting example(s) of such an oligonucleotide include: WV-8473.

In some embodiments of an oligonucleotide, e.g., an oligonucleotide having an asymmetric format: a first wing comprises: S, and two or more consecutive O, and, and two or more consecutive S, and; and/or a second wing comprises: S, and two or more consecutive O, and S. Non-limiting example(s) of such an oligonucleotide include: WV-8472.

In some embodiments of an oligonucleotide, e.g., an oligonucleotide having an asymmetric format: a first wing comprises: S, and two or more consecutive O, and S; and/or a second wing comprises: two or more consecutive S. Non-limiting example(s) of such an oligonucleotide include: WV-8587, WV-9395, WV-9397, WV-9399, WV-9394, WV-9396, WV-9398, WV-11967, WV-7606.

In some embodiments of an oligonucleotide, e.g., an oligonucleotide having an asymmetric format: a first wing comprises: S, and two or more consecutive O, and S; and/or a second wing comprises: two or more consecutive S. Non-limiting example(s) of such an oligonucleotide include: WV-8012, WV-8586, WV-9508, WV-9505, WV-9509, WV-12893, WV-14087, WV-7605, WV-8011, WV-8569, WV-8614, WV-9530, WV-8615, WV-9531, WV-8568, WV-8585, WV-8601, WV-8653, WV-8661.

In some embodiments of an oligonucleotide, e.g., an oligonucleotide having an asymmetric format: a first wing comprises: S, and two or more consecutive O, and S; and/or a second wing comprises: two or more consecutive S. Non-limiting example(s) of such an oligonucleotide include: WV-8669, WV-8681, WV-8685, WV-8606, WV-8654, WV-8662, WV-8670, WV-8682, WV-8686, WV-8584, WV-9507, WV-8583, WV-8619, WV-9506, WV-9532, WV-8582, WV-8602, WV-8605, WV-8616, WV-8655, WV-8663, WV-8671, WV-8683.

In some embodiments of an oligonucleotide, e.g., an oligonucleotide having an asymmetric format: a first wing comprises: S, and two or more consecutive O, and S; and/or a second wing comprises: two or more consecutive S. Non-limiting example(s) of such an oligonucleotide include: WV-8687.

In some embodiments of an oligonucleotide, e.g., an oligonucleotide having an asymmetric format: a first wing comprises: S, and two or more consecutive O, and S; and/or a second wing comprises: two or more consecutive S, and O, and two or more consecutive S, and. Non-limiting example(s) of such an oligonucleotide include: WV-9059, WV-8455, WV-8454, WV-8692.

In some embodiments of an oligonucleotide, e.g., an oligonucleotide having an asymmetric format: a first wing comprises: S, and two or more consecutive O, and S; and/or a second wing comprises: two or more consecutive S, and O, and two or more consecutive S, and. Non-limiting example(s) of such an oligonucleotide include: WV-8691.

In some embodiments of an oligonucleotide, e.g., an oligonucleotide having an asymmetric format: a first wing comprises: S, and two or more consecutive O, and S; and/or a second wing comprises: two or more consecutive S, and, and two or more consecutive O, and S. Non-limiting example(s) of such an oligonucleotide include: WV-8126.

In some embodiments of an oligonucleotide, e.g., an oligonucleotide having an asymmetric format: a first wing comprises: S, and two or more consecutive O, and S; and/or a second wing comprises: two or more consecutive S, and, and two or more consecutive O, and S. Non-limiting example(s) of such an oligonucleotide include: WV-8118.

In some embodiments of an oligonucleotide, e.g., an oligonucleotide having an asymmetric format: a first wing comprises: S, and two or more consecutive O, and S; and/or a second wing comprises: SO, and two or more consecutive S. Non-limiting example(s) of such an oligonucleotide include: WV-9058.

In some embodiments of an oligonucleotide, e.g., an oligonucleotide having an asymmetric format: a first wing comprises: S, and two or more consecutive O, and S; and/or a second wing comprises: S, and two or more consecutive O, and, and two or more consecutive S, and. Non-limiting example(s) of such an oligonucleotide include: WV-8593, WV-7604.

In some embodiments of an oligonucleotide, e.g., an oligonucleotide having an asymmetric format: a first wing comprises: S, and two or more consecutive O, and S; and/or a second wing comprises: S, and two or more consecutive O, and, and two or more consecutive S, and. Non-limiting example(s) of such an oligonucleotide include: WV-8010.

In some embodiments of an oligonucleotide, e.g., an oligonucleotide having an asymmetric format: a first wing comprises: S, and two or more consecutive O, and S; and/or a second wing comprises: S, and two or more consecutive O, and, and two or more consecutive S, and. Non-limiting example(s) of such an oligonucleotide include: WV-8592, WV-7603, WV-8009, WV-8695, WV-8591, WV-8694, WV-8590, WV-8589.

In some embodiments of an oligonucleotide, e.g., an oligonucleotide having an asymmetric format: a first wing comprises: S, and two or more consecutive O, and S; and/or a second wing comprises: S, and two or more consecutive O, and, and two or more consecutive S, and. Non-limiting example(s) of such an oligonucleotide include: WV-8588.

In some embodiments of an oligonucleotide, e.g., an oligonucleotide having an asymmetric format: a first wing comprises: S, and two or more consecutive O, and S; and/or a second wing comprises: S, and two or more consecutive O, and S. Non-limiting example(s) of such an oligonucleotide include: WV-8083, WV-8102, WV-11965, WV-7124, WV-7130, WV-8101, WV-8453, WV-8452, WV-8100, WV-8246, WV-8603, WV-8608, WV-8099, WV-8098, WV-8097, WV-8248.

In some embodiments of an oligonucleotide, e.g., an oligonucleotide having an asymmetric format: a first wing comprises: S, and two or more consecutive O, and S; and/or a second wing comprises: S, and two or more consecutive O, and S. Non-limiting example(s) of such an oligonucleotide include: WV-8250.

In some embodiments of an oligonucleotide, e.g., an oligonucleotide having an asymmetric format: a first wing comprises: S, and two or more consecutive O, and S; and/or a second wing comprises: S, and two or more consecutive Xn, and S. Non-limiting example(s) of such an oligonucleotide include: WV-13303.

In some embodiments of an oligonucleotide, e.g., an oligonucleotide having an asymmetric format: a first wing comprises: S, and two or more consecutive O, and R; and/or a second wing comprises: two or more consecutive S.

Non-limiting example(s) of such an oligonucleotide include: WV-12110, WV-12111, WV-13306, WV-13310, WV-9886, WV-9892, WV-11960.

In some embodiments of an oligonucleotide, e.g., an oligonucleotide having an asymmetric format: a first wing comprises: S, and two or more consecutive O, and R; and/or a second wing comprises: two or more consecutive S. Non-limiting example(s) of such an oligonucleotide include: WV-9893.

In some embodiments of an oligonucleotide, e.g., an oligonucleotide having an asymmetric format: a first wing comprises: S, and two or more consecutive O, and R; and/or a second wing comprises: R, and two or more consecutive S. Non-limiting example(s) of such an oligonucleotide include: WV-9888.

In some embodiments of an oligonucleotide, e.g., an oligonucleotide having an asymmetric format: a first wing comprises: S, and two or more consecutive O, and R; and/or a second wing comprises: R, and two or more consecutive S. Non-limiting example(s) of such an oligonucleotide include: WV-9895.

In some embodiments of an oligonucleotide, e.g., an oligonucleotide having an asymmetric format: a first wing comprises: S, and two or more consecutive O, and R; and/or a second wing comprises: R, and two or more consecutive S. Non-limiting example(s) of such an oligonucleotide include: WV-9896.

In some embodiments of an oligonucleotide, e.g., an oligonucleotide having an asymmetric format: a first wing comprises: S, and two or more consecutive O, and R; and/or a second wing comprises: R, and two or more consecutive O, and S. Non-limiting example(s) of such an oligonucleotide include: WV-9889.

In some embodiments of an oligonucleotide, e.g., an oligonucleotide having an asymmetric format: a first wing comprises: S, and two or more consecutive O, and R; and/or a second wing comprises: R, and two or more consecutive O, and S. Non-limiting example(s) of such an oligonucleotide include: WV-9890.

In some embodiments of an oligonucleotide, e.g., an oligonucleotide having an asymmetric format: a first wing comprises: S, and two or more consecutive O; and/or a second wing comprises: two or more consecutive S. Non-limiting example(s) of such an oligonucleotide include: WV-12101.

In some embodiments of an oligonucleotide, e.g., an oligonucleotide having an asymmetric format: a first wing comprises: S, and two or more consecutive O; and/or a second wing comprises: two or more consecutive S. Non-limiting example(s) of such an oligonucleotide include: WV-12112.

In some embodiments of an oligonucleotide, e.g., an oligonucleotide having an asymmetric format: a first wing comprises: S, and two or more consecutive O; and/or a second wing comprises: two or more consecutive O, and S. Non-limiting example(s) of such an oligonucleotide include: WV-12100.

In some embodiments of an oligonucleotide, e.g., an oligonucleotide having an asymmetric format: a first wing comprises: S, and two or more consecutive Xn, and S; and/or a second wing comprises: two or more consecutive S. Non-limiting example(s) of such an oligonucleotide include: WV-11533.

In some embodiments of an oligonucleotide, e.g., an oligonucleotide having an asymmetric format: a first wing comprises: S, and two or more consecutive Xn, and S; and/or a second wing comprises: two or more consecutive S. Non-limiting example(s) of such an oligonucleotide include: WV-11532.

In some embodiments of an oligonucleotide, e.g., an oligonucleotide having an asymmetric format: a first wing comprises: S, and two or more consecutive Xn, and S; and/or a second wing comprises: two or more consecutive S. Non-limiting example(s) of such an oligonucleotide include: WV-13312.

In some embodiments of an oligonucleotide, e.g., an oligonucleotide having an asymmetric format: a first wing comprises: S, and two or more consecutive Xn, and S; and/or a second wing comprises: S, and two or more consecutive Xn, and S. Non-limiting example(s) of such an oligonucleotide include: WV-13304.

In some embodiments of an oligonucleotide, e.g., an oligonucleotide having an asymmetric format: a first wing comprises: S, and two or more consecutive Xn, and R; and/or a second wing comprises: two or more consecutive S. Non-limiting example(s) of such an oligonucleotide include: WV-13307.

In some embodiments of an oligonucleotide, e.g., an oligonucleotide having an asymmetric format: a first wing comprises: S, and two or more consecutive Xn, and R; and/or a second wing comprises: two or more consecutive S. Non-limiting example(s) of such an oligonucleotide include: WV-13311.

In some embodiments of an oligonucleotide, e.g., an oligonucleotide having an asymmetric format: a first wing comprises: two or more consecutive R, and; and/or a second wing comprises: S, and two or more consecutive R, and. Non-limiting example(s) of such an oligonucleotide include: WV-8313.

In some embodiments of an oligonucleotide, e.g., an oligonucleotide having an asymmetric format: a first wing comprises: two or more consecutive R, and; and/or a second wing comprises: two or more consecutive R, and. Non-limiting example(s) of such an oligonucleotide include: WV-7601.

In some embodiments of an oligonucleotide, e.g., an oligonucleotide having an asymmetric format: a first wing comprises: two or more consecutive R, and; and/or a second wing comprises: two or more consecutive R, and. Non-limiting example(s) of such an oligonucleotide include: WV-8317.

In some embodiments of an oligonucleotide, e.g., an oligonucleotide having an asymmetric format: a first wing comprises: two or more consecutive R, and; and/or a second wing comprises: two or more consecutive R, and. Non-limiting example(s) of such an oligonucleotide include: WV-7657.

In some embodiments of an oligonucleotide, e.g., an oligonucleotide having an asymmetric format: a first wing comprises: two or more consecutive R, and OR; and/or a second wing comprises: R, and two or more consecutive O, and, and two or more consecutive R, and. Non-limiting example(s) of such an oligonucleotide include: WV-8322.

In some embodiments of an oligonucleotide, e.g., an oligonucleotide having an asymmetric format: a first wing comprises: two or more consecutive R, and, and two or more consecutive O, and R; and/or a second wing comprises: R, and two or more consecutive O, and, and two or more consecutive R, and. Non-limiting example(s) of such an oligonucleotide include: WV-8321.

In some embodiments of an oligonucleotide, e.g., an oligonucleotide having an asymmetric format: a first wing comprises: two or more consecutive R, and, and two or more consecutive O, and R; and/or a second wing comprises: R, and two or more consecutive O, and, and two or more consecutive R, and. Non-limiting example(s) of such an oligonucleotide include: WV-8329.

In some embodiments of an oligonucleotide, e.g., an oligonucleotide having an asymmetric format: a first wing comprises: R, and two or more consecutive O, and R; and/or a second wing comprises: two or more consecutive S. Non-limiting example(s) of such an oligonucleotide include: WV-8575, WV-8008, WV-13308, WV-8007, WV-8471, WV-8470, WV-8573, WV-8572, WV-8571.

In some embodiments of an oligonucleotide, e.g., an oligonucleotide having an asymmetric format: a first wing comprises: R, and two or more consecutive O, and R; and/or a second wing comprises: two or more consecutive S. Non-limiting example(s) of such an oligonucleotide include: WV-8570.

In some embodiments of an oligonucleotide, e.g., an oligonucleotide having an asymmetric format: a first wing comprises: R, and two or more consecutive O, and R; and/or a second wing comprises: two or more consecutive S, and, and two or more consecutive O, and S. Non-limiting example(s) of such an oligonucleotide include: WV-8469.

In some embodiments of an oligonucleotide, e.g., an oligonucleotide having an asymmetric format: a first wing comprises: R, and two or more consecutive O, and R; and/or a second wing comprises: two or more consecutive S, and, and two or more consecutive O, and S. Non-limiting example(s) of such an oligonucleotide include: WV-8468.

In some embodiments of an oligonucleotide, e.g., an oligonucleotide having an asymmetric format: a first wing comprises: R, and two or more consecutive O, and R; and/or a second wing comprises: S, and two or more consecutive O, and, and two or more consecutive S, and. Non-limiting example(s) of such an oligonucleotide include: WV-8581, WV-8006, WV-8580, WV-8005, WV-8579, WV-8578, WV-8577.

In some embodiments of an oligonucleotide, e.g., an oligonucleotide having an asymmetric format: a first wing comprises: R, and two or more consecutive O, and R; and/or a second wing comprises: S, and two or more consecutive O, and, and two or more consecutive S, and. Non-limiting example(s) of such an oligonucleotide include: WV-8576.

In some embodiments of an oligonucleotide, e.g., an oligonucleotide having an asymmetric format: a first wing comprises: R, and two or more consecutive O, and R; and/or a second wing comprises: S, and two or more consecutive O, and S. Non-limiting example(s) of such an oligonucleotide include: WV-8456, WV-8467.

In some embodiments of an oligonucleotide, e.g., an oligonucleotide having an asymmetric format: a first wing comprises: R, and two or more consecutive O, and R; and/or a second wing comprises: S, and two or more consecutive O, and S. Non-limiting example(s) of such an oligonucleotide include: WV-8466.

In some embodiments of an oligonucleotide, e.g., an oligonucleotide having an asymmetric format: a first wing comprises: R, and two or more consecutive O, and R; and/or a second wing comprises: S, and two or more consecutive O, and R. Non-limiting example(s) of such an oligonucleotide include: WV-8312.

In some embodiments of an oligonucleotide, e.g., an oligonucleotide having an asymmetric format: a first wing comprises: R, and two or more consecutive O, and R; and/or a second wing comprises: R, and two or more consecutive S. Non-limiting example(s) of such an oligonucleotide include: WV-14552.

In some embodiments of an oligonucleotide, e.g., an oligonucleotide having an asymmetric format: a first wing comprises: R, and two or more consecutive O, and R; and/or a second wing comprises: R, and two or more consecutive O, and R. Non-limiting example(s) of such an oligonucleotide include: WV-7658, WV-7659.

In some embodiments of an oligonucleotide, e.g., an oligonucleotide having an asymmetric format: a first wing comprises: R, and two or more consecutive O, and R; and/or a second wing comprises: R, and two or more consecutive O, and R. Non-limiting example(s) of such an oligonucleotide include: WV-8316.

In some embodiments of an oligonucleotide, e.g., an oligonucleotide having an asymmetric format: a first wing comprises: R, and two or more consecutive Xn, and R; and/or a second wing comprises: two or more consecutive S. Non-limiting example(s) of such an oligonucleotide include: WV-13305.

In some embodiments of an oligonucleotide, e.g., an oligonucleotide having an asymmetric format: a first wing comprises: R, and two or more consecutive Xn, and R; and/or a second wing comprises: two or more consecutive S. Non-limiting example(s) of such an oligonucleotide include: WV-13309.

In some embodiments of an oligonucleotide, e.g., an oligonucleotide having an asymmetric format: a first wing comprises: R, and two or more consecutive Xn, and R; and/or a second wing comprises: two or more consecutive S. Non-limiting example(s) of such an oligonucleotide include: WV-13313.

In some embodiments of an oligonucleotide, e.g., an oligonucleotide having an asymmetric format: a first wing comprises: O, and two or more consecutive X; and/or a second wing comprises: two or more consecutive X. Non-limiting example(s) of such an oligonucleotide include: WV-8810, WV-8448, WV-8809.

In some embodiments of an oligonucleotide, e.g., an oligonucleotide having an asymmetric format: a first wing comprises: OX, and two or more consecutive O, and; and/or a second wing comprises: two or more consecutive X. Non-limiting example(s) of such an oligonucleotide include: WV-12105, WV-12109, WV-10243, WV-10245, WV-10249, WV-10252, WV-8600, WV-8613.

In some embodiments of an oligonucleotide, e.g., an oligonucleotide having an asymmetric format: a first wing comprises: OX, and two or more consecutive O, and; and/or a second wing comprises: two or more consecutive X. Non-limiting example(s) of such an oligonucleotide include: WV-8628, WV-8632, WV-8640, WV-8648, WV-8668, WV-8676, WV-8680, WV-8689, WV-8697, WV-9529, WV-9593, WV-9860, WV-9868, WV-9871.

In some embodiments of an oligonucleotide, e.g., an oligonucleotide having an asymmetric format: a first wing comprises: OX, and two or more consecutive O, and; and/or a second wing comprises: two or more consecutive X. Non-limiting example(s) of such an oligonucleotide include: WV-9873.

In some embodiments of an oligonucleotide, e.g., an oligonucleotide having an asymmetric format: a first wing comprises: OX, and two or more consecutive O, and; and/or a second wing comprises: X, and two or more consecutive O, and X. Non-limiting example(s) of such an oligonucleotide include: WV-8132.

In some embodiments of an oligonucleotide, e.g., an oligonucleotide having an asymmetric format: a first wing comprises: O, and two or more consecutive S; and/or a second wing comprises: two or more consecutive S. Non-limiting example(s) of such an oligonucleotide include: WV-8043.

In some embodiments of an oligonucleotide, e.g., an oligonucleotide having an asymmetric format: a first wing comprises: O, and two or more consecutive S; and/or a second wing comprises: S, and two or more consecutive R, and. Non-limiting example(s) of such an oligonucleotide include: WV-8044, WV-8257.

In some embodiments of an oligonucleotide, e.g., an oligonucleotide having an asymmetric format: a first wing comprises: O, and two or more consecutive S; and/or a second wing comprises: S, and two or more consecutive R, and. Non-limiting example(s) of such an oligonucleotide include: WV-8259.

In some embodiments of an oligonucleotide, e.g., an oligonucleotide having an asymmetric format: a first wing comprises: O, and two or more consecutive S; and/or a second wing comprises: S, and two or more consecutive O, and S. Non-limiting example(s) of such an oligonucleotide include: WV-8045.

In some embodiments of an oligonucleotide, e.g., an oligonucleotide having an asymmetric format: a first wing comprises: O, and two or more consecutive S; and/or a second wing comprises: S, and two or more consecutive O, and S. Non-limiting example(s) of such an oligonucleotide include: WV-8046.

In some embodiments of an oligonucleotide, e.g., an oligonucleotide having an asymmetric format: a first wing comprises: O, and two or more consecutive S; and/or a second wing comprises: S, and two or more consecutive O, and R. Non-limiting example(s) of such an oligonucleotide include: WV-8047.

In some embodiments of an oligonucleotide, e.g., an oligonucleotide having an asymmetric format: a first wing comprises: O, and two or more consecutive S; and/or a second wing comprises: S, and two or more consecutive O, and R. Non-limiting example(s) of such an oligonucleotide include: WV-8048.

In some embodiments of an oligonucleotide, e.g., an oligonucleotide having an asymmetric format: a first wing comprises: OS, and two or more consecutive O, and; and/or a second wing comprises: two or more consecutive S. Non-limiting example(s) of such an oligonucleotide include: WV-12099, WV-12103, WV-10244, WV-9872, WV-10250, WV-9869, WV-10251, WV-11958.

In some embodiments of an oligonucleotide, e.g., an oligonucleotide having an asymmetric format: a first wing comprises: OS, and two or more consecutive O, and; and/or a second wing comprises: two or more consecutive S. Non-limiting example(s) of such an oligonucleotide include: WV-11962, WV-9870, WV-11114, WV-12503, WV-13809, WV-14349, WV-9696, WV-9697, WV-9698, WV-9380, WV-9381, WV-9421, WV-9062, WV-9063, WV-8610, WV-8629, WV-9526, WV-9590.

In some embodiments of an oligonucleotide, e.g., an oligonucleotide having an asymmetric format: a first wing comprises: OS, and two or more consecutive O, and; and/or a second wing comprises: two or more consecutive S. Non-limiting example(s) of such an oligonucleotide include: WV-8611, WV-9527, WV-9591, WV-8562, WV-8564, WV-8620, WV-8637, WV-8645, WV-8665, WV-8673, WV-8677, WV-8597, WV-8625, WV-8638, WV-8646.

In some embodiments of an oligonucleotide, e.g., an oligonucleotide having an asymmetric format: a first wing comprises: OS, and two or more consecutive O, and; and/or a second wing comprises: two or more consecutive S. Non-limiting example(s) of such an oligonucleotide include: WV-8666, WV-8674, WV-8678, WV-8618, WV-9528, WV-9592, WV-8563, WV-8565, WV-8596, WV-8612, WV-8621, WV-8624, WV-8639, WV-8647, WV-8667, WV-8675.

In some embodiments of an oligonucleotide, e.g., an oligonucleotide having an asymmetric format: a first wing comprises: OS, and two or more consecutive O, and; and/or a second wing comprises: two or more consecutive S. Non-limiting example(s) of such an oligonucleotide include: WV-8679.

In some embodiments of an oligonucleotide, e.g., an oligonucleotide having an asymmetric format: a first wing comprises: OS, and two or more consecutive O, and; and/or a second wing comprises: two or more consecutive S, and O, and two or more consecutive S, and. Non-limiting example(s) of such an oligonucleotide include: WV-9285.

In some embodiments of an oligonucleotide, e.g., an oligonucleotide having an asymmetric format: a first wing comprises: OS, and two or more consecutive O, and; and/or a second wing comprises: two or more consecutive S, and O, and two or more consecutive S, and. Non-limiting example(s) of such an oligonucleotide include: WV-9286.

In some embodiments of an oligonucleotide, e.g., an oligonucleotide having an asymmetric format: a first wing comprises: OS, and two or more consecutive O, and; and/or a second wing comprises: S, and two or more consecutive O, and S. Non-limiting example(s) of such an oligonucleotide include: WV-8566.

In some embodiments of an oligonucleotide, e.g., an oligonucleotide having an asymmetric format: a first wing comprises: OS, and two or more consecutive O, and; and/or a second wing comprises: S, and two or more consecutive O, and S. Non-limiting example(s) of such an oligonucleotide include: WV-8599.

In some embodiments of an oligonucleotide, e.g., an oligonucleotide having an asymmetric format: a first wing comprises: OS, and two or more consecutive O, and; and/or a second wing comprises: S, and two or more consecutive O, and S. Non-limiting example(s) of such an oligonucleotide include: WV-8567.

In some embodiments of an oligonucleotide, e.g., an oligonucleotide having an asymmetric format: a first wing comprises: OS, and two or more consecutive O, and; and/or a second wing comprises: R, and two or more consecutive S. Non-limiting example(s) of such an oligonucleotide include: WV-10246, WV-9874, WV-10253, WV-9861, WV-10254.

In some embodiments of an oligonucleotide, e.g., an oligonucleotide having an asymmetric format: a first wing comprises: OS, and two or more consecutive O, and; and/or a second wing comprises: R, and two or more consecutive S. Non-limiting example(s) of such an oligonucleotide include: WV-9862.

In some embodiments of an oligonucleotide, e.g., an oligonucleotide having an asymmetric format: a first wing comprises: OS, and two or more consecutive O, and; and/or a second wing comprises: R, and two or more consecutive O, and S. Non-limiting example(s) of such an oligonucleotide include: WV-9859.

In some embodiments of an oligonucleotide, e.g., an oligonucleotide having an asymmetric format: a first wing comprises: OS, and two or more consecutive O, and; and/or a second wing comprises: R, and two or more consecutive O, and S. Non-limiting example(s) of such an oligonucleotide include: WV-9670.

In some embodiments of an oligonucleotide, e.g., an oligonucleotide having an asymmetric format: a first wing comprises: OS, and two or more consecutive Xn, and; and/or a second wing comprises: two or more consecutive S. Non-limiting example(s) of such an oligonucleotide include: WV-12504.

In some embodiments of an oligonucleotide, e.g., an oligonucleotide having an asymmetric format: a first wing comprises: OS, and two or more consecutive Xn, and; and/or a second wing comprises: two or more consecutive S. Non-limiting example(s) of such an oligonucleotide include: WV-12505.

In some embodiments of an oligonucleotide, e.g., an oligonucleotide having an asymmetric format: a first wing comprises: OR, and two or more consecutive O, and; and/or a second wing comprises: two or more consecutive S. Non-limiting example(s) of such an oligonucleotide include: WV-8560.

In some embodiments of an oligonucleotide, e.g., an oligonucleotide having an asymmetric format: a first wing comprises: two or more consecutive O, and X; and/or a second wing comprises: XX, and two or more consecutive O, and. Non-limiting example(s) of such an oligonucleotide include: WV-980.

In some embodiments, an oligonucleotide, e.g., an oligonucleotide having an asymmetric format can comprise any internucleotidic linkage described herein or known in the art.

A non-limiting example of an internucleotidic linkage or unmodified internucleotidic linkage is a phosphodiester; non-limiting examples of modified internucleotidic linkages include those in which one or more oxygen of a phosphodiester has been replaced by, as non-limiting examples, sulfur (as in a phosphorothioate), H, alkyl, or another moiety or element which is not oxygen. A non-limiting example of an internucleotidic linkage is a moiety which does not a comprise a phosphorus but serves to link two sugars. A non-limiting example of an internucleotidic linkage is a moiety which does not a comprise a phosphorus but serves to link two sugars in the backbone of an oligonucleotide. Disclosed herein are additional non-limiting examples of nucleotides, modified nucleotides, nucleotide analogs, internucleotidic linkages, modified internucleotidic linkages, bases, modified bases, and base analogs, sugars, modified sugars, and sugar analogs, and nucleosides, modified nucleosides, and nucleoside analogs.

In some embodiments, an internucleotidic linkage which has the structure of Formula I:

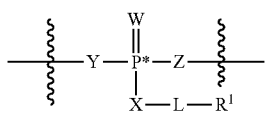

(I)

wherein:
P* is a symmetric phosphorus atom, or asymmetric phosphorus atom that is either Rp or Sp;
W is 0, S or Se;
each of X, Y and Z is independently —O—, —S—, —N(-L-R$_1$)—, or L;
L is a covalent bond or an optionally substituted, linear or branched C$_1$-C$_{10}$ alkylene, wherein one or more methylene units of L are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—;
R$^1$ is halogen, R, or an optionally substituted C$_1$-C$_{50}$ aliphatic wherein one or more methylene units are optionally and independently replaced by an optionally substituted group selected from C$_1$-C$_6$ alkylene, C$_1$-C$_6$ alkenylene, —C≡C—, a C$_1$-C$_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$— —SC(O)—, —C(O)S—, —OC(O)—, and —C(O)O—
each R' is independently —R, —C(O)R, —CO$_2$R, or —SO$_2$R, or:
two R' are taken together with their intervening atoms to form an optionally substituted aryl, carbocyclic, heterocyclic, or heteroaryl ring;
Cy- is an optionally substituted bivalent ring selected from phenylene, carbocyclylene, arylene, heteroarylene, and heterocyclylene;
each R is independently hydrogen, or an optionally substituted group selected from C$_1$-C$_6$ aliphatic, carbocyclyl, aryl, heteroaryl, and heterocyclyl; and
each

independently represents a connection to a nucleoside.

In some embodiments, L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
R$^1$ is halogen, R, or an optionally substituted C$_1$-C$_{50}$ aliphatic wherein one or more methylene units are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;

Cy- is an optionally substituted bivalent ring selected from phenylene, carbocyclylene, arylene, heteroarylene, and heterocyclylene;

each R is independently hydrogen, or an optionally substituted group selected from $C_1$-$C_6$ aliphatic, phenyl, carbocyclyl, aryl, heteroaryl, and heterocyclyl; and each

independently represents a connection to a nucleoside.

In some embodiments, a chirally controlled oligonucleotide comprises one or more modified internucleotidic phosphorus linkages. In some embodiments, a chirally controlled oligonucleotide comprises, e.g., a phosphorothioate or a phosphorothioate triester linkage. In some embodiments, a chirally controlled oligonucleotide comprises a phosphorothioate triester linkage. In some embodiments, a chirally controlled oligonucleotide comprises at least two phosphorothioate triester linkages. In some embodiments, a chirally controlled oligonucleotide comprises at least three phosphorothioate triester linkages. In some embodiments, a chirally controlled oligonucleotide comprises at least four phosphorothioate triester linkages. In some embodiments, a chirally controlled oligonucleotide comprises at least five phosphorothioate triester linkages. Examples of such modified internucleotidic phosphorus linkages are described further herein.

In some embodiments, a linkage of Formula I is chiral. In some embodiments, the present disclosure provides a chirally controlled oligonucleotide comprising one or more modified internucleotidic linkages of Formula I. In some embodiments, the present disclosure provides a chirally controlled oligonucleotide comprising one or more modified internucleotidic linkages of Formula I, and wherein individual internucleotidic linkages of Formula I within the oligonucleotide have different P-modifications relative to one another. In some embodiments, the present disclosure provides a chirally controlled oligonucleotide comprising one or more modified internucleotidic linkages of Formula I, and wherein individual internucleotidic linkages of Formula I within the oligonucleotide have different —X-L-R' relative to one another. In some embodiments, the present disclosure provides a chirally controlled oligonucleotide comprising one or more modified internucleotidic linkages of Formula I, and wherein individual internucleotidic linkages of Formula I within the oligonucleotide have different X relative to one another. In some embodiments, the present disclosure provides a chirally controlled oligonucleotide comprising one or more modified internucleotidic linkages of Formula I, and wherein individual internucleotidic linkages of Formula I within the oligonucleotide have different -L-$R^1$ relative to one another. In some embodiments, a chirally controlled oligonucleotide is an oligonucleotide in a provided composition that is of the particular oligonucleotide type. In some embodiments, a chirally controlled oligonucleotide is an oligonucleotide in a provided composition that has the common base sequence and length, the common pattern of backbone linkages, and the common pattern of backbone chiral centers. In some embodiments, a chirally controlled oligonucleotide is an oligonucleotide in a chirally controlled composition that is of the particular oligonucleotide type, and the chirally controlled oligonucleotide is of the type. In some embodiments, a chirally controlled oligonucleotide is an oligonucleotide in a provided composition that comprises a non-random or controlled level of a plurality of oligonucleotides that share a common base sequence, a common pattern of backbone linkages, and a common pattern of backbone chiral centers, and the chirally controlled oligonucleotide shares the common base sequence, the common pattern of backbone linkages, and the common pattern of backbone chiral centers.

In some embodiments, the present disclosure provides a chirally controlled oligonucleotide having an asymmetric format, wherein at least two of the individual internucleotidic linkages within the oligonucleotide have different stereochemistry and/or different P-modifications relative to one another. In some embodiments, the present disclosure provides a chirally controlled oligonucleotide, wherein at least two of the individual internucleotidic linkages within the oligonucleotide have different stereochemistry relative to one another, and wherein at least a portion of the structure of the chirally controlled oligonucleotide is characterized by a repeating pattern of alternating stereochemistry.

In some embodiments, the present disclosure provides a chirally controlled oligonucleotide having an asymmetric format, wherein at least two of the individual internucleotidic linkages within the oligonucleotide have different P-modifications relative to one another, in that they have different X atoms in their -XL$R^1$ moieties, and/or in that they have different L groups in their -XL$R^1$ moieties, and/or that they have different $R^1$ atoms in their -XL$R^1$ moieties, wherein XL$R^1$ is equivalent to X-L-$R^1$ and X, L, and $R^1$ are as defined in Formula I.

In some embodiments, a chirally controlled oligonucleotide comprises different internucleotidic phosphorus linkages. In some embodiments, a chirally controlled oligonucleotide comprises at least one phosphate diester internucleotidic linkage and at least one modified internucleotidic linkage. In some embodiments, a chirally controlled oligonucleotide comprises at least one phosphate diester internucleotidic linkage and at least one phosphorothioate triester linkage. In some embodiments, a chirally controlled oligonucleotide comprises at least one phosphate diester internucleotidic linkage and at least two phosphorothioate triester linkages. In some embodiments, a chirally controlled oligonucleotide comprises at least one phosphate diester internucleotidic linkage and at least three phosphorothioate triester linkages. In some embodiments, a chirally controlled oligonucleotide comprises at least one phosphate diester internucleotidic linkage and at least four phosphorothioate triester linkages. In some embodiments, a chirally controlled oligonucleotide comprises at least one phosphate diester internucleotidic linkage and at least five phosphorothioate triester linkages. Examples of such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, an oligonucleotide can comprise any internucleotidic linkage described herein or known in the art.

In some embodiments, the present disclosure provides oligonucleotides comprising one or more modified internucleotidic linkages independently having the structure of Formula I, disclosed herein. In some embodiments, a modified internucleotidic linkage is phosphorothioate. Examples of internucleotidic linkages having the structure of Formula I are widely known in the art.

In some embodiments, the present disclosure provides a chirally controlled oligonucleotide having the sequence of any oligonucleotide disclosed herein, wherein at least one internucleotidic linkage has a chiral linkage phosphorus. In some embodiments, the present disclosure provides a chirally controlled oligonucleotide having the sequence of any oligonucleotide disclosed herein, wherein at least one internucleotidic linkage has the structure of Formula I. In some embodiments, the present disclosure provides a chirally controlled oligonucleotide having the sequence of any oligonucleotide disclosed herein, wherein each internucleotidic linkage has the structure of Formula I. In some embodiments, the present disclosure provides a chirally controlled oligonucleotide having the sequence of any oligonucleotide disclosed herein, wherein at least one internucleotidic linkage has the structure of Formula I-c. In some embodiments, the present disclosure provides a chirally controlled oligonucleotide having the sequence of any oligonucleotide disclosed herein, wherein each internucleotidic linkage has the structure of Formula I-c. In some embodiments, the present disclosure provides a chirally controlled oligonucleotide having the sequence of any oligonucleotide disclosed herein, wherein at least one internucleotidic linkage is

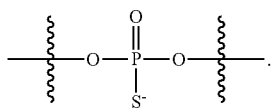 [SMILES: *OP(=O)([S-])O*]

In some embodiments, the present disclosure provides a chirally controlled oligonucleotide having the sequence of any oligonucleotide disclosed herein, wherein each internucleotidic linkage is

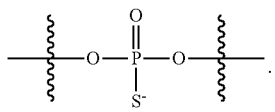

In some embodiments, each of the consecutive nucleoside units is independently preceded and/or followed by a modified internucleotidic linkage. In some embodiments, each of the consecutive nucleoside units is independently preceded and/or followed by a phosphorothioate linkage. In some embodiments, each of the consecutive nucleoside units is independently preceded and/or followed by a chirally controlled modified internucleotidic linkage. In some embodiments, each of the consecutive nucleoside units is independently preceded and/or followed by a chirally controlled phosphorothioate linkage. In some embodiments, a modified internucleotidic linkage has a structure of Formula I. In some embodiments, a modified internucleotidic linkage has a structure of Formula I-a.

In some embodiments, a modified internucleotidic linkage has a structure of Formula I. In some embodiments, a modified internucleotidic linkage has a structure of Formula I-a.

In some embodiments, a chirally controlled oligonucleotide is designed such that one or more nucleotides comprise a phosphorus modification prone to "autorelease" under certain conditions. That is, under certain conditions, a particular phosphorus modification is designed such that it self-cleaves from the oligonucleotide to provide, e.g., a phosphate diester such as those found in naturally occurring DNA and RNA. In some embodiments, such a phosphorus modification has a structure of $-O-L-R^1$, wherein each of L and $R^1$ is independently described in the present disclosure. In some embodiments, an autorelease group comprises a morpholino group. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a phosphate diester as is found in naturally occurring DNA and RNA.

In some embodiments, a chiral internucleotidic linkage has the structure of Formula I, disclosed herein. In some embodiments, a chiral internucleotidic linkage is phosphorothioate. In some embodiments, each chiral internucleotidic linkage in a single oligonucleotide of a provided composition independently has the structure of Formula I, disclosed herein. In some embodiments, each chiral internucleotidic linkage in a single oligonucleotide of a provided composition is a phosphorothioate.

In some embodiments, a chirally controlled oligonucleotide is designed such that the resulting pharmaceutical properties are improved through one or more particular modifications at phosphorus. It is well documented in the art that certain oligonucleotides are rapidly degraded by nucleases and exhibit poor cellular uptake through the cytoplasmic cell membrane (Poijarvi-Virta et al., Curr. Med. Chem. (2006), 13(28); 3441-65; Wagner et al., Med. Res. Rev. (2000), 20(6):417-51; Peyrottes et al., Mini Rev. Med. Chem. (2004), 4(4):395-408; Gosselin et al., (1996), 43(1): 196-208; Bologna et al., (2002), Antisense & Nucleic Acid Drug Development 12:33-41). For instance, Vives et al., (Nucleic Acids Research (1999), 27(20):4071-76) found that tert-butyl SATE pro-oligonucleotides displayed markedly increased cellular penetration compared to the parent oligonucleotide.

In some embodiments, the present disclosure provides a chirally controlled oligonucleotide, wherein at least two of the individual internucleotidic linkages within the oligonucleotide have different stereochemistry and/or different P-modifications relative to one another. In certain embodiments, the present disclosure provides a chirally controlled oligonucleotide, wherein at least two individual internucleotidic linkages within the oligonucleotide have different P-modifications relative to one another. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate diester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphorothioate triester internucleotidic linkage. In certain embodiments, the present disclosure provides a chirally controlled oligonucleotide, wherein at least two of the individual internucleotidic linkages within the oligonucleotide have different P-modifications relative to one another, and wherein the chirally controlled oligonucleotide comprises at least one phosphate diester internucleotidic linkage and at least one phosphorothioate triester internucleotidic linkage.

In some embodiments, provided oligonucleotides are capable of directing a decrease in the expression, level and/or activity of a target gene or its gene product. In some embodiments, a target gene comprises a repeat expansion. In some embodiments, provided oligonucleotides comprise any internucleotidic linkage described herein or known in the art.

In some embodiments, an oligonucleotide can comprise any internucleotidic linkage described herein or known in the art.

A non-limiting example of an internucleotidic linkage or unmodified internucleotidic linkage is a phosphodiester; non-limiting examples of modified internucleotidic linkages include those in which one or more oxygen of a phosphodiester has been replaced by, as non-limiting examples, sulfur (as in a phosphorothioate), H, alkyl, or another moiety or element which is not oxygen. A non-limiting example of an internucleotidic linkage is a moiety which does not a comprise a phosphorus but serves to link two sugars. A non-limiting example of an internucleotidic linkage is a moiety which does not a comprise a phosphorus but serves to link two sugars in the backbone of an oligonucleotide. Disclosed herein are additional non-limiting examples of nucleotides, modified nucleotides, nucleotide analogs, internucleotidic linkages, modified internucleotidic linkages, bases, modified bases, and base analogs, sugars, modified sugars, and sugar analogs, and nucleosides, modified nucleosides, and nucleoside analogs.

In some embodiments, the present disclosure provides a chirally controlled oligonucleotide, wherein at least two of the individual internucleotidic linkages within the oligonucleotide have different stereochemistry and/or different P-modifications relative to one another. In some embodiments, the present disclosure provides a chirally controlled oligonucleotide, wherein at least two of the individual internucleotidic linkages within the oligonucleotide have different stereochemistry relative to one another, and wherein at least a portion of the structure of the chirally controlled oligonucleotide is characterized by a repeating pattern of alternating stereochemistry.

In some embodiments, a chirally controlled oligonucleotide comprises one or more modified internucleotidic phosphorus linkages. Examples of such modified internucleotidic phosphorus linkages are described further herein.

In some embodiments, a chirally controlled oligonucleotide comprises different internucleotidic phosphorus linkages. In some embodiments, a chirally controlled oligonucleotide comprises at least one phosphate diester internucleotidic linkage and at least one modified internucleotidic linkage. Examples of such modified internucleotidic phosphorus linkages are described further herein.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, the present disclosure provides compositions comprising or consisting of a plurality of provided oligonucleotides (e.g., chirally controlled oligonucleotide compositions). In some embodiments, all such provided oligonucleotides are of the same type, i.e., all have the same base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR$^1$" groups in Formula I, disclosed herein). In some embodiments, all oligonucleotides of the same type are identical. In many embodiments, however, provided compositions comprise a plurality of oligonucleotides types, typically in pre-determined relative amounts.

In some embodiments, an oligonucleotide can comprise any internucleotidic linkage described herein or known in the art. In some embodiments, an oligonucleotide can comprise any internucleotidic linkage described herein or known in the art in combination with any other structural element or modification described herein, including but not limited to, base sequence or portion thereof, sugar, base (nucleobase); stereochemistry or combination or pattern thereof, additional chemical moiety, including but not limited to, a targeting moiety, a carbohydrate moiety, etc.; additional chemical moiety, including but not limited to, a targeting moiety, etc.; format or any structural element thereof, and/or any other structural element or modification described herein; and in some embodiments, the present disclosure pertains to multimers of any such oligonucleotides.

In some embodiments, the present disclosure provides oligonucleotides comprising one or more modified internucleotidic linkages independently having the structure of Formula I, disclosed herein.

In some embodiments of Formula I, P in $T^{LD}$ is P*. In some embodiments, P* is an asymmetric phosphorus atom and is either Rp or Sp. In some embodiments, P* is Rp. In other embodiments, P* is Sp. In some embodiments, an oligonucleotide comprises one or more internucleotidic linkages of Formula I wherein each P* is independently Rp or Sp. In some embodiments, an oligonucleotide comprises one or more internucleotidic linkages of Formula I wherein each P* is Rp. In some embodiments, an oligonucleotide comprises one or more internucleotidic linkages of Formula I wherein each P* is Sp. In some embodiments, an oligonucleotide comprises at least one internucleotidic linkage of Formula I wherein P* is Rp. In some embodiments, an oligonucleotide comprises at least one internucleotidic linkage of Formula I wherein P* is Sp. In some embodiments, an oligonucleotide comprises at least one internucleotidic linkage of Formula I wherein P* is Rp, and at least one internucleotidic linkage of Formula I wherein P* is Sp.

In some embodiments of Formula I, W is O, S, or Se. In some embodiments, W is O. In some embodiments, W is S. In some embodiments, W is Se. In some embodiments, an oligonucleotide comprises at least one internucleotidic linkage of Formula I wherein W is O. In some embodiments, an oligonucleotide comprises at least one internucleotidic linkage of Formula I wherein W is S. In some embodiments, an oligonucleotide comprises at least one internucleotidic linkage of Formula I wherein W is Se.

In some embodiments of Formula I, an oligonucleotide comprises at least one internucleotidic linkage of Formula I wherein W is O. In some embodiments, an oligonucleotide comprises at least one internucleotidic linkage of Formula I wherein W is S.

In some embodiments, each R is independently hydrogen, or an optionally substituted group selected from $C_1$-$C_6$ aliphatic, phenyl, carbocyclyl, aryl, heteroaryl, and heterocyclyl.

In some embodiments, R is hydrogen. In some embodiments, R is an optionally substituted group selected from $C_1$-$C_6$ aliphatic, phenyl, carbocyclyl, aryl, heteroaryl, and heterocyclyl.

In some embodiments, R is an optionally substituted $C_1$-$C_6$ aliphatic. In some embodiments, R is an optionally substituted $C_1$-$C_6$ alkyl. In some embodiments, R is optionally substituted, linear or branched hexyl. In some embodiments, R is optionally substituted, linear or branched pentyl. In some embodiments, R is optionally substituted, linear or branched butyl. In some embodiments, R is optionally substituted, linear or branched propyl. In some embodiments, R is optionally substituted ethyl. In some embodiments, R is optionally substituted methyl.

In some embodiments, R is optionally substituted phenyl. In some embodiments, R is substituted phenyl. In some embodiments, R is phenyl.

In some embodiments, R is optionally substituted carbocyclyl. In some embodiments, R is optionally substituted $C_3$-$C_{10}$ carbocyclyl. In some embodiments, R is optionally substituted monocyclic carbocyclyl. In some embodiments, R is optionally substituted cycloheptyl. In some embodiments, R is optionally substituted cyclohexyl. In some embodiments, R is optionally substituted cyclopentyl. In some embodiments, R is optionally substituted cyclobutyl. In some embodiments, R is an optionally substituted cyclopropyl. In some embodiments, R is optionally substituted bicyclic carbocyclyl.

In some embodiments, R is an optionally substituted aryl. In some embodiments, R is an optionally substituted bicyclic aryl ring.

In some embodiments, R is an optionally substituted heteroaryl. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-3 heteroatoms independently selected from nitrogen, sulfur, and oxygen. In some embodiments, R is an optionally substituted 6 membered monocyclic heteroaryl ring having 1-3 heteroatoms independently selected from nitrogen, oxygen, and sulfur.

In some embodiments, R is an optionally substituted 5-membered monocyclic heteroaryl ring having 1 heteroatom selected from nitrogen, oxygen, and sulfur. In some embodiments, R is selected from pyrrolyl, furanyl, and thienyl.

In some embodiments, R is an optionally substituted 5-membered heteroaryl ring having 2 heteroatoms independently selected from nitrogen, oxygen, and sulfur. In certain embodiments, R is an optionally substituted 5-membered heteroaryl ring having 1 nitrogen atom, and an additional heteroatom selected from sulfur and oxygen. Example R groups include optionally substituted pyrazolyl, imidazolyl, thiazolyl, isothiazolyl, oxazolyl or isoxazolyl.

In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having 2 nitrogen atoms. In certain embodiments, R is an optionally substituted 6-membered heteroaryl ring having 1 nitrogen. Example R groups include optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. According to one aspect, R is an optionally substituted 6,6-fused heteroaryl ring having 2 heteroatoms independently selected from nitrogen, oxygen, and sulfur. In some embodiments, R is a quinazoline or a quinoxaline.

In some embodiments, R is an optionally substituted heterocyclyl. In some embodiments, R is an optionally substituted 3-7 membered saturated or partially unsaturated heterocyclic ring having 1-2 heteroatoms independently selected from nitrogen, oxygen, and sulfur. In some embodiments, R is a substituted 3-7 membered saturated or partially unsaturated heterocyclic ring having 1-2 heteroatoms independently selected from nitrogen, oxygen, and sulfur. In some embodiments, R is an unsubstituted 3-7 membered saturated or partially unsaturated heterocyclic ring having 1-2 heteroatoms independently selected from nitrogen, oxygen, and sulfur.

In some embodiments, R is an optionally substituted heterocyclyl. In some embodiments, R is an optionally substituted 6 membered saturated or partially unsaturated heterocyclic ring having 1-2 heteroatoms independently selected from nitrogen, oxygen, and sulfur. In some embodiments, R is an optionally substituted 6 membered partially unsaturated heterocyclic ring having 2 heteroatoms independently selected from nitrogen, oxygen, and sulfur. In some embodiments, R is an optionally substituted 6 membered partially unsaturated heterocyclic ring having 2 oxygen atom.

In certain embodiments, R is a 3-7 membered saturated or partially unsaturated heterocyclic ring having 1-2 heteroatoms independently selected from nitrogen, oxygen, and sulfur. In certain embodiments, R is oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl. In some embodiments, R is an optionally substituted 5-membered saturated or partially unsaturated heterocyclic ring having 1-2 heteroatoms independently selected from nitrogen, oxygen, and sulfur.

In some embodiments, a structure of Formula I is a structure of Formula I as described in WO2017/210647.-In some embodiments, the internucleotidic linkage of Formula I has the structure of Formula I-a:

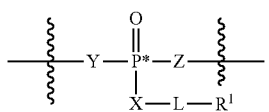

(I-a)

wherein each variable is independently described in the present disclosure, as in Formula I.

In some embodiments, the internucleotidic linkage of Formula I has the structure of Formula I-b:

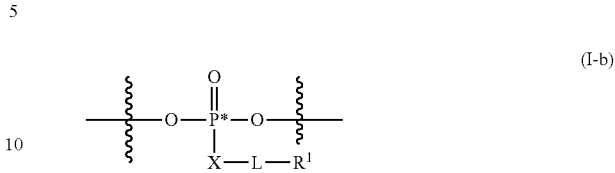

(I-b)

wherein each variable is independently described in the present disclosure, as in Formula I.

In some embodiments, the internucleotidic linkage of Formula I is an phosphorothioate triester linkage having the structure of Formula I-c:

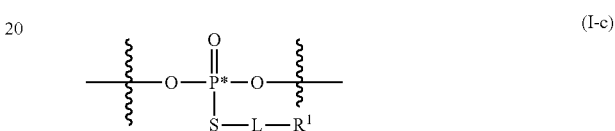

(I-c)

wherein:
P* is an asymmetric phosphorus atom and is either Rp or Sp;
L is a covalent bond or an optionally substituted, linear or branched $C_1$-$C_{10}$ alkylene, wherein one or more methylene units of L are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—; $R^1$ is halogen, R, or an optionally substituted $C_1$-$C_{50}$ aliphatic wherein one or more methylene units are optionally and independently replaced by an optionally substituted $C_1$-$C_6$ alkylene, $C_1$-$C_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
each R' is independently —R, —C(O)R, —CO$_2$R, or —SO$_2$R, or:
two R' on the same nitrogen are taken together with their intervening atoms to form an optionally substituted heterocyclic or heteroaryl ring, or
two R' on the same carbon are taken together with their intervening atoms to form an optionally substituted aryl, carbocyclic, heterocyclic, or heteroaryl ring;
-Cy- is an optionally substituted bivalent ring selected from phenylene, carbocyclylene, arylene, heteroarylene, and heterocyclylene;
each R is independently hydrogen, or an optionally substituted group selected from $C_1$-$C_6$ aliphatic, phenyl, carbocyclyl, aryl, heteroaryl, and heterocyclyl;
each

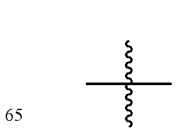

independently represents a connection to a nucleoside; and R¹ is not —H when L is a covalent bond.

In some embodiments, the internucleotidic linkage having the structure of Formula I is

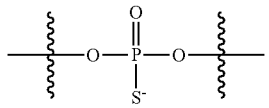 [SMILES: *OP(=O)([S-])O*]

or an internucleotidic linkage as shown in the art, e.g., WO2017/210647.

In some embodiments, the present disclosure provides a chirally controlled oligonucleotide comprising one or more phosphate diester linkages, and one or more modified internucleotide linkages having the formula of I-a, I-b, or I-c.

In some embodiments, a modified internucleotidic linkage has the structure of. In some embodiments, a modified internucleotidic linkage has the structure of I-a. In some embodiments, a modified internucleotidic linkage has the structure of I-b. In some embodiments, a modified internucleotidic linkage has the structure of I-c.

In some embodiments, a modified internucleotidic linkage is phosphorothioate. Examples of internucleotidic linkages having the structure of Formula I are widely known in the art, including but not limited to those described in US 20110294124, US 20120316224, US 20140194610, US 20150211006, US 20150197540, WO 2015107425, PCT/US2016/043542, and PCT/US2016/043598, each of which is incorporated herein by reference. In some embodiments, a modified internucleotidic linkage is a vinylphosphonate. Whittaker et al. 2008 Tetrahedron Letters 49: 6984-6987.

Non-limiting examples of internucleotidic linkages also include those described in the art, including, but not limited to, those described in any of: Gryaznov, S.; Chen, J.-K. J. Am. Chem. Soc. 1994, 116, 3143, Jones et al. J. Org. Chem. 1993, 58, 2983, Koshkin et al. 1998 Tetrahedron 54: 3607-3630, Lauritsen et al. 2002 Chem. Comm. 5: 530-531, Lauritsen et al. 2003 Bioo. Med. Chem. Lett. 13: 253-256, Mesmaeker et al. Angew. Chem., Int. Ed. Engl. 1994, 33, 226, Petersen et al. 2003 TRENDS Biotech. 21: 74-81, Schultz et al. 1996 Nucleic Acids Res. 24: 2966, Ts'o et al. Ann. N. Y. Acad. Sci. 1988, 507, 220, and Vasseur et al. J. Am. Chem. Soc. 1992, 114, 4006.

In some embodiments, a modified internucleotidic linkage is a non-negatively charged internucleotidic linkage. In some embodiments, a modified internucleotidic linkage is a neutral internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of:

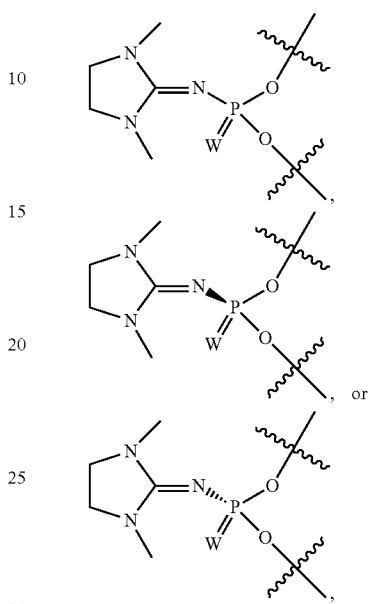

wherein W is O or S. In some embodiments, W is O. In some embodiments, W is S. In some embodiments, a non-negatively charged internucleotidic linkage is stereochemically controlled.

In some embodiments, an internucleotidic linkage comprising a triazole moiety (e.g., an optionally substituted triazolyl group) in a provided oligonucleotide, e.g., a C9orf72 oligonucleotide, has the structure of:

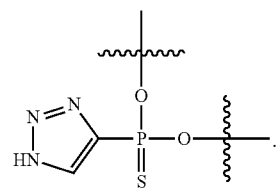

In some embodiments, an internucleotidic linkage comprising a triazole moiety has the formula of

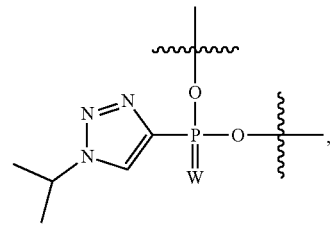

where W is O or S. In some embodiments, an internucleotidic linkage comprising an alkyne moiety (e.g., an optionally substituted alkynyl group) has the formula of:

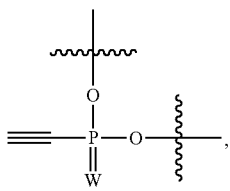

wherein W is O or S. In some embodiments, an internucleotidic linkage comprises a cyclic guanidine moiety. In some embodiments, an internucleotidic linkage comprising a cyclic guanidine moiety has the structure of:

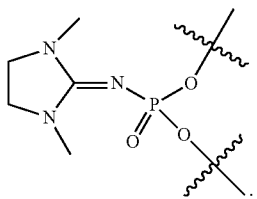 [SMILES: *OP(=O)(N=C1N(C)CCN1C)O*]

In some embodiments, a neutral internucleotidic linkage or internucleotidic linkage comprising a cyclic guanidine moiety is stereochemically controlled.

In some embodiments, a C9orf72 oligonucleotide comprises a lipid moiety In some embodiments, an internucleotidic linkage comprises a Tmg group

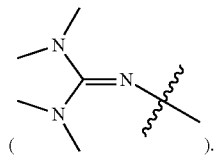 [SMILES: *N=C(N(C)C)N(C)C]

In some embodiments, an internucleotidic linkage comprises a Tmg group and has the structure of

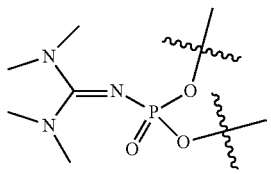 [SMILES: *OP(=O)(N=C(N(C)C)N(C)C)O*]

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage has the structure of formula I, I-a, I-b, I-c, I-n-1, I-n-2, I-n-3, II, II-a-1, II-a-2, II-b-1, II-b-2, II-c-1, II-c-2, II-d-1, II-d-2, etc., or a salt form thereof. In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted triazolyl group. In some embodiments, a non-negatively charged internucleotidic linkage comprises an unsubstituted triazolyl group, e.g.,

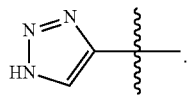

In some embodiments, a non-negatively charged internucleotidic linkage comprises a substituted triazolyl group, e.g.,

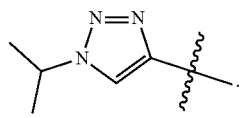 [SMILES: *c1cn(C(C)C)nn1]

In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 1-4 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

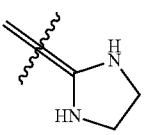 [SMILES: *=C1NCCN1]

group. In some embodiments, a non-negatively charged internucleotidic linkage comprises an substituted

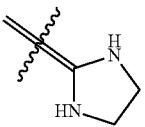 [SMILES: *=C1NCCN1]

group. In some embodiments, a non-negatively charged internucleotidic linkage comprises a

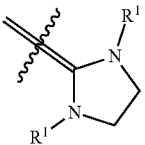

group. In some embodiments, each $R^1$ is independently optionally substituted $C_{1-6}$ alkyl. In some embodiments, each $R^1$ is independently methyl.

In some embodiments, a modified internucleotidic linkage, e.g., a non-negatively charged internucleotidic linkage, comprises a triazole or alkyne moiety, each of which is optionally substituted. In some embodiments, a modified internucleotidic linkage comprises a triazole moiety. In some embodiments, a modified internucleotidic linkage comprises a unsubstituted triazole moiety. In some embodiments, a modified internucleotidic linkage comprises a substituted triazole moiety. In some embodiments, a modified internucleotidic linkage comprises an alkyl moiety. In some embodiments, a modified internucleotidic linkage comprises an optionally substituted alkynyl group. In some embodiments, a modified internucleotidic linkage comprises an unsubstituted alkynyl group. In some embodiments, a modified internucleotidic linkage comprises a substituted alkynyl group. In some embodiments, an alkynyl group is directly bonded to a linkage phosphorus.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage. In some embodiments, an oligonucleotide comprises at least one phosphorothioate internucleotidic linkage and at least one non-negatively charged internucleotidic linkage. In some embodiments, an oligonucleotide comprises at least one phosphorothioate internucleotidic linkage, at least one natural phosphate linkage, and at least one non-negatively charged internucleotidic linkage. In some embodiments, oligonucleotides comprise one or more, e.g., 1, 2, 3, 4, 5, 6, 7, 8, 9, 10, 11, 12, 13, 14, 15, 16, 17, 18, 19, 20 or more non-negatively charged internucleotidic linkages. In some embodiments, a non-negatively charged internucleotidic linkage is not negatively charged in that at a given pH in an aqueous solution less than 50%, 40%, 40%, 30%, 20%, 10%, 5%, or 1% of the internucleotidic linkage exists in a negatively charged salt form. In some embodiments, a pH is about pH 7.4. In some embodiments, a pH is about 4-9. In some embodiments, the percentage is less than 10%. In some embodiments, the percentage is less than 5%. In some embodiments, the percentage is less than 1%. In some embodiments, an internucleotidic linkage is a non-negatively charged internucleotidic linkage in that the neutral form of the internucleotidic linkage has no pKa that is no more than about 1, 2, 3, 4, 5, 6, or 7 in water. In some embodiments, no pKa is 7 or less. In some embodiments, no pKa is 6 or less. In some embodiments, no pKa is 5 or less. In some embodiments, no pKa is 4 or less. In some embodiments, no pKa is 3 or less. In some embodiments, no pKa is 2 or less. In some embodiments, no pKa is 1 or less. In some embodiments, pKa of the neutral form of an internucleotidic linkage can be represented by pKa of the neutral form of a compound having the structure of $CH_3$— the internucleotidic linkage —$CH_3$. For example, pKa of the neutral form of an internucleotidic linkage having the structure of formula I may be represented by the pKa of the neutral form of a compound having the structure of

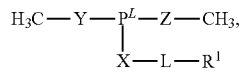

pKa of

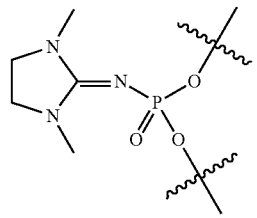 [SMILES: *OP(=O)(N=C1N(C)CCN1C)O*]

can be represented by pKa

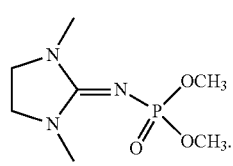

In some embodiments, a non-negatively charged internucleotidic linkage is a neutral internucleotidic linkage. In some embodiments, a non-negatively charged internucleotidic linkage is a positively-charged internucleotidic linkage. In some embodiments, a non-negatively charged internucleotidic linkage comprises a guanidine moiety. In some embodiments, a non-negatively charged internucleotidic linkage comprises a heteroaryl base moiety. In some embodiments, a non-negatively charged internucleotidic linkage comprises a triazole moiety. In some embodiments, a non-negatively charged internucleotidic linkage comprises an alkynyl moiety.

In some embodiments, a non-negatively charged internucleotidic linkage has the structure of formula I, I-a, I-b, I-c, I-n-1, I-n-2, I-n-3, II, II-a-1, II-a-2, II-b-1, II-b-2, II-c-1, II-c-2, II-d-1, II-d-2, or a salt form thereof (not negatively charged). In some embodiments, an internucleotidic linkage, e.g., a non-negatively charged internucleotidic linkage, has the structure of formula I-n-1 or a salt form thereof:

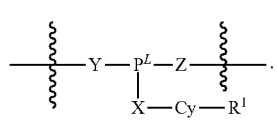

I-n-1

In some embodiments, X is a covalent bond and —X-Cy-R$^1$ is -Cy-R$^1$. In some embodiments, -Cy- is an optionally substituted bivalent group selected from a 5-20 membered heteroaryl ring having 1-10 heteroatoms, and a 3-20 membered heterocyclyl ring having 1-10 heteroatoms. In some embodiments, -Cy- is an optionally substituted bivalent 5-20 membered heteroaryl ring having 1-10 heteroatoms. In some embodiments, -Cy-R$^1$ is optionally substituted 5-20 membered heteroaryl ring having 1-10 heteroatoms, wherein at least one heteroatom is nitrogen. In some embodiments, -Cy-R$^1$ is optionally substituted 5-membered heteroaryl ring having 1-4 heteroatoms, wherein at least one heteroatom is nitrogen. In some embodiments, -Cy-R$^1$ is optionally substituted 6-membered heteroaryl ring having 1-4 heteroatoms, wherein at least one heteroatom is nitrogen. In some embodiments, -Cy-R$_1$ is optionally substituted triazolyl.

In some embodiments, an internucleotidic linkage, e.g., a non-negatively charged internucleotidic linkage, has the structure of formula I-n-2 or a salt form thereof:

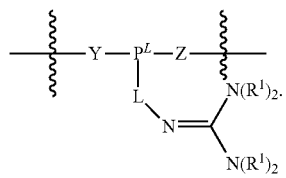

I-n-2

In some embodiments, R$^1$ is R'. In some embodiments, L is a covalent bond. In some embodiments, an internucleotidic linkage, e.g., a non-negatively charged internucleotidic linkage, has the structure of formula I-n-3 or a salt form thereof:

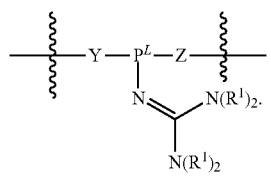

I-n-3

In some embodiments, two R' on different nitrogen atoms are taken together to form a ring as described. In some embodiments, a formed ring is 5-membered. In some embodiments, a formed ring is 6-membered. In some embodiments, a formed ring is substituted. In some embodiments, the two R' group that are not taken together to form a ring are each independently R. In some embodiments, the two R' group that are not taken together to form a ring are each independently hydrogen or an optionally substituted C$_{1-6}$ aliphatic. In some embodiments, the two R' group that are not taken together to form a ring are each independently hydrogen or an optionally substituted C$_{1-6}$ alkyl. In some embodiments, the two R' group that are not taken together to form a ring are the same. In some embodiments, the two R' group that are not taken together to form a ring are different. In some embodiments, both of them are —CH$_3$.

In some embodiments, a internucleotidic linkage, e.g., a non-negatively charged internucleotidic linkage, has the structure of formula II or a salt form thereof:

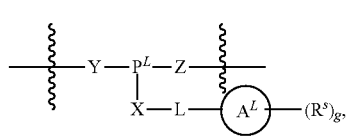

II or a salt form thereof, wherein:

P$^L$ is P(=W), P, or P→B(R')$_3$;

W is O, N(-L-R$^5$), S or Se;

each of X, Y and Z is independently —O—, —S—, —N(-L-R$^5$)—, or L;

Ring A$^L$ is an optionally substituted 3-20 membered monocyclic, bicyclic or polycyclic ring having 0-10 heteroatoms;

each R$^s$ is independently —H, halogen, —CN, —N$_3$, —NO, —NO$_2$, -L-R', -L-Si(R)$_3$, -L-OR', -L-SR', -L-N(R')$_2$, —O-L-R', —O-L-Si(R)$_3$, —O-L-OR', —O-L-SR', or —O-L-N(R')$_2$;

g is 0-20;

each L is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced with C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more CH or carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each Cy$^L$ is independently an optionally substituted trivalent or tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)₂R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or, two or more R groups on the same atom are optionally and independently taken together with the atom to form an optionally substituted, 3-30 membered, monocyclic, bicyclic or polycyclic ring having, in addition to the atom, 0-10 heteroatoms, or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

In some embodiments, a internucleotidic linkage, e.g., a non-negatively charged internucleotidic linkage of formula II, has the structure of formula II-a-1 or a salt form thereof:

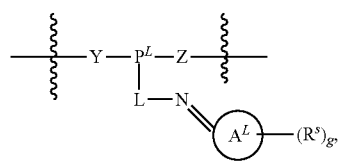

II-a-1 or a salt form thereof.

In some embodiments, a internucleotidic linkage, e.g., a non-negatively charged internucleotidic linkage of formula II, has the structure of formula II-a-2 or a salt form thereof:

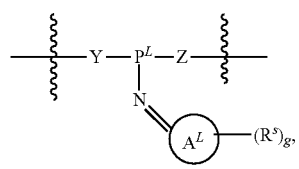

II-a-2 or a salt form thereof.

In some embodiments, $A^L$ is bonded to —N= or L through a carbon atom. In some embodiments, an internucleotidic linkage, e.g., a non-negatively charged internucleotidic linkage of formula II or II-a-1, II-a-2, has the structure of formula II-b-1 or a salt form thereof:

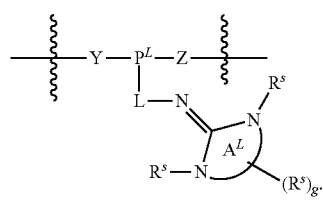

II-b-1

In some embodiments, a structure of formula II-a-1 or II-a-2 may be referred to a structure of formula II-a. In some embodiments, a structure of formula II-b-1 or II-b-2 may be referred to a structure of formula II-b. In some embodiments, a structure of formula II-c-1 or II-c-2 may be referred to a structure of formula II-c. In some embodiments, a structure of formula II-d-1 or II-d-2 may be referred to a structure of formula II-d.

In some embodiments, $A^L$ is bonded to —N= or L through a carbon atom. In some embodiments, an internucleotidic linkage, e.g., a non-negatively charged internucleotidic linkage of formula II or II-a-1, II-a-2, has the structure of formula II-b-2 or a salt form thereof

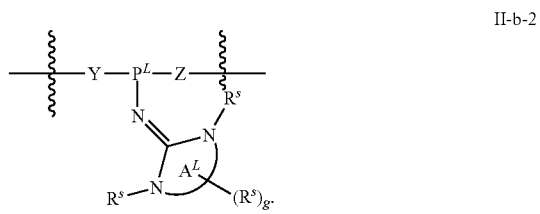

II-b-2

In some embodiments, Ring $A^L$ is an optionally substituted 3-20 membered monocyclic ring having 0-10 heteroatoms (in addition to the two nitrogen atoms for formula II-b). In some embodiments, Ring $A^L$ is an optionally substituted 5-membered monocyclic saturated ring.

In some embodiments, an internucleotidic linkage, e.g., a non-negatively charged internucleotidic linkage of formula II, II-a, or II-b, has the structure of formula II-c-1 or a salt form thereof:

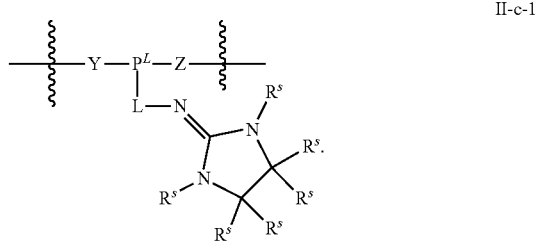

II-c-1

In some embodiments, an internucleotidic linkage, e.g., a non-negatively charged internucleotidic linkage of formula II, II-a, or II-b, has the structure of formula II-c-2 or a salt form thereof:

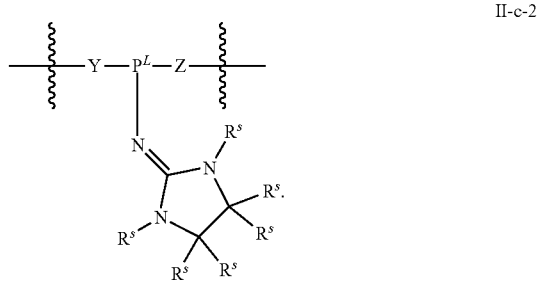

II-c-2

In some embodiments, an internucleotidic linkage, e.g., a non-negatively charged internucleotidic linkage of formula II, II-a, II-b, or II-c has the structure of formula II-d-1 or a salt form thereof:

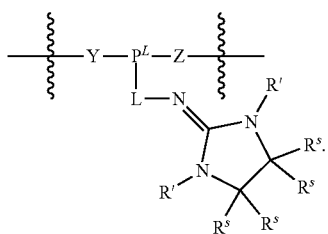

In some embodiments, an internucleotidic linkage, e.g., a non-negatively charged internucleotidic linkage of formula II, II-a, II-b, or II-c has the structure of formula II-d-2 or a salt form thereof:

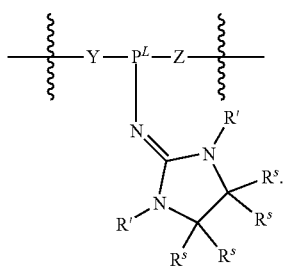

II-d-2

In some embodiments, each R' is independently optionally substituted $C_{1-6}$ aliphatic. In some embodiments, each R' is independently optionally substituted $C_{1-6}$ alkyl. In some embodiments, each R' is independently —$CH_3$. In some embodiments, each $R^s$ is —H.

In some embodiments, a non-negatively charged internucleotidic linkage has the structure of

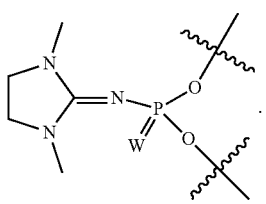

In some embodiments, a non-negatively charged internucleotidic linkage has the structure of

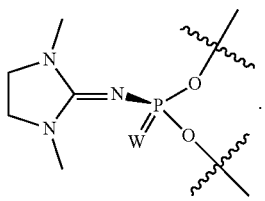

In some embodiments, a non-negatively charged internucleotidic linkage has the structure of

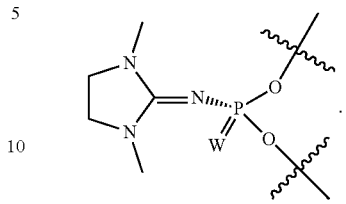

In some embodiments, a non-negatively charged internucleotidic linkage has the structure of

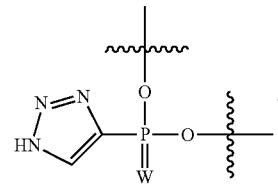

In some embodiments, a non-negatively charged internucleotidic linkage has the structure of

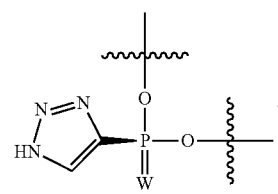

In some embodiments, a non-negatively charged internucleotidic linkage has the structure of

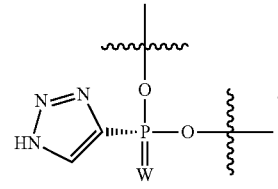

In some embodiments, a non-negatively charged internucleotidic linkage has the structure of

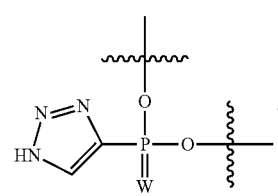

In some embodiments, a non-negatively charged internucleotidic linkage has the structure of

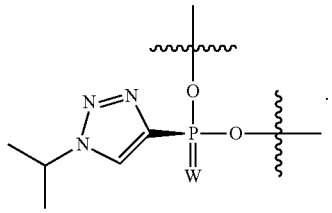

In some embodiments, a non-negatively charged internucleotidic linkage has the structure of

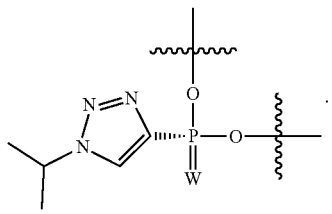

In some embodiments, a non-negatively charged internucleotidic linkage has the structure of

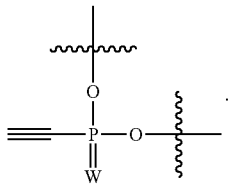

In some embodiments, a non-negatively charged internucleotidic linkage has the structure of

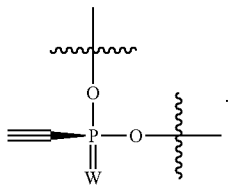

In some embodiments, a non-negatively charged internucleotidic linkage has the structure of

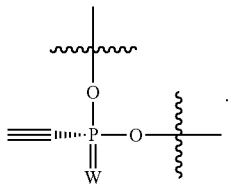

In some embodiments, W is O. In some embodiments, W is S.

In some embodiments, each LP independently has the structure of formula I, I-a, I-b, I-c, I-n-1, I-n-2, I-n-3, II, II-a-1, II-a-2, II-b-1, II-b-2, II-c-1, II-c-2, II-d-1, II-d-2, or a salt form thereof.

In some embodiments, the present disclosure provides oligonucleotides comprising one or more non-negatively charged internucleotidic linkages. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage has the structure of formula I-n-1, I-n-2, I-n-3, II, II-a-1, II-a-2, II-b-1, II-b-2, II-c-1, II-c-2, II-d-1, II-d-2, or a salt form thereof.

In some embodiments, a non-negatively charged internucleotidic linkage comprises a triazole moiety. In some embodiments, a non-negatively charged internucleotidic linkage comprises an optionally substituted triazolyl group. In some embodiments, a non-negatively charged internucleotidic linkage has the structure of

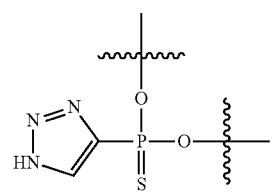

In some embodiments, a non-negatively charged internucleotidic linkage has the structure of

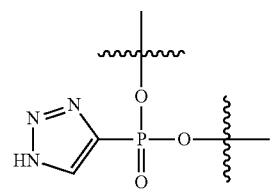

In some embodiments, a non-negatively charged internucleotidic linkage comprises a substituted triazolyl group. In some embodiments, a non-negatively charged internucleotidic linkage has the structure of

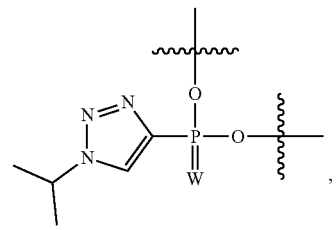

wherein W is O or S. In some embodiments, a non-negatively charged internucleotidic linkage comprises an optionally substituted alkynyl group. In some embodiments, a non-negatively charged internucleotidic linkage has the structure of

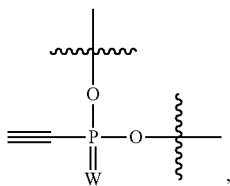

wherein W is O or S.

In some embodiments, the present disclosure provides oligonucleotides comprising an internucleotidic linkage, e.g., a non-negatively charged internucleotidic linkage, which comprises a cyclic guanidine moiety. In some embodiments, an internucleotidic linkage comprises a cyclic guanidine and has the structure of:

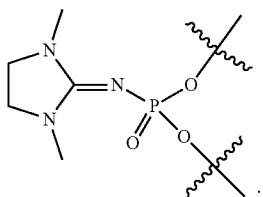 [SMILES: *OP(=O)(N=C1N(C)CCN1C)O*]

In some embodiments, an internucleotidic linkage, e.g., a non-negatively charged internucleotidic linkage, comprising a cyclic guanidine is stereochemically controlled.

In some embodiments, a non-negatively charged internucleotidic linkage, or a neutral internucleotidic linkage, is or comprising a structure selected from

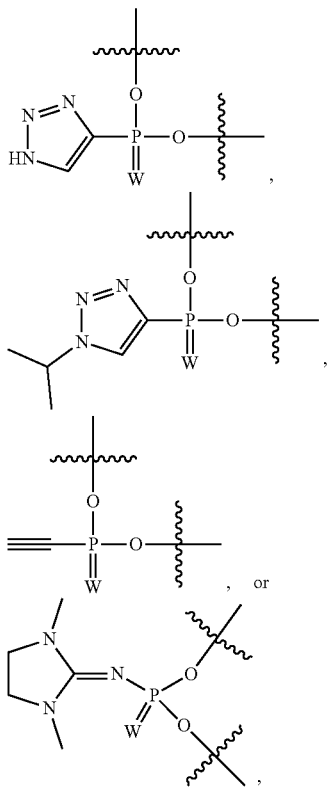

wherein W is O or S. In some embodiments, a non-negatively charged internucleotidic linkage is a chirally controlled internucleotidic linkage. In some embodiments, a neutral internucleotidic linkage is a chirally controlled internucleotidic linkage. In some embodiments, a nucleic acid or an oligonucleotide comprising a modified internucleotidic linkage comprising a cyclic guanidine moiety is a siRNA, double-strained siRNA, single-stranded siRNA, gapmer, skipmer, blockmer, antisense oligonucleotide, antagomir, microRNA, pre-microRNs, antimir, supermir, ribozyme, U1 adaptor, RNA activator, RNAi agent, decoy oligonucleotide, triplex forming oligonucleotide, aptamer or adjuvant.

In some embodiments, an oligonucleotide comprises a neutral internucleotidic linkage and a chirally controlled internucleotidic linkage. In some embodiments, an oligonucleotide comprises a neutral internucleotidic linkage and a chirally controlled internucleotidic linkage which is a phosphorothioate in the Rp or Sp configuration. In some embodiments, the present disclosure provides an oligonucleotide comprising one or more non-negatively charged internucleotidic linkages and one or more phosphorothioate internucleotidic linkage, wherein each phosphorothioate internucleotidic linkage in the oligonucleotide is independently a chirally controlled internucleotidic linkage. In some embodiments, the present disclosure provides an oligonucleotide comprising one or more neutral internucleotidic linkages and one or more phosphorothioate internucleotidic linkage, wherein each phosphorothioate internucleotidic linkage in the oligonucleotide is independently a chirally controlled internucleotidic linkage. In some embodiments, a provided oligonucleotide comprises at least 5, 6, 7, 8, 9, 10, 11, 12, 13, 14, 15, 16, 17, 18, 19, 20 or more chirally controlled phosphorothioate internucleotidic linkages.

Without wishing to be bound by any particular theory, the present disclosure notes that a neutral internucleotidic linkage can be more hydrophobic than a phosphorothioate internucleotidic linkage (PS), which is more hydrophobic than a phosphodiester linkage (natural phosphate linkage, PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be bound by any particular theory, the present disclosure notes that incorporation of one or more neutral internucleotidic linkages can be utilized to modulate melting temperature between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as exon skipping or gene knockdown. In some embodiments, an oligonucleotide capable of mediating knockdown of level of a nucleic acid or a product encoded thereby comprises one or more non-negatively charged internucleotidic linkages. In some embodiments, an oligonucleotide capable of mediating knockdown of expression of a target gene comprises one or more non-negatively charged internucleotidic linkages. In some embodiments, an oligonucleotide capable of mediating knockdown of expression of a target gene comprises one or more neutral internucleotidic linkages.

In some embodiments, a non-negatively charged internucleotidic linkage is not chirally controlled. In some embodiments, a non-negatively charged internucleotidic linkage is chirally controlled. In some embodiments, a non-negatively charged internucleotidic linkage is chirally controlled and its linkage phosphorus is Rp. In some embodiments, a non-negatively charged internucleotidic linkage is chirally controlled and its linkage phosphorus is Sp.

In some embodiments, a provided oligonucleotide comprises 1, 2, 3, 4, 5, 6, 7, 8, 9, 10, or more non-negatively charged internucleotidic linkages. In some embodiments, a provided oligonucleotide comprises 1, 2, 3, 4, 5, 6, 7, 8, 9, 10, or more neutral internucleotidic linkages. In some embodiments, each of non-negatively charged internucleotidic linkage and/or neutral internucleotidic linkages is optionally and independently chirally controlled. In some embodiments, each non-negatively charged internucleotidic linkage in an oligonucleotide is independently a chirally controlled internucleotidic linkage. In some embodiments, each neutral internucleotidic linkage in an oligonucleotide is independently a chirally controlled internucleotidic linkage. In some embodiments, at least one non-negatively charged internucleotidic linkage/neutral internucleotidic linkage has the structure of

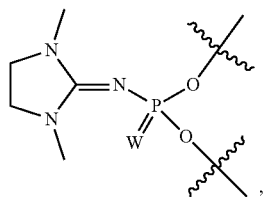

wherein W is O or S. In some embodiments, at least one non-negatively charged internucleotidic linkage/neutral internucleotidic linkage has the structure of

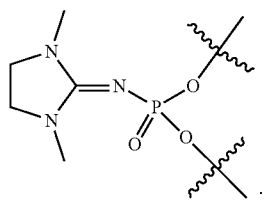 [SMILES: *OP(=O)(N=C1N(C)CCN1C)O*]

In some embodiments, at least one non-negatively charged internucleotidic linkage/neutral internucleotidic linkage has the structure of

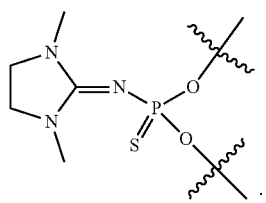 [SMILES: *OP(=S)(N=C1N(C)CCN1C)O*]

In some embodiments, at least one non-negatively charged internucleotidic linkage/neutral internucleotidic linkage has the structure of

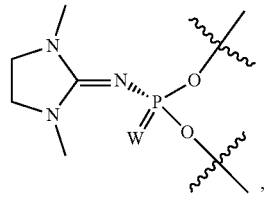

wherein W is O or S. In some embodiments, at least one non-negatively charged internucleotidic linkage/neutral internucleotidic linkage has the structure of

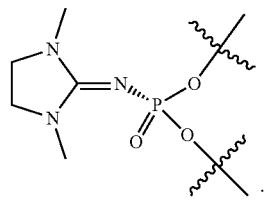

In some embodiments, at least one non-negatively charged internucleotidic linkage/neutral internucleotidic linkage has the structure of

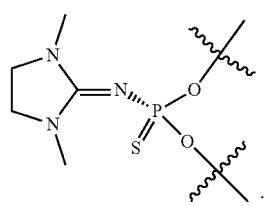

In some embodiments, at least one non-negatively charged internucleotidic linkage/neutral internucleotidic linkage has the structure of

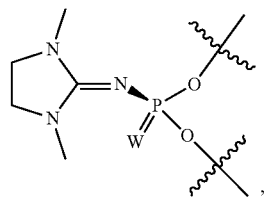

wherein W is O or S. In some embodiments, at least one non-negatively charged internucleotidic linkage/neutral internucleotidic linkage has the structure of

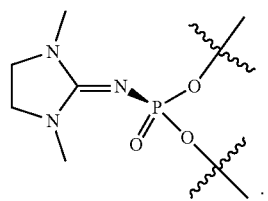

In some embodiments, at least one non-negatively charged internucleotidic linkage/neutral internucleotidic linkage has the structure of

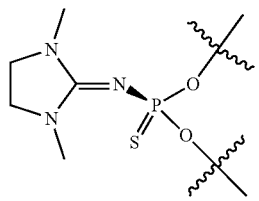

In some embodiments, a provided oligonucleotide comprises at least one non-negatively charged internucleotidic linkage wherein its linkage phosphorus is in Rp configuration, and at least one non-negatively charged internucleotidic linkage wherein its linkage phosphorus is in Sp configuration.

In some embodiments, an oligonucleotide or a block or region thereof (e.g., a 5'-end region, a 5'-wing, a middle region, a core region, a 3'-end region, a 3'-ring, etc.) comprises one or more, e.g., 1, 2, 3, 4, 5, 6, 7, 8, 9, 10, 11, 12, 13, 14, 15, 16, 17, 18, 19, 20 or more, non-negatively charged internucleotidic linkages as described in the present disclosure. In some embodiments, a provided oligonucleotide comprises two or more, e.g., 2, 3, 4, 5, 6, 7, 8, 9, 10, 11, 12, 13, 14, 15, 16, 17, 18, 19, 20 or more, consecutive non-negatively charged internucleotidic linkages. In some embodiments, a block or region comprises two or more, e.g., 2, 3, 4, 5, 6, 7, 8, 9, 10, 11, 12, 13, 14, 15, 16, 17, 18, 19, 20 or more, consecutive non-negatively charged internucleotidic linkages. In some embodiments, the number is 1. In some embodiments, the number is 2. In some embodiments, the number is 3. In some embodiments, the number is 4. In some embodiments, the number is 5. In some embodiments, the number is 6. In some embodiments, the number is 7. In some embodiments, the number is 8. In some embodiments, the number is 9. In some embodiments, the number is 10 or more. In some embodiments, each internucleotidic linkage between nucleoside units in a block, e.g., a 5'-end region, a 5'-wing, is a non-negatively charged internucleotidic linkage except the first internucleotidic linkage between two nucleoside units of the block from the 5'-end of the block. In some embodiments, each internucleotidic linkage between nucleoside units in a block, e.g., a 3'-end region, a 3'-wing, is a non-negatively charged internucleotidic linkage except the first internucleotidic linkage between two nucleoside units of the block from the 3'-end of the block. In some embodiments, each internucleotidic linkage between nucleoside units in a region, e.g., a 5'-end region, a 5'-wing, is a non-negatively charged internucleotidic linkage except the first internucleotidic linkage between two nucleoside units of the region from the 5'-end of the region. In some embodiments, each internucleotidic linkage between nucleoside units in a region, e.g., a 3'-end region, a 3'-wing, is a non-negatively charged internucleotidic linkage except the first internucleotidic linkage between two nucleoside units of the region from the 3'-end of the region. In some embodiments, each internucleotidic linkage in a region or block, e.g., a 5'-end region, a 5'-wing, a middle region, a core region, a 3'-end region, a 3'-ring, etc., is independently a non-negatively charged internucleotidic linkage, a natural phosphate internucleotidic linkage or a Rp chiral internucleotidic linkage. In some embodiments, each internucleotidic linkage in a region or block is independently a non-negatively charged internucleotidic linkage, a natural phosphate internucleotidic linkage or a Rp phosphorothioate internucleotidic linkage. In some embodiments, about 40%, 45%, 50%, 55%, 60%, 65%, 70%, 75%, 80%, 85%, 90%, 95% or more of internucleotidic linkages of an oligonucleotide or a region or block, e.g., a 5'-end region, a 5'-wing, a middle region, a core region, a 3'-end region, a 3'-ring, etc., is independently a non-negatively charged internucleotidic linkage, a natural phosphate internucleotidic linkage or a Rp chiral internucleotidic linkage. In some embodiments, about 40%, 45%, 50%, 55%, 60%, 65%, 70%, 75%, 80%, 85%, 90%, 95% or more of internucleotidic linkages of an oligonucleotide or a region or block is independently a non-negatively charged internucleotidic linkage, a natural phosphate internucleotidic linkage or a Rp phosphorothioate internucleotidic linkage. In some embodiments, about 40%, 45%, 50%, 55%, 60%, 65%, 70%, 75%, 80%, 85%, 90%, 95% or more of internucleotidic linkages of an oligonucleotide or a region or block is independently a non-negatively charged internucleotidic linkage or a natural phosphate internucleotidic linkage. In some embodiments, about 40%, 45%, 50%, 55%, 60%, 65%, 70%, 75%, 80%, 85%, 90%, 95% or more of internucleotidic linkages of an oligonucleotide or a region or block is independently a non-negatively charged internucleotidic linkage. In some embodiments, the percentage is 45% or more. In some embodiments, the percentage is 50% or more. In some embodiments, the percentage is 60% or more. In some embodiments, the percentage is 70% or more. In some embodiments, the percentage is 80% or more. In some embodiments, the percentage is 90% or more. In some embodiments, a region or block is a wing. In some embodiments, a region or block is a 5'-wing. In some embodiments, a region or block is a 3'-wing. In some embodiments, a region or block is a core. As described herein, a region or block, e.g., a wing, a core, etc., can have various lengths, e.g., comprising 2, 3, 4, 5, 6, 7, 8, 9, 10, 11, 12, 13, 14, 15, 16, 17, 18, 19, 20 or more nucleobases. In some embodiments, each nucleobase is independently optionally substituted A, T, C, G, U or an optionally substituted tautomer of A, T, C, G, or U.

Oligonucleotides of the provided technologies can be of various lengths. In some embodiments, provided oligonucleotides comprise 5, 6, 7, 8, 9, 10, 11, 12, 13, 14, 15, 16, 17, 18, 19, 20, 21, 22, 23, 24, 25, 26, 27, 28, 29, 30, 40, 50 or more bases. In some embodiments, provided oligonucleotides comprise 10, 11, 12, 13, 14, 15, 16, 17, 18, 19, 20, 21, 22, 23, 24, 25, 26, 27, 28, 29, 30, 40, 50 or more bases. In some embodiments, provided oligonucleotides comprise 15, 16, 17, 18, 19, 20, 21, 22, 23, 24, 25, 26, 27, 28, 29, 30, 40, 50 or more bases.

In some embodiments, the present disclosure provides a chirally controlled oligonucleotide comprising at least one phosphate diester internucleotidic linkage and at least one phosphorothioate triester linkage having the structure of Formula I-c. In some embodiments, the present disclosure provides a chirally controlled oligonucleotide comprising at least one phosphate diester internucleotidic linkage and at least two phosphorothioate triester linkages having the structure of Formula I-c. In some embodiments, the present disclosure provides a chirally controlled oligonucleotide comprising at least one phosphate diester internucleotidic linkage and at least three phosphorothioate triester linkages having the structure of Formula I-c. In some embodiments, the present disclosure provides a chirally controlled oligonucleotide comprising at least one phosphate diester internucleotidic linkage and at least four phosphorothioate triester linkages having the structure of Formula I-c. In some embodiments, the present disclosure provides a chirally controlled oligonucleotide comprising at least one phosphate diester internucleotidic linkage and at least five phosphorothioate triester linkages having the structure of Formula I-c. In some embodiments, the present disclosure provides a chirally controlled oligonucleotide comprising a non-negatively charged internucleotidic linkage having the structure of formula I-n-1, I-n-2, I-n-3, II, II-a-1, II-a-2, II-b-1, II-b-2, II-c-1, II-c-2, II-d-1, II-d-2, or a salt form thereof.

In some embodiments, the present disclosure provides a chirally controlled oligonucleotide comprising a sequence found in any oligonucleotide disclosed herein. In some embodiments, the present disclosure provides a chirally controlled oligonucleotide comprising a sequence found in any oligonucleotide disclosed herein, wherein one or more U is replaced with T or vice versa. In some embodiments, the present disclosure provides a chirally controlled oligonucleotide comprising a sequence found in any oligonucleotide disclosed herein, wherein the said sequence has over 50% identity with the sequence of any oligonucleotide disclosed herein. In some embodiments, the present disclosure provides a chirally controlled oligonucleotide comprising a sequence found in any oligonucleotide disclosed herein, wherein the said sequence has over 60% identity with the sequence of any oligonucleotide disclosed herein. In some embodiments, the present disclosure provides a chirally controlled oligonucleotide comprising a sequence found in any oligonucleotide disclosed herein, wherein the said sequence has over 70% identity with the sequence of any oligonucleotide disclosed herein. In some embodiments, the present disclosure provides a chirally controlled oligonucleotide comprising a sequence found in any oligonucleotide disclosed herein, wherein the said sequence has over 80% identity with the sequence of any oligonucleotide disclosed herein. In some embodiments, the present disclosure provides a chirally controlled oligonucleotide comprising a sequence found in any oligonucleotide disclosed herein, wherein the said sequence has over 90% identity with the sequence of any oligonucleotide disclosed herein. In some embodiments, the present disclosure provides a chirally controlled oligonucleotide comprising a sequence found in any oligonucleotide disclosed herein, wherein the said sequence has over 95% identity with the sequence of any oligonucleotide disclosed herein. In some embodiments, the present disclosure provides a chirally controlled oligonucleotide comprising the sequence of any oligonucleotide disclosed herein. In some embodiments, the present disclosure provides a chirally controlled oligonucleotide having the sequence of any oligonucleotide disclosed herein. In some embodiments, the present disclosure provides a chirally controlled oligonucleotide comprising a sequence found in any oligonucleotide disclosed herein, wherein the oligonucleotides have a pattern of backbone linkages, pattern of backbone chiral centers, and/or pattern of backbone phosphorus modifications described herein.

In some embodiments, the present disclosure provides a chirally controlled oligonucleotide comprising a sequence (or a portion of at least 10 contiguous bases thereof) found in any oligonucleotide disclosed herein, wherein at least one internucleotidic linkage has a chiral linkage phosphorus. In some embodiments, the present disclosure provides a chirally controlled oligonucleotide comprising a sequence found in any oligonucleotide disclosed herein, wherein at least one internucleotidic linkage has the structure of Formula I. In some embodiments, the present disclosure provides a chirally controlled oligonucleotide comprising a sequence (or a portion of at least 10 contiguous bases thereof) found in any oligonucleotide disclosed herein, wherein each internucleotidic linkage has the structure of Formula I. In some embodiments, the present disclosure provides a chirally controlled oligonucleotide comprising a sequence (or a portion of at least 10 contiguous bases thereof) found in any oligonucleotide disclosed herein, wherein at least one internucleotidic linkage has the structure of Formula I-c. In some embodiments, the present disclosure provides a chirally controlled oligonucleotide comprising a sequence (or a portion of at least 10 contiguous bases thereof) found in any oligonucleotide disclosed herein, wherein each internucleotidic linkage has the structure of Formula I-c. In some embodiments, the present disclosure provides a chirally controlled oligonucleotide comprising a sequence (or a portion of at least 10 contiguous bases thereof) found in any oligonucleotide disclosed herein, wherein at least one internucleotidic linkage is

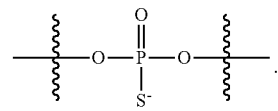

In some embodiments, the present disclosure provides a chirally controlled oligonucleotide comprising a sequence (or a portion of at least 10 contiguous bases thereof) found in any oligonucleotide disclosed herein, wherein each internucleotidic linkage is

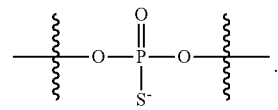

In some embodiments, the present disclosure provides a chirally controlled oligonucleotide comprising a sequence (or a portion of at least 10 contiguous bases thereof) found in any oligonucleotide disclosed herein, wherein at least one internucleotidic linkage is

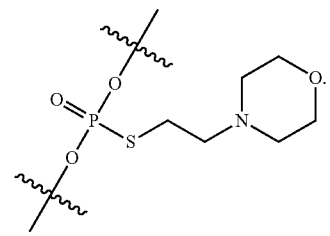

In some embodiments, the present disclosure provides a chirally controlled oligonucleotide comprising a sequence (or a portion of at least 10 contiguous bases thereof) found in any oligonucleotide disclosed herein, wherein each internucleotidic linkage is

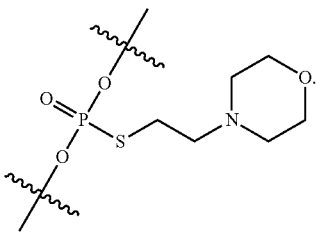

In some embodiments, a modification at a linkage phosphorus is characterized by its ability to be transformed to a phosphate diester, such as those present in naturally occurring DNA and RNA, by one or more esterases, nucleases, and/or cytochrome P450 enzymes, including but not limited to: CYP1A1, CYP1A2, CYP1B1 (Family: CYP1); CYP2A6, CYP2A7, CYP2A13, CYP2B6, CYP2C8, CYP2C9, CYP2C18, CYP2C19, CYP2D6, CYP2E1, CYP2F1, CYP2J2, CYP2R1, CYP2S1, CYP2U1, CYP2W1 (CYP2); CYP3A4, CYP3A5, CYP3A7, CYP3A43 (CYP3); CYP4A11, CYP4A22, CYP4B1, CYP4F2, CYP4F3, CYP4F8, CYP4F11, CYP4F12, CYP4F22, CYP4V2, CYP4X1, CYP4Z1 (CYP4); CYP5A1 (CYP5); CYP7A1, CYP7B1 (CYP7); CYP8A1 (prostacyclin synthase), CYP8B1 (bile acid biosynthesis) (CYP8); CYP11A1, CYP11B1, CYP11B2 (CYP11); CYP17A1 (CYP17); CYP19A1 (CYP19); CYP20A1 (CYP20); CYP21A2 (CYP21); CYP24A1 (CYP24); CYP26A1, CYP2XXX1, CYP26C1 (CYP26); CYP27A1 (bile acid biosynthesis), CYP27B1 (vitamin D3 1-alpha hydroxylase, activates vitamin D3), CYP27C1 (unknown function) (CYP27); CYP39A1 (CYP39); CYP46A1 (CYP46); or CYP51A1 (lanosterol 14-alpha demethylase) (CYP51).

In some embodiments, a modification at phosphorus results in a P-modification moiety characterized in that it acts as a pro-drug, e.g., the P-modification moiety facilitates delivery of an oligonucleotide to a desired location prior to removal. For instance, in some embodiments, a P-modification moiety results from PEGylation at the linkage phosphorus. One of skill in the relevant arts will appreciate that various PEG chain lengths are useful and that the selection of chain length will be determined in part by the result that is sought to be achieved by PEGylation. For instance, in some embodiments, PEGylation is effected in order to reduce RES uptake and extend in vivo circulation lifetime of an oligonucleotide.

In some embodiments, a PEGylation reagent for use in accordance with the present disclosure is of a molecular weight of about 300 g/mol to about 100,000 g/mol. In some embodiments, a PEGylation reagent is of a molecular weight of about 300 g/mol to about 10,000 g/mol. In some embodiments, a PEGylation reagent is of a molecular weight of about 300 g/mol to about 5,000 g/mol. In some embodiments, a PEGylation reagent is of a molecular weight of about 500 g/mol. In some embodiments, a PEGylation reagent of a molecular weight of about 1000 g/mol. In some embodiments, a PEGylation reagent is of a molecular weight of about 3000 g/mol. In some embodiments, a PEGylation reagent is of a molecular weight of about 5000 g/mol.

In certain embodiments, a PEGylation reagent is PEG500. In certain embodiments, a PEGylation reagent is PEG1000. In certain embodiments, a PEGylation reagent is PEG3000. In certain embodiments, a PEGylation reagent is PEG5000.

In some embodiments, a P-modification moiety is characterized in that it acts as an agent which promotes cell entry and/or endosomal escape, such as a membrane-disruptive lipid or peptide.

In some embodiments, a P-modification moiety is characterized in that it acts as a targeting agent. In some embodiments, a P-modification moiety is or comprises a targeting agent. The phrase "targeting agent," as used herein, is an entity that is associates with a payload of interest (e.g., with an oligonucleotide or oligonucleotide composition) and also interacts with a target site of interest so that the payload of interest is targeted to the target site of interest when associated with the targeting agent to a materially greater extent than is observed under otherwise comparable conditions when the payload of interest is not associated with the targeting agent. A targeting agent may be, or comprise, any of a variety of chemical moieties, including, for example, small molecule moieties, nucleic acids, polypeptides, carbohydrates, etc. Targeting agents are described further by Adarsh et al., "Organelle Specific Targeted Drug Delivery—A Review," International Journal of Research in Pharmaceutical and Biomedical Sciences, 2011, p. 895.

Examples of such targeting agents include, but are not limited to, proteins (e.g. Transferrin), oligopeptides (e.g., cyclic and acylic RGD-containing oligopeptides), antibodies (monoclonal and polyclonal antibodies, e.g. IgG, IgA, IgM, IgD, IgE antibodies), sugars/carbohydrates (e.g., monosaccharides and/or oligosaccharides (mannose, mannose-6-phosphate, galactose, and the like)), vitamins (e.g., folate), or other small biomolecules. In some embodiments, a targeting moiety is a steroid molecule (e.g., bile acids including cholic acid, deoxycholic acid, dehydrocholic acid; cortisone; digoxigenin; testosterone; cholesterol; cationic steroids such as cortisone having a trimethylaminomethyl hydrazide group attached via a double bond at the 3-position of the cortisone ring, etc.). In some embodiments, a targeting moiety is a lipophilic molecule (e.g., alicyclic hydrocarbons, saturated and unsaturated fatty acids, waxes, terpenes, and polyalicyclic hydrocarbons such as adamantine and buckminsterfullerenes). In some embodiments, a lipophilic molecule is a terpenoid such as vitamin A, retinoic acid, retinal, or dehydroretinal. In some embodiments, a targeting moiety is a peptide.

In some embodiments, a P-modification moiety is a targeting agent of formula —X-L-R$^1$ wherein each of X, L, and R$^1$ are as defined in Formula I, disclosed herein.

In some embodiments, a P-modification moiety is characterized in that it facilitates cell specific delivery.

In some embodiments, a P-modification moiety is characterized in that it falls into one or more of the above-described categories. For instance, in some embodiments, a P-modification moiety acts as a PK enhancer and a targeting ligand. In some embodiments, a P-modification moiety acts as a pro-drug and an endosomal escape agent. One of skill in the relevant arts would recognize that numerous other such combinations are possible and are contemplated by the present disclosure.

In some embodiments, a carbocyclyl, aryl, heteroaryl, or heterocyclyl group, or a bivalent or polyvalent group thereof, is a $C_3$-$C_{30}$ carbocyclyl, aryl, heteroaryl, or heterocyclyl group, or a bivalent and/or polyvalent group thereof.

In some embodiments, a pattern of backbone chiral centers of a provided oligonucleotide or a region thereof (e.g., a core) comprises or is (Sp)m(Rp)n, (Rp)n(Sp)m, (Op)n(Sp)m, (Np)t[(Op)n(Sp)m]y, (Sp)t[(Op)n(Sp)m]y, (Np)t[(Rp)n(Sp)m]y, or (Sp)t[(Rp)n(Sp)m]y, wherein each variable is as described in the present disclosure. In some embodiments, y is 1. In some embodiments, a pattern of backbone chiral centers comprises or is (Sp)m(Rp)n, (Rp)n(Sp)m, (Np)t(Rp)n(Sp)m, (Sp)t(Rp)n(Sp)m, (Np)t[(Rp)n(Sp)m]2, (Sp)t[(Rp)n(Sp)m]2, (Np)t(Op)n(Sp)m, (Sp)t(Op)n(Sp)m, (Np)t[(Op)

n(Sp)m]2, or (Sp)t[(Op)n(Sp)m]2. In some embodiments, y is 2. In some embodiments, a pattern is (Np)t(Op/Rp)n(Sp)m(Op/Rp)n(Sp)m. In some embodiments, a pattern is (Np)t(Op/Rp)n(Sp)1-5(Op/Rp)n(Sp)m. In some embodiments, a pattern is (Np)t(Op/Rp)n(Sp)2-5(Op/Rp)n(Sp)m. In some embodiments, a pattern is (Np)t(Op/Rp)n(Sp)2(Op/Rp)n(Sp)m. In some embodiments, a pattern is (Np)t(Op/Rp)n(Sp)3(Op/Rp)n(Sp)m. In some embodiments, a pattern is (Np)t(Op/Rp)n(Sp)4(Op/Rp)n(Sp)m. In some embodiments, a pattern is (Np)t(Op/Rp)n(Sp)5(Op/Rp)n(Sp)m. In some embodiments, Np is Sp. In some embodiments, (Op/Rp) is Op. In some embodiments, (Op/Rp) is Rp. In some embodiments, Np is Sp and (Op/Rp) is Rp. In some embodiments, Np is Sp and (Op/Rp) is Op. In some embodiments, Np is Sp and at least one (Op/Rp) is Rp, and at least one (Op/Rp) is Op. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, at least one t>1, and at least one m>2. In some embodiments, at one n is 1, at least one t is no less than 1, and at least one m is no less than 2. In some embodiments, at one n is 1, at least one t is no less than 2, and at least one m is no less than 3. In some embodiments, each n is 1. In some embodiments, at least one t>1. In some embodiments, at least one t>2. In some embodiments, at least one t>3. In some embodiments, at least one t>4. In some embodiments, at least one m>1. In some embodiments, at least one m>2. In some embodiments, at least one m>3. In some embodiments, at least one m>4. In some embodiments, a pattern of backbone chiral centers comprises one or more achiral natural phosphate linkages. In some embodiments, the sum of m, t, and n (or m and n if no t in a pattern) is no less than 5, 6, 7, 8, 9, 10, 11, 12, 13, 14, 15, 16, 17, 18, 19 or 20. In some embodiments, the sum is 5. In some embodiments, the sum is 6. In some embodiments, the sum is 7. In some embodiments, the sum is 8. In some embodiments, the sum is 9 In some embodiments, the sum is 10. In some embodiments, the sum is 11. In some embodiments, the sum is 12. In some embodiments, the sum is 13. In some embodiments, the sum is 14. In some embodiments, the sum is 15.

In some embodiments, a nucleotidic unit comprising Op is $Nu^O$ as described in the present disclosure. For example, in some embodiments, $Nu^O$ comprises a 5'-substitution/modification as described in the present disclosure, e.g., —$C(R^{5s})_2$ as described in the present disclosure. In some embodiments, —$C(R^{5s})_2$ is 5MRd as described in the present disclosure. In some embodiments, —$C(R^{5s})_2$ is 5MSd as described in the present disclosure.

In some embodiments, a pattern of backbone chiral centers comprises or is (Rp)n(Sp)m. In some embodiments, a pattern of backbone chiral centers comprises or is (Sp)t(Rp)n. In some embodiments, a pattern of backbone chiral centers comprises or is (Np)t(Rp)n(Sp)m. In some embodiments, a pattern of backbone chiral centers comprises or is (Sp)t(Sp)m, optionally with n achiral phosphate diester internucleotidic linkages and/or stereorandom (non-chirally controlled) chiral internucleotidic linkages between the section having (Sp)t and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)t(Rp)n(Sp)m. In some embodiments, each of t and m is independently equal to or greater than 1, 2, 3, 4, 5, 6, 7, 8, 9, 10, 11, 12, 13, 14, 15, 16, 17, 18, 19 or 20.

In some embodiments, a common pattern of backbone chiral centers in a provided oligonucleotide comprises a pattern of $i^o$-$i^s$-$i^o$-$i^s$-$i^o$, $i^o$-$i^s$-$i^s$-$i^s$-$i^o$, $i^o$-$i^s$-$i^s$-$i^s$-$i^o$-$i^s$, $i^s$-$i^o$-$i^s$-$i^o$, $i^s$-$i^o$-$i^s$-$i^o$, $i^s$-$i^o$-$i^s$-$i^o$-$i^s$, $i^s$-$i^o$-$i^s$-$i^o$-$i^s$-$i^o$, $i^s$-$i^o$-$i^s$-$i^o$-$i^s$-$i^o$-$i^s$, $i^s$-$i^o$-$i^s$-$i^s$-$i^s$-$i^o$, $i^s$-$i^s$-$i^o$-$i^s$-$i^s$-$i^s$-$i^o$-$i^s$, $i^s$-$i^s$-$i^s$-$i^o$-$i^s$-$i^o$-$i^s$-$i^s$, $i^s$-$i^s$-$i^s$-$i^o$-$i^s$-, $i^s$-$i^s$-$i^s$-$i^s$, $i^s$-$i^s$-$i^s$-$i^s$-$i^s$, $i^s$-$i^s$-$i^s$-$i^s$, $i^s$-$i^s$-$i^s$-$i^s$-$i^s$-$i^s$, $i^s$-$i^s$-$i^s$-$i^s$-$i^s$-$i^s$-$i^s$, $i^s$-$i^s$-$i^s$-$i^s$-$i^s$-$i^s$-$i^s$-$i^s$, or $i^r$-$i^r$-$i^r$, wherein $i^s$ represents an internucleotidic linkage in the Sp configuration; $i^o$ represents an achiral internucleotidic linkage; and $i^r$ represents an internucleotidic linkage in the Rp configuration.

In some embodiments, a common pattern of backbone chiral centers comprises a pattern of OSOSO, OSSSO, OSSSOS, SOSO, SOSO, SOSOS, SOSOSO, SOSOSOSO, SOSSSO, SSOSSSOSS, SSSOSOSSS, SSSSOSOSSSS, SSSSS, SSSSSS, SSSSSSS, SSSSSSSS, SSSSSSSSS, or RRR, wherein S represents a phosphorothioate of the Sp configuration, O represents a phosphodiester, and R represents a phosphorothioate of the Rp configuration.

In some embodiments, the non-chiral center is a linkage phosphorus of a phosphodiester linkage. In some embodiments, the chiral center in a Sp configuration is a linkage phosphorus of a phosphorothioate linkage. In some embodiments, the chiral center in a Rp configuration is a linkage phosphorus of a phosphorothioate linkage.

As defined herein, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is greater than 25.

In some embodiments, a pattern of backbone chiral centers of a provided oligonucleotide or a region thereof comprises a repeating pattern. In some embodiments, a repeating pattern is (Sp)m(Rp)n, wherein n is 1-10, and m is independently described in the present disclosure. In some embodiments, a repeating pattern is (Rp)n(Sp)m, wherein n is 1-10, and m is independently described in the present disclosure. In some embodiments, a repeating pattern is (Op)n(Sp)m, wherein n is 1-10, and m is independently described in the present disclosure. In some embodiments, (Rp)n(Sp)m is $(Rp)(Sp)_2$. In some embodiments, (Sp)n(Rp)m is $(Sp)_2(Rp)$. In some embodiments, (Op)n(Sp)m is (Op)(Sp)2.

In some embodiments, a repeating pattern is (Np)t(Rp)n(Sp)m, wherein n is 1-10, t is 1-50, Np is independently Rp or Sp, and m is as described in the present disclosure. In some embodiments, the present disclosure provides a C9orf72 oligonucleotide or an oligonucleotide type whose pattern of backbone chiral centers comprises (Np)t(Rp)n(Sp)m. In some embodiments, the present disclosure provides a C9orf72 oligonucleotide of an oligonucleotide type whose pattern of backbone chiral centers comprises (Np)t(Rp)n(Sp)m. In some embodiments, a repeating pattern is (Np)m(Rp)n(Sp)t, wherein n is 1-10, t is 1-50, Np is independently Rp or Sp, and m is as described in the present disclosure. In some embodiments, the present disclosure provides a C9orf72 oligonucleotide of an oligonucleotide type whose pattern of backbone chiral centers comprises (Np)m(Rp)n(Sp)t. In some embodiments, the present disclosure provides a C9orf72 oligonucleotide of an oligonucleotide type whose pattern of backbone chiral centers comprises (Np)m(Rp)n(Sp)t. In some embodiments, Np is Rp. In some embodiments, Np is Sp. In some embodiments, all Np are the same. In some embodiments, all Np are Sp. In some embodiments, at least one Np is different from the other Np. In some embodiments, t is 2.

As defined herein, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

As defined herein, t is 1-50. In some embodiments, t is 1. In some embodiments, t is 2-50. In some embodiments, t is 2, 3, 4, 5, 6, 7 or 8. In some embodiments, t is 3, 4, 5, 6, 7 or 8. In some embodiments, t is 4, 5, 6, 7 or 8. In some embodiments, t is 5, 6, 7 or 8. In some embodiments, t is 6, 7 or 8. In some embodiments, t is 7 or 8. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20. In some embodiments, t is 21. In some embodiments, t is 22. In some embodiments, t is 23. In some embodiments, t is 24. In some embodiments, t is 25. In some embodiments, t is greater than 25.

In some embodiments, at least one of m and t is greater than 2. In some embodiments, at least one of m and t is greater than 3. In some embodiments, at least one of m and t is greater than 4. In some embodiments, at least one of m and t is greater than 5. In some embodiments, at least one of m and t is greater than 6. In some embodiments, at least one of m and t is greater than 7. In some embodiments, at least one of m and t is greater than 8. In some embodiments, at least one of m and t is greater than 9. In some embodiments, at least one of m and t is greater than 10. In some embodiments, at least one of m and t is greater than 11. In some embodiments, at least one of m and t is greater than 12. In some embodiments, at least one of m and t is greater than 13. In some embodiments, at least one of m and t is greater than 14. In some embodiments, at least one of m and t is greater than 15. In some embodiments, at least one of m and t is greater than 16. In some embodiments, at least one of m and t is greater than 17. In some embodiments, at least one of m and t is greater than 18. In some embodiments, at least one of m and t is greater than 19. In some embodiments, at least one of m and t is greater than 20. In some embodiments, at least one of m and t is greater than 21. In some embodiments, at least one of m and t is greater than 22. In some embodiments, at least one of m and t is greater than 23. In some embodiments, at least one of m and t is greater than 24. In some embodiments, at least one of m and t is greater than 25.

In some embodiments, each one of m and t is greater than 2. In some embodiments, each one of m and t is greater than 3. In some embodiments, each one of m and t is greater than 4. In some embodiments, each one of m and t is greater than 5. In some embodiments, each one of m and t is greater than 6. In some embodiments, each one of m and t is greater than 7. In some embodiments, each one of m and t is greater than 8. In some embodiments, each one of m and t is greater than 9. In some embodiments, each one of m and t is greater than 10. In some embodiments, each one of m and t is greater than 11. In some embodiments, each one of m and t is greater than 12. In some embodiments, each one of m and t is greater than 13. In some embodiments, each one of m and t is greater than 14. In some embodiments, each one of m and t is greater than 15. In some embodiments, each one of m and t is greater than 16. In some embodiments, each one of m and t is greater than 17. In some embodiments, each one of m and t is greater than 18. In some embodiments, each one of m and t is greater than 19. In some embodiments, each one of m and t is greater than 20.

In some embodiments, the sum of m and t is greater than 3. In some embodiments, the sum of m and t is greater than 4. In some embodiments, the sum of m and t is greater than 5. In some embodiments, the sum of m and t is greater than 6. In some embodiments, the sum of m and t is greater than 7. In some embodiments, the sum of m and t is greater than 8. In some embodiments, the sum of m and t is greater than 9. In some embodiments, the sum of m and t is greater than 10. In some embodiments, the sum of m and t is greater than 11. In some embodiments, the sum of m and t is greater than 12. In some embodiments, the sum of m and t is greater than 13. In some embodiments, the sum of m and t is greater than 14. In some embodiments, the sum of m and t is greater than 15. In some embodiments, the sum of m and t is greater than 16. In some embodiments, the sum of m and t is greater than 17. In some embodiments, the sum of m and t is greater than 18. In some embodiments, the sum of m and t is greater than 19. In some embodiments, the sum of m and t is greater than 20. In some embodiments, the sum of m and t is greater than 21. In some embodiments, the sum of m and t is greater than 22. In some embodiments, the sum of m and t is greater than 23. In some embodiments, the sum of m and t is greater than 24. In some embodiments, the sum of m and t is greater than 25.

In some embodiments, n is 1, and at least one of m and t is greater than 1. In some embodiments, n is 1 and each of m and t is independently greater than 1. In some embodiments, m>n and t>n. In some embodiments, (Sp)m(Rp)n(Sp)t is (Sp)$_2$Rp(Sp)$_2$. In some embodiments, (Sp)t(Rp)n(Sp)m is (Sp)$_2$Rp(Sp)$_2$. In some embodiments, (Sp)t(Rp)n(Sp)m is SpRp(Sp)$_2$. In some embodiments, (Np)t(Rp)n(Sp)m is (Np)tRp(Sp)m. In some embodiments, (Np)t(Rp)n(Sp)m is (Np)$_2$Rp(Sp)m. In some embodiments, (Np)t(Rp)n(Sp)m is (Rp)$_2$Rp(Sp)m. In some embodiments, (Np)t(Rp)n(Sp)m is (Sp)$_2$Rp(Sp)m. In some embodiments, (Np)t(Rp)n(Sp)m is RpSpRp(Sp)m. In some embodiments, (Np)t(Rp)n(Sp)m is SpRpRp(Sp)m.

In some embodiments, n is 1, and at least one of m and t is greater than 1. In some embodiments, n is 1 and each of m and t is independently greater than 1. In some embodiments, m>n and t>n. In some embodiments, (Sp)m(Op)n (Sp)t is (Sp)$_2$Op(Sp)$_2$. In some embodiments, (Sp)t(Op)n(Sp)m is (Sp)$_2$Op(Sp)$_2$. In some embodiments, (Sp)t(Op)n(Sp)m is SpOp(Sp)$_2$. In some embodiments, (Np)t(Op)n(Sp)m is (Np)tOp(Sp)m. In some embodiments, (Np)t(Op)n(Sp)m is (Np)$_2$Op(Sp)m. In some embodiments, (Np)t(Op)n(Sp)m is (Op)$_2$Op(Sp)m. In some embodiments, (Np)t(Op)n(Sp)m is (Sp)$_2$Op(Sp)m. In some embodiments, (Np)t(Op)n(Sp)m is RpSpOp(Sp)m. In some embodiments, (Np)t(Op)n(Sp)m is SpRpOp(Sp)m.

In some embodiments, (Sp)t(Rp)n(Sp)m is SpRpSpSp. In some embodiments, (Sp)t(Rp)n(Sp)m is (Sp)$_2$Rp(Sp)$_2$. In some embodiments, (Sp)t(Rp)n(Sp)m is (Sp)$_3$Rp(Sp)$_3$. In some embodiments, (Sp)t(Rp)n(Sp)m is (Sp)$_4$Rp(Sp)$_4$. In some embodiments, (Sp)t(Rp)n(Sp)m is (Sp)tRp(Sp)s. In some embodiments, (Sp)t(Rp)n(Sp)m is SpRp(Sp)s. In some embodiments, (Sp)t(Rp)n(Sp)m is (Sp)$_2$Rp(Sp)$_5$. In some embodiments, (Sp)t(Rp)n(Sp)m is (Sp)$_3$Rp(Sp)$_5$. In some embodiments, (Sp)t(Rp)n(Sp)m is (Sp)$_4$Rp(Sp)$_5$. In some embodiments, (Sp)t(Rp)n(Sp)m is (Sp)$_5$Rp(Sp)$_5$.

In some embodiments, (Sp)t(Op)n(Sp)m is SpOpSpSp. In some embodiments, (Sp)t(Op)n(Sp)m is (Sp)$_2$Op(Sp)$_2$. In some embodiments, (Sp)t(Op)n(Sp)m is (Sp)$_3$Op(Sp)$_3$. In some embodiments, (Sp)t(Op)n(Sp)m is (Sp)$_4$Op(Sp)$_4$. In some embodiments, (Sp)t(Op)n(Sp)m is (Sp)tOp(Sp)s. In some embodiments, (Sp)t(Op)n(Sp)m is SpOp(Sp)s. In some embodiments, (Sp)t(Op)n(Sp)m is (Sp)$_2$Op(Sp)$_5$. In some embodiments, (Sp)t(Op)n(Sp)m is (Sp)$_3$Op(Sp)$_5$. In some embodiments, (Sp)t(Op)n(Sp)m is (Sp)$_4$Op(Sp)$_5$. In some embodiments, (Sp)t(Op)n(Sp)m is (Sp)$_5$Op(Sp)$_5$.

The present invention demonstrates, among other things, that individual stereoisomers of a particular oligonucleotide can show different stability and/or activity from each other. In some embodiments, inclusion of particular pattern of backbone chiral centers, e.g., those described in the present disclosure comprising OpSpSp, within an oligonucleotide can surprisingly change the cleavage pattern of a nucleic acid polymer when such an oligonucleotide is utilized for cleaving said nucleic acid polymer. In some embodiments, a pattern of backbone chiral centers provides unexpectedly high cleavage efficiency of a target nucleic acid polymer. In some embodiments, a pattern of backbone chiral centers provides new cleavage sites. In some embodiments, a pattern of backbone chiral centers increase cleavage (e.g., percentage, rate, absolute amount, etc.) at a cleavage site. In some embodiments, a pattern of backbone chiral centers decrease cleavage (e.g., percentage, rate, absolute amount, etc.) at a cleavage site. In some embodiments, a pattern of backbone chiral centers provides fewer cleavage sites, for example, by blocking certain existing cleavage sites. Even more unexpectedly, in some embodiments, a pattern of backbone chiral centers provides cleavage predominantly at only one site of a target nucleic acid polymer within the sequence that is complementary to an oligonucleotide utilized for cleavage. In some embodiments, higher cleavage efficiency is achieved by selecting a pattern of backbone chiral centers to minimize the number of cleavage sites. In some embodiments, a pattern of backbone chiral centers of the oligonucleotide improves cleavage of a target nucleic acid polymer. In some embodiments, a pattern of backbone chiral centers increases selectivity. In some embodiments, a pattern of backbone chiral centers minimizes off-target effect. In some embodiments, a pattern of backbone chiral centers increase selectivity, e.g., cleavage selectivity among target sequences differing by point mutations or single nucleotide polymorphisms (SNPs). In some embodiments, a pattern of backbone chiral centers increase selectivity, e.g., cleavage selectivity among target sequences differing by only one point mutation or single nucleotide polymorphism (SNP). In some embodiments, the present disclosure provides oligonucleotides whose pattern of backbone chiral centers comprising (Op)n(Sp)m, (Np)t[(Op)n(Sp)m]y, or (Sp)t[(Op)n(Sp)m]y, wherein n is 1 and m is 2 or greater. In some embodiments, the present disclosure provides oligonucleotides whose pattern of backbone chiral centers comprising (Op)n(Sp)m, wherein n is 1 and m is 2. In some embodiments, the present disclosure provides chirally controlled oligonucleotide compositions of oligonucleotides wherein the oligonucleotides have the same base sequence, the same pattern of backbone linkages, and the same pattern of backbone chiral centers of the oligonucleotides which comprises (Op)n(Sp)m, (Np)t[(Op)n(Sp)m]y, or (Sp)t[(Op)n(Sp)m]y, wherein n is 1 and m is 2 or greater. In some embodiments, the present disclosure provides chirally controlled oligonucleotide compositions of a plurality of oligonucleotides wherein the oligonucleotides have the same base sequence, the same pattern of backbone linkages, and the same pattern of backbone chiral centers of the oligonucleotides which comprises (Op)n(Sp)m, wherein n is 1 and m is 2. In some embodiments, oligonucleotides of the plurality have the same constitution. In some embodiments, oligonucleotides of the plurality are structurally identical. In some embodiments, at least 0.1%, 0.5%, 1%, 5%, 10%, 15%, 20%, 25%, 30%, 35%, 40%, 45%, 50%, 55%, 60%, 65%, 70%, 75%, 80%, 85%, 90%, or 95% of all oligonucleotides in the composition that have the same base sequence are oligonucleotides of the plurality. In some embodiments, the percentage is at least 5%. In some embodiments, the percentage is at least 10%. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 70%. In some embodiments, the percentage is at least 80%. In some embodiments, the percentage is at least 90%.

In some embodiments, the present invention provides a method for controlled cleavage of a nucleic acid polymer, comprising providing a chirally controlled oligonucleotide composition of the present disclosure, wherein the nucleic acid polymer is cleaved in a cleavage pattern that is different than a reference cleavage pattern. In some embodiments, a provided chirally controlled oligonucleotide composition is of a plurality of oligonucleotides whose common pattern of backbone chiral centers comprises (Op)n(Sp)m, (Np)t[(Op)n(Sp)m]y, or (Sp)t[(Op)n(Sp)m]y, wherein n is 1 and m is 2 or greater.

In some embodiments, a reference cleavage pattern is a cleavage pattern of a reference composition (e.g., non-chirally controlled oligonucleotide composition, a chirally controlled oligonucleotide composition of oligonucleotides having a different pattern of backbone chiral centers (e.g., not containing (Op/Rp)(Sp)m), etc.). As appreciated by those skilled in the art, a cleavage pattern of a nucleic acid polymer includes the number of cleavage sites, the locations of the cleavage sites, and the percentage of cleavage at each sites.

In some embodiments, the present invention provides a method for changing a first cleavage pattern of a nucleic acid polymer resulted from using a first oligonucleotide composition, comprising providing a second composition which is a chirally controlled oligonucleotide composition of the present disclosure, wherein the second composition provides a second cleavage pattern that is different than the first cleavage pattern. In some embodiments, a provided chirally controlled oligonucleotide composition is of a plurality of oligonucleotides whose common pattern of backbone chiral centers comprises (Op)n(Sp)m, (Np)t[(Op)n(Sp)m]y, or (Sp)t[(Op)n(Sp)m]y, wherein n is 1 and m is 2 or greater. In some embodiments, a second cleavage pattern has a different cleavage site. In some embodiments, a second cleavage pattern has fewer cleavage sites. In some embodiments, a second cleavage pattern has a predominant cleavage site (e.g., at least 50%, 55%, 60%, 65%, 70%, 75%, 80%, 85%, 90%, or 95% cleavage) that is different than and/or absent from the first cleavage pattern.

In some embodiments, the present disclosure provides a method for altering a cleavage pattern observed when a nucleic acid polymer whose nucleotide sequence includes a target sequence is contacted with a reference oligonucleotide composition that comprises oligonucleotides having a particular base sequence and length, which particular base sequence is or comprises a sequence that is complementary to the target sequence, the method comprising providing a chirally controlled oligonucleotide composition of the present disclosure, which chirally controlled oligonucleotide composition comprises a plurality of oligonucleotides whose base sequence is or comprises the particular base sequence, and whose common pattern of backbone chiral centers comprises (Op)n(Sp)m, (Np)t[(Op)n(Sp)m]y, or (Sp)t[(Op)n(Sp)m]y, wherein n is 1 and m is 2 or greater.

In some embodiments, a nucleic acid polymer is RNA. In some embodiments, a nucleic acid polymer is an oligonucleotide. In some embodiments, a nucleic acid polymer is an RNA oligonucleotide. In some embodiments, a nucleic acid polymer is a transcript. In some embodiments, oligonucleotides of a provided chirally controlled oligonucleotide composition form duplexes with a nucleic acid polymer to be cleaved.

In some embodiments, a provided chirally controlled oligonucleotide composition comprising oligonucleotides with a common pattern of backbone chiral centers provides unexpectedly high selectivity so that nucleic acid polymers that have only small sequence variations within a target region can be selectively targeted. In some embodiments, a nucleic acid polymer is a transcript from an allele. In some embodiments, transcripts from different alleles can be selectively targeted by provided chirally controlled oligonucleotide compositions.

Figure 2:
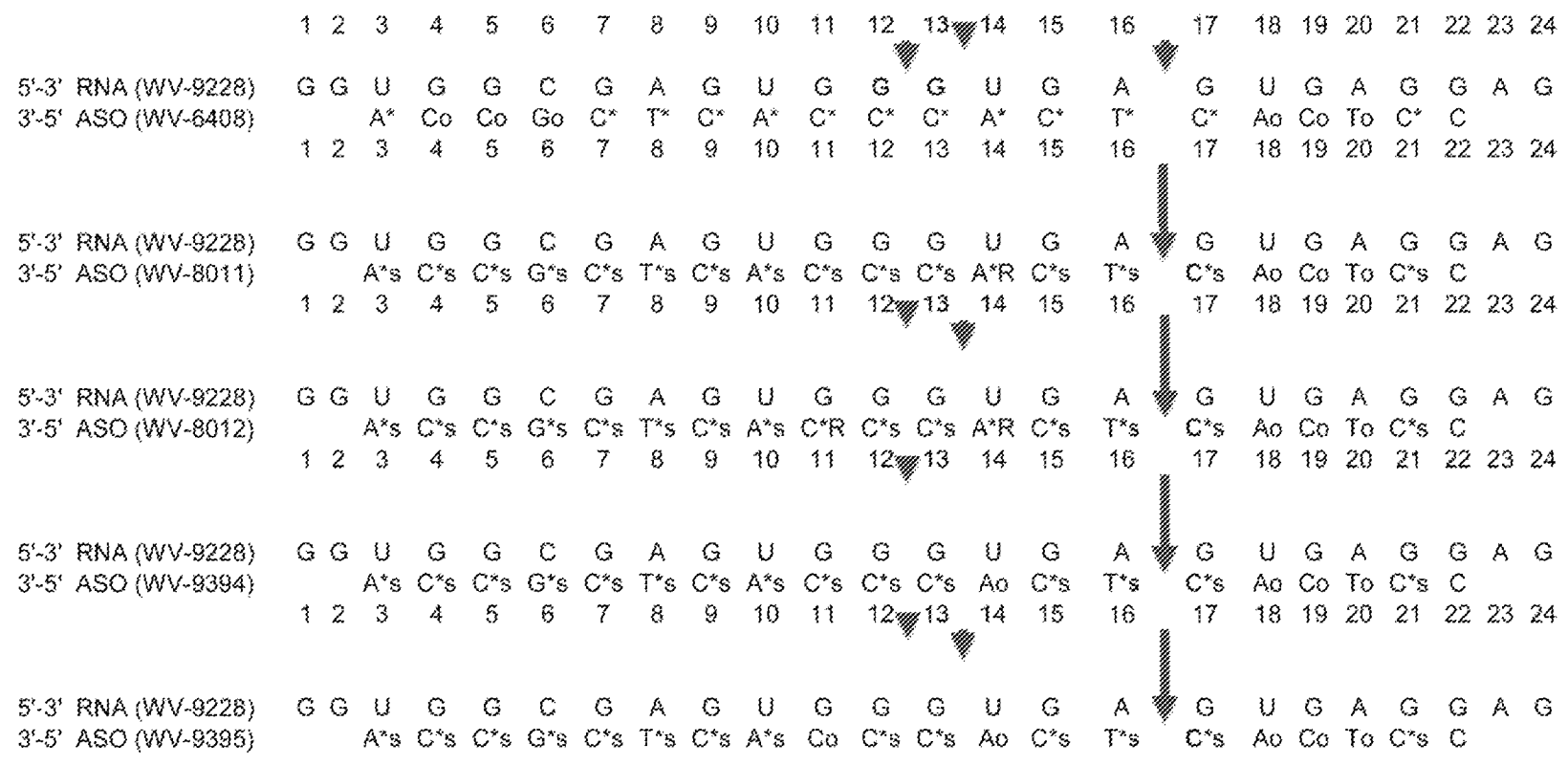

In some embodiments, provided chirally controlled oligonucleotide compositions and methods thereof enables precise control of cleavage sites within a target sequence. In some embodiments, a cleavage site is around a sequence of OpSpSp backbone chiral centers. In some embodiments, a cleavage site is upstream of and near a sequence of OpSpSp backbone chiral centers. In some embodiments, a cleavage site is within 5 base pairs upstream of a sequence of OpSpSp backbone chiral centers. In some embodiments, a cleavage site is within 4 base pairs upstream of a sequence of OpSpSp backbone chiral centers. In some embodiments, a cleavage site is within 3 base pairs upstream of a sequence of OpSpSp backbone chiral centers. In some embodiments, a cleavage site is within 2 base pairs upstream of a sequence of OpSpSp backbone chiral centers. In some embodiments, a cleavage site is within 1 base pair upstream of a sequence of OpSpSp backbone chiral centers. In some embodiments, a cleavage site is downstream of and near a sequence of OpSpSp backbone chiral centers. In some embodiments, a cleavage site is within 5 base pairs downstream of a sequence of OpSpSp backbone chiral centers. In some embodiments, a cleavage site is within 4 base pairs downstream of a sequence of OpSpSp backbone chiral centers. In some embodiments, a cleavage site is within 3 base pairs downstream of a sequence of OpSpSp backbone chiral centers. In some embodiments, a cleavage site is within 2 base pairs downstream of a sequence of OpSpSp backbone chiral centers. In some embodiments, a cleavage site is within 1 base pair downstream of a sequence of OpSpSp backbone chiral centers. Among other things, the present invention therefore provides control of cleavage sites with in a target sequence. As extensively described in the present disclosure, a sequence of OpSpSp backbone chiral centers can be found in a single or repeating units of (Np)m(Op)n(Sp)t, (Np)t(Op)n(Sp)m, (Sp)m(Op)n(Sp)t, (Sp)t(Op)n(Sp)m, (Op)n(Sp)m, (Op)m(Sp)n, (Sp)mOp and/or Op(Sp)m, each of which is independently as defined above and described herein. In some embodiments, a provided chirally controlled oligonucleotide composition creates a new cleavage site 2 base pairs downstream of OpSpSp backbone chiral centers in a target molecule wherein said new cleavage site does not exist if a reference (e.g., chirally uncontrolled) oligonucleotide composition is used (cannot be detected). In some embodiments, a provided chirally controlled oligonucleotide composition enhances cleavage at a cleavage site 2 base pairs downstream of OpSpSp backbone chiral centers in a target molecule (e.g., see FIG. 2), wherein cleavage at such a site occurs at a higher percentage than when a reference (e.g., chirally uncontrolled) oligonucleotide composition is used. In some embodiments, cleavage at such a site by a provided chirally controlled oligonucleotide composition is at least 2, 3, 4, 5, 6, 7, 8, 9, 10, 20, 30, 40, 50, 60, 70, 80, 90, 100, 200, 500 or 1000 fold of that by a reference oligonucleotide composition (for example, when measured by percentage of cleavage at a site). In some embodiments, a provided chirally controlled oligonucleotide composition provides accelerated cleavage at a cleavage site 2 base pairs downstream of OpSpSp backbone chiral centers in a target molecule (e.g., see FIG. 2), compared to when a reference (e.g., chirally uncontrolled) oligonucleotide composition is used. In some embodiments, cleavage by a provided chirally controlled oligonucleotide composition is at least 2, 3, 4, 5, 6, 7, 8, 9, 10, 20, 30, 40, 50, 60, 70, 80, 90, 100, 200, 500 or 1000 fold faster than that by a reference oligonucleotide composition. In some embodiments, a cleavage site of a provided chirally controlled oligonucleotide composition 2 base pairs downstream of OpSpSp backbone chiral centers in a target molecule (e.g., see FIG. 2) is a cleavage site when a reference (e.g., chirally uncontrolled) oligonucleotide composition is used. In some embodiments, a cleavage site of a provided chirally controlled oligonucleotide composition 2 base pairs downstream of OpSpSp backbone chiral centers in a target molecule (e.g., see FIG. 2) is within one base pair of a cleavage site when a reference (e.g., chirally uncontrolled) oligonucleotide composition is used. In some embodiments, a cleavage site of a provided chirally controlled oligonucleotide composition 2 base pairs downstream of OpSpSp backbone chiral centers in a target molecule (e.g., see FIG. 2) is within 2 base pairs of a cleavage site when a reference (e.g., chirally uncontrolled) oligonucleotide composition is used. In some embodiments, it is within 3 base pairs. In some embodiments, it is within 4 base pairs. In some embodiments, it is within 5 base pairs. In some embodiments, a cleavage site of a provided chirally controlled oligonucleotide composition 2 base pairs downstream of OpSpSp backbone chiral centers in a target molecule is one of the major cleavage sites when a reference (e.g., chirally uncontrolled) oligonucleotide composition is used. In some embodiments, such a site is the cleavage site with the highest cleavage percentage when a reference (e.g., chirally uncontrolled) oligonucleotide composition is used. In some embodiments, a cleavage site of a provided chirally controlled oligonucleotide composition 2 base pairs downstream of OpSpSp backbone chiral centers in a target molecule is one of the cleavage sites with higher cleavage rate when a reference (e.g., chirally uncontrolled) oligonucleotide composition is used. In some embodiments, such a site is the cleavage site with the highest cleavage rate when a reference (e.g., chirally uncontrolled) oligonucleotide composition is used.

In some embodiments, a provided chirally controlled oligonucleotide composition enhances cleavage at one or more sites, e.g., relative to a reference (e.g., chirally uncontrolled/stereorandom) oligonucleotide composition. In some embodiments, a provided chirally controlled oligonucleotide composition selectively enhances cleavage at a single site relative to a reference (e.g., chirally uncontrolled/stereorandom) composition. In some embodiments, a chirally controlled oligonucleotide composition enhances cleavage at a site by providing a higher cleavage rate. In some embodiments, a chirally controlled oligonucleotide composition enhances cleavage at a site by providing a higher percentage of cleavage at said site. Percentage of cleavage at a site can be determined by various methods widely known and practiced in the art. In some embodiments, percentage of cleavage at a site is determined by analysis of cleavage products, for example, as by HPLC-MS. In some embodiments, enhancement is relative to a reference oligonucleotide composition. In some embodiments, enhancement is relative to another cleavage site. In some embodiments, a provided chirally controlled oligonucleotide composition enhances cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition enhances cleavage at a site that is a preferred cleavage site of an enzyme. In some embodiments, a provided chirally controlled oligonucleotide composition enhances cleavage at a site that is not a preferred cleavage site of a reference oligonucleotide composition. In some embodiments, a provided chirally controlled oligonucleotide composition enhances cleavage at a site that is not a cleavage site of a reference oligonucleotide composition, effectively creating a new cleavage site which does not exist when a reference oligonucleotide composition is used. In some embodiments, a provided chirally controlled oligonucleotide composition enhances cleavage at a site within 5 base pairs from a targeted mutation or SNP, thereby increasing selective cleavage of the undesired target oligonucleotide. In some embodiments, a provided chirally controlled oligonucleotide composition enhances cleavage at a site within 4 base pairs from a targeted mutation or SNP, thereby increasing selective cleavage of the undesired target oligonucleotide. In some embodiments, a provided chirally controlled oligonucleotide composition enhances cleavage at a site within 3 base pairs from a targeted mutation or SNP, thereby increasing selective cleavage of the undesired target oligonucleotide. In some embodiments, a provided chirally controlled oligonucleotide composition enhances cleavage at a site within 2 base pairs from a targeted mutation or SNP, thereby increasing selective cleavage of the undesired target oligonucleotide. In some embodiments, a provided chirally controlled oligonucleotide composition enhances cleavage at a site immediately upstream or downstream targeted characteristic sequence elements (e.g., a mutation, a SNP, etc.) thereby increasing selective cleavage of the undesired target oligonucleotide.

In some embodiments, a provided chirally controlled oligonucleotide composition suppresses cleavage at one or more sites, e.g., relative to a reference (e.g., chirally uncontrolled/stereorandom) oligonucleotide composition. In some embodiments, a chirally controlled oligonucleotide composition suppresses cleavage at a site by providing a lower cleavage rate. In some embodiments, a chirally controlled oligonucleotide composition suppresses cleavage at a site by providing a lower percentage of cleavage at said site. In some embodiments, suppression is relative to a reference oligonucleotide composition. In some embodiments, suppression is relative to another cleavage site. In some embodiments, a provided chirally controlled oligonucleotide composition suppresses cleavage at a site that is a preferred cleavage site of a reference oligonucleotide composition. In some embodiments, a preferred cleavage site, or a group of preferred cleavage sites, is a site or sites that have relatively higher percentage of cleavage compared to one or more other cleavage sites. In some embodiments, preferred cleavage sites can indicate preference of an enzyme. For example, for RNase H, when a DNA oligonucleotide is used, resulting cleavage sites may indicate preference of RNase H. In some embodiments, a provided chirally controlled oligonucleotide composition suppresses cleavage at a site that is a preferred cleavage site of an enzyme. In some embodiments, a provided chirally controlled oligonucleotide composition suppresses cleavage at a site that is not a preferred cleavage site of a reference oligonucleotide composition. In some embodiments, a provided chirally controlled oligonucleotide composition suppresses all cleavage sites of a reference oligonucleotide composition. In some embodiments, a provided chirally controlled oligonucleotide composition generally enhances cleavage of target oligonucleotides. In some embodiments, a provided chirally controlled oligonucleotide composition generally suppresses cleavage of non-target oligonucleotides. In some embodiments, a provided chirally controlled oligonucleotide composition enhances cleavage of target oligonucleotides and suppresses cleavage of non-target oligonucleotides. In a subject comprising a diseased tissue comprising a mutation or SNP, a target oligonucleotide for cleavage can be transcripts with a mutation or SNP, while a non-target oligonucleotide can be normal transcripts without a mutation or SNP, such as those expressed in healthy tissues.

In some embodiments, the present invention provides a method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of: contacting a sample comprising transcripts of the target nucleic acid sequence with a chirally controlled oligonucleotide composition comprising a plurality of oligonucleotides that have 1) a common base sequence;
2) a common pattern of backbone linkages;
3) a common pattern of backbone chiral centers;

wherein the common base sequence for the oligonucleotides of the particular oligonucleotide type is or comprises a sequence that is complementary to the characteristic sequence element that defines a particular allele. In some embodiments, the present disclosure provides a method for selective suppression of a transcript from a target nucleic acid sequence for which one or more similar sequences exist within a population, each of which contains a specific nucleotide characteristic sequence element that defines the target nucleic acid sequence relative to the similar sequences, the method comprising steps of:

contacting a sample comprising transcripts of the target nucleic acid sequence with a chirally controlled oligonucleotide composition comprising a plurality of oligonucleotides that have 1) a common base sequence;
2) a common pattern of backbone linkages;
3) a common pattern of backbone chiral centers;

wherein the common base sequence for the oligonucleotides of the particular oligonucleotide type is or comprises a sequence that is complementary to the characteristic sequence element that defines the target nucleic acid sequence. In some embodiments, a similar sequence shares at least 80%, 85%, 90%, 95%, 96%, 97%, 98%, or 99% but less than 100% homology with the target nucleic acid sequence within the portion of the sequence that is complementary to the common base sequence. In some embodiments, a similar sequence differs at no more than 5, 4, 3, 2, or 1 nucleobases from (but not identical with) the target nucleic acid sequence within the portion of the sequence that is complementary to the common base sequence. In some embodiments, a similar sequence differs at only 1 nucleobases from the target nucleic acid sequence within the portion of the sequence that is complementary to the common base sequence. In some embodiments, the common pattern of backbone chiral centers comprises (Op)n(Sp)m, (Np)t[(Op)n(Sp)m]y, or (Sp)t[(Op)n(Sp)m]y, wherein each variable is as described in the present disclosure, and n is 1 and m is 2 or greater. In some embodiments, oligonucleotides of the plurality comprise an asymmetric format. In some embodiments, when the composition is contacted with a system comprising transcripts of both the target allele and another allele of the same nucleic acid sequence, transcripts of the particular allele are suppressed at a greater level (e.g., at least 1.5, 2, 3, 4, or 5 fold) than a level of suppression observed for another allele of the same nucleic acid sequence. In some embodiments, when the composition is contacted with a system comprising transcripts of the same target nucleic acid sequence, it shows suppression of transcripts of the particular allele at a level that is:

a) greater than when the composition is absent;
b) greater than a level of suppression observed for another allele of the same nucleic acid sequence; or
c) both greater than when the composition is absent, and greater than a level of suppression observed for another allele of the same nucleic acid sequence.

In some embodiments, the contacting is performed under conditions determined to permit the composition to suppress transcripts of the particular allele.

In some embodiments, a transcript is suppressed by cleavage of said transcript. In some embodiments, a specific nucleotide characteristic sequence element is in an intron. In some embodiments, a specific nucleotide characteristic sequence element is in an exon. In some embodiments, a specific nucleotide characteristic sequence element is partially in an exon and partially in an intron. In some embodiments, a specific nucleotide characteristic sequence element is or comprises a mutation that differentiates an allele from other alleles. In some embodiments, a mutation is or comprises a deletion. In some embodiments, a mutation is or comprises an insertion. In some embodiments, a mutation is or comprises a point mutation. In some embodiments, a specific nucleotide characteristic sequence element is or comprises a single nucleotide polymorphism (SNP) that differentiates an allele from other alleles. In some embodiments, a specific nucleotide characteristic sequence element is or comprises one or more nucleobases that differentiate a target nucleic acid sequence from similar sequence(s) in a genome and/or products encoded thereby.

In some embodiments, suppression of transcripts of a particular allele is at a level that is greater than when the composition is absent. In some embodiments, suppression of transcripts of a particular allele is at a level that is at least 1.1 fold relative to when the composition is absent, in that transcripts from the particular allele are detected in amounts that are at least 1.1 fold lower when the composition is present relative to when it is absent. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than a level of suppression observed for another allele of the same nucleic acid sequence. In some embodiments, suppression of transcripts of a particular allele is at a level that is at least 1.1 fold greater than a level of suppression observed for another allele of the same nucleic acid sequence. In some embodiments, a level is at least 1.2 fold. In some embodiments, a level is at least 1.3 fold. In some embodiments, a level is at least 1.4 fold. In some embodiments, a level is at least 1.5 fold. In some embodiments, a level is at least 1.6 fold. In some embodiments, a level is at least 1.7 fold. In some embodiments, a level is at least 1.8 fold. In some embodiments, a level is at least 1.9 fold. In some embodiments, a level is at least 2 fold. In some embodiments, a level is at least 3 fold. In some embodiments, a level is at least 4 fold. In some embodiments, a level is at least 5 fold. In some embodiments, a level is at least 6 fold. In some embodiments, a level is at least 7 fold. In some embodiments, a level is at least 8 fold. In some embodiments, a level is at least 9 fold. In some embodiments, a level is at least 10 fold. In some embodiments, a level is at least 11 fold. In some embodiments, a level is at least 12 fold. In some embodiments, a level is at least 13 fold. In some embodiments, a level is at least 14 fold. In some embodiments, a level is at least 15 fold. In some embodiments, a level is at least 20 fold. In some embodiments, a level is at least 30 fold. In some embodiments, a level is at least 40 fold. In some embodiments, a level is at least 50 fold. In some embodiments, a level is at least 75 fold. In some embodiments, a level is at least 100 fold. In some embodiments, a level is at least 150 fold. In some embodiments, a level is at least 200 fold. In some embodiments, a level is at least 300 fold. In some embodiments, a level is at least 400 fold. In some embodiments, a level is at least 500 fold. In some embodiments, a level is at least 750 fold. In some embodiments, a level is at least 1000 fold. In some embodiments, a level is at least 5000 fold.

In some embodiments, suppression of transcripts of a particular allele is at a level that is greater than when the composition is absent, and at a level that is greater than a level of suppression observed for another allele of the same nucleic acid sequence. In some embodiments, suppression of transcripts of a particular allele is at a level that is at least 1.1 fold relative to when the composition is absent, and at least 1.1 fold greater than a level of suppression observed for another allele of the same nucleic acid sequence. In some embodiments, each fold is independently as described above.

In some embodiments, a system is a composition comprising a transcript. In some embodiments, a system is a composition comprising transcripts from different alleles. In some embodiments, a system can be in vivo or in vitro, and in either way can comprise one or more cells, tissues, organs or organisms. In some embodiments, a system comprises one or more cells. In some embodiments, a system comprises one or more tissues. In some embodiments, a system comprises one or more organs. In some embodiments, a system comprises one or more organisms. In some embodiments, a system is a subject.

In some embodiments, suppression of a transcript, or suppression of expression of an allele from which a transcript is transcribed, can be measured in in vitro assay. In some embodiments, a sequence from a transcript and comprising a specific nucleotide characteristic sequence element is used in assays instead of the full-length transcript. In some embodiments, an assay is a biochemical assay. In some embodiments, an assay is a biochemical assay wherein a nucleic acid polymer, for example, a transcript or a sequence from a transcript and comprising a specific nucleotide characteristic sequence element, is tested for cleavage by an enzyme in the presence of a chirally controlled oligonucleotide composition.

In some embodiments, a provided chirally controlled oligonucleotide composition is administered to a subject. In some embodiments, a subject is an animal. In some embodiments, a subject is a plant. In some embodiments, a subject is a human.

In some embodiments, for allele-specific suppression of transcripts from a particular allele, transcripts are cleaved at a site near a sequence difference, for example a mutation, within a specific nucleotide characteristic sequence element, which sequence difference differentiates transcripts from a particular allele from transcripts from the other alleles. In some embodiments, transcripts are selectively cleaved at a site near such a sequence difference. In some embodiments, transcripts are cleaved at a higher percentage at a site near such a sequence difference that when a chirally uncontrolled oligonucleotide composition is used. In some embodiments, transcripts are cleaved at the site of a sequence difference. In some embodiments, transcripts are cleaved only at the site of a sequence difference within a specific nucleotide characteristic sequence element. In some embodiments, transcripts are cleaved at a site within 5 base pairs downstream or upstream a sequence difference. In some embodiments, transcripts are cleaved at a site within 4 base pairs downstream or upstream a sequence difference. In some embodiments, transcripts are cleaved at a site within 3 base pairs downstream or upstream a sequence difference. In some embodiments, transcripts are cleaved at a site within 2 base pairs downstream or upstream a sequence difference. In some embodiments, transcripts are cleaved at a site within 1 base pair downstream or upstream a sequence difference. In some embodiments, transcripts are cleaved at a site within 5 base pairs downstream a sequence difference. In some embodiments, transcripts are cleaved at a site within 4 base pairs downstream a sequence difference. In some embodiments, transcripts are cleaved at a site within 3 base pairs downstream a sequence difference. In some embodiments, transcripts are cleaved at a site within 2 base pairs downstream a sequence difference. In some embodiments, transcripts are cleaved at a site within 1 base pair downstream a sequence difference. In some embodiments, transcripts are cleaved at a site within 5 base pairs upstream a sequence difference. In some embodiments, transcripts are cleaved at a site within 4 base pairs upstream a sequence difference. In some embodiments, transcripts are cleaved at a site within 3 base pairs upstream a sequence difference. In some embodiments, transcripts are cleaved at a site within 2 base pairs upstream a sequence difference. In some embodiments, transcripts are cleaved at a site within 1 base pair upstream a sequence difference. Such precise control of cleavage patterns, and the resulting highly selective suppression of transcripts from a particular allele, would not be possible without chirally controlled oligonucleotide compositions and methods thereof provided by Applicant in this disclosure.

Figure 3:
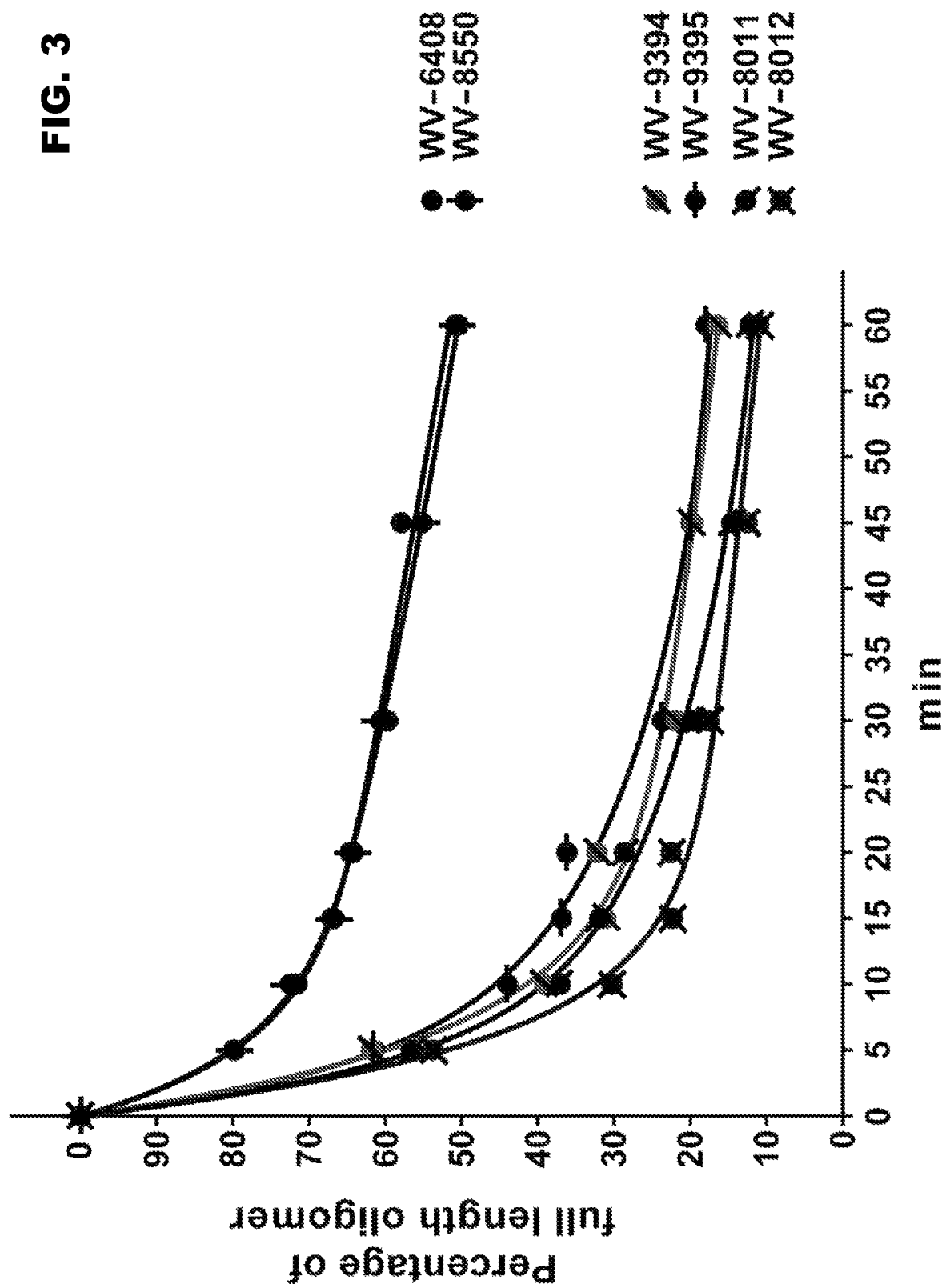
FIG. 3. Example cleavage data by provided oligonucleotides.

In some embodiments, as demonstrated (e.g., FIG. 2 and FIG. 3) provided oligonucleotide or composition can increase cleavage rate at one or more cleavage sites and/or the overall cleavage rate. In some embodiments, a rate increase is at least 1.5, 2, 3, 4, 5, 6, 7, 8, 9, 10, 20, 30, 40, 50, 60, 70, 80, 90, 100, 200, 500 or 1000 fold. In some embodiments, a provided oligonucleotide or composition provides a lower level of remaining, un-cleaved target nucleic acid polymer compared to a reference oligonucleotide composition. In some embodiments, it is at least 1.5, 2, 3, 4, 5, 6, 7, 8, 9, 10, 20, 30, 40, 50, 60, 70, 80, 90, 100, 200, 500 or 1000 fold lower.

In some embodiments, a nucleobase complementary to a characteristic sequence element (e.g., a mutation, a SNP, etc.) is located at position 1, 2, 3, 4, 5, 6, 7, 8, 9, 10, 11, 12, 13, 14, 15, 16, 17, 18, 19, or 20 or further from the 5'-end of an oligonucleotide. In some embodiments, a nucleobase complementary to a characteristic sequence element is located at position 1, 2, 3, 4, 5, 6, 7, 8, 9, 10, 11, 12, 13, 14, 15, 16, 17, 18, 19, or 20 from the 3'-end of an oligonucleotide. In some embodiments, a nucleobase complementary to a characteristic sequence element is located at position 4, 5, 6, 7, 8, 9, 10, 11, 12, 13, 14, 15, 16, 17, 18, 19, or 20 or further from the 3'-end of an oligonucleotide. In some embodiments, a nucleobase complementary to a characteristic sequence element is located at position 5, 6, 7, 8, 9, 10, 11, 12, 13, 14, 15, 16, 17, 18, 19, or 20 or further from the 3'-end of an oligonucleotide. In some embodiments, a nucleobase complementary to a characteristic sequence element is located at position 1, 2, 3, 4, 5, 6, 7, 8, 9, 10, 11, 12, 13, 14, 15, 16, 17, 18, 19, or 20 or further from the 5'-end of a core. In some embodiments, a nucleobase complementary to a characteristic sequence element is located at position 1, 2, 3, 4, 5, 6, 7, 8, 9, 10, 11, 12, 13, 14, 15, 16, 17, 18, 19, or 20 or further from the 3'-end of a core. In some embodiments, a nucleobase complementary to a characteristic sequence element is located at position 3, 4, 5, 6, 7, 8, 9, 10, 11, 12, 13, 14, 15, 16, 17, 18, 19, or 20 or further from the 3'-end of a core. In some embodiments, a nucleobase complementary to a characteristic sequence element is located at position 4, 5, 6, 7, 8, 9, 10, 11, 12, 13, 14, 15, 16, 17, 18, 19, or 20 or further from the 3'-end of a core. In some embodiments, a nucleobase complementary to a characteristic sequence element is located at position 5, 6, 7, 8, 9, 10, 11, 12, 13, 14, 15, 16, 17, 18, 19, or 20 or further from the 3'-end of a core. In some embodiments, a core comprises no 2'-modification that is 2'-OR. In some embodiments, a core comprises no 2'-substitution (two H at the 2' position). In some embodiments, a nucleobase complementary to a characteristic sequence element is bonded to an internucleotidic linkage that is 0, 1, 2 or 3 internucleotidic linkage away from the second internucleotidic linkage upstream of OpSpSp (the underlined Np: NpNpOpSpSp). In some embodiments, it is 0 internucleotidic linkage away (bonded to the underlined Np: NpNpOpSpSp).

When a mismatch is positioned near or next to a cleavage site, cleavage of a target nucleic acid at the cleavage site can be significantly decreased. In some embodiments, overall cleavage (e.g., rate and/or extent, etc.) is decreased, for example, when a cleavage site near or next to a mismatch is a major cleavage site. In some embodiments, provided oligonucleotides selectively suppress target nucleic acids and/or products encoded thereby whose characteristic sequence elements are complementary to provided oligonucleotides over similar nucleic acids whose characteristic sequence elements are not complementary to provided oligonucleotides. For example, in some embodiments, a characteristic sequence element is or comprises a SNP, and provided oligonucleotides selectively suppression transcripts and/or products encoded thereby of an allele whose characteristic SNP nucleobase matches the corresponding nucleobase in the provided oligonucleotides, over another allele whose characteristic SNP nucleobase does not match the corresponding nucleobase in the provided oligonucleotides. Similarly, sequences whose characteristic sequence elements are or comprises mutations, naturally occurring similar sequences whose characteristic sequence elements are or comprises nucleobases that are different among the similar sequences, etc., can be differentiated and selectively targeted.

In some embodiments, a characteristic sequence element is or comprises a SNP. In some embodiments, a characteristic sequence element is or comprises a mutation. In some embodiments, a characteristic sequence element is or comprises a point mutation. In some embodiments, a characteristic sequence element is or comprises a nucleobase that differentiates two or more naturally occurring sequences (e.g., genetic sequences having similar base sequences).

Nucleobases

In some embodiments, provided oligonucleotides comprise natural nucleobases. In some embodiments, provided oligonucleotides comprise unnatural nucleobases. In some embodiments, provided oligonucleotides are capable of directing a decrease in the expression, level and/or activity of a target gene or its gene product. In some embodiments, a target gene comprises a repeat expansion. In some embodiments, provided oligonucleotides comprise any nucleobase described herein or known in the art, e.g., WO2017/062862, US20180216108, US20170037399, and U.S. Pat. No. 9,982,257, the nucleobases of each of which is incorporated herein by reference.

In some embodiments, a nucleobase present in a provided oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen and sulfur;

(3) one or more double bonds in a nucleobase are independently hydrogenated; or (4) one or more aryl or heteroaryl rings are independently inserted into a nucleobase.

In some embodiments, a modified nucleobase is a modified nucleobase as shown in the art, e.g., WO2017/210647. Modified nucleobases also include expanded-size nucleobases in which one or more aryl rings, such as phenyl rings, have been added. Nucleic base replacements described in the Glen Research catalog (Glen Research, Sterling, Va.); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the nucleic acids described herein. In some embodiments, an expanded-size nucleobase is an expanded-size nucleobase as shown in the art, e.g., WO2017/210647 Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, Org. Lett., 2002, 4, 4377-4380. In some embodiments, a porphyrin-derived ring is a porphyrin-derived ring as shown in the art, e.g., WO2017/219647 In some embodiments, a modified nucleobase is a modified nucleobase as shown in the art, e.g., WO2017/219647 In some embodiments, a modified nucleobase is fluorescent. Examples of such fluorescent modified nucleobases include phenanthrene, pyrene, stillbene, isoxanthine, isozanthopterin, terphenyl, terthiophene, benzoterthiophene, coumarin, lumazine, tethered stillbene, benzo-uracil, and naphthouracil, as shown in the art, e.g., WO2017/210647 In some embodiments, a nucleobase or modified nucleobase is selected from: C5-propyne T, C5-propyne C, C5-Thiazole, Phenoxazine, 2-Thio-thymine, 5-Triazolylphenyl-thymine, Diaminopurine, and N2-Aminopropylguanine.

In some embodiments, a modified nucleobase is selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Example United States patents that teach the preparation of certain of the above noted modified nucleobases as well as other modified nucleobases include without limitation, US2003/0158403, U.S. Pat. Nos. 3,687,808; 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594, 121; 5,596,091; 5,614,617; 5,645,985; 5,681,941; 5,750,692; 5,763,588; 5,830,653; and 6,005,096.

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One representative example of such a universal base is 3-nitropyrrole.

In some embodiments, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2"-O-methylcytidine; 5-carboxymethylaminomethyl-2-thiouridine; 5-carboxymethylaminomethyluridine; dihydrouridine; 2"-O-methylpseudouridine; beta,D-galactosylqueosine; 2"-O-methylguanosine; N$^6$-isopentenyladenosine; 1-methyladenosine; 1-methylpseudouridine; 1-methylguanosine; 1-methylinosine; 2,2-dimethylguanosine; 2-methyladenosine; 2-methylguanosine; N$^7$-methylguanosine; 3-methyl-cytidine; 5-methylcytidine; 5-hydroxymethylcytidine; 5-formylcytosine; 5-carboxylcytosine; N$^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-N$^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2"-O-methyl-5-methyluridine; and 2"-O-methyluridine.

In some embodiments, nucleosides include 6-modified bicyclic nucleosides that have either (R) or (S)-chirality at the 6-position and include the analogs described in U.S. Pat. No. 7,399,845. In other embodiments, nucleosides include 5"-modified bicyclic nucleosides that have either (R) or (S)-chirality at the 5-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the modified nucleobases, sugars, and internucleotidic linkages of each of which are incorporated by reference.

In some embodiments, a base is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)—, one or more =CH— are independently and optionally replaced with =N—, and one or more =O are independently and optionally replaced with =S, =N(-L-R$^1$), or =C(-L-R$^1$)$_2$, wherein two or more -L-R$^1$ are optionally taken together with their intervening atoms to form a 3-30 membered bicyclic or polycyclic ring having 0-10 heteroatom ring atoms. In some embodiments, a modified base is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)—, one or more =CH— are independently and optionally replaced with =N—, and one or more =O are independently and optionally replaced with =S, =N(-L-R$^1$), or =C(-L-R$^1$)$_2$, wherein two or more -L-R$^1$ are optionally taken together with their intervening atoms to form a 3-30 membered bicyclic or polycyclic ring having 0-10 heteroatom ring atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a nucleoside is any described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; or WO 2016/079181.

Example nucleobases are also described in US 20110294124, US 20120316224, US 20140194610, US 20150211006, US 20150197540, WO 2015107425, PCT/US2016/043542, and PCT/US2016/043598, each of which is incorporated herein by reference.

In some embodiments, each nucleobase is independently A, T, C, G, or U, or an optionally substituted A, T, C, G, or U, or an optionally substituted tautomer of A, T, C, G, or U.

Additional Chemical Moieties in Oligonucleotides Having an Asymmetric Format

In some embodiments, the present disclosure provides oligonucleotides comprising additional chemistry moieties, optionally connected to the oligonucleotide moiety through a linker. In some embodiments, the present disclosure provides oligonucleotides comprising (R$^D$b-L$^{M1}$-L$^{M2}$-L$^{M3}$-, wherein:

each RD is independently a chemical moiety;

each of L$^{M1}$, L$^{M2}$, and L$^{M3}$ is independently a covalent bond, or a bivalent or multivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring; and b is 1-1000.

In some embodiments, each of L$^{M1}$, L$^{M2}$, and L$^{M3}$ is independently a covalent bond, or a bivalent or multivalent, optionally substituted, linear or branched group selected from a C$_{1-10}$ aliphatic group and a C$_{1-10}$ heteroaliphatic group having 1-5 heteroatoms, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$.

In some embodiments, $L^{M1}$ comprises one or more —N(R')— and one or more —C(O)—. In some embodiments, a linker or $L^{M1}$ is or comprises
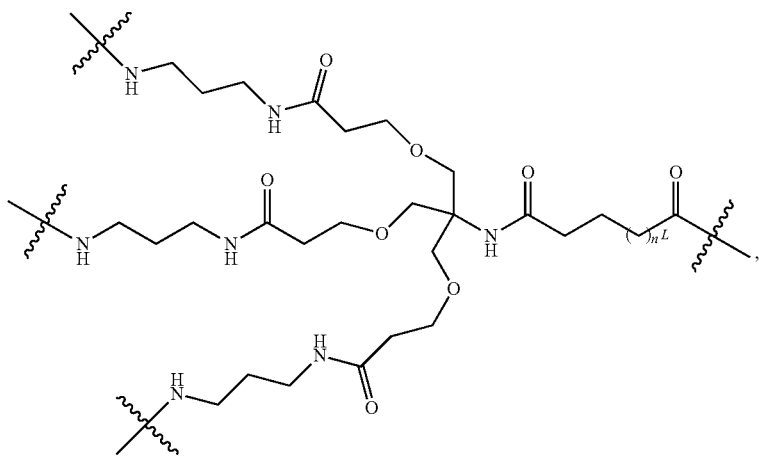
wherein $n^L$ is 1-8. In some embodiments, a linker or -$L^{M1}$-$L^{M2}$-$L^{M3}$- is
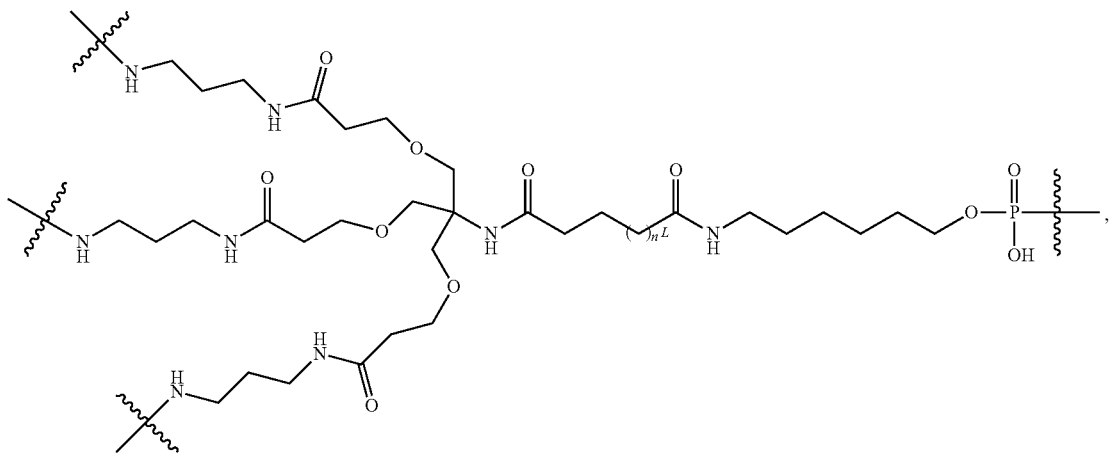
or a salt form thereof, wherein $n^L$ is 1-8. In some embodiments, a liner or -$L^{M1}$-$L^{M2}$-$L^{M3}$- is
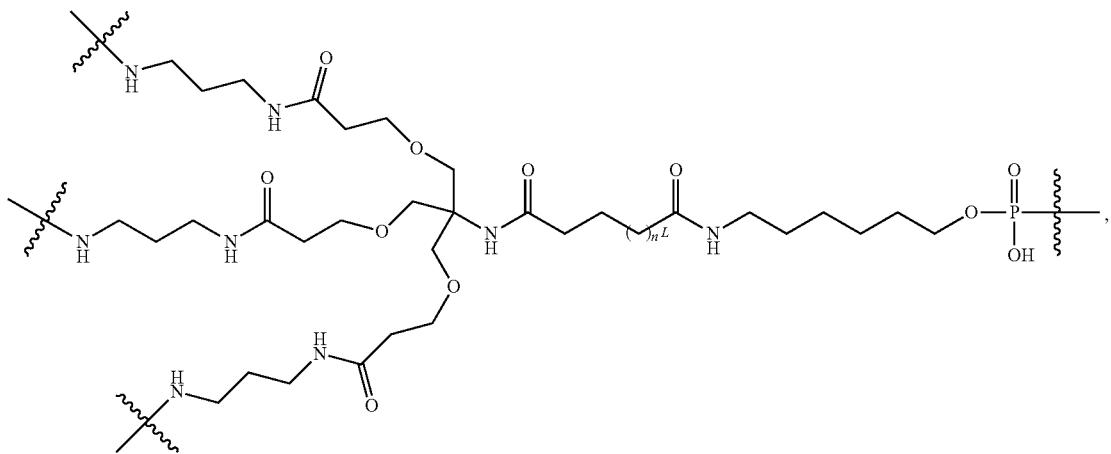

or a salt form thereof, wherein:
$n^L$ is
each amino group independently connects to a moiety; and
the P atom connects to the 5′-OH of the oligonucleotide.
In some embodiments, the moiety and the linker, or $(R^D)b$-$L^{M1}$-$L^{M2}$-$L^{M3}$-, is or comprises
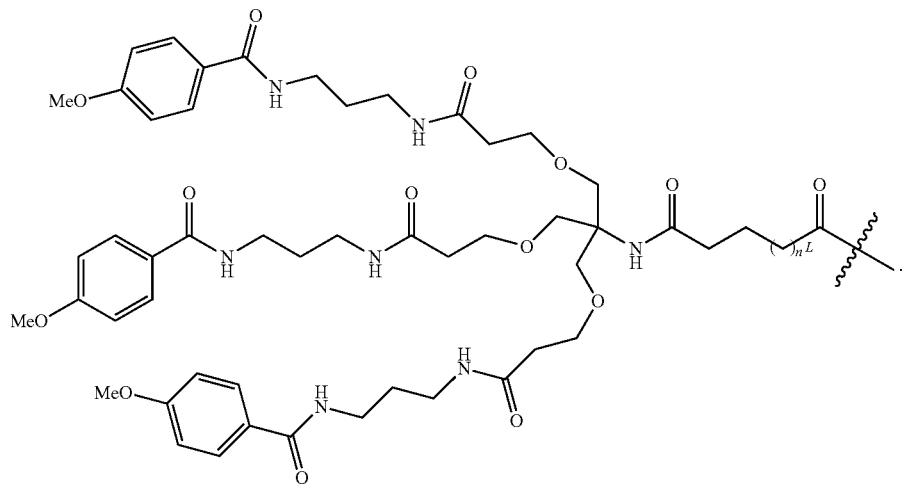
In some embodiments, the moiety and the linker, or $(R^D)b$-$L^{M1}$-$L^{M2}$-$L^{M3}$-, is or comprises
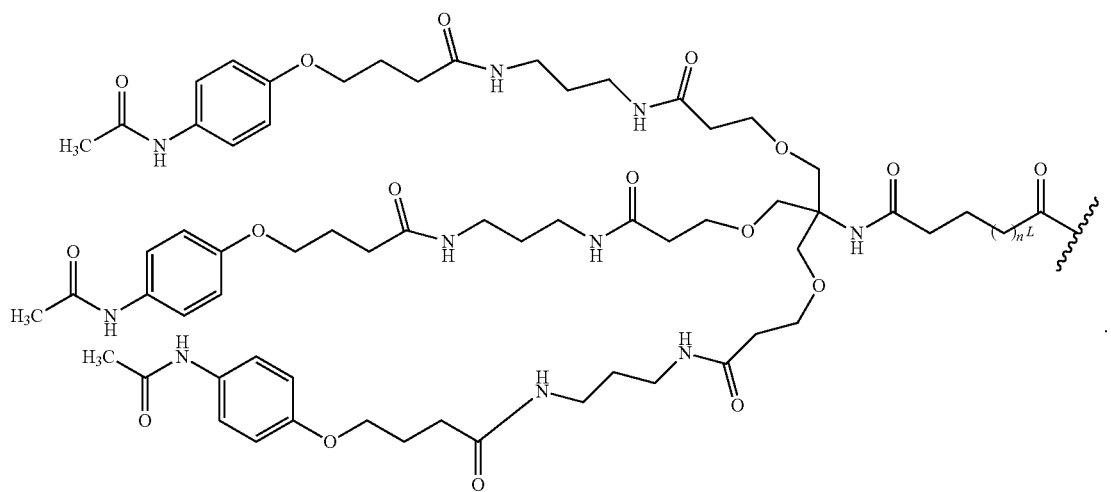

In some embodiments, the moiety and the linker, or $(R^D)b$-$L^{M1}$-$L^{M2}$-$L^{M3}$-, is or comprises
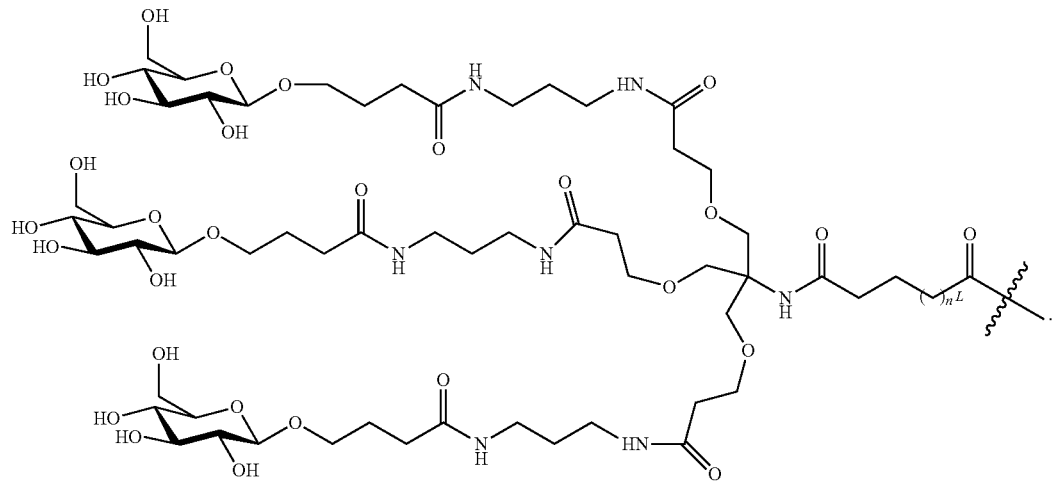
In some embodiments, the moiety and the linker, or $(R^D)b$-$L^{M1}$-$L^{M2}$-$L^{M3}$-, is or comprises
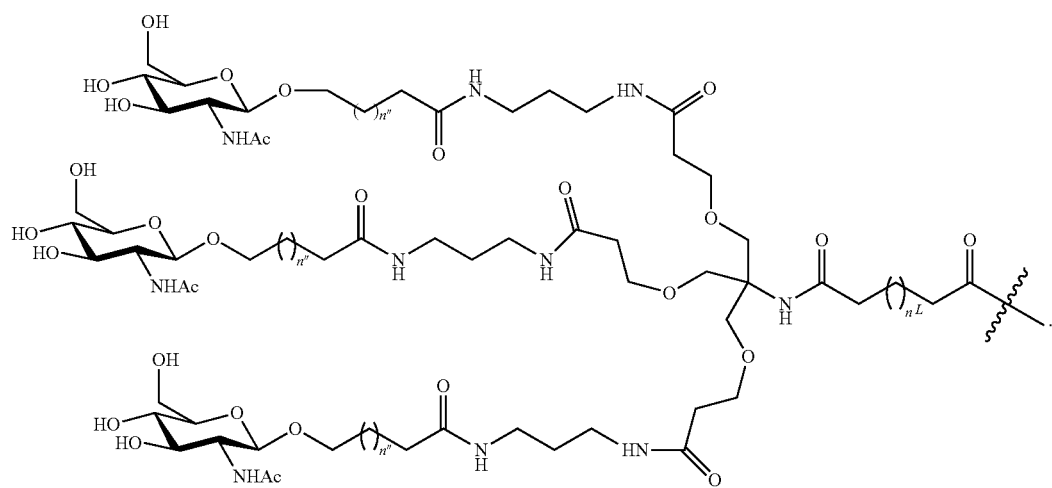

In some embodiments, the moiety and the linker, or $(R^D)b\text{-}L^{M1}\text{-}L^{M2}\text{-}L^{M3}\text{-}$, is or comprises
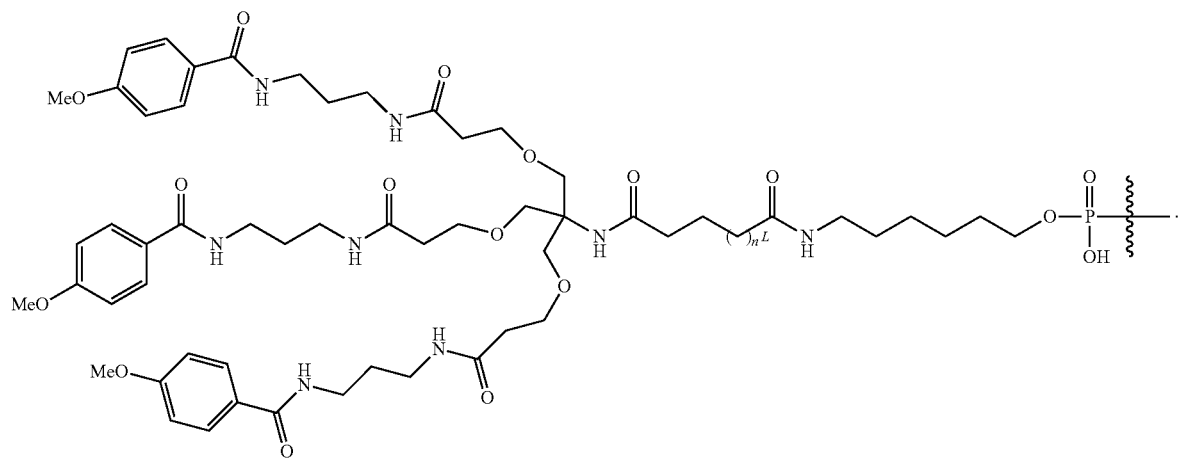
In Some embodiments, the moiety and the linker, or $(R^D)b\text{-}L^{M1}\text{-}L^{M2}\text{-}L^{M3}\text{-}$, is or comprises
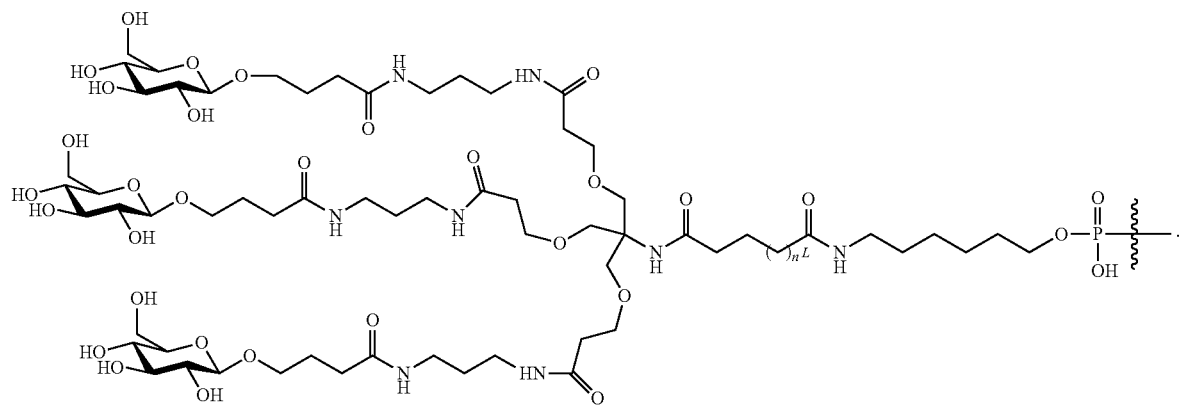
In some embodiments, the moiety and the linker, or $(R^D)b\text{-}L^{M1}\text{-}L^{M2}\text{-}L^{M3}\text{-}$, is or comprises
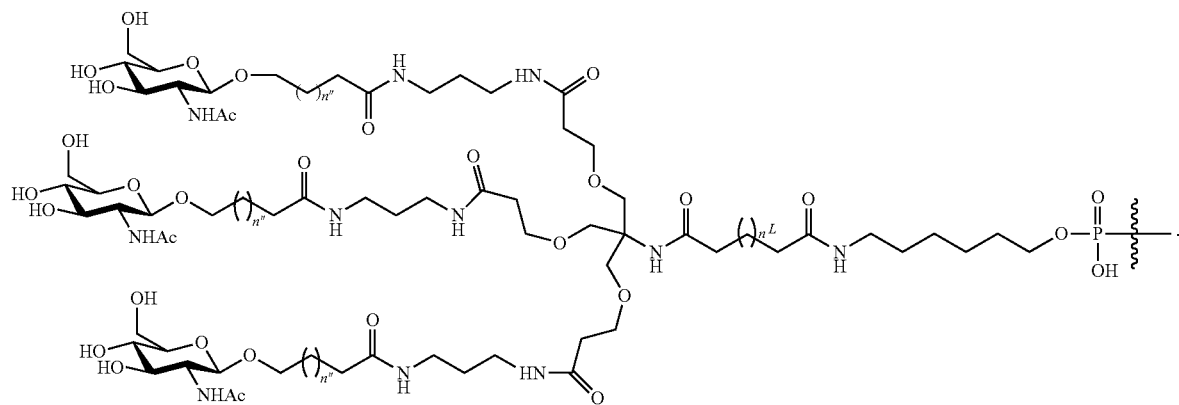

In some embodiments, the linker, or $L^{M1}$, is or comprises
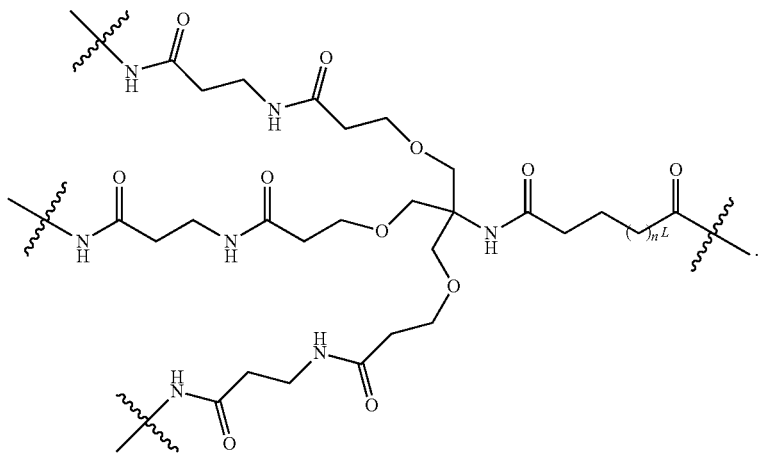
In some embodiments, the moiety and linker, or $(R^D)b\text{-}L^{M1}\text{-}L^{M2}\text{-}L^{M3}\text{-}$, is or comprises:
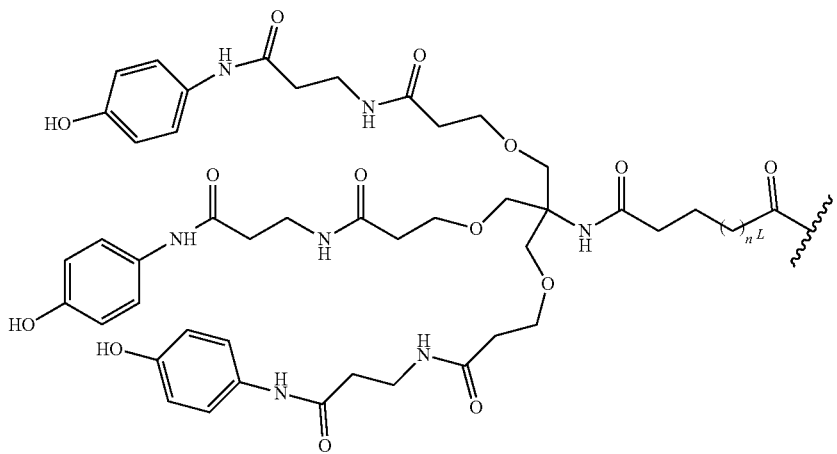
In some embodiments, the moiety and linker, or $(R^D)b\text{-}L^{M1}\text{-}L^{M2}\text{-}L^{M3}\text{-}$, is or comprises:
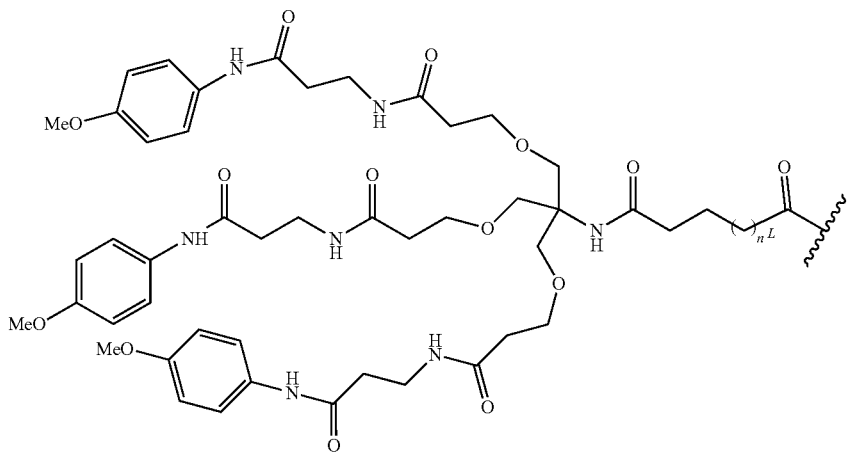

In some embodiments, $n^L$ is 1-8. In some embodiments, $n^L$ is 1, 2, 3, 4, 5, 6, 7, or 8. In some embodiments, $n^L$ is 1. In some embodiments, $n^L$ is 2. In some embodiments, $n^L$ is 3. In some embodiments, $n^L$ is 4. In some embodiments, $n^L$ is 5. In some embodiments, $n^L$ is 6. In some embodiments, $n^L$ is 7. In some embodiments, $n^L$ is 8.

In some embodiments, $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$. In some embodiments, $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, or —P(O)(R')—. In some embodiments, $L^{M2}$ is a covalent bond, or a bivalent, optionally substituted, linear or branched $C_{1-10}$ aliphatic wherein one or more methylene units are optionally and independently replaced with $C_{1-6}$ alkylene, $C_{1-6}$ alkenylene, —C≡C—, —C(R')$_2$—, —O—, —S—, —N(R')—, or —C(O)—. In some embodiments, $L^{M2}$ is —NH—(CH$_2$)$_6$—, wherein —NH— is bonded to $L^{M1}$.

In some embodiments, $L^{M3}$ is —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')—, —OP(O)(SR')—, —OP(O)(R')—, —OP(O)(NR')—, —OP(S)(OR')—, —OP(S)(SR')—, —OP(S)(R')—, —OP(S)(NR')—, —OP(R')—, —OP(OR')—, —OP(SR')—, —OP(NR')—, or —OP(OR')[B(R')$_3$]—. In some embodiments, $L^{M3}$ is —OP(O)(OR')—, or —OP(O)(SR')—, wherein —O— is bonded to $L^{M2}$. In some embodiments, the P atom is connected to a sugar unit, a nucleobase unit, or an internucleotidic linkage. In some embodiments, the P atom is connected to a —OH group through formation of a P—O bond. In some embodiments, the P atom is connected to the 5'-OH group through formation of a P—O bond.

In some embodiments, $L^{M1}$ is a covalent bond. In some embodiments, $L^{M2}$ is a covalent bond. In some embodiments, $L^{M3}$ is a covalent bond. In some embodiments, $L^{M1}$ is $L^{M2}$ as described in the present disclosure. In some embodiments, $L^{M1}$ is $L^{M3}$ as described in the present disclosure. In some embodiments, $L^{M2}$ is $L^{M1}$ as described in the present disclosure. In some embodiments, $L^{M2}$ is $L^{M3}$ as described in the present disclosure. In some embodiments, $L^{M3}$ is $L^{M1}$ as described in the present disclosure. In some embodiments, $L^{M3}$ is $L^{M2}$ as described in the present disclosure. In some embodiments, $L^M$ is $L^{M1}$ as described in the present disclosure. In some embodiments, $L^M$ is $L^{M2}$ as described in the present disclosure. In some embodiments, $L^M$ is $L^{M3}$ as described in the present disclosure. In some embodiments, $L^M$ is $L^{M1}$-$L^{M2}$, wherein each of $L^{M1}$ and $L^{M2}$ is independently as described in the present disclosure. In some embodiments, $L^M$ is $L^{M1}$-$L^{M3}$, wherein each of $L^{M1}$ and $L^{M3}$ is independently as described in the present disclosure. In some embodiments, $L^M$ is $L^{M2}$-$L^{M3}$, wherein each of $L^{M2}$ and $L^{M3}$ is independently as described in the present disclosure. In some embodiments, $L^M$ is $L^{M1}$-$L^{M2}$-$L^{M3}$, wherein each of $L^{M1}$, $L^{M2}$ and $L^{M3}$ is independently as described in the present disclosure.

In some embodiments, each $R^D$ is independently a chemical moiety as described in the present disclosure. In some embodiments, $R^D$ is targeting moiety. In some embodiments, $R^D$ is or comprises a carbohydrate moiety. In some embodiments, $R^D$ is or comprises a lipid moiety. In some embodiments, $R^D$ is or comprises a ligand moiety for, e.g., cell receptors such as a sigma receptor, an asialoglycoprotein receptor, etc. In some embodiments, a ligand moiety is or comprises an anisamide moiety, which may be a ligand moiety for a sigma receptor. In some embodiments, a ligand moiety is or comprises a GalNAc moiety, which may be a ligand moiety for an asialoglycoprotein receptor. In some embodiments, $R^D$ is selected from optionally substituted phenyl,

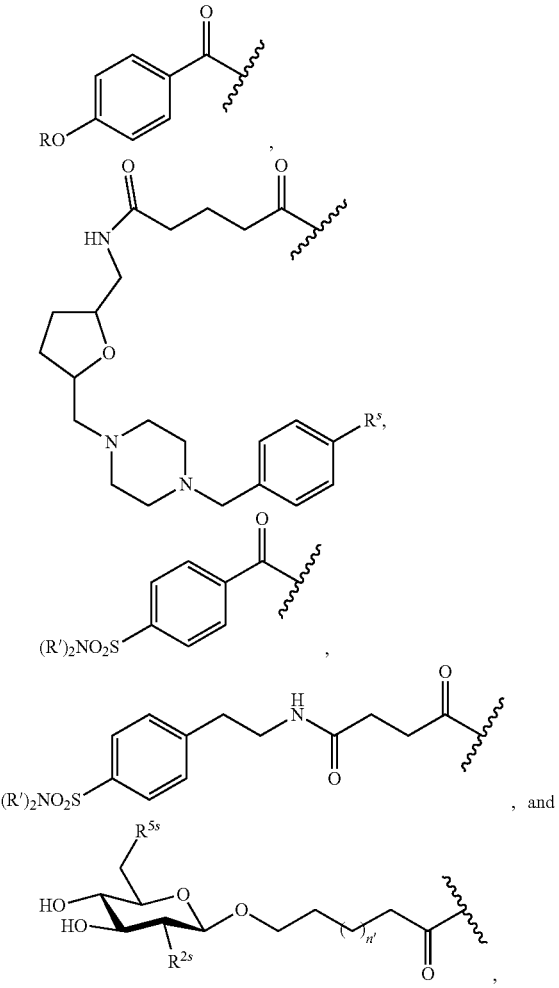

, and wherein n' is 0 or 1, and each other variable is independently as described in the present disclosure. In some embodiments, $R^s$ is F. In some embodiments, $R^s$ is OMe. In some embodiments, $R^s$ is OH. In some embodiments, $R^s$ is NHAc. In some embodiments, $R^s$ is NHCOCF$_3$. In some embodiments, R' is H. In some embodiments, R is H. In some embodiments, $R^{2s}$ is NHAc, and $R^{5s}$ is OH. In some embodiments, $R^{2s}$ is p-anisoyl, and $R^{5s}$ is OH. In some embodiments, $R^{2s}$ is NHAc and $R^{5s}$ is p-anisoyl. In some embodiments, $R^{2s}$ is OH, and $R^{5s}$ is p-anisoyl. In some embodiments, $R^D$ is selected from

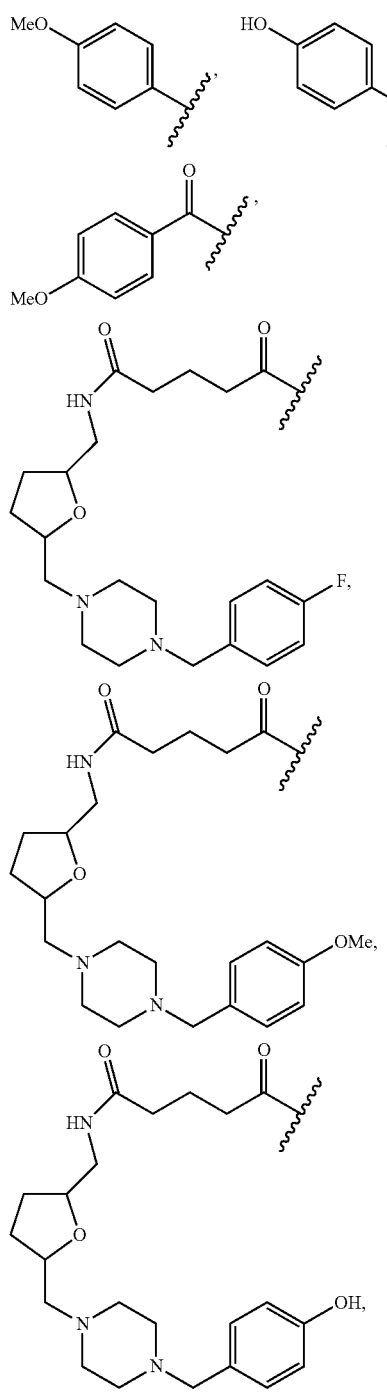

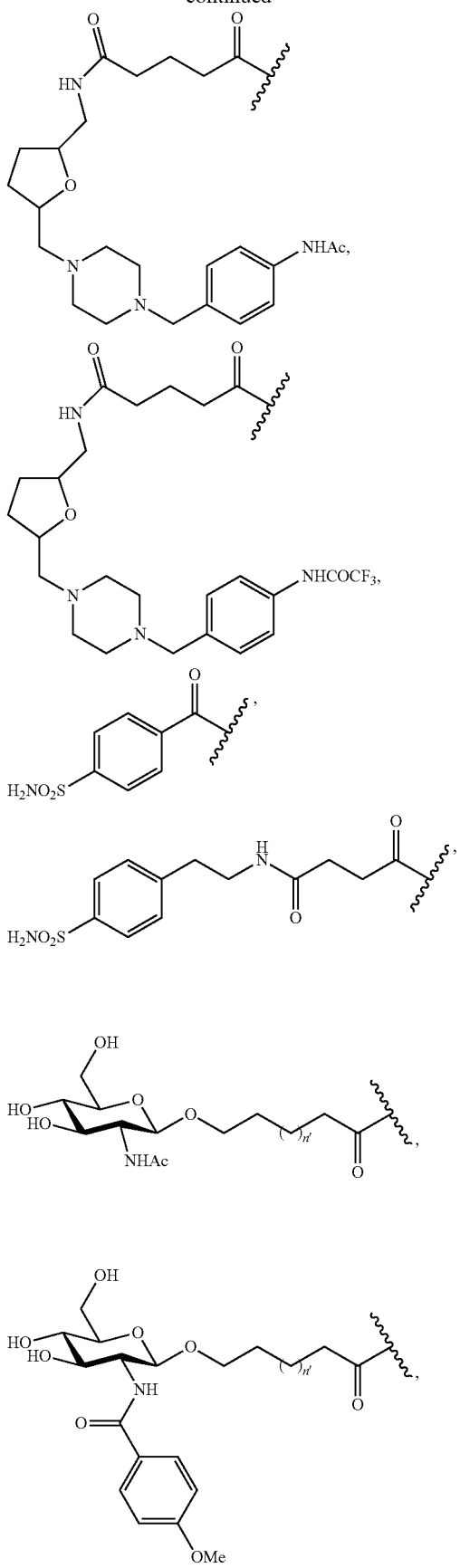

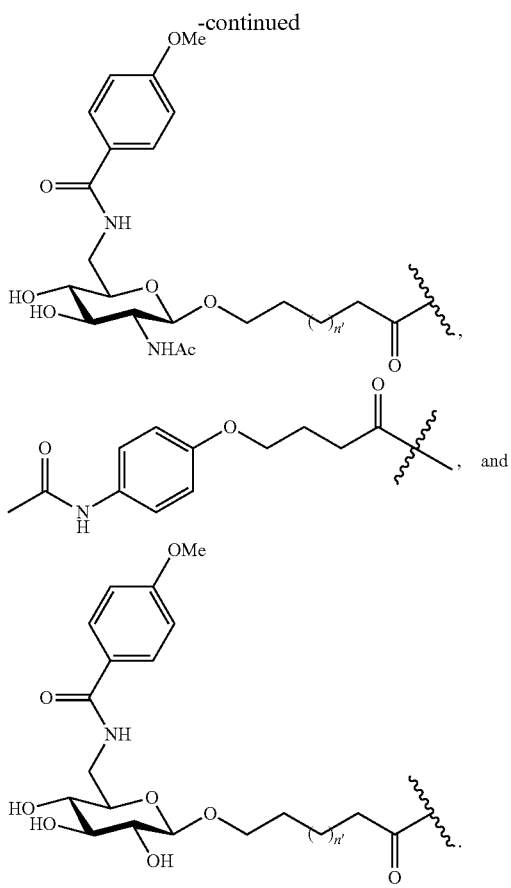

Further embodiments of $R^D$ include additional chemical moiety embodiments, e.g., those described herein.

In some embodiments, n' is 1. In some embodiments, n' is 0.

In some embodiments, n" is 1. In some embodiments, n" is 2.

In some embodiments, an oligonucleotide having an asymmetric format comprises a base (e.g., nucleobase) residue or variant thereof illustrated in US 2011/0294124, US 2015/0211006, US 2015/0197540, and WO 2015/107425.

In some embodiments, BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, a natural nucleobase moiety, and a modified nucleobase moiety. In some embodiments, BA is optionally substituted $C_{5-30}$ heteroaryl having 1-10 heteroatoms independently selected from oxygen, nitrogen, and sulfur. In some embodiments, BA is optionally substituted natural nucleobases and tautomers thereof. In some embodiments, BA is protected natural nucleobases and tautomers thereof. Various nucleobase protecting groups for oligonucleotide synthesis are known and can be utilized in accordance with the present disclosure. In some embodiments, BA is an optionally substituted nucleobase selected from adenine, cytosine, guanosine, thymine, and uracil, and tautomers thereof. In some embodiments, BA is an optionally protected nucleobase selected from adenine, cytosine, guanosine, thymine, and uracil, and tautomers thereof.

In some embodiments, BA is optionally substituted $C_{3-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{3-30}$ cycloaliphatic, $C_{6-30}$ aryl, $C_{3-30}$ heterocyclyl, and $C_{5-30}$ heteroaryl. In some embodiments, BA is an optionally substituted group selected from $C_{3-30}$ cycloaliphatic, $C_{6-30}$ aryl, $C_{3-30}$ heterocyclyl, $C_{5-30}$ heteroaryl, and a natural nucleobase moiety.

In some embodiments, BA is connected through an aromatic ring. In some embodiments, BA is connected through a heteroatom. In some embodiments, BA is connected through a ring heteroatom of an aromatic ring. In some embodiments, BA is connected through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is natural nucleobase A, T, C, U, or G. In some embodiments, BA is an optionally substituted group selected from natural nucleobases A, T, C, U, and G.

In some embodiments, BA is an optionally substituted group, which group is formed by removing a —H from

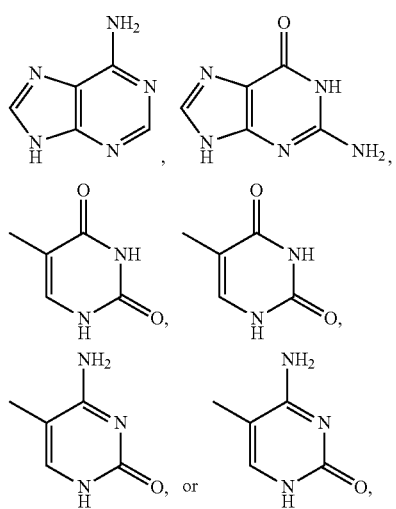

or a tautomer thereof. In some embodiments BA is an optionally substituted group, which group is formed by removing a —H from

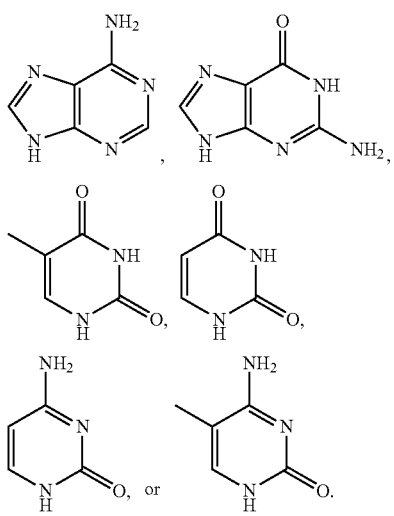

In some embodiments, BA is an optionally substituted group which group is selected from

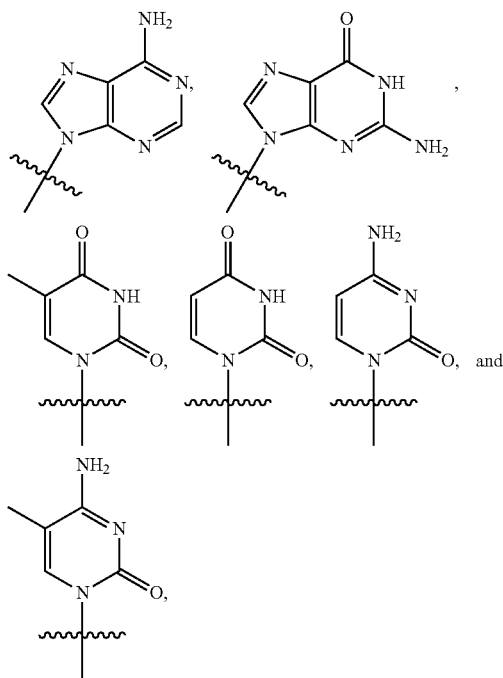

and tautomeric forms thereof. In some embodiments, BA is an optionally substituted group which group is selected from

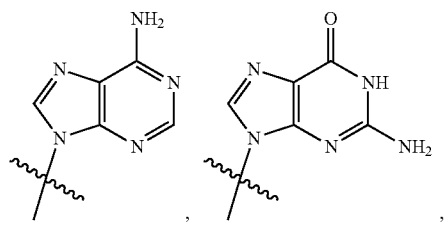

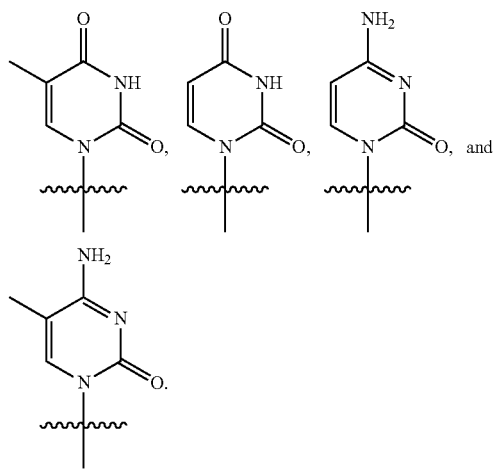

In some embodiments, BA is an optionally substituted group, which group is formed by removing a —H from

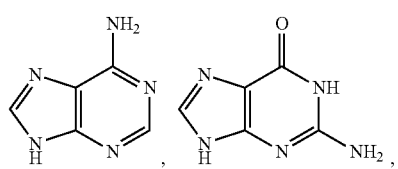

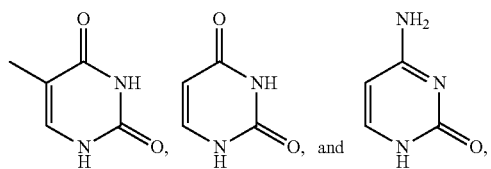

and tautomers thereof. In some embodiments, BA is an optionally substituted group, which group is formed by removing a —H from

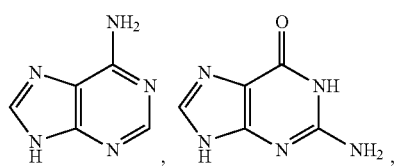

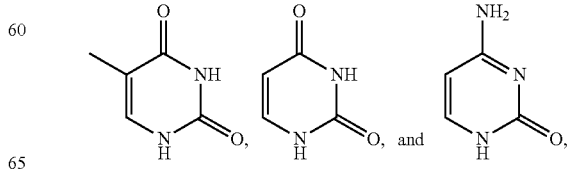

In some embodiments, BA is an optionally substituted group which group is selected from

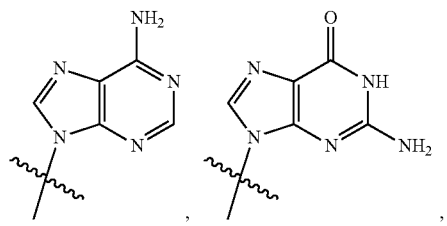

,

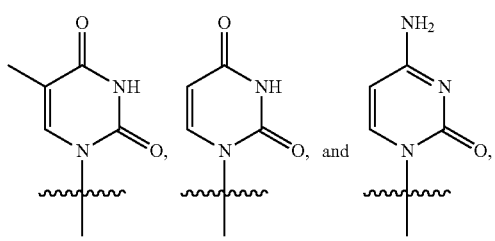

and tautomeric forms thereof. In some embodiments, BA is an optionally substituted group which group is selected from

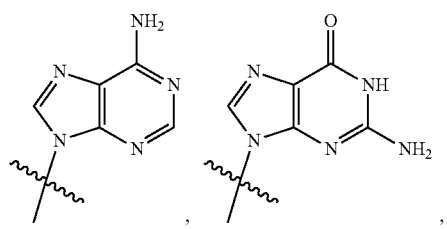

,

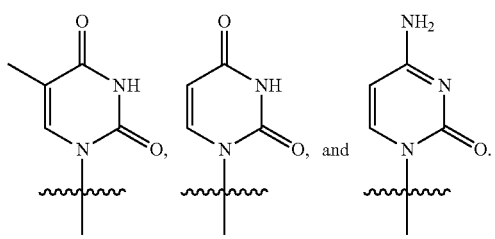

In some embodiments, BA is optionally substituted

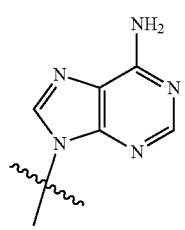 [SMILES: *n1cnc2c(N)ncnc21]

or a tautomeric form thereof. In some embodiments, BA is optionally substituted

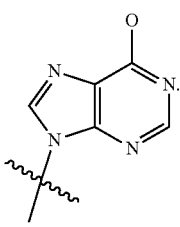 [SMILES: *n1cnc2c(O)ncnc21]

In some embodiments, BA is optionally substituted

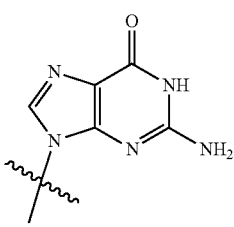 [SMILES: *n1cnc2c(=O)[nH]c(N)nc21]

or a tautomeric form thereof. In some embodiments, BA is optionally substituted

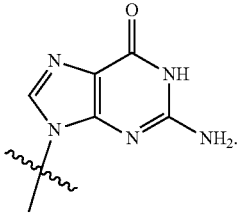 [SMILES: *n1cnc2c(=O)[nH]c(N)nc21]

In some embodiments, BA is optionally substituted

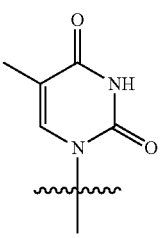

or a tautomeric form thereof. In some embodiments, BA is optionally substituted

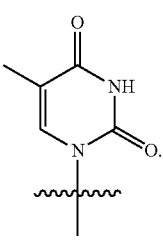

In some embodiments, BA is optionally substituted

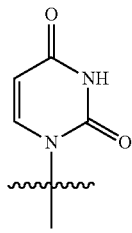

or a tautomeric form thereof. In some embodiments, BA is optionally substituted

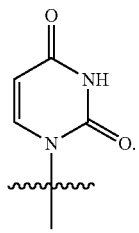

In some embodiments, BA is optionally substituted

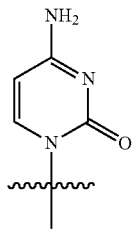

or a tautomeric form thereof. In some embodiments, BA is optionally substituted

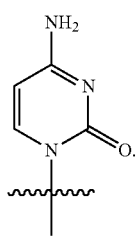

In some embodiments, BA is

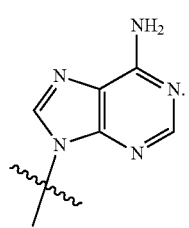 [SMILES: *n1cnc2c(N)ncnc21]

In some embodiments, BA is

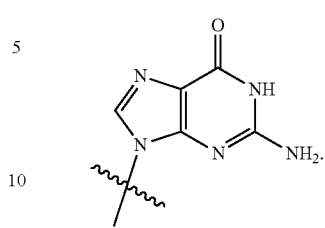

In some embodiments, BA is

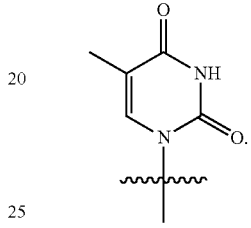

In some embodiments, BA is

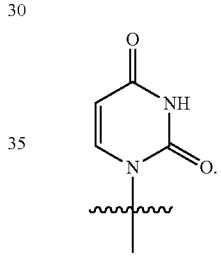

In some embodiments, BA is

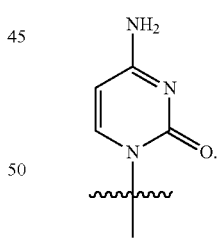

In some embodiments, BA of the 5'-end nucleoside unit of a provided oligonucleotide, e.g., an oligonucleotide of formula VIII, is an optionally substituted group, which group is formed by removing a —H from

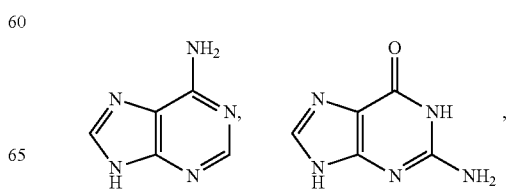

-continued

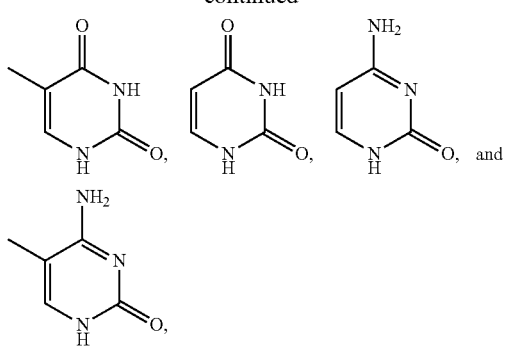

In some embodiments, BA of the 5'-end nucleoside unit is an optionally substituted group which group is selected from

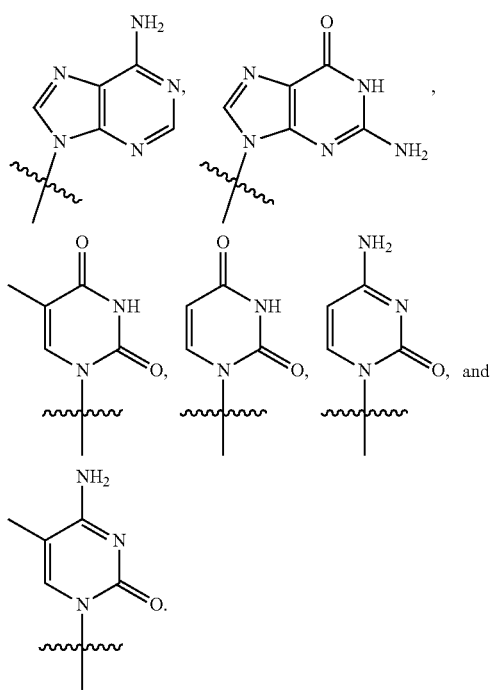

In some embodiments, BA of the 5'-end nucleoside unit is an optionally substituted group, which group is formed by removing a —H from

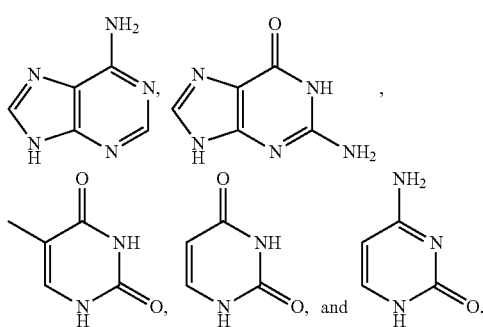

In some embodiments, BA of the 5'-end nucleoside unit is an optionally substituted group which group is selected from

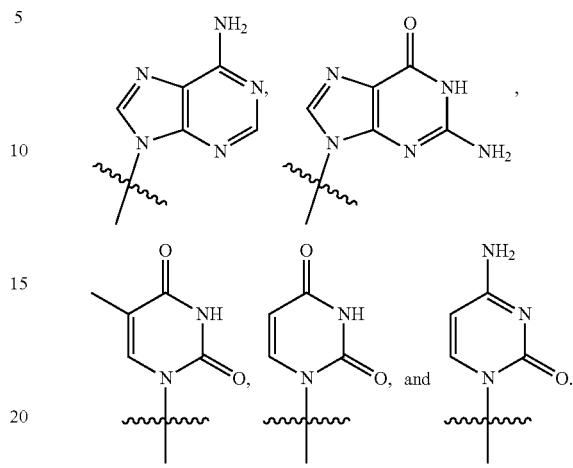

In some embodiments, BA of the 5'-end nucleoside unit is optionally substituted

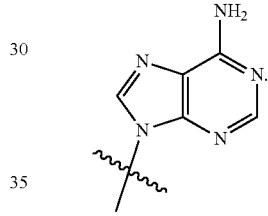

In some embodiments, BA of the 5'-end nucleoside unit is optionally substituted

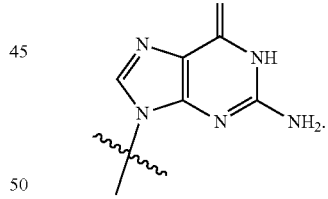

In some embodiments, BA of the 5'-end nucleoside unit is optionally substituted

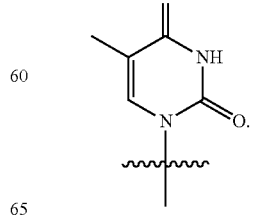

In some embodiments, BA of the 5'-end nucleoside unit is optionally substituted

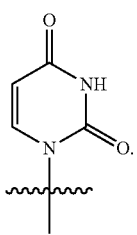 [SMILES: *n1ccc(=O)[nH]c1=O]

In some embodiments, BA of the 5'-end nucleoside unit is optionally substituted

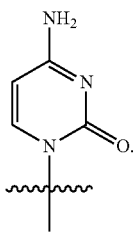 [SMILES: *n1ccc(N)nc1=O]

In some embodiments, BA of the 5'-end nucleoside unit is

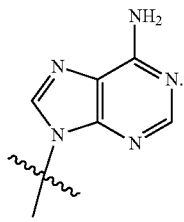 [SMILES: *n1cnc2c(N)ncnc21]

In some embodiments, BA of the 5'-end nucleoside unit is

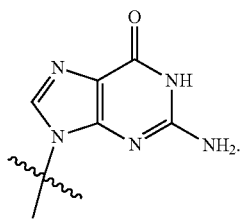 [SMILES: *n1cnc2c(=O)[nH]c(N)nc21]

In some embodiments, BA of the 5'-end nucleoside unit is

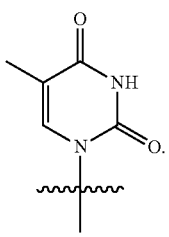 [SMILES: *n1cc(C)c(=O)[nH]c1=O]

In some embodiments, BA of the 5'-end nucleoside unit is

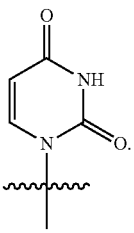 [SMILES: *n1ccc(=O)[nH]c1=O]

In some embodiments, BA of the 5'-end nucleoside unit is

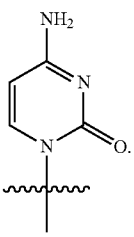 [SMILES: *n1ccc(N)nc1=O]

In some embodiments, BA is

 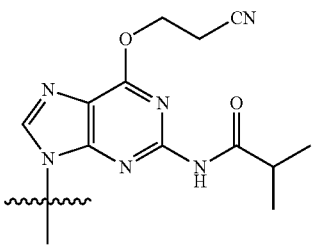,

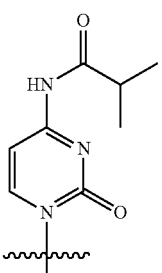 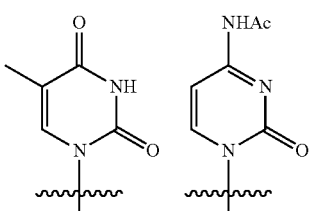,

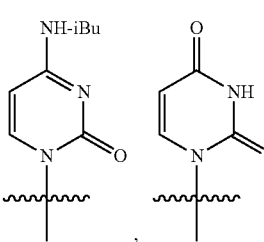, or

-continued
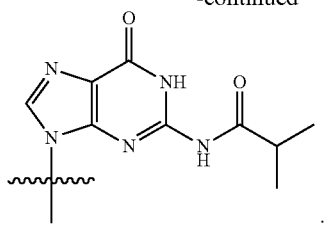
In some embodiments, BA is
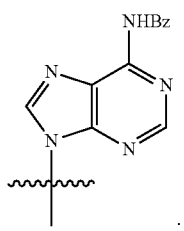
In some embodiments, BA is
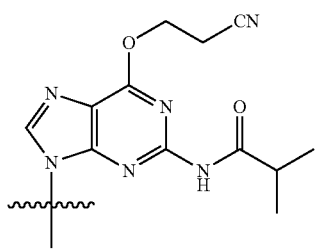
or
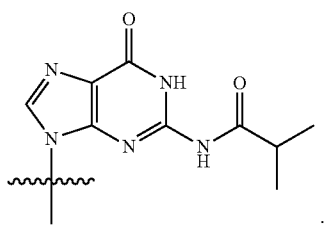
In some embodiments, BA is
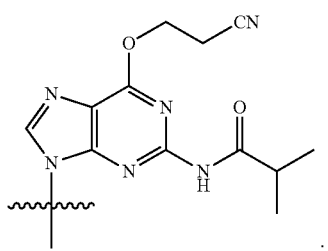 [SMILES: *n1cnc2c(OCCC#N)nc(NC(=O)C(C)C)nc21]
In some embodiments, BA is
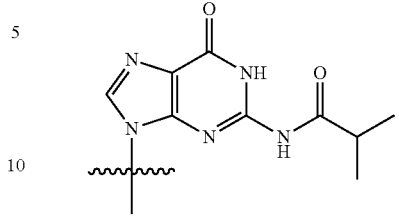
In some embodiments, BA is
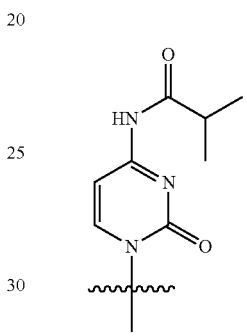
In some embodiments, BA is
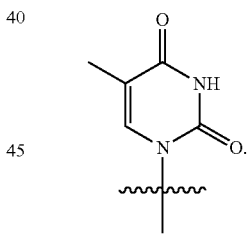
In some embodiments, BA is
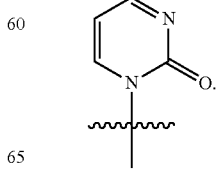

In some embodiments, BA is

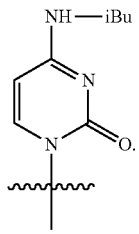

In some embodiments, BA is

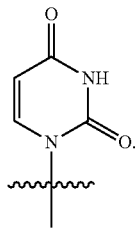

In some embodiments, a protection group is -Ac. In some embodiments, a protection group is -Bz. In some embodiments, a protection group is -iBu for nucleobase.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, BA is an optionally substituted cytosine residue. In some embodiments, BA is a protected cytosine residue. In some embodiments, BA is an optionally substituted thymine residue. In some embodiments, BA is a protected thymine residue. In some embodiments, BA is an optionally substituted uracil residue. In some embodiments, BA is a protected uracil residue. In some embodiments, BA is an optionally substituted 5-methylcytosine residue. In some embodiments, BA is a protected 5-methylcytosine residue.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference. In some embodiments, BA is a modified nucleobase illustrated in WO 2017/192679.

In some embodiments, each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-R', —O-L$^s$-Si(R)$_3$, —O-L$^s$-OR', —O-L$^s$-SR', or —O-L$^s$-N(R')$_2$ as described in the present disclosure. In some embodiments, $R^s$ is —H. In some embodiments, $R^s$ is not —H.

In some embodiments, $R^s$ is R', wherein R is as described in the present disclosure. In some embodiments, $R^s$ is R, wherein R is as described in the present disclosure. In some embodiments, $R^s$ is optionally substituted $C_{1-30}$ heteroaliphatic. In some embodiments, $R^s$ comprises one or more silicon atoms. In some embodiments, $R^s$ is —CH$_2$Si(Ph)$_2$CH$_3$.

In some embodiments, $R^s$ is -L$^s$-R'. In some embodiments, $R^s$ is -L$^s$-R' wherein -L$^s$- is a bivalent, optionally substituted $C_{1-30}$ heteroaliphatic group. In some embodiments, $R^s$ is —CH$_2$Si(Ph)$_2$CH$_3$.

In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —N$_3$. In some embodiments, $R^s$ is —NO. In some embodiments, $R^s$ is —NO$_2$. In some embodiments, $R^s$ is -L$^s$-Si(R)$_3$. In some embodiments, $R^s$ is —Si(R)$_3$. In some embodiments, $R^s$ is -L$^s$-R'. In some embodiments, $R^s$ is -R'. In some embodiments, $R^s$ is -L$^s$-OR'. In some embodiments, $R^s$ is —OR'. In some embodiments, $R^s$ is -L$^s$-SR'. In some embodiments, $R^s$ is —SR'. In some embodiments, $R^s$ is -L$^s$-N(R')$_2$. In some embodiments, $R^s$ is —N(R')$_2$. In some embodiments, $R^s$ is —O-L$^s$-R'. In some embodiments, $R^s$ is —O-L$^s$-Si(R)$_3$. In some embodiments, $R^s$ is —O-L$^s$-OR'. In some embodiments, $R^s$ is —O-L$^s$-SR'. In some embodiments, $R^s$ is —O-L$^s$-N(R')$_2$. In some embodiments, $R^s$ is a 2'-modification as described in the present disclosure. In some embodiments, $R^s$ is —OR, wherein R is as described in the present disclosure. In some embodiments, $R^s$ is —OR, wherein R is optionally substituted $C_{1-6}$ aliphatic. In some embodiments, $R^s$ is —OMe. In some embodiments, $R^s$ is —OCH$_2$CH$_2$OMe.

In some embodiments, s is 0-20. In some embodiments, s is 1-20. In some embodiments, s is 1-5. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, $L^s$ is L, wherein L is as described in the present disclosure. In some embodiments, L is a bivalent optionally substituted methylene group.

As described herein, each L is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$.

In some embodiments, L is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched C$_{1-30}$ aliphatic group, wherein one or more methylene units are optionally and independently replaced by an optionally substituted group selected from C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with Cy$^L$. In some embodiments, L is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with Cy$^L$. In some embodiments, L is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L is a covalent bond. In some embodiments, L is optionally substituted bivalent C$_{1-30}$ aliphatic. In some embodiments, L is optionally substituted bivalent C$_{1-30}$ heteroaliphatic having 1-10 heteroatoms independently selected from boron, oxygen, nitrogen, sulfur, phosphorus and silicon.

In some embodiments, aliphatic moieties, e.g. those of L, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc. In some embodiments, heteroaliphatic moieties, e.g. those of L, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc.

In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with —S(O)$_2$—. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with —P(OR')[B(R')$_3$]—. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, each of which may independently be an internucleotidic linkage.

In some embodiments, L, e.g., when connected to R, is —CH$_2$—. In some embodiments, L is —C(R)$_2$—, wherein at least one R is not hydrogen. In some embodiments, L is —CHR—. In some embodiments, R is hydrogen. In some embodiments, L is —CHR—, wherein R is not hydrogen. In some embodiments, C of —CHR— is chiral. In some embodiments, L is —(R)—CHR—, wherein C of —CHR— is chiral. In some embodiments, L is —(S)—CHR—, wherein C of —CHR— is chiral. In some embodiments, R is optionally substituted C$_{1-6}$ aliphatic. In some embodiments, R is optionally substituted C$_{1-6}$ alkyl. In some embodiments, R is optionally substituted C$_{1-5}$ aliphatic. In some embodiments, R is optionally substituted C$_{1-5}$ alkyl. In some embodiments, R is optionally substituted C$_{1-4}$ aliphatic. In some embodiments, R is optionally substituted C$_{1-4}$ alkyl. In some embodiments, R is optionally substituted C$_{1-3}$ aliphatic. In some embodiments, R is optionally substituted C$_{1-3}$ alkyl. In some embodiments, R is optionally substituted C$_2$ aliphatic. In some embodiments, R is optionally substituted methyl. In some embodiments, R is C$_{1-6}$ aliphatic. In some embodiments, R is C$_{1-6}$ alkyl. In some embodiments, R is C$_{1-5}$ aliphatic. In some embodiments, R is C$_{1-5}$ alkyl. In some embodiments, R is C$_{1-4}$ aliphatic. In some embodiments, R is C$_{1-4}$ alkyl. In some embodiments, R is C$_{1-3}$ aliphatic. In some embodiments, R is C$_{1-3}$ alkyl. In some embodiments, R is C$_2$ aliphatic. In some embodiments, R is methyl. In some embodiments, R is C$_{1-6}$ haloaliphatic. In some embodiments, R is C$_{1-6}$ haloalkyl. In some embodiments, R is C$_{1-5}$ haloaliphatic. In some embodiments, R is C$_{1-5}$ haloalkyl. In some embodiments, R is C$_{1-4}$ haloaliphatic. In some embodiments, R is C$_{1-4}$ haloalkyl. In some embodiments, R is C$_{1-3}$ haloaliphatic. In some embodiments, R is C$_{1-3}$ haloalkyl. In some embodiments, R is C$_2$ haloaliphatic. In some embodiments, R is methyl substituted with one or more halogen. In some embodiments, R is —CF$_3$. In some embodiments, L is optionally substituted —CH=CH—. In some embodiments, L is optionally substituted (E)-CH=CH—. In some embodiments, L is optionally substituted (Z)—CH=CH—. In some embodiments, L is —C≡C—.

In some embodiments, L comprises at least one phosphorus atom. In some embodiments, at least one methylene unit of L is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—.

In some embodiments, Cy$^L$ is an optionally substituted tetravalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon.

In some embodiments, Cy$^L$ is monocyclic. In some embodiments, Cy$^L$ is bicyclic. In some embodiments, Cy$^L$ is polycyclic.

In some embodiments, Cy$^L$ is saturated. In some embodiments, Cy$^L$ is partially unsaturated. In some embodiments, Cy$^L$ is aromatic. In some embodiments, Cy$^L$ is or comprises a saturated ring moiety. In some embodiments, Cy$^L$ is or comprises a partially unsaturated ring moiety. In some embodiments, Cy$^L$ is or comprises an aromatic ring moiety.

In some embodiments, Cy$^L$ is an optionally substituted C$_{3-20}$ cycloaliphatic ring as described in the present disclosure (for example, those described for R but tetravalent). In some embodiments, a ring is an optionally substituted saturated C$_{3-20}$ cycloaliphatic ring. In some embodiments, a ring is an optionally substituted partially unsaturated C$_{3-20}$ cycloaliphatic ring. A cycloaliphatic ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is an optionally substituted cyclopropyl moiety. In some embodiments, a ring is an optionally substituted cyclobutyl moiety. In some embodiments, a ring is an optionally substituted cyclopentyl moiety. In some embodiments, a ring is an optionally substituted cyclohexyl moiety. In some embodiments, a ring is an optionally substituted cycloheptyl moiety. In some embodiments, a ring is an optionally substituted cyclooctanyl moiety. In some embodiments, a cycloaliphatic ring is a cycloalkyl ring. In some embodiments, a cycloaliphatic ring is monocyclic. In some embodiments, a cycloaliphatic ring is bicyclic. In some embodiments, a cycloaliphatic ring is polycyclic. In some embodiments, a ring is a cycloaliphatic moiety as described in the present disclosure for R with more valences.

In some embodiments, Cy$^L$ is an optionally substituted 6-20 membered aryl ring. In some embodiments, a ring is an optionally substituted tetravalent phenyl moiety. In some embodiments, a ring is a tetravalent phenyl moiety. In some embodiments, a ring is an optionally substituted naphthalene moiety. A ring can be of different size as described in the present disclosure. In some embodiments, an aryl ring is 6-membered. In some embodiments, an aryl ring is 10-membered. In some embodiments, an aryl ring is 14-membered. In some embodiments, an aryl ring is monocyclic. In some embodiments, an aryl ring is bicyclic. In some embodiments, an aryl ring is polycyclic. In some embodiments, a ring is an aryl moiety as described in the present disclosure for R with more valences.

In some embodiments, Cy$^L$ is an optionally substituted 5-20 membered heteroaryl ring having 1-10 heteroatoms independently selected from oxygen, nitrogen, sulfur, phosphorus and silicon. In some embodiments, Cy$^L$ is an optionally substituted 5-20 membered heteroaryl ring having 1-10 heteroatoms independently selected from oxygen, nitrogen, and sulfur. In some embodiments, as described in the present disclosure, heteroaryl rings can be of various sizes and contain various numbers and/or types of heteroatoms. In some embodiments, a heteroaryl ring contains no more than one heteroatom. In some embodiments, a heteroaryl ring contains more than one heteroatom. In some embodiments, a heteroaryl ring contains no more than one type of heteroatom. In some embodiments, a heteroaryl ring contains more than one type of heteroatoms. In some embodiments, a heteroaryl ring is 5-membered. In some embodiments, a heteroaryl ring is 6-membered. In some embodiments, a heteroaryl ring is 8-membered. In some embodiments, a heteroaryl ring is 9-membered. In some embodiments, a heteroaryl ring is 10-membered. In some embodiments, a heteroaryl ring is monocyclic. In some embodiments, a heteroaryl ring is bicyclic. In some embodiments, a heteroaryl ring is polycyclic. In some embodiments, a heteroaryl ring is a nucleobase moiety, e.g., A, T, C, G, U, etc. In some embodiments, a ring is a heteroaryl moiety as described in the present disclosure for R with more valences.

In some embodiments, $Cy^L$ is a 3-20 membered heterocyclyl ring having 1-10 heteroatoms independently selected from oxygen, nitrogen, sulfur, phosphorus and silicon. In some embodiments, $Cy^L$ is a 3-20 membered heterocyclyl ring having 1-10 heteroatoms independently selected from oxygen, nitrogen, and sulfur. In some embodiments, a heterocyclyl ring is saturated. In some embodiments, a heterocyclyl ring is partially unsaturated. A heterocyclyl ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. Heterocyclyl rings can contain various numbers and/or types of heteroatoms. In some embodiments, a heterocyclyl ring contains no more than one heteroatom. In some embodiments, a heterocyclyl ring contains more than one heteroatom. In some embodiments, a heterocyclyl ring contains no more than one type of heteroatom. In some embodiments, a heterocyclyl ring contains more than one type of heteroatoms. In some embodiments, a heterocyclyl ring is monocyclic. In some embodiments, a heterocyclyl ring is bicyclic. In some embodiments, a heterocyclyl ring is polycyclic. In some embodiments, a ring is a heterocyclyl moiety as described in the present disclosure for R with more valences.

As readily appreciated by a person having ordinary skill in the art, many suitable ring moieties are extensively described in and can be used in accordance with the present disclosure, for example, those described for R (which may have more valences for $Cy^L$).

In some embodiments, $Cy^L$ is a sugar moiety in a nucleic acid. In some embodiments, $Cy^L$ is an optionally substituted furanose moiety. In some embodiments, $Cy^L$ is a pyranose moiety. In some embodiments, $Cy^L$ is an optionally substituted furanose moiety found in DNA. In some embodiments, $Cy^L$ is an optionally substituted furanose moiety found in RNA. In some embodiments, $Cy^L$ is an optionally substituted 2'-deoxyribofuranose moiety. In some embodiments, $Cy^L$ is an optionally substituted ribofuranose moiety. In some embodiments, substitutions provide sugar modifications as described in the present disclosure. In some embodiments, an optionally substituted 2'-deoxyribofuranose moiety and/or an optionally substituted ribofuranose moiety comprise substitution at a 2'-position. In some embodiments, a 2'-position is a 2'-modification as described in the present disclosure. In some embodiments, a 2'-modification is —F. In some embodiments, a 2'-modification is —OR, wherein R is as described in the present disclosure. In some embodiments, R is not hydrogen. In some embodiments, $Cy^L$ is a modified sugar moiety, such as a sugar moiety in LNA. In some embodiments, $Cy^L$ is a modified sugar moiety, such as a sugar moiety in ENA. In some embodiments, $Cy^L$ is a terminal sugar moiety of an oligonucleotide, connecting an internucleotidic linkage and a nucleobase. In some embodiments, $Cy^L$ is a terminal sugar moiety of an oligonucleotide, for example, when that terminus is connected to a solid support optionally through a linker. In some embodiments, $Cy^L$ is a sugar moiety connecting two internucleotidic linkages and a nucleobase. Example sugars and sugar moieties are extensively described in the present disclosure.

In some embodiments, $Cy^L$ is a nucleobase moiety. In some embodiments, a nucleobase is a natural nucleobase, such as A, T, C, G, U, etc. In some embodiments, a nucleobase is a modified nucleobase. In some embodiments, $Cy^L$ is optionally substituted nucleobase moiety selected from A, T, C, G, U, and 5 mC. Example nucleobases and nucleobase moieties are extensively described in the present disclosure.

In some embodiments, two $Cy^L$ moieties are bonded to each other, wherein one $Cy^L$ is a sugar moiety and the other is a nucleobase moiety. In some embodiments, such a sugar moiety and nucleobase moiety forms a nucleoside moiety. In some embodiments, a nucleoside moiety is natural. In some embodiments, a nucleoside moiety is modified. In some embodiments, $Cy^L$ is an optionally substituted natural nucleoside moiety selected from adenosine, 5-methyluridine, cytidine, guanosine, uridine, 5-methylcytidine, 2'-deoxyadenosine, thymidine, 2'-deoxycytidine, 2'-deoxyguanosine, 2'-deoxyuridine, and 5-methyl-2'-deoxycytidine. Example nucleosides and nucleosides moieties are extensive described in the present disclosure.

In some embodiments, for example in $L^s$, $Cy^L$ is an optionally substituted nucleoside moiety bonded to an internucleotidic linkage, for example, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, —OP(OR')[B(R')$_3$]O—, etc., which may form an optionally substituted nucleotidic unit. Example nucleotides and nucleosides moieties are extensive described in the present disclosure.

In some embodiments, each Ring A is independently an optionally substituted 3-20 membered monocyclic, bicyclic or polycyclic ring having 0-10 heteroatoms independently selected from oxygen, nitrogen, sulfur, phosphorus and silicon. In some embodiments, Ring A is an optionally substituted ring, which ring is as described in the present disclosure. In some embodiments, a ring is

In some embodiments, a ring is

In some embodiments, Ring A is or comprises a ring of a sugar moiety. In some embodiments, Ring A is or comprises a ring of a modified sugar moiety.

In some embodiments, a sugar unit is of the structure

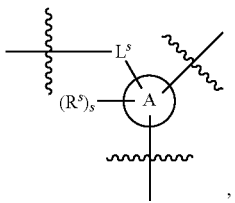

, wherein each variable is independently as described in the present disclosure. In some embodiments, a nucleoside unit is of the structure

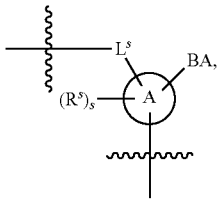

, wherein each variable is independently as described in the present disclosure. In some embodiments, a nucleotide unit, e.g., $Nu^M$, $Nu^O$, etc., is of the structure

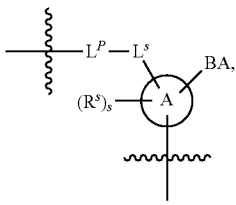

, wherein each variable is independently as described in the present disclosure. In some embodiments, for $Nu^O$, $L^P$ is a natural phosphate linkage, and $L^s$ is —$C(R^{5s})_2$— as described in the present disclosure.

In some embodiments, $L^s$ is —$C(R^{5s})_2$—

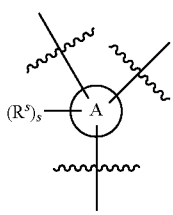

and is as described in the present disclosure. In some embodiments,

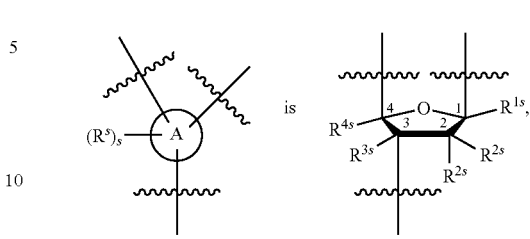

BA is connected at $C_1$, and each of $R^{1s}$, $R^{2s}$, $R^{3s}$, $R^{4s}$ and $R^{5s}$ is independently as described in the present disclosure. In some embodiments,

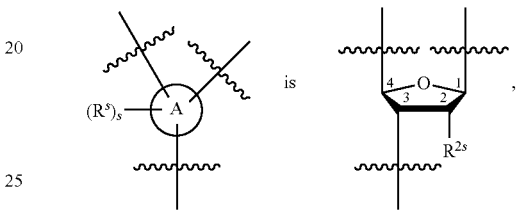

wherein $R^{2s}$ is as described in the present disclosure. In some embodiments,

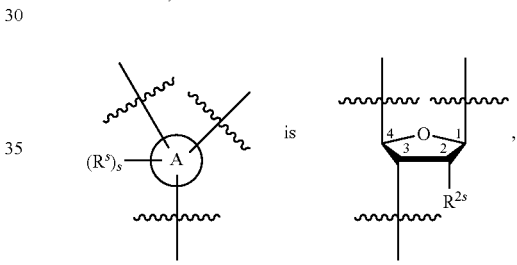

wherein $R^{2s}$ is not —OH. In some embodiments,

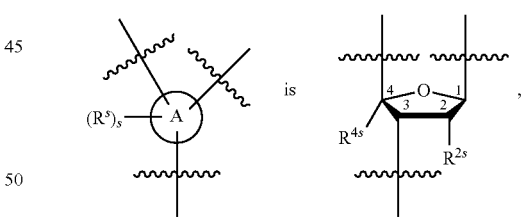

wherein $R^{2s}$ and $R^{4s}$ are R, and the two R groups are taken together with their intervening atoms to form an optionally substituted ring. In some embodiments,

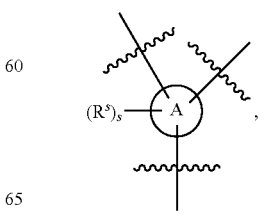

, or Ring A, is optionally substituted

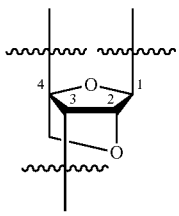

In some embodiments,

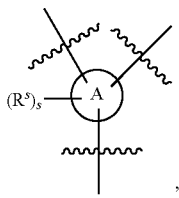

or Ring A, is

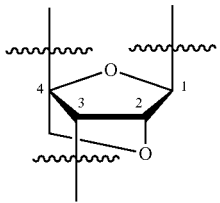

In some embodiments,

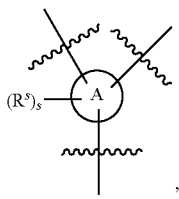

or Ring A, is

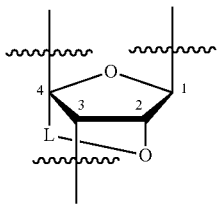

In some embodiments, each of $R^{1s}$, $R^{2s}$, $R^{3s}$, $R^{4s}$, and $R^{5s}$ is independently $R^s$, wherein $R^s$ is as described in the present disclosure.

In some embodiments, $R^{1s}$ is $R^s$ wherein $R^s$ is as described in the present disclosure. In some embodiments, $R^{1s}$ is at 1'-position (BA is at 1'-position). In some embodiments, $R^{1s}$ is —H. In some embodiments, $R^{1s}$ is —F. In some embodiments, $R^{1s}$ is —Cl. In some embodiments, $R^s$ is —Br. In some embodiments, $R^s$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is L-L-N(R')$_2$. In some embodiments, $R^{1s}$ is —N(R')$_2$. In some embodiments, $R^{1s}$ is —OR', wherein R' is optionally substituted C$_{1-6}$ aliphatic. In some embodiments, $R^{1s}$ is —OR', wherein R' is optionally substituted C$_{1-6}$ alkyl. In some embodiments, $R^{1s}$ is —OMe. In some embodiments, $R^{1s}$ is -MOE. In some embodiments, $R^{1s}$ is hydrogen. In some embodiments, $R^s$ at one 1'-position is hydrogen, and $R^s$ at the other 1'-position is not hydrogen as described herein. In some embodiments, $R^s$ at both 1'-positions are hydrogen. In some embodiments, $R^s$ at one 1'-position is hydrogen, and the other 1'-position is connected to an internucleotidic linkage. In some embodiments, $R^{1s}$ is —F. In some embodiments, $R^{1s}$ is —Cl. In some embodiments, $R^{1s}$ is —Br. In some embodiments, $R^{1s}$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1s}$ is -L-N(R')$_2$. In some embodiments, $R^{1s}$ is —N(R')$_2$. In some embodiments, $R^{1s}$ is —OR', wherein R' is optionally substituted C$_{1-6}$ aliphatic. In some embodiments, $R^{1s}$ is —OR', wherein R' is optionally substituted C$_{1-6}$ alkyl. In some embodiments, $R^{1s}$ is —OH. In some embodiments, $R^{1s}$ is —OMe. In some embodiments, $R^{1s}$ is -MOE. In some embodiments, $R^{1s}$ is hydrogen. In some embodiments, one $R^{1s}$ at a 1'-position is hydrogen, and the other $R^{1s}$ at the other 1'-position is not hydrogen as described herein. In some embodiments, $R^{1s}$ at both 1'-positions are hydrogen. In some embodiments, $R^{1s}$ is —O-L$^s$-OR'. In some embodiments, $R^{1s}$ is —O-L$^s$-OR', wherein L$^s$ is optionally substituted C$_{1-6}$ alkylene, and R' is optionally substituted C$_{1-6}$ aliphatic. In some embodiments, $R^{1s}$ is —O-(optionally substituted C$_{1-6}$ alkylene)-OR'. In some embodiments, $R^{1s}$ is —O-(optionally substituted C$_{1-6}$ alkylene)-OR', wherein R' is optionally substituted C$_{1-6}$ alkyl. In some embodiments, $R^{1s}$ is —OCH$_2$CH$_2$OMe.

In some embodiments, $R^{2s}$ is $R^s$ wherein $R^s$ is as described in the present disclosure. In some embodiments, if there are two $R^{2s}$ at the 2'-position, one $R^{2s}$ is —H and the other is not. In some embodiments, $R^{2s}$ is at 2'-position (BA is at 1'-position). In some embodiments, $R^{2s}$ is —H. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is L-L-N(R')$_2$. In some embodiments, $R^{2s}$ is —N(R')$_2$. In some embodiments, $R^{2s}$ is —OR', wherein R' is optionally substituted C$_{1-6}$ aliphatic. In some embodiments, $R^{2s}$ is —OR', wherein R' is optionally substituted C$_{1-6}$ alkyl. In some embodiments, $R^{2s}$ is —OMe. In some embodiments, $R^{2s}$ is -MOE. In some embodiments, $R^{2s}$ is hydrogen. In some embodiments, $R^s$ at one 2'-position is hydrogen, and $R^s$ at the other 2'-position is not hydrogen as described herein. In some embodiments, $R^s$ at both 2'-positions are hydrogen. In some embodiments, $R^s$ at one 2'-position is hydrogen, and the other 2'-position is connected to an internucleotidic linkage. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is -L-N(R')$_2$. In some embodiments, $R^{2s}$ is —N(R')$_2$. In some embodiments, $R^{2s}$ is —OR', wherein R' is optionally substituted $C_{1-6}$ aliphatic. In some embodiments, $R^{2s}$ is —OR', wherein R' is optionally substituted $C_{1-6}$ alkyl. In some embodiments, $R^{2s}$ is —OH. In some embodiments, $R^{2s}$ is —OMe. In some embodiments, $R^{2s}$ is -MOE. In some embodiments, $R^{2s}$ is hydrogen. In some embodiments, one $R^{2s}$ at a 2'-position is hydrogen, and the other $R^{2s}$ at the other 2'-position is not hydrogen as described herein. In some embodiments, $R^{2s}$ at both 2'-positions are hydrogen. In some embodiments, $R^{2s}$ is —O-L$^s$-OR'. In some embodiments, $R^{2s}$ is —O-L$^s$-OR', wherein L$^s$ is optionally substituted $C_{1-6}$ alkylene, and R' is optionally substituted $C_{1-6}$ aliphatic. In some embodiments, $R^{2s}$ is —O-(optionally substituted $C_{1-6}$ alkylene)-OR'. In some embodiments, $R^{2s}$ is —O-(optionally substituted $C_{1-6}$ alkylene)-OR', wherein R' is optionally substituted $C_{1-6}$ alkyl. In some embodiments, $R^{2s}$ is —OCH$_2$CH$_2$OMe.

In some embodiments, $R^{3s}$ is $R^s$ wherein $R^s$ is as described in the present disclosure. In some embodiments, $R^{3s}$ is at 3'-position (BA is at 1'-position). In some embodiments, $R^{3s}$ is —H. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —N$_3$. In some embodiments, $R^{3s}$ is —NO. In some embodiments, $R^{3s}$ is —NO$_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^s$ is —SR'. In some embodiments, $R^{3s}$ is -L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OMe. In some embodiments, $R^{3s}$ is -MOE. In some embodiments, $R^{3s}$ is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —N$_3$. In some embodiments, $R^{3s}$ is —NO. In some embodiments, $R^{3s}$ is —NO$_2$. In some embodiments, $R^{3s}$ is -L-R'. In some embodiments, $R^s$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is L-L-N(R')$_2$. In some embodiments, $R^{3s}$ is —N(R')$_2$. In some embodiments, $R^{3s}$ is —OR', wherein R' is optionally substituted $C_{1-6}$ aliphatic. In some embodiments, $R^{3s}$ is —OR', wherein R' is optionally substituted $C_{1-6}$ alkyl. In some embodiments, $R^{3s}$ is —OH. In some embodiments, $R^{3s}$ is —OMe. In some embodiments, $R^{3s}$ is -MOE. In some embodiments, $R^{3s}$ is hydrogen.

In some embodiments, $R^{4s}$ is $R^s$ wherein $R^s$ is as described in the present disclosure. In some embodiments, $R^{4s}$ is at 4'-position (BA is at 1'-position). In some embodiments, $R^{4s}$ is —H. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —N$_3$. In some embodiments, $R^{4s}$ is —NO. In some embodiments, $R^{4s}$ is —NO$_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is -L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OMe. In some embodiments, $R^{4s}$ is -MOE. In some embodiments, $R^{4s}$ is hydrogen. In some embodiments, $R^s$ at one 4'-position is hydrogen, and $R^s$ at the other 4'-position is not hydrogen as described herein. In some embodiments, $R^s$ at both 4'-positions are hydrogen. In some embodiments, $R^s$ at one 4'-position is hydrogen, and the other 4'-position is connected to an internucleotidic linkage. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —N$_3$. In some embodiments, $R^{4s}$ is —NO. In some embodiments, $R^{4s}$ is —NO$_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is L-L-N(R')$_2$. In some embodiments, $R^{4s}$ is —N(R')$_2$. In some embodiments, $R^{4s}$ is —OR', wherein R' is optionally substituted $C_{1-6}$ aliphatic. In some embodiments, $R^{4s}$ is —OR', wherein R' is optionally substituted $C_{1-6}$ alkyl. In some embodiments, $R^{4s}$ is —OH. In some embodiments, $R^{4s}$ is —OMe. In some embodiments, $R^{4s}$ is -MOE. In some embodiments, $R^{4s}$ is hydrogen.

In some embodiments, $R^{5s}$ is $R^s$ wherein $R^s$ is as described in the present disclosure. In some embodiments, $R^{5s}$ is R' wherein R' is as described in the present disclosure. In some embodiments, $R^{5s}$ is —H. In some embodiments, two or more $R^{5s}$ are connected to the same carbon atom, and at least one is not —H. In some embodiments, $R^{5s}$ is not —H. In some embodiments, $R^{5s}$ is —F. In some embodiments, $R^{5s}$ is —Cl. In some embodiments, $R^{5s}$ is —Br. In some embodiments, $R^{5s}$ is —I. In some embodiments, $R^{5s}$ is —CN. In some embodiments, $R^{5s}$ is —N$_3$. In some embodiments, $R^{5s}$ is —NO. In some embodiments, $R^{5s}$ is —NO$_2$. In some embodiments, $R^{5s}$ is -L-R'. In some embodiments, $R^{5s}$ is —R'. In some embodiments, $R^{5s}$ is -L-OR'. In some embodiments, $R^{5s}$ is —OR'. In some embodiments, $R^{5s}$ is -L-SR'. In some embodiments, $R^{5s}$ is —SR'. In some embodiments, $R^{5s}$ is L-L-N(R')$_2$. In some embodiments, $R^{5s}$ is —N(R')$_2$. In some embodiments, $R^{5s}$ is —OR', wherein R' is optionally substituted $C_{1-6}$ aliphatic. In some embodiments, $R^{5s}$ is —OR', wherein R' is optionally substituted $C_{1-6}$ alkyl. In some embodiments, $R^{5s}$ is —OH. In some embodiments, $R^{5s}$ is —OMe. In some embodiments, $R^{5s}$ is -MOE. In some embodiments, $R^{5s}$ is hydrogen.

In some embodiments, $R^{5s}$ is optionally substituted $C_{1-6}$ aliphatic as described in the present disclosure, e.g., $C_{1-6}$ aliphatic embodiments described for R or other variables. In some embodiments, $R^{5s}$ is optionally substituted $C_{1-6}$ alkyl. In some embodiments, $R^{5s}$ is methyl. In some embodiments, $R^{5s}$ is ethyl.

In some embodiments, $R^{5s}$ is a protected hydroxyl group suitable for oligonucleotide synthesis. In some embodiments, $R^{5s}$ is —OR', wherein R' is optionally substituted $C_{1-6}$ aliphatic. In some embodiments, $R^{5s}$ is DMTrO-. Example protecting groups are widely known for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, protecting groups of each of which are hereby incorporated by reference.

In some embodiments, two or more of $R^{1s}$, $R^{2s}$, $R^{3s}$, $R^{4s}$, and $R^{5s}$ are R and can be taken together with intervening atom(s) to form a ring as described in the present disclosure. In some embodiments, $R^{2s}$ and $R^{4s}$ are R taken together to form a ring, and a sugar moiety can be a bicyclic sugar moiety, e.g., a LNA sugar moiety.

In some embodiments, $L^s$ is —C($R^{5s}$)$_2$—, wherein each $R^{5s}$ is independently as described in the present disclosure. In some embodiments, one of $R^{5s}$ is H and the other is not H. In some embodiments, none of $R^{5s}$ is H. In some embodiments, $L^s$ is —CHR$^{5s}$—, wherein each $R^{5s}$ is independently as described in the present disclosure. In some embodiments, —C($R^{5s}$)$_2$ is 5'-C, optionally substituted, of a sugar moiety. In some embodiments, the C of —C($R^{5s}$)$_2$— is connected to linkage phosphorus and a sugar wing moiety. In some embodiments, the C of —C($R^{5s}$)$_2$— is of R configuration. In some embodiments, the C of —C($R^{5s}$)$_2$— is of S configuration. As described in the present disclosure, in some embodiments, $R^{5s}$ is optionally substituted $C_{1-6}$ aliphatic; in some embodiments, $R^{5s}$ is methyl.

In some embodiments, provided compounds comprise one or more bivalent or multivalent optionally substituted rings, e.g., Ring A, As, $A^L$, -Cy-, $Cy^L$, those formed by two or more R groups (R and (combinations of) variables that can be R) taken together, etc. In some embodiments, a ring is a cycloaliphatic, aryl, heteroaryl, or heterocyclyl group as described for R but bivalent or multivalent. As appreciated by those skilled in the art, ring moieties described for one variable, e.g., Ring A, can also be applicable to other variables, e.g., $Cy^L$, if requirements of the other variables, e.g., number of heteroatoms, valence, etc., are satisfied. Example rings are extensively described in the present disclosure.

In some embodiments, a ring, e.g., in Ring A, R, etc. which is optionally substituted, is a 3-20 membered monocyclic, bicyclic or polycyclic ring having 0-10 heteroatoms independently selected from oxygen, nitrogen, sulfur, phosphorus and silicon.

In some embodiments, a ring can be of any size within its range, e.g., 3, 4, 5, 6, 7, 8, 9, 10, 11, 12, 13, 14, 15, 16, 17, 18, 19, or 20-membered.

In some embodiments, a ring is monocyclic. In some embodiments, a ring is saturated and monocyclic. In some embodiments, a ring is monocyclic and partially saturated. In some embodiments, a ring is monocyclic and aromatic.

In some embodiments, a ring is bicyclic. In some embodiments, a ring is polycyclic. In some embodiments, a bicyclic or polycyclic ring comprises two or more monocyclic ring moieties, each of which can be saturated, partially saturated, or aromatic, and each which can contain no or 1-10 heteroatoms. In some embodiments, a bicyclic or polycyclic ring comprises a saturated monocyclic ring. In some embodiments, a bicyclic or polycyclic ring comprises a saturated monocyclic ring containing no heteroatoms. In some embodiments, a bicyclic or polycyclic ring comprises a saturated monocyclic ring comprising one or more heteroatoms. In some embodiments, a bicyclic or polycyclic ring comprises a partially saturated monocyclic ring. In some embodiments, a bicyclic or polycyclic ring comprises a partially saturated monocyclic ring containing no heteroatoms. In some embodiments, a bicyclic or polycyclic ring comprises a partially saturated monocyclic ring comprising one or more heteroatoms. In some embodiments, a bicyclic or polycyclic ring comprises an aromatic monocyclic ring. In some embodiments, a bicyclic or polycyclic ring comprises an aromatic monocyclic ring containing no heteroatoms. In some embodiments, a bicyclic or polycyclic ring comprises an aromatic monocyclic ring comprising one or more heteroatoms. In some embodiments, a bicyclic or polycyclic ring comprises a saturated ring and a partially saturated ring, each of which independently contains one or more heteroatoms. In some embodiments, a bicyclic ring comprises a saturated ring and a partially saturated ring, each of which independently comprises no, or one or more heteroatoms. In some embodiments, a bicyclic ring comprises an aromatic ring and a partially saturated ring, each of which independently comprises no, or one or more heteroatoms. In some embodiments, a polycyclic ring comprises a saturated ring and a partially saturated ring, each of which independently comprises no, or one or more heteroatoms. In some embodiments, a polycyclic ring comprises an aromatic ring and a partially saturated ring, each of which independently comprises no, or one or more heteroatoms. In some embodiments, a polycyclic ring comprises an aromatic ring and a saturated ring, each of which independently comprises no, or one or more heteroatoms. In some embodiments, a polycyclic ring comprises an aromatic ring, a saturated ring, and a partially saturated ring, each of which independently comprises no, or one or more heteroatoms. In some embodiments, a ring comprises at least one heteroatom. In some embodiments, a ring comprises at least one nitrogen atom. In some embodiments, a ring comprises at least one oxygen atom. In some embodiments, a ring comprises at least one sulfur atom.

As appreciated by those skilled in the art in accordance with the present disclosure, a ring is typically optionally substituted. In some embodiments, a ring is unsubstituted. In some embodiments, a ring is substituted. In some embodiments, a ring is substituted on one or more of its carbon atoms. In some embodiments, a ring is substituted on one or more of its heteroatoms. In some embodiments, a ring is substituted on one or more of its carbon atoms, and one or more of its heteroatoms. In some embodiments, two or more substituents can be located on the same ring atom. In some embodiments, all available ring atoms are substituted. In some embodiments, not all available ring atoms are substituted. In some embodiments, in provided structures where rings are indicated to be connected to other structures (e.g., Ring A in

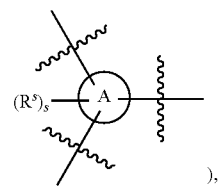

),

"optionally substituted" is to mean that, besides those structures already connected, remaining substitutable ring positions, if any, are optionally substituted.

In some embodiments, a ring is a bivalent or multivalent $C_{3-30}$ cycloaliphatic ring. In some embodiments, a ring is a bivalent or multivalent $C_{3-20}$ cycloaliphatic ring. In some embodiments, a ring is a bivalent or multivalent $C_{3-10}$ cycloaliphatic ring. In some embodiments, a ring is a bivalent or multivalent 3-30 membered saturated or partially unsaturated carbocyclic ring. In some embodiments, a ring is a bivalent or multivalent 3-7 membered saturated or partially unsaturated carbocyclic ring. In some embodiments, a ring is a bivalent or multivalent 3-membered saturated or partially unsaturated carbocyclic ring. In some embodiments, a ring is a bivalent or multivalent 4-membered saturated or partially unsaturated carbocyclic ring. In some embodiments, a ring is a bivalent or multivalent 5-membered saturated or partially unsaturated carbocyclic ring. In some embodiments, a ring is a bivalent or multivalent 6-membered saturated or partially unsaturated carbocyclic ring. In some embodiments, a ring is a bivalent or multivalent 7-membered saturated or partially unsaturated carbocyclic ring. In some embodiments, a ring is a bivalent or multivalent cyclohexyl ring. In some embodiments, a ring is a bivalent or multivalent cyclopentyl ring. In some embodiments, a ring is a bivalent or multivalent cyclobutyl ring. In some embodiments, a ring is a bivalent or multivalent cyclopropyl ring.

In some embodiments, a ring is a bivalent or multivalent $C_{6-30}$ aryl ring. In some embodiments, a ring is a bivalent or multivalent phenyl ring.

In some embodiments, a ring is a bivalent or multivalent 8-10 membered bicyclic saturated, partially unsaturated or aryl ring. In some embodiments, a ring is a bivalent or multivalent 8-10 membered bicyclic saturated ring. In some embodiments, a ring is a bivalent or multivalent 8-10 membered bicyclic partially unsaturated ring. In some embodiments, a ring is a bivalent or multivalent 8-10 membered bicyclic aryl ring. In some embodiments, a ring is a bivalent or multivalent naphthyl ring.

In some embodiments, a ring is a bivalent or multivalent 5-30 membered heteroaryl ring having 1-10 heteroatoms independently selected from oxygen, nitrogen, sulfur, phosphorus and silicon. In some embodiments, a ring is a bivalent or multivalent 5-30 membered heteroaryl ring having 1-10 heteroatoms independently selected from oxygen, nitrogen, and sulfur. In some embodiments, a ring is a bivalent or multivalent 5-30 membered heteroaryl ring having 1-5 heteroatoms independently selected from oxygen, nitrogen, sulfur, phosphorus and silicon. In some embodiments, a ring is a bivalent or multivalent 5-30 membered heteroaryl ring having 1-5 heteroatoms independently selected from oxygen, nitrogen, and sulfur.

In some embodiments, a ring is a bivalent or multivalent 5-6 membered monocyclic heteroaryl ring having 1-4 heteroatoms independently selected from nitrogen, oxygen, and sulfur. In some embodiments, a ring is a bivalent or multivalent 5-6 membered monocyclic heteroaryl ring having 1-3 heteroatoms independently selected from nitrogen, sulfur, and oxygen.

In some embodiments, a ring is a bivalent or multivalent 5-membered monocyclic heteroaryl ring having 1-4 heteroatoms independently selected from nitrogen, oxygen or sulfur. In some embodiments, a ring is a bivalent or multivalent 6-membered monocyclic heteroaryl ring having 1-4 heteroatoms independently selected from nitrogen, oxygen, and sulfur.

In certain embodiments, a ring is a bivalent or multivalent 8-10 membered bicyclic heteroaryl ring having 1-4 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-5 heteroatoms independently selected from nitrogen, oxygen, and sulfur. In certain embodiments, a ring is a bivalent or multivalent 6,6-fused heteroaryl ring having 1-4 heteroatoms independently selected from nitrogen, oxygen, and sulfur.

In some embodiments, a ring is a bivalent or multivalent 3-30 membered heterocyclic ring having 1-10 heteroatoms independently selected from oxygen, nitrogen, sulfur, phosphorus and silicon. In some embodiments, a ring is a bivalent or multivalent 3-7 membered saturated or partially unsaturated heterocyclic ring having 1-3 heteroatoms independently selected from nitrogen, oxygen, and sulfur. In certain embodiments, a ring is a bivalent or multivalent 5-7 membered partially unsaturated monocyclic ring having 1-3 heteroatoms independently selected from nitrogen, oxygen, and sulfur. In certain embodiments, a ring is a bivalent or multivalent 5-6 membered partially unsaturated monocyclic ring having 1-3 heteroatoms independently selected from nitrogen, oxygen, and sulfur. In certain embodiments, a ring is a bivalent or multivalent 5-membered partially unsaturated monocyclic ring having 1-3 heteroatoms independently selected from nitrogen, oxygen, and sulfur. In certain embodiments, a ring is a bivalent or multivalent 6-membered partially unsaturated monocyclic ring having 1-3 heteroatoms independently selected from nitrogen, oxygen, and sulfur. In certain embodiments, a ring is a bivalent or multivalent 7-membered partially unsaturated monocyclic ring having 1-3 heteroatoms independently selected from nitrogen, oxygen, and sulfur. In some embodiments, a ring is a bivalent or multivalent 3-membered heterocyclic ring having one heteroatom selected from nitrogen, oxygen or sulfur. In some embodiments, a ring is a bivalent or multivalent 4-membered heterocyclic ring having 1-3 heteroatoms independently selected from nitrogen, oxygen, and sulfur. In some embodiments, a ring is a bivalent or multivalent 5-membered heterocyclic ring having 1-3 heteroatoms independently selected from nitrogen, oxygen, and sulfur. In some embodiments, a ring is a bivalent or multivalent 6-membered heterocyclic ring having 1-3 heteroatoms independently selected from nitrogen, oxygen, and sulfur. In some embodiments, a ring is a bivalent or multivalent 7-membered heterocyclic ring having 1-3 heteroatoms independently selected from nitrogen, oxygen, and sulfur.

In some embodiments, a ring is a bivalent or multivalent 7-10 membered bicyclic saturated or partially unsaturated heterocyclic ring having 1-5 heteroatoms independently selected from nitrogen, oxygen, and sulfur. In some embodiments, a ring is a bivalent or multivalent 8-10 membered bicyclic heteroaryl ring having 1-5 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In certain embodiments, a ring is a bivalent or multivalent 6,6-fused heteroaryl ring having 1-5 heteroatoms independently selected from nitrogen, oxygen, and sulfur.

In some embodiments, a ring formed by two or more groups taken together, which is typically optionally substituted, is a monocyclic saturated 5-7 membered ring having no additional heteroatoms in addition to intervening heteroatoms, if any. In some embodiments, a ring formed by two or more groups taken together is a monocyclic saturated 5-membered ring having no additional heteroatoms in addition to intervening heteroatoms, if any. In some embodiments, a ring formed by two or more groups taken together is a monocyclic saturated 6-membered ring having no additional heteroatoms in addition to intervening heteroatoms, if any. In some embodiments, a ring formed by two or more groups taken together is a monocyclic saturated 7-membered ring having no additional heteroatoms in addition to intervening heteroatoms, if any.

In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, and sulfur. In some embodiments, a ring formed by two or more groups taken together is a bicyclic and saturated 8-10 membered bicyclic ring having no additional heteroatoms in addition to intervening heteroatoms, if any. In some embodiments, a ring formed by two or more groups taken together is a bicyclic and saturated 8-membered bicyclic ring having no additional heteroatoms in addition to intervening heteroatoms, if any. In some embodiments, a ring formed by two or more groups taken together is a bicyclic and saturated 9-membered bicyclic ring having no additional heteroatoms in addition to intervening heteroatoms, if any. In some embodiments, a ring formed by two or more groups taken together is a bicyclic and saturated 10-membered bicyclic ring having no additional heteroatoms in addition to intervening heteroatoms, if any. In some embodiments, a ring formed by two or more groups taken together is bicyclic and comprises a 5-membered ring fused to a 5-membered ring. In some embodiments, a ring formed by two or more groups taken together is bicyclic and comprises a 5-membered ring fused to a 6-membered ring. In some embodiments, the 5-membered ring comprises one or more intervening nitrogen, phosphorus and oxygen atoms as ring atoms. In some embodiments, a ring formed by two or more groups taken together comprises a ring system having the backbone structure of

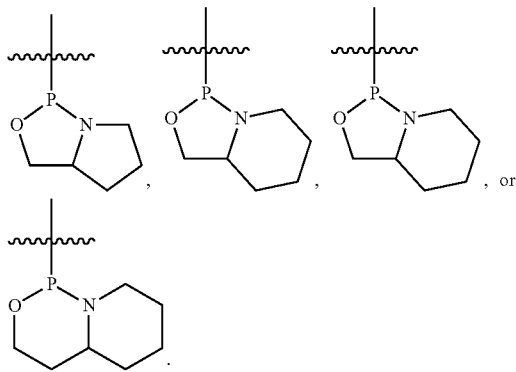

In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, and sulfur.

In some embodiments, a ring formed by two or more groups taken together is monocyclic, bicyclic or polycyclic and comprises a 5-10 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-9 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-8 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-7 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-6 membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 6-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 7-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 8-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 9-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 10-membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 6-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 7-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 8-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 9-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 10-membered ring whose ring atoms consist of carbon atoms and the intervening nitrogen, phosphorus and oxygen atoms.

In some embodiments, rings described herein are unsubstituted. In some embodiments, rings described herein are substituted. In some embodiments, substituents are selected from those described in example compounds provided in the present disclosure.

As described herein, each $L^P$ is independently an internucleotidic linkage as described in the present disclosure, e.g., a natural phosphate linkage, a phosphorothioate diester linkage, a modified internucleotidic linkage, a chiral internucleotidic linkage, etc.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is —$(CH_2)_2CN$.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

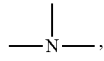

—N=, ≡N, —S—, —S(O)—, —S(O)₂—, —O—, =O,

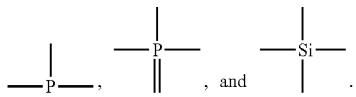, and

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, $P^L$ is P(=W). In some embodiments, $P^L$ is P. In some embodiments, $P^L$ is P→B(R')$_3$. In some embodiments, p of $P^L$ is chiral. In some embodiments, p of $P^L$ is Rp. In some embodiments, P of $P^L$ is Sp. In some embodiments, a linkage of formula I is a phosphate linkage or a salt form thereof. In some embodiments, a linkage of formula I is a phosphorothioate linkage or a salt form thereof. In some embodiments, $P^L$ is P*(=W), wherein P* is a chiral linkage phosphorus. In some embodiments, $P^L$ is P*(=O), wherein P* is a chiral linkage phosphorus.

In some embodiments, W is O. In some embodiments, W is S. In some embodiments, W is Se.

In some embodiments, R' is —R, —C(O)R, —CO$_2$R, or —SO$_2$R, wherein R is as described in the present disclosure.

In some embodiments, R' is —R, wherein R is as defined and described above and herein. In some embodiments, R' is hydrogen.

In some embodiments, R' is —C(O)R, wherein R is as described in the present disclosure. In some embodiments, R' is —CO$_2$R, wherein R is as described in the present disclosure. In some embodiments, R' is —SO$_2$R, wherein R is as described in the present disclosure.

In some embodiments, two R' on the same nitrogen are taken together with their intervening atoms to form an optionally substituted heterocyclic or heteroaryl ring. In some embodiments, two R' on the same carbon are taken together with their intervening atoms to form an optionally substituted aryl, carbocyclic, heterocyclic, or heteroaryl ring.

In some embodiments, -Cy- is an optionally substituted bivalent ring selected from phenylene, carbocyclylene, arylene, heteroarylene, and heterocyclylene.

In some embodiments, -Cy- is optionally substituted phenylene. In some embodiments, -Cy- is optionally substituted carbocyclylene. In some embodiments, -Cy- is optionally substituted arylene. In some embodiments, -Cy- is optionally substituted heteroarylene. In some embodiments, -Cy- is optionally substituted heterocyclylene.

In some embodiments, each of X, Y and Z is independently —O—, —S—, —N(-L-R$^1$)—, or L, wherein each of L and R$^1$ is independently as defined above and described below.

In some embodiments, X is —O—. In some embodiments, X is —S—. In some embodiments, X is —O— or —S—. In some embodiments, a C9orf72 oligonucleotide comprises at least one internucleotidic linkage of Formula I wherein X is —O—. In some embodiments, a C9orf72 oligonucleotide comprises at least one internucleotidic linkage of Formula I wherein X is —S—. In some embodiments, a C9orf72 oligonucleotide comprises at least one internucleotidic linkage of Formula I wherein X is —O—, and at least one internucleotidic linkage of Formula I wherein X is —S—. In some embodiments, a C9orf72 oligonucleotide comprises at least one internucleotidic linkage of Formula I wherein X is —O—, and at least one internucleotidic linkage of Formula I wherein X is —S—, and at least one internucleotidic linkage of Formula I wherein L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, X is —N(-L-R')—. In some embodiments, X is —N(R')—. In some embodiments, X is —N(R')—. In some embodiments, X is —N(R)—. In some embodiments, X is —NH—.

In some embodiments, X is L. In some embodiments, X is a covalent bond. In some embodiments, X is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, X is an optionally substituted C$_1$-C$_{10}$ alkylene or C$_1$-C$_{10}$ alkenylene. In some embodiments, X is methylene.

In some embodiments, Y is —O—. In some embodiments, Y is —S—.

In some embodiments, Y is —N(-L-R')—. In some embodiments, Y is —N(R')—. In some embodiments, Y is —N(R')—. In some embodiments, Y is —N(R)—. In some embodiments, Y is —NH—.

In some embodiments, Y is L. In some embodiments, Y is a covalent bond. In some embodiments, Y is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Y is an optionally substituted C$_1$-C$_{10}$ alkylene or C$_1$-C$_{10}$ alkenylene. In some embodiments, Y is methylene.

In some embodiments, Z is —O—. In some embodiments, Z is —S—.

In some embodiments, Z is —N(-L-R')—. In some embodiments, Z is —N(R')—. In some embodiments, Z is —N(R')—. In some embodiments, Z is —N(R)—. In some embodiments, Z is —NH—.

In some embodiments, Z is L. In some embodiments, Z is a covalent bond. In some embodiments, Z is or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, Z is an optionally substituted C$_1$-C$_{10}$ alkylene or C$_1$-C$_{10}$ alkenylene. In some embodiments, Z is methylene.

In some embodiments, L is a covalent bond or an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, L is a covalent bond. In some embodiments, L is an optionally substituted, linear or branched C$_1$-C$_{10}$ alkylene, wherein one or more methylene units of L are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—.

In some embodiments, R$^1$ is halogen, R, or an optionally substituted C$_1$-C$_{50}$ aliphatic wherein one or more methylene units are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently described in the present disclosure. In some embodiments, R$^1$ is halogen, R, or an optionally substituted C$_1$-C$_{10}$ aliphatic wherein one or more methylene units are optionally and independently replaced by an optionally substituted C$_1$-C$_6$ alkylene, C$_1$-C$_6$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—, wherein each variable is independently described in the present disclosure.

In some embodiments, R$^1$ is hydrogen. In some embodiments, R$^1$ is halogen. In some embodiments, R$^1$ is —F. In some embodiments, $R^1$ is —Cl. In some embodiments, $R^1$ is —Br. In some embodiments, $R^1$ is —I.

In some embodiments, $R^1$ is R wherein R is as described in the present disclosure.

In some embodiments, $R^1$ is an optionally substituted group selected from $C_1$-$C_{50}$ aliphatic, phenyl, carbocyclyl, aryl, heteroaryl, and heterocyclyl.

In some embodiments, $R^1$ is an optionally substituted $C_1$-$C_{50}$ aliphatic. In some embodiments, $R^1$ is an optionally substituted $C_1$-$C_{10}$ aliphatic. In some embodiments, $R^1$ is an optionally substituted $C_1$-$C_6$ aliphatic. In some embodiments, $R^1$ is an optionally substituted $C_1$-$C_6$ alkyl. In some embodiments, $R^1$ is optionally substituted, linear or branched hexyl. In some embodiments, $R^1$ is optionally substituted, linear or branched pentyl. In some embodiments, $R^1$ is optionally substituted, linear or branched butyl. In some embodiments, $R^1$ is optionally substituted, linear or branched propyl. In some embodiments, $R^1$ is optionally substituted ethyl. In some embodiments, $R^1$ is optionally substituted methyl.

In some embodiments, $R^1$ is optionally substituted phenyl. In some embodiments, $R^1$ is substituted phenyl. In some embodiments, $R^1$ is phenyl.

In some embodiments, $R^1$ is optionally substituted carbocyclyl. In some embodiments, $R^1$ is optionally substituted $C_3$-$C_{10}$ carbocyclyl. In some embodiments, $R^1$ is optionally substituted monocyclic carbocyclyl. In some embodiments, $R^1$ is optionally substituted cycloheptyl. In some embodiments, R' is optionally substituted cyclohexyl. In some embodiments, $R^1$ is optionally substituted cyclopentyl. In some embodiments, $R^1$ is optionally substituted cyclobutyl. In some embodiments, $R^1$ is an optionally substituted cyclopropyl. In some embodiments, $R^1$ is optionally substituted bicyclic carbocyclyl.

In some embodiments, $R^1$ is an optionally substituted aryl. In some embodiments, $R^1$ is an optionally substituted bicyclic aryl ring.

In some embodiments, $R^1$ is an optionally substituted heteroaryl. In some embodiments, $R^1$ is an optionally substituted 5-6 membered monocyclic heteroaryl ring having 1-3 heteroatoms independently selected from nitrogen, sulfur, and oxygen. In some embodiments, $R^1$ is a substituted 5-6 membered monocyclic heteroaryl ring having 1-3 heteroatoms independently selected from nitrogen, oxygen, and sulfur. In some embodiments, $R^1$ is an unsubstituted 5-6 membered monocyclic heteroaryl ring having 1-3 heteroatoms independently selected from nitrogen, sulfur, and oxygen. In certain embodiments, $R^1$ is an optionally substituted 8-10 membered bicyclic heteroaryl ring having 1-4 heteroatoms independently selected from nitrogen, oxygen, and sulfur.

In some embodiments, $R^1$ is an optionally substituted heterocyclyl. In some embodiments, $R^1$ is an optionally substituted 3-7 membered saturated or partially unsaturated heterocyclic ring having 1-2 heteroatoms independently selected from nitrogen, oxygen, and sulfur. In some embodiments, $R^1$ is a substituted 3-7 membered saturated or partially unsaturated heterocyclic ring having 1-2 heteroatoms independently selected from nitrogen, oxygen, and sulfur. In some embodiments, $R^1$ is an unsubstituted 3-7 membered saturated or partially unsaturated heterocyclic ring having 1-2 heteroatoms independently selected from nitrogen, oxygen, and sulfur.

In certain embodiments, $R^1$ is an optionally substituted 5-6 membered partially unsaturated monocyclic ring having 1-2 heteroatoms independently selected from nitrogen, oxygen, and sulfur. In certain embodiments, $R^1$ is an optionally substituted tetrahydropyridinyl, dihydrothiazolyl, dihydrooxazolyl, or oxazolinyl group.

In some embodiments, $R^1$ is an optionally substituted 8-10 membered bicyclic saturated or partially unsaturated heterocyclic ring having 1-4 heteroatoms independently selected from nitrogen, oxygen, and sulfur. In some embodiments, $R^1$ is an optionally substituted indolinyl. In some embodiments, $R^1$ is an optionally substituted isoindolinyl. In some embodiments, $R^1$ is an optionally substituted 1, 2, 3, 4-tetrahydroquinoline. In some embodiments, R' is an optionally substituted 1, 2, 3, 4-tetrahydroisoquinoline.

Ring $A^L$ can be either be monovalent, bivalent or polyvalent. In some embodiments, Ring $A^L$ is monovalent (e.g., when g is 0 and no substitution). In some embodiments, Ring $A^L$ is bivalent. In some embodiments, Ring $A^L$ is polyvalent. In some embodiments, Ring $A^L$ is bivalent and is -Cy-. In some embodiments, Ring $A^L$ is an optionally substituted bivalent triazole ring. In some embodiments, Ring $A^L$ is trivalent and is $Cy^L$. In some embodiments, Ring $A^L$ is tetravalent and is $Cy^L$. In some embodiments, Ring $A^L$ is optionally substituted

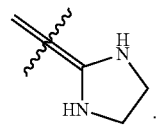 [SMILES: *=C1NCCN1]

In some embodiments, —X-L-R' is optionally substituted alkynyl. In some embodiments, —X-L-$R^1$ is —C≡CH. In some embodiments, an alkynyl group, e.g., —C≡CH, can react with a number of reagents through various reactions to provide further modifications. For example, in some embodiments, an alkynyl group can react with azides through click chemistry. In some embodiments, an azide has the structure of $R^1$—$N_3$.

In some embodiments, g is 0-20. In some embodiments, g is 1-20. In some embodiments, g is 1-5. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In some embodiments, g is 11. In some embodiments, g is 12. In some embodiments, g is 13. In some embodiments, g is 14. In some embodiments, g is 15. In some embodiments, g is 16. In some embodiments, g is 17. In some embodiments, g is 18. In some embodiments, g is 19. In some embodiments, g is 20.

In some embodiments,

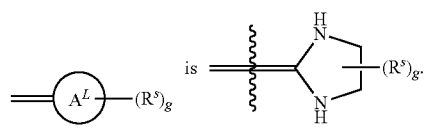

In some embodiments,

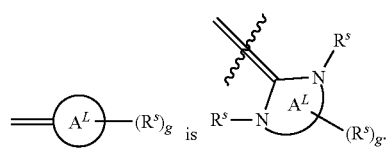

In some embodiments,

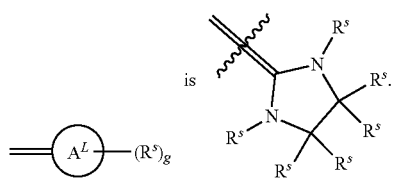

is

In some embodiments, the present disclosure provides multimers of oligonucleotides. In some embodiments, at least one of the monomer is an oligonucleotide. In some embodiments, a multimer is a multimer of the same oligonucleotides. In some embodiments, a multimer is a multimer of structurally different oligonucleotides. In some embodiments, each oligonucleotide of a multimer performs its functions independently through its own pathways, e.g., RNA interference (RNAi), RNase H dependent, etc.

In some embodiments, the present disclosure provides salts of oligonucleotides, and pharmaceutical compositions thereof. In some embodiments, a salt is a pharmaceutically acceptable salt. In some embodiments, each hydrogen ion that may be donated to a base (e.g., under conditions of an aqueous solution, a pharmaceutical composition, etc.) is replaced by a non-H$^+$ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. In some embodiments, a provided salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate diester linkage (acid form —O—P(O)(SH)—O—), if any, exists as its sodium salt form (—O—P(O)(SNa)—O—).

In some embodiments, a provided compound, e.g., a provided oligonucleotide, has a purity of 60%-100%. In some embodiments, a purity is at least 60%, 65%, 70%, 75%, 80%, 85%, 90%, 91%, 92%, 93%, 94%, 95%, 96%, 97%, 98%, or 99%. In some embodiments, a purity is at least 60%. In some embodiments, a purity is at least 70%. In some embodiments, a purity is at least 80%. In some embodiments, a purity is at least 85%. In some embodiments, a purity is at least 90%. In some embodiments, a purity is at least 91%. In some embodiments, a purity is at least 92%. In some embodiments, a purity is at least 93%. In some embodiments, a purity is at least 94%. In some embodiments, a purity is at least 95%. In some embodiments, a purity is at least 96%. In some embodiments, a purity is at least 97%. In some embodiments, a purity is at least 98%. In some embodiments, a purity is at least 99%. In some embodiments, a purity is at least 99.5%.

Various linker, carbohydrate moieties and targeting moieties, including many known in the art, can be utilized in accordance with the present disclosure. In some embodiments, a carbohydrate moiety is a targeting moiety. In some embodiments, a targeting moiety is a carbohydrate moiety.

In some embodiments, a provided oligonucleotide is an altmer. In some embodiments, a provided oligonucleotide is a P-modification altmer. In some embodiments, a provided oligonucleotide is a stereoaltmer.

In some embodiments, a provided oligonucleotide is a blockmer. In some embodiments, a provided oligonucleotide is a P-modification blockmer. In some embodiments, a provided oligonucleotide is a stereoblockmer.

In some embodiments, a provided oligonucleotide having an asymmetric format is a gapmer.

In some embodiments, a provided oligonucleotide having an asymmetric format is a skipmer.

In some embodiments, a provided oligonucleotide comprises one or more optionally substituted nucleobases. In some embodiments, a provided oligonucleotide comprises one or more optionally substituted natural nucleobases. In some embodiments, a provided oligonucleotide comprises one or more optionally substituted modified nucleobases. In some embodiments, a provided oligonucleotide comprises one or more 5-methylcytidine; 5-hydroxymethylcytidine, 5-formylcytosine, or 5-carboxylcytosine. In some embodiments, a provided oligonucleotide comprises one or more 5-methylcytidine.

In some embodiments, each nucleobase of a provided oligonucleotide is independently an optionally substituted or protected nucleobase of adenine, cytosine, guanosine, thymine, or uracil. In some embodiments, each BA is independently an optionally substituted or protected nucleobase of adenine, cytosine, guanosine, thymine, or uracil. As appreciated by those skilled in the art, various protected nucleobases, including those widely known in the art, for example, those used in oligonucleotide preparation (e.g., protected nucleobases of WO/2010/064146, WO/2011/005761, WO/2013/012758, WO/2014/010250, US2013/0178612, WO/2014/012081, WO/2015/107425, WO2017/015555, and WO2017/062862, protected nucleobases of each of which are incorporated herein by reference), and can be utilized in accordance with the present disclosure.

In some embodiments, a provided oligonucleotide, e.g., an oligonucleotide having an asymmetric format is single-stranded oligonucleotide. In some embodiments, a provided single-stranded oligonucleotide further comprises one or more additional strands which are partially or completely complementary to the single-stranded oligonucleotide.

In some embodiments, a provided oligonucleotide, e.g., an oligonucleotide having an asymmetric format is a hybridized oligonucleotide strand. In certain embodiments, a provided oligonucleotide is a partially hybridized oligonucleotide strand. In certain embodiments, a provided oligonucleotide is a completely hybridized oligonucleotide strand. In certain embodiments, a provided oligonucleotide is a double-stranded oligonucleotide. In certain embodiments, a provided oligonucleotide is a triple-stranded oligonucleotide (e.g., a triplex).

In some embodiments, a provided oligonucleotide, e.g., an oligonucleotide having an asymmetric format is chimeric. For example, in some embodiments, a provided oligonucleotide (e.g., an oligonucleotide which has a base sequence which comprises, consists of, or comprises a portion of a base sequence of an oligonucleotide disclosed herein) is DNA-RNA chimera, DNA-LNA chimera, a chimera comprising any two or more of DNA, RNA, LNA, 2'-modified sugars, etc.

In some embodiments, an oligonucleotide, e.g., an oligonucleotide having an asymmetric format can comprise a chemical structure described in WO2012/030683.

In some embodiments, a provided oligonucleotide, e.g., an oligonucleotide having an asymmetric format comprises a nucleic acid analog, e.g., GNA, LNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), and Morpholino.

In some embodiments, a provided oligonucleotide is about 2-500 nucleotide units in length. In some embodiments, a provided oligonucleotide is about 5-500 nucleotide units in length. In some embodiments, a provided oligonucleotide is about 10-50 nucleotide units in length. In some embodiments, a provided oligonucleotide is about 15-50 nucleotide units in length. In some embodiments, each nucleotide unit independently comprises a heteroaryl nucleobase unit (e.g., adenine, cytosine, guanosine, thymine, and uracil, each of which is optionally and independently substituted or protected), a sugar unit comprising a 5-10 membered heterocyclyl ring, and an internucleotidic linkage having the structure of formula I, disclosed herein.

In some embodiments, oligonucleotides of an oligonucleotide type characterized by 1) a common base sequence and length, 2) a common pattern of backbone linkages, and 3) a common pattern of backbone chiral centers, have the same chemical structure. For example, they have the same base sequence, the same pattern of nucleoside modifications, the same pattern of backbone linkages (i.e., pattern of internucleotidic linkage types, for example, phosphate, phosphorothioate, etc), the same pattern of backbone chiral centers (i.e. pattern of linkage phosphorus stereochemistry (Rp/Sp)), and the same pattern of backbone phosphorus modifications (e.g., pattern of "—XLR$^1$" groups in Formula I, disclosed herein).

In some embodiments, provided oligonucleotides, e.g., an oligonucleotide having an asymmetric format can direct a decrease in the expression, level and/or activity of a target gene or its gene product. In some embodiments, provided oligonucleotides can direct a decrease in the expression, level and/or activity of a target gene or its gene product and has a base sequence which consists of, comprises, or comprises a portion (e.g., a span of 10, 11, 12, 13, 14, 15, 16, 17, 18, 19 or more contiguous bases) of the base sequence of any oligonucleotide disclosed herein, and the oligonucleotide comprises at least one non-naturally-occurring modification of a base, sugar and/or internucleotidic linkage.

In some embodiments, a provided composition comprises an oligonucleotide. In some embodiments, a provided oligonucleotide, e.g., an oligonucleotide having an asymmetric format comprises one or more carbohydrate moieties. In some embodiments, a carbohydrate moiety is attached to an oligonucleotide chain. In some embodiments, a provided oligonucleotide comprises one or more targeting moieties. Non-limiting examples of additional chemical moieties which can be conjugated to an oligonucleotide are shown in Example 1.

In some embodiments, provided oligonucleotides can direct a decrease in the expression, level and/or activity of a target gene or its gene product. In some embodiments, provided oligonucleotides can direct a decrease in the expression, level and/or activity of a target gene or its gene product via RNase H-mediated knockdown. In some embodiments, provided oligonucleotides can direct a decrease in the expression, level and/or activity of a target gene or its gene product by sterically blocking translation after binding to a target gene mRNA, and/or by altering or interfering with mRNA splicing. In some embodiments, a target gene comprises a hexanucleotide repeat expansion.

In some embodiments, an oligonucleotide, e.g., an oligonucleotide having an asymmetric format is an antisense transcript specific inhibitor or an agent capable of specifically inhibiting the expression of antisense transcript or gene and/or its expression product or gene product. For example, oligonucleotides include nucleic acids (including antisense compounds), including but not limited to antisense oligonucleotides (ASOs), oligonucleotides, double- and single-stranded siRNAs; and oligonucleotide can be co-administered or be used as part of a treatment regiment along with aptamers, antibodies, peptides, small molecules, and/or other agents capable of inhibiting the expression of antisense transcript or gene and/or its expression product or gene product, or a gene or gene product which increases the expression, activity and/or level of a transcript comprising a repeat expansion or its gene product, or a gene or gene product which is associated with a disorder. In some embodiments, a gene product is a RNA (e.g., a mRNA or pre-mRNA) transcribed from a gene, a protein translated from a RNA transcript, or a focus. A protein translated from a RNA transcript includes any such protein, including but not limited to, or a dipeptide repeat containing protein. A focus is a complex comprising, for example, a transcript or a portion thereof, including but not limited to, one comprising a hexanucleotide repeat expansion-containing region, complexed with one or more RNA-binding proteins. In some embodiments, an intron comprising a hexanucleotide repeat expansion is spliced from a pre-mRNA, and this is bound by various RNA-binding proteins, producing a focus (plural: foci), wherein the RNA-binding proteins are sequestered from their normal function(s).

In some embodiments, a provided oligonucleotide, e.g., an oligonucleotide having an asymmetric format has a base sequence (or a portion thereof), pattern of chemical modification (or a portion thereof), structural element or a portion thereof, or a format or portion thereof described herein.

In some embodiments, a provided oligonucleotide, e.g., an oligonucleotide having an asymmetric format is capable of directing a decrease in the expression, level and/or activity of a target gene or its gene product has a base sequence (or a portion thereof), pattern of chemical modification (or a portion thereof), structural element or a portion thereof, or a format or portion thereof described herein. In some embodiments, a provided oligonucleotide capable of directing a decrease in the expression, level and/or activity of a target gene or its gene product has the base sequence (or a portion thereof), pattern of chemical modification (or a portion thereof), format of any oligonucleotide disclosed herein, e.g., in Table 1A or in the Figures, or otherwise disclosed herein, or a structural element or format or portion thereof described herein.

In some embodiments, a target of an oligonucleotide is a RNA which is not a mRNA.

In some embodiments, compared to a reference condition, provided oligonucleotides and compositions thereof are surprisingly effective. In some embodiments, desired biological effects (e.g., as measured by decreased levels of undesired mRNA, proteins, etc.) can be enhanced by more than 5, 10, 15, 20, 25, 30, 40, 50, or 100 fold. In some embodiments, a change is measured by increase of a desired mRNA level compared to a reference condition. In some embodiments, a change is measured by decrease of an undesired mRNA level compared to a reference condition. In some embodiments, a reference condition is absence of oligonucleotide treatment. In some embodiments, a reference condition is a stereorandom composition of oligonucleotides having the same base sequence and chemical modifications.

In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a first plurality, comprise base modifications, sugar modifications, and/or internucleotidic linkage modifications, wherein the oligonucleotides contain an enriched level of deuterium. In some embodiments, provided oligonucleotides are labeled with deuterium (replacing —$^1$H with —$^2$H) at one or more positions. In some embodiments, one or more $^1$H of an oligonucleotide or any moiety conjugated to the oligonucleotide (e.g., a targeting moiety, etc.) is substituted with $^2$H. Such oligonucleotides can be used in any composition or method described herein.

In some embodiments, the present disclosure provides an oligonucleotide composition comprising a first plurality of oligonucleotides which:

1) have a common base sequence complementary to a target sequence in a transcript; and
2) comprise one or more modified sugar moieties and modified internucleotidic linkages.

In some embodiments, a common base sequence and length may be referred to as a common base sequence. In some embodiments, oligonucleotides having a common base sequence may have the same pattern of nucleoside modifications, e.g., sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkages. A pattern of backbone chiral centers of an oligonucleotide can be designated by a combination of linkage phosphorus stereochemistry (Rp/Sp) from 5' to 3'. As exemplified above, locations of non-chiral linkages may be obtained, for example, from pattern of backbone linkages.

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, at least two couplings of a nucleotide monomer have a diastereoselectivity lower than about 60:40, 70:30, 80:20, 85:15, 90:10, 91:9, 92:8, 97:3, 98:2, or 99:1. In some embodiments, at least three couplings of a nucleotide monomer have a diastereoselectivity lower than about 60:40, 70:30, 80:20, 85:15, 90:10, 91:9, 92:8, 97:3, 98:2, or 99:1. In some embodiments, at least four couplings of a nucleotide monomer have a diastereoselectivity lower than about 60:40, 70:30, 80:20, 85:15, 90:10, 91:9, 92:8, 97:3, 98:2, or 99:1. In some embodiments, at least five couplings of a nucleotide monomer have a diastereoselectivity lower than about 60:40, 70:30, 80:20, 85:15, 90:10, 91:9, 92:8, 97:3, 98:2, or 99:1. In some embodiments, each coupling of a nucleotide monomer independently has a diastereoselectivity lower than about 60:40, 70:30, 80:20, 85:15, 90:10, 91:9, 92:8, 97:3, 98:2, or 99:1. In some embodiments, in a stereorandom or racemic preparations, at least one internucleotidic linkage has a diastereoselectivity lower than about 60:40, 70:30, 80:20, 85:15, 90:10, 91:9, 92:8, 97:3, 98:2, or 99:1. In some embodiments, at least two internucleotidic linkages have a diastereoselectivity lower than about 60:40, 70:30, 80:20, 85:15, 90:10, 91:9, 92:8, 97:3, 98:2, or 99:1. In some embodiments, at least three internucleotidic linkages have a diastereoselectivity lower than about 60:40, 70:30, 80:20, 85:15, 90:10, 91:9, 92:8, 97:3, 98:2, or 99:1. In some embodiments, at least four internucleotidic linkages have a diastereoselectivity lower than about 60:40, 70:30, 80:20, 85:15, 90:10, 91:9, 92:8, 97:3, 98:2, or 99:1. In some embodiments, at least five internucleotidic linkages have a diastereoselectivity lower than about 60:40, 70:30, 80:20, 85:15, 90:10, 91:9, 92:8, 97:3, 98:2, or 99:1. In some embodiments, each internucleotidic linkage independently has a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, a diastereoselectivity is lower than about 92:8. In some embodiments, a diastereoselectivity is lower than about 93:7. In some embodiments, a diastereoselectivity is lower than about 94:6. In some embodiments, a diastereoselectivity is lower than about 95:5. In some embodiments, a diastereoselectivity is lower than about 96:4. In some embodiments, a diastereoselectivity is lower than about 97:3. In some embodiments, a diastereoselectivity is lower than about 98:2. In some embodiments, a diastereoselectivity is lower than about 99:1. In some embodiments, at least one coupling has a diastereoselectivity lower than about 90:10. In some embodiments, at least two couplings have a diastereoselectivity lower than about 90:10. In some embodiments, at least three couplings have a diastereoselectivity lower than about 90:10. In some embodiments, at least four couplings have a diastereoselectivity lower than about 90:10. In some embodiments, at least five couplings have a diastereoselectivity lower than about 90:10. In some embodiments, each coupling independently has a diastereoselectivity lower than about 90:10. In some embodiments, at least one internucleotidic linkage has a diastereoselectivity lower than about 90:10. In some embodiments, at least two internucleotidic linkages have a diastereoselectivity lower than about 90:10. In some embodiments, at least three internucleotidic linkages have a diastereoselectivity lower than about 90:10. In some embodiments, at least four internucleotidic linkages have a diastereoselectivity lower than about 90:10. In some embodiments, at least five internucleotidic linkages have a diastereoselectivity lower than about 90:10. In some embodiments, each internucleotidic linkage independently has a diastereoselectivity lower than about 90:10.

In some embodiments, a chirally controlled internucleotidic linkage, such as those of oligonucleotides of chirally controlled oligonucleotide compositions, has a diastereoselectivity of 90:10 or more. In some embodiments, each chirally controlled internucleotidic linkage, such as those of oligonucleotides of chirally controlled oligonucleotide compositions, has a diastereoselectivity of 90:10 or more. In some embodiments, the selectivity is 91:9 or more. In some embodiments, the selectivity is 92:8 or more. In some embodiments, the selectivity is 97:3 or more. In some embodiments, the selectivity is 94:6 or more. In some embodiments, the selectivity is 95:5 or more. In some embodiments, the selectivity is 96:4 or more. In some embodiments, the selectivity is 97:3 or more. In some embodiments, the selectivity is 98:2 or more. In some embodiments, the selectivity is 99:1 or more.

Confirmation that a stereocontrolled oligonucleotide (e.g., one prepared by a method described herein or in the art) comprises the intended stereocontrolled (chirally controlled) internucleotidic linkage, and/or determination of the diastereoselectivity of an oligonucleotide composition or an internucleotidic linkage, can be performed using a variety of suitable technologies. Useful technologies include, as non-limiting examples: NMR (e.g., 1D (one-dimensional) and/or 2D (two-dimensional) $^1$H-$^{31}$P HETCOR (heteronuclear correlation spectroscopy)), HPLC, RP-HPLC, mass spectrometry, LC-MS, and/or stereospecific nucleases.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage.

In some embodiments, the present disclosure provides chirally controlled (and/or stereochemically pure) oligonucleotide compositions comprising a first plurality of oligonucleotides defined by having:

1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type. In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type that share:

1) a common base sequence and length;
2) a common pattern of backbone linkages; and
3) a common pattern of backbone chiral centers.

In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have identical structures.

In some embodiments, oligonucleotides of an oligonucleotide type have a common pattern of backbone phosphorus modifications and a common pattern of sugar modifications. In some embodiments, oligonucleotides of an oligonucleotide type have a common pattern of backbone phosphorus modifications and a common pattern of base modifications. In some embodiments, oligonucleotides of an oligonucleotide type have a common pattern of backbone phosphorus modifications and a common pattern of nucleoside modifications. In some embodiments, oligonucleotides of an oligonucleotide type are identical.

In some embodiments, an oligonucleotide is a substantially pure preparation of an oligonucleotide type in that oligonucleotides in the composition that are not of the oligonucleotide type are impurities form the preparation process of said oligonucleotide type, in some case, after certain purification procedures.

In some embodiments, oligonucleotides having a common base sequence and length, a common pattern of backbone linkages, and a common pattern of backbone chiral centers have a common pattern of backbone phosphorus modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have a common pattern of backbone phosphorus modifications and a common pattern of sugar modifications. In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers are identical.

In some embodiments, oligonucleotides in provided compositions have a common pattern of backbone phosphorus modifications. In some embodiments, a common base sequence is a base sequence of an oligonucleotide type. In some embodiments, a provided composition is an oligonucleotide composition that is chirally controlled and contains a non-random or controlled level of a first plurality of oligonucleotides of an individual oligonucleotide type, wherein an oligonucleotide type is defined by:

1) base sequence;
2) pattern of backbone linkages;
3) pattern of backbone chiral centers; and
4) pattern of backbone phosphorus modifications.

As noted above and understood in the art, in some embodiments, the base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, a particular oligonucleotide type may be defined by
1A) base identity;
1B) pattern of base modification;
1C) pattern of sugar modification;
2) pattern of backbone linkages;
3) pattern of backbone chiral centers; and
4) pattern of backbone phosphorus modifications,
wherein the oligonucleotide has an asymmetrical format. Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, purity of an oligonucleotide can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed may be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%. In some embodiments, a coupling step has a stereoselectivity of virtually 100% in that all detectable product from the coupling step by an analytical method (e.g., NMR, HPLC, etc) has the intended stereoselectivity.

In some embodiments, provided chirally controlled (and/or stereochemically pure) preparations are of oligonucleotides that include one or more modified backbone linkages, bases, and/or sugars.

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

As a person having ordinary skill in the art understands, provided oligonucleotide compositions and methods have various uses as known by a person having ordinary skill in the art. Methods for assessing provided compositions, and properties and uses thereof, are also widely known and practiced by a person having ordinary skill in the art. Example properties, uses, and/or methods include but are not limited to those described in WO/2014/012081 and WO/2015/107425.

In some embodiments, a provided compound, e.g., oligonucleotide and/or compositions thereof, can modulate activities and/or functions of a target (e.g., a target gene). In some embodiments, a target gene is a gene with respect to which expression and/or activity of one or more gene products (e.g., RNA and/or protein products) are intended to be altered. In many embodiments, a target gene is intended to be inhibited. Thus, when an oligonucleotide as described herein acts on a particular target gene, presence and/or activity of one or more gene products of that gene are altered when the oligonucleotide is present as compared with when it is absent.

In some embodiments, a target is a specific allele (e.g., a pathological allele) with respect to which expression and/or activity of one or more products (e.g., RNA and/or protein products) are intended to be altered. In many embodiments, a target allele is one whose presence and/or expression is associated with (e.g., related to or correlated with) the presence, incidence, and/or severity, of one or more diseases and/or conditions, e.g., a disorder. Alternatively or additionally, in some embodiments, a target allele is one for which alteration of level and/or activity of one or more gene products correlates with improvement (e.g., delay of onset, reduction of severity, responsiveness to other therapy, etc) in one or more aspects of a disease and/or condition. In some such embodiments, oligonucleotides and methods thereof as described herein may preferentially or specifically target the pathological allele relative to the non-pathological allele, e.g., one or more less-associated/unassociated allele(s). In some embodiments, a pathological allele of a target gene comprises a mutation.

In some embodiments, a target sequence is a sequence to which an oligonucleotide as described herein binds. In many embodiments, a target sequence is identical to, or is an exact complement of, a sequence of a provided oligonucleotide, or of consecutive residues therein (e.g., a provided oligonucleotide includes a target-binding sequence that is identical to, or an exact complement of, a target sequence). In some embodiments, a small number of differences/mismatches is tolerated between (a relevant portion of) an oligonucleotide and its target sequence. In many embodiments, a target sequence is present within a target gene. In many embodiments, a target sequence is present within a transcript (e.g., an mRNA and/or a pre-mRNA) produced from a target gene. In some embodiments, a target sequence includes one or more allelic sites (i.e., positions within a target gene at which allelic variation occurs). In some such embodiments, a provided oligonucleotide binds to one allele preferentially or specifically relative to one or more other alleles.

In some embodiments, a target-binding sequence is identical to, or is an exact complement of, a target sequence of one allele. In some embodiments, a target-binding sequence is identical to a target sequence of one allele. In some embodiments, a target-binding sequence is an exact complement of a target sequence of one allele. In some embodiments, a provided oligonucleotide binds preferentially to a disease-associated allele. In some embodiments, a provided oligonucleotide binds preferentially to a disease-associated allele, and comprises a target-binding sequence which is identical to, or is an exact complement of, a target sequence of a disease-associated allele but not other allele(s). For example, in some embodiments, an oligonucleotide (or a target-binding sequence portion thereof) provided herein has a sequence that is identical to, or an exact complement of a particular allelic version of a target sequence. In some embodiments, a target sequence is a sequence of a particular allele. In some embodiments, an oligonucleotide (or a target-binding sequence portion thereof) provided herein has a sequence that is identical to, or an exact complement of an allelic site of a disease-associated allele.

Oligonucleotides, e.g., oligonucleotides having an asymmetric format designed to target any of several different gene targets have been designed, constructed and/or tested.

Oligonucleotides, e.g., those having an asymmetric format designed to target Malat1, C9orf72, PNPLA3, APOC3, and at least four other gene targets (all of which are separate and distinct gene targets, requiring the use of different base sequences for target specificity) have been designed, constructed and/or tested.

Sequences and data pertaining to the activity of various oligonucleotides are disclosed herein.

Oligonucleotides as examples were designed, constructed and/or tested, which target any of various different genes: C9orf72, Malat1, APOC3, and PNPLA3. Various of these oligonucleotides are described herein (e.g., in Table 1), and the activity of many of these oligonucleotides is shown (e.g., in the Examples and elsewhere herein).

As non-limiting examples, certain oligonucleotides targeting Malat1 were designed, constructed and/or tested.

In some embodiments, Malat1 is a gene or gene product thereof (including, but not limited to, a transcript or protein) also known as: MALAT1, HCN, LINC00047, MALAT-1, NCRNA00047, NEAT2, PRO2853, mascRNA, metastasis associated lung adenocarcinoma transcript 1 (non-protein coding), or metastasis associated lung adenocarcinoma transcript 1; or Human Entrez 378938.

An increase in the level, activity, and/or expression of Malat1 or a mutation in Malat1 is associated with various types of cancer, including but not limited to: lung cancer, pancreatic cancer, and cervical cancer.

Oligonucleotides which target Malat1 include, as non-limiting examples: 8097, WV-8098, WV-8099, WV-8100, WV-8101, WV-8102, WV-8109, WV-8552, WV-8553, WV-8554, WV-8555, WV-8556, WV-8557, WV-8570, WV-8571, WV-8572, WV-8573, WV-8574, WV-8575, WV-8576, WV-8577, WV-8578, WV-8579, WV-8580, WV-8581, WV-8582, WV-8583, WV-8584, WV-8585, WV-8586, WV-8587, WV-8588, WV-8589, WV-8590, WV-8591, WV-8592, WV-8593, WV-9058, WV-9059, WV-9060, WV-9061, WV-9696, WV-9697, WV-9698, WV-11114, WV-11533, WV-12110, WV-12111, WV-12112, WV-12113, WV-12114, WV-12503, WV-12504, WV-12505, WV-13303, WV-13304, WV-13809, WV-14087, WV-14349, WV-14556, WV-14557, WV-14558, WV-14559, WV-14560, WV-14561, WV-14562, WV-14563, WV-14564, WV-14733, WV-14734, WV-14735, WV-14736, WV-14737, WV-14771, WV-15310, WV-15311, WV-15312, WV-15313, WV-15314, WV-15315, WV-15316, WV-15317, WV-15318, WV-15319, WV-15320, WV-15321, WV-15351, WV-15352, WV-15353, WV-15354, WV-15355, WV-15356, WV-15357, WV-15358, WV-15359, WV-15360, WV-15361, WV-15362, WV-15363, WV-15364, WV-15365, WV-15562, WV-15563, WV-15863, WV-15864, and WV-15887. These oligonucleotides are described in Table 1B.

As non-limiting examples, oligonucleotides targeting C9orf72 were designed, constructed and/or tested.

In some embodiments, C9orf72 (chromosome 9 open reading frame 72) is a gene or its gene product, also designated as, C9, ALSFTD, FTDALS, FTDALS1, DENNL72; External IDs: MGI: 1920455 HomoloGene: 10137 GeneCards: is also informally designated C9. Orthologs: Species: Human Entrez: 203228; Ensembl: ENSG00000147894; UniProt: Q96LT7; RefSeq (mRNA): NM_145005 NM_001256054 NM_018325; RefSeq (protein): NP_001242983 NP_060795 NP_659442; Location (UCSC): Chr 9: 27.55-27.57 Mb; Species: Mouse Entrez: 73205; Ensembl: ENSMUSG00000028300; UniProt: Q6DFW0; RefSeq (mRNA): NM_001081343; RefSeq (protein): NP_00107481; Location (UCSC): Chr 4: 35.19-35.23 Mb. Nucleotides which encode C9orf72 include, without limitation, GENBANK Accession No. NM_001256054.1; GENBANK Accession No. NT_008413.18; GENBANK Accession No. BQ068108.1; GENBANK Accession No. NM_018325.3; GENBANK Accession No. DN993522.1; GENBANK Accession No. NM_145005.5; GENBANK Accession No. DB079375.1; GENBANK Accession No. BU194591.1; Sequence Identifier 4141_014_A 5; Sequence Identifier 4008_73_A; and GENBANK Accession No. NT_008413.18. C9orf72 reportedly is a 481 amino acid protein with a molecular mass of 54328 Da, which may undergo post-translational modifications of ubiquitination and phosphorylation. The expression levels of C9orf72 reportedly may be highest in the central nervous system and the protein localizes in the cytoplasm of neurons as well as in presynaptic terminals. C9orf72 reportedly plays a role in endosomal and lysosomal trafficking regulation and has been shown to interact with RAB proteins that are involved in autophagy and endocytic transport. C9orf72 reportedly activates RAB5, a GTPase that mediates early endosomal trafficking. Mutations in C9orf72 reportedly have been associated with ALS and FTD. DeJesus-Hernandez et al. 2011 Neuron 72: 245-256; Renton et al. 2011 Neuron 72: 257-268; and Itzcovich et al. 2016. Neurobiol. Aging. Volume 40, Pages 192.e13-192.e15. A C9orf72 mutation, e.g., a hexanucleotide repeat expansion (e.g., (GGGGCC)n) in C9orf72, reportedly may be present in subjects suffering from a neurological disease or disorder.

Various alternative transcripts of C9orf72 include V3, V2 and V1. In some embodiments, transcripts V3 and V1 are mutant transcripts which comprise an expanded hexanucleotide repeat. In some embodiments, V3 is the major C9orf72 transcript comprising a disease-related mutation. In some embodiments, V1 is reportedly transcribed at very low levels (around 1% of the total transcripts) and does not contribute significantly to the levels of transcripts comprising hexanucleotide repeat expansions or to the levels of transcripts detected in assays for V3 transcripts. In some embodiments, V2 transcript is wild-type and does not comprise a disease-associated mutation (e.g., a hexanucleotide repeat expansion).

In some embodiments, a C9orf72-related disorder is a disorder or disease associated with or caused by abnormal expression of the gene, and/or activity and/or level of a gene product (e.g., a transcript, a protein, etc.), including but not limited to a transcript containing a repeat expansion, or a gene product thereof. Examples of-related disorders include: amyotrophic lateral sclerosis (ALS), frontotemporal dementia (FTD), corticobasal degeneration syndrome (CBD), atypical Parkinsonian syndrome, olivopontocerebellar degeneration (OPCD), primary lateral sclerosis (PLS), progressive muscular atrophy (PMA), Huntington's disease (HD) phenocopy, Alzheimer's disease (AD), bipolar disorder, schizophrenia, or other non-motor disorders. Cooper-Knock et al. 2015 Neurother. 12: 326-339; Souza et al. Arq. Neuropsiquiatr. 2015 March; 73(3):246-56.

Oligonucleotides having an asymmetrical format which target C9orf72 include, as non-limiting examples: WV-8005, WV-8006, WV-8007, WV-8008, WV-8009, WV-8010, WV-8011, WV-8012, WV-8115, WV-8116, WV-8118, WV-8119, WV-8120, WV-8121, WV-8123, WV-8124, WV-8125, WV-8126, WV-8127, WV-8128, WV-8129, WV-8314, WV-8452, WV-8453, WV-8454, WV-8455, WV-8456, WV-8466, WV-8467, WV-8468, WV-8469, WV-8470, WV-8471, WV-8472, WV-8473, WV-8474, WV-8475, WV-8476, WV-8547, WV-8548, WV-8549, WV-8550, WV-8551, WV-8568, WV-8569, WV-8594, WV-8595, WV-8691, WV-8692, WV-8693, WV-8694, WV-8695, WV-8696, WV-9062, WV-9063, WV-9285, WV-9286, WV-9380, WV-9381, WV-9394, WV-9395, WV-9396, WV-9397, WV-9398, WV-9399, WV-9421, WV-9421, WV-9486, WV-9487, WV-9488, WV-9489, WV-9490, WV-9491, WV-9492, WV-9494, WV-9505, WV-9506, WV-9507, WV-9508, WV-9509, WV-9510, WV-12581, WV-12582, WV-12583, WV-13305, WV-13306, WV-13307, WV-13308, WV-13309, WV-13310, WV-13311, WV-13312, WV-13313, WV-13803, WV-13804, WV-13805, WV-14552, WV-14553, WV-14554, WV-14555, WV-14758, WV-14772, WV-15049, WV-15050, and WV-15051. These oligonucleotides are described in Table 1A.

As non-limiting examples, oligonucleotides targeting PNPLA3 were designed, constructed and/or tested.

In some embodiments, PNPLA3 is a gene, or a gene product thereof (including, but not limited to, a transcript or protein), also known as: PNPLA3, adiponutrin, ADPN, C22orf20, acylglycerol O-acyltransferase or calcium-independent phospholipase A2-epsilon, iPLA(2)epsilon, patatin-like phospholipase domain-containing 3; External IDs: MGI: 2151796; HomoloGene: 11883; GeneCards: PNPLA3; Species; Human: Entrez; 80339; Ensembl; ENSG00000100344; UniProt; Q9NST1; RefSeq (mRNA); NM_025225; RefSeq (protein); NP_079501; Location (UCSC); Chr 22: 43.92-43.96 Mb; Species; Mouse: Entrez; 116939; Ensembl; ENSMUSG00000041653; UniProt; Q91WW7; RefSeq (mRNA); NM_054088; RefSeq (protein); NP_473429.2 NP_473429; Location (UCSC); Chr 15: 84.17-84.19 Mb. Patatin-like phospholipase domain-containing protein 3 (PNPLA3) also known as adiponutrin (ADPN), acylglycerol O-acyltransferase or calcium-independent phospholipase A2-epsilon (iPLA2-epsilon) is reportedly an enzyme that in humans is encoded by the PNPLA3 gene. PNPLA3 encodes a 481 amino acid protein that belongs to the patatin-like phospholipase family. The progenitor of this family, patatin, is reportedly a major protein of potato tubers and has nonspecific lipid acyl hydrolase activity. A variant (I148M) in PNPLA3 (Patatin-like phospholipase domain containing 3) was reportedly strongly associated with increased hepatic fat levels and with hepatic inflammation. A marker of PNPLA3-1148M is reportedly SNP rs738409, and another SNP, rs738408, is a silent mutation and 2 bp away. The association between PNPLA3-1148M and hepatic fat content reportedly remained highly significant after adjusting for BMI, diabetes status, ethanol use, as well as global and local ancestry, and was associated with a significant increase in liver TG content in all three ethnic groups. The frequencies of the PNPLA3-1148M allele reportedly mirrored the relative prevalence of NAFLD in the three ethnic groups; the highest frequency was in Hispanics (0.49), with lower frequencies observed in European Americans (0.23) and African-Americans (0.17). Collins et al. 2003 Genome Res. 13 (1): 27-36; Collins et al. 2005 Genome Biol. 5 (10): R84; Dunham et al. 1999 Nature. 402 (6761): 489-95; Gerhard et al. 2004 Genome Res. 14 (10B): 2121-7; Jenkins et al. 2005 J. Biol. Chem. 279 (47): 48968-75; Kienesberger et al. 2009 J. Lipid Res. 50 Suppl.: S63-8; Lake et al. 2006 J. Lipid Res. 46 (11): 2477-87; Liu et al. 2004 J. Clin. Endocrinol. Metab. 89 (6): 2684-9; Strausberg et al. 2003 Proc. Natl. Acad. Sci. U.S.A. 99 (26): 16899-903; Wilson et al. 2006 J Lipid Res. 47 (9): 1940-9.

In some embodiments, a mutation in PNPLA3 is related to or associated with a disease or disorder.

In some embodiments, a PNPLA3-related disorder is a disorder related to, caused and/or associated with abnormal or excessive activity, level and/or expression or abnormal tissue or inter- or intracellular distribution of an PNPLA3 gene or a gene product thereof. Non-limiting examples of an PNPLA3-related disorder include: liver disease, fatty liver (e.g., accumulation of fat in the liver, or an increase in or supra-normal hepatic fat), hepatic steatosis (e.g., simple fatty liver), steatohepatitis, hepatitis, nonalcoholic fatty liver disease (e.g., NAFLD), and/or one or more disease and/or one or more symptom or condition associated with or secondary to a liver disease, including but not limited to: inflammation, destruction of liver cells (e.g., hepatocellular necrosis), scarring of the liver (e.g., fibrosis), irreversible, advanced scarring of the liver (e.g., cirrhosis), insulin resistance, diabetes, dyslipidemia, increased protein activity in the hedgehog (Hh) signaling pathway, fatigue, weakness, nausea, abdominal pain, spider-like blood vessels, jaundice, itching, edema, ascites, mental confusion, obesity, hepatocellular carcinoma.

In some embodiments, non-limiting examples of a PNPLA3-related disorder include: hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertriglyceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD).

In some embodiments, non-limiting examples of a PNPLA3-related disorder include: fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma.

Oligonucleotides which target PNPLA3 include, as non-limiting examples: WV-8043, WV-8044, WV-8045, WV-8046, WV-8047, WV-8048, WV-8083, WV-8132, WV-8246, WV-8248, WV-8250, WV-8257, WV-8259, WV-8560, WV-8562, WV-8563, WV-8564, WV-8565, WV-8567, WV-8596, WV-8597, WV-8600, WV-8601, WV-8602, WV-8605, WV-8606, WV-8609, WV-8620, WV-8621, WV-8624, WV-8625, WV-8628, WV-8689, WV-8690, WV-8697, WV-8844, WV-8845, WV-8846, WV-8847, WV-8848, WV-8849, WV-8850, WV-8851, WV-8852, WV-8853, WV-8854, WV-8855, WV-8856, WV-8857, WV-8858, WV-8859, WV-8860, WV-9441, WV-9442, WV-9443, WV-9444, WV-9445, WV-9860, WV-9861, WV-9862, WV-9868, WV-9869, WV-9870, WV-9891, WV-9892, WV-9893, WV-9894, WV-9895, WV-9896, WV-10249, WV-10250, WV-10251, WV-10252, WV-10253, WV-10254, WV-11958, WV-11960, WV-11962, WV-12099, WV-12101, WV-12103, WV-12105, WV-12107, and WV-12109. These oligonucleotides are described in Table 1C.

As non-limiting examples, oligonucleotides targeting APOC3 were designed, constructed and/or tested.

In some embodiments, APOC3 is a gene, or a gene product thereof (including, but not limited to, a transcript or protein), also known as APOCIII, ApocIII, HALP2, apolipoprotein C3; OMIM: 107720; MGI: 88055; HomoloGene: 81615; or GeneCards: 345; or Human APOC3: Entrez 345; Ensembl: ENSG00000110245; UniProt: P02656; RefSeq (mRNA): NM_000040; RefSeq (protein): NP_000031.1; Location (UCSC): Chr 11: 116.83-116.83 Mb; Mouse Entrez 11814; Ensembl: ENSMUSG00000032081; UniProt: P33622; RefSeq (mRNA): NM_023114 NM_001289755 NM_001289756 NM_001289833; RefSeq (protein): NP_001276685.1 NP_075603.1; Location (UCSC): Chr 9: 46.23-46.24 Mb. APOC3 reportedly inhibits lipoprotein lipase and hepatic lipase; it is reported to inhibit hepatic uptake of triglyceride-rich particles. An increase in APOC3 levels reportedly induces the development of hypertriglyceridemia. Scientific papers reportedly suggest an intracellular role for APOC3 in promoting the assembly and secretion of triglyceride-rich VLDL particles from hepatic cells under lipid-rich conditions. However, two naturally-occurring point mutations in human APOC3 coding sequence, namely Ala23Thr and Lys58Glu, reportedly abolish the intracellular assembly and secretion of triglyceride-rich VLDL particles from hepatic cells. Two novel susceptibility haplotypes (specifically, P2-S2-X1 and P1-S2-X1) have been reportedly discovered in ApoAI-CIII-AIV gene cluster on chromosome 11q23; these reportedly confer approximately threefold higher risk of coronary heart disease in normal as well as non-insulin diabetes mellitus. APOC3 delays the catabolism of triglyceride rich particles. Elevations of APOC3 found in genetic variation studies may predispose patients to non-alcoholic fatty liver disease. APOC3 expression has reportedly been implicated in various disorders, including but not limited to: atherosclerosis or dyslipidemia, elevated triglyceride levels, elevated cholesterol levels, elevated free fatty acids, and diabetes. Vaith et al. 1978 Biochimica et Biophysica Acta. 541 (2): 234-40; Nicolardi et al. 2013 Journal of Proteome Research. 12 (5): 2260-8; Mendivil et al. 2010 Arteriosclerosis, Thrombosis, and Vascular Biology. 30 (2): 239-45; Sundaram et al. 2010 Journal of Lipid Research. 51 (1): 150-161; Sundaram et al. 2010 Journal of Lipid Research. 51 (6): 1524-1534; Qin et al. August 2011 The Journal of Biological Chemistry. 286 (31): 27769-27780; Singh et al. November 2008 International Journal of Cardiology. 130 (3): e93-5; Singh et al. June 2007 Diabetes & Vascular Disease Research. 4 (2): 124-29.

In some embodiments, a mutation in APOC3 is related to or associated with a disease or disorder.

In some embodiments, an APOC3-related disorder is a disorder related to, caused and/or associated with abnormal or excessive activity, level and/or expression of, a deleterious mutation in, or abnormal tissue or inter- or intracellular distribution of an APOC3 gene or a gene product thereof. In some embodiments, non-limiting examples of an APOC3-related disorder include: heart disease, atherosclerosis, dyslipidemia, elevated triglyceride levels (hypertriglyceridemia), elevated cholesterol levels (hypercholesterolemia), cardiovascular disease, metabolic syndrome, obesity and diabetes, premature chronic heart disease (CHD), eruptive xanthoma, hepatosplenomegaly, pancreatitis, aneurysm, angina, arrhythmia, atherosclerosis, cerebrovascular disease (stroke), hypertension, and hyperlipidemia. In some embodiments, non-limiting examples of an APOC3-related disorder include: hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertriglyceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD). portal hypertension, hepatic protein synthetic capability, hyperbilirubinemia, or encephalopathy. fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma.

In some embodiments, non-limiting examples of an APOC3-related disorder include: hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertriglyceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD).

In some embodiments, non-limiting examples of an APOC3-related disorder include: fatty liver, nonalcoholic fatty liver disease, nonalcoholic steatohepatitis, nonalcoholic steatohepatitis with liver fibrosis, nonalcoholic steatohepotitis with cirrhosis, or nonalcoholic steatohepatitis with cirrhosis and hepatocellular carcinoma.

Oligonucleotides target APOC3 include, as non-limiting examples: WV-8610, WV-8611, WV-8612, WV-8613, WV-8614, WV-8615, WV-8616, WV-8617, WV-8618, WV-8619, WV-8629, WV-8632, WV-8637, WV-8638, WV-8639, WV-8640, WV-8645, WV-8646, WV-8647, WV-8648, WV-8653, WV-8654, WV-8655, WV-8656, WV-8661, WV-8662, WV-8663, WV-8664, WV-8665, WV-8666, WV-8667, WV-8668, WV-8669, WV-8670, WV-8671, WV-8672, WV-8673, WV-8674, WV-8675, WV-8676, WV-8677, WV-8678, WV-8679, WV-8680, WV-8681, WV-8682, WV-8683, WV-8684, WV-8685, WV-8686, WV-8687, WV-8688, WV-9526, WV-9527, WV-9528, WV-9529, WV-9530, WV-9531, WV-9532, WV-9533, WV-9590, WV-9591, WV-9592, WV-9593, WV-9871, WV-9872, WV-9873, WV-9874, WV-9885, WV-9886, WV-9887, WV-9888, WV-10243, WV-10244, WV-10245, WV-10246, WV-12947, WV-12948, WV-12949, WV-12950, WV-12951, WV-12952, WV-12953, WV-12954, WV-12955, WV-12956, WV-12957, WV-12958, WV-12959, WV-12960, WV-12961, WV-12962, WV-12963, WV-12964, WV-12965, WV-12966, WV-12967, WV-12968, WV-12969, WV-12970, WV-12971, WV-12972, WV-12973, WV-12974, WV-12975, WV-12976, WV-12977, WV-12978, WV-12979, WV-12980, WV-12981, WV-12982, WV-12983, WV-12984, WV-12985, WV-12986, WV-12987, WV-12988, WV-12989, WV-12990, WV-12991, WV-12992, WV-12993, WV-12994, WV-12995, WV-12996, WV-12997, WV-12998, WV-12999, WV-13000, WV-13001, WV-13002, WV-13003, WV-13004, WV-13005, WV-13006, WV-13007, and WV-13008. These oligonucleotides are described in Table 1D.

Oligonucleotides were also designed to target each of at least four different gene targets which are not Malat1, C9orf72, PNPLA3 or APOC3, and shown to efficaciously decrease the expression, level and/or activity of the target gene or its gene product (data not shown).

Oligonucleotides were thus designed, constructed and/or tested which have a variety of different base sequences, and which target a variety of different targets, related to a variety of different diseases.

In some embodiments, provided oligonucleotides are capable of directing a decrease in the expression, level and/or activity of a gene or its gene product. In some embodiments, a target gene comprises a repeat expansion. In some embodiments, provided oligonucleotides can comprise any base sequence described herein, or portion thereof, wherein a portion is a span of at least 15 contiguous bases, or a span of at least 15 contiguous bases with 1-5 mismatches.

In some embodiments, the base sequence of an oligonucleotide has a sufficient length and identity to a transcript target to mediate target-specific knockdown. In some embodiments, the oligonucleotide is complementary to a portion of a transcript target sequence.

In some embodiments, the base sequence of an oligonucleotide is complementary to that of a target transcript. As used herein, "target transcript sequence," "target sequence", "target gene", and the like, refer to a contiguous portion of the nucleotide sequence of an mRNA molecule formed during the transcription of a gene, including mRNA that is a product of RNA processing of a primary transcription product.

The terms "complementary," "fully complementary" and "substantially complementary" herein may be used with respect to the base matching between an oligonucleotide and a target sequence, as will be understood from the context of their use. In some embodiments, the base sequence of an oligonucleotide is complementary to that of a target sequence when each base of the oligonucleotide is capable of base-pairing with a sequential base on the target strand, when maximally aligned. As a non-limiting example, if a target sequence has, for example, a base sequence of 5'-GCAUAGCGAGCGAGGGAAAAC-3' (SEQ ID NO: 2), an oligonucleotide with a base sequence of 5'GUUUUCC-CUCGCUCGCUAUGC-3' (SEQ ID NO: 3) is complementary or fully complementary to such a target sequence. It is noted, of course, that substitution of T for U, or vice versa, does not alter the amount of complementarity.

As used herein, a polynucleotide that is "substantially complementary" to a target sequence is largely or mostly complementary but not 100% complementary. In some embodiments, a sequence (e.g., an oligonucleotide) which is substantially complementary has 1, 2, 3, 4 or 5 mismatches from a sequence which is 100% complementary to the target sequence.

The present disclosure presents, in Table 1 and elsewhere, various oligonucleotides, each of which has a defined base sequence. In some embodiments, the disclosure encompasses any oligonucleotide having a base sequence which is, comprises, or comprises a portion of the base sequence of any of oligonucleotide disclosed herein. In some embodiments, the disclosure encompasses any oligonucleotide having a base sequence which is, comprises, or comprises a portion of the base sequence of any oligonucleotide disclosed herein, which has any chemical modification, stereochemistry, format, structural feature (e.g., any structure or pattern of modification or portion thereof), and/or any other modification described herein (e.g., conjugation with another moiety, such as a targeting moiety, carbohydrate moiety, etc.; and/or multimerization). In some embodiments, a "portion" (e.g., of a base sequence or a pattern of modifications), is at least 5, 6, 7, 8, 9, 10, 11, 12, 13, 14, 15, 16, 17, 18, 19, or 20 long. In some embodiments, a "portion" of a base sequence is at least 5 nt long. In some embodiments, a "portion" of a base sequence is at least 10 nt long. In some embodiments, a "portion" of a base sequence is at least 15 nt long. In some embodiments, a "portion" of a base sequence is at least 20 nt long.

Non-limiting examples of oligonucleotides are described in detail below, in Table 1, including all subparts, such as Table 1A, Table 1B, etc.

TABLE 1A

C9orf72 Oligonucleotides.

| WAVE ID | Modified Sequence | Base sequence | Stereochemistry / Internucleotidic Linkages |
|---|---|---|---|
| WV-3536 | Teo * Aeo * m5Ceo * Aeo * Geo * G * m5C * T * G * m5C * G * G * T * T * G * Teo * Teo * Teo * m5Ceo * m5Ceo | TACAGGCTGCGGTTGTTTCC | XXXXXXXXXXXXXXXXXXX |
| WV-3542 | m5Ceo * m5Ceo * Teo * Teo * m5Ceo * m5C * m5C * T * G * A * A * G * G * T * T * m5Ceo * m5Ceo * Teo * m5Ceo * m5Ceo | CCTTCCCTGAAGGTTCCTCC | XXXXXXXXXXXXXXXXXXX |
| WV-3662 | mG * mUmGmCmU * G * C * G * A * T * C * C * C * C * A * mUmUmCmC * mA | GUGCUGCGAUCCCCAUUCCA | XOOOXXXXXXXXXXXXOOOX |
| WV-3688 | mC * mCmUmCmA * C * T * C * A * C * C * C * A * C * T * mCmGmCmC * mA | CCUCACUCACCCACUCGCCA | XOOOXXXXXXXXXXXXOOOX |
| WV-3690 | mG * mCmCmAmG * G * A * T * G * C * C * G * C * C * T * mCmCmUmC * mA | GCCAGGAUGCCGCCUCCUCA | XOOOXXXXXXXXXXXXOOOX |
| WV-6408 | m5Ceo * m5CeoTeom5CeoAeo * C * T * C * A * C * C * C * A * C * T * m5CeoGeom5Ceom5Ceo * Aeo | CCTCACTCACCCACTCGCCA | XOOOXXXXXXXXXXXXOOOX |
| WV-6474 | mG * mCmCmGmC * C * T * C * C * T * C * A * C * T * C * mAmCmCmC * mA | GCCGCCUCCUCACUCACCCA | XOOOXXXXXXXXXXXXOOOX |
| WV-6936 | mA * mCmCmGmG * G * C * A * G * C * A * G * G * G * A * mCmGmGmC * mU | ACCGGGCAGCAGGGACGGCU | XOOOXXXXXXXXXXXXOOOX |
| WV-6951 | mG * mUmUmCmA * C * C * C * T * C * A * G * C * G * A * mGmUmAmC * mU | GUUCACCCUCAGCGAGUACU | XOOOXXXXXXXXXXXXOOOX |
| WV-6952 | mC * mUmUmGmU * T * C * A * C * C * C * T * C * A * G * mCmGmAmG * mU | CUUGUCACCCUCAGCGAGU | XOOOXXXXXXXXXXXXOOOX |
| WV-6969 | mG * mAmGmCmU * T * G * C * T * A * C * A * G * G * C * mUmGmCmG * mG | GAGCUGCUACAGGCUGCGG | XOOOXXXXXXXXXXXXOOOX |
| WV-6976 | mG * mCmGmCmG * A * C * T * C * C * T * G * A * G * T * mUmCmCmA * mG | GCGCGACUCCUGAGUUCCAG | XOOOXXXXXXXXXXXXOOOX |
| WV-6981 | mC * mAmGmGmA * T * G * C * C * G * C * C * T * C * C * mUmCmAmC * mU | CAGGAUGCCGCCUCCUCACU | XOOOXXXXXXXXXXXXOOOX |
| WV-6982 | mC * mCmAmGmG * A * T * G * C * C * G * C * C * T * C * mCmUmCmA * mC | CCAGGAUGCCGCCUCCUCAC | XOOOXXXXXXXXXXXXOOOX |
| WV-6989 | mG * mCmCmAmC * C * C * G * C * C * A * G * G * A * T * mGmCmCmG * mC | GCCACCCGCCAGGAUGCCGC | XOOOXXXXXXXXXXXXOOOX |
| WV-7002 | mC * mGmCmCmU * C * T * T * C * C * C * G * G * C * A * mGmCmCmG * mA | CGCCUCUUCCCGGCAGCCGA | XOOOXXXXXXXXXXXXOOOX |
| WV-7027 | Aeo * m5Ceom5CeoGeoGeo * G * m5C * A * G * m5C * A * G * G * G * A * m5CeoGeoGeom5Ceo * Teo | XOOOXXXXXXXXXXXXOOOX | ACCGGGCAGCAGGGACGGCT |
| WV-7118 | Geo * TeoGeom5CeoTeo * G * m5C * G * A * T * m5C * m5C * m5C * m5C * A * TeoTeom5Ceom5Ceo * Aeo | GTGCTGCGATCCCCATTCCA | XOOOXXXXXXXXXXXXOOOX |
| WV-7124 | mC *S mCmUmCmA *S C *S T *S C *S R A *S C *S C *R C *S A *S C *S T *S mCmGmCmC *S mA | CCUCACUCACCCACUCGCCA | SOOOSSSRSSRSSSSOOOS |

TABLE 1A-continued

C9orf72 Oligonucleotides.

| WAVE ID | Modified Sequence | Base sequence | Stereochemistry / Internucleotidic Linkages |
|---|---|---|---|
| WV-7130 | m5Ceo *S m5CeoTeom5CeoAeo *S C *S T *S C *R A *S C *S C *R C *S A *S C *S T *S m5CeoGeom5Ceom5Ceo *S Aeo | CCTCACTCACCCACTCGCCA | SOOOSSSRSSRSSSSOOOS |
| WV-7601 | m5Ceo *R m5Ceo *R Teo *R m5Ceo *R Aeo *R C *S T *S C *R A *S C *S C *R C *S A *S C *S T *R m5Ceo * RGeo *R m5Ceo *R m5Ceo *R Aeo | CCTCACTCACCCACTCGCCA | RRRRRSSRSSRSSSRRRRR |
| WV-7603 | mC *S mCmUmCmA *S C *S T *S C *R A *S C *S C *S C *S A *S C *S T *S mCmGmC *S mC *S mA | CCUCACTCACCCACTCGCCA | SOOOSSSRSSSSSSSOOSS |
| WV-7604 | mC *S mCmUmCmA *S C *S T *S C *R A *S C *S C *R C *S A *S C *S T *S mCmGmC *S mC *S mA | CCUCACTCACCCACTCGCCA | SOOOSSSRSSRSSSOOSS |
| WV-7605 | mC *S mCmUmCmA *S C *S T *S C *R A *S C *S C *S C *S A *S C *S T * SmC * SmG *S mC *S mC *S mA | CCUCACTCACCCACTCGCCA | SOOOSSSRSSSSSSSSSSS |
| WV-7606 | mC *S mCmUmCmA *S C *S T *S C *R A *S C *S C *R C *S A *S C *S T * SmC * SmG *S mC *S mC *S mA | CCUCACTCACCCACTCGCCA | SOOOSSSRSSRSSSSSSS |
| WV-7657 | m5Ceo *R m5Ceo *R Teo *R m5Ceo *R Aeo *R C *S T *S C *S A *S C *S C *R C *S A *S C *S T *R m5Ceo * RGeo *R m5Ceo *R m5Ceo *R Aeo | CCTCACTCACCCACTCGCCA | RRRRRSSSSRSSSRRRRR |
| WV-7658 | m5Ceo *R m5CeoTeom5CeoAeo *R C *S T *S C *R A *S C *S C *R C *S A *S C *S T *R m5CeoGeom5Ceom5Ceo *R Aeo | CCTCACTCACCCACTCGCCA | ROOORSSRSSRSSSROOOR |
| WV-7659 | m5Ceo *R m5CeoTeom5CeoAeo *R C *S T *S C *R A *S C *S C *S C *S A *S C *S T *R m5CeoGeom5Ceom5Ceo *R Aeo | CCTCACTCACCCACTCGCCA | ROOORSSRSSSSSSROOOR |
| WV-8005 | m5Ceo *R m5CeoTeom5CeoAeo *R C *S T *S C *R A *S C *S C *S C *S A *S C *S T *S mCmGmC *S mC *S mA | CCTCACTCACCCACTCGCCA | ROOORSSRSSSSSSSOOSS |
| WV-8006 | m5Ceo *R m5CeoTeom5CeoAeo *R C *S T *S C *R A *S C *S C *R C *S A *S C *S T *S mCmGmC *S mC *S mA | CCTCACTCACCCACTCGCCA | ROOORSSRSSRSSSSOOSS |
| WV-8007 | m5Ceo *R m5CeoTeom5CeoAeo *R C *S T *S C *R A *S C *S C *S C *S A *S C *S T * SmC *S mG *S mC *S mC *S mA | CCTCACTCACCCACTCGCCA | ROOORSSRSSSSSSSSSSS |
| WV-8008 | m5Ceo *R m5CeoTeom5CeoAeo *R C *S T *S C *R A *S C *S C *R C *S A *S C *S T * SmC *S mG *S mC *S mC *S mA | CCTCACTCACCCACTCGCCA | ROOORSSRSSRSSSSSSSS |
| WV-8009 | mC *S m5CeoTeom5CeomA *S C *S T *S C *R A *S C *S C *S C *S A *S C *S T *S mCmGmC *S mC *S mA | CCTCACTCACCCACTCGCCA | SOOOSSSRSSSSSSSOOSS |
| WV-8010 | mC *S m5CeoTeom5CeomA *S C *S T *S C *R A *S C *S C *R C *S A *S C *S T *S mCmGmC *S mC *S mA | CCTCACTCACCCACTCGCCA | SOOOSSSRSSRSSSOOSS |
| WV-8011 | mC *S m5CeoTeom5CeomA *S C *S T *S C *R A *S C *S C *S C *S A *S C *S T * SmC *S mG *S mC *S mC *S mA | CCTCACTCACCCACTCGCCA | SOOOSSSRSSSSSSSSSSS |
| WV-8012 | mC *S m5CeoTeom5CeomA *S C *S T *S C *R A *S C *S C *R C *S A *S C *S T *S mC *S mG *S mC *S mC *S mA | CCTCACTCACCCACTCGCCA | SOOOSSSRSSRSSSSSSS |
| WV-8114 | mA *S mC *S mC *S mGmG *S G *S C *S A *S G *S C *R A *S G *S G *R G *S A * SmC *S mGmGmC *S mU | ACCGGGCAGCAGGGACGGCU | SSSOSSSSSRSSRSSSOOS |

TABLE 1A-continued

C9orf72 Oligonucleotides.

| WAVE ID | Modified Sequence | Base sequence | Stereochemistry / Internucleotidic Linkages |
|---|---|---|---|
| WV-8115 | mA *S m5CeomC *S mGmG *S G *S C *S A *S G *S C *R A *S G *S G *R G *S A * SmC *S mGmGmC *S mU | ACCGGGCAGCAGGGACGGCU | SOSOSSSSSRSSRSSSOOS |
| WV-8116 | mA *S mC *S m5CeomGmG *S G *S C *S A *S G *S C *R A *S G *S G *R G *S A * SmC *S mGmGmC *S mU | ACCGGGCAGCAGGGACGGCU | SSOOSSSSSRSSRSSSOOS |
| WV-8117 | mA *S mC *S mC *S mGmG *S G *S C *S A *S G *S C *R A *S G *S G *R G *S A *S m5CeomGmGmC *S mU | ACCGGGCAGCAGGGACGGCU | SSSOSSSSSRSSRSSOOOS |
| WV-8118 | mA *S m5Ceom5CeomGmG *S G *S C *S A *S G *S C *R A *S G *S G *R G *S A * SmC *S mGmGmC *S mU | ACCGGGCAGCAGGGACGGCU | SOOOSSSSSRSSRSSSOOS |
| WV-8119 | mA *S m5CeomC *S mGmG *S G *S C *S A *S G *S C *R A *S G *S G *R G *S A *S m5CeomGmGmC *S mU | ACCGGGCAGCAGGGACGGCU | SOSOSSSSSRSSRSSSOOOS |
| WV-8120 | mA *S mC *S m5CeomGmG *S G *S C *S A *S G *S C *R A *S G *S G *R G *S A *S m5CeomGmGmC *S mU | ACCGGGCAGCAGGGACGGCU | SSOOSSSSSRSSRSSSOOOS |
| WV-8121 | mA *S m5Ceo *S m5CeomGmG *S G *S C *S A *S G *S C *R A *S G *S G *R G *S A *S m5CeomGmGmC *S mU | ACCGGGCAGCAGGGACGGCU | SSOOSSSSSRSSRSSSOOOS |
| WV-8122 | mA *S mC *S mC *S mGmG *S G *S C *S A *S G *R C *S A *S G *R G *S G *S A * SmC *S mGmGmC *S mU | ACCGGGCAGCAGGGACGGCU | SSSOSSSSSRSSRSSSSOOS |
| WV-8123 | mA *S m5CeomC *S mGmG *S G *S C *S A *S G *R C *S A *S G *R G *S G *S A * SmC *S mGmGmC *S mU | ACCGGGCAGCAGGGACGGCU | SOSOSSSSSRSSRSSSSOOS |
| WV-8124 | mA *S mC *S m5CeomGmG *S G *S C *S A *S G *R C *S A *S G *R G *S G *S A * SmC *S mGmGmC *S mU | ACCGGGCAGCAGGGACGGCU | SSOOSSSSSRSSRSSSSOOS |
| WV-8125 | mA *S mC *S mC *S mGmG *S G *S C *S A *S G *R C *S A *S G *R G *S G *S A *S m5CeomGmGmC *S mU | ACCGGGCAGCAGGGACGGCU | SSSOSSSSSRSSRSSSOOOS |
| WV-8126 | mA *S m5Ceom5CeomGmG *S G *S C *S A *S G *R C *S A *S G *R G *S G *S A * SmC *S mGmGmC *S mU | ACCGGGCAGCAGGGACGGCU | SOOOSSSSSRSSRSSSSOOS |
| WV-8127 | mA *S m5CeomC *S mGmG *S G *S C *S A *S G *R C *S A *S G *R G *S G *S A *S m5CeomGmGmC *S mU | ACCGGGCAGCAGGGACGGCU | SOSOSSSSSRSSRSSSOOOS |
| WV-8128 | mA *S mC *S m5CeomGmG *S G *S C *S A *S G *R C *S A *S G *R G *S G *S A *S m5CeomGmGmC *S mU | ACCGGGCAGCAGGGACGGCU | SSOOSSSSSRSSRSSSOOOS |
| WV-8129 | mA *S m5Ceo *S m5CeomGmG *S G *S C *S A *S G *R C *S A *S G *R G *S G *S A *S m5CeomGmGmC *S mU | ACCGGGCAGCAGGGACGGCU | SSOOSSSSSRSSRSSSOOOS |
| WV-8311 | mA *S mC *S mC *S mG *S mG *S G *S C *S A *S G *S C *R A *S G *S G *R G *S A *S mC *S mG *S mG *S mC *S mU | ACCGGGCAGCAGGGACGGCU | SSSSSSSSSRSSRSSSSSS |
| WV-8312 | Aeo *R m5Ceom5CeoGeoGeo *R G *S C *S A *S G *S C *R A *S G *S G *R G *S A *S m5CeoGeoGeom5Ceo *R Teo | ACCGGGCAGCAGGGACGGCT | ROOORSSSRSSRSSOOOR |
| WV-8313 | Aeo *R m5Ceo *R m5Ceo * RGeo * RGeo *R G *S C *S A *S G *S C *R A *S G *S G *R G *S A *S m5Ceo * RGeo * RGeo *R m5Ceo *R Teo | ACCGGGCAGCAGGGACGGCT | RRRRRSSSRSSRSSRRRR |

TABLE 1A-continued

C9orf72 Oligonucleotides.

| WAVE ID | Modified Sequence | Base sequence | Stereochemistry / Internucleotidic Linkages |
|---|---|---|---|
| WV-8314 | mA *S mC *S mC *S mGmG *S G *S C *S A *S G *S C *R A *S G *S G *R G *S A *S m5CeoGeoGeom5Ceo *R Teo | ACCGGGCAGCAGGGACGGCT | SSSOSSSSSRSSRSSOOOR |
| WV-8315 | mA *S mC *S mC *S mG *S mG *S G *S C *S A *S G *R C *S A *S G *R G *S G *S A *S mC *S mG *S mG *S mC *S mU | ACCGGGCAGCAGGGACGGCU | SSSSSSSSSRSSRSSSSSSS |
| WV-8316 | Aeo *R m5Ceom5CeoGeoGeo *R G *S C *S A *S G *R C *S A *S G *R G *S G *S A *R m5CeoGeoGeom5Ceo *R Teo | ACCGGGCAGCAGGGACGGCT | ROOORSSSRSSRSSROOOR |
| WV-8317 | Aeo *R m5Ceo *R m5Ceo * RGeo * RGeo *R G *S C *S A *S G *R C *S A *S G *R G *S G *S A *R m5Ceo * RGeo * RGeo *R m5Ceo *R Teo | ACCGGGCAGCAGGGACGGCT | RRRRRSSSRSSRSSRRRRR |
| WV-8318 | mA *S mC *S mC *S mG *S mG *S G *S C *S A *S G *R C *S A *S G *R G *S G *S A *R m5CeoGeoGeom5Ceo *R Teo | ACCGGGCAGCAGGGACGGCT | SSSSSSSSSRSSRSSROOOR |
| WV-8321 | m5Ceo *R m5Ceo *R Teom5CeoAeo *R C *S T *S C *R A *S C *S C *R C *S A *S C *S T *R m5CeoGeom5Ceo *R m5Ceo *R Aeo | CCTCACTCACCCACTCGCCA | RROORSSRSSRSSSROORR |
| WV-8322 | m5Ceo *R m5Ceo *R Teo *R m5CeoAeo *R C *S T *S C *S A *S C *S C *R C *S A *S C *S T *R m5CeoGeom5Ceo *R m5Ceo *R Aeo | CCTCACTCACCCACTCGCCA | RRRORSSSSRSSSROORR |
| WV-8329 | m5Ceo *R m5Ceo *R Teom5CeoAeo *R C *S T *S C *S A *S C *S C *R C *S A *S C *S T *R m5CeoGeom5Ceo *R m5Ceo *R Aeo | CCTCACTCACCCACTCGCCA | RROORSSRSSRSSSROORR |
| WV-8452 | mC *S m5CeoTeom5CeomA *S C *S T *S C *R A *S C *S C *S C *S A *S C *S T *S m5CeomGm5CeomC *S mA | CCTCACTCACCCACTCGCCA | SOOOSSSRSSSSSSSSOOOS |
| WV-8453 | mC *S m5CeoTeom5CeomA *S C *S T *S C *R A *S C *S C *R C *S A *S C *S T *S m5CeomGm5CeomC *S mA | CCTCACTCACCCACTCGCCA | SOOOSSSRSSSRSSSSOOOS |
| WV-8454 | mC *S m5CeoTeom5CeomA *S C *S T *S C *R A *S C *S C *S C *S A *S C *S T * SmC *S mGmC *S mC *S mA | CCTCACTCACCCACTCGCCA | SOOOSSSRSSSSSSSSOSS |
| WV-8455 | mC *S m5CeoTeom5CeomA *S C *S T *S C *R A *S C *S C *R C *S A *S C *S T *S mC *S mGmC *S mC *S mA | CCTCACTCACCCACTCGCCA | SOOOSSSRSSSRSSSSSOSS |
| WV-8456 | m5Ceo *R m5CeoTeom5CeoAeo *R C *S T *S C *R A *S C *S C *S C *S A *S C *S T *S m5CeomGm5CeomC *S mA | CCTCACTCACCCACTCGCCA | ROOORSSRSSSSSSSSOOOS |
| WV-8466 | Aeo *R m5Ceom5CeoGeoGeo *R G *S C *S A *S G *S C *R A *S G *S G *R G *S A *S mCmGmGmC *S mU | ACCGGGCAGCAGGGACGGCU | ROOORSSSSRSSRSSOOOS |
| WV-8467 | Aeo *R m5Ceom5CeoGeoGeo *R G *S C *S A *S G *R C *S A *S G *R G *S G *S A *S mCmGmGmC *S mU | ACCGGGCAGCAGGGACGGCU | ROOORSSSRSSRSSSOOOS |
| WV-8468 | Aeo *R m5Ceom5CeoGeoGeo *R G *S C *S A *S G *S C *R A *S G *S G *R G *S A * SmC *S mGmGmC *S mU | ACCGGGCAGCAGGGACGGCU | ROOORSSSSRSSRSSSOOS |
| WV-8469 | Aeo *R m5Ceom5CeoGeoGeo *R G *S C *S A *S G *R C *S A *S G *R G *S G *S A * SmC *S mGmGmC *S mU | ACCGGGCAGCAGGGACGGCU | ROOORSSSRSSRSSSSOOS |
| WV-8470 | Aeo *R m5Ceom5CeoGeoGeo *R G *S C *S A *S G *S C *R A *S G *S G *R G *S A * SmC *S mG *S mG *S mC *S mU | ACCGGGCAGCAGGGACGGCU | ROOORSSSSRSSRSSSSSSS |

TABLE 1A-continued

C9orf72 Oligonucleotides.

| WAVE ID | Modified Sequence | Base sequence | Stereochemistry / Internucleotidic Linkages |
|---|---|---|---|
| WV-8471 | Aeo *R m5Ceom5CeoGeoGeo *R G *S C *S A *S G *R C *S A *S G *R G *S G *S A * SmC *S mG *S mG *S mC *S mU | ACCGGGCAGCAGGGACGGCU | ROOORSSSRSSSRSSSSSSS |
| WV-8472 | mA *S m5Ceom5CeomG *S mG *S G *S C *S A *S G *S C *R A *S G *S G *R G *S A *S mCmGmGmC *S mU | ACCGGGCAGCAGGGACGGCU | SOOSSSSSSRSSRSSOOOS |
| WV-8473 | mA *S m5Ceom5CeomG *S mG *S G *S C *S A *S G *R C *S A *S G *R G *S G *S A *S mCmGmGmC *S mU | ACCGGGCAGCAGGGACGGCU | SOOSSSSSSRSSRSSSOOOS |
| WV-8474 | mA *S m5Ceom5CeomG *S mG *S G *S C *S A *S G *S C *R A *S G *S G *R G *S A * SmC *S mGmGmC *S mU | ACCGGGCAGCAGGGACGGCU | SOOSSSSSSRSSRSSSSOOS |
| WV-8475 | mA *S m5Ceom5CeomG *S mG *S G *S C *S A *S G *R C *S A *S G *R G *S G *S A * SmC *S mGmGmC *S mU | ACCGGGCAGCAGGGACGGCU | SOOSSSSSSRSSRSSSSSOOS |
| WV-8476 | mA *S m5Ceom5CeomG *S mG *S G *S C *S A *S G *S C *R A *S G *S G *R G *S A * SmC *S mG *S mG *S mC *S mU | ACCGGGCAGCAGGGACGGCU | SOOSSSSSSRSSRSSSSSSS |
| WV-8547 | m5Ceo * m5CeoTeom5CeoAeo * C * T * C * A * C * C * C * A * C * T * mCmGmC * mC * mA | CCTCACTCACCCACTCGCCA | XOOOXXXXXXXXXXXOOXX |
| WV-8548 | m5Ceo * m5CeoTeom5CeoAeo * C * T * C * A * C * C * C * A * C * T * mC * mG * mC * mC * mA | CCTCACTCACCCACTCGCCA | XOOOXXXXXXXXXXXXXXX |
| WV-8549 | mC * m5CeoTeom5CeomA * C * T * C * A * C * C * C * A * C * T * mCmGmC * mC * mA | CCTCACTCACCCACTCGCCA | XOOOXXXXXXXXXXXOOXX |
| WV-8550 | mC * m5CeoTeom5CeomA * C * T * C * A * C * C * C * A * C * T * mC * mG * mC * mC * mA | CCTCACTCACCCACTCGCCA | XOOOXXXXXXXXXXXXXXX |
| WV-8551 | mC * m5CeoTeom5CeomA * C * T * C * A * C * C * C * A * C * T * mC * mGmC * mC * mA | CCTCACTCACCCACTCGCCA | XOOOXXXXXXXXXXXXXOXX |
| WV-8568 | mA *S m5Ceom5CeoGeomG *S G *S C *S A *S G *S C *R A *S G *S G *R G *S A * SmC *S mG *S mG *S mC *S mU | ACCGGGCAGCAGGGACGGCU | SOOOSSSSRSSRSSSSSSS |
| WV-8569 | mA *S m5Ceom5CeoGeomG *S G *S C *S A *S G *R C *S A *S G *R G *S G *S A *S mG *S mG *S mC *S mU | ACCGGGCAGCAGGGACGGCU | SOOOSSSSSRSSRSSSSSSS |
| WV-8594 | Aeo * m5Ceom5CeoGeoGeo * G * C * A * G * C * A * G * G * G * A * mC * mG * mG * mC * mU | ACCGGGCAGCAGGGACGGCU | XOOOXXXXXXXXXXXXXXX |
| WV-8595 | mA * m5Ceom5CeoGeomG * G * C * A * G * C * A * G * G * G * A * mC * mG * mG * mC * mU | ACCGGGCAGCAGGGACGGCU | XOOOXXXXXXXXXXXXXXX |
| WV-8691 | mA *S m5Ceom5CeoGeomG *S G *S C *S A *S G *S C *R A *S G *S G *R G *S A * SmC *S mGmG *S mC *S mU | ACCGGGCAGCAGGGACGGCU | SOOOSSSSSRSSRSSSOSS |
| WV-8692 | mA *S m5Ceom5CeoGeomG *S G *S C *S A *S G *R C *S A *S G *R G *S G *S A * SmC *S mGmG *S mC *S mU | ACCGGGCAGCAGGGACGGCU | SOOOSSSSSRSSRSSSSOSS |
| WV-8693 | mA * m5Ceom5CeoGeomG * G * C * A * G * C * A * G * G * G * A * mC * mGmG * mC * mU | ACCGGGCAGCAGGGACGGCU | XOOOXXXXXXXXXXXXOXX |
| WV-8694 | mA *S m5Ceom5CeoGeomG *S G *S C *S A *S G *R C *S A *S G *S G *R G *S A *S mCmGmG *S mC *S mU | ACCGGGCAGCAGGGACGGCU | SOOOSSSSSRSSRSSSOOSS |

TABLE 1A-continued

C9orf72 Oligonucleotides.

| WAVE ID | Modified Sequence | Base sequence | Stereochemistry / Internucleotidic Linkages |
|---|---|---|---|
| WV-8695 | mA *S m5Ceom5CeoGeomG *S G *S C *S A *S G *R C *S A *S G *R G *S G *S A *S mCmGmG *S mC *S mU | ACCGGGCAGCAGGGACGGCU | SOOOSSSSRSSRSSSOOSS |
| WV-8696 | mA * m5Ceom5CeoGeomG * G * C * A * G * C * A * G * G * G * A * mCmGmG * mC * mU | ACCGGGCAGCAGGGACGGCU | XOOOXXXXXXXXXXXOOXX |
| WV-9062 | L001mC *S m5CeoTeom5CeomA *S C *S T *S C *R A *S C *S C *S C *S A *S C *S T * SmC *S mG *S mC *S mC *S mA | CCTCACTCACCCACTCGCCA | OSOOOSSSRSSSSSSSSSSS |
| WV-9063 | Mod007L001mC *S m5CeoTeom5CeomA *S C *S T *S C *R A *S C *S C *S C *S A *S C *S T *S mC *S mG *S mC *S mC *S mA | CCTCACTCACCCACTCGCCA | OSOOOSSSRSSSSSSSSSSS |
| WV-9285 | L001mC *S m5CeoTeom5CeomA *S C *S T *S C *R A *S C *S C *S C *R C *S A *S C *S T * SmC *S mGmC *S mC *S mA | CCTCACTCACCCACTCGCCA | OSOOOSSSRSSRSSSSOSS |
| WV-9286 | Mod007L001mC *S m5CeoTeom5CeomA *S C *S T *S C *R A *S C *S C *S C *R C *S A *S C *S T *S mC *S mGmC *S mC *S mA | CCTCACTCACCCACTCGCCA | OSOOOSSSRSSRSSSSOSS |
| WV-9380 | L001mC *S m5CeoTeom5CeomA *S C *S T *S C *R A *S C *S C *S C *R C *S A *S C *S T * SmC *S mG *S mC *S mC *S mA | CCTCACTCACCCACTCGCCA | OSOOOSSSRSSRSSSSSSS |
| WV-9381 | Mod007L001mC *S m5CeoTeom5CeomA *S C *S T *S C *R A *S C *S C *S C *R C *S A *S C *S T *S mC *S mG *S mC *S mC *S mA | CCTCACTCACCCACTCGCCA | OSOOOSSSRSSRSSSSSSS |
| WV-9394 | mC *S m5CeoTeom5CeomA *S C *S T *S CA *S C *S C *S C *S A *S C *S T * SmC * SmG *S mC *S mC *S mA | CCTCACTCACCCACTCGCCA | SOOOSSSOSSSSSSSSSSS |
| WV-9395 | mC *S m5CeoTeom5CeomA *S C *S T *S CA *S C *S CC *S A *S C *S T * SmC * SmG *S mC *S mC *S mA | CCTCACTCACCCACTCGCCA | SOOOSSSOSSOSSSSSSSS |
| WV-9396 | mC *S m5CeoTeom5CeomA *S C *S T *S C5MSdA *S C *S C *S C *S A *S C *S T *S mC *S mG *S mC *S mC *S mA | CCTCACTCACCCACTCGCCA | SOOOSSSOSSSSSSSSSSS |
| WV-9397 | mC *S m5CeoTeom5CeomA *S C *S T *S C5MSdA *S C *S C5MSdC *S A *S C *S T *S mC *S mG *S mC *S mC *S mA | CCTCACTCACCCACTCGCCA | SOOOSSSOSSOSSSSSSSS |
| WV-9398 | mC *S m5CeoTeom5CeomA *S C *S T *S C5MRdA *S C *S C *S C *S A *S C *S T *S mC *S mG *S mC *S mC *S mA | CCTCACTCACCCACTCGCCA | SOOOSSSOSSSSSSSSSSS |
| WV-9399 | mC *S m5CeoTeom5CeomA *S C *S T *S C5MRdA *S C *S C5MRdC *S A *S C *S T *S mC *S mG *S mC *S mC *S mA | CCTCACTCACCCACTCGCCA | SOOOSSSOSSOSSSSSSSS |
| WV-9421 | Mod059L001mC *S m5CeoTeom5CeomA *S C *S T *S C *R A *S C *S C *R C *S A *S C *S T *S mC *S mG *S mC *S mC *S mA | CCTCACTCACCCACTCGCCA | OSOOOSSSRSSRSSSSSSS |
| WV-9486 | mU * Aeom5Ceom5CeoC * G * C * G * C * C * T * C * T * C * mC * mC * mG * mG * mC | UACCCGCGCCTCTTCCCGGC | XOOOXXXXXXXXXXXXXXX |
| WV-9487 | mC * TeoAeom5CeoC * C * G * C * G * C * C * T * C * T * T * mC * mC * mC * mG * mG | CTACCCGCGCCTCTTCCCGG | XOOOXXXXXXXXXXXXXXX |
| WV-9488 | mG * GeoGeom5CeomU * C * T * C * C * T * C * A * G * A * G * mC * mU * mC * mG * mA | GGGCUCTCCTCAGAGCUCGA | XOOOXXXXXXXXXXXXXXX |
| WV-9489 | mG * GeoGeoTeomG * T * C * G * G * C * T * T * T * C * mG * mC * mC * mU * mC | GGGTGTCGGGCTTTCGCCUC | XOOOXXXXXXXXXXXXXXX |
| WV-9490 | mG * m5CeoAeoTeomC * C * G * G * G * C * C * C * G * G * mG * mC * mU * mU * mC | GCATCCGGGCCCGGGCUUC | XOOOXXXXXXXXXXXXXXX |

TABLE 1A-continued

C9orf72 Oligonucleotides.

| WAVE ID | Modified Sequence | Base sequence | Stereochemistry / Internucleotidic Linkages |
|---|---|---|---|
| WV-9491 | mC * m5CeoTeoTeomC * C * C * T * G * A * A * G * G * T * T * mC * mC * mU * mC * mC | CCTTCCCTGAAGGTTCCUCC | XOOOXXXXXXX XXXXXXXX |
| WV-9492 | mC * m5Ceom5CeoGeomG * C * C * C * C * T * A * G * C * G * C * mG * mC * mG * mA * mC | CCCGGCCCCTAGCGCGCGAC | XOOOXXXXXXX XXXXXXXX |
| WV-9493 | m5Ceo * m5Ceom5CeoGeoGeo * C * C * C * C * T * A * G * C * G * C * Geom5CeoGeoAeo * m5Ceo | CCCGGCCCCTAGCGCGCGAC | XOOOXXXXXXX XXXXOOOX |
| WV-9494 | mG * TeoGeom5CeomU * G * C * G * A * T * C * C * C * C * A * mU * mU * mC * mC * mA | GTGCUGCGATCCCAUUCCA | XOOOXXXXXXX XXXXXXXX |
| WV-9505 | mC * Sm5CeoTeom5CeomA * SC * ST * SC * RA * SC * SC * SC * RA * SC * ST * SmC * SmG * SmC * SmC * SmA | CCTCACTCACCCACTCGCCA | SOOOSSS RSSSRSSSSSSS |
| WV-9506 | mC * Sm5CeoTeom5CeomA * SC * ST * SC * SA * SC * SC * SC * RA * SC * ST * SmC * SmG * SmC * SmC * SmA | CCTCACTCACCCACTCGCCA | SOOOSSS SSSSRSSSSSSS |
| WV-9507 | mC * Sm5CeoTeom5CeomA * SC * ST * SC * SA * SC * SC * RC * SA * SC * ST * SmC * SmG * SmC * SmC * SmA | CCTCACTCACCCACTCGCCA | SOOOSSS SSSSRSSSSSSS |
| WV-9508 | mC * Sm5CeoTeom5CeomA * SC * ST * SC * RA * SC * SC * RC * SA * SC * ST * SfC *SfG *SfC *SfC *SfA | CCTCACTCACCCACTCGCCA | SOOOSSS RSSSRSSSSSSS |
| WV-9509 | mC * Sm5CeoTeom5CeomA * SC * ST * SC * RA * SC * SC * SC * RA * SC * ST * SfC *SfG *SfC *SfC *SfA | CCTCACTCACCCACTCGCCA | SOOOSSS RSSSRSSSSSSS |
| WV-9510 | mC * m5CeoTeom5CeomA * C * T * C * A * C * C * C * A * C * T * fC * fG * fC * fC * fA | CCTCACTCACCCACTCGCCA | XOOOXXXXXXX XXXXXXXX |
| WV-9694 | mC * mCmCmGmG * C * C * C * C * T * A * G * C * G * C * mGmCmGmA * mC | CCCGGCCCCTAGCGCGCGAC | XOOOXXXXXXX XXXXOOOX |
| WV-9695 | mU * mAmCmAmG * G * C * T * G * C * G * G * T * T * G * mUmUmUmC * mC | UACAGGCTGCGGTTGUUUCC | XOOOXXXXXXX XXXXOOOX |
| WV-10406 | mG * AeoTeoGeomC * C * G * C * C * T * C * C * T * C * A * mC * mU * mC * mA * mC | GATGCCGCCTCCTCACUCAC | XOOOXXXXXXX XXXXXXXX |
| WV-10407 | mA * TeoGeom5CeomC * G * C * C * T * C * C * T * C * A * C * mU * mC * mA * mC * mC | ATGCCGCCTCCTCACUCACC | XOOOXXXXXXX XXXXXXXX |
| WV-10408 | mU * Geom5Ceom5CeomG * C * C * T * C * C * T * C * A * C * T * mC * mA * mC * mC * mC | UGCCGCCTCCTCACTCACCC | XOOOXXXXXXX XXXXXXXX |
| WV-10409 | mG * m5Ceom5CeoGeomC * C * T * C * C * T * C * A * C * T * C * mA * mC * mC * mC * mA | GCCGCCTCCTCACTCACCCA | XOOOXXXXXXX XXXXXXXX |
| WV-10410 | mC * m5CeoGeom5CeomC * T * C * C * T * C * A * C * T * C * A * mC * mC * mC * mA * mC | CCGCCTCCTCACTCACCCAC | XOOOXXXXXXX XXXXXXXX |
| WV-10411 | mC * Geom5Ceom5CeomU * C * C * T * C * A * C * T * C * A * C * mC * mC * mA * mC * mU | CGCCUCCTCACTCACCCACU | XOOOXXXXXXX XXXXXXXX |
| WV-10412 | mG * m5Ceom5CeoTeomC * C * T * C * A * C * T * C * A * C * C * mC * mA * mC * mU * mC | GCCTCCTCACTCACCCACUC | XOOOXXXXXXX XXXXXXXX |
| WV-10413 | mC * m5CeoTeom5CeomC * T * C * A * C * T * C * A * C * C * C * mA * mC * mU * mC * mG | CCTCCTCACTCACCCACUCG | XOOOXXXXXXX XXXXXXXX |
| WV-10414 | mC * Teom5Ceom5CeomU * C * A * C * T * C * A * C * C * C * A * mC * mU * mC * mG * mC | CTCCUCACTCACCCACUCGC | XOOOXXXXXXX XXXXXXXX |
| WV-10415 | mU * m5Ceom5CeoTeomC * A * C * T * C * A * C * C * C * A * C * mU * mC * mG * mC * mC | UCCTCACTCACCCACUCGCC | XOOOXXXXXXX XXXXXXXX |
| WV-10416 | mC * Teom5CeoAeomC * T * C * A * C * C * C * A * C * T * C * mG * mC * mC * mA * mC | CTCACTCACCCACTCGCCAC | XOOOXXXXXXX XXXXXXXX |
| WV-10417 | mC * Aeom5CeoTeomC * A * C * C * C * A * C * T * C * G * C * mC * mA * mC * mC * mG | CACTCACCCACTCGCCACCG | XOOOXXXXXXX XXXXXXXX |

TABLE 1A-continued

C9orf72 Oligonucleotides.

| WAVE ID | Modified Sequence | Base sequence | Stereochemistry / Internucleotidic Linkages |
|---|---|---|---|
| WV-10418 | mA * m5CeoTeom5CeomA * C * C * A * C * T * C * G * C * C * mA * mC * mC * mG * mC | ACTCACCCACTCGCCACCGC | XOOOXXXXXXX XXXXXXXX |
| WV-10419 | mC * Teom5CeoAeomC * C * C * A * C * T * C * G * C * C * A * mC * mC * mG * mC * mC | CTCACCCACTCGCCACCGCC | XOOOXXXXXXX XXXXXXXX |
| WV-10420 | mU * m5CeoAeom5CeomC * C * A * C * T * C * G * C * C * A * C * mC * mG * mC * mC * mU | UCACCCACTCGCCACCGCCU | XOOOXXXXXXX XXXXXXXX |
| WV-10421 | mC * Aeom5Ceom5CeomC * A * C * T * C * G * C * C * A * C * C * mG * mC * mC * mU * mG | CACCCACTCGCCACCGCCUG | XOOOXXXXXXX XXXXXXXX |
| WV-10422 | mA * m5Ceom5Ceom5CeomA * C * T * C * G * C * C * A * C * C * G * mC * mC * mU * mG * mC | ACCCACTCGCCACCGCCUGC | XOOOXXXXXXX XXXXXXXX |
| WV-10423 | mC * m5Ceom5CeoAeomC * T * C * G * C * C * A * C * C * G * C * mC * mU * mG * mC * mG | CCCACTCGCCACCGCCUGCG | XOOOXXXXXXX XXXXXXXX |
| WV-10424 | mC * m5CeoAeom5CeomU * C * G * C * C * A * C * C * G * C * C * mU * mG * mC * mG * mC | CCACUCGCCACCGCCUGCGC | XOOOXXXXXXX XXXXXXXX |
| WV-10425 | mU * m5CeoAeom5CeomU * C * A * C * C * C * A * C * T * C * G * mC * mC * mA * mC * mC | UCACUCACCCACTCGCCACC | XOOOXXXXXXX XXXXXXXX |
| WV-10426 | fC * fC * fU * fC * fA * fC * mU * mC * mA * mC * mC * mA * mC * fU * fC * fG * fC * fC * fA | CCUCACUCACCCACUCGCCA | XXXXXXXXXXX XXXXXXXX |
| WV-10427 | m5Ceo * m5Ceo * m5Ceo * Geo * Geo * C * C * C * C * T * A * G * C * G * C * Geo * m5Ceo * Geo * Aeo * m5Ceo | CCCGGCCCCTAGCGCGCGAC | XXXXXXXXXXX XXXXXXXX |
| WV-11532 | mC * Sm5Ceon001Teon001m5Ceon001mA * SC * ST * SC * RA * SC * SC * RC * SA * SC * ST * SmC * SmG * SmC * SmC * SmA | CCTCACTCACCCACTCGCCA | SnXnXnXSSSR SSRSSSSSSSS |
| WV-11963 | mC * mCmUmCmA * C * T * C * A * C * C * C * A * C * BrdU * mCmGmCmC * mA | CCUCACTCACCCACTCGCCA | XOOOXXXXXXX XXXXOOOX |
| WV-11964 | m5Ceo * m5CeoTeom5CeoAeo * C * T * C * A * C * C * C * A * C * BrdU * m5CeoGeom5Ceom5Ceo * Aeo | CCTCACTCACCCACTCGCCA | XOOOXXXXXXX XXXXOOOX |
| WV-11965 | m5Ceo * Sm5CeoTeom5CeoAeo * SC * ST * SC * RA * SC * SC * RC * SA * SC *SBrdU * Sm5CeoGeom5Ceom5Ceo * S Aeo | CCTCACTCACCCACTCGCCA | SOOOSSS RSSRSSSSOOOS |
| WV-11966 | mC * m5CeoTeom5CeomA * C * T * C * A * C * C * C * A * C * BrdU * mC * mG * mC * mC * mA | CCTCACTCACCCACTCGCCA | XOOOXXXXXXX XXXXXXX |
| WV-11967 | mC * Sm5CeoTeom5CeomA * SC * ST * SC * RA * SC * SC * RC * SA * SC *SBrdU * SmC * SmG * SmC * SmC * SmA | CCTCACTCACCCACTCGCCA | SOOOSSS RSSRSSSSSSSS |
| WV-12048 | rUrGrGrCrGrArGrUrGrGrGrUrGrArGrUrGrArGrG | UGGCGAGUGGGUGAGUGAGG | OOOOOOOO OOOOOOOO |
| WV-12439 | m5Ceo * Teom5CeoAeom5Ceo * T * C * A * C * C * C * A * C * T * C * mG * mC * mC * mA * mC | CTCACTCACCCACTCGCCAC | XOOOXXXXXXX XXXXXXXX |
| WV-12440 | Teo * m5Ceom5CeoTeom5Ceo * A * C * T * C * A * C * C * C * A * C * mU * mC * mG * mC * mC | TCCTCACTCACCCACUCGCC | XOOOXXXXXXX XXXXXXXX |
| WV-12441 | Teo * Geom5Ceom5CeoGeo * C * C * T * C * A * C * T * C * A * C * mC * mA * mC * mC * mC | TGCCGCCTCCTCACTCACCC | XOOOXXXXXXX XXXXXXXX |
| WV-12442 | Geo * m5CeoGeom5CeoGeo * A * C * T * C * C * T * G * A * G * T * mU * mC * mC * mA * mG | GCGCGACTCCTGAGTUCCAG | XOOOXXXXXXX XXXXXXXX |
| WV-12443 | Geo * AeoGeom5CeoTeo * T * G * C * T * A * C * A * G * G * C * mU * mG * mC * mG * mG | GAGCTTGCTACAGGCUGCGG | XOOOXXXXXXX XXXXXXXX |
| WV-12444 | m5Ceo * AeoGeoGeoAeo * T * G * C * C * G * C * C * T * C * C * mU * mC * mA * mC * mU | CAGGATGCCGCCTCCUCACU | XOOOXXXXXXX XXXXXXXX |

TABLE 1A-continued

C9orf72 Oligonucleotides.

| WAVE ID | Modified Sequence | Base sequence | Stereochemistry / Internucleotidic Linkages |
|---|---|---|---|
| WV-12445 | mC * mU * mC * mA * mC * T * C * A * C * C * C * A * C * T * C * Geom5Ceom5CeoAeo * m5Ceo | CUCACTCACCCACTCGCCAC | XXXXXXXXXX XXXXOOOX |
| WV-12446 | mC * mC * mU * mC * mA * C * T * C * A * C * C * C * A * C * T * m5CeoGeom5Ceom5Ceo * Aeo | CCUCACTCACCCACTCGCCA | XXXXXXXXXX XXXXOOOX |
| WV-12447 | mU * mC * mC * mU * mC * A * C * T * C * A * C * C * C * A * C * Teom5CeoGeom5Ceo * m5Ceo | UCCUCACTCACCCACTCGCC | XXXXXXXXXX XXXXOOOX |
| WV-12448 | mU * mG * mC * mC * mG * C * C * T * C * C * T * C * A * C * T * m5CeoAeom5Ceom5Ceo * m5Ceo | UGCCGCCTCCTCACTCACCC | XXXXXXXXXX XXXXOOOX |
| WV-12449 | mG * mC * mG * mC * mG * A * C * T * C * C * T * G * A * G * T * Teom5Ceom5CeoAeo * Geo | GCGCGACTCCTGAGTTCCAG | XXXXXXXXXX XXXXOOOX |
| WV-12450 | mG * mA * mG * mC * mU * T * G * C * T * A * C * A * G * G * C * TeoGeom5CeoGeo * Geo | GAGCUTGCTACAGGCTGCGG | XXXXXXXXXX XXXXOOOX |
| WV-12451 | mC * mA * mG * mG * mA * T * G * C * C * G * C * C * T * C * C * Teom5CeoAeom5Ceo * Teo | CAGGATGCCGCCTCCTCACT | XXXXXXXXXX XXXXOOOX |
| WV-12480 | m5Ceo * Teom5CeoAeom5Ceo * T * C * A * C * C * C * A * C * T * C * Geom5Ceom5CeoAeo * m5Ceo | CTCACTCACCCACTCGCCAC | XOOOXXXXXX XXXXOOOX |
| WV-12481 | Teo * m5Ceom5CeoTeom5Ceo * A * C * T * C * A * C * C * C * A * C * Teom5CeoGeom5Ceo * m5Ceo | TCCTCACTCACCCACTCGCC | XOOOXXXXXX XXXXOOOX |
| WV-12482 | Teo * Geom5Ceom5CeoGeo * C * C * T * C * C * T * C * A * C * T * m5CeoAeom5Ceom5Ceo * m5Ceo | TGCCGCCTCCTCACTCACCC | XOOOXXXXXX XXXXOOOX |
| WV-12483 | Geo * m5CeoGeom5CeoGeo * A * C * T * C * C * T * G * A * G * T * Teom5Ceom5CeoAeo * Geo | GCGCGACTCCTGAGTTCCAG | XOOOXXXXXX XXXXOOOX |
| WV-12484 | Geo * AeoGeom5CeoTeo * T * G * C * T * A * C * A * G * G * C * TeoGeom5CeoGeo * Geo | GAGCTTGCTACAGGCTGCGG | XOOOXXXXXX XXXXOOOX |
| WV-12485 | m5Ceo * AeoGeoGeoAeo * mA * T * G * C * C * G * C * C * T * C * C * Teom5CeoAeom5Ceo * Teo | CAGGAATGCCGCCTCCTCACT | XOOOXXXXXX XXXXOOOX |
| WV-12486 | m5Ceo * AeoGeoGeoAeo * T * G * C * C * G * C * C * T * CAGGATGCCGCCTCCTCACT * C * Teom5CeoAeom5Ceo * Teo | CAGGATGCCGCCTCCTCACT | XOOOXXXXXX XXXXOOOX |
| WV-12581 | mC * m5CeoTeom5CeomA * mC * mU * mC * mA * mC * mC * mC * mA * mC * mU * mC * mG * mC * mC * mA | CCTCACUCACCCACUCGCCA | XOOOXXXXXX XXXXXXXX |
| WV-12582 | m51C * m5CeoTeom5CeomA * mC * mU * mC * mA * mC * mC * mC * mA * mC * mU * mC * mG * mC * mC * 1A | CCTCACUCACCCACUCGCCA | XOOOXXXXXX XXXXXXXX |
| WV-12583 | fC * m5CeoTeom5CeofA * mC * mU * mC * mA * mC * mC * mC * mA * mC * mU * fC * fG * fC * fC * fA | CCTCACUCACCCACUCGCCA | XOOOXXXXXX XXXXXXXX |
| WV-12893 | mC * Sm5CeoTeom5CeomA * SC * ST * SC * RA * SC * SC * SC * SA * SC * SBrdU * SmC * SmG * SmC * SmC * SmA | CCTCACTCACCCACTCGCCA | SOOOSSS RSSSSSSSSS SS |
| WV-13305 | m5Ceo * Rm5Ceon001Teon001m5Ceon001Aeo *R C *S T * SC * RA * SC * SC * SC * RC * SA * SC * ST * SmC * SmG * SmC * SmC * SmA | CCTCACTCACCCACTCGCCA | RnXnXnXRSSRS SRSSSSSSSS |
| WV-13306 | m5Ceo * Sm5CeoTeom5CeoAeo * RC * ST * SC * RA * SC * SC * RC * SA * SC * ST * SmC * SmG * SmC * SmC * SmA | CCTCACTCACCCACTCGCCA | SOOORSSRSS RSSSSSSS |
| WV-13307 | m5Ceo * Sm5Ceon001Teon001m5Ceon001Aeo * RC * ST * SC * RA * SC * SC * RC * SA * SC * ST * SmC * SmG * SmC * SmC * SmA | CCTCACTCACCCACTCGCCA | SnXnXnXRSSR SSRSSSSSSSS |
| WV-13308 | m5Ceo * Rm5CeoTeom5CeoAeo * RC * ST * SC * RA * SC * SC * SC * RA * SC * ST * SmC * SmG * SmC * SmC * SmA | CCTCACTCACCCACTCGCCA | ROOORSSRSSS RSSSSSSS |
| WV-13309 | m5Ceo * Rm5Ceon001Teon001m5Ceon001Aeo * RC * ST * SC * RA * SC * SC * SC * RA * SC * ST * SmC * SmG * SmC * SmC * SmA | CCTCACTCACCCACTCGCCA | RnXnXnXRSSRSSS RSSSSSSS |

TABLE 1A-continued

C9orf72 Oligonucleotides.

| WAVE ID | Modified Sequence | Base sequence | Stereochemistry / Internucleotidic Linkages |
|---|---|---|---|
| WV-13310 | m5Ceo * Sm5CeoTeom5CeoAeo * RC * ST * SC * RA * SC * SC * SC * RA * SC * ST * SmC * SmG * SmC * SmC * SmA | CCTCACTCACCCACTCGCCA | SOOORSSRSSSRSSSSSSS |
| WV-13311 | m5Ceo * Sm5Ceon001Teon001m5Ceon001Aeo * RC * ST * SC * RA * SC * SC * SC * RA * SC * ST * SmC * SmG * SmC * SmC * SmA | CCTCACTCACCCACTCGCCA | SnXnXnXRSSRSSSRSSSSSSSS |
| WV-13312 | mc * Sm5Ceon001Teon001m5Ceon001mA * SC * ST * SC * RA * SC * SC * SC * SA * SC * ST * SmC * SmG * SmC * SmC * SmA | CCTCACTCACCCACTCGCCA | SnXnXnXSSSRSSSSSSSSSS |
| WV-13313 | m5Ceo * Rm5Ceon001Teon001m5Ceon001Aeo * RC * ST * SC * RA * SC * SC * SC * SA * SC * ST * SmC * SmG * SmC * SmC * SmA | CCTCACTCACCCACTCGCCA | RnXnXnXRSSRSSSSSSSSSSS |
| WV-13803 | Teo * Geon001m5Ceon001m5Ceon001Geo * C * C * T * C * C * T * C * A * C * T * mC * mA * mC * mC * mC | TGCCGCCTCCTCACTCACCC | XnXnXnXXXXXXXXXXXXXXXX |
| WV-13804 | Teo * Geom5Ceom5CeoGeo * C * C * T * C * C * T * C * A * C * T * mCn001mAn001mCn001mC * mc | TGCCGCCTCCTCACTCACCC | XOOOXXXXXXXXXXXnXnXnXX |
| WV-13805 | Teo * Geon001m5Ceon001m5Ceon001Geo * C * C * T * C * C * T * C * A * C * T * mCn001mAn001mCn001mC * mc | TGCCGCCTCCTCACTCACCC | XnXnXnXXXXXXXXXXXXnXnXnXX |
| WV-14552 | m5Ceo * Rm5CeoTeom5CeoAeo * RC * ST * SC * RA * SC * SC * RC * SA * SC * ST * Rm5Ceo * SmG * SmC * SmC * SmA | CCTCACTCACCCACTCGCCA | ROOORSSRSSRSSSRSSSSS |
| WV-14553 | m5Ceo * Rm5Ceon001Teon001m5Ceon001Aeo * RC * ST * SC * RA * SC * SC * RC * SA * SC * ST * Rm5Ceo * SmG * SmC * SmC * SmA | CCTCACTCACCCACTCGCCA | RnXnXnXRSSRSSRSSSRSSSS |
| WV-14554 | m5Ceo * Rm5CeoTeom5CeoAeo * RC * ST * SC * RA * SC * SC * SC * RA * SC * ST * Rm5Ceo * SmG * SmC * SmC * SmA | CCTCACTCACCCACTCGCCA | ROOORSSRSSSRSSSRSSSSS |
| WV-14555 | m5Ceo * Rm5Ceon001Teon001m5Ceon001Aeo * RC * ST * SC * RA * SC * SC * SC * RA * SC * ST * Rm5Ceo * SmG * SmC * SmC * SmA | CCTCACTCACCCACTCGCCA | RnXnXnXRSSRSSSRSSSRSSSSS |
| WV-14758 | mC * Sm5CeoTeom5CeomA * SC * ST * SC * RA * SC * SC * RC * SA * SC * ST * SmCmGmCmCmA | CCTCACTCACCCACTCGCCA | SOOOSSSRSSRSSSSOOOO |
| WV-14772 | mC * Sm5CeoTeom5CeomA * SC * ST * SC * SA * SC * SC * SC * SA * SC * ST * SmC * SmG * SmC * SmC * SmA | CCTCACTCACCCACTCGCCA | SOOOSSSSSSSSSSSSSSS SSS |
| WV-15049 | mU * Sm5CeoTeom5CeomA * SC * ST * SC * RA * SC * SC * RC * SA * SC * ST * SmU * SmG * SmU * SmU * SmA | UCTCACTCACCCACTUGUUA | SOOOSSSRSSRSSSSSSSSS |
| WV-15050 | mU * Sm5CeoTeom5CeomA * SC * ST * SC * RA * SC * SC * RC * SA * SC * ST * SmG * SmA * SmC * SmU * SmC | UCTCACTCACCCACTGACUC | SOOOSSSRSSRSSSSSSSSS |
| WV-15051 | mC * Sm5CeoTeom5CeomA * SG * SG * RC * ST * SG * RG * ST * ST * RA * ST * SmC * SmG * SmC * SmC * SmA | CCTCAGGCTGGTTATCGCCA | SOOOSSRSSRSSRSSSSSSSS |
| WV-8444 | L001mA * mCmCmGmG * G * C * A * G * C * A * G * G * G * A * mCmGmGmC * mU | ACCGGGCAGCAGGGACGGCU | OXOOOXXXXXXXXXXXOOX |
| WV-8445 | Mod024L001mA * mCmCmGmG * G * C * A * G * C * A * G * G * G * A * mCmGmGmC * mU | ACCGGGCAGCAGGGACGGCU | OXOOOXXXXXXXXXXXOOX |
| WV-8446 | Mod059L001mA * mCmCmGmG * G * C * A * G * C * A * G * G * G * A * mCmGmGmC * mU | ACCGGGCAGCAGGGACGGCU | OXOOOXXXXXXXXXXXOOX |
| WV-8447 | Mod007L001mA * mCmCmGmG * G * C * A * G * C * A * G * G * G * A * mCmGmGmC * mU | ACCGGGCAGCAGGGACGGCU | OXOOOXXXXXXXXXXXOOX |

TABLE 1B

Malat1 Oligonucleotides.

| WAVE ID | Sequence | Naked Sequence | Stereochemistry |
|---|---|---|---|
| WV-3174 | mU * mG * mC * mC * mA * G * G * C * T * G * T * T * A * T * mG * mA * mC * mU * mC | UGCCAGGCTG GTTATGACUC | XXXXXXXXXX XXXXXXXX |
| WV-8103 | mU * SmGmC * SmC * SmA * SG * SG * SC * ST * SG * SG * ST * ST * RA * ST * SmGmAmC * SmU * SmC | UGCCAGGCTG GTTATGACUC | SOSSSSSSSSSS RSSOOSS |
| WV-8104 | mU * SmGmC * SmC * SmA * SG * SG * SC * ST * SG * SG * ST *RT * SA * ST * SmGmAmC * SmU * SmC | UGCCAGGCTG GTTATGACUC | SOSSSSSSSSSR SSSOOSS |
| WV-8105 | mU * SmGmC * SmC * SmA * SG * SG * SC * ST * SG * SG *RT * ST * SA * ST * SmGmAmC * SmU * SmC | UGCCAGGCTG GTTATGACUC | SOSSSSSSSSRS SSSOOSS |
| WV-8106 | mU * SmGmC * SmC * SmA * SG * SG * SC * ST * SG * RG * ST * ST * RA * ST * SmGmAmC * SmU * SmC | UGCCAGGCTG GTTATGACUC | SOSSSSSSSRSS RSSOOSS |
| WV-8107 | mU * SmGmC * SmC * SmA * SG * SG * SC *RT * SG * SG *RT * ST * SA * ST * SmGmAmC * SmU * SmC | UGCCAGGCTG GTTATGACUC | SOSSSSSRSSRS SSSOOSS |
| WV-8108 | mU * SmGmC * SmC * SmA * SG * SG * RC * ST * SG * RG * ST * ST * RA * ST * SmGmAmC * SmU * SmC | UGCCAGGCTG GTTATGACUC | SOSSSSRSSRSS RSSOOSS |
| WV-8110 | mU * mGmC * mC * mA * G * G * C * T * G * T * T * A * T * mGmAmC * mU * mC | UGCCAGGCTG GTTATGACUC | XOXXXXXXXXXX XXOOXX |
| WV-8097 | mU * SmGm5Ceom5CeomA * SG * SG * SC * ST * SG * SG * ST * ST * RA * ST * SmGmAm5CeomU * SmC | UGCCAGGCTG GTTATGACUC | SOOOSSSSSSS SRSSOOOS |
| WV-8098 | mU * SmGm5Ceom5CeomA * SG * SG * SC * ST * SG * SG * ST *RT * SA * ST * SmGmAm5CeomU * SmC | UGCCAGGCTG GTTATGACUC | SOOOSSSSSSS RSSSOOOS |
| WV-8099 | mU * SmGm5Ceom5CeomA * SG * SG * SC * ST * SG * SG *RT * ST * SA * ST * SmGmAm5CeomU * SmC | UGCCAGGCTG GTTATGACUC | SOOOSSSSSSR SSSSOOOS |
| WV-8100 | mU * SmGm5Ceom5CeomA * SG * SG * SC * ST * SG * RG * ST * ST * RA * ST * SmGmAm5CeomU * SmC | UGCCAGGCTG GTTATGACUC | SOOOSSSSSRS SRSSOOOS |
| WV-8101 | mU * SmGm5Ceom5CeomA * SG * SG * SC *RT * SG * SG *RT * ST * SA * ST * SmGmAm5CeomU * SmC | UGCCAGGCTG GTTATGACUC | SOOOSSSRSSR SSSSOOOS |
| WV-8102 | mU * SmGm5Ceom5CeomA * SG * SG * RC * ST * SG * RG * ST * ST * RA * ST * SmGmAm5CeomU * SmC | UGCCAGGCTG GTTATGACUC | SOOOSSRSSRS SRSSOOOS |
| WV-8109 | mU * mGm5Ceom5CeomA * G * G * C * T * G * T * T * A * T * mGmAm5CeomU * mC | UGCCAGGCTG GTTATGACUC | XOOOXXXXXXX XXXX OOOX |
| WV-8448 | Mod059L001mU * mG * mC * mC * mA * G * G * C * T * G * T * T * A * T * mG * mA * mC * mU * mC | UGCCAGGCTG GTTATGACUC | OXXXXXXXXXX XXXXXXXX |
| WV-8552 | Teo * Geom5Ceom5CeoAeo * G * G * C * T * G * T * T * A * T * mG * mA * mC * mU * mC | TGCCAGGCTG GTTATGACUC | XOOOXXXXXXX XXX XXXX |
| WV-8553 | mU * Geom5Ceom5Ceo * mA * G * G * C * T * G * T * T * A * T * mG * mA * mC * mU * mC | UGCCAGGCTG GTTATGACUC | XOOXXXXXXXX XXX XXXXX |
| WV-8554 | Teo * Geom5Ceom5CeoAeo * G * G * C * T * G * T * T * A * T * mGmAmC * mU * mC | TGCCAGGCTG GTTATGACUC | XOOOXXXXXXX XXXX OOXX |
| WV-8555 | mU * Geom5Ceom5Ceo * mA * G * G * C * T * G * T * T * A * T * mGmAmC * mU * mC | UGCCAGGCTG GTTATGACUC | XOOXXXXXXXX XXX XOOXX |
| WV-8556 | mU * Geom5Ceom5CeomA * G * G * C * T * G * T * T * A * T * mG * mA * mC * mU * mC | UGCCAGGCTG GTTATGACUC | XOOOXXXXXXX XX XXXX |
| WV-8557 | mU * Geom5Ceom5CeomA * G * G * C * T * G * T * T * A * T * mGmAmC * mU * mC | UGCCAGGCTG GTTATGACUC | XOOOXXXXXXX XX OOXX |
| WV-8570 | Teo * RGeom5Ceom5CeoAeo * RG * SG * SC * ST * SG * SG * ST * ST * RA * ST * SmG * SmA * SmC * SmU * SmC | TGCCAGGCTG GTTATGACUC | ROOORSSSSSSR SSSSSS |
| WV-8571 | Teo * RGeom5Ceom5CeoAeo * RG * SG * SC * ST * SG * SG * ST *RT * SA * ST * SmG * SmA * SmC * SmU * SmC | TGCCAGGCTG GTTATGACUC | ROOORSSSSSR SSSSSS |
| WV-8572 | Teo * RGeom5Ceom5CeoAeo * RG * SG * SC * ST * SG * SG *RT * ST * SA * ST * SmG * SmA * SmC * SmU * SmC | TGCCAGGCTG GTTATGACUC | ROOORSSSSRS SSSSSS |

TABLE 1B-continued

Malat1 Oligonucleotides.

| WAVE ID | Sequence | Naked Sequence | Stereochemistry |
|---|---|---|---|
| WV-8573 | Teo * RGeom5Ceom5CeoAeo * RG * SG * SC * ST * SG * RG * ST * ST * RA * ST * SmG * SmA * SmC * SmU * SmC | TGCCAGGCTGGTTATGACUC | ROOORSSSSRSSRSSSSSS |
| WV-8574 | Teo * RGeom5Ceom5CeoAeo * RG * SG *SC *RT * SG * SG *RT * ST * SA * ST * SmG * SmA * SmC * SmU * SmC | TGCCAGGCTGGTTATGACUC | ROOORSSRSSRSSSSSSSS |
| WV-8575 | Teo * RGeom5Ceom5CeoAeo * RG * SG * RC * ST * SG * RG * ST * ST * RA * ST * SmG * SmA * SmC * SmU * SmC | TGCCAGGCTGGTTATGACUC | ROOORSRSSRSSRSSSSSS |
| WV-8576 | Teo * RGeom5Ceom5CeoAeo * RG * SG * SC * ST * SG * SG * ST * ST * RA * ST * SmGmAmC * SmU * SmC | TGCCAGGCTGGTTATGACUC | ROOORSSSSSSSRSSOOSS |
| WV-8577 | Teo * RGeom5Ceom5CeoAeo * RG * SG * SC * ST * SG * SG * ST *RT * SA * ST * SmGmAmC * SmU * SmC | TGCCAGGCTGGTTATGACUC | ROOORSSSSSSRSSSOOSS |
| WV-8578 | Teo * RGeom5Ceom5CeoAeo * RG * SG * SC * ST * SG * SG *RT * ST * SA * ST * SmGmAmC * SmU * SmC | TGCCAGGCTGGTTATGACUC | ROOORSSSSSRSSSSOOSS |
| WV-8579 | Teo * RGeom5Ceom5CeoAeo * RG * SG * SC * ST * SG * RG * ST * ST * RA * ST * SmGmAmC * SmU * SmC | TGCCAGGCTGGTTATGACUC | ROOORSSSSRSSSSOOSS |
| WV-8580 | Teo * RGeom5Ceom5CeoAeo * RG * SG *SC *RT * SG * SG *RT * ST * SA * ST * SmGmAmC * SmU * SmC | TGCCAGGCTGGTTATGACUC | ROOORSSRSSRSSSSOOSS |
| WV-8581 | Teo * RGeom5Ceom5CeoAeo * RG * SG * RC * ST * SG * RG * ST * ST * RA * ST * SmGmAmC * SmU * SmC | TGCCAGGCTGGTTATGACUC | ROOORSRSSRSSRSSOOSS |
| WV-8582 | mU * SGeom5Ceom5CeomA * SG * SG * SC * ST * SG * SG * ST * ST * RA * ST * SmG * SmA * SmC * SmU * SmC | UGCCAGGCTGGTTATGACUC | SOOOSSSSSSSSRSSSSSS |
| WV-8583 | mU * SGeom5Ceom5CeomA * SG * SG * SC * ST * SG * SG * ST *RT * SA * ST * SmG * SmA * SmC * SmU * SmC | UGCCAGGCTGGTTATGACUC | SOOOSSSSSSSRSSSSSSS |
| WV-8584 | mU * SGeom5Ceom5CeomA * SG * SG * SC * ST * SG * SG *RT * ST * SA * ST * SmG * SmA * SmC * SmU * SmC | UGCCAGGCTGGTTATGACUC | SOOOSSSSSSRSSSSSSSS |
| WV-8585 | mU * SGeom5Ceom5CeomA * SG * SG * SC * ST * SG * RG * ST * ST * RA * ST * SmG * SmA * SmC * SmU * SmC | UGCCAGGCTGGTTATGACUC | SOOOSSSSSRSSRSSSSSS |
| WV-8586 | mU * SGeom5Ceom5CeomA * SG * SG * SC *RT * SG * SG *RT * ST * SA * ST * SmG * SmA * SmC * SmU * SmC | UGCCAGGCTGGTTATGACUC | SOOOSSSRSSRSSSSSSSS |
| WV-8587 | mU * SGeom5Ceom5CeomA * SG * SG * RC * ST * SG * RG * ST * ST * RA * ST * SmG * SmA * SmC * SmU * SmC | UGCCAGGCTGGTTATGACUC | SOOOSSRSSRSSRSSSSSS |
| WV-8588 | mU * SGeom5Ceom5CeomA * SG * SG * SC * ST * SG * SG * ST * ST * RA * ST * SmGmAmC * SmU * SmC | UGCCAGGCTGGTTATGACUC | SOOOSSSSSSSSSRSSOOSS |
| WV-8589 | mU * SGeom5Ceom5CeomA * SG * SG * SC * ST * SG * SG * ST *RT * SA * ST * SmGmAmC * SmU * SmC | UGCCAGGCTGGTTATGACUC | SOOOSSSSSSSRSSSOOSS |
| WV-8590 | mU * SGeom5Ceom5CeomA * SG * SG * SC * ST * SG * SG *RT * ST * SA * ST * SmGmAmC * SmU * SmC | UGCCAGGCTGGTTATGACUC | SOOOSSSSSSRSSSSOOSS |
| WV-8591 | mU * SGeom5Ceom5CeomA * SG * SG * SC * ST * SG * RG * ST * ST * RA * ST * SmGmAmC * SmU * SmC | UGCCAGGCTGGTTATGACUC | SOOOSSSSSRSSRSSOOSS |
| WV-8592 | mU * SGeom5Ceom5CeomA * SG * SG * SC *RT * SG * SG *RT * ST * SA * ST * SmGmAmC * SmU * SmC | UGCCAGGCTGGTTATGACUC | SOOOSSSRSSRSSSSOOSS |
| WV-8593 | mU * SGeom5Ceom5CeomA * SG * SG * RC * ST * SG * RG * ST * ST * RA * ST * SmGmAmC * SmU * SmC | UGCCAGGCTGGTTATGACUC | SOOOSSRSSRSSRSSOOSS |
| WV-8809 | Mod053L001Geo * Geo * Geo * Teo * m5Ceo * A * G * C * T * G * C * C * A * A * T * Geo * m5Ceo * Teo * Aeo * Geo | GGGTCAGCTGCCAATGCTAG | OXXXXXXXXXXXXXXXXXX |
| WV-8810 | Mod059L001Geo * Geo * Geo * Teo * m5Ceo * A * G * C * T * G * C * C * A * A * T * Geo * m5Ceo * Teo * Aeo * Geo | GGGTCAGCTGCCAATGCTAG | OXXXXXXXXXXXXXXXXXX |
| WV-9058 | mU * SGeom5Ceom5CeomA * SG * SG * RC * ST * SG * RG * ST * ST * RA * ST * SmGmA * SmC * SmU * SmC | UGCCAGGCTGGTTATGACUC | SOOOSSRSSRSSRSSOSSS |
| WV-9059 | mU * SGeom5Ceom5CeomA * SG * SG * RC * ST * SG * RG * ST * ST * RA * ST * SmG * SmAmC * SmU * SmC | UGCCAGGCTGGTTATGACUC | SOOOSSRSSRSSRSSSOSS |

TABLE 1B-continued

Malat1 Oligonucleotides.

| WAVE ID | Sequence | Naked Sequence | Stereochemistry |
|---|---|---|---|
| WV-9060 | mU * Geom5Ceom5CeomA * G * G * C * T * G * T * T * A * T * mGmA * mC * mU * mC | UGCCAGGCTG GTTATGACUC | XOOOXXXXXXXX XXX OXXX |
| WV-9061 | mU * Geom5Ceom5CeomA * G * G * C * T * G * T * T * A * T * mG * mAmC * mU * mC | UGCCAGGCTG GTTATGACUC | XOOOXXXXXXXX XXX XOXX |
| WV-9696 | L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSRS SRSSSSSS |
| WV-9697 | Mod007L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-9698 | Mod059L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-11114 | Mod091L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-11533 | mU * SGeon001m5Ceon001m5Ceon001mA * SG * SG * RC * ST * SG * RG * ST * ST * RA * ST * SmG * SmA * SmC * SmU * SmC | UGCCAGGCTG GTTATGACUC | SnXnXnXSSRSS RSSRSSSSSS |
| WV-12110 | mU * SGeom5Ceom5CeoAeo * RG * SG * RC * ST * SG * RG * ST * ST * RA * ST * SmG * SmA * SmC * SmU * SmC | UGCCAGGCTG GTTATGACUC | SOOORSRSSR SSRSSSSSS |
| WV-12111 | mU * SGeom5Ceom5CeoAeo * RG * SG * RC * ST * SG * RG * ST * ST * SA * ST * SmG * SmA * SmC * SmU * SmC | UGCCAGGCTG GTTATGACUC | SOOORSRSSR SSSSSSSSS |
| WV-12112 | mU * SGeom5Ceom5CeoAeoG * SG * RC * ST * SG * RG * ST * ST * RA * ST * SmG * SmA * SmC * SmU * SmC | UGCCAGGCTG GTTATGACUC | SOOOOSRSSR SSRSSSSSS |
| WV-12113 | mU * Geom5Ceom5CeoAeo * G * G * C * T * G * T * T * A * T * mG * mA * mC * mU * mC | UGCCAGGCTG GTTATGACUC | XOOOOXXXXXXX XXXX XXXX |
| WV-12114 | mU * Geom5Ceom5CeoAeoG * G * C * T * G * T * T * A * T * mG * mA * mC * mU * mC | UGCCAGGCTG GTTATGACUC | XOOOOXXXXX XXXXXX XXX |
| WV-12503 | Mod001L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-12504 | Mod001L001mU * SGeon001m5Ceon001m5Ceon001mA * SG * SG * RC * ST * SG * RG * ST * ST * RA * ST * SmG * SmA * SmC * SmU * SmC | UGCCAGGCTG GTTATGACUC | OSnXnXnXSSR SSRSRSSSSSS |
| WV-12505 | L001mU * SGeon001m5Ceon001m5Ceon001mA * SG * SG * RC * ST * SG * RG * ST * ST * RA * ST * SmG * SmA * SmC * SmU * SmC | UGCCAGGCTG GTTATGACUC | OSnXnXnXSSR SSRSSRSSSSSS |
| WV-13303 | mU * SGeom5Ceom5CeomA * SG * SG * RC * ST * SG * RG * ST * ST * RA * ST * SmGn001mAn001mCn001mU * SmC | UGCCAGGCTG GTTATGACUC | SOOOSSRSSRSS RSSnXnXnXS |
| WV-13304 | mU * SGeon001m5Ceon001m5Ceon001mA * SG * SG * RC * ST * SG * RG * ST * ST * RA * ST * SmGn001mAn001mCn001mU * SmC | UGCCAGGCTG GTTATGACUC | SnXnXnXSSRSSR SSRSSnXnXnXS |
| WV-13809 | Mod097L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-14087 | mU * SGeom5Ceom5CeomA * SG * SG * SC *RT * SG * SG * ST * ST * SA * ST * SmG * SmA * SmC * SmU * SmC | UGCCAGGCTG GTTATGACUC | SOOOSSRSSSS SSSSSSS |
| WV-14349 | Mod098L001mU * SGeom5Ceom5CeomA * SG * SG * RC * ST * SG * RG * ST * ST * RA * ST * SmG * SmA * SmC * SmU * SmC | UGCCAGGCTG GTTATGACUC | OSOOOSSRSSR SSRSSSSSS |
| WV-14556 | mUn001Geon001m5Ceon001m5CeomA * SG * SG * RC * ST * SG * RG * ST * ST * RA * ST * SmG * SmA * SmC * SmU * SmC | UGCCAGGCTG GTTATGACUC | nXnXnXOSSRSS RSSRSSSSSS |
| WV-14557 | mUn001Geon001m5Ceom5Ceon001mA * SG * SG * RC * ST * SG * RG * ST * ST * RA * ST * SmG * SmA * SmC * SmU * SmC | UGCCAGGCTG GTTATGACUC | nXnXOnXSSRSS RSSRSSSSSS |
| WV-14558 | mUn001Geon001m5Ceom5CeomAn001G * SG * RC * ST * SG * RG * ST * ST * RA * ST * SmG * SmA * SmC * SmU * SmC | UGCCAGGCTG GTTATGACUC | nXnXOOnXSSRSS RSSRSSSSSS |
| WV-14559 | mUn001Geom5Ceon001m5Ceon001mA * SG * SG * RC * ST * SG * RG * ST * ST * RA * ST * SmG * SmA * SmC * SmU * SmC | UGCCAGGCTG GTTATGACUC | nXOnXnXSSRSS RSSRSSSSSS |
| WV-14560 | mUn001Geom5Ceon001m5CeomAn001G * SG * RC * ST * SG * RG * ST * ST * RA * ST * SmG * SmA * SmC * SmU * SmC | UGCCAGGCTG GTTATGACUC | nXOnXOnXSRS SRSSRSSSSSSS |

TABLE 1B-continued

Malat1 Oligonucleotides.

| WAVE ID | Sequence | Naked Sequence | Stereochemistry |
|---|---|---|---|
| WV-14561 | mUn001Geom5Ceom5Ceon001mAn001G * SG * RC * ST * SG * RG * ST * ST * RA * ST * SmG * SmA * SmC * SmU * SmC | UGCCAGGCTGGTTATGACUC | nXOOnXnXSRSSRSSRSSSSSSS |
| WV-14562 | mU * SGeon001m5Ceon001m5CeomAn001G * SG * RC * ST * SG * RG * ST * ST * RA * ST * SmG * SmA * SmC * SmU * SmC | UGCCAGGCTGGTTATGACUC | SnXnXOnXSRSSRSSRSSSSSSS |
| WV-14563 | mU * SGeon001m5Ceon5Ceon001mAn001G * SG * RC * ST * SG * RG * ST * ST * RA * ST * SmG * SmA * SmC * SmU * SmC | UGCCAGGCTGGTTATGACUC | SnXOnXnXSRSSRSSRSSSSSSS |
| WV-14564 | mU * SGeom5Ceon001m5Ceon001mAn001G * SG * RC * ST * SG * RG * ST * ST * RA * ST * SmG * SmA * SmC * SmU * SmC | UGCCAGGCTGGTTATGACUC | SOnXnXnXSRSSRSSRSSSSSSS |
| WV-14733 | mU * SGeom5Ceom5CeomA * SG * SG * SC * ST * SG * SG * ST * ST * SA * ST * SmG * SmA * SmC * SmU * SmC | UGCCAGGCTGGTTATGACUC | SOOOSSSSSSSSSSSSSS |
| WV-14734 | mU * RGeom5Ceom5CeomA * SG * SG * RC * ST * SG * RG * ST * ST * RA * ST * SmG * SmA * SmC * SmU * SmC | UGCCAGGCTGGTTATGACUC | ROOOSSRSSRSSRSSSSSSS |
| WV-14735 | mU * SGeom5Ceom5CeomA * RG * SG * RC * ST * SG * RG * ST * ST * RA * ST * SmG * SmA * SmC * SmU * SmC | UGCCAGGCTGGTTATGACUC | SOOORSRSSRSSRSSSSSSS |
| WV-14736 | mU * SGeom5Ceom5CeomA * SG * SG * RC * ST * SG * RG * ST * ST * RA * ST * RmG * SmA * SmC * SmU * SmC | UGCCAGGCTGGTTATGACUC | SOOOSSRSSRSSRSSRSSSSS |
| WV-14737 | mU * SGeom5Ceom5CeomA * SG * SG * RC * ST * SG * RG * ST * ST * RA * ST * SmG * SmA * SmC * SmU * RmC | UGCCAGGCTGGTTATGACUC | SOOOSSRSSRSSRSSSSSSSR |
| WV-14771 | mU * Geon001m5Ceon001m5Ceon001mA * G * G * C * T * G * T * T * A * T * mG * mA * mC * mU * mC | UGCCAGGCTGGTTATGACUC | XnXnXnXXXXXXXXXXX XXXXX |
| WV-15310 | mU * RGeom5Ceom5CeomA * SG * SG * SC * ST * SG * SG * ST * ST * SA * ST * SmG * SmA * SmC * SmU * SmC | UGCCAGGCTGGTTATGACUC | ROOOSSSSSSSSSSSSSSS |
| WV-15311 | mU * SGeom5Ceom5CeomA * RG * SG * SC * ST * SG * SG * ST * ST * SA * ST * SmG * SmA * SmC * SmU * SmC | UGCCAGGCTGGTTATGACUC | SOOORSSSSSSSSSSSSSS |
| WV-15312 | mU * SGeom5Ceom5CeomA * SG * RG * SC * ST * SG * SG * ST * ST * SA * ST * SmG * SmA * SmC * SmU * SmC | UGCCAGGCTGGTTATGACUC | SOOOSRSSSSSSSSSSSSS |
| WV-15313 | mU * SGeom5Ceom5CeomA * SG * SG * RC * ST * SG * SG * ST * ST * SA * ST * SmG * SmA * SmC * SmU * SmC | UGCCAGGCTGGTTATGACUC | SOOOSSRSSSSSSSSSSSS |
| WV-15314 | mU * SGeom5Ceom5CeomA * SG * SG * SC * ST * RG * SG * ST * ST * SA * ST * SmG * SmA * SmC * SmU * SmC | UGCCAGGCTGGTTATGACUC | SOOOSSSSRSSSSSSSSSS |
| WV-15315 | mU * SGeom5Ceom5CeomA * SG * SG * SC * ST * SG * RG * ST * ST * SA * ST * SmG * SmA * SmC * SmU * SmC | UGCCAGGCTGGTTATGACUC | SOOOSSSSSRSSSSSSSSS |
| WV-15316 | mU * SGeom5Ceom5CeomA * SG * SG * SC * ST * SG * SG * ST * ST * SA *RT * SmG * SmA * SmC * SmU * SmC | UGCCAGGCTGGTTATGACUC | SOOOSSSSSSSSSSRSSSSS |
| WV-15317 | mU * SGeom5Ceom5CeomA * SG * SG * SC * ST * SG * SG * ST * ST * SA * ST * RmG * SmA * SmC * SmU * SmC | UGCCAGGCTGGTTATGACUC | SOOOSSSSSSSSSSSRSSSS |
| WV-15318 | mU * SGeom5Ceom5CeomA * SG * SG * SC * ST * SG * SG * ST * ST * SA * ST * SmG * RmA * SmC * SmU * SmC | UGCCAGGCTGGTTATGACUC | SOOOSSSSSSSSSSSSRSSS |
| WV-15319 | mU * SGeom5Ceom5CeomA * SG * SG * SC * ST * SG * SG * ST * ST * SA * ST * SmG * SmA * RmC * SmU * SmC | UGCCAGGCTGGTTATGACUC | SOOOSSSSSSSSSSSSSRSS |
| WV-15320 | mU * SGeom5Ceom5CeomA * SG * SG * SC * ST * SG * SG * ST * ST * SA * ST * SmG * SmA * SmC * RmU * SmC | UGCCAGGCTGGTTATGACUC | SOOOSSSSSSSSSSSSSSRS |
| WV-15321 | mU * SGeom5Ceom5CeomA * SG * SG * SC * ST * SG * SG * ST * ST * SA * ST * SmG * SmA * SmC * SmU * RmC | UGCCAGGCTGGTTATGACUC | SOOOSSSSSSSSSSSSSSSR |
| WV-15351 | mU * SGeom5Ceom5CeomA * SG * SGn001C * ST * SGn001G * ST * STn001A * ST * SmG * SmA * SmC * SmU * SmC | UGCCAGGCTGGTTATGACUC | SOOOSSnXSSnXSSnXSSSSSSS |
| WV-15352 | mU * SGeom5Ceom5CeomA * SG * SGn001C * ST * SG * RG * ST * ST * RA * ST * SmG * SmA * SmC * SmU * SmC | UGCCAGGCTGGTTATGACUC | SOOOSSnXSSRSSRSSSSSSS |
| WV-15353 | mU * SGeom5Ceom5CeomA * SG * SG * RC * ST * SGn001G * ST * ST * RA * ST * SmG * SmA * SmC * SmU * SmC | UGCCAGGCTGGTTATGACUC | SOOOSSRSSnXSSRSSSSSSS |

TABLE 1B-continued

Malat1 Oligonucleotides.

| WAVE ID | Sequence | Naked Sequence | Stereochemistry |
|---|---|---|---|
| WV-15354 | mU * SGeom5Ceom5CeomA * SG * SG * RC * ST * SG * RG * ST * STn001A * ST * SmG * SmA * SmC * SmU * SmC | UGCCAGGCTG GTTATGACUC | SOOOSSRSSRS SnXSSSSSS |
| WV-15355 | mU * SGeom5Ceom5CeomA * SG * SG * RCn001Tn001G * RGn001Tn001T * RAn001Tn001mG * SmA * SmC * SmU * SmC | UGCCAGGCTG GTTATGACUC | SOOOSSRnXnX RnXnXRnXnXSSSS |
| WV-15356 | mU * SGeom5Ceom5CeomA * SG * SG * RCn001Tn001G * RG * ST * ST * RA * ST * SmG * SmA * SmC * SmU * SmC | UGCCAGGCTG GTTATGACUC | SOOOSSRnXnX RSSRSSSSSS |
| WV-15357 | mU * SGeom5Ceom5CeomA * SG * SG * RC * ST * SG * RGn001Tn001T * RA * ST * SmG * SmA * SmC * SmU * SmC | UGCCAGGCTG GTTATGACUC | SOOOSSRSSRnX nXRSSSSSS |
| WV-15358 | mU * SGeom5Ceom5CeomA * SG * SG * RC * ST * SG * RG * ST * ST * RAn001Tn001mG * SmA * SmC * SmU * SmC | UGCCAGGCTG GTTATGACUC | SOOOSSRSSRSS RnXnXSSSS |
| WV-15359 | mU * SGeom5Ceom5CeomA * SG * SG * SC * ST * SG * SG * ST * STn001An001Tn001mG * SmA * SmC * SmU * SmC | UGCCAGGCTG GTTATGACUC | SOOOSSSSSSSS nXnXnXSSSS |
| WV-15360 | mU * SGeom5Ceom5CeomA * SG * SG * SC * ST * SG * SG * ST * STn001A * ST * SmG * SmA * SmC * SmU * SmC | UGCCAGGCTG GTTATGACUC | SOOOSSSSSSSS nXSSSSSS |
| WV-15361 | mU * SGeom5Ceom5CeomA * SG * SG * SC * ST * SG * SG * ST * ST * RA * STn001mGn001mA * SmC * SmU * SmC | UGCCAGGCTG GTTATGACUC | SOOOSSSSSSSS RSnXnXSSS |
| WV-15362 | mU * SGeom5Ceom5CeomA * SG * SG * SC * ST * SG * SG * ST * ST * RAn001T * SmG * SmA * SmC * SmU * SmC | UGCCAGGCTG GTTATGACUC | SOOOSSSSSSSS RnXSSSSS |
| WV-15363 | mU * SGeom5Ceom5CeomA * SG * SG * SC * ST * SG * SG * ST * ST * RA * STn001mG * SmA * SmC * SmU * SmC | UGCCAGGCTG GTTATGACUC | SOOOSSSSSSSS RSnXSSSS |
| WV-15364 | mU * SGeom5Ceom5CeomA * SG * SG * SC * ST * SG * SG * ST * ST * RAn001Tn001mGmA * SmC * SmU * SmC | UGCCAGGCTG GTTATGACUC | SOOOSSSSSSSS RnXnXOSSS |
| WV-15365 | mU * SGeom5Ceom5CeomA * SG * SG * SC * ST * SG * SG * ST * ST * RAn001Tn001mG * SmA * SmC * SmU * SmC | UGCCAGGCTG GTTATGACUC | SOOOSSSSSSSS RnXnXSSSS |
| WV-15562 | mU * SGeon001Rm5Ceon001Rm5Ceon001RmA * SG * SG * RC * ST * SG * RG * ST * ST * RA * ST * SmG * SmA * SmC * SmU * SmC | UGCCAGGCTG GTTATGACUC | SnRnRnSSRSS RSSRSSSSSS |
| WV-15563 | mU * SGeon001Sm5Ceon001Sm5Ceon001SmA * SG * SG * RC * ST * SG * RG * ST * ST * RA * ST * SmG * SmA * SmC * SmU * SmC | UGCCAGGCTG GTTATGACUC | SnSnSnSSSRSS RSSRSSSSSS |
| WV-15863 | Mod001L001mU * SGeom5Ceom5CeomA * SG * SG * RC * ST * SG * RG * ST * ST * RA * ST * SmGn001mAn001mCn001mU * SmC | UGCCAGGCTG GTTATGACUC | OSOOOSSRSS RSSRSSnXnXnXS |
| WV-15864 | L001mU * SGeom5Ceom5CeomA * SG * SG * RC * ST * SG * RG * ST * ST * RA * ST * SmGn001mAn001mCn001mU * SmC | UGCCAGGCTG GTTATGACUC | OSOOOSSRSS RSSRSSnXnXnXS |
| WV-15887 | mU * SGeon002Sm5Ceon002Sm5Ceon002SmA * SG * SG * RC * ST * SG * RG * ST * ST * RA * ST * SmG * SmA * SmC * SmU * SmC | UGCCAGGCTG GTTATGACUC | SnSnSnSSSRSS RSSRSSSSSS |
| WV-7557 | L001mU * mG * mC * mC * mA * G * G * C * T * G * G * T * T * A * T * mG * mA * mC * mU * mC | UGCCAGGCTGG TTATGACUC | OXXXXXXXXXX XXXXXXXX |
| WV-7558 | Mod027L001mU * mG * mC * mC * mA * G * G * C * T * G * G * T * T * A * T * mG * mA * mC * mU * mC | UGCCAGGCTGG TTATGACUC | OXXXXXXXXXX XXXXXXXX |
| WV-7559 | Mod028L001mU * mG * mC * mC * mA * G * G * C * T * G * G * T * T * A * T * mG * mA * mC * mU * mC | UGCCAGGCTGG TTATGACUC | OXXXXXXXXXX XXXXXXXX |
| WV-7560 | Mod007L001mU * mG * mC * mC * mA * G * G * C * T * G * G * T * T * A * T * mG * mA * mC * mU * mC | UGCCAGGCTGG TTATGACUC | OXXXXXXXXXX XXXXXXXX |
| WV-8896 | Mod024mU * mG * mC * mC * mA * G * G * C * T * G * G * T * T * A * T * mG * mA * mC * mU * mC | UGCCAGGCTGG TTATGACUC | XXXXXXXXXX XXXXXXXX |
| WV-8587 | mU * SGeom5Ceom5CeomA * SG * SG * RC * ST * SG * RG * ST * ST * RA * ST * SmG * SmA * SmC * SmU * SmC | UGCCAGGCTGG TTATGACUC | SOOOSS RSSRSSR SSSSSS |
| WV-14733 | mU * SGeom5Ceom5CeomA * SG * SG * SC * ST * SG * SG * ST * ST * SA * ST * SmG * SmA * SmC * SmU * SmC | UGCCAGGCTGG TTATGACUC | SOOOSS SSSSS SSSSS SSS |
| WV-15351 | mU * SGeom5Ceom5CeomA * SG * SGn001C * ST * SGn001G * ST * STn001A * ST * SmG * SmA * SmC * SmU * SmC | UGCCAGGCTGG TTATGACUC | SOOOSS nXSSnXSSnX SSSSS S |

TABLE 1B-continued

Malat1 Oligonucleotides.

| WAVE ID | Sequence | Naked Sequence | Stereochemistry |
|---|---|---|---|
| WV-15352 | mU * SGeom5Ceom5CeomA * SG * SGn001C * ST * SG * RG * ST * ST * RA * ST * SmG * SmA * SmC * SmU * SmC | UGCCAGGCTGG TTATGACUC | SOOOSS nXSSRSSR SSSSS S |
| WV-15353 | mU * SGeom5Ceom5CeomA * SG * SG * RC * ST * SGn001G * ST * ST * RA * ST * SmG * SmA * SmC * SmU * SmC | UGCCAGGCTGG TTATGACUC | SOOOSS RSSnXSSR SSSSS S |
| WV-15354 | mU * SGeom5Ceom5CeomA * SG * SG * RC * ST * SG * RG * ST * STn001A * ST * SmG * SmA * SmC * SmU * SmC | UGCCAGGCTGG TTATGACUC | SOOOSS RSSRSSnX SSSSS S |
| WV-15356 | mU * SGeom5Ceom5CeomA * SG * SG * RCn001Tn001G * RG * ST * ST * RA * ST * SmG * SmA * SmC * SmU * SmC | UGCCAGGCTGG TTATGACUC | SOOOSS RnXnXRSSR SSSSS S |
| WV-15357 | mU * SGeom5Ceom5CeomA * SG * SG * RC * ST * SG * RGn001Tn001T * RA * ST * SmG * SmA * SmC * SmU * SmC | UGCCAGGCTGG TTATGACUC | SOOOSS RSSRnXnXR SSSSS S |
| WV-15358 | mU * SGeom5Ceom5CeomA * SG * SG * RC * ST * SG * RG * ST * ST * RAn001Tn001mG * SmA * SmC * SmU * SmC | UGCCAGGCTGG TTATGACUC | SOOOSS RSSRSSRnXnXSSSS |
| WV-8582 | mU * SGeom5Ceom5CeomA * SG * SG * SC * ST * SG * SG * ST * ST * RA * ST * SmG * SmA * SmC * SmU * SmC | UGCCAGGCTGG TTATGACUC | SOOOSS SSSSS SR SSSSS S |
| WV-15359 | mU * SGeom5Ceom5CeomA * SG * SG * SC * ST * SG * SG * ST * STn001An001Tn001mG * SmA * SmC * SmU * SmC | UGCCAGGCTGG TTATGACUC | SOOOSS SSSSS SnXnXnXSSSS |
| WV-15360 | mU * SGeom5Ceom5CeomA * SG * SG * SC * ST * SG * SG * ST * STn001A * ST * SmG * SmA * SmC * SmU * SmC | UGCCAGGCTGG TTATGACUC | SOOOSS SSSSS SnX SSSSS S |
| WV-15361 | mU * SGeom5Ceom5CeomA * SG * SG * SC * ST * SG * SG * ST * ST * RA * STn001mGn001mA * SmC * SmU * SmC | UGCCAGGCTGG TTATGACUC | SOOOSS SSSSS SRSnXnXSSSS |
| WV-15362 | mU * SGeom5Ceom5CeomA * SG * SG * SC * ST * SG * SG * ST * ST * RAn001T * SmG * SmA * SmC * SmU * SmC | UGCCAGGCTGG TTATGACUC | SOOOSS SSSSS SRnX SSSSS |
| WV-15363 | mU * SGeom5Ceom5CeomA * SG * SG * SC * ST * SG * SG * ST * ST * RA * STn001mG * SmA * SmC * SmU * SmC | UGCCAGGCTGG TTATGACUC | SOOOSS SSSSS SRSnXSSSSS |
| WV-14556 | mUn001Geon001m5Ceon001m5CeomA * SG * SG * RC * ST * SG * RG * ST * ST * RA * ST * SmG * SmA * SmC * SmU * SmC | UGCCAGGCTGG TTATGACUC | nXnXnXOSSRSSRSSR SSSSS S |
| WV-14557 | mUn001Geon001m5Ceom5Ceon001mA * SG * SG * RC * ST * SG * RG * ST * ST * RA * ST * SmG * SmA * SmC * SmU * SmC | UGCCAGGCTGG TTATGACUC | nXnXOnXSSRSSRSSR SSSSS S |
| WV-14558 | mUn001Geon001m5Ceom5CeomAn001G * SG * RC * ST * SG * RG * ST * ST * RA * ST * SmG * SmA * SmC * SmU * SmC | UGCCAGGCTGG TTATGACUC | nXnXOOnXSSRSSRSSR SSSSS S |
| WV-14559 | mUn001Geom5Ceon001m5Ceon001mA * SG * SG * RC * ST * SG * RG * ST * ST * RA * ST * SmG * SmA * SmC * SmU * SmC | UGCCAGGCTGG TTATGACUC | nXOnXnXSSRSSRSSR SSSSS S |
| WV-14560 | mUn001Geom5Ceon001m5CeomAn001G * SG * RC * ST * SG * RG * ST * ST * RA * ST * SmG * SmA * SmC * SmU * SmC | UGCCAGGCTGG TTATGACUC | nXOnXOnXSSRSSRSSR SSSSS S |
| WV-14561 | mUn001Geom5Ceom5Ceon001mAn001G * SG * RC * ST * SG * RG * ST * ST * RA * ST * SmG * SmA * SmC * SmU * SmC | UGCCAGGCTGG TTATGACUC | nXOOnXnXSSRSSRSSR SSSSS S |
| WV-11533 | mU * SGeon001m5Ceon001m5Ceon001mA * SG * SG * RC * ST * SG * RG * ST * ST * RA * ST * SmG * SmA * SmC * SmU * SmC | UGCCAGGCTGG TTATGACUC | SnXnXnXSSRSSRSSR SSSSS S |
| WV-14562 | mU * SGeon001m5Ceon001m5CeomAn001G * SG * RC * ST * SG * RG * ST * ST * RA * ST * SmG * SmA * SmC * SmU * SmC | UGCCAGGCTGG TTATGACUC | SnXnXOnXSSRSSRSSR SSSSS S |
| WV-14563 | mU * SGeon001m5Ceom5Ceon001mAn001G * SG * RC * ST * SG * RG * ST * ST * RA * ST * SmG * SmA * SmC * SmU * SmC | UGCCAGGCTGG TTATGACUC | SnXOnXnXSSRSSRSSR SSSSS S |
| WV-14564 | mU * SGeom5Ceon001m5Ceon001mAn001G * SG * RC * ST * SG * RG * ST * ST * RA * ST * SmG * SmA * SmC * SmU * SmC | UGCCAGGCTGG TTATGACUC | SOnXnXnXSRSSRSSR SSSSS S |
| WV-14349 | Mod098L001mU * SGeom5Ceom5CeomA * SG * SG * RC * ST * SG * RG * ST * ST *RA *ST * SmG * SmA * SmC * SmU * SmC | UGCCAGGCTGG TTATGACUC | OSOOOSS RSSRSSR SSSSS S |

WV-7557, WV-7558, WV-7559, WV-7560, and WV-8896 are also described in the Examples.

TABLE 1C

| | PNPLA3 oligonucleotides | | |
|---|---|---|---|
| WV-8844 | mU * mG * mU * mA * mG * A * A * A * G * G * C * A * T * G * A * mAGeom5CeoAeo * mG | UGUAGAAAGGCA TGAAGCAG | XXXXXXXXXXXX XXXOOOX |
| WV-8846 | mU * mG * mU * mA * mG * A * A * A * G * G * C * A * T * G * A * AeoGeom5CeoAeo * Geo | UGUAGAAAGGCA TGAAGCAG | XXXXXXXXXXXX XXXOOOX |
| WV-9441 | mU * GeoTeoAeomG * A * A * A * G * G * A * T * G * A * mA * mG * mC * mA * mG | UGTAGAAAGGGA TGAAGCAG | XOOOXXXXXXXX XXXXX XXX |
| WV-9431 | Teo * Geo * Teo * Aeo * Geo * A * A * A * G * G * G * A * T * G * A Aeo * Geo * m5Ceo * Aeo * Geo | TGTAGAAAGGGA TGAAGCAG | XXXXXXXXXXXX XXXXXXX |
| WV-9436 | Teo * GeoTeoAeoGeo * A * A * A * G * G * G * A * T * G * A * AeoGeom5CeoAeo * Geo | TGTAGAAAGGGA TGAAGCAG | XOOOXXXXXXXX XXXXOOOX |
| WV-8845 | Teo * GeoTeoAeoGeo * A * A * A * G * C * A * T * G * A * mA * mG * mC * mA * mG | TGTAGAAAGGCA TGAAGCAG | XOOOXXXXXXXX XXXXX XXX |
| WV-8083 | mG * SmGmAm5CeomC * ST * SG * RA * SG * SG * RA * ST * SG * RG * SA * Sm5Ceom5CeomGmC * SmG | GGACCTGAGGATG GACCGCG | SOOOSSRSSRS SRSSOOOS |
| WV-8259 | L001mG * SmG * SmA * SmC * SmC * ST * SG * RA * SG * SG * SA * ST * SG * RG * SA * Sm5Ceo * Rm5Ceo * RGeo * Rm5Ceo * RGeo | GGACCTGAGGATG GACCGCG | OSSSSSSRSSSSS RSSRRRR |
| WV-8043 | Mod001L001mG * SmG * SmA * SmC * SmC * ST * SG * RA * SG * SG * RA * ST * SG * RG * SA * Sm5Ceo * Sm5Ceo * SGeo * Sm5Ceo * SGeo | GGACCTGAGGATG GACCGCG | OSSSSSSRSSRSS RSSSSSS |
| WV-8044 | Mod001L001mG * SmG * SmA * SmC * SmC * ST * SG * RA * SG * SG * RA * ST * SG * RG * SA * Sm5Ceo * Rm5Ceo * RGeo * Rm5Ceo * RGeo | GGACCTGAGGATG GACCGCG | OSSSSSSRSSRSS RSSRRRR |
| WV-8257 | L001mG * SmG * SmA * SmC * SmC * ST * SG * RA * SG * SG * RA * ST * SG * RG * SA * Sm5Ceo * Rm5Ceo * RGeo * Rm5Ceo * RGeo | GGACCTGAGGATG GACCGCG | OSSSSSSRSSRSS RSSRRRR |
| WV-8045 | Mod001L001mG * SmG * SmA * SmC * SmC * ST * SG * RA * SG * SG * RA * ST * SG * RG * SA * Sm5Ceom5CeoGeom5Ceo * SGeo | GGACCTGAGGATG GACCGCG | OSSSSSSRSSRSS RSSOOOS |
| WV-8046 | Mod001L001mG * SmG * SmA * SmC * SmC * ST * SG * RA * SG * SG * RA * ST * SG * RG * SA * Sm5Ceom5CeoGeom5Ceo * SGeo | GGACCTGAGGATG GACCGCG | OSSSSSSRSSRSS RSSOOOS |
| WV-8047 | Mod001L001mG * SmG * SmA * SmC * SmC * ST * SG * RA * SG * SG * RA * ST * SG * RG * SA * Sm5Ceom5CeoGeom5Ceo * RGeo | GGACCTGAGGATG GACCGCG | OSSSSSSRSSRSS RSSOOOR |
| WV-8048 | Mod001L001mG * SmG * SmA * SmC * SmC * ST * SG * RA * SG * SG * RA * ST * SG * RG * SA * Sm5Ceom5CeoGeom5Ceo * RGeo | GGACCTGAGGATG GACCGCG | OSSSSSSRSSRSS RSSOOOR |
| WV-8847 | mC * mU * mG * mU * mA * G * A * A * A * G * G * C * A * T * G * mAAeoGeom5Ceo * mA | CUGUAGAAAGGCA TGAAGCA | XXXXXXXXXXXX XXXOOOX |
| WV-8849 | mC * mU * mG * mU * mA * G * A * A * A * G * G * C * A * T * G * AeoAeoGeom5Ceo * Aeo | CUGUAGAAAGGCA TGAAGCA | XXXXXXXXXXXX XXXOOOX |
| WV-8807 | rCrUrGrCrUrUrCrArUrGrCrCrUrUrUrCrUrArCrArGrUrGrG | CUGCUUCAUGCCU UUCUACAGUGG | OOOOOOOOOOOO OOOOOOOOOOO |
| WV-8808 | rCrUrGrCrUrUrCrArUrCrCrCrCrUrUrUrCrUrArCrArGrUrGrG | CUGCUUCAUCCCC UUCUACAGUGG | OOOOOOOOOOOOO OOOOOOOOOO |
| WV-9432 | m5Ceo * Teo * Geo * Teo * Aeo * G * A * A * A * G * G * G * A * T * CTGTAGAAAGGGA * Aeo * Aeo * Geo * m5Ceo * Aeo | CTGTAGAAAGGGA TGAAGCA | XXXXXXXXXXXX XXXXXXX |
| WV-9442 | mC * TeoGeoTeomA * G * A * A * A * G * G * G * A * T * G * mA * mA * mG * mC * mA | CTGTAGAAAGGGA TGAAGCA | XOOOXXXXXXXX XXXXX XXX |
| WV-9437 | m5Ceo * TeoGeoTeoAeo * G * A * A * A * G * G * G * A * T * G * AeoAeoGeom5Ceo * Aeo | CTGTAGAAAGGGA TGAAGCA | XOOOXXXXXXXX XXXXOOOX |
| WV-8609 | mC * TeoGeoTeomA * G * A * A * A * G * G * C * A * T * G * mA * mA * mG * mC * mA | CTGTAGAAAGGCA TGAAGCA | XOOOXXXXXXXX XXXXX XXX |
| WV-8848 | m5Ceo * TeoGeoTeoAeo * G * A * A * A * G * G * C * A * T * G * mA * mA * mG * mC * mA | CTGTAGAAAGGCA TGAAGCA | XOOOXXXXXXXX XXXXX XXX |
| WV-9891 | mC * TeoGeo-TeoAeo * G * A * A * A * G * G * C * A * T * G * mA * mA * mG * mC * mA | CTGTAGAAAGGCA TGAAGCA | XOOOXXXXXXXX XXXXX XXX |
| WV-9894 | mC * TeoGeoTeoAeo * G * A * A * A * G * G * C * A * T * G * Aeo * mA * mG * mC * mA | CTGTAGAAAGGCA TGAAGCA | XOOOXXXXXXXX XXXXX XXX |

TABLE 1C-continued

PNPLA3 oligonucleotides

| | | | |
|---|---|---|---|
| WV-7805 | m5Ceo * TeoGeoTeoAeo * G * A * A * A * G * G * C * A * T * G * AeoAeoGeom5Ceo * Aeo | CTGTAGAAAGGCA TGAAGCA | XOOOXXXXXXX XXXXOOOX |
| WV-8605 | mC * STeoGeoTeomA * SG * SA * SA * SA * SG * SG * SC * SA * RT * SG * SmA * SmA * SmG * SmC * SmA | CTGTAGAAAGGCA TGAAGCA | SOOOSSSSSSS RSSSSSS |
| WV-8606 | mC * STeoGeoTeomA * SG * SA * SA * SA * SG * RG * SC * SA * ST * SG * SmA * SmA * SmG * SmC * SmA | CTGTAGAAAGGCA TGAAGCA | SOOOSSSSRS SSSSSSS |
| WV-8608 | m5Ceo * STeoGeoTeoAeo * SG * SA * SA * SA * SG * RG * SC * SA * ST * SG * SAeoAeoGeom5Ceo * SAeo | CTGTAGAAAGGCA TGAAGCA | SOOOSSSSRS SSSSOOOS |
| WV-8601 | mC * STeoGeoTeomA * SG * SA * SA * SA * SG * RG * SC * SA * RT * SG * SmA * SmA * SmG * SmC * SmA | CTGTAGAAAGGCA TGAAGCA | SOOOSSSSRS SRSSSSS |
| WV-8246 | m51C * STeomGTeomA * SG * SA * SA * SA * SG * RG * SC * SA * RT * SG * SmAmAmGmC * S1A | CTGTAGAAAGGCA TGAAGCA | SOOOSSSSRS SRSSOOOS |
| WV-8603 | m5Ceo * STeoGeoTeoAeo * SG * SA * SA * SA * SG * RG * SC * SA * RT * SG * SAeoAeoGeom5Ceo * SAeo | CTGTAGAAAGGCA TGAAGCA | SOOOSSSSRS SRSSOOOS |
| WV-9893 | mC * STeoGeoTeoAeo * RG * SA * SA * SA * SG * RG * SC * SA * ST * SG * SmA * SmA * SmG * SmC * SmA | CTGTAGAAAGGCA TGAAGCA | SOOORSSSSRS SSSSSSS |
| WV-11960 | m51C * STeoGeoTeoAeo * RG * SA * SA * SA * SG * RG * SC * SA * ST * SG * SmA * SmA * SmG * SmC * S1A | CTGTAGAAAGGCA TGAAGCA | SOOORSSSSRS SSSSSSS |
| WV-9896 | mC * STeoGeoTeoAeo * RG * SA * SA * SA * SG * RG * SC * SA * ST * SG * RAeo * SmA * SmG * SmC * SmA | CTGTAGAAAGGCA TGAAGCA | SOOORSSSSRS SSSRSSSS |
| WV-9890 | m5Ceo * STeoGeoTeoAeo * RG * SA * SA * SA * SG * RG * SC * SA * ST * SG * RAeoAeoGeom5Ceo * SAeo | CTGTAGAAAGGCA TGAAGCA | SOOORSSSSRS SSSROOOS |
| WV-9892 | mC * STeoGeoTeoAeo * RG * SA * SA * SA * SG * RG * SC * SA * RT * SG * SmA * SmA * SmG * SmC * SmA | CTGTAGAAAGGCA TGAAGCA | SOOORSSSSRS SRSSSSS |
| WV-9895 | mC * STeoGeoTeoAeo * RG * SA * SA * SA * SG * RG * SC * SA * RT * SG * RAeo * SmA * SmG * SmC * SmA | CTGTAGAAAGGCA TGAAGCA | SOOORSSSSRS SRSRSSSS |
| WV-9889 | m5Ceo * STeoGeoTeoAeo * RG * SA * SA * SA * SG * RG * SC * SA * RT * SG * RAeoAeoGeom5Ceo * SAeo | CTGTAGAAAGGCA TGAAGCA | SOOORSSSSRS SRSROOOS |
| WV-8600 | Mod001L001mC * TeoGeoTeomA * G * A * A * A * G * G * C * A * T * G * mA * mA * mG * mC * mA | CTGTAGAAAGGCA TGAAGCA | OXOOOXXXXXXX XXXXX XXX |
| WV-8628 | L001mC * TeoGeoTeomA * G * A * A * A * G * G * C * A * T * G * mA * mA * mG * mC * mA | CTGTAGAAAGGCA TGAAGCA | OXOOOXXXXXXX XXXXX XXX |
| WV-9860 | Mod001L001mC * TeoGeoTeoAeo * G * A * A * A * G * G * C * A * T * G * Aeo * mA * mG * mC * mA | CTGTAGAAAGGCA TGAAGCA | OXOOOXXXXXXX XXXXX XXX |
| WV-9868 | Mod001L001mC * TeoGeoTeoAeo * G * A * A * A * G * G * C * A * T * G * mA * mA * mG * mC * mA | CTGTAGAAAGGCA TGAAGCA | OXOOOXXXXXXX XXXXX XXX |
| WV-10249 | L001mC * TeoGeoTeoAeo * G * A * A * A * G * G * C * A * T * G * mA * mA * mG * mC * mA | CTGTAGAAAGGCA TGAAGCA | OXOOOXXXXXXX XXXXX XXX |
| WV-10252 | L001mC * TeoGeo-TeoAeo * G * A * A * A * G * G * C * A * T * G * Aeo * mA * mG * mC * mA | CTGTAGAAAGGCA TGAAGCA | OXOOOXXXXXXX XXXXX XXX |
| WV-8132 | Mod001L001m5Ceo * TeoGeoTeoAeo * G * A * A * A * G * G * C * A * T * G * AeoAeoGeom5Ceo * Aeo | CTGTAGAAAGGCA TGAAGCA | OXOOOXXXXXXX XXXXOOOX |
| WV-8596 | Mod001L001mC * STeoGeoTeomA * SG * SA * SA * SA * SG * SG * SC * SA * RT * SG * SmA * SmA * SmG * SmC * SmA | CTGTAGAAAGGCA TGAAGCA | OSOOOSSSSSSS RSSSSSS |
| WV-8624 | L001mC * STeoGeoTeomA * SG * SA * SA * SA * SG * SG * SC * SA * RT * SG * SmA * SmA * SmG * SmC * SmA | CTGTAGAAAGGCA TGAAGCA | OSOOOSSSSSSS RSSSSSS |
| WV-8597 | Mod001L001mC * STeoGeoTeomA * SG * SA * SA * SA * SG * RG * SC * SA * ST * SG * SmA * SmA * SmG * SmC * SmA | CTGTAGAAAGGCA TGAAGCA | OSOOOSSSSRS SSSSSSS |
| WV-8625 | L001mC * STeoGeoTeomA * SG * SA * SA * SA * SG * RG * SC * SA * ST * SG * SmA * SmA * SmG * SmC * SmA | CTGTAGAAAGGCA TGAAGCA | OSOOOSSSSRS SSSSSSS |

TABLE 1C-continued

PNPLA3 oligonucleotides

| | | | |
|---|---|---|---|
| WV-8599 | Mod001L001m5Ceo * STeoGeoTeoAeo * SG * SA * SA * SA * SG * RG * SC * SA * ST * SG * SAeoAeoGeom5Ceo * SAeo | CTGTAGAAAGGCA TGAAGCA | OSOOOSSSSSRS SSSSOOOS |
| WV-8562 | Mod001L001mC * STeoGeoTeomA * SG * SA * SA * SA * SG * RG * SC * SA * RT * SG * SAeo * SAeo * SGeo * Sm5Ceo * SAeo | CTGTAGAAAGGCA TGAAGCA | OSOOOSSSSSRS SRSSSSSS |
| WV-8564 | Mod001L001mC * STeoGeoTeomA * SG * SA * SA * SA * SG * RG * SC * SA * RT * SG * SmA * SmA * SmG * SmC * SmA | CTGTAGAAAGGCA TGAAGCA | OSOOOSSSSSRS SRSSSSSS |
| WV-8620 | L001mC * STeoGeoTeomA * SG * SA * SA * SA * SG * RG * SC * SA * RT * SG * SmA * SmA * SmG * SmC * SmA | CTGTAGAAAGGCA TGAAGCA | OSOOOSSSSSRS SRSSSSSS |
| WV-8566 | Mod001L001m5Ceo * STeoGeoTeoAeo * SG * SA * SA * SA * SG * RG * SC * SA * RT * SG * SAeoAeoGeom5Ceo * SAeo | CTGTAGAAAGGCA TGAAGCA | OSOOOSSSSSRS SRSSOOOS |
| WV-9870 | Mod001L001mC * STeoGeoTeoAeo * RG * SA * SA * SA * SG * RG * SC * SA * ST * SG * SmA * SmA * SmG * SmC * SmA | CTGTAGAAAGGCA TGAAGCA | OSOOORSSSSRS SSSSSSSS |
| WV-10251 | L001mC * STeoGeoTeoAeo * RG * SA * SA * SA * SG * RG * SC * SA * ST * SG * SmA * SmA * SmG * SmC * SmA | CTGTAGAAAGGCA TGAAGCA | OSOOORSSSSRS SSSSSSSS |
| WV-11958 | Mod001L001m51C * STeoGeoTeoAeo * RG * SA * SA * SA * SG * RG * SC * SA * ST * SG * SmA * SmA * SmG * SmC * S1A | CTGTAGAAAGGCA TGAAGCA | OSOOORSSSSRS SSSSSSSS |
| WV-11962 | L001m51C * STeoGeoTeoAeo * RG * SA * SA * SA * SG * RG * SC * SA * ST * SG * SmA * SmA * SmG * SmC * S1A | CTGTAGAAAGGCA TGAAGCA | OSOOORSSSSRS SSSSSSSS |
| WV-9862 | Mod001L001mC * STeoGeoTeoAeo * RG * SA * SA * SA * SG * RG * SC * SA * ST * SG * RAeo * SmA * SmG * SmC * SmA | CTGTAGAAAGGCA TGAAGCA | OSOOORSSSSRS SSSRSSSS |
| WV-10254 | L001mC * STeoGeoTeoAeo * RG * SA * SA * SA * SG * RG * SC * SA * ST * SG * RAeo * SmA * SmG * SmC * SmA | CTGTAGAAAGGCA TGAAGCA | OSOOORSSSSRS SSSRSSSS |
| WV-9670 | Mod001L001m5Ceo * STeoGeoTeoAeo * RG * SA * SA * SA * SG * RG * SC * SA * ST * SG * RAeoAeoGeom5Ceo * SAeo | CTGTAGAAAGGCA TGAAGCA | OSOOORSSSSRS SSSROOOS |
| WV-9869 | Mod001L001mC * STeoGeoTeoAeo * RG * SA * SA * SA * SG * RG * SC * SA * RT * SG * SmA * SmA * SmG * SmC * SmA | CTGTAGAAAGGCA TGAAGCA | OSOOORSSSSRS SRSSSSSS |
| WV-10250 | L001mC * STeoGeoTeoAeo * RG * SA * SA * SA * SG * RG * SC * SA * RT * SG * SmA * SmA * SmG * SmC * SmA | CTGTAGAAAGGCA TGAAGCA | OSOOORSSSSRS SRSSSSSS |
| WV-9861 | Mod001L001mC * STeoGeoTeoAeo * RG * SA * SA * SA * SG * RG * SC * SA * RT * SG * RAeo * SmA * SmG * SmC * SmA | CTGTAGAAAGGCA TGAAGCA | OSOOORSSSSRS SRSRSSSS |
| WV-10253 | L001mC * STeoGeoTeoAeo * RG * SA * SA * SA * SG * RG * SC * SA * RT * SG * RAeo * SmA * SmG * SmC * SmA | CTGTAGAAAGGCA TGAAGCA | OSOOORSSSSRS SRSRSSSS |
| WV-9859 | Mod001L001m5Ceo * STeoGeoTeoAeo * RG * SA * SA * SA * SG * RG * SC * SA * RT * SG * RAeoAeoGeom5Ceo * SAeo | CTGTAGAAAGGCA TGAAGCA | OSOOORSSSSRS SRSROOOS |
| WV-8560 | Mod001L001m5Ceo * RTeoGeoTeoAeo * RG * SA * SA * SA * SG * RG * SC * SA * RT * SG * SmA * SmA * SmG * SmC * SmA | CTGTAGAAAGGCA TGAAGCA | OROOORSSSSRS SRSSSSSS |
| WV-980 | mCmGmAmAm5C * A * T * G * A * m5C * m5C * T * m5C * m5C * mGmCmAmC | CGAACATGACCTC CGCAC | OOOOXXXXXXXX XXOO |
| WV-9445 | mc * m5CeoAeom5CeomU * G * T * A * G * A * A * G * G * mA * mU * mG * mA * mA | CCACUGTAGAAAG GGA UGAA | XOOOXXXXXXXX XXXXX XXX |
| WV-8690 | mc * m5CeoAeom5CeomU * G * T * A * G * A * A * G * G * C * mA * mU * mG * mA * mA | CCACUGTAGAAAG GCAUGAA | XOOOXXXXXXXX XXXXX XXX |
| WV-8602 | mc * Sm5CeoAeom5CeomU * SG * ST * SA * SG * SA * SA * SA * SG * RG * SC * SmA * SmU * SmG * SmA * SmA | CCACUGTAGAAAG GCAUGAA | SOOOSSSSSSSS RSSSSSS |
| WV-8689 | Mod001L001mC * m5CeoAeom5CeomU * G * T * A * G * A * A * A * G * G * C * mA * mU * mG * mA * mA | CCACUGTAGAAAG GCAUGAA | OXOOOXXXXXXXX XXXXX XXX |
| WV-8697 | L001mC * m5CeoAeom5CeomU * G * T * A * G * A * A * A * G * G * C * mA * mU * mG * mA * mA | CCACUGTAGAAAG GCAUGAA | OXOOOXXXXXXXX XXXXX XXX |
| WV-8565 | Mod001L001mC * Sm5CeoAeom5CeomU * SG * ST * SA * SG * SA * SA * SA * SG * RG * SC * SmA * SmU * SmG * SmA * SmA | CCACUGTAGAAAG GCAUGAA | OSOOOSSSSSSSS RSSSSSS |
| WV-8621 | L001mC * Sm5CeoAeom5CeomU * SG * ST * SA * SG * SA * SA * SA * SG * RG * SC * SmA * SmU * SmG * SmA * SmA | CCACUGTAGAAAG GCAUGAA | OSOOOSSSSSSSS RSSSSSS |

TABLE 1C-continued

PNPLA3 oligonucleotides

| | | | |
|---|---|---|---|
| WV-8858 | mC * mC * mA * mC * mU * G * T * A * G * A * A * A * G * G * C * mATeoGeoAeo * mA | CCACUGTAGAAAG GCATGAA | XXXXXXXXXXX XXXOOOX |
| WV-8860 | mC * mC * mA * mC * mU * G * T * A * G * A * A * A * G * G * C * AeoTeoGeoAeo * Aeo | CCACUGTAGAAAG GCATGAA | XXXXXXXXXXX XXXOOOX |
| WV-8248 | mc * Sm5CeomAm5CeomU * SG * ST * SA * SG * SA * SA * SA * SG * RG * SC * SmATeomGmA * SmA | CCACUGTAGAAAG GCATGAA | SOOOSSSSSSS RSSOOOS |
| WV-8250 | m51C * Sm5CeomAm5CeomU * SG * ST * SA * SG * SA * SA * SA * SG * RG * SC * SmATeomGmA * S1A | CCACUGTAGAAAG GCATGAA | SOOOSSSSSSS RSSOOOS |
| WV-8563 | Mod001L001mC * Sm5CeoAeom5CeomU * SG * ST * SA * SG * SA * SA * SA * SG * RG * SC * SAeo * STeo * SGeo * SAeo * SAeo | CCACUGTAGAAAG GCATGAA | OSOOOSSSSSSSS RSSSSSS |
| WV-9435 | m5Ceo * m5Ceo * Aeo * m5Ceo * Teo * G * T * A * G * A * A * A * G * * G * Aeo * Teo * Geo * Aeo * Aeo | CCACTGTAGAAAG GGA TGAA | XXXXXXXXXXX XXXXXXX |
| WV-9440 | m5Ceo * m5CeoAeom5CeoTeo * G * T * A * G * A * A * A * G * G * AeoTeoGeoAeo * Aeo | CCACTGTAGAAAG GGA TGAA | XOOOXXXXXXX XXXXOOOX |
| WV-8859 | m5Ceo * m5CeoAeom5CeoTeo * G * T * A * G * A * A * A * G * G * C * mA * mU * mG * mA * mA | CCACTGTAGAAAG GCA TGAA | XOOOXXXXXXX XXXXX XXX |
| WV-8567 | Mod001L001m5Ceo * Sm5CeoAeom5CeoTeo * SG * ST * SA * SG * SA * SA * SA * SG * RG * SC * SAeoTeoGeoAeo * SAeo | CCACTGTAGAAAG GCA TGAA | OSOOOSSSSSSSS RSSOOOS |
| WV-8855 | mC * mA * mC * mU * mG * T * A * G * A * A * A * G * G * C * A * mUGeoAeoAeo * mG | CACUGTAGAAAGG CAUGAAG | XXXXXXXXXXX XXXOOOX |
| WV-8857 | mC * mA * mC * mU * mG * T * A * G * A * A * A * G * G * C * A * TeoGeoAeoAeo * Geo | CACUGTAGAAAGG CATGAAG | XXXXXXXXXXX XXXOOOX |
| WV-9444 | mC * Aeom5CeoTeomG * T * A * G * A * A * A * G * G * A * mU * mG CACTGTAGAAAGG * mA * mA * mG | GAUGAAG | XOOOXXXXXXX XXXXX XXX |
| WV-9434 | m5Ceo * Aeo * m5Ceo * Teo * Geo * T * A * G * A * A * A * G * G * G CACTGTAGAAAGG A * Teo * Geo * Aeo * Aeo * Geo | GATGAAG | XXXXXXXXXXX XXXXXXX |
| WV-9439 | m5Ceo * Aeom5CeoTeoGeo * T * A * G * A * A * A * G * G * A * TeoGeoAeoAeo * Geo | CACTGTAGAAAGG GATGAAG | XOOOXXXXXXX XXXXOOOX |
| WV-8854 | mC * Aeom5CeoTeomG * T * A * G * A * A * A * G * G * C * A * mU * mG CACTGTAGAAAGG * mA * mA * mG | CAUGAAG | XOOOXXXXXXX XXXXX XXX |
| WV-8856 | m5Ceo * Aeom5CeoTeoGeo * T * A * G * A * A * A * G * G * C * A * mU CACTGTAGAAAGG mG * mA * mA * mG | CAUGAAG | XOOOXXXXXXX XXXXX XXX |
| WV-12107 | mC * Aeom5CeoTeoGeoTeoAeo * G * A * A * A * G * G * C * A * T * G * CACTGTAGAAAGG mA * mA * mG * mC * mA * mG * mG | CATGAAGCAGG | XOOOOOXXXXX XXXXXXX XXXXX |
| WV-12101 | mC * SAeom5CeoTeoGeoTeoAeo * RG * SA * SA * SA * SG * RG * SC * SA * ST * SG * SmA * SmA * SmG * SmC * SmA * SmG * SmG | CACTGTAGAAAGG CATGAAGCAGG | SOOOOORSSS SRSSSSSSSSSSS |
| WV-12100 | m5Ceo * SAeom5CeoTeoGeoTeoAeo * RG * SA * SA * SA * SG * RG * SC * SA * ST * SG * RAeoAeoGeom5CeoAeoGeo * SGeo | CACTGTAGAAAGG CATGAAGCAGG | SOOOOORSSS SRSSSSROOOOOS |
| WV-12105 | Mod001L001mC * Aeom5CeoTeoGeoTeoAeo * G * A * A * A * G * G * C * A * T * G * mA * mA * mG * mC * mA * mG * mG | CACTGTAGAAAGG CATGAAGCAGG | OXOOOOOXXXXX XXXXXXX XXXXX |
| WV-12109 | L001mC * Aeom5CeoTeoGeoTeoAeo * G * A * A * A * G * G * C * A * T * G * mA * mA * mG * mC * mA * mG * mG | CACTGTAGAAAGG CATGAAGCAGG | OXOOOOOXXXXX XXXXXXX XXXXX |
| WV-12099 | Mod001L001mC * SAeom5CeoTeoGeoTeoAeo * RG * SA * SA * SA * SG * RG * SC * SA * ST * SG * SmA * SmA * SmG * SmC * SmA * SmG * SmG | CACTGTAGAAAGG CATGAAGCAGG | OSOOOOORSSS SRSSSSSSSSSSS |
| WV-12103 | L001mC * SAeom5CeoTeoGeoTeoAeo * RG * SA * SA * SA * SG * RG * SC * SA * ST * SG * SmA * SmA * SmG * SmC * SmA * SmG * SmG | CACTGTAGAAAGG CATGAAGCAGG | OSOOOOORSSS SRSSSSSSSSSSS |
| WV-3421 | mA * mGmGmCmU * G * G * A * T * C * C * T * C * C * mc mAmCmGmU | AGGCUGGGATCCT CCACGUC | XOOOXXXXXXX XXXXOOOX |
| WV-8851 | mA * mC * mU * mG * mU * A * G * A * A * A * G * G * C * A * T * mGAeoAeoGeo * mC | ACUGTAGAAAGGC ATGAAGC | XXXXXXXXXXX XXXOOOX |
| WV-8853 | mA * mC * mU * mG * mU * A * G * A * A * A * G * G * C * A * T * GeoAeoAeoGeo * m5Ceo | ACUGTAGAAAGGC ATGAAGC | XXXXXXXXXXX XXXOOOX |

TABLE 1C-continued

PNPLA3 oligonucleotides

| WV-9443 | mA * m5CeoTeoGeomU * A * G * A * A * A * G * G * A * T * mG * mA * mA * mG * mC | ACTGUAGAAAGGG ATGAAGC | XOOOXXXXXXX XXXXX XXX |
| WV-8850 | mA * m5CeoTeoGeomU * A * G * A * A * A * G * G * C * A * T * mG * mA * mA * mG * mC | ACTGUAGAAAGGC ATGAAGC | XOOOXXXXXXX XXXXX XXX |
| WV-9433 | Aeo * m5Ceo * Teo * Geo * Teo * A * G * A * A * A * G * G * G * A * Teo * Geo * Aeo * Aeo * Geo * m5Ceo | ACTGTAGAAAGGG ATGAAGC | XXXXXXXXXXXX XXXXXXX |
| WV-9438 | Aeo * m5CeoTeoGeoTeo * A * G * A * A * A * G * G * G * A * T * GeoAeoAeoGeo * m5Ceo | ACTGTAGAAAGGG ATGAAGC | XOOOXXXXXXX XXXXOOOX |
| WV-8852 | Aeo * m5CeoTeoGeoTeo * A * G * A * A * A * G * G * C * A * T * mG * mA * mA * mG * mC | ACTGTAGAAAGGC ATGAAGC | XOOOXXXXXXX XXXXX XXX |

TABLE 1D

APOC3 oligonucleotides.

| WV-8610 | Mod001L001mA * SGeom5CeoTeomU * SC * ST * ST * SG * RT * SC * SC * RA * SG * SC * SmU * SmU * SmU * SmA * SmU | AGCTUCTTGTCC AGCUUUAU | OSOOOSSSS RSSRSSSSSSS |
| WV-8611 | Mod001L001mA * SGeom5CeoTeomU * SC * ST * ST * SG * RT * SC * SC * SA * SG * SC * SmU * SmU * SmU * SmA * SmU | AGCTUCTTGTCC AGCUUUAU | OSOOOSSSS RSSSSSSSSS |
| WV-8612 | Mod001L001mA * SGeom5CeoTeomU * SC * ST * ST * SG * ST * SC * SC * SA * RG * SC * SmU * SmU * SmU * SmA * SmU | AGCTUCTTGTCC AGCUUUAU | OSOOOSSSS SSSSRSSSSSS |
| WV-8613 | Mod001L001mA * Geom5CeoTeomU * C * T * T * G * T * C * C * A * G * C * mU * mU * mU * mA * mU | AGCTUCTTGTCC AGCUUUAU | OXOOOXXXX XXXXXXXXXX |
| WV-8614 | mA * SGeom5CeoTeomU * SC * ST * ST * SG * RT * SC * SC * RA * SG * SC * SmU * SmU * SmU * SmA * SmU | AGCTUCTTGTCC AGCUUUAU | SOOOSSSS RSSRSSSSSSS |
| WV-8615 | mA * SGeom5CeoTeomU * SC * ST * ST * SG * RT * SC * SC * SA * SG * SC * SmU * SmU * SmU * SmA * SmU | AGCTUCTTGTCC AGCUUUAU | SOOOSSSS RSSSSSSSSS |
| WV-8616 | mA * SGeom5CeoTeomU * SC * ST * ST * SG * ST * SC * SC * SA * RG * SC * SmU * SmU * SmU * SmA * SmU | AGCTUCTTGTCC AGCUUUAU | SOOOSSSS SSSSRSSSSSS |
| WV-8617 | mA * Geom5CeoTeomU * C * T * T * G * T * C * C * A * G * C * mU * mU * mU * mA * mU | AGCTUCTTGTCC AGCUUUAU | XOOOXXXX XXXXXXXXXX |
| WV-8618 | Mod001L001mA * SGeom5CeoTeomU * SC * ST * ST * SG * ST * SC * SC * RA * SG * SC * SmU * SmU * SmU * SmA * SmU | AGCTUCTTGTCC AGCUUUAU | OSOOOSSSS SSSSRSSSSSS |
| WV-8619 | mA * SGeom5CeoTeomU * SC * ST * ST * SG * ST * SC * SC * RA * SG * SC * SmU * SmU * SmU * SmA * SmU | AGCTUCTTGTCC AGCUUUAU | SOOOSSSS SSSSRSSSSSS |
| WV-8629 | L001mA * SGeom5CeoTeomU * SC * ST * ST * SG * RT * SC * SC * RA * SG * SC * SmU * SmU * SmU * SmA * SmU | AGCTUCTTGTCC AGCUUUAU | OSOOOSSSS RSSRSSSSSSS |
| WV-8632 | L001mA * Geom5CeoTeomU * C * T * T * G * T * C * C * A * G * C * mU * mU * mU * mA * mU | AGCTUCTTGTCC AGCUUUAU | OXOOOXXXX XXXXXXXXXX |
| WV-8637 | Mod001L001m5Ceo * STeoTeoGeoTeo * SC * SC * SA * SG * SC * RT * ST * ST * RA * ST * SmU * SmG * SmG * SmG * SmA | CTTGTCCAGCTT TATUGGGA | OSOOOSSSS SRSSRSSSSSS |
| WV-8638 | Mod001L001m5Ceo * STeoTeoGeoTeo * SC * SC * SA * SG * SC * RT * ST * ST * SA * ST * SmU * SmG * SmG * SmG * SmA | CTTGTCCAGCTT TATUGGGA | OSOOOSSSS SRSSSSSSSS |
| WV-8639 | Mod001L001m5Ceo * STeoTeoGeoTeo * SC * SC * SA * SG * SC * ST * ST * ST * RA * ST * SmU * SmG * SmG * SmG * SmA | CTTGTCCAGCTT TATUGGGA | OSOOOSSSS SSSSRSSSSSS |
| WV-8640 | Mod001L001m5Ceo * TeoTeoGeoTeo * C * C * A * G * C * T * T * T * T * A * T * mU * mG * mG * mG * mA | CTTGTCCAGCTT TATUGGGA | OXOOOXXXX XXXXXXXXXX |
| WV-8645 | Mod001L001Aeo * STeoAeoGeom5Ceo * SA * SG * SC * ST * ST * RC * ST * ST * RG * ST * Sm5C * Sm5C * SmA * SmG * Sm5C | ATAGCAGCTTCT TGTCCAGC | OSOOOSSSS SRSSRSSSSSS |
| WV-8646 | Mod001L001Aeo * STeoAeoGeom5Ceo * SA * SG * SC * ST * ST * RC * ST * ST * SG * ST * Sm5C * Sm5C * SmA * SmG * Sm5C | ATAGCAGCTTCT TGTCCAGC | OSOOOSSSS SRSSSSSSSS |
| WV-8647 | Mod001L001Aeo * STeoAeoGeom5Ceo * SA * SG * SC * ST * ST * SC * ST * ST * RG * ST * Sm5C * Sm5C * SmA * SmG * Sm5C | ATAGCAGCTTCT TGTCCAGC | OSOOOSSSS SSSSRSSSSSS |

TABLE 1D-continued

APOC3 oligonucleotides.

| WV-8648 | Mod001L001Aeo * TeoAeoGeom5Ceo * A * G * C * T * T * C * T * T * G * T * m5C * m5C * mA * mG * m5C | ATAGCAGCTTCT TGTCCAGC | OXOOOXXXX XXXXXXXXXX |
|---|---|---|---|
| WV-8653 | m5Ceo * STeoTeoGeoTeo * SC * SC * SA * SG * SC * RT * ST * ST * RA * ST * SmU * SmG * SmG * SmG * SmA | CTTGTCCAGCTT TATUGGGA | SOOOSSSS SRSSRSSSSSS |
| WV-8654 | m5Ceo * STeoTeoGeoTeo * SC * SC * SA * SG * SC * RT * ST * ST * SA * ST * SmU * SmG * SmG * SmG * SmA | CTTGTCCAGCTT TATUGGGA | SOOOSSSS SRSSSSSSSS |
| WV-8655 | m5Ceo * STeoTeoGeoTeo * SC * SC * SA * SG * SC * ST * ST * ST * RA * ST * SmU * SmG * SmG * SmG * SmA | CTTGTCCAGCTT TATUGGGA | SOOOSSSS SSSSRSSSSSS |
| WV-8656 | m5Ceo * TeoTeoGeoTeo * C * C * A * G * C * T * T * T * A * T * mU * mG * mG * mG * mA | CTTGTCCAGCTT TATUGGGA | XOOOXXXX XXXXXXXXXX |
| WV-8661 | Aeo * STeoAeoGeom5Ceo * SA * SG * SC * ST * ST * RC * ST * ST * RG * ST * Sm5C * Sm5C * SmA * SmG * Sm5C | ATAGCAGCTTCT TGTCCAGC | SOOOSSSS SRSSRSSSSSS |
| WV-8662 | Aeo * STeoAeoGeom5Ceo * SA * SG * SC * ST * ST * RC * ST * ST * SG * ST * Sm5C * Sm5C * SmA * SmG * Sm5C | ATAGCAGCTTCT TGTCCAGC | SOOOSSSS SRSSSSSSSS |
| WV-8663 | Aeo * STeoAeoGeom5Ceo * SA * SG * SC * ST * ST * SC * ST * ST * RG * ST * Sm5C * Sm5C * SmA * SmG * Sm5C | ATAGCAGCTTCT TGTCCAGC | SOOOSSSS SSSSRSSSSSS |
| WV-8664 | Aeo * TeoAeoGeom5Ceo * A * G * C * T * T * C * T * T * G * T * m5C * m5C * mA * mG * m5C | ATAGCAGCTTCT TGTCCAGC | XOOOXXXX XXXXXXXXXX |
| WV-8665 | Mod001L001Aeo * STeoAeoGeom5Ceo * SA * SG * SC * ST * ST * RC * ST * ST * RG * ST * SmC * SmC * SmA * SmG * SmC | ATAGCAGCTTCT TGTCCAGC | OSOOOSSSS SRSSRSSSSSS |
| WV-8666 | Mod001L001Aeo * STeoAeoGeom5Ceo * SA * SG * SC * ST * ST * RC * ST * ST * SG * ST * SmC * SmC * SmA * SmG * SmC | ATAGCAGCTTCT TGTCCAGC | OSOOOSSSS SRSSSSSSSS |
| WV-8667 | Mod001L001Aeo * STeoAeoGeom5Ceo * SA * SG * SC * ST * ST * SC * ST * ST * RG * ST * SmC * SmC * SmA * SmG * SmC | ATAGCAGCTTCT TGTCCAGC | OSOOOSSSS SSSSRSSSSSS |
| WV-8668 | Mod001L001Aeo * TeoAeoGeom5Ceo * A * G * C * T * T * C * T * T * G * T * mC * mC * mA * mG * mC | ATAGCAGCTTCT TGTCCAGC | OXOOOXXXX XXXXXXXXXX |
| WV-8669 | Aeo * STeoAeoGeom5Ceo * SA * SG * SC * ST * ST * RC * ST * ST * RG * ST * SmC * SmC * SmA * SmG * SmC | ATAGCAGCTTCT TGTCCAGC | SOOOSSSS SRSSRSSSSSS |
| WV-8670 | Aeo * STeoAeoGeom5Ceo * SA * SG * SC * ST * ST * RC * ST * ST * SG * ST * SmC * SmC * SmA * SmG * SmC | ATAGCAGCTTCT TGTCCAGC | SOOOSSSS SRSSSSSSSS |
| WV-8671 | Aeo * STeoAeoGeom5Ceo * SA * SG * SC * ST * ST * SC * ST * ST * RG * ST * SmC * SmC * SmA * SmG * SmC | ATAGCAGCTTCT TGTCCAGC | SOOOSSSS SSSSRSSSSSS |
| WV-8672 | Aeo * TeoAeoGeom5Ceo * A * G * C * T * T * C * T * T * G * T * mC * mC * mA * mG * mC | ATAGCAGCTTCT TGTCCAGC | XOOOXXXX XXXXXXXXXX |
| WV-8673 | Mod001L001mC * STeoTeoGeomU * SC * SC * SA * SG * SC * RT * ST * ST * RA * ST * SmU * SmG * SmG * SmG * SmA | CTTGUCCAGCTT TATUGGGA | OSOOOSSSS SRSSRSSSSSS |
| WV-8674 | Mod001L001mC * STeoTeoGeomU * SC * SC * SA * SG * SC * RT * ST * ST * SA * ST * SmU * SmG * SmG * SmG * SmA | CTTGUCCAGCTT TATUGGGA | OSOOOSSSS SRSSSSSSSS |
| WV-8675 | Mod001L001mC * STeoTeoGeomU * SC * SC * SA * SG * SC * ST * ST * ST * RA * ST * SmU * SmG * SmG * SmG * SmA | CTTGUCCAGCTT TATUGGGA | OSOOOSSSS SSSSRSSSSSS |
| WV-8676 | Mod001L001mC * TeoTeoGeomU * C * C * A * G * C * T * T * T * A * T * mU * mG * mG * mG * mA | CTTGUCCAGCTT TATUGGGA | OXOOOXXXX XXXXXXXXXX |
| WV-8677 | Mod001L001mA * STeoAeoGeomC * SA * SG * SC * ST * ST * RC * ST * ST * RG * ST * SmC * SmC * SmA * SmG * SmC | ATAGCAGCTTCT TGTCCAGC | OSOOOSSSS SRSSRSSSSSS |
| WV-8678 | Mod001L001mA * STeoAeoGeomC * SA * SG * SC * ST * ST * RC * ST * ST * SG * ST * SmC * SmC * SmA * SmG * SmC | ATAGCAGCTTCT TGTCCAGC | OSOOOSSSS SRSSSSSSSS |
| WV-8679 | Mod001L001mA * STeoAeoGeomC * SA * SG * SC * ST * ST * SC * ST * ST * RG * ST * SmC * SmC * SmA * SmG * SmC | ATAGCAGCTTCT TGTCCAGC | OSOOOSSSS SSSSRSSSSSS |
| WV-8680 | Mod001L001mA * TeoAeoGeomC * A * G * C * T * T * C * T * T * G * T * mC * mC * mA * mG * mC | ATAGCAGCTTCT TGTCCAGC | OXOOOXXXX XXXXXXXXXX |
| WV-8681 | mC * STeoTeoGeomU * SC * SC * SA * SG * SC * RT * ST * ST * RA * ST * SmU * SmG * SmG * SmG * SmA | CTTGUCCAGCTT TATUGGGA | SOOOSSSS SRSSRSSSSSS |

TABLE 1D-continued

APOC3 oligonucleotides.

| WV-8682 | mc * STeoTeoGeomU * SC * SC * SA * SG * SC * RT * ST * ST * SA * ST * SmU * SmG * SmG * SmG * SmA | CTTGUCCAGCTT TATUGGGA | SOOOSSSS SRSSSSSSSSS |
|---|---|---|---|
| WV-8683 | mc * STeoTeoGeomU * SC * SC * SA * SG * SC * ST * ST * ST * RA * ST * SmU * SmG * SmG * SmG * SmA | CTTGUCCAGCTT TATUGGGA | SOOOSSSS SSSSRSSSSSS |
| WV-8684 | mc * TeoTeoGeomU * C * C * A * G * C * T * T * T * A * T * mU * mG * mG * mG * mA | CTTGUCCAGCTT TATUGGGA | XOOOXXXX XXXXXXXXXX |
| WV-8685 | mA * STeoAeoGeomC * SA * SG * SC * ST * ST * RC * ST * ST * RG * ST * SmC * SmC * SmA * SmG * SmC | ATAGCAGCTTCT TGTCCAGC | SOOOSSSS SRSSRSSSSSS |
| WV-8686 | mA * STeoAeoGeomC * SA * SG * SC * ST * ST * RC * ST * ST * SG * ST * SmC * SmC * SmA * SmG * SmC | ATAGCAGCTTCT TGTCCAGC | SOOOSSSS SRSSSSSSSSS |
| WV-8687 | mA * STeoAeoGeomC * SA * SG * SC * ST * ST * SC * ST * ST * RG * ST * SmC * SmC * SmA * SmG * SmC | ATAGCAGCTTCT TGTCCAGC | SOOOSSSS SSSSRSSSSSS |
| WV-8688 | mA * TeoAeoGeomC * A * G * C * T * T * C * T * T * G * T * mc * mc * mA * mG * mc | ATAGCAGCTTCT TGTCCAGC | XOOOXXXX XXXXXXXXXX |
| WV-9526 | Mod001L001mA * SGeom5CeoTeomU * SC * ST * ST * SG * RT * SC * SC * RA * SG * SC * SfU * SfU * SfU * SfA * SfU | AGCTUCTTGTCC AGCUUUAU | OSOOOSSSS RSSRSSSSSSS |
| WV-9527 | Mod001L001mA * SGeom5CeoTeomU * SC * ST * ST * SG * RT * SC * SC * SA * SG * SC * SfU * SfU * SfU * SfA * SfU | AGCTUCTTGTCC AGCUUUAU | OSOOOSSSS RSSSSSSSSSS |
| WV-9528 | Mod001L001mA * SGeom5CeoTeomU * SC * ST * ST * SG * ST * SC * SC * RA * SG * SC * SfU * SfU * SfU * SfA * SfU | AGCTUCTTGTCC AGCUUUAU | OSOOOSSSS SSSRSSSSSSS |
| WV-9529 | Mod001L001mA * Geom5CeoTeomU * C * T * T * G * T * C * C * A * G * C * fU * fU * fU * fA * fU | AGCTUCTTGTCC AGCUUUAU | OXOOOXXXX XXXXXXXXXX |
| WV-9530 | mA * SGeom5CeoTeomU * SC * ST * ST * SG * RT * SC * SC * RA * SG * SC * SfU * SfU * SfU * SfA * SfU | AGCTUCTTGTCC AGCUUUAU | SOOOSSSS RSSRSSSSSSS |
| WV-9531 | mA * SGeom5CeoTeomU * SC * ST * ST * SG * RT * SC * SC * SA * SG * SC * SfU * SfU * SfU * SfA * SfU | AGCTUCTTGTCC AGCUUUAU | SOOOSSSS RSSSSSSSSSS |
| WV-9532 | mA * SGeom5CeoTeomU * SC * ST * ST * SG * ST * SC * SC * RA * SG * SC * SfU * SfU * SfU * SfA * SfU | AGCTUCTTGTCC AGCUUUAU | SOOOSSSS SSSRSSSSSSS |
| WV-9533 | mA * Geom5CeoTeomU * C * T * T * G * T * C * C * A * G * C * fU * fU * fU * fA * fU | AGCTUCTTGTCC AGCUUUAU | XOOOXXXX XXXXXXXXXX |
| WV-9590 | L001mA * SGeom5CeoTeomU * SC * ST * ST * SG * RT * SC * SC * RA * SG * SC * SfU * SfU * SfU * SfA * SfU | AGCTUCTTGTCC AGCUUUAU | OSOOOSSSS RSSRSSSSSSS |
| WV-9591 | L001mA * SGeom5CeoTeomU * SC * ST * ST * SG * RT * SC * SC * SA * SG * SC * SfU * SfU * SfU * SfA * SfU | AGCTUCTTGTCC AGCUUUAU | OSOOOSSSS RSSSSSSSSSS |
| WV-9592 | L001mA * SGeom5CeoTeomU * SC * ST * ST * SG * ST * SC * SC * RA * SG * SC * SfU * SfU * SfU * SfA * SfU | AGCTUCTTGTCC AGCUUUAU | OSOOOSSSS SSSRSSSSSSS |
| WV-9593 | L001mA * Geom5CeoTeomU * C * T * T * G * T * C * C * A * G * C * fU * fU * fU * fA * fU | AGCTUCTTGTCC AGCUUUAU | OXOOOXXXX XXXXXXXXXX |
| WV-9871 | Mod001L001mA * Geom5CeoTeoTeo * C * T * T * G * T * C * C * A * G * C * mU * mU * mU * mA * mU | AGCTTCTTGTCC AGCUUUAU | OXOOOXXXX XXXXXXXXXX |
| WV-9872 | Mod001L001mA * SGeom5CeoTeoTeo * RC * ST * ST * SG * RT * SC * SC * RA * SG * SC * SmU * SmU * SmU * SmA * SmU | AGCTTCTTGTCC AGCUUUAU | OSOOORSSSR SSRSSSSSSS |
| WV-9873 | Mod001L001mA * Geom5CeoTeoTeo * C * T * T * G * T * C * C * A * G * C * Teo * mU * mU * mA * mU | AGCTTCTTGTCC AGCUUUAU | OXOOOXXXX XXXXXXXXXX |
| WV-9874 | Mod001L001mA * SGeom5CeoTeoTeo * RC * ST * ST * SG * RT * SC * SC * RA * SG * SC * RTeo * SmU * SmU * SmA * SmU | AGCTTCTTGTCC AGCUUUAU | OSOOORSSS RSSRSSRSSSSS |
| WV-9885 | mA * Geom5CeoTeoTeo * C * T * T * G * T * C * C * A * G * C * mU * mU * mU * mA * mU | AGCTTCTTGTCC AGCUUUAU | XOOOXXXX XXXXXXXXXX |
| WV-9886 | mA * SGeom5CeoTeoTeo * RC * ST * ST * SG * RT * SC * SC * RA * SG * SC * SmU * SmU * SmU * SmA * SmU | AGCTTCTTGTCC AGCUUUAU | SOOORSSSR SSRSSSSSSS |
| WV-9887 | mA * Geom5CeoTeoTeo * C * T * T * G * T * C * C * A * G * C * Teo * mU * mU * mA * mU | AGCTTCTTGTCC AGCUUUAU | XOOOXXXX XXXXXXXXXX |

TABLE 1D-continued

APOC3 oligonucleotides.

| | | | |
|---|---|---|---|
| WV-9888 | mA * SGeom5CeoTeoTeo * RC * ST * ST * SG * RT * SC * SC * RA * SG * SC * RTeo * SmU * SmU * SmA * SmU | AGCTTCTTGTCCAGCTUUAU | SOOORSSSRSSRSSRSSSS |
| WV-10243 | L001mA * Geom5CeoTeoTeo * C * T * T * G * T * C * C * A * G * C * mU * mU * mU * mA * mU | AGCTTCTTGTCCAGCUUUAU | OXOOOXXXXXXXXXXXXXX |
| WV-10244 | L001mA * SGeom5CeoTeoTeo * RC * ST * ST * SG * RT * SC * SC * RA * SG * SC * SmU * SmU * SmU * SmA * SmU | AGCTTCTTGTCCAGCUUUAU | OSOOORSSSRSSRSSSSSSS |
| WV-10245 | L001mA * Geom5CeoTeoTeo * C * T * T * G * T * C * C * A * G * C * Teo * mU * mU * mA * mU | AGCTTCTTGTCCAGCUUUAU | OXOOOXXXXXXXXXXXXXX |
| WV-10246 | L001mA * SGeom5CeoTeoTeo * RC * ST * ST * SG * RT * SC * SC * RA * SG * SC * RTeo * SmU * SmU * SmA * SmU | AGCTTCTTGTCCAGCUUUAU | OSOOORSSSRSSRSSRSSSS |
| WV-12947 | Geo * m5CeoAeom5CeoTeo * G * A * G * A * A * T * A * C * T * G * mU * mC * mC * mC * mU | GCACTGAGAATACTGUCCCU | XOOOXXXXXXXXXXXXXX |
| WV-12948 | m5Ceo * Aeom5CeoTeoGeo * A * G * A * A * T * A * C * T * G * T * mC * mC * mC * mU * mU | CACTGAGAATACTGTCCCUU | XOOOXXXXXXXXXXXXXX |
| WV-12949 | Aeo * m5CeoTeoGeoAeo * G * A * A * T * A * C * T * G * T * C * mC * mC * mU * mU * mU | ACTGAGAATACTGTCCCUUU | XOOOXXXXXXXXXXXXXX |
| WV-12950 | m5Ceo * TeoGeoAeoGeo * A * A * T * A * C * T * G * T * C * C * mC * mU * mU * mU * mU | CTGAGAATACTGTCCCUUUU | XOOOXXXXXXXXXXXXXX |
| WV-12951 | Teo * GeoAeoGeoAeo * A * T * A * C * T * G * T * C * C * C * mU * mU * mU * mU * mA | TGAGAATACTGTCCCUUUUA | XOOOXXXXXXXXXXXXXX |
| WV-12952 | Geo * AeoGeoAeoAeo * T * A * C * T * G * T * C * C * C * T * mU * mU * mU * mA * mA | GAGAATACTGTCCCUUUAA | XOOOXXXXXXXXXXXXXX |
| WV-12953 | Aeo * GeoAeoAeoTeo * A * C * T * G * T * C * C * C * T * T * mU * mU * mA * mA * mG | AGAATACTGTCCCUUUAAG | XOOOXXXXXXXXXXXXXX |
| WV-12954 | Geo * AeoAeoTeoAeo * C * T * G * T * C * C * C * T * T * T * mU * mA * mA * mG * mC | GAATACTGTCCCTTTUAAGC | XOOOXXXXXXXXXXXXXX |
| WV-12955 | Aeo * AeoTeoAeom5Ceo * T * G * T * C * C * C * T * T * T * T * mA * mA * mG * mC * mA | AATACTGTCCCTTTTTAAGCA | XOOOXXXXXXXXXXXXXX |
| WV-12956 | Aeo * TeoAeom5CeoTeo * G * T * C * C * C * T * T * T * T * A * mA * mG * mC * mA * mA | ATACTGTCCCTTTTTAAGCAA | XOOOXXXXXXXXXXXXXX |
| WV-12957 | Teo * Aeom5CeoTeoGeo * T * C * C * C * T * T * T * T * A * A * mG * mC * mA * mA * mC | TACTGTCCCTTTTAAGCAAC | XOOOXXXXXXXXXXXXXX |
| WV-12958 | Aeo * m5CeoTeoGeoTeo * C * C * C * T * T * T * T * A * A * G * mC * mA * mA * mC * mC | ACTGTCCCTTTTAAGCAACC | XOOOXXXXXXXXXXXXXX |
| WV-12959 | m5Ceo * TeoGeoTeom5Ceo * C * C * T * T * T * T * A * A * G * C * mA * mA * mC * mC * mU | CTGTCCCTTTTAAGCAACCU | XOOOXXXXXXXXXXXXXX |
| WV-12960 | Teo * GeoTeom5Ceom5Ceo * C * T * T * T * T * A * A * G * C * A * mA * mC * mC * mU * mA | TGTCCCTTTTAAGCAACCUA | XOOOXXXXXXXXXXXXXX |
| WV-12961 | Geo * Teom5Ceom5Ceom5Ceo * T * T * T * T * A * A * G * C * A * A * mC * mC * mU * mA * mC | GTCCCTTTTAAGCAACCUAC | XOOOXXXXXXXXXXXXXX |
| WV-12962 | Teo * m5Ceom5Ceom5CeoTeo * T * T * T * A * A * G * C * A * A * C * mC * mU * mA * mC * mA | TCCCTTTTAAGCAACCUACA | XOOOXXXXXXXXXXXXXX |
| WV-12963 | m5Ceo * m5Ceom5CeoTeoTeo * T * T * A * A * G * C * A * A * C * C * mU * mA * mC * mA * mG | CCCTTTTAAGCAACCUACAG | XOOOXXXXXXXXXXXXXX |
| WV-12964 | m5Ceo * m5CeoTeoTeoTeo * T * A * A * G * C * A * A * C * C * T * mA * mC * mA * mG * mG | CCTTTTAAGCAACCUACAGG | XOOOXXXXXXXXXXXXXX |
| WV-12965 | m5Ceo * TeoTeoTeoTeo * A * A * G * C * A * A * C * C * T * A * mC * mA * mG * mG * mG | CTTTTAAGCAACCUACAGGG | XOOOXXXXXXXXXXXXXX |
| WV-12966 | Teo * TeoTeoTeoAeo * A * G * C * A * A * C * C * T * A * C * mA * mG * mG * mG * mG | TTTTAAGCAACCTACAGGGG | XOOOXXXXXXXXXXXXXX |
| WV-12967 | Teo * TeoTeoAeoAeo * G * C * A * A * C * C * T * A * C * A * mG * mG * mG * mG * mC | TTTAAGCAACCTACAGGGGC | XOOOXXXXXXXXXXXXXX |

TABLE 1D-continued

APOC3 oligonucleotides.

| WV- | Sequence | Target | Pattern |
|---|---|---|---|
| WV-12968 | Teo * TeoAeoAeoGeo * C * A * A * C * C * T * A * C * A * G * mG * mG * mG * mC * mA | TTAAGCAACCTACAGGGGCA | XOOOXXXX XXXXXXXXXX |
| WV-12969 | Teo * AeoAeoGeom5Ceo * A * A * C * C * T * A * C * A * G * G * mG * mG * mC * mA * mG | TAAGCAACCTACAGGGGCAG | XOOOXXXX XXXXXXXXXX |
| WV-12970 | Aeo * AeoGeom5CeoAeo * A * C * C * T * A * C * A * G * G * G * mG * mC * mA * mG * mC | AAGCAACCTACAGGGGCAGC | XOOOXXXX XXXXXXXXXX |
| WV-12971 | Aeo * Geom5CeoAeoAeo * C * C * T * A * C * A * G * G * G * G * mC * mA * mG * mC * mC | AGCAACCTACAGGGGCAGCC | XOOOXXXX XXXXXXXXXX |
| WV-12972 | Geo * m5CeoAeoAeom5Ceo * C * T * A * C * A * G * G * G * G * C * mA * mG * mC * mC * mC | GCAACCTACAGGGGCAGCCC | XOOOXXXX XXXXXXXXXX |
| WV-12973 | m5Ceo * AeoAeom5Ceom5Ceo * T * A * C * A * G * G * G * G * C * A * mG * mC * mC * mC * mU | CAACCTACAGGGGCAGCCCU | XOOOXXXX XXXXXXXXXX |
| WV-12974 | Aeo * Aeom5Ceom5CeoTeo * A * C * A * G * G * G * G * C * A * G * mC * mC * mC * mU * mG | AACCTACAGGGGCAGCCCUG | XOOOXXXX XXXXXXXXXX |
| WV-12975 | Aeo * m5Ceom5CeoTeoAeo * C * A * G * G * G * G * C * A * G * C * mC * mC * mU * mG * mG | ACCTACAGGGGCAGCCCUGG | XOOOXXXX XXXXXXXXXX |
| WV-12976 | Aeo * Geom5CeoTeoTeo * C * T * T * G * T * C * C * A * G * C * mU * mU * mU * mA * mU | AGCTTCTTGTCCAGCUUUAU | XOOOXXXX XXXXXXXXXX |
| WV-12977 | mG * mC * mA * mC * mU * G * A * G * A * A * T * A * C * T * G * Teom5Ceom5Ceom5Ceo * Teo | GCACUGAGAATACTGTCCCT | XXXXXXXXXX XXXOOOX |
| WV-12978 | mC * mA * mC * mU * mG * A * G * A * A * T * A * C * T * G * T * m5Ceom5Ceom5CeoTeo * Teo | CACUGAGAATACTGTGTCCCTT | XXXXXXXXXX XXXOOOX |
| WV-12979 | mA * mC * mU * mG * mA * G * A * A * T * A * C * T * G * T * C * m5Ceom5CeoTeoTeo * Teo | ACUGAGAATACTGTCCCTTT | XXXXXXXXXX XXXOOOX |
| WV-12980 | mC * mU * mG * mA * mG * A * A * T * A * C * T * G * T * C * C * m5CeoTeoTeoTeo * Teo | CUGAGAATACTGTCCCTTTT | XXXXXXXXXX XXXOOOX |
| WV-12981 | mU * mG * mA * mG * mA * A * T * A * C * T * G * T * C * C * C * TeoTeoTeoTeo * Aeo | UGAGAATACTGTCCCTTTTA | XXXXXXXXXX XXXOOOX |
| WV-12982 | mG * mA * mG * mA * mA * T * A * C * T * G * T * C * C * C * T * TeoTeoTeoAeo * Aeo | GAGAATACTGTCCCTTTTAA | XXXXXXXXXX XXXOOOX |
| WV-12983 | mA * mG * mA * mA * mU * A * C * T * G * T * C * C * C * T * T * TeoTeoAeoAeo * Geo | AGAAUACTGTCCCTTTTAAG | XXXXXXXXXX XXXOOOX |
| WV-12984 | mG * mA * mA * mU * mA * C * T * G * T * C * C * C * T * T * T * TeoAeoAeoGeo * m5Ceo | GAAUACTGTCCCTTTTAAGC | XXXXXXXXXX XXXOOOX |
| WV-12985 | mA * mA * mU * mA * mC * T * G * T * C * C * C * T * T * T * T * AeoAeoGeom5Ceo * Aeo | AAUACTGTCCCTTTTAAGCA | XXXXXXXXXX XXXOOOX |
| WV-12986 | mA * mU * mA * mC * mU * G * T * C * C * C * T * T * T * T * A * AeoGeom5CeoAeo * Aeo | AUACUGTCCCTTTTAAGCAA | XXXXXXXXXX XXXOOOX |
| WV-12987 | mU * mA * mC * mU * mG * T * C * C * C * T * T * T * T * A * A * Geom5CeoAeoAeo * m5Ceo | UACUGTCCCTTTTAAGCAAC | XXXXXXXXXX XXXOOOX |
| WV-12988 | mA * mC * mU * mG * mU * C * C * C * T * T * T * T * A * A * G * m5CeoAeoAeom5Ceo * m5Ceo | ACUGUCCCTTTTAAGCAACC | XXXXXXXXXX XXXOOOX |
| WV-12989 | mC * mU * mG * mU * mC * C * C * T * T * T * T * A * A * G * C * AeoAeom5Ceom5Ceo * Teo | CUGUCCCTTTTAAGCAACCT | XXXXXXXXXX XXXOOOX |
| WV-12990 | mU * mG * mU * mC * mC * C * T * T * T * T * A * A * G * C * A * Aeom5Ceom5CeoTeo * Aeo | UGUCCCTTTTAAGCAACCTA | XXXXXXXXXX XXXOOOX |
| WV-12991 | mG * mU * mC * mC * mC * T * T * T * T * A * A * G * C * A * A * m5Ceom5CeoTeoAeo * m5Ceo | GUCCCTTTTAAGCAACCTAC | XXXXXXXXXX XXXOOOX |

TABLE 1D-continued

APOC3 oligonucleotides.

| | | | |
|---|---|---|---|
| WV-12992 | mU * mC * mC * mC * mU * T * T * T * A * A * G * C * A * A * C * m5CeoTeoAeom5Ceo * Aeo | UCCCUUTTAAGCAACCTACA | XXXXXXXXXXXXXXXOOOX |
| WV-12993 | mC * mC * mC * mU * mU * T * T * A * A * G * C * A * A * C * C * TeoAeom5CeoAeo * Geo | CCCUUTTAAGCAACCTACAG | XXXXXXXXXXXXXXXOOOX |
| WV-12994 | mC * mC * mU * mU * mU * T * A * A * G * C * A * A * C * C * T * Aeom5CeoAeoGeo * Geo | CCUUUTAAGCAACCTACAGG | XXXXXXXXXXXXXXXOOOX |
| WV-12995 | mC * mU * mU * mU * mU * A * A * G * C * A * A * C * C * T * A * m5CeoAeoGeoGeo * Geo | CUUUUAAGCAACCTACAGGG | XXXXXXXXXXXXXXXOOOX |
| WV-12996 | mU * mU * mU * mU * mA * A * G * C * A * A * C * C * T * A * C * AeoGeoGeoGeo * Geo | UUUUAAGCAACCTACAGGGG | XXXXXXXXXXXXXXXOOOX |
| WV-12997 | mU * mU * mU * mA * mA * G * C * A * A * C * C * T * A * C * A * GeoGeoGeoGeo * m5Ceo | UUUAAGCAACCTACAGGGGC | XXXXXXXXXXXXXXXOOOX |
| WV-12998 | mU * mU * mA * mA * mG * C * A * A * C * C * T * A * C * A * G * GeoGeoGeom5Ceo * Aeo | UUAAGCAACCTACAGGGGCA | XXXXXXXXXXXXXXXOOOX |
| WV-12999 | mU * mA * mA * mG * mC * A * A * C * C * T * A * C * A * G * G * GeoGeom5CeoAeo * Geo | UAAGCAACCTACAGGGGCAG | XXXXXXXXXXXXXXXOOOX |
| WV-13000 | mA * mA * mG * mC * mA * A * C * C * T * A * C * A * G * G * G * Geom5CeoAeoGeo * m5Ceo | AAGCAACCTACAGGGGCAGC | XXXXXXXXXXXXXXXOOOX |
| WV-13001 | mA * mG * mC * mA * mA * C * C * T * A * C * A * G * G * G * G * m5CeoAeoGeom5Ceo * m5Ceo | AGCAACCTACAGGGGCAGCC | XXXXXXXXXXXXXXXOOOX |
| WV-13002 | mG * mC * mA * mA * mC * C * T * A * C * A * G * G * G * G * C * AeoGeom5Ceom5Ceo * m5Ceo | GCAACCTACAGGGGCAGCCC | XXXXXXXXXXXXXXXOOOX |
| WV-13003 | mC * mA * mA * mC * mC * T * A * C * A * G * G * G * G * C * A * Geom5Ceom5Ceom5Ceo * Teo | CAACCTACAGGGGCAGCCCT | XXXXXXXXXXXXXXXOOOX |
| WV-13004 | mA * mA * mC * mC * mU * A * C * A * G * G * G * G * C * A * G * m5Ceom5Ceom5CeoTeo * Geo | AACCUACAGGGGCAGCCCTG | XXXXXXXXXXXXXXXOOOX |
| WV-13005 | mA * mC * mC * mU * mA * C * A * G * G * G * G * C * A * G * C * m5Ceom5CeoTeoGeo * Geo | ACCUACAGGGGCAGCCCTGG | XXXXXXXXXXXXXXXOOOX |
| WV-13006 | mC * mU * mU * mG * mU * C * C * A * G * C * T * T * T * A * T * TeoGeoGeoGeo * Aeo | CUUGUCCAGCTTTATTGGGA | XXXXXXXXXXXXXXXOOOX |
| WV-13007 | mA * mG * mC * mU * mU * C * T * T * G * T * C * C * A * G * C * TeoTeoTeoAeo * Teo | AGCUUCTTGTCCAGCTTT AT | XXXXXXXXXXXXXXXOOOX |
| WV-13008 | mA * mU * mA * mG * mC * A * G * C * T * T * C * T * T * G * T * m5Ceom5CeoAeoGeo * m5Ceo | AUAGCAGCTTCTTGTCCA GC | XXXXXXXXXXXXXXXOOOX |

Key to Table 1 (including all subparts, such as Table 1A, Table 1B, etc.):

The present disclosure notes that some sequences, due to their length, are divided into multiple lines in Table 1 (e.g., WV-9421, WV-9399, WV-9398, WV-9397, WV-9396, etc.); however, these sequences, as are all oligonucleotides in Table 1, are single-stranded (unless otherwise noted).

Moieties and modifications listed in the Tables (or compounds used to construct oligonucleotides comprising these moieties or modifications: 1: LNA sugar moieties (2'-O—CH$_2$-4'), e.g., 1A [

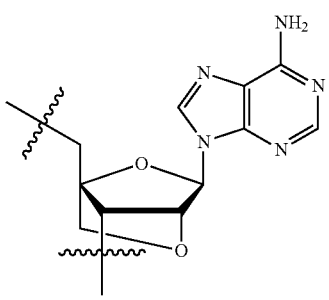 [SMILES: *C[C@]12CO[C@@H](C1*)[C@H](n1cnc3c(N)ncnc31)O2]

if between 5'-end group(s) and internucleotidic linkage, or between internucleotidic linkages

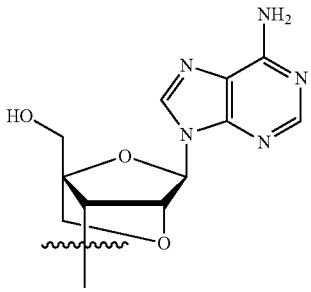 [SMILES: *C1[C@@H]2OC[C@]1(CO)O[C@H]2n1cnc2c(N)ncnc21]

if at 5'-end and without 5'-end groups; or

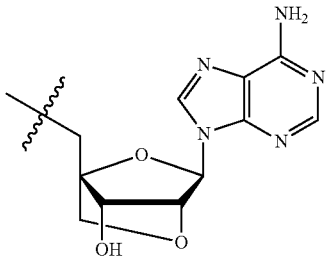 [SMILES: *C[C@]12CO[C@@H](C1O)[C@H](n1cnc3c(N)ncnc31)O2]

if at 3'-end (e.g., in WV-12575)]; and m51C [

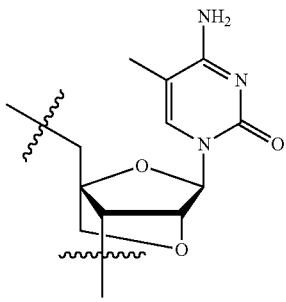 [SMILES: *C[C@]12CO[C@@H](C1*)[C@H](n1cc(C)c(N)nc1=O)O2]

if between 5'-end group(s) and internucleotidic linkages, or between internucleotidic linkages;

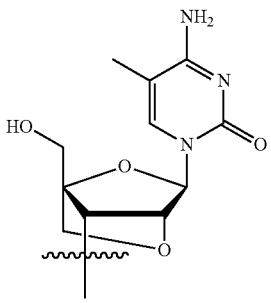

if at 5'-end and without 5'-end groups (e.g., in WV-12575); or

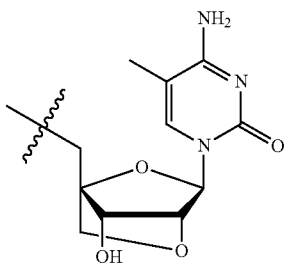 [SMILES: *C[C@]12CO[C@@H](C1O)[C@H](n1cc(C)c(N)nc1=O)O2]

if at 3'-end]

m: 2'-OMe m5: methyl at 5-position of C (nucleobase is 5-methylcytosine)

m5Ceo: 5-methyl 2'-O-methoxyethyl C

5MRd: 5'-methyl group wherein the 5'-C is in the Rp configuration, 2'-deoxy

5MSd: 5'-methyl group wherein the 5'-C is in the Sp configuration, 2'-deoxy

OMe: 2'-OMe eo: 2'-MOE (2'-OCH$_2$CH$_2$OCH$_3$)

F, f: 2'-F;

r: 2'-OH;

O, PO: phosphodiester (phosphate); can be an end group, or a linkage, e.g., a linkage between linker and oligonucleotide chain, an internucleotidic linkage, etc. Phosphodiesters indicated in the Stereochemistry/Internucleotidic Linkages column are not reproduced in the Modified Sequence column; if no internucleotidic linkage is indicated in the Modified Sequence column, it is a phosphodiester *, PS: Phosphorothioate; this can be an end group, or a linkage, e.g., a linkage between linker and oligonucleotide chain, an internucleotidic linkage, etc.

R, Rp: Phosphorothioate in Rp conformation; note that *R indicates a single phosphorothioate in the Rp conformation S, Sp: Phosphorothioate in Sp conformation; note that *S indicates a single phosphorothioate in the Sp conformation n001:

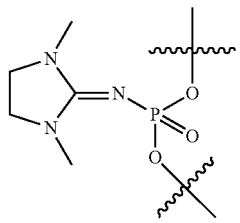 [SMILES: *OP(=O)(N=C1N(C)CCN1C)O*]

nX: stereorandom n001

X: Stereorandom phosphorothioate

L001: —NH—(CH$_2$)$_6$-linker (also known as a C6 linker, C6 amine linker or C6 amino linker), connected to Mod, if any, through —NH—, and the 5'-end of the oligonucleotide chain through either a phosphate linkage (O or PO) or phosphorothioate linkage (* if the phosphorothioate not chirally controlled; can also be Sp if chirally controlled and has an Sp configuration, and Rp if chirally controlled and has an Rp configuration) as illustrated. If no Mod is present, L001 is connected to —H, e.g., in WV-9380 or WV-9285. For example, in WV-9381, L001 is connected to Mod007 through —NH— (forming an amide group —C(O)—NH—), and is connected to the oligonucleotide chain through a phosphate linkage (indicated by bold underlined in <u>O</u>SO<u>O</u>OSSSRSSRSSSSSSSS); in WV-9062, L001 is not connected to any Mod, but to —H, through —NH—, and is connected to the oligonucleotide chain through a phosphate linkage (indicated by bold underlined in <u>O</u>SO<u>O</u>OSSSRSSSSSSSSSSS).

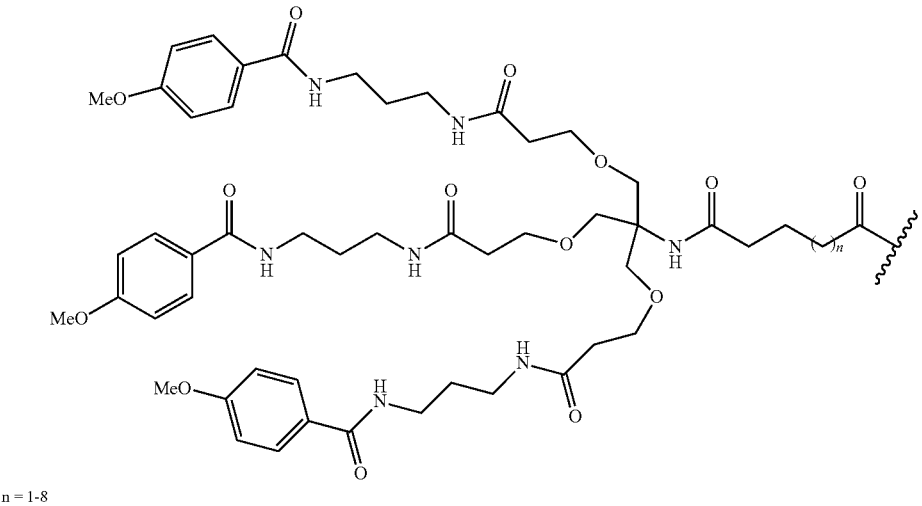

Mod007 n = 1-8

In Mod007, n=8.

BrdU: a nucleoside unit wherein the nucleobase is BrU

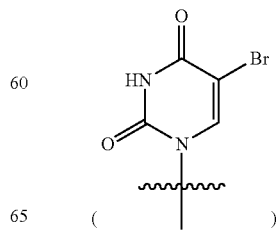

and wherein the sugar is 2-deoxyribose (as widely found in natural DNA; 2'-deoxy (d));

In some embodiments, a provided oligonucleotide capable of directing a decrease in the expression, level

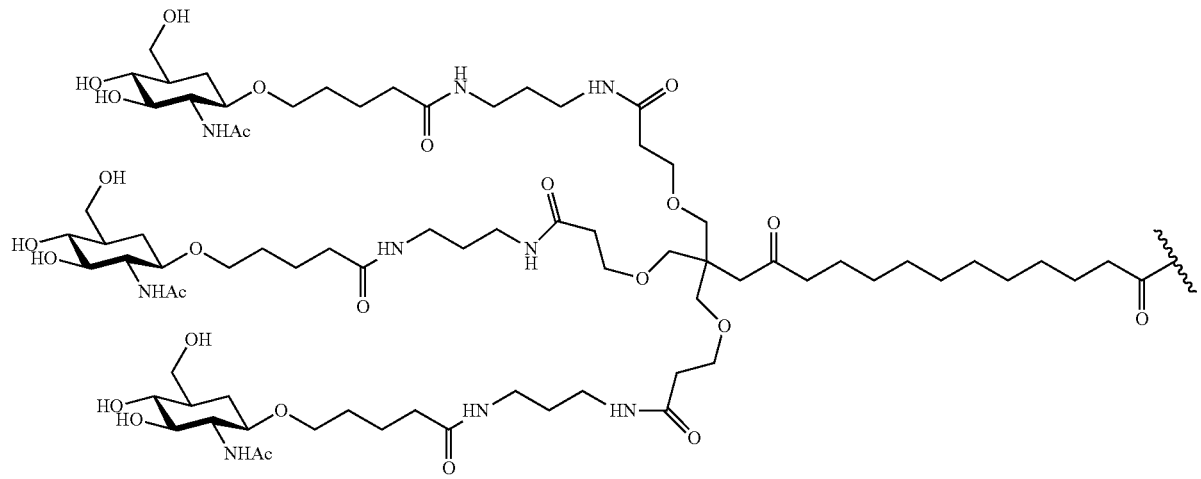
Mod024

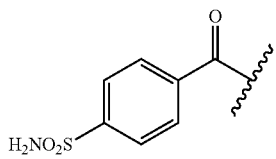
Mod027

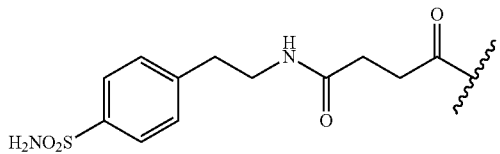
Mod028

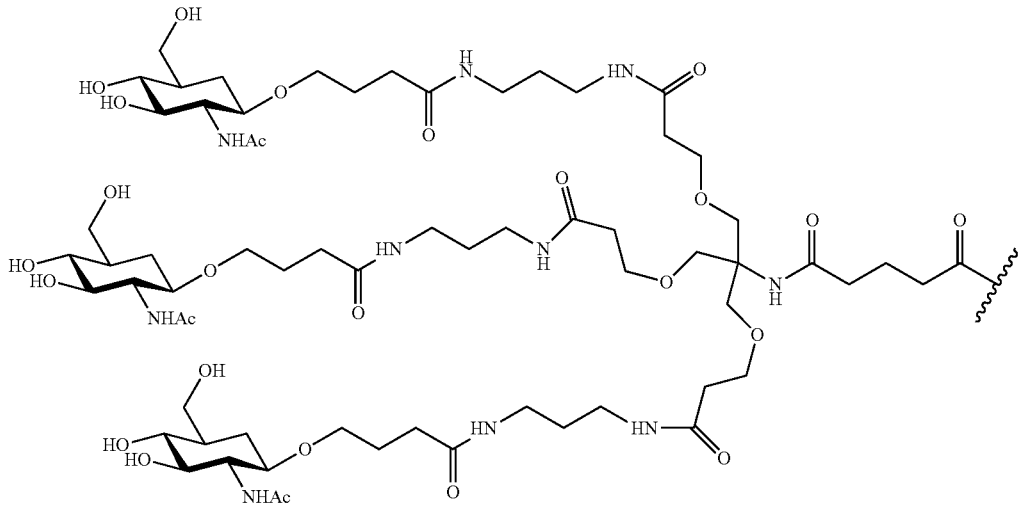
Mod059

In some embodiments, provided oligonucleotides can direct a decrease in the expression, level and/or activity of a target gene or its gene product. In some embodiments, a target gene comprises a mutation and is associated or related to a disorder or disease.

In some embodiments, a provided oligonucleotide has a structural element or format or portion thereof described herein.

and/or activity of a target gene or its gene product has a structural element or format or portion thereof described herein.

In some embodiments, a provided oligonucleotide capable of directing a decrease in the expression, level and/or activity of a target gene or its gene product has the format of any oligonucleotide disclosed herein, e.g., in Table 1 or in the Figures, or otherwise disclosed herein, or a structural element or format or portion thereof.

In some embodiments, the present disclosure provides an oligonucleotide composition comprising a first plurality of oligonucleotides, wherein:

oligonucleotides of the first plurality have the same base sequence; and oligonucleotides of the first plurality comprise one or more modified sugar moieties, or comprise one or more natural phosphate linkages and one or more modified internucleotidic linkages.

In some embodiments, provided compositions alter transcript knockdown so that an undesired target and/or biological function are suppressed. In some embodiments, in such cases provided composition can also induce cleavage of the transcript after hybridization.

In some embodiments, compared to a reference condition, provided chirally controlled oligonucleotide compositions are surprisingly effective. In some embodiments, desired biological effects (e.g., as measured by increased levels of desired mRNA, proteins, etc., decreased levels of undesired mRNA, proteins, etc.) can be enhanced by more than 5, 10, 15, 20, 25, 30, 40, 50, or 100 fold. In some embodiments, a change is measured by increase of a desired mRNA level compared to a reference condition.

In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a first plurality, comprise base modifications, sugar modifications, and/or internucleotidic linkage modifications, wherein the oligonucleotides contain an enriched level of deuterium. In some embodiments, provided oligonucleotides are labeled with deuterium (replacing —$^1$H with —$^2$H) at one or more positions. In some embodiments, one or more $^1$H of an oligonucleotide or any moiety conjugated to the oligonucleotide (e.g., a targeting moiety, etc.) is substituted with $^2$H. Such oligonucleotides can be used in any composition or method described herein.

In some embodiments, the present disclosure provides an oligonucleotide composition comprising a first plurality of oligonucleotides which:

1) have a common base sequence complementary to a target sequence in a transcript; and 2) comprise one or more modified sugar moieties and modified internucleotidic linkages, wherein the oligonucleotides have an asymmetrical format.

In some embodiments, the present disclosure provides an oligonucleotide composition comprising a first plurality of oligonucleotides capable of directing knockdown, wherein an oligonucleotides type is defined by:

1) base sequence;
2) pattern of backbone linkages;
3) pattern of backbone chiral centers; and
4) pattern of backbone phosphorus modifications, which composition is chirally controlled in that it is enriched, relative to a substantially racemic preparation of oligonucleotides having the same base sequence, for oligonucleotides of the particular oligonucleotide type, the oligonucleotide composition being characterized in that, when it is contacted with the transcript in a knockdown system, knockdown-mediated knockdown of the transcript is improved relative to that observed under reference conditions selected from the group consisting of absence of the composition, presence of a reference composition, and combinations thereof, wherein the oligonucleotides have an asymmetrical format.

In some embodiments, the present disclosure provides an oligonucleotide composition comprising a first plurality of oligonucleotides, wherein: oligonucleotides of the first plurality have the same base sequence; oligonucleotides of the first plurality comprise structural elements (a) 2, 3, 4, 5, 6, 7, 8, 9, 10, 11, 12, 13, 14, 15, 16, 17, 18, 19, 20 or more nucleoside units comprising 2'-F, 2'-OMe, 2'-deoxy and/or 2'-MOE modified sugar moieties; (b) 2, 3, 4, 5, 6, 7, 8, 9, 10, 11, 12, 13, 14, 15, 16, 17, 18, 19, 20 or more modified internucleotidic linkages, (c) 2, 3, 4, 5, 6, 7, 8, 9, 10, 11, 12, 13, 14, 15, 16, 17, 18, 19, 20 or more chirally controlled modified internucleotidic linkages, and (d) 2, 3, 4, 5, 6, 7, 8, 9, 10 or more natural phosphate linkages. In some embodiments, the oligonucleotides of the first plurality comprise structural elements (a), (b) and (c). In some embodiments, the oligonucleotides of the first plurality comprise structural elements (b), (c) and (d). In some embodiments, the oligonucleotides of the first plurality comprise structural elements (a), (b) and (d). In some embodiments, the oligonucleotides of the first plurality comprise structural elements (a), (c) and (d). In some embodiments, the oligonucleotides of the first plurality comprise structural elements (a) and (b). In some embodiments, the oligonucleotides of the first plurality comprise structural elements (a) and (c). In some embodiments, the oligonucleotides of the first plurality comprise structural elements (a) and (d). In some embodiments, the oligonucleotides of the first plurality comprise structural elements (b) and (c). In some embodiments, the oligonucleotides of the first plurality comprise structural elements (b) and (d). In some embodiments, the oligonucleotides of the first plurality comprise structural elements (c) and (d).

In some embodiments, a modified internucleotidic linkage has a structure of Formula I. In some embodiments, a modified internucleotidic linkage has a structure of Formula I-a.

As demonstrated in the present disclosure, in some embodiments, a provided oligonucleotide composition is characterized in that, when it is contacted with the transcript in a knockdown system, knockdown-mediated knockdown of the transcript is improved relative to that observed under reference conditions selected from the group consisting of absence of the composition, presence of a reference composition, and combinations thereof. In some embodiments, knockdown is increased 10%, 20%, 30%, 40%, 50%, 60%, 70%, 80%, 90%, 100%, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000 fold or more. In some embodiments, as exemplified in the present disclosure, levels of the plurality of oligonucleotides, e.g., a first plurality of oligonucleotides, in provided compositions are pre-determined.

In some embodiments, a common base sequence and length may be referred to as a common base sequence. In some embodiments, oligonucleotides having a common base sequence may have the same pattern of nucleoside modifications, e.g., sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkages. A pattern of backbone chiral centers of an oligonucleotide can be designated by a combination of linkage phosphorus stereochemistry (Rp/Sp) from 5' to 3'. As exemplified above, locations of non-chiral linkages may be obtained, for example, from pattern of backbone linkages.

In some embodiments, the present disclosure provides an oligonucleotide composition comprising a first plurality of oligonucleotides capable of directing knockdown, wherein oligonucleotides are of a particular oligonucleotide type characterized by:
1) a common base sequence and length;
2) a common pattern of backbone linkages; and
3) a common pattern of backbone chiral centers;
which composition is chirally controlled in that it is enriched, relative to a substantially racemic preparation of oligonucleotides having the same base sequence and length, for oligonucleotides of the particular oligonucleotide type.

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1.

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage.

In some embodiments, the present disclosure provides chirally controlled (and/or stereochemically pure) oligonucleotide compositions comprising a first plurality of oligonucleotides defined by having:
1) a common base sequence and length;
2) a common pattern of backbone linkages; and
3) a common pattern of backbone chiral centers, which composition is a substantially pure preparation of a single oligonucleotide in that at least about 10% of the oligonucleotides in the composition have the common base sequence and length, the common pattern of backbone linkages, and the common pattern of backbone chiral centers.

In some embodiments, a sugar moiety without a 2'-modification is a sugar moiety found in a natural DNA nucleoside.

A person of ordinary skill in the art understands that various regions of a target transcript can be targeted by provided compositions and methods. In some embodiments, a base sequence of provided oligonucleotides comprises an intron sequence. In some embodiments, a base sequence of provided oligonucleotides comprises an exon sequence. In some embodiments, a base sequence of provided oligonucleotides comprises an intron and an exon sequence.

As understood by a person having ordinary skill in the art, provided oligonucleotides and compositions, among other things, can target a great number of nucleic acid polymers. For instance, in some embodiments, provided oligonucleotides and compositions may target a transcript of a nucleic acid sequence, wherein a common base sequence of oligonucleotides (e.g., a base sequence of an oligonucleotide type) comprises or is a sequence complementary to a sequence of the transcript.

In some embodiments, a similar sequence has greater than 60%, 65%, 70%, 75%, 80%, 85%, 90%, 91%, 92%, 93%, 94%, 95%, 96%, 97%, 98% or 99% sequence identity with a target sequence. In some embodiments, a target sequence is a disease-causing copy of a nucleic acid sequence comprising one or more mutations, and a similar sequence is a copy not causing the disease (wild type). In some embodiments, a target sequence comprises a mutation, wherein a similar sequence is the corresponding wild-type sequence. In some embodiments, a target sequence is a mutant allele, while a similar sequence is a wild-type allele. In some embodiments, a target sequence is in an intron comprising a hexanucleotide repeat expansion. In some embodiments, the region of a target sequence that is complementary to a common base sequence of a provided oligonucleotide composition differs from the corresponding region of a similar sequence at less than 5, less than 4, less than 3, less than 2, or only 1 base pairs.

In some embodiments, a common base sequence comprises or is a sequence complementary to a characteristic sequence element. In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments, a characteristic sequence element is or comprises a mutation. In some embodiments, characteristic sequence element is or comprises a point mutation. In some embodiments, characteristic sequence element is or comprises a SNP.

Among other things, the present disclosure recognizes that a base sequence may have impact on oligonucleotide properties. In some embodiments, a base sequence may have impact on cleavage pattern of a C9orf72 target when oligonucleotides having the base sequence are utilized for suppressing a C9orf72 target, e.g., through a pathway involving RNase H: for example, structurally similar (all phosphorothioate linkages, all stereorandom) oligonucleotides have different sequences may have different cleavage patterns.

As a person having ordinary skill in the art understands, provided C9orf72 oligonucleotide compositions and methods have various uses as known by a person having ordinary skill in the art. Methods for assessing provided compositions, and properties and uses thereof, are also widely known and practiced by a person having ordinary skill in the art. Example properties, uses, and/or methods include but are not limited to those described in WO/2014/012081 and WO/2015/107425.

In some embodiments, a chiral internucleotidic linkage has the structure of Formula I. In some embodiments, a chiral internucleotidic linkage is phosphorothioate. In some embodiments, each chiral internucleotidic linkage in a single oligonucleotide of a provided composition independently has the structure of Formula I. In some embodiments, each chiral internucleotidic linkage in a single oligonucleotide of a provided composition is a phosphorothioate.

In some embodiments, C9orf72 oligonucleotides of the present disclosure comprise one or more modified sugar moieties. In some embodiments, C9orf72 oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198, WO2014/012081 and WO/2015/107425, the sugar and base modifications of each of which are incorporated herein by reference.

In some embodiments, a sugar modification is a 2'-modification. Commonly used 2'-modifications include but are not limited to 2'-OR$^1$, wherein R$^1$ is not hydrogen. In some embodiments, a modification is 2'-OR, wherein R is optionally substituted aliphatic. In some embodiments, a modification is 2'-OMe. In some embodiments, a modification is 2'-O-MOE. In some embodiments, the present disclosure demonstrates that inclusion and/or location of particular chirally pure internucleotidic linkages can provide stability improvements comparable to or better than those achieved through use of modified backbone linkages, bases, and/or sugars. In some embodiments, a provided single oligonucleotide of a provided composition has no modifications on the sugars. In some embodiments, a provided single oligonucleotide of a provided composition has no modifications on 2'-positions of the sugars (i.e., the two groups at the 2'-position are either —H/—H or —H/—OH). In some embodiments, a provided single oligonucleotide of a provided composition does not have any 2'-MOE modifications.

In some embodiments, a 2'-modification is —O-L- or -L- which connects the 2'-carbon of a sugar moiety to another carbon of a sugar moiety. In some embodiments, a 2'-modification is —O-L- or -L- which connects the 2'-carbon of a sugar moiety to the 4'-carbon of a sugar moiety. In some embodiments, a 2'-modification is S-cEt. In some embodiments, a modified sugar moiety is an LNA moiety.

In some embodiments, a locked nucleic acid or LNA or LNA nucleoside or LNA nucleotide is or comprises a nucleic acid monomer having a bridge connecting two carbon atoms between the 4' and 2' position of the nucleoside sugar unit, thereby forming a bicyclic sugar. Examples of such a bicyclic sugar include but are not limited to alpha-L-Methyleneoxy (4'-CH$_2$—O-2') LNA, beta-D-Methyleneoxy (4'-CH$_2$—O-2') LNA, Ethyleneoxy (4'-(CH$_2$)$_2$—O-2') LNA, Aminooxy (4'-CH$_2$—O—N(R)-2') LNA, and Oxyamino (4'-CH$_2$—N(R)—O-2') LNA. In some embodiments, R is R$_1$ or R$_2$.

In some embodiments, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group. Non-limiting examples of 4'-2' bridging groups encompassed within the definition of LNA include, but are not limited to one of formulae: —[C(R$_1$)(R$_2$)]$_n$—, —[C(R$_1$)(R$_2$)]n-O—, —C(R$_1$R$_2$)—N(R$_1$)—O— or C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl. Also included within the definition of LNA are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. In some embodiments, in the case of the bicylic sugar moiety having an ethylene bridging group in this position, the term ethyleneoxy (4'-CH$_2$CH$_2$—O-2') LNA is used. alpha-L-methyleneoxy (4'-CH$_2$—O-2'), an isomer of methyleneoxy (4'-CH$_2$—O-2') LNA, is also encompassed within the definition of LNA, as used herein.

In some embodiments, a 2'-modification is —F. In some embodiments, a 2'-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, an antisense oligonucleotide (ASO) is or comprises an oligonucleotide selected from the group consisting of: any oligonucleotide disclosed herein, and any oligonucleotide of any format described herein. Those skilled in the art, reading the present specification, will appreciate that the present disclosure specifically does not exclude the possibility that any oligonucleotide described herein which is labeled as an antisense oligonucleotide (ASO) may also or alternatively operate through another mechanism (e.g., as a knockdown utilizing RISC); the disclosure also notes that various oligonucleotides may operate via different mechanisms (utilizing RNase H, sterically blocking translation or other post-transcriptional processes, changing the conformation of a target nucleic acid, etc.).

Provided oligonucleotides and compositions may be prepared by various technologies, e.g., those described in WO2017/062862, US20180216108, US20170037399, and U.S. Pat. No. 9,982,257. In some embodiments, modifying comprises use of click chemistry, e.g., wherein an alkyne group of an oligonucleotide, e.g., of an internucleotidic linkage, is reacted with an azide. Various reagents and conditions for click chemistry can be utilized in accordance with the present disclosure. In some embodiments, an azid has the structure of R$^1$—N$_3$, wherein R$^1$ is as described in the present disclosure. In some embodiments, $R^1$ is optionally substituted $C_{1-6}$ alkyl. In some embodiments, $R^1$ is isopropyl. In some embodiments, a P(III) linkage (e.g., formed after a coupling step of an oligonucleotide synthesis cycle) can be converted into a non-negatively charged internucleotidic linkage by reacting the P(III) linkage with an azide or an azido imidazolinium salt (e.g., a compound comprising

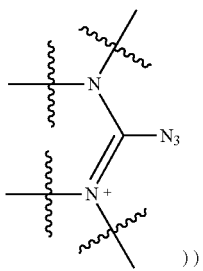

)) under suitable conditions. In some embodiments, an azido imidazolinium salt is a salt of $PF_6^-$. In some embodiments, an azido imidazolinium salt is a slat of

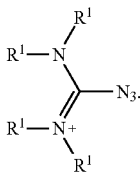

In some embodiments, an azido imidazolinium salt is 2-azido-1,3-dimethylimidazolinium hexafluorophosphate. In some embodiments, a P(III) linkage is reacted with an electrophile having the structure of $R-G^Z$, wherein R is as described in the present disclosure, and $G^Z$ is a leaving group, e.g., —Cl, —Br, —I, —OTf, —Oms, —OTosyl, etc. In some embodiments, R is —$CH_3$. In some embodiments, R is —$CH_2CH_3$. In some embodiments, R is —$CH_2CH_2CH_3$. In some embodiments, R is —$CH_2OCH_3$. In some embodiments, R is $CH_3CH_2OCH_2$—. In some embodiments, R is $PhCH_2OCH_2$—. In some embodiments, R is HC≡C—$CH_2$—. In some embodiments, R is $H_3$C—C≡C—$CH_2$—. In some embodiments, R is $CH_2$=$CHCH_2$—. In some embodiments, R is $CH_3SCH_2$—. In some embodiments, R is —$CH_2COOCH_3$. In some embodiments, R is —$CH_2COOCH_2CH_3$. In some embodiments, R is —$CH_2CONHCH_3$.

Biological Applications

As described herein, provided compositions and methods are capable of improving knockdown of RNA, including knockdown of RNA transcripts. In some embodiments, provided compositions and methods provide improved knockdown of transcripts (including but not limited to those comprising a repeat expansion) compared to a reference condition selected from the group consisting of absence of the composition, presence of a reference composition, and combinations thereof.

In some embodiment, an oligonucleotide is capable of preferentially decreasing (knocking down) the expression, level and/or activity of a mutant (e.g., disorder-associated) gene or gene product thereof relative to that of a wild-type (e.g., not disorder-associated) gene or gene product (e.g., the oligonucleotide is capable of mediating allele-specific knockdown). In some embodiments, an oligonucleotide is capable of decreasing (knocking down) the expression, level and/or activity of both a mutant (e.g., disorder-associated) and wild-type (e.g., not disorder-associated) gene or gene product (e.g., the oligonucleotide is pan-specific).

Preferential knockdown of mutant C9orf72 (e.g., repeat expansion-containing C9orf72 transcripts) by various oligonucleotides was tested. C9orf72 oligonucleotides WV-3688, WV-6408, WV-7658, WV-7659, WV-8011 and WV-8012 were all able to preferentially knock down the level of repeat expansion-containing RNA transcripts relative to the level of non-repeat expansion-containing RNA transcripts (e.g., total transcripts, most of which are normal transcripts which do not comprise a repeat expansion). Total transcripts include V2, V3 and V1, both normal (healthy, without repeat expansions) and mutant (pathological, comprising a repeat expansion). V1 is reportedly transcribed at very low levels (around 1% of the total transcripts) and does not contribute significantly to the levels of transcripts comprising hexanucleotide repeat expansions or to the levels of transcripts detected in assays for V3 transcripts.

In some embodiments, the present disclosure provides a method of treating a disease by administering a composition comprising a first plurality of oligonucleotides sharing a common base sequence comprising a common base sequence, which nucleotide sequence is complementary to a target sequence in the target transcript, the improvement that comprises using as the oligonucleotide composition a stereocontrolled oligonucleotide composition characterized in that, when it is contacted with the transcript in an oligonucleotide or a knockdown system, RNase H-mediated knockdown of the transcript is improved relative to that observed under a reference condition selected from the group consisting of absence of the composition, presence of a reference composition, and combinations thereof.

Evaluation and Testing of Efficacy of Oligonucleotides

Various techniques and tools, including but not limited to many known in the art, can be used for evaluation and testing of oligonucleotides.

In some embodiments, evaluation and testing of efficacy of oligonucleotides can be performed by quantifying a change or improvement in the level, activity, expression, allele-specific expression and/or intracellular distribution of a target nucleic acid or a corresponding gene product following delivery of an oligonucleotide. In some embodiments, delivery can be via a transfection agent or without a transfection agent (e.g., gymnotic).

In some embodiments, evaluation and testing of efficacy of oligonucleotides can be performed by quantifying a change in the level, activity, expression and/or intracellular of a gene product (including but not limited to a transcript, DPR or focus) following introduction of an oligonucleotide. Gene products include RNA produced from a gene or locus.

In some embodiments, the present disclosure provides a method of identifying and/or characterizing an oligonucleotide composition, the method comprising steps of:

providing at least one composition comprising a first plurality of oligonucleotides; and assessing delivery relative to a reference composition.

In some embodiments, the present disclosure provides a method of identifying and/or characterizing an oligonucleotide composition, the method comprising steps of:

providing at least one composition comprising a first plurality of oligonucleotides; and assessing cellular uptake relative to a reference composition.

In some embodiments, properties of a provided oligonucleotide compositions are compared to a reference oligonucleotide composition.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications.

In some embodiments, a reference composition is a composition of oligonucleotides having the same base sequence but different chemical modifications, including but not limited to chemical modifications described herein. In some embodiments, a reference composition is a composition of oligonucleotides having the same base sequence but different patterns of internucleotidic linkages and/or stereochemistry of internucleotidic linkages and/or chemical modifications.

Various methods are known in the art for the detection of gene products, the expression, level and/or activity of which might be altered after introduction or administration of an oligonucleotide. As non-limiting examples: transcripts and their knockdown can be quantified with qPCR, protein levels can be determined via Western blot, RNA foci by FISH (fluorescence in situ hybridization), DPRs by Western blot, ELISA, or mass spectrometry. Commercially available antibodies include anti-C9orf72 antibody GT779 (1:2000; GeneTex, Irvine, Calif.). In addition, functional assays can be performed on motor neurons (MN) expressing wild-type and/or mutant by Electrophysiology and NMJ formation.

In some embodiments, evaluation and testing of efficacy of oligonucleotides can be performed in vitro in a cell.

In some embodiments, evaluation of an oligonucleotide can be performed in an animal. In some embodiments, an animal is a mouse.

In some embodiments, target nucleic acid levels can be quantitated by any method known in the art, many of which can be accomplished with kits and materials which are commercially available, and which methods are well known and routine in the art. Such methods include, e.g., Northern blot analysis, competitive polymerase chain reaction (PCR), or quantitative real-time PCR. RNA analysis can be performed on total cellular RNA or poly(A)+ mRNA. Probes and primers are designed to hybridize to a nucleic acid. Methods for designing real-time PCR probes and primers are well known in the art.

In some embodiments, evaluation and testing of efficacy of oligonucleotides can be performed using a luciferase assay. A non-limiting example of such an assay is detailed in the Examples.

In some embodiments, a protein level can be evaluated or quantitated in any method known in the art, including, but not limited to, enzyme-linked immunosorbent assay (ELISA), Western blot analysis (immunoblotting), immunocytochemistry, fluorescence-activated cell sorting (FACS), immunohistochemistry, immunoprecipitation, protein activity assays (for example, caspase activity assays), and quantitative protein assays. Antibodies useful for the detection of mouse, rat, monkey, and human are commercially available; additional antibodies to can be generated via methods known in the art.

Examples assays for detecting levels of an oligonucleotide are described herein. This assay can be used to detect, as non-limiting examples, an oligonucleotide or any other nucleic acid of interest, including nucleic acids or other oligonucleotides which do not target and nucleic acids.

Evaluation and testing of efficacy of oligonucleotides can be performed in vivo. In some embodiments, oligonucleotides can be evaluated and/or tested in animals. In some embodiments, oligos can be evaluated and/or tested in humans and/or other animals to mediate a change or improvement in the level, activity, expression, allele-specific expression and/or intracellular distribution and/or to prevent, treat, ameliorate or slow the progress of a disorder or at least one symptom of a disorder.

In some embodiments, the testing of the efficacy of an oligonucleotide be accomplished by contacting a motor neuron cell from a subject with a neurological disease with the oligonucleotide and determining whether the motor neuron cell degenerates. If the motor neuron cell does not degenerate, the oligonucleotide may be capable of reducing or inhibiting motor neuron degeneration. The motor neuron cell may be derived from a pluripotent stem cell. The pluripotent stem cell may have been reprogrammed from a cell from the subject. The cell from the subject may be a somatic cell, for example. The somatic cell may be a fibroblast, a lymphocyte, or a keratinocyte, for example. The assessment of whether a motor neuron cell degenerates or not may be based on a comparison to a control. In some embodiments, the control level may be a predetermined or reference value, which is employed as a benchmark against which to assess the measured and/or visual result. The predetermined or reference value may be a level in a sample (e.g. motor neuron cell) from a subject not suffering from a neurological disease or from a sample from a subject suffering from a neurological disease but wherein the motor neuron cell is not contacted with the oligonucleotide. The predetermined or reference value may be a level in a sample from a subject suffering from a neurological disease. In any of these screening methods, the cell from the subject having the neurological disease may comprise the (GGGGCC)n hexanucleotide expansion in.

The efficacy of can also be tested in suitable test animals, such as those described in, as non-limiting examples: Peters et al. 2015 Neuron. 88(5):902-9; O'Rourke et al. 2015 Neuron. 88(5): 892-901; and Liu et al. 2016 Neuron. 90(3): 521-34. In some embodiments, a test animal is a C9-BAC mouse. The efficacy of can also be tested in C9-BAC transgenic mice with 450 repeat expansions, which were also described in Jiang et al. 2016 Neuron 90, 1-16.

In some embodiments, in a test animal, levels of various transcripts can be determined, as can be protein level, RNA foci, and levels of DPRs (dipeptide repeat proteins). Tests can be performed on oligonucleotides and in comparison with reference oligonucleotides. Several oligonucleotides disclosed herein are capable of reducing the percentage of cells comprising RNAi foci and the average number of foci per cell (data shown below and data not shown). Several oligonucleotides disclosed herein are capable of reducing the level of DPRs such as polyGP. All of oligonucleotides WV-6408, WV-8009, WV-8010, WV-8011, and WV-8012, some of which are oligonucleotides having an asymmetric format, reduced the level of polyGP (pGP, a dipeptide repeat protein) in the hippocampus of C9-BAC mice (data not shown). In addition, oligonucleotides WV-8549 and WV-8551 also reduced polyGP levels in the mouse hippocampus (data not shown).

In some embodiments, an oligonucleotide is capable of reducing the extent or rate of neurodegeneration caused by ALS, FTD or other-related disorder. In some embodiments, in addition to an improvement, or at least reduction in the extent or rate of deterioration of any nervous system tissue, in behavioral symptoms, therapeutic efficacy of an oligonucleotide in a subject or other animal can also be monitored with brain scans, e.g., CAT scan, functional MRI, or PET scan, or other methods known in the art.

Various assays for analysis of oligonucleotides are described herein, for example in the Examples, and include, inter alia, Reporter assay (Luciferase Assay), e.g., performed in an ALS neuron, and measuring, for example, analysis of V3/intron expression, activity and/or level; stability assay; TLR9 assay; Complement assay; PD (Pharmacodynamics) (C9-BAC, icv or Intracerebroventricular injection), e.g., PD and/or efficacy tested in-BAC (C9-BAC) mouse model; in vivo procedures, including but not limited to injection into a lateral ventricle or other areas of the central nervous system (including but not limited to cortex and spinal cord) of a test animal, such as a mouse; analysis of number of foci and/or number of cells comprising foci: PolyGP (or pGP or DPR assay).

Oligonucleotides which have been evaluated and tested for efficacy in decreasing have various uses, including administration for use in treatment or prevention of a disorder or a symptom thereof.

In some embodiments, provided oligonucleotides are capable of directing a decrease in the expression, level and/or activity of a target gene or a gene product thereof. In some embodiments, an-related disorder is a disorder related to, caused and/or associated with abnormal or excessive activity, level and/or expression of, a deleterious mutation in, or abnormal tissue or inter- or intracellular distribution of an gene or a gene product thereof.

Without wishing to be bound by any particular theory or terminology, the present specification notes that, with the understanding of-related diseases constantly evolving, the exact labeling of various-related diseases is also reportedly evolving. In some embodiments, oligonucleotides are useful for decreasing levels of hexanucleotide repeat-containing mutant alleles of (at the protein and/or mRNA level) and/or decrease the level of dipeptide repeat proteins produced from hexanucleotide-repeat-containing mutant mRNA, wherein the oligonucleotides are useful for treating a related disease.

The present disclosure pertains to methods of using oligonucleotides disclosed herein which are capable of targeting and useful for treating and/or manufacturing a treatment for a disorder. In some embodiments, a base sequence of an oligonucleotide can comprise or consist of a base sequence which has a specified maximum number of mismatches from a specified base sequence.

In some embodiments, the present disclosure pertains to the use of a composition of comprising an oligonucleotide for the manufacture of a medicament for treating a neurodegenerative disease.

In some embodiments, the present disclosure pertains to a method of treating or ameliorating an-related disorder in a patient thereof, the method comprising the step of administering to the patient a therapeutically effective amount of an oligonucleotide.

In some embodiments, the present disclosure pertains to a method comprising administering to an animal a composition comprising an oligonucleotide.

In some embodiments, the animal is a subject, e.g., a human.

In some embodiments, a subject or patient suitable for treatment of a disorder, such as administration of an oligonucleotide, can be identified or diagnosed by a health care professional In some embodiments, the composition prevents, treats, ameliorates, or slows progression of at least one symptom of a disorder.

In some embodiments, an animal or human is suffering from a symptom of a disorder.

In some embodiments, the present disclosure pertains to a method for decreasing gene expression in a mammal in need thereof, the method comprising: administering to the mammal a nucleic acid-lipid particle comprising a provided oligonucleotide.

In some embodiments, the present disclosure pertains to a method for treating and/or ameliorating one or more symptoms associated with a disorder in a mammal in need thereof, the method comprising: administering to the mammal a therapeutically effective amount of a nucleic acid-lipid particle comprising an oligonucleotide.

In some embodiments, the present disclosure pertains to a method of inhibiting expression in a cell, the method comprising: (a) contacting the cell with an oligonucleotide; and (b) maintaining the cell produced in step (a) for a time sufficient to obtain degradation of the mRNA transcript of an gene, thereby inhibiting expression of the gene in the cell.

In some embodiments, expression is inhibited by at least 30%.

In some embodiments, the present disclosure pertains to a method of treating a disorder mediated by expression comprising administering to a human in need of such treatment a therapeutically effective amount of an oligonucleotide.

In some embodiments, administration causes a decrease in the expression, activity and/or level of a transcript containing a repeat expansion or a gene product thereof.

In some embodiments, the present disclosure pertains to a method comprising the steps of: Providing a system comprising two or more different splicing products of the same mRNA, wherein at least one splicing product is disease-associated and at least one splicing product is non-disease-associated; introducing into a system an oligonucleotide, wherein the oligonucleotide is complementary to a sequence which is present in the at least one disease-associated splicing product, but not present in the at least one non-disease-associated splicing product, wherein the oligonucleotide is capable of reducing the expression, level and/or activity of the disease-associated splicing product relative to the expression, level and/or activity of the non-disease-associated splicing product.

In some embodiments of the method, a provided oligonucleotide is complementary to an intron-exon junction present on the disease-associated splicing product but not present on the non-disease-associated splicing product.

In some embodiments, a second therapeutic agent is a dsRNA or siRNA which comprises a strand which has a sequence which comprises at least 15 contiguous nt of the sequence of any oligonucleotide disclosed herein.

Pharmaceutical Compositions

In some embodiments, the present disclosure provides pharmaceutical compositions comprising a provided compound, e.g., a provided oligonucleotide, or a pharmaceutically acceptable salt thereof, and a pharmaceutical carrier.

When used as therapeutics, a provided oligonucleotide or oligonucleotide composition described herein is administered as a pharmaceutical composition. In some embodiments, the pharmaceutical composition is suitable for administration of an oligonucleotide to an area of the body affected by a disorder, including but not limited to the central nervous system. In some embodiments, the pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers.

In some embodiments, a provided oligonucleotide having an asymmetric format is conjugated to an additional chemical moiety suitable for use in delivery to the central nervous system, selected from: glucose, GluNAc (N-acetyl amine glucosamine) and anisamide, and a molecule of any of the structures of:

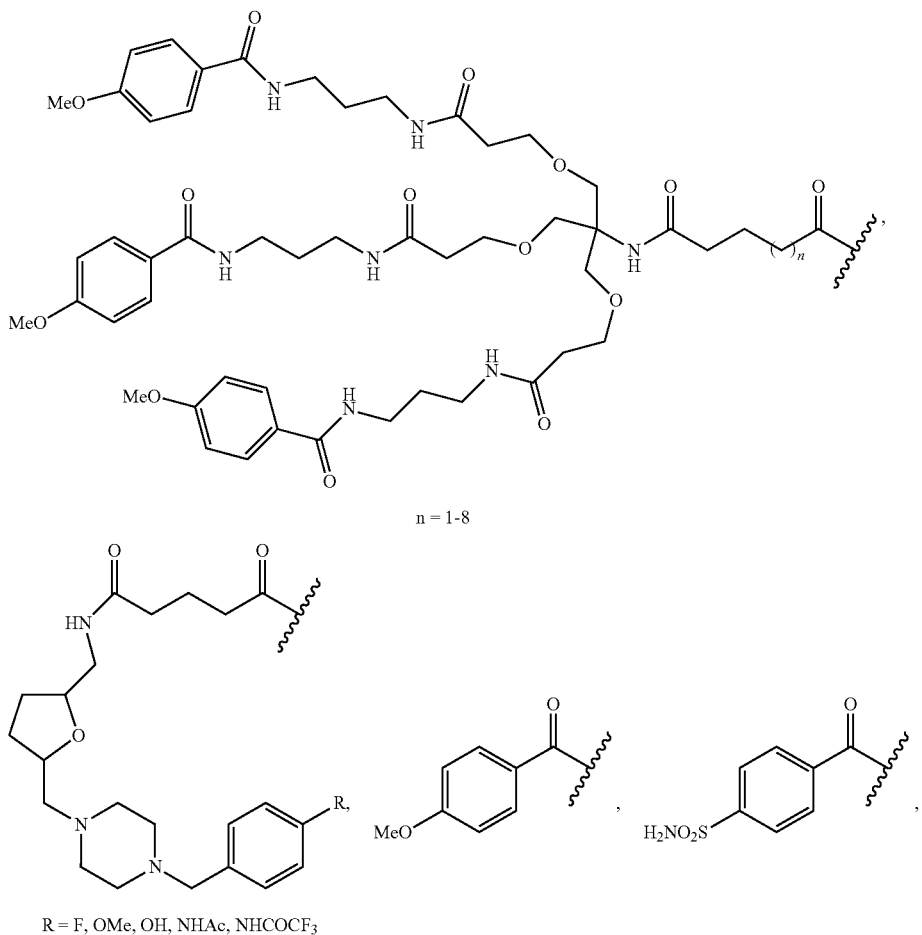

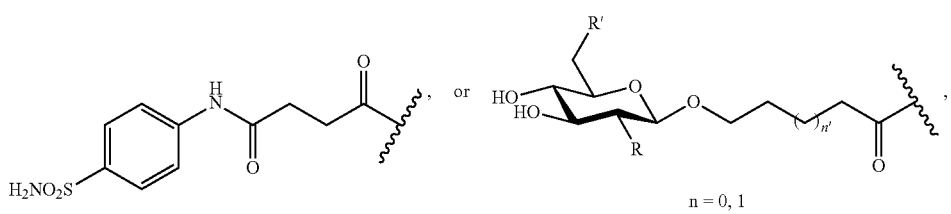

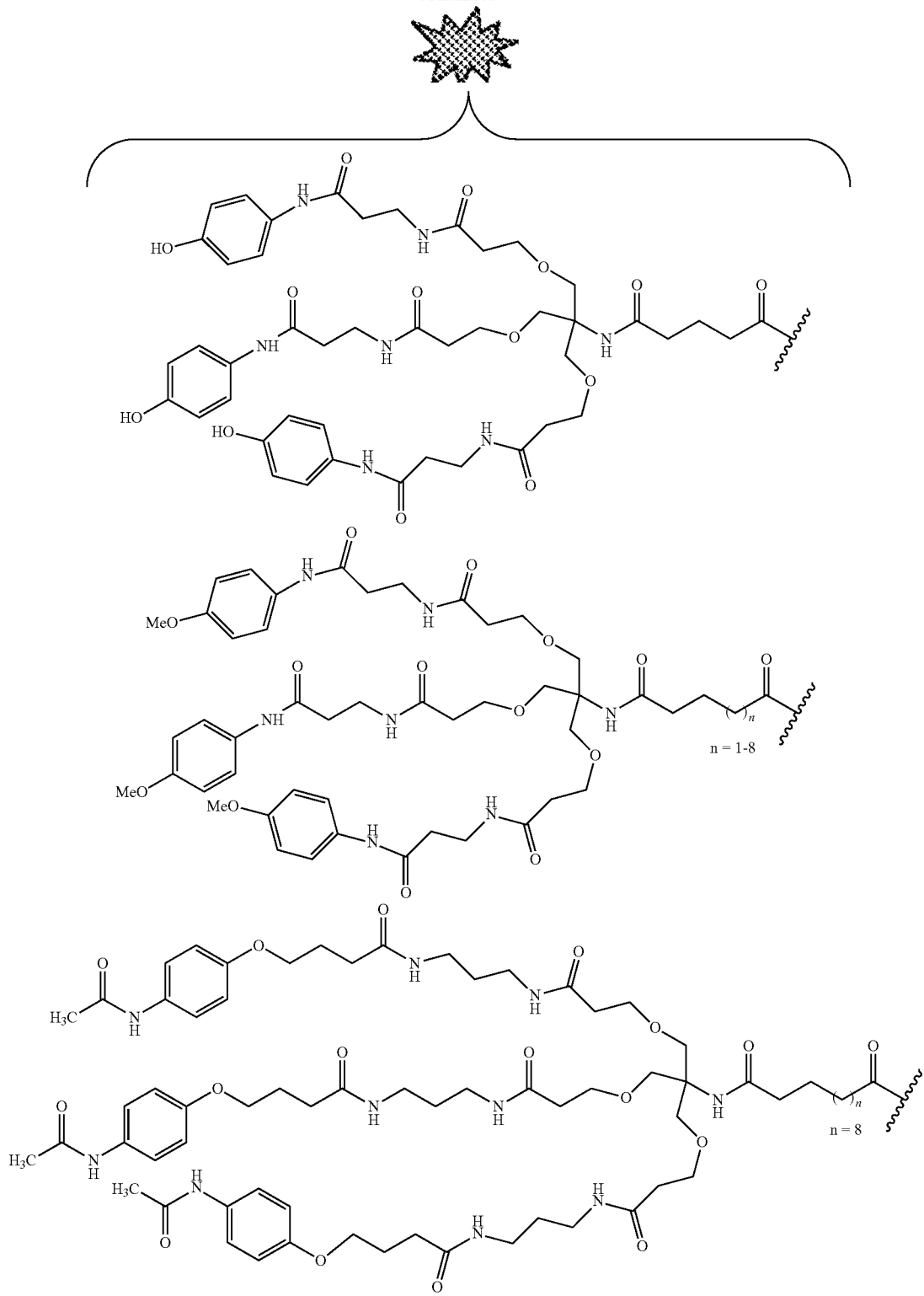

which are described in more detail in Example 1 and Example 2.

In some embodiments, an additional chemical moiety conjugated to an oligonucleotide is capable of targeting the oligonucleotide to a cell in the nervous system.

In some embodiments, an additional chemical moiety conjugated to a provided oligonucleotide comprises anisamide or a derivative or analog thereof and is capable of targeting the provided oligonucleotide to a cell expressing a particular receptor, such as the sigma 1 receptor.

In some embodiments, a provided oligonucleotide is formulated for administration to a body cell and/or tissue expressing its target.

In some embodiments, an additional chemical moiety conjugated to an oligonucleotide is capable of targeting the oligonucleotide to a cell in the nervous system.

In some embodiments, an additional chemical moiety conjugated to an oligonucleotide comprises anisamide or a derivative or analog thereof and is capable of targeting the oligonucleotide to a cell expressing a particular receptor, such as the sigma 1 receptor.

In some embodiments, a provided oligonucleotide is formulated for administration to a body cell and/or tissue expressing. In some embodiments, such a body cell and/or tissue is a neuron or a cell and/or tissue of the central nervous system. In some embodiments, broad distribution of oligonucleotides and compositions, described herein, within the central nervous system may be achieved with intraparenchymal administration, intrathecal administration, or intracerebroventricular administration.

In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGylated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly(lactic acid), liquid depot, polymer micelles, quantum dots and lipoplexes. In some embodiments, an oligonucleotide is conjugated to another molecular.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate. In some embodiments, provided oligonucleotides are provided as salts. In some embodiments, a salt is an ammonium salt. In some embodiments, a salt is a metal ion salt, such as sodium, calcium, etc. In some embodiments, a salt is a sodium salt. In some embodiments, a salt is a calcium salt. In some embodiments, all acidic internucleotidic linkages (e.g., phosphate, phosphorothioate, etc.) exist as salt forms, such as sodium salts. In some embodiments, an oligonucleotide is formulated as a salt of a single ion, e.g., a sodium salt. In some embodiments, an oligonucleotide is formulated as a mixed salt, e.g., comprising two or more types of ions (e.g., sodium and calcium, sodium and ammonium, etc.). As appreciated by those skilled in the art, oligonucleotides comprising acidic linkages (e.g., phosphate, phosphorothioate, etc.) may exist as salt forms at certain pH and may be formulated as various types of salts.

In some embodiments, a provided oligonucleotide is formulated in a pharmaceutical composition described in U.S. Applications No. 61/774,759; 61/918,175, filed Dec. 19, 2013; 61/918,927; 61/918,182; 61/918941; 62/025224; 62/046,487; or International Applications No. PCT/US04/042911; PCT/EP2010/070412; or PCT/I B2014/059503.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of an active compound into preparations which can be used pharmaceutically. The preparations formulated for oral administration may be in the form of tablets, dragees, capsules, or solutions.

Pharmaceutical preparations for oral use can be obtained by combining an active compound with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active compound may be dissolved or suspended in suitable liquids, such as fatty oils, liquid paraffin, or liquid polyethylene glycols (PEGs). In addition, stabilizers may be added.

A composition can be obtained by combining an active compound with a lipid. In some embodiments, the lipid is conjugated to an active compound. In some embodiments, the lipid is not conjugated to an active compound. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, an active compound is any oligonucleotide or other nucleic acid described herein. In some embodiments, an active compound is a nucleic acid of a sequence comprising or consisting of any sequence of any nucleic acid listed in Table 1. In some embodiments, a composition comprises a lipid and an active compound, and further comprises another component selected from: another lipid, and a targeting compound or moiety. In some embodiments, a lipid includes, without limitation: an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; and a targeting lipid; and any other lipid described herein or reported in the art. In some embodiments, a composition comprises a lipid and a portion of another lipid capable of mediating at least one function of another lipid. In some embodiments, a targeting compound or moiety is capable of targeting a compound (e.g., a composition comprising a lipid and a active compound) to a particular cell or tissue or subset of cells or tissues. In some embodiments, a targeting moiety is designed to take advantage of cell- or tissue-specific expression of particular targets, receptors, proteins, or other subcellular components; In some embodiments, a targeting moiety is a ligand (e.g., a small molecule, antibody, peptide, protein, carbohydrate, aptamer, etc.) that targets a composition to a cell or tissue, and/or binds to a target, receptor, protein, or other subcellular component.

Certain example lipids for use in preparation of a composition for delivery of an active compound allow (e.g., do not prevent or interfere with) the function of an active compound. Non-limiting example lipids include: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

As described in the present disclosure, lipid conjugation, such as conjugation with fatty acids, may improve one or more properties of oligonucleotides.

In some embodiments, a composition for delivery of an active compound is capable of targeting an active compound to particular cells or tissues, as desired. In some embodiments, a composition for delivery of an active compound is capable of targeting an active compound to a muscle cell or tissue. In some embodiments, the present disclosure pertains to compositions and methods related to delivery of active compounds, wherein the compositions comprise an active compound a lipid. In various embodiments to a muscle cell or tissue, the lipid is selected from: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

Depending upon the particular disorder to be treated or prevented, additional therapeutic agents, which are normally administered to treat or prevent that condition, may be administered together with C9orf oligonucleotides of this disclosure.

In some embodiments, a second therapeutic agent administered with a first oligonucleotide is a second, different, oligonucleotide.

In some embodiments, oligonucleotides disclosed herein can be used for a method for the prevention and/or treatment of a disorder or a symptom thereof, or for the manufacture of medicament for use in such a method.

Certain example embodiments (embodiments 1-431) are provided below:

1. A composition comprising an oligonucleotide, wherein the oligonucleotide comprises at least one modification of a sugar, base or internucleotidic linkage, and the base sequence of the oligonucleotide comprises at least 15 contiguous bases of a base sequence of an oligonucleotide disclosed in the specification, and the oligonucleotide is capable of decreasing the level, activity and/or expression of a C9orf72 gene or a C9orf72 gene product.

2. The composition of embodiment 1, wherein the oligonucleotide reduces level of a C9orf72 transcript when administered to a system comprises the transcript.

3. The composition of embodiment 1, wherein the oligonucleotide reduces level of a repeat expansion-containing C9orf72 transcript when administered to a system comprises the C9orf72 transcript.

4. The composition of embodiment 3, wherein the repeat expansion-containing C9orf72 transcript comprises at least 30, 50, 100, 150, 200, 300, 400, 500, 600, 700, 800, 900, or 1000 GGGGCC repeats (SEQ ID NO: 600).

5. The composition of embodiment 1, wherein the oligonucleotide reduces level of a repeat-expansion-containing C9orf72 transcript at a greater extent than it reduces level of a non-repeat-expansion-containing C9orf72 transcript, or it does not reduce level of a non-repeat-expansion-containing C9orf72 transcript, when administered to a system comprises repeat-expansion-containing C9orf72 transcript and a non-repeat-expansion-containing C9orf72 transcript.

6. The composition of embodiment 5, wherein the reduction of level of the repeat-expansion-containing C9orf72 transcript as measured by percentage is at least 1.1, 1.2, 1.3, 1.4, 1.5, 1.6, 1.7, 1.8, 1.9, 2, 2.5, 3, 4, 5, 6, 7, 8, 9, or 10 fold of the reduction of level of the non-repeat-expansion-containing C9orf72 transcript as measured by percentage.

7. The composition of any one of embodiments 2-6, wherein the system is a cell, tissue or organ.

8. The composition of any one of embodiments 2-6, wherein the system is a cell expressing a C9orf72 transcript.

9. The composition of any one of embodiments 2-6, wherein the system is a cell expressing a repeat-expansion-containing C9orf72 transcript.

10. The composition of any one of embodiments 2-6, wherein the system is a cell expressing a non-repeat-expansion-containing C9orf72 transcript.

11. The composition of embodiment 1, wherein the oligonucleotide hybridizes a site in C9orf72 exon 1a, intron 1, exon 1b, or exon 2.

12. The composition of embodiment 1, wherein the oligonucleotide hybridizes a site in a C9orf72 intron 1.

13. The composition of embodiment 1, wherein the oligonucleotide is capable of mediating preferential knockdown of a repeat expansion-containing C9orf72 RNA transcript relative to a non-repeat expansion-containing C9orf72 RNA transcript.

14. The composition of embodiment 1, wherein the oligonucleotide is capable of mediating preferential knockdown of a repeat expansion-containing V3 C9orf72 RNA transcript relative to a non-repeat expansion-containing C9orf72 RNA transcript.

15. The composition of embodiment 1, wherein the base sequence of the oligonucleotide comprises the base sequence of a C9orf72 oligonucleotide disclosed herein.

16. The composition of embodiment 1, wherein the single-stranded oligonucleotide has a length of 15 to 49 nucleotides.

17. The composition of embodiment 1, wherein the single-stranded oligonucleotide has a length of 17 to 25 nucleotides.

18. The composition of embodiment 1, wherein the single-stranded oligonucleotide has a length of 19 to 23 nucleotides.

19. The composition of embodiment 1, wherein the base sequence of the oligonucleotide is the base sequence of a C9orf72 oligonucleotide disclosed herein.

20. The composition of embodiment 1, wherein the base sequence of the oligonucleotide is the base sequence of a C9orf72 oligonucleotide disclosed herein, and wherein the pattern of sugars or sugar modifications and/or the pattern of internucleotidic linkages is the pattern of sugars or sugar modifications and/or pattern of internucleotidic linkages of the disclosed C9orf72 oligonucleotide.

21. The composition of embodiment 1, wherein the base sequence of the oligonucleotide is the base sequence of a C9orf72 oligonucleotide disclosed herein, and wherein the pattern of sugars or sugar modifications and the pattern of internucleotidic linkages is the pattern of sugars or sugar modifications and/or pattern of internucleotidic linkages of the disclosed C9orf72 oligonucleotide.

22. The composition of any of the preceding embodiments, wherein the oligonucleotide comprises at least one internucleotidic linkage wherein the linkage phosphorus is in the Sp configuration.

23. The composition of any of the preceding embodiments, wherein the oligonucleotide comprises at least one internucleotidic linkage wherein the linkage phosphorus is in the Rp configuration.

24. The composition of any of the preceding embodiments, wherein the oligonucleotide comprises comprise at least one phosphorothioate.

25. The composition of any of the preceding embodiments, wherein the oligonucleotide comprises at least one phosphorothioate in the Sp configuration.

26. The composition of any of the preceding embodiments, wherein the oligonucleotide comprises at least one phosphorothioate in the Rp configuration.

27. The composition of any of the preceding embodiments, wherein the oligonucleotide comprises a core and at least one wing.

28. The composition of any of the preceding embodiments, wherein the oligonucleotide comprises a core and at least two wings.

29. A composition comprising a single-stranded oligonucleotide, wherein the oligonucleotide comprises a core, a first wing and a second wing, wherein the pattern of sugar modifications and/or pattern of internucleotidic linkages of the first wing differ from the pattern of sugar modifications and/or pattern of internucleotidic linkages of the first wing, respectively.

30. The composition of embodiment 20, wherein the first and/or second wing comprise a modification.

31. The composition of embodiment 20, wherein the first and/or second wing comprise a sugar modification.

32. The composition of embodiment 20, wherein the first and/or second wing comprise a sugar modification selected from 2'-MOE, 2'-OMe, 2'-F and LNA.

33. The composition of embodiment 20, wherein the first and/or second wing comprise a sugar modification selected from 2'-MOE, 2'-OMe, 2'-F and LNA.

34. The composition of embodiment 20, wherein the first wing comprises a 2'-OMe and the second wing does not.

35. The composition of embodiment 20, wherein the second wing comprises a 2'-MOE and the first wing does not.

36. The composition of embodiment 20, wherein the first wing comprises a 2'-OMe and the second wing does not and wherein the second wing comprises a 2'-MOE and the first wing does not.

37. The composition of embodiment 20, wherein the first and/or second wing comprise an internucleotidic linkage selected from phosphodiester, phosphorothioate in the Sp configuration and phosphorothioate in the Rp configuration.

38. The composition of embodiment 20, wherein the first and second wing each comprise a phosphodiester and a phosphorothioate in the Sp configuration.

39. The composition of embodiment 20, wherein the first and second wing each comprise a phosphodiester and two or more phosphorothioates in the Sp configuration.

40. The composition of embodiment 20, wherein the first wing is 5' to the core, and the second wing is 3' to the core.

41. The composition of embodiment 20, wherein the second wing is 5' to the core, and the first wing is 3' to the core.

42. The composition of any of the preceding embodiments, wherein the oligonucleotide targets C9orf72.

43. A composition comprising oligonucleotides of a particular oligonucleotide type characterized by:
   a) a common base sequence;
   b) a common pattern of backbone linkages;
   c) a common pattern of backbone chiral centers;
   which composition is chirally controlled in that it is enriched, relative to a substantially racemic preparation of oligonucleotides having the same common base sequence, for oligonucleotides of the particular oligonucleotide type; and wherein the oligonucleotide targets C9orf72.

44. A chirally controlled oligonucleotide composition having a region of complementarity to an C9orf72 RNA and comprising oligonucleotides which have:
   a) a common base sequence;
   b) a common pattern of backbone linkages, which comprises at least one chiral internucleotidic linkage comprising a chiral linkage phosphorus;
   which composition is chirally controlled in that the composition is enriched, relative to a substantially racemic preparation of oligonucleotides having the same common base sequence and the same common pattern of backbone linkages, for oligonucleotides that have a) the common base sequence, b) the common pattern of backbone linkages; and
   c) a specific stereochemical configuration selected from Rp and Sp at the chiral linkage phosphorus of the at least one chiral internucleotidic linkage (chirally controlled internucleotidic linkage);
   wherein the oligonucleotides comprise a nucleotidic unit which comprises a 2'-substituent.

45. The composition of any one of the preceding embodiments, wherein the oligonucleotides comprise a carbohydrate moiety.

46. The composition of any one of the preceding embodiments, wherein the oligonucleotides comprise a carbohydrate moiety selected from Glucose, GluNAc and anisamide.

47. A method of decreasing the activity, expression and/or level of a C9orf72 target gene or its gene product in a cell, comprising the step of introducing into the cell a composition of any of preceding embodiments, wherein the base sequence of the oligonucleotide comprises at least 15 contiguous bases of the base sequence of a C9orf72 oligonucleotide disclosed herein.

48. A method for preferential knockdown of a repeat expansion-containing C9orf72 RNA transcript relative to a non-repeat expansion-containing C9orf72 RNA transcript in a cell, the method comprising steps of:
   contacting a cell comprising the repeat expansion-containing C9orf72 RNA transcript and the non-repeat expansion-containing C9orf72 RNA transcript with an oligonucleotide,
   wherein the oligonucleotide comprises a sequence present in or complementary to a sequence in the repeat expansion-containing C9orf72 RNA transcript,
   wherein the oligonucleotide directs preferential knockdown of a repeat expansion-containing C9orf72 RNA transcript relative to a non-repeat expansion-containing C9orf72 RNA transcript in a cell.

49. The method of embodiment 40, wherein the repeat expansion-containing C9orf72 RNA transcript is knocked down by at least 20% relative to a non-repeat expansion-containing C9orf72 RNA transcript.

50. The method of embodiment 40, wherein the repeat expansion-containing C9orf72 RNA transcript is knocked down by at least 30% relative to a non-repeat expansion-containing C9orf72 RNA transcript.

51. The method of embodiment 40, wherein the repeat expansion-containing C9orf72 RNA transcript is knocked down by at least 40% relative to a non-repeat expansion-containing C9orf72 RNA transcript.

52. The method of embodiment 40, wherein the repeat expansion-containing C9orf72 RNA transcript is knocked down by at least 50% relative to a non-repeat expansion-containing C9orf72 RNA transcript.

53. The method of embodiment 40, wherein the repeat expansion-containing C9orf72 RNA transcript is knocked down by at least 60% relative to a non-repeat expansion-containing C9orf72 RNA transcript.

54. A method for preferential knockdown of a repeat expansion-containing C9orf72 RNA transcript relative to a non-repeat expansion-containing C9orf72 RNA transcript in a subject, the method comprising steps of:
    administering an oligonucleotide to the subject, wherein the subject has a genotype comprising a repeat expansion-containing C9orf72 RNA transcript and a non-repeat expansion-containing C9orf72 RNA transcript with an oligonucleotide,
    wherein the oligonucleotide comprises a sequence present in or complementary to a sequence in the repeat expansion-containing C9orf72 RNA transcript,
    wherein the oligonucleotide directs preferential knockdown of a repeat expansion-containing C9orf72 RNA transcript relative to a non-repeat expansion-containing C9orf72 RNA transcript in a cell.

55. The composition of any of the preceding embodiments, wherein the oligonucleotide is conjugated via a linker to a second oligonucleotide.

56. The composition of any of the preceding embodiments, wherein the oligonucleotide is capable of directing RNA interference and is conjugated via a linker to a second oligonucleotide, which is also capable of directing RNA interference.

57. The composition of any of the preceding embodiments, wherein the oligonucleotide is capable of directing RNase H-mediated knockdown and is conjugated via a linker to a second oligonucleotide, which is capable of directing RNA interference.

58. The composition of any of the preceding embodiments, wherein the oligonucleotide comprises two 2'-F.

59. The composition of any of the preceding embodiments, and wherein the oligonucleotide comprises a span of continuous 2'-deoxy sugars.

60. The composition of any of the preceding embodiments, and wherein the oligonucleotide comprises a span of at least 5 continuous 2'-deoxy sugars.

61. The composition of any of the preceding embodiments, and wherein the oligonucleotide comprises a span of at least 6 continuous 2'-deoxy sugars.

62. The composition of any of the preceding embodiments, and wherein the oligonucleotide comprises a span of at least 7 continuous 2'-deoxy sugars.

63. The composition of any of the preceding embodiments, and wherein the oligonucleotide comprises a span of at least 8 continuous 2'-deoxy sugars.

64. The composition of any of the preceding embodiments, and wherein the oligonucleotide comprises a span of at least 9 continuous 2'-deoxy sugars.

65. The composition of any of the preceding embodiments, and wherein the oligonucleotide comprises a span of at least 10 continuous 2'-deoxy sugars.

66. The composition of any of the preceding embodiments, and wherein the span of continuous 2'-deoxy sugars is the core.

67. The composition of any of the preceding embodiments, wherein the oligonucleotide comprises a LNA.

68. The composition of any of the preceding embodiments, wherein the oligonucleotide comprises a LNA and an internucleotidic linkage which is chirally controlled.

69. The composition of any of the preceding embodiments, wherein the oligonucleotide comprises a LNA and a phosphorothioate in the Sp configuration.

70. The composition of any of the preceding embodiments, wherein the oligonucleotide comprises a LNA and a phosphorothioate in the Rp configuration.

71. The composition of any of the preceding embodiments, wherein the oligonucleotide comprises a LNA and a phosphorothioate in the Rp configuration and a phosphorothioate in the Sp configuration.

72. The composition of any of the preceding embodiments, wherein the oligonucleotide comprises any sequence, structure or format (or portion thereof) disclosed herein.

73. The composition of any of the preceding embodiments, wherein the oligonucleotide is at least partially complementary to a second oligonucleotide further comprised in the composition, and where the oligonucleotide and the second oligonucleotide form at least partially form a duplex.

74. The composition of any of the preceding embodiments, wherein the oligonucleotide is at least partially complementary to a second oligonucleotide further comprised in the composition, and where the oligonucleotide and the second oligonucleotide form at least partially form a double-stranded oligonucleotide.

75. The composition of any of the preceding embodiments, wherein the oligonucleotide is complementary to a second oligonucleotide further comprised in the composition, and where the oligonucleotide and the second oligonucleotide form a duplex.

76. The composition of any of the preceding embodiments, wherein the oligonucleotide is complementary to a second oligonucleotide further comprised in the composition, and where the oligonucleotide and the second oligonucleotide form a double-stranded oligonucleotide.

77. The composition of any one of the preceding embodiments, wherein the composition is disposed within a container, wherein the container is a vial.

78. The composition of any one of the preceding embodiments, wherein the composition is disposed within a container, wherein the container is a syringe.

79. An oligonucleotide as described in any one of the previous embodiments.

80. A method for treating a C9orf72-related disorder in a subject, comprising the step of administering to the subject a therapeutically effective amount of the composition of any of preceding embodiments, wherein the oligonucleotide specifically targets C9orf72.

81. The method of any of the preceding embodiments, wherein the C9orf72-related disorder is selected from: amyotrophic lateral sclerosis (ALS), frontotemporal dementia (FTD), corticobasal degeneration syndrome (CBD), atypical Parkinsonian syndrome, olivopontocerebellar degeneration (OPCD), or Alzheimer's disease.

82. The method of any of the preceding embodiments, wherein the composition further comprises a pharmaceutically acceptable carrier.

83. The method of any of the preceding embodiments, wherein the method further comprises a step of administering a second agent to treat the C9orf72-related disorder.

84. The method of any of the preceding embodiments, wherein the second agent comprises an oligonucleotide which specifically targets C9orf72.

85. The method of any of the preceding embodiments, wherein the steps of administering the composition and the second agent are simultaneously, concurrent, separate or sequential.

86. A method of decreasing the expression and/or level of a target gene or its gene product in a subject comprising the step of administering to the subject a therapeutically effective amount of a composition of any of preceding embodiments, comprising the step of administering to the subject a therapeutically effective amount of a composition of any of preceding embodiments, wherein the oligonucleotide specifically targets C9orf72.

87. The method of any of the preceding embodiments, wherein the C9orf72-related disorder is selected from: amyotrophic lateral sclerosis (ALS), frontotemporal dementia (FTD), corticobasal degeneration syndrome (CBD), atypical Parkinsonian syndrome, olivopontocerebellar degeneration (OPCD), or Alzheimer's disease.

88. The method of any of the preceding embodiments, wherein the composition further comprises a pharmaceutically acceptable carrier.

89. The method of any of the preceding embodiments, wherein the method further comprises a step of administering a second agent to treat the C9orf72-related disorder.

90. The method of any of the preceding embodiments, wherein the second agent comprises an oligonucleotide which specifically targets C9orf72.

91. The method of any of the preceding embodiments, wherein the steps of administering the composition and the second agent are simultaneously, concurrent, separate or sequential.

92. The use of a composition of any of the preceding embodiments or a pharmaceutically acceptable salt thereof for the preparation of a pharmaceutical composition for treating a C9orf72-related disorder.

93. The use of a composition of any of the preceding embodiments or a pharmaceutically acceptable salt thereof for the preparation or manufacture of a pharmaceutical composition or medicament for treating a C9orf72-related disorder.

94. The use of a composition of any of the preceding embodiments or a pharmaceutically acceptable salt thereof for the preparation or manufacture of a pharmaceutical composition or medicament for treating a disorder.

95. An oligonucleotide comprising a region of consecutive nucleotidic units:

$(Nu^M)t[(Nu^O)n(Nu^M)m]y$ wherein:
each $Nu^M$ is independently a nucleotidic unit comprising a modified internucleotidic linkage;
each $Nu^O$ is independently a nucleotidic unit comprising a natural phosphate linkage; each of t, n, and m is independently 1-20; and
y is 1-10.

96. The oligonucleotide of embodiment 95, wherein y is 1.
97. The oligonucleotide of embodiment 95, wherein y is 2.
98. The oligonucleotide of any one of embodiments 95-97, wherein at least one n is 1.
99. The oligonucleotide of any one of embodiments 95-97, wherein each n is 1.

100. The oligonucleotide of any one of embodiments 95-99, wherein t is 2-20.
101. The oligonucleotide of any one of embodiments 95-100, wherein at least one m is 2-20.
102. The oligonucleotide of any one of embodiments 95-100, wherein each m is 2-20.
103. The oligonucleotide of any one of embodiments 95-102, wherein the sum of t, m, and n is no less than 5, 6, 7, 8, 9, 10, 11, 12, 13, 14, 15, 16, 17, 18, 19, 20, 25, or 30.
104. The oligonucleotide of any one of embodiments 95-103, wherein each of $Nu^M$ is independently of the structure

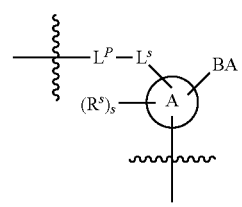

or a salt form thereof.

105. The oligonucleotide of any one of 95-104, wherein at least one $Nu^O$ is a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms.

106. The oligonucleotide of any one of 95-104, wherein each $Nu^O$ is independently a nucleotidic unit comprising a natural phosphate linkage, wherein the natural phosphate linkage is bonded to a 5'-nucleotidic unit and a carbon atom of the sugar unit of the nucleotidic unit, wherein the carbon atom is bonded to less than two hydrogen atoms.

107. The oligonucleotide of any one of embodiments 95-106, wherein at least one $Nu^O$ comprises a structure of $—C(R^{5s})_2—$, which structure is directly boned to the natural phosphate linkage of $Nu^O$ and a ring moiety of the sugar unit of $Nu^O$.

108. The oligonucleotide of any one of embodiments 95-106, wherein each $Nu^O$ independently comprises a structure of $—C(R^{5s})_2—$, which structure is directly boned to the natural phosphate linkage of $Nu^O$ and a ring moiety of the sugar unit of $Nu^O$.

109. The oligonucleotide of any one of the preceding embodiments, wherein each $Nu^O$ independently has the structure of formula N-I:

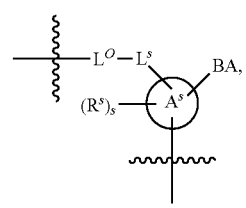

N-I or a salt form thereof, wherein:
BA is an optionally substituted group selected from $C_{1-30}$ cycloaliphatic, $C_{6-30}$ aryl, $C_{5-30}$ heteroaryl having 1-10 heteroatoms, $C_{3-30}$ heterocyclyl having 1-10 heteroatoms, a natural nucleobase moiety, and a modified nucleobase moiety;

$L^O$ is a natural phosphate linkage;

$L^s$ is —C(R$^{5s}$)$_2$—, or L;

each R$^{5s}$ and R$^s$ is independently —F, —Cl, —Br, —I, —CN, —N$_3$, —NO, —NO$_2$, -L-R', -L-OR', -L-SR', -L-N(R')$_2$, —O-L-OR', —O-L-SR', or —O-L-N(R')$_2$;

each L is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring; Ring A is an optionally substituted 3-20 membered monocyclic, bicyclic or polycyclic ring having 0-10 heteroatoms;

s is 0-20;

each R' is independently —R, —C(O)R, —C(O)OR, or —S(O)$_2$R; and each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

110. The oligonucleotide of embodiment 109, wherein L$^s$ is —C(R$^{5s}$)$_2$—.

111. The oligonucleotide of any one of embodiments 109-110, wherein at least one Nu$^O$ has the structure of formula N-I, wherein one R$^{5s}$ is —H, and the other R$^{5s}$ is not —H.

112. The oligonucleotide of any one of embodiments 109-110, wherein each Nu$^O$ independently has the structure of formula N-I, wherein one R$^{5s}$ is —H, and the other R$^{5s}$ is not —H.

113. The oligonucleotide of any one of embodiments 107-111, wherein one R$^{5s}$ is optionally substituted C$_{1-6}$ aliphatic.

114. The oligonucleotide of any one of embodiments 107-112, wherein one R$^{5s}$ is optionally substituted C$_{1-6}$ alkyl.

115. The oligonucleotide of any one of embodiments 107-114, wherein one R$^{5s}$ is optionally substituted C$_{1-6}$ methyl.

116. The oligonucleotide of any one of embodiments 107-115, wherein one R$^{5s}$ is —CH$_3$.

117. The oligonucleotide of any one of embodiments 107-116, wherein the C of —C(R$^{5s}$)$_2$— is chiral and has a R configuration.

118. The oligonucleotide of any one of embodiments 107-116, wherein the C of —C(R$^{5s}$)$_2$— is chiral and has a S configuration.

119. The oligonucleotide of any one of embodiments 109-110, wherein at least one Nu$^O$ has the structure of formula N—I, wherein both R$^{5s}$ are —H.

120. The oligonucleotide of any one of embodiments 109-110, wherein each Nu$^O$ independently has the structure of formula N—I, wherein both R$^{5s}$ are —H.

121. The oligonucleotide of any one of embodiments 109-119, wherein has the structure of wherein each of R$^{1s}$, R$^{2s}$, R$^{3s}$, and R$^{4s}$ is independently R$^s$.

122. The oligonucleotide of embodiment 23, wherein R$^{1s}$ is H.

123. The oligonucleotide of any one of embodiments 121-122, wherein both R$^{2s}$ are H.

124. The oligonucleotide of any one of embodiments 121-122, wherein one R$^{2s}$ is H, and the other R$^{2s}$ is —F, —Cl, —Br, —I, or —OR';

125. The oligonucleotide of any one of embodiments 121-122, wherein one R$^{2s}$ is H, and the other R$^{2s}$ is —F, or —OR', wherein R' is optionally substituted C$_{1-3}$ alkyl.

126. The oligonucleotide of any one of embodiments 121-122, wherein one R$^{2s}$ is H, and the other R$^{2s}$ is —F, or —OR', wherein R' is methyl or 2'-methyoxyethyl.

127. The oligonucleotide of any one of embodiments 121-123, wherein R$^{3s}$ is H.

128. The oligonucleotide of any one of embodiments 121-126, wherein R$^{4s}$ is H.

129. The oligonucleotide of any one of the preceding embodiments, wherein each Nu$^M$ independently comprises a modified internucleotidic linkage having the structure of formula I:

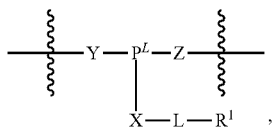

or a salt form thereof, wherein the structure of formula I is not an natural phosphate linkage.

130. The oligonucleotide of any one of the preceding embodiments, wherein the modified internucleotidic linkage of at least one Nu$^M$ is chiral and diastereomerically pure.

131. The oligonucleotide of any one of the preceding embodiments, wherein the modified internucleotidic linkage of each Nu$^M$ is chiral and diastereomerically pure.

132. The oligonucleotide of any one of the preceding embodiments, wherein the region of consecutive nucleotidic units comprises a pattern of backbone chiral centers (linkage phosphorus) of:

(Sp)$t$[(Op)$n$(Sp)$m$]$y$, wherein:
Sp indicates the S configuration of a chiral linkage phosphorus of a chiral modified internucleotidic linkage;
each of t, n, and m is independently 1-20;
y is 1-10; and
Op indicates an achiral linkage phosphorus of a natural phosphate linkage.

133. The oligonucleotide of any one of the preceding embodiments, wherein the region of consecutive nucleotidic units comprises a pattern of backbone chiral centers (linkage phosphorus) of:

(Np)$t$[(Op)$n$(Sp)$m$]$y$, wherein:
Np is either Rp or Sp;
Sp indicates the S configuration of a chiral linkage phosphorus of a chiral modified internucleotidic linkage;
Op indicates an achiral linkage phosphorus of a natural phosphate linkage; and
Rp indicates the S configuration of a chiral linkage phosphorus of a chiral modified internucleotidic linkage;
each of t, n, and m is independently 1-20;
y is 1-10; and
each wing independently comprises one or more nucleobases.

134. The oligonucleotide of any one of the preceding embodiments, wherein the region of consecutive nucleotidic units comprises a pattern of backbone chiral centers (linkage phosphorus) of:

[(Op)$n$(Sp)$m$]$y$, wherein:
Sp indicates the S configuration of a chiral linkage phosphorus of a chiral modified internucleotidic linkage;
each of n and m is independently 1-20;
y is 1-10; and
Op indicates an achiral linkage phosphorus of a natural phosphate linkage.

135. The oligonucleotide of any one of the preceding embodiments, wherein the oligonucleotide is of a wing-core-wing structure, wherein:
the core is the region of consecutive nucleotidic units (Nu$^M$)t[(Nu$^O$)n(Nu$^M$)m]y;
each wing independently comprises one or more nucleobases.

136. An oligonucleotide comprising a pattern of backbone chiral centers (linkage phosphorus) of:

(Np)$t$[(Op)$n$(Sp)$m$]$y$, wherein:
Np is either Rp or Sp;
Sp indicates the S configuration of a chiral linkage phosphorus of a chiral modified internucleotidic linkage;
Op indicates an achiral linkage phosphorus of a natural phosphate linkage; and
Rp indicates the S configuration of a chiral linkage phosphorus of a chiral modified internucleotidic linkage;
each of t, n, and m is independently 1-20;
y is 1-10; and
each wing independently comprises one or more nucleobases.

137. An oligonucleotide comprising a pattern of backbone chiral centers (linkage phosphorus) of:
(Sp)t[(Op)n(Sp)m]y,
wherein:
Sp indicates the S configuration of a chiral linkage phosphorus of a chiral modified internucleotidic linkage;
Op indicates an achiral linkage phosphorus of a natural phosphate linkage; and
each of t, n, and m is independently 1-20;
y is 1-10; and
each wing independently comprises one or more nucleobases.

138. An oligonucleotide comprising a pattern of backbone chiral centers (linkage phosphorus) of:

(Op)$n$(Sp)$m$, wherein:
Sp indicates the S configuration of a chiral linkage phosphorus of a chiral modified internucleotidic linkage;
Op indicates an achiral linkage phosphorus of a natural phosphate linkage; and
each of n and m is independently 1-20; and
each wing independently comprises one or more nucleobases.

139. An oligonucleotide of or comprising a wing-core-wing structure, or a wing-core structure, or a core-wing structure, wherein the core comprises a pattern of backbone chiral centers (linkage phosphorus) of:

(Sp)$t$[(Op/Rp)$n$(Sp)$m$]$y$, wherein:
Sp indicates the S configuration of a chiral linkage phosphorus of a chiral modified internucleotidic linkage;
Op indicates an achiral linkage phosphorus of a natural phosphate linkage;
each of t, n, and m is independently 1-20;
y is 1-10; and
each wing independently comprises one or more nucleobases.

140. An oligonucleotide of or comprising a wing-core-wing structure, or a wing-core structure, or a core-wing structure, wherein the core comprises a pattern of backbone chiral centers (linkage phosphorus) of:

(Op)$n$(Sp)$m$, wherein:
Sp indicates the S configuration of a chiral linkage phosphorus of a chiral modified internucleotidic linkage;
Op indicates an achiral linkage phosphorus of a natural phosphate linkage; and
each of n and m is independently 1-20; and
each wing independently comprises one or more nucleobases.

141. An oligonucleotide of or comprising a wing-core-wing structure, or a wing-core structure, or a core-wing structure, wherein the core comprises a pattern of backbone chiral centers (linkage phosphorus) of:

(Np)$t$[(Op/Rp)$n$(Sp)$m$]$y$, wherein:
Np is either Rp or Sp;
Sp indicates the S configuration of a chiral linkage phosphorus of a chiral modified internucleotidic linkage;
Op indicates an achiral linkage phosphorus of a natural phosphate linkage; and
Rp indicates the S configuration of a chiral linkage phosphorus of a chiral modified internucleotidic linkage;
each of t, n, and m is independently 1-20;
y is 1-10; and
each wing independently comprises one or more nucleobases.

142. The oligonucleotide of embodiment 136-138, wherein the oligonucleotide is of a wing-core-wing structure.

143. The oligonucleotide of any one of embodiments 133-142, wherein Np is Sp.

144. The oligonucleotide of any one of embodiments 136-142, wherein the pattern comprises at least one Rp.

145. The oligonucleotide of any one of 136-144, wherein the pattern comprises at least one Op.

146. The oligonucleotide of any one of embodiments 136-142, wherein the pattern is (Np)t[(Op)n(Sp)m]y.

147. The oligonucleotide of any one of embodiments 136-142, wherein the pattern is (Np)t[(Rp)n(Sp)m]y.

148. The oligonucleotide of any one of embodiments 132-147, wherein at least one n is 1.

149. The oligonucleotide of any one of embodiments 132-147, wherein each n is 1.

150. The oligonucleotide of any one of embodiments 132-149, wherein y is 1.

151. The oligonucleotide of any one of embodiments 132-149, wherein y is 2.

152. The oligonucleotide of any one of embodiments 132-151, wherein t is 2-20.

153. The oligonucleotide of any one of embodiments 132-152, wherein at least one m is 2-20.

154. The oligonucleotide of any one of embodiments 132-152, wherein at least one m is 3, 4, 5, 6, 7, 8, 9, or 10.

155. The oligonucleotide of any one of embodiments 132-154, wherein each m is independently 2-20.

156. The oligonucleotide of any one of embodiments 135-155, wherein the two wings comprise different sugar modifications.

157. The oligonucleotide of any one of embodiments 135-155, wherein one wing comprises a sugar modification that is not in the other wing.

158. The oligonucleotide of any one of embodiments 135-157, wherein the two rings comprise different internucleotidic linkages.

159. The oligonucleotide of any one of embodiments 135-157, wherein one wing comprises a type internucleotidic linkage that is not in the other wing.

160. The oligonucleotide of any one of embodiments 135-159, wherein nucleoside units of the core comprise no 2'-substitutions (two —H at 2' position).

161. The oligonucleotide of any one of embodiments 135-160, wherein nucleoside units of the core comprise no sugar modifications.

162. The oligonucleotide of any one of embodiments 135-161, wherein each wing nucleoside unit independently comprises a sugar modification.

163. The oligonucleotide of any one of embodiments 135-162, wherein each wing nucleoside unit independently comprises a sugar modification, wherein the sugar modification is a 2'-modification.

164. The oligonucleotide of any one of embodiments 135-163, wherein nucleoside units of the same wing comprise the same sugar modification.

165. The oligonucleotide of any one of embodiments 135-163, wherein nucleoside units of the same wing comprise different sugar modifications.

166. The oligonucleotide of any one of embodiments 135-163, wherein each nucleoside unit in a wing comprising a pyrimidine nucleobase comprises a 2'-OR$^1$ modification, wherein R' is substituted $C_{1-3}$ alkyl.

167. The oligonucleotide of any one of embodiments 135-166, wherein each nucleoside unit in a wing comprising a pyrimidine nucleobase comprises a 2'-MOE modification.

168. The oligonucleotide of any one of embodiments 135-167, wherein each nucleoside unit in a wing comprising a purine nucleobase comprises a 2'-OMe modification.

169. The oligonucleotide of any one of embodiments 135-168, wherein a wing comprises one or more natural phosphate linkages and one or more modified internucleotidic linkage.

170. The oligonucleotide of embodiment 169, wherein each modified internucleotidic linkage independently has the structure of formula I.

171. The oligonucleotide of embodiment 169, wherein each modified internucleotidic linkage is a phosphorothioate diester linkage.

172. The oligonucleotide of any one of embodiments 170-171, wherein each modified internucleotidic linkage comprises a chiral linkage phosphorus atom of Rp or Sp configuration.

173. The oligonucleotide of any one of embodiments 170-171, wherein each modified internucleotidic linkage comprises a chiral linkage phosphorus atom of Sp configuration.

174. The oligonucleotide of any one of embodiments 170-171, wherein the first internucleotidic linkage of the wing is a modified internucleotidic linkage.

175. The oligonucleotide of embodiment 174, wherein the first internucleotidic linkage of the wing links the 5'-end nucleoside unit of the oligonucleotide and the 5'-second nucleoside units of the oligonucleotide.

176. The oligonucleotide of embodiment 174, wherein the first internucleotidic linkage of the wing links the 3'-end nucleoside unit of the core and the 5'-end nucleoside unit of the wing.

177. The oligonucleotide of any one of embodiments 169-176, wherein a nucleoside unit in the wing comprising a pyrimidine nucleobase comprises a 2'-OR$^1$ modification, wherein R' is substituted $C_{1-3}$ alkyl.

178. The oligonucleotide of any one of embodiments 169-176, wherein a nucleoside unit in the wing comprising a pyrimidine nucleobase comprises a 2'-MOE modification.

179. The oligonucleotide of any one of embodiments 169-178, wherein a nucleoside unit in the wing comprising a pyrimidine nucleobase comprises a 2'-MOE modification, and is linked to its 3'-nucleoside unit through a natural phosphate linkage.

180. The oligonucleotide of any one of embodiments 169-176, wherein each nucleoside unit in the wing that is not the 5'-end or the 3'-end nucleoside and comprises a pyrimidine nucleobase comprises a 2'-OR$^1$ modification, wherein R' is substituted $C_{1-3}$ alkyl.

181. The oligonucleotide of any one of embodiments 169-176, wherein a nucleoside unit in the wing that is not the 5'-end or the 3'-end nucleoside and comprises a pyrimidine nucleobase comprises a 2'-MOE modification.

182. The oligonucleotide of any one of embodiments 169-178, wherein a nucleoside unit in the wing that is not the 5'-end or the 3'-end nucleoside and comprises a pyrimidine nucleobase comprises a 2'-MOE modification, and is linked to its 3'-nucleoside unit through a natural phosphate linkage.

183. The oligonucleotide of any one of embodiments 169-182, wherein the 5'-end nucleoside unit of the wing comprises a purine nucleobase and a 2'-OR$^1$ modification, wherein R' is substituted $C_{1-3}$ alkyl, wherein the 5'-end nucleoside is linked to its 3'-nucleoside unit through a natural phosphate linkage.

184. The oligonucleotide of any one of embodiments 169-183, wherein the 5'-end nucleoside unit of the wing comprises a purine nucleobase and a 2'-MOE modification, wherein the 5'-end nucleoside is linked to its 3'-nucleoside unit through a natural phosphate linkage.

185. The oligonucleotide of any one of embodiments 169-182, wherein the 5'-end nucleoside unit of the wing comprises a purine nucleobase and a 2'-OMe modification, wherein the 5'-end nucleoside is linked to its 3'-nucleoside unit through a modified internucleotidic linkage.

186. The oligonucleotide of any one of embodiments 169-182, wherein the 5'-end nucleoside unit of the wing comprises a purine nucleobase and a 2'-OMe modification, wherein the 5'-end nucleoside is linked to its 3'-nucleoside unit through a phosphorothioate diester linkage.

187. The oligonucleotide of any one of embodiments 169-182, wherein the 5'-end nucleoside unit of the wing comprises a purine nucleobase and a 2'-OMe modification, wherein the 5'-end nucleoside is linked to its 3'-nucleoside unit through a Sp phosphorothioate diester linkage.

188. The oligonucleotide of any one of embodiments 169-187, comprising a wing that contains no natural phosphate linkages.

189. The oligonucleotide of any one of embodiments 169-187, comprising a wing that contains fewer natural phosphate linkages than the other wing.

190. The oligonucleotide of any one of embodiments 169-187, wherein one wing contains more modified internucleotidic linkages linking two wing nucleoside units than the other.

191. The oligonucleotide of any one of embodiments 169-190, comprising a wing that contains no 2'-OR$^1$ modification, wherein R' is substituted $C_{1-3}$ alkyl.

192. The oligonucleotide of any one of embodiments 188-191, wherein each nucleoside unit of the wing comprises a 2'-OMe modification.

193. The oligonucleotide of any one of embodiments 169-190, wherein a nucleoside unit in the wing comprising a pyrimidine nucleobase comprises a 2'-OR$^1$ modification, wherein R' is substituted $C_{1-3}$ alkyl.

194. The oligonucleotide of any one of embodiments 169-190, wherein a nucleoside unit in the wing comprising a pyrimidine nucleobase comprises a 2'-MOE modification.

195. The oligonucleotide of any one of embodiments 169-190, wherein a nucleoside unit in the wing comprising a pyrimidine nucleobase comprises a 2'-MOE modification, and is linked to its 3'-nucleoside unit through a natural phosphate linkage.

196. The oligonucleotide of any one of embodiments 169-190, wherein a nucleoside unit in the wing that is not the 5'-end or the 3'-end nucleoside and comprises a pyrimidine nucleobase comprises a 2'-OR$^1$ modification, wherein R' is substituted $C_{1-3}$ alkyl.

197. The oligonucleotide of any one of embodiments 169-190, wherein a nucleoside unit in the wing that is not the 5'-end or the 3'-end nucleoside and comprises a pyrimidine nucleobase comprises a 2'-MOE modification.

198. The oligonucleotide of any one of embodiments 169-190, wherein each nucleoside unit in the wing that is not the 5'-end or the 3'-end nucleoside and comprises a pyrimidine nucleobase comprises a 2'-MOE modification, and is linked to its 3'-nucleoside unit through a natural phosphate linkage.

199. The oligonucleotide of any one of embodiments 169-190, wherein each nucleoside unit in the wing that is not the 5'-end or the 3'-end nucleoside and comprises a pyrimidine nucleobase comprises a 2'-OR$^1$ modification, wherein R' is substituted $C_{1-3}$ alkyl.

200. The oligonucleotide of any one of embodiments 169-190, wherein each nucleoside unit in the wing that is not the 5'-end or the 3'-end nucleoside and comprises a pyrimidine nucleobase comprises a 2'-MOE modification.

201. The oligonucleotide of any one of embodiments 169-190, wherein each nucleoside unit in the wing that is not the 5'-end or the 3'-end nucleoside and comprises a pyrimidine nucleobase comprises a 2'-MOE modification, and is linked to its 3'-nucleoside unit through a natural phosphate linkage.

202. The oligonucleotide of any one of embodiments 196-201, wherein the 5'-end nucleoside unit of the wing comprises a purine nucleobase and a 2'-OR$^1$ modification, wherein R' is substituted $C_{1-3}$ alkyl, wherein the 5'-end nucleoside is linked to its 3'-nucleoside unit through a natural phosphate linkage.

203. The oligonucleotide of any one of embodiments 196-201, wherein the 5'-end nucleoside unit of the wing comprises a purine nucleobase and a 2'-MOE modification, wherein the 5'-end nucleoside is linked to its 3'-nucleoside unit through a natural phosphate linkage.

204. The oligonucleotide of any one of embodiments 196-201, wherein the 5'-end nucleoside unit of the wing comprises a purine nucleobase and a 2'-OMe modification, wherein the 5'-end nucleoside is linked to its 3'-nucleoside unit through a modified internucleotidic linkage.

205. The oligonucleotide of any one of embodiments 196-201, wherein the 5'-end nucleoside unit of the wing comprises a purine nucleobase and a 2'-OMe modification, wherein the 5'-end nucleoside is linked to its 3'-nucleoside unit through a phosphorothioate diester linkage.

206. The oligonucleotide of any one of embodiments 196-201, wherein the 5'-end nucleoside unit of the wing comprises a purine nucleobase and a 2'-OMe modification, wherein the 5'-end nucleoside is linked to its 3'-nucleoside unit through a Sp phosphorothioate diester linkage.

207. The oligonucleotide of any one of embodiments 196-206, wherein the wing comprises a nucleoside unit comprising a purine nucleobase, wherein the internucleotidic linkage linking the nucleoside to its 3'-nucleoside is a natural phosphate linkage.

208. The oligonucleotide of any one of embodiments 196-206, wherein each nucleoside unit comprising a purine nucleobase in the wing is independently linked to its 3'-nucleoside, if any, through a natural phosphate linkage.

209. The oligonucleotide of any one of embodiments 196-206, wherein the wing comprises a nucleoside unit comprising a purine nucleobase, wherein the internucleotidic linkage linking the nucleoside to its 3'-nucleoside is a modified internucleotidic linkage.

210. The oligonucleotide of any one of embodiments 196-206, wherein each nucleoside unit comprising a purine nucleobase in the wing is independently linked to its 3'-nucleoside, if any, through a modified internucleotidic linkage.

211. The oligonucleotides of any one of embodiments 95-163, wherein the oligonucleotide comprises two wings, wherein the first wing comprising a first sugar modification that is not in a second wing, which first sugar modification is 2'-OR$^1$, wherein R' is substituted $C_{1-6}$ alkyl or a LNA sugar modification.

212. The oligonucleotide of embodiment 211, wherein the first sugar modification is 2'-MOE.

213. The oligonucleotide of any one of embodiments 211-212, wherein a nucleoside unit comprising a first sugar modification comprises a pyrimidine nucleobase.

214. The oligonucleotide of any one of embodiments 211-212, wherein each nucleoside unit comprising a first sugar modification, if the nucleoside unit is not the 5'-end nucleoside unit of the oligonucleotide, independently comprises a pyrimidine nucleobase.

215. The oligonucleotide of any one of embodiments 211-212, wherein a pyrimidine nucleobase is optionally substituted T, C or U.

216. The oligonucleotide of any one of embodiments 211-215, wherein a pyrimidine nucleobase is T, C, U or 5 mC.

217. The oligonucleotide of any one of embodiments 211-215, wherein each nucleoside unit of the first ring comprises a 2'-MOE modification.

218. The oligonucleotide of any one of 211-216, wherein a nucleoside unit comprising a first sugar modification is immediately followed by a natural phosphate linkage, if the nucleoside unit is not the 3'-end nucleoside unit of the wing.

219. The oligonucleotide of any one of embodiments 211-216, wherein the first wing comprises a purine nucleobase.

220. The oligonucleotide of embodiment 219, wherein the nucleoside unit comprising a purine nucleobase comprises a 2'-modification that is not 2'-OR$^1$, wherein R' is substituted $C_{1-6}$ alkyl or a LNA sugar modification.

221. The oligonucleotide of embodiment 219, wherein the nucleoside unit comprising a purine nucleobase comprises a 2'-OMe modification.

222. The oligonucleotide of any one of embodiments 211-221, wherein the first wing comprises one or more natural phosphate linkages and one or more modified internucleotidic linkage.

223. The oligonucleotide of embodiment 222, wherein each internucleotidic linkage linking two nucleoside units of the first wing is a natural phosphate linkage, if the internucleotidic linkage is not the 5'-end or 3'-end internucleotidic linkage of the oligonucleotide.

224. The oligonucleotide of any one of embodiments 222-223, wherein the first internucleotidic linkage of the first wing if it is the first internucleotidic linkage (5'-end internucleotidic linkage) of the oligonucleotide, or the last internucleotidic linkage of the first wing if it is the last internucleotidic linkage (3'-end internucleotidic linkage) of the oligonucleotide, is a modified internucleotidic linkage.

225. The oligonucleotide of any one of embodiments 222-224, wherein the internucleotidic linkage connecting the first wing and the core is a modified internucleotidic linkage.

226. The oligonucleotide of any one of embodiments 222-225, wherein a modified internucleotidic linkage is an internucleotidic linkage of formula I.

227. The oligonucleotide of any one of embodiments 222-226, wherein a modified internucleotidic linkage is a chiral internucleotidic linkage of formula I.

228. The oligonucleotide of any one of embodiments 222-227, wherein a modified internucleotidic linkage is a phosphorothioate linkage.

229. The oligonucleotide of any one of embodiments 222-228, wherein the modified oligonucleotide is Sp.

230. The oligonucleotide of any one of embodiments 222-228, wherein the modified oligonucleotide is Rp.

231. The oligonucleotide of any one of embodiments 211-230, wherein the oligonucleotide comprises a second wing, wherein the second wing comprises a second sugar modification, which is not 2'-OR$^1$, wherein R' is substituted $C_{1-6}$ alkyl or a LNA sugar modification.

232. The oligonucleotide of embodiment 231, wherein the second wing comprises no 2'-OR$^1$, wherein R' is substituted $C_{1-6}$ alkyl or a LNA sugar modification.

233. The oligonucleotide of embodiment 231, wherein each sugar unit of the second wing independently comprises a second sugar modification.

234. The oligonucleotide of any one of embodiments 231-233, wherein a sugar modification is 2'-OR$^1$, wherein R' is unsubstituted, linear, $C_{1-3}$ aliphatic or haloaliphatic.

235. The oligonucleotide of any one of embodiments 231-233, wherein a sugar modification is 2'-OR$^1$, wherein R' is unsubstituted, linear, $C_{1-3}$ alkyl or haloalkyl.

236. The oligonucleotide of any one of embodiments 231-235, wherein a sugar modification is 2'-OR$^1$, wherein R' is methyl.

237. The oligonucleotide of any one of embodiments 231-236, wherein the second wing comprises no 2'-OR$^1$, wherein R' is substituted $C_{1-6}$ alkyl or a LNA sugar modification.

238. The oligonucleotide of any one of embodiments 231-237, wherein the second wing comprises no natural phosphate linkage.

239. The oligonucleotide of any one of embodiments 231-238, wherein the internucleotidic linkage connecting the second wing and the core is a modified internucleotidic linkage.

240. The oligonucleotide of any one of embodiments 231-239, wherein each internucleotidic linkage of the second wing is independently a modified internucleotidic linkage.

241. The oligonucleotide of any one of embodiments 231-240, wherein a modified internucleotidic linkage is an internucleotidic linkage of formula I.

242. The oligonucleotide of any one of embodiments 231-241, wherein a modified internucleotidic linkage is a chiral internucleotidic linkage of formula I.

243. The oligonucleotide of any one of embodiments 231-242, wherein a modified internucleotidic linkage is a phosphorothioate linkage.

244. The oligonucleotide of any one of embodiments 231-243, wherein the modified oligonucleotide is Sp.

245. The oligonucleotide of any one of embodiments 231-243, wherein the modified oligonucleotide is Rp.

246. The oligonucleotide of any one of embodiments 135-245, wherein the core comprise 5, 6, 7, 8, 9, 10, 11, 12, 13, 14, 15, 16, 17, 18, 19, 20 or more nucleoside units.

247. The oligonucleotide of any one of embodiments 135-245, wherein the core comprise 8, 9, 10, 11, 12, 13, 14, 15, 16, 17, 18, 19, 20 or more nucleoside units.

248. The oligonucleotide of any one of embodiments 135-247, wherein each wing independently comprise 1, 2, 3, 4, 5, 6, 7, 8, 9, 10, 11, 12, 13, 14, 15, 16, 17, 18, 19, or 20 nucleoside units.

249. The oligonucleotide of any one of embodiments 135-247, wherein each wing independently comprise 13, 4, 5, 6, 7, 8, 9, or 10 nucleoside units.

250. The oligonucleotide of any one of embodiments 135-249, wherein each wing has the same number of nucleoside units.

251. The oligonucleotide of any one of embodiments 135-249, wherein each wing has 5 nucleoside units.

252. The oligonucleotide of any one of embodiments 135-251, wherein each C in a wing is replaced with 5 mC.

253. A compound having the structure of formula O-I:

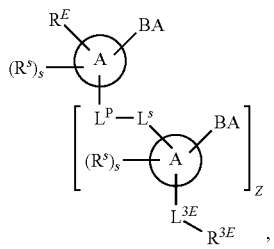

O-I or a salt thereof, wherein:

$R^E$ is a 5'-end group;

each BA is independently an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus, boron and silicon, a natural nucleobase moiety, and a modified nucleobase moiety;

each $R^s$ is independently —F, —Cl, —Br, —I, —CN, —N$_3$, —NO, —NO$_2$, -L-R', -L-OR', -L-SR', -L-N(R')$_2$, —O-L-OR', —O-L-SR', or —O-L-N(R')$_2$;

s is 0-20;

$L^s$ is —C($R^{5s}$)$_2$—, or L;

each L is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon;

each Ring A is independently an optionally substituted 3-20 membered monocyclic, bicyclic or polycyclic ring having 0-10 heteroatoms independently selected from oxygen, nitrogen, sulfur, phosphorus and silicon;

each $L^P$ is independently an internucleotidic linkage;

z is 1-1000;

$L^{3E}$ is L or -L-L-;

$R^{3E}$ is —R', -L-R', —OR', or a solid support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms independently selected from oxygen, nitrogen, sulfur, phosphorus and silicon.

254. The oligonucleotide of any one of the preceding embodiments, wherein the oligonucleotide is a compound of embodiment 253.

255. The oligonucleotide of embodiment 253 or 246, wherein $R^E$ is $R^{5s}$-$L^s$-.

256. The oligonucleotide of embodiment 255, wherein $R^E$ is HO-$L^s$-.

257. The oligonucleotide of any one of embodiments 253-255, wherein $L^s$ is —C($R^{5s}$)—.

258. The oligonucleotide of embodiment 257, wherein for at least one $L^s$, one $R^{5s}$ is —H, and the other $R^{5s}$ is not —H.

259. The oligonucleotide of embodiment 258, wherein the other $R^{5s}$ is optionally substituted $C_{1-6}$ aliphatic.

260. The oligonucleotide of embodiment 258, wherein the other $R^{5s}$ is methyl.

261. The oligonucleotide of embodiment 257, wherein for at least one $L^s$, both $R^{5s}$ are —H.

262. The oligonucleotide of any one of embodiments 253-261, wherein each BA is independently optionally substituted A, T, C, G or U.

263. The oligonucleotide of any one of embodiments 253-261, wherein each BA is independently A, T, C, 5 mC, or G or U.

264. The oligonucleotide of any one of embodiments 253-263, wherein z is no less than 15.

265. The oligonucleotide of any one of embodiments 253-264, wherein $L^{3E}$ is a covalent bond.

266. The oligonucleotide of any one of embodiments 253-265, wherein $R^{3E}$ is —OH.

267. The oligonucleotide of any one of embodiments 253-266, wherein

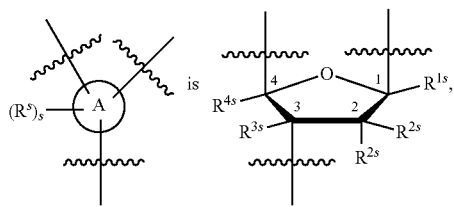

and BA is connected at C1.

268. The oligonucleotide of any one of embodiments 253-266, wherein

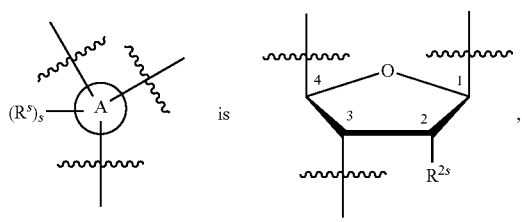

and BA is connected at C1.

269. The oligonucleotide of any one of embodiments 253-266, wherein

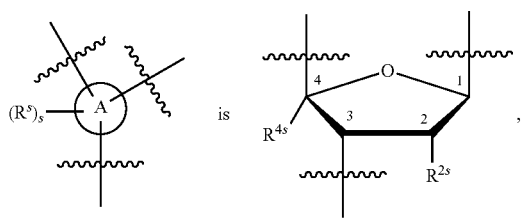

and BA is connected at C1.

270. The oligonucleotide of any one of embodiments 253-266, wherein one

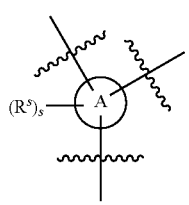

is optionally substituted

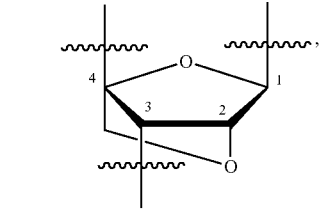 [SMILES: *C1[C@@H]2OC[C@]1(*)O[C@H]2*]

and BA is connected at C1.

271. The oligonucleotide of any one of embodiments 253-270, wherein each $L^P$ independently has the structure of formula I:

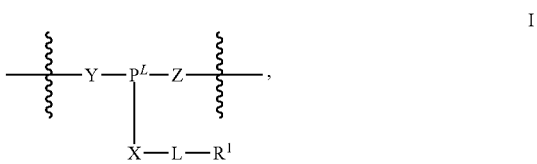

or a salt form thereof, wherein:

$P^L$ is P(=W), P, or P→B(R')$_3$;

W is O, S or Se;

$R^1$ is -L-R, halogen, —CN, —NO$_2$, —Si(R')$_3$, —OR', —SR', or —N(R')$_2$;

each of X, Y and Z is independently —O—, —S—, —N(-L-R$^1$)—, or L;

each R' is independently —R, —C(O)R, —C(O)OR, or —S(O)$_2$R;

each L is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus, boron and silicon, wherein one or more methylene units are optionally and independently replaced with C$_{1-6}$ alkylene, C$_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy$^L$;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms independently selected from oxygen, nitrogen, sulfur, phosphorus and silicon.

272. The oligonucleotide of any one of embodiments 253-271, wherein $P^L$ is P(=W).

273. The oligonucleotide of any one of embodiments 253-272, wherein $P^L$ is P(=O).

274. The oligonucleotide of any one of embodiments 253-273, wherein Y is O.

275. The oligonucleotide of any one of embodiments 253-274, wherein Z is O.

276. The oligonucleotide of any one of embodiments 253-275, wherein X is O or S.

277. The oligonucleotide of any one of embodiments 253-276, wherein L is a covalent bond.

278. The oligonucleotide of any one of embodiments 253-277, wherein $R^1$ is —H.

279. The oligonucleotide of any one of the preceding embodiments, wherein each sugar unit independently has the structure of

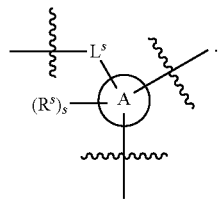

280. The oligonucleotide of any one of the preceding embodiments, wherein each nucleoside unit independently has the structure of

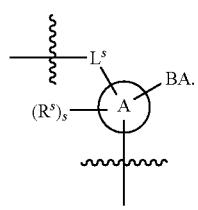

281. The oligonucleotide of any one of the preceding embodiments, wherein each nucleotide unit independently has the structure of

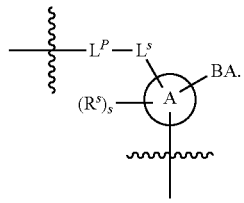

282. The oligonucleotide of any of the preceding embodiments, wherein the oligonucleotide is conjugated to a chemical moiety through a linker.

283. The oligonucleotide of any of the preceding embodiments, wherein the oligonucleotide is conjugated to a carbohydrate moiety through a linker.

284. The oligonucleotide of any of the preceding embodiments, wherein the oligonucleotide is conjugated to a target moiety through a linker.

285. The oligonucleotide of any of embodiments 254-284, wherein the moiety is or comprises a ligand moiety of a receptor.

286. The oligonucleotide of embodiment 285, wherein the receptor is a sigma-receptor.

287. The oligonucleotide of embodiment 285, wherein the receptor is a sigma 1-receptor.

288. The oligonucleotide of embodiment 286-287, wherein the ligand is an anisamide.

289. The oligonucleotide of embodiment 285, wherein the receptor is asialoglycoprotein receptor.

290. The oligonucleotide of any one of embodiments 254-289, wherein the moiety and the linker has the structure of:

$(R^D)b\text{-}L^{M1}\text{-}L^{M2}\text{-}L^{M3}\text{-}$, wherein:

each $R^D$ is independently a chemical moiety;

each of $L^{M1}$, $L^{M2}$, and $L^{M3}$ is independently is a covalent bond, or a bivalent or multivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring, and a 3-20 membered heterocyclyl ring; and b is 1-1000.

291. An oligonucleotide comprising one or more structures of:

$(R^D)b\text{-}L^{M1}\text{-}L^{M2}\text{-}L^{M3}\text{-}$, wherein:

each of $L^{M1}$, $L^{M2}$, and $L^{M3}$ is independently is a covalent bond, or a bivalent or multivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

each $Cy^L$ is independently an optionally substituted tetravalent group selected from a $C_{3-20}$ cycloaliphatic ring, a $C_{6-20}$ aryl ring, a 5-20 membered heteroaryl ring, and a 3-20 membered heterocyclyl ring; and b is 1-1000.

292. The oligonucleotide of embodiment 290 or 291, wherein b is 1, and $L^{M1}$ is bivalent.

293. The oligonucleotide of embodiment 290 or 291, wherein b is 3, and $L^{M1}$ is tetravalent.

294. The oligonucleotide of any one of embodiments 290-293, wherein $L^{M1}$ comprises one or more —N(R')— and one or more —C(O)—.

295. The oligonucleotide of any one of embodiments 290-294, wherein $L^{M2}$ is a covalent bond, or a bivalent, optionally substituted, linear or branched group selected from a $C_{1-10}$ aliphatic group and a $C_{1-10}$ heteroaliphatic group having 1-5 heteroatoms, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$.

296. The oligonucleotide of any one of embodiments 290-294, wherein $L^{M2}$ is a covalent bond, or a bivalent, optionally substituted, linear or branched $C_{1-10}$ aliphatic wherein one or more methylene units are optionally and independently replaced with $C_{1-6}$ alkylene, $C_{1-6}$ alkenylene, —C≡C—, —C(R')$_2$—, —O—, —S—, —N(R')—, or —C(O)—.

297. The oligonucleotide of any one of embodiments 290-296, wherein $L^{M2}$-NH—(CH$_2$)$_6$—, wherein —NH— is bonded to $L^{M1}$.

298. The oligonucleotide of any one of embodiments 290-297, wherein $L^{M3}$ is —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')—, —OP(O)(SR')—, —OP(O)(R')—, —OP(O)(NR')—, —OP(S)(OR')—, —OP(S)(SR')—, —OP(S)(R')—, —OP(S)(NR')—, —OP(R')—, —OP(OR')—, —OP(SR')—, —OP(NR')—, or —OP(OR')[B(R')$_3$]—.

299. The oligonucleotide of any one of embodiments 290-297, wherein $L^{M3}$ is —OP(O)(OR')—, or —OP(O)(SR')—, wherein —O— is bonded to $L^{M2}$.

300. The oligonucleotide of any one of embodiments 298-299, wherein the P atom is connected to a sugar unit, a nucleobase unit, or an internucleotidic linkage.

301. The oligonucleotide of any one of embodiments 298-300, wherein the P atom is connected to a —OH group through formation of a P—O bond.

302. A compound having the structure:

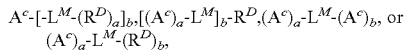

or a salt thereof, wherein:

each $A^C$ is independently an oligonucleotide moiety (e.g., $[H]_a$-$A^c$ or $[H]_b$-$A^c$ is an oligonucleotide);

a is 1-1000;

b is 1-1000;

$L^M$ is a multivalent linker; and each $R^D$ is independently a chemical moiety.

303. The oligonucleotide of embodiment 302, wherein the compound has the structure of $A^c$-$[-L^M$-$(R^D)_a]_b$ or a salt thereof.

304. The oligonucleotide of embodiment 302, wherein the compound has the structure of $[(A^c)_a$-$L^M]_b$-$R^D$ or a salt thereof.

305. The oligonucleotide of embodiment 302, wherein the compound has the structure of $(A^c)_a$-$L^M$-$(A^c)_b$ or a salt thereof.

306. The oligonucleotide of embodiment 302, wherein the compound has the structure of $(A^c)_a$-$L^M$-$(R^D)_b$ or a salt thereof.

307. The oligonucleotide of any one of embodiments 302-306, wherein $[H]_a$-$A^c$ or $[H]_b$-$A^c$ is an oligonucleotide of any one of embodiments 1-281.

308. The oligonucleotide of any one of embodiments 302-306, wherein the oligonucleotide is an oligonucleotide of any one of embodiments 282-301.

309. The oligonucleotide of any one of 302-308, wherein each $L^M$ is independently a covalent bond, or a bivalent or multivalent, optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$.

310. The oligonucleotide of any one of 302-308, wherein $L^M$ is -$L^{M1}$-$L^{M2}$-$L^{M3}$-.

311. The oligonucleotide of any one of embodiments 298-301, wherein the P atom is connected to the 5'-OH group through formation of a P—O bond.

312. The oligonucleotide of any of the preceding embodiments, wherein the oligonucleotide is conjugated to a lipid moiety through a linker.

313. The oligonucleotide of any one of embodiments 254-311, wherein the moiety or $R^D$ is selected from: optionally substituted phenyl,

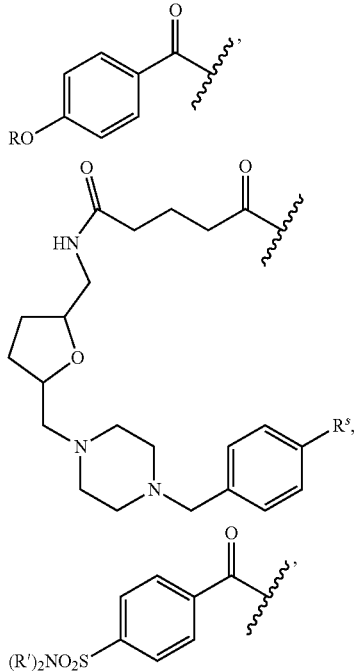

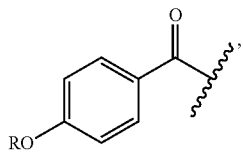

314. An oligonucleotide comprising one or more chemical moieties selected from:

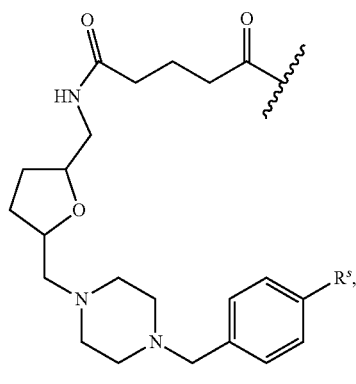

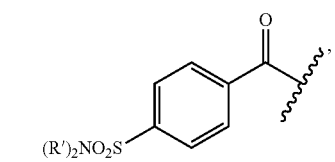

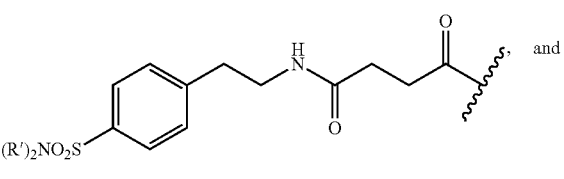

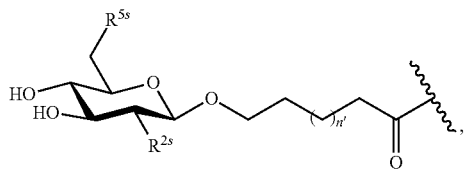

wherein n' is 0 or 1.

315. The oligonucleotide of any one of embodiments 313-314, wherein n' is 0.

316. The oligonucleotide of any one of embodiments 313-314, wherein n' is 1.

317. The oligonucleotide of any one of embodiments 313-316, wherein the moiety or RD is selected from:

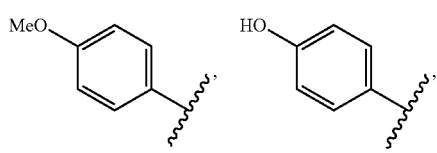

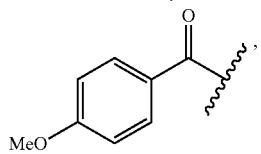

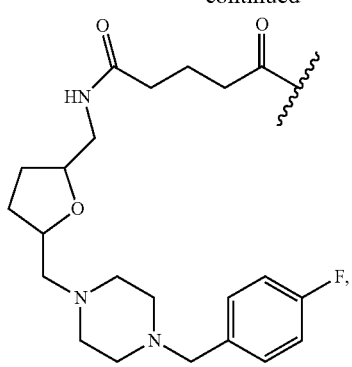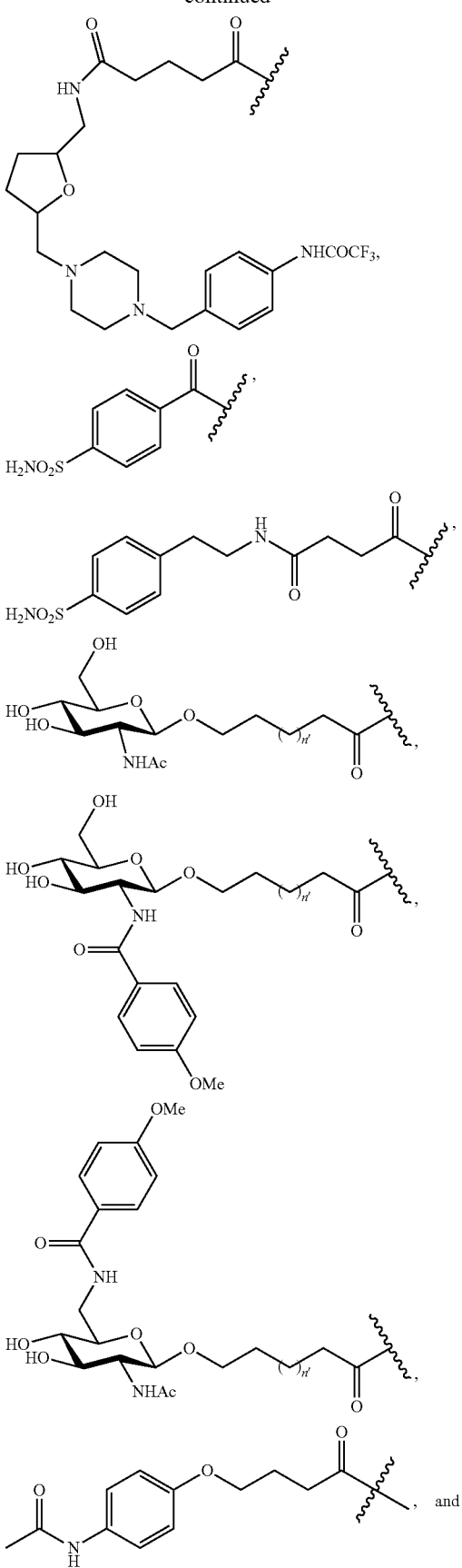

425
-continued
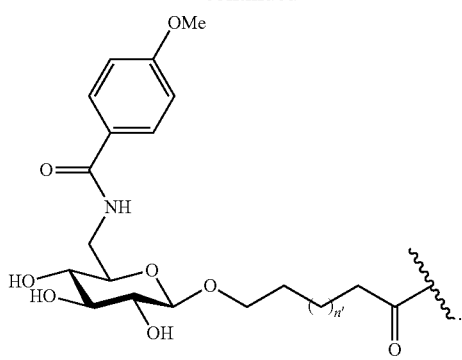
318. The oligonucleotide of any one of embodiments 313-316, wherein the moiety or $R^D$ is selected from:
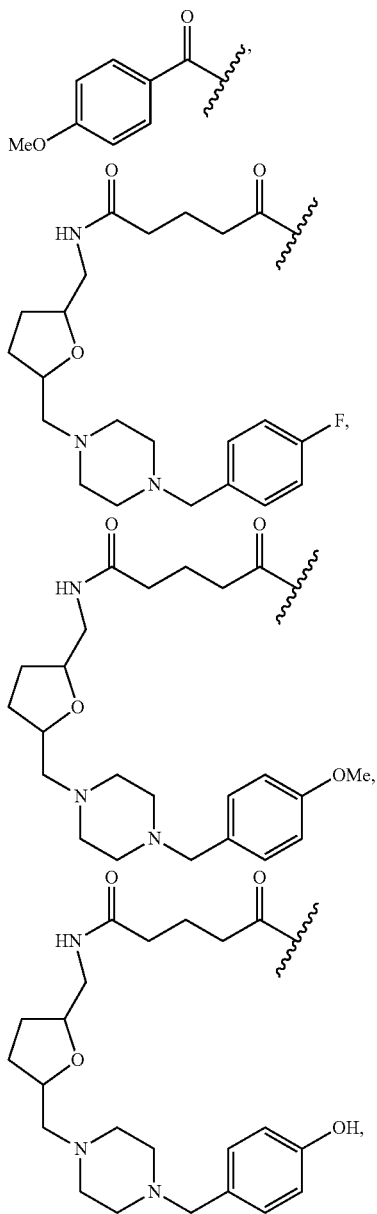
426
-continued
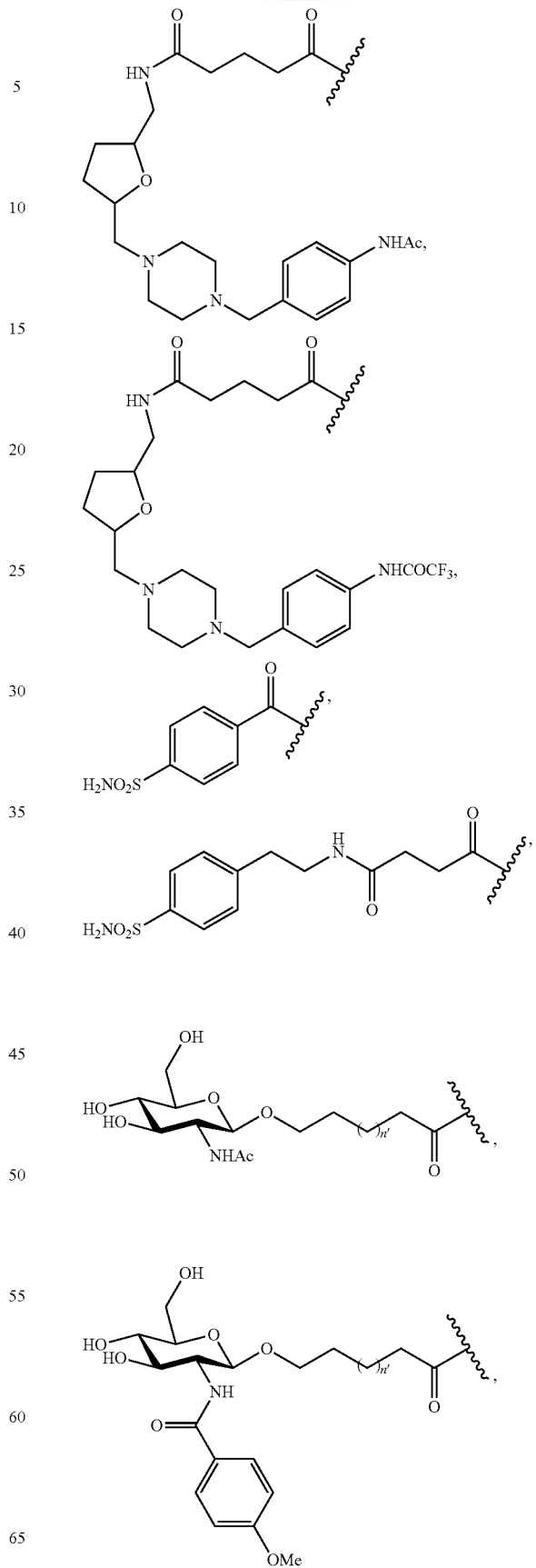

427
-continued

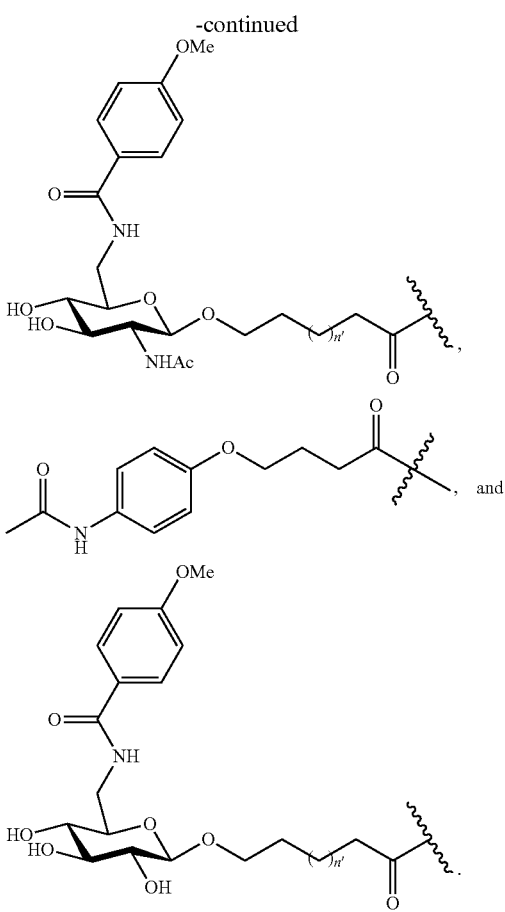

319. The oligonucleotide of any one of embodiments 254-318, wherein the linker is $L^M$, wherein $L^M$ is a covalent bond, or a bivalent or multivalent, optionally substituted, linear or branched group selected from a $C_{1-100}$ aliphatic group and a $C_{1-100}$ heteroaliphatic group having 1-30 heteroatoms, wherein one or more methylene units are optionally and independently replaced with $C_{1-6}$ alkylene, $C_{1-6}$ alkenylene, —C≡C—, —C(R')$_2$—, —O—, —S—, —SS—, —N(R')—, —C(O)—, —C(S)—, —C(NR')—, —C(O) N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$.

320. The oligonucleotide of embodiment 319, wherein $L^M$ is multivalent, and connects two or more moieties to the oligonucleotide.

321. The oligonucleotide of embodiment 319, wherein $L^M$ is tetravalent, and connects three moieties to the oligonucleotide.

322. The oligonucleotide of any one of embodiments 254-322, wherein the linker or $L^{M1}$ is or comprises:

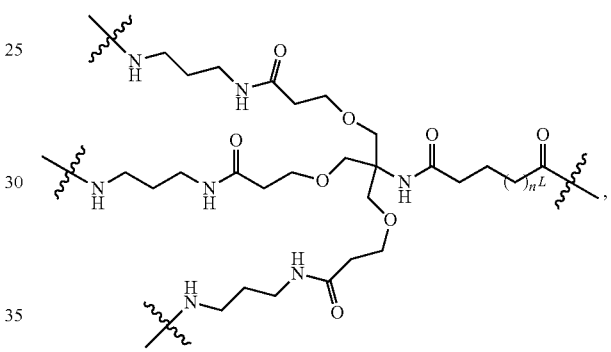

wherein $n^L$ is 1-8.

323. The oligonucleotide of any one of embodiments 254-322, wherein the linker or -$L^{M1}$-$L^{M2}$-$L^{M3}$-is:

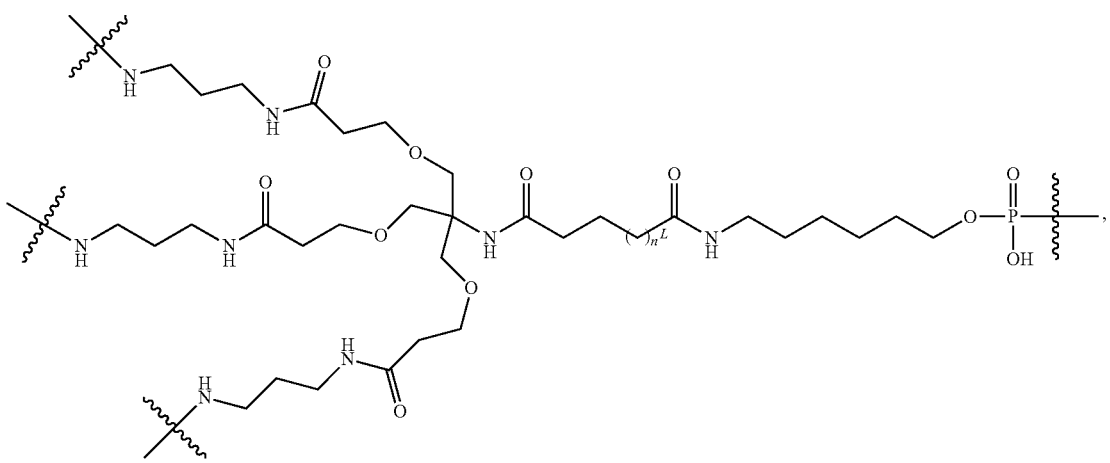

or a salt form thereof, wherein $n^L$ is 1-8.

324. The oligonucleotide of any one of embodiments 254-323, wherein the linker or -$L^{M1}$-$L^{M2}$-$L^{M3}$-is

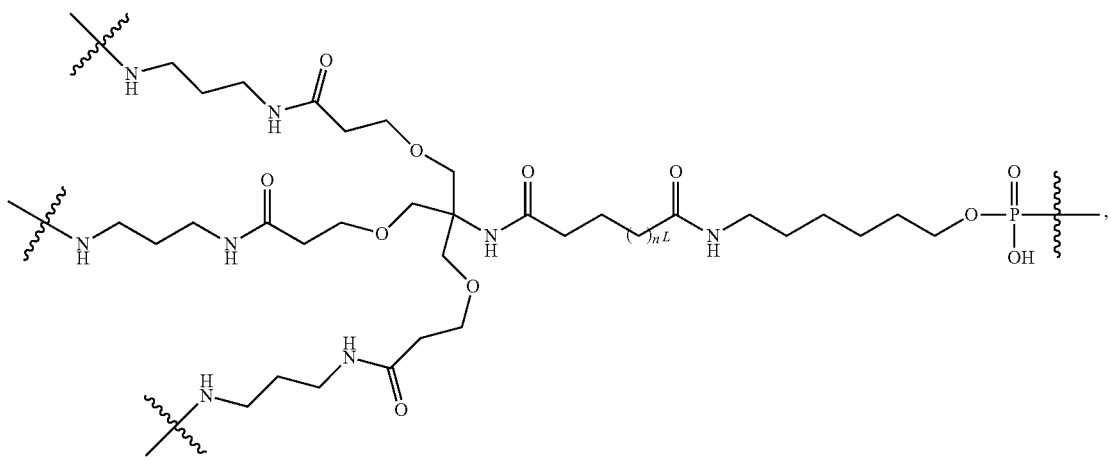

or a salt form thereof, wherein:

$n^L$ is 1-8.

each amino group independently connects to a moiety; and the P atom connects to the 5'-OH of the oligonucleotide.

325. The oligonucleotide of any one of embodiments 254-324, wherein the moiety and the linker, or $(R^D)b\text{-}L^{M1}\text{-}L^{M2}\text{-}L^{M3}\text{-}$, is or comprises:

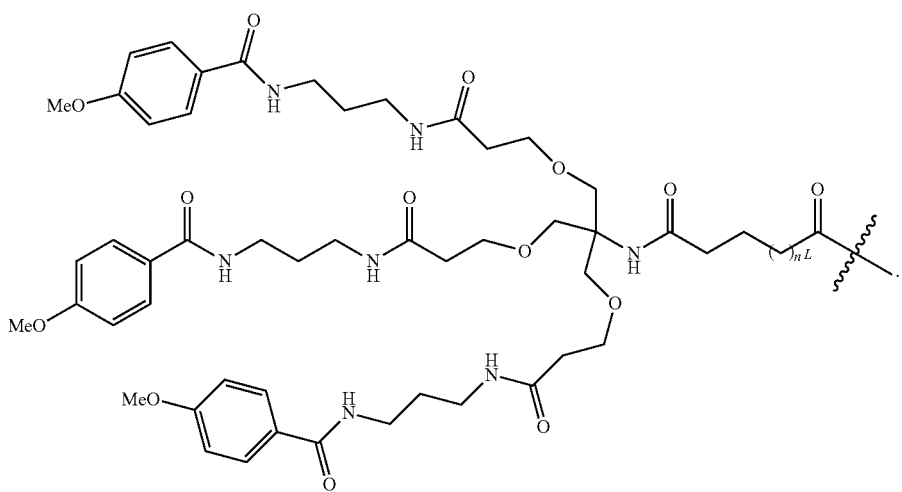

326. The oligonucleotide of any one of embodiments 254-324, wherein the moiety and the linker, or $(R^D)b\text{-}L^{M1}\text{-}L^{M2}\text{-}L^{M3}\text{-}$, is or comprises:

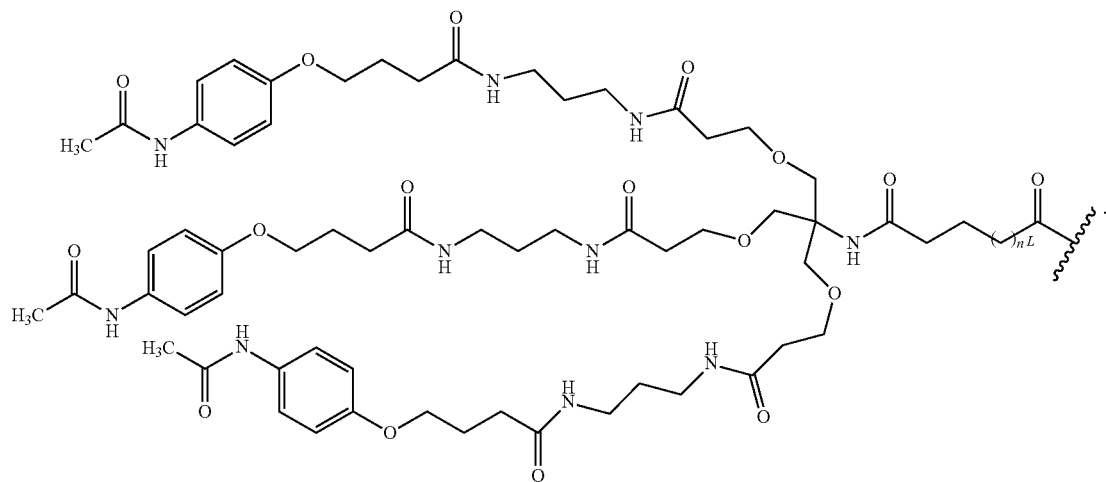
327. The oligonucleotide of any one of embodiments 254-324, wherein the moiety and the linker, or $(R^D)b\text{-}L^{M1}\text{-}L^{M2}\text{-}L^{M3}\text{-}$, is or comprises:
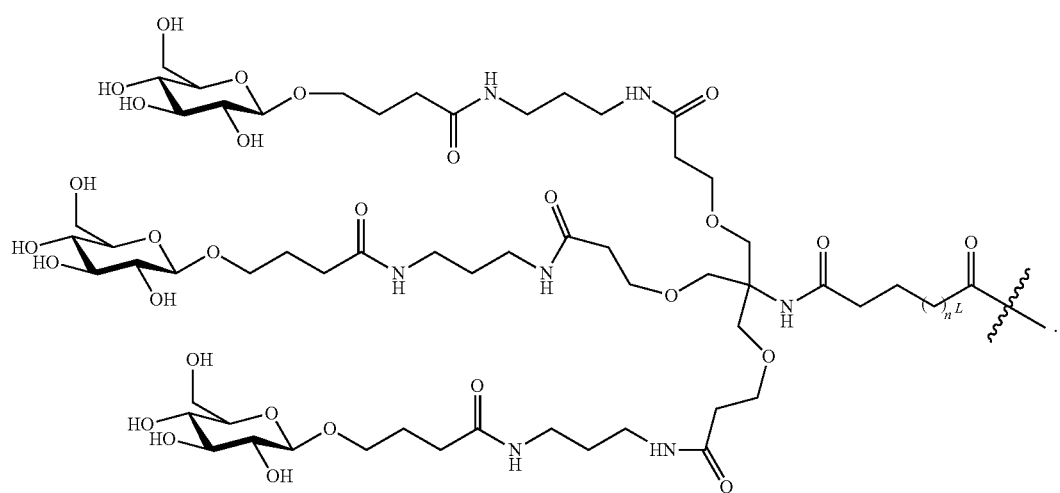
328. The oligonucleotide of any one of embodiments 254-324, wherein the moiety and the linker, or $(R^D)b\text{-}L^{M1}\text{-}L^{M2}\text{-}L^{M3}\text{-}$, is or comprises:

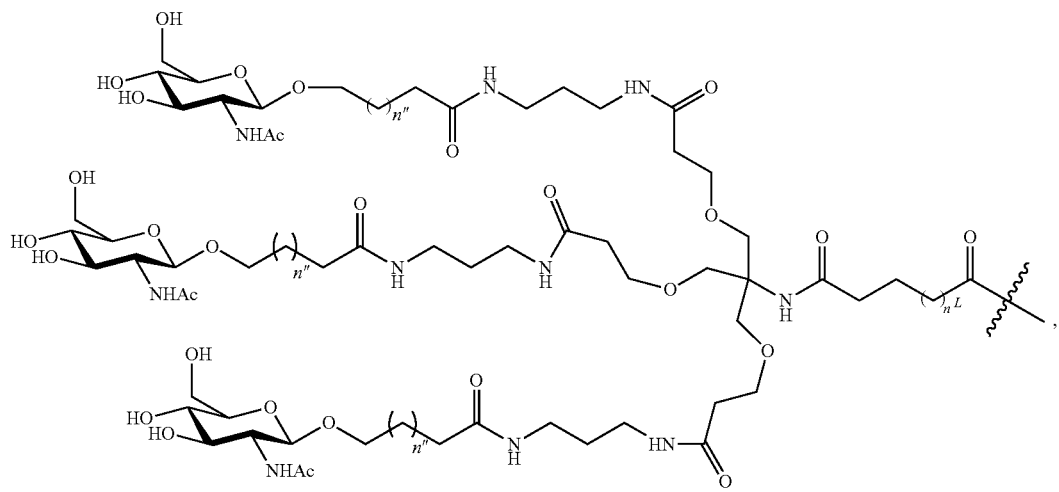

wherein n" is 1 or 2.

329. The oligonucleotide of embodiment 328, wherein n" is 1.

330. The oligonucleotide of embodiment 328, wherein n" is 2.

331. The oligonucleotide of any one of embodiments 254-324, wherein the moiety and the linker, or $(R^D)b\text{-}L^{M1}\text{-}L^{M2}\text{-}L^{M3}$, is:

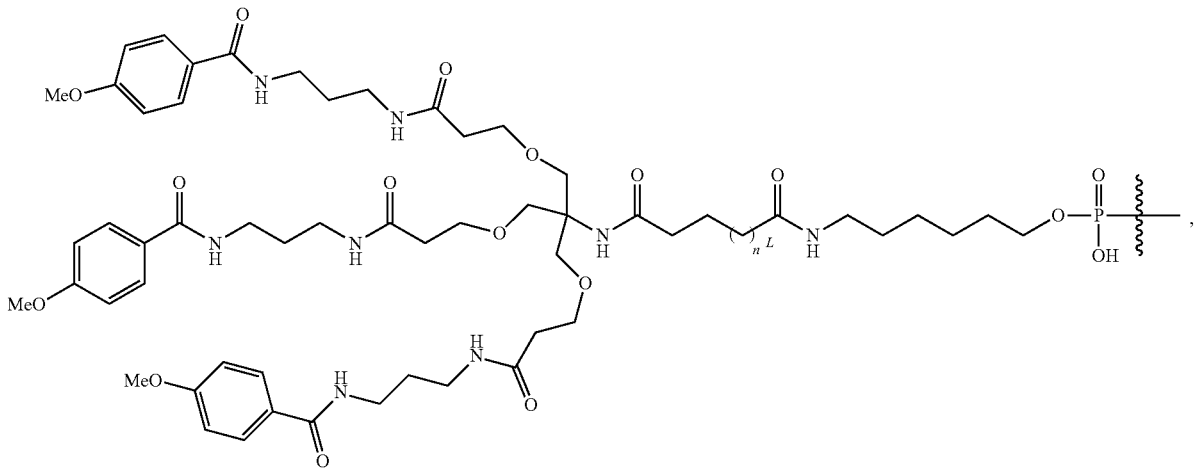

or a salt form thereof.

332. The oligonucleotide of any one of embodiments 254-324, wherein the moiety and the linker, or $(R^D)b\text{-}L^{M1}\text{-}L^{M2}\text{-}L^{M3}\text{-}$, is:

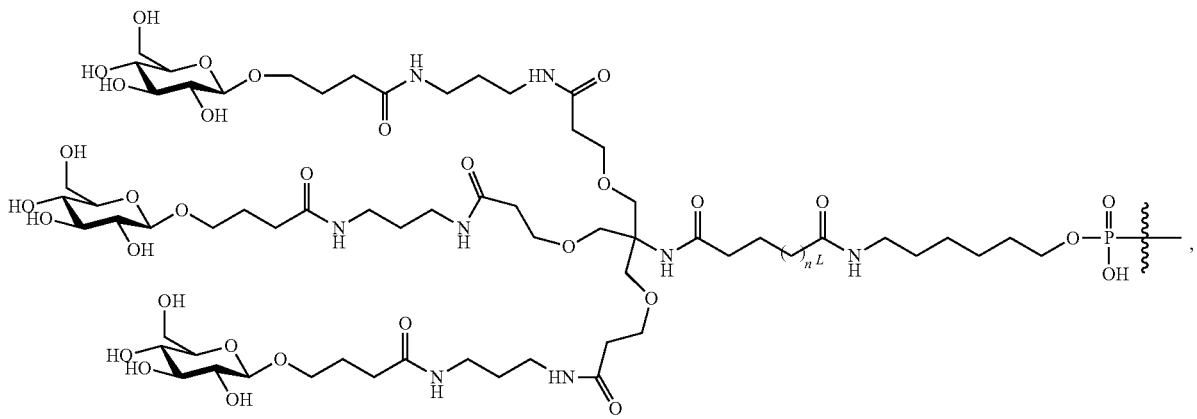
or a salt form thereof.
333. The oligonucleotide of any one of embodiments 254-324, wherein the moiety and the linker, or $(R^D)b-L^{M1}-L^{M2}-L^{M3}-$, is:
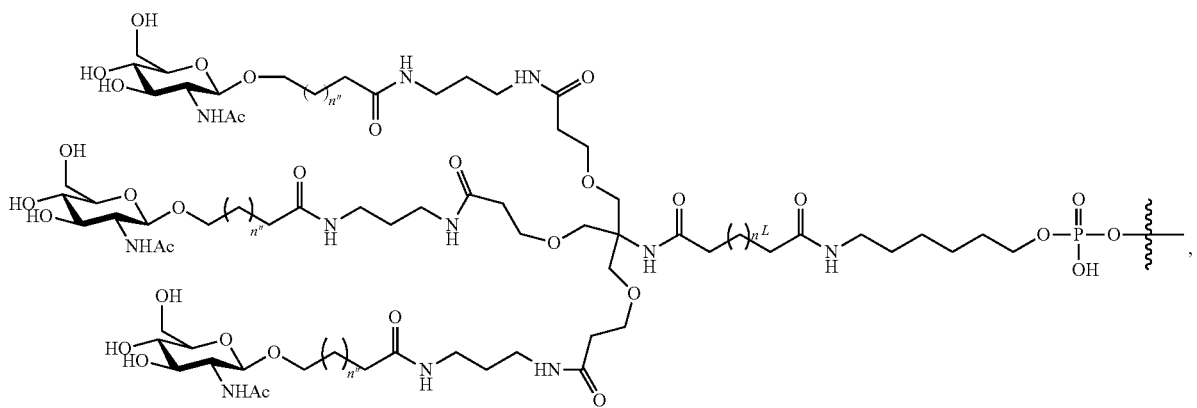
or a salt form thereof, wherein n" is 1 or 2.
334. The oligonucleotide of embodiment 333, wherein n" is 1.
335. The oligonucleotide of embodiment 333, wherein n" is 2.
336. The oligonucleotide of any one of embodiments 254-321, wherein the linker, or $L^{M1}$, is or comprises:

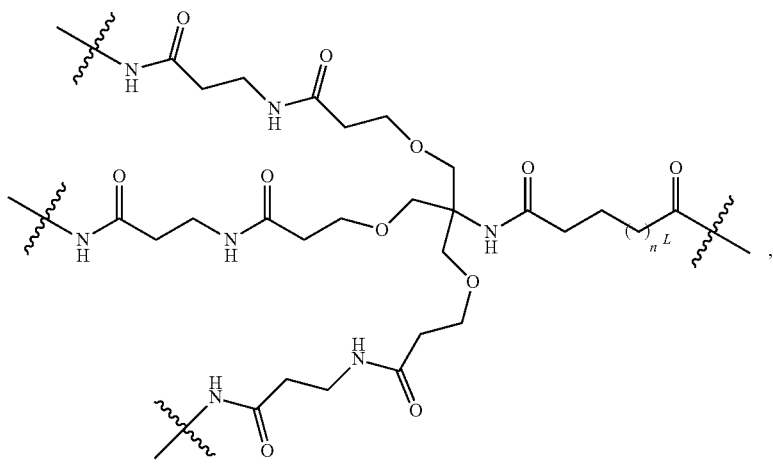
wherein $n^L$ is 1-8.
337. The oligonucleotide of embodiment 336, wherein the moiety and linker, or $(R^D)b-L^{M1}-L^{M2}-L^{M3}-$, is or comprises:
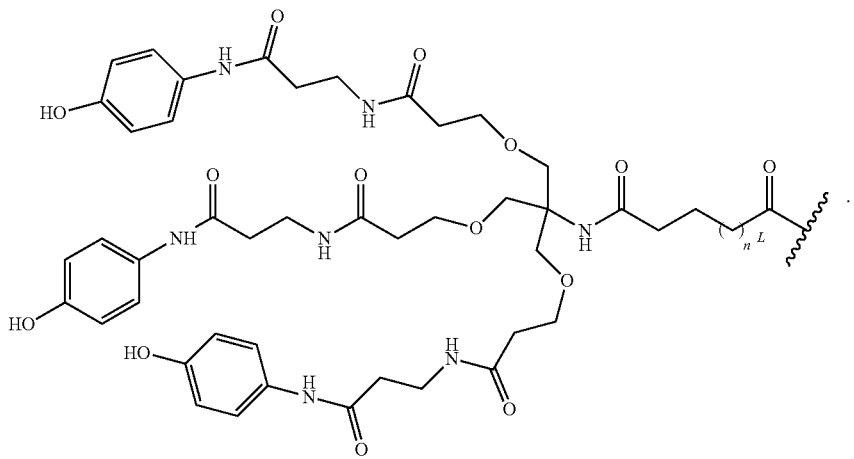
338. The oligonucleotide of embodiment 336, wherein the moiety and linker, or $(R^D)b-L^{M1}-L^{M2}-L^{M3}-$, is or comprises:
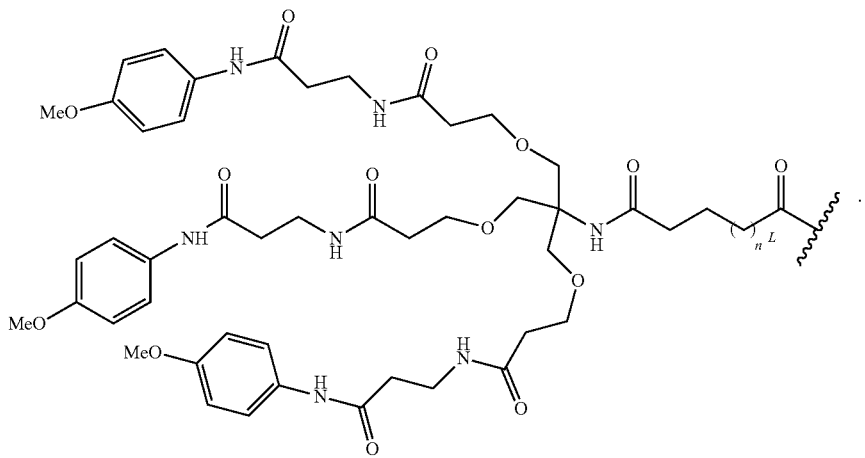

339. The oligonucleotide of embodiment 319-335, wherein $n^L$ is 1.

340. The oligonucleotide of embodiment 319-335, wherein $n^L$ is 8.

341. The oligonucleotide of any one of the preceding embodiments, wherein a heteroatom is selected from oxygen, nitrogen, sulfur, boron, silicon, and phosphorus.

342. The oligonucleotide of any one of the preceding embodiments, wherein a heteroatom is selected from oxygen, nitrogen, sulfur, and phosphorus.

343. The oligonucleotide of any one of the preceding embodiments, wherein a heteroatom is selected from oxygen, nitrogen, and sulfur.

344. The oligonucleotide of any one of the preceding embodiments, wherein an Op linkage phosphorus of Op(Sp)m is bonded to the 3'-position of the $3^{rd}$, $4^{th}$, $5^{th}$, $6^{th}$, $7^{th}$, $8^{th}$, $9^{th}$, $10^{th}$, $11^{th}$, $12^{th}$ or further nucleoside of the core counting from the 5'-end of the core.

345. The oligonucleotide of any one of the preceding embodiments, wherein an Op linkage phosphorus of Op(Sp)m is bonded to the 3'-position of the $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$ or further nucleoside of the oligonucleotide counting from the 5'-end of the oligonucleotide.

346. The oligonucleotide of any one of the preceding embodiments, wherein the oligonucleotide comprises 1, 2, 3, 4, 5, 6, 7, 8, 9, 10 or more non-negatively charged internucleotidic linkages.

347. The oligonucleotide of any one of the preceding embodiments, wherein the oligonucleotide comprises 1, 2, 3, 4, 5, 6, 7, 8, 9, 10 or more chirally controlled non-negatively charged internucleotidic linkages.

348. The oligonucleotide of any one of the preceding embodiments, wherein the oligonucleotide comprises 2, 3, 4, 5, 6, 7, 8, 9, 10 or more consecutive non-negatively charged internucleotidic linkages.

349. The oligonucleotide of any one of the preceding embodiments, wherein the oligonucleotide comprises 2, 3, 4, 5, 6, 7, 8, 9, 10 or more consecutive chirally controlled non-negatively charged internucleotidic linkages.

350. The oligonucleotide of any one of the preceding embodiments, wherein the oligonucleotide comprises a wing-core-wing, core-wing, or wing-core structure, and wherein a wing comprises 1, 2, 3, 4, 5, 6, 7, 8, 9, 10 or more non-negatively charged internucleotidic linkages.

351. The oligonucleotide of any one of the preceding embodiments, wherein the oligonucleotide comprises a wing-core-wing, core-wing, or wing-core structure, and wherein a wing comprises 1, 2, 3, 4, 5, 6, 7, 8, 9, 10 or more chirally controlled non-negatively charged internucleotidic linkages.

352. The oligonucleotide of any one of the preceding embodiments, wherein the oligonucleotide comprises a wing-core-wing, core-wing, or wing-core structure, and wherein a wing comprises 2, 3, 4, 5, 6, 7, 8, 9, 10 or more consecutive non-negatively charged internucleotidic linkages.

353. The oligonucleotide of any one of the preceding embodiments, wherein the oligonucleotide comprises a wing-core-wing, core-wing, or wing-core structure, and wherein a wing comprises 2, 3, 4, 5, 6, 7, 8, 9, 10 or more consecutive chirally controlled non-negatively charged internucleotidic linkages.

354. The oligonucleotide of any one of the preceding embodiments, wherein the oligonucleotide comprises or consists of a wing-core-wing structure, and wherein only one wing comprise one or more non-negatively charged internucleotidic linkages.

355. The oligonucleotide of any one of the preceding embodiments, wherein the oligonucleotide comprises a wing-core-wing, core-wing, or wing-core structure, and wherein a core comprises 1, 2, 3, 4, 5, 6, 7, 8, 9, 10 or more non-negatively charged internucleotidic linkages.

356. The oligonucleotide of any one of the preceding embodiments, wherein the oligonucleotide comprises a wing-core-wing, core-wing, or wing-core structure, and wherein a core comprises 1, 2, 3, 4, 5, 6, 7, 8, 9, 10 or more chirally controlled non-negatively charged internucleotidic linkages.

357. The oligonucleotide of any one of the preceding embodiments, wherein the oligonucleotide comprises a wing-core-wing, core-wing, or wing-core structure, and wherein a core comprises 2, 3, 4, 5, 6, 7, 8, 9, 10 or more consecutive non-negatively charged internucleotidic linkages.

358. The oligonucleotide of any one of the preceding embodiments, wherein the oligonucleotide comprises a wing-core-wing, core-wing, or wing-core structure, and wherein a core comprises 2, 3, 4, 5, 6, 7, 8, 9, 10 or more consecutive chirally controlled non-negatively charged internucleotidic linkages.

359. The oligonucleotide of any one of the preceding embodiments, wherein each of the non-negatively charged internucleotidic linkages independently has the structure of formula II, II-a-1, II-a-2, II-b-1, II-b-2, II-c-1, II-c-2, II-d-1, II-d-2, or a salt form thereof.

360. The oligonucleotide of any one of the preceding embodiments, wherein each of the non-negatively charged internucleotidic linkages independently has the structure of formula TI, TI-a-1, II-a-2, I-b-1, II-b-2, II-c-1, II-c-2, II-d-1, II-d-2, or a salt form thereof.

361. The oligonucleotide of any one of the preceding embodiments, having a purity of at least 50%, 60%, 70%, 80%, 85%, 90%, 95%, 96%, 97%, 98%, or 99%.

362. The oligonucleotide of any one of the preceding embodiments, having a diastereomeric purity of at least 50%, 60%, 70%, 80%, 85%, 90%, 95%, 96%, 97%, 98%, or 99%.

363. The oligonucleotide of any one of the preceding embodiments, wherein the base sequence of the oligonucleotide comprises a sequence targeting a C9orf72 intro sequence.

364. The oligonucleotide of any one of the preceding embodiments, wherein the base sequence of the oligonucleotide comprises a sequence targeting a C9orf72 intro 1 sequence.

365. The oligonucleotide of any one of the preceding embodiments, wherein the base sequence of the oligonucleotide comprises a sequence selected from Table 1A, or a portion thereof, wherein the portion is of 10, 11, 12, 13, 14, 15, 16, 17, 18, or 19 consecutive bases.

366. The oligonucleotide of any one of embodiments 363-365, wherein the oligonucleotide preferentially reduce level of a disease-associated C9orf72 product.

367. The oligonucleotide of embodiment 366, wherein the product is a transcript comprising expanded GGGGCC repeats.

368. The oligonucleotide of embodiment 366, wherein the product is a transcript comprising at least 30, 50, 100, 200, 300, 400, or 500 GGGGCC repeats (SEQ ID NO: 601).

369. The oligonucleotide of embodiment 366, wherein the product is an antisense transcript comprising expanded GGGGCC repeats.

370. The oligonucleotide of embodiment 366, wherein the product is an antisense transcript comprising expanded GGGGCC repeats.

371. The oligonucleotide of embodiment 366, wherein the product is a dipeptide repeat protein.

372. A pharmaceutical composition comprising an oligonucleotide of any one of the preceding embodiments or a pharmaceutically acceptable salt thereof.

373. The composition of embodiment 372, wherein the composition comprises a sodium salt of an oligonucleotide of any one of embodiments 1-371.

374. An oligonucleotide composition comprising a plurality of oligonucleotides which have:
   a) a common base sequence;
   b) a common pattern of backbone linkages, which comprises at least one chiral internucleotidic linkage comprising a chiral linkage phosphorus;
   which composition is chirally controlled in that the composition is enriched, relative to a substantially racemic preparation of oligonucleotides having the same common base sequence and the same common pattern of backbone linkages, for oligonucleotides that have a) the common base sequence; b) the common pattern of backbone linkages; and c) a specific stereochemical configuration selected from Rp and Sp at the chiral linkage phosphorus of the at least one chiral internucleotidic linkage (chirally controlled internucleotidic linkage),
   wherein each oligonucleotide of the plurality is independently an oligonucleotide of any of embodiments 1-371 or a salt thereof.

375. The composition of embodiment 374, wherein each chiral internucleotidic linkage comprising a chiral linkage phosphorus is independently a chirally controlled internucleotidic linkage.

376. An oligonucleotide composition comprising a plurality of oligonucleotides which have:
   a) a common base sequence;
   b) a common pattern of backbone linkages;
   c) a common pattern of backbone chiral centers;
   which composition is chirally controlled in that level of the plurality of oligonucleotides in the composition is not random; and
   wherein each oligonucleotide of the particular oligonucleotide type is independently an oligonucleotide of any of embodiments 1-371 or a salt thereof.

377. An oligonucleotide composition comprising oligonucleotides of a particular oligonucleotide type characterized by:
   a) a common base sequence;
   b) a common pattern of backbone linkages;
   c) a common pattern of backbone chiral centers;
   which composition is chirally controlled in that it is enriched, relative to a substantially racemic preparation of oligonucleotides having the same common base sequence, for oligonucleotides of the particular oligonucleotide type; and
   wherein each oligonucleotide of the particular oligonucleotide type is independently an oligonucleotide of any of embodiments 1-371 or a salt thereof.

378. The composition of any one of embodiments 374-377, wherein the common pattern of backbone chiral centers comprises at least one Rp.

379. The composition of any one of embodiments 374-378, wherein the common pattern of backbone chiral centers comprises at least one Sp.

380. The composition of any one of embodiments 374-379, wherein oligonucleotides of the plurality or type are of the same constitution.

381. The composition of any one of embodiments 374-380, wherein at least 0.1%, 0.5%, 1%, 5%, 10%, 15%, 20%, 25%, 30%, 35%, 40%, 45%, 50%, 55%, 60%, 65%, 70%, 75%, 80%, 85%, 90%, or 95% of all oligonucleotides in the composition that have common base sequence are oligonucleotides of the plurality or type.

382. The composition of any one of embodiments 374-381, wherein at least 0.1%, 0.5%, 1%, 5%, 10%, 15%, 20%, 25%, 30%, 35%, 40%, 45%, 50%, 55%, 60%, 65%, 70%, 75%, 80%, 85%, 90%, or 95% of all oligonucleotides in the composition have the common base sequence.

383. The composition of any one of embodiments 381 or 382, wherein the percentage is at least 5%.

384. The composition of any one of embodiments 381 or 382, wherein the percentage is at least 10%.

385. The composition of any one of embodiments 381 or 382, wherein the percentage is at least 20%.

386. The composition of any one of embodiments 381 or 382, wherein the percentage is at least 50%.

387. The composition of any one of embodiments 381 or 382, wherein the percentage is at least 75%.

388. The composition of any one of embodiments 381 or 382, wherein the percentage is at least 90%.

389. The composition of any one of embodiments 374-388, wherein the common pattern of backbone chiral centers comprises at least one Op.

390. A method for controlled cleavage of a nucleic acid target, comprising contacting the nucleic acid target with an oligonucleotide or composition of any one of the preceding embodiments.

391. A method for selective suppression of a transcript from a target nucleic acid sequence for which one or more similar sequences exist within a population, each of which contains a specific nucleotide characteristic sequence element that defines the target nucleic acid sequence relative to the similar sequences, the method comprising steps of:
   contacting a sample comprising transcripts of the target nucleic acid sequence with a chirally controlled oligonucleotide composition comprising a plurality of oligonucleotides that have
      1) a common base sequence;
      2) a common pattern of backbone linkages;
      3) a common pattern of backbone chiral centers;
   wherein the common base sequence for the oligonucleotides of the particular oligonucleotide type is or comprises a sequence that is complementary to the characteristic sequence element that defines the target nucleic acid sequence.

392. The method of embodiment 391, wherein a characteristic sequence element is or comprises one or more nucleobases that differentiate the target nucleic acid sequence from similar sequence(s) in a genome and/or products encoded thereby.

393. The method of embodiment 391, wherein a characteristic sequence element is a nucleobase that differentiates the target nucleic acid sequence from similar sequence(s) in a genome and/or products encoded thereby.

394. The method of any one of embodiments 391-393, wherein a similar sequence shares at least 80%, 85%, 90%, 95%, 96%, 97%, 98%, or 99% but less than 100% homology with the target nucleic acid sequence within the portion of the sequence that is complementary to the common base sequence.

395. The method of any one of embodiments 391-393, wherein a similar sequence differs at no more than 5, 4, 3, 2, or 1 nucleobases from but not identical with the target nucleic acid sequence within the portion of the sequence that is complementary to the common base sequence.

396. The method of any one of embodiments 391-393, wherein a similar sequence differs at only 1 nucleobases from the target nucleic acid sequence within the portion of the sequence that is complementary to the common base sequence.

397. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
    contacting a sample comprising transcripts of the target nucleic acid sequence with a chirally controlled oligonucleotide composition comprising a plurality of oligonucleotides that have
    1) a common base sequence;
    2) a common pattern of backbone linkages;
    3) a common pattern of backbone chiral centers;
wherein the common base sequence for the oligonucleotides of the particular oligonucleotide type is or comprises a sequence that is complementary to the characteristic sequence element that defines a particular allele.

398. The method of any one of embodiments 391-397, wherein a characteristic sequence element is a SNP.

399. The method of any one of embodiments 391-397, wherein a characteristic sequence element is a mutation.

400. The method of any one of embodiments 391-399, wherein the composition provides suppression of the transcript at a level that is greater than when the composition is absent.

401. The method of any one of embodiments 391-400, wherein the composition provides suppression of the transcript at a level that is greater than a level of suppression observed for another allele or a similar sequence.

402. The method of any one of embodiments 390-401, wherein the chirally controlled oligonucleotide composition is a chirally controlled oligonucleotide composition of an oligonucleotide of any one of embodiments 1-371 or a composition of any one of embodiments 372-389.

403. The method of any one of embodiments 391-402, wherein a nucleobase that is complementary to the characteristic sequence element is located at position 3, 4, 5, 6, 7, 8, 9, or 10 or further from the 3'-end of the oligonucleotide.

404. The method of any one of embodiments 391-402, wherein a nucleobase that is complementary to the characteristic sequence element is located at position 3, 4, 5, 6, 7, 8, 9, or 10 or further from the 5'-end of the oligonucleotide.

405. The method of any one of embodiments 391-402, wherein a nucleobase that is complementary to the characteristic sequence element is located at position 3, 4, 5, 6, 7, 8, 9, or 10 or further from the 3'-end of the core of the oligonucleotide.

406. The method of any one of embodiments 391-402, wherein a nucleobase that is complementary to the characteristic sequence element is located at position 1, 2, 3, 4, 5, 6, 7, 8, 9, or 10 or further from the 5'-end of the core of the oligonucleotide.

407. A method for reducing a level of a transcript or a protein encoded thereby in a system, comprising administering an oligonucleotide or a composition of any one of the preceding embodiments.

408. The method of embodiment 407, wherein the system is a cell.

409. The method of embodiment 407, wherein the system is a tissue.

410. The method of embodiment 407, wherein the system is an organ.

411. The method of embodiment 407, wherein the system is an organism.

412. The method of embodiment 407, wherein the system is a subject.

413. The method of embodiment 407, wherein the method preferentially reduces level of disease-associated transcript or protein over a non-disease associated transcript or protein.

414. The method of any one of the preceding embodiments, wherein a transcript is a C9orf72 transcript comprising expanded GGGGCC repeats.

415. The method of any one of the preceding embodiments, wherein a transcript is a C9orf72 transcript comprising at least 30, 50, 100, 200, 300, 400, or 500 GGGGCC repeats (SEQ ID NO: 601).

416. The method of any one of the preceding embodiments, wherein the method reduce level of a protein.

417. The method of any one of the preceding embodiments, wherein the method reduce level of dipeptide repeat protein related to C9orf72 expanded repeats.

418. The method of any one of the preceding embodiments, wherein the method reduce level of foci related to C9orf72 expanded repeats.

419. The method of any one of embodiments 407-413, wherein a transcript is a Malat1 transcript.

420. The method of any one of embodiments 407-413, wherein level of a transcript of Malat1 and/or a protein encoded thereby is reduced.

421. The method of any one of embodiments 407-413, wherein a transcript is a PNPLA3 transcript.

422. The method of any one of embodiments 407-413, wherein level of a transcript of PNPLA3 and/or a protein encoded thereby is reduced.

423. The method of any one of embodiments 407-413, wherein a transcript is an ApoC3 transcript.

424. The method of any one of embodiments 407-413, wherein level of a transcript of ApoC3 and/or a protein encoded thereby is reduced.

425. A method, comprising administering to a subject suffering from or susceptible to a condition, disorder, and/or disease related to C9orf72 expanded repeats an oligonucleotide or composition of any one of the preceding embodiments.

426. The method of embodiment 425, wherein the condition, disorder, and/or disease is amyotrophic lateral sclerosis (ALS), frontotemporal dementia (FTD), corticobasal degeneration syndrome (CBD), atypical Parkinsonian syndrome, olivopontocerebellar degeneration (OPCD), or Alzheimer's disease.

427. The method of embodiment 425, wherein the condition, disorder, and/or disease is amyotrophic lateral sclerosis (ALS).

428. The method of embodiment 425, wherein the condition, disorder, and/or disease is frontotemporal dementia (FTD).

429. A method, comprising administering to a subject suffering from or susceptible to a condition, disorder, and/or disease related to Malat1 expanded repeats an oligonucleotide or composition of any one of the preceding embodiments.

430. A method, comprising administering to a subject suffering from or susceptible to a condition, disorder, and/or disease related to PNPLA3 expanded repeats an oligonucleotide or composition of any one of the preceding embodiments.

431. A method, comprising administering to a subject suffering from or susceptible to a condition, disorder, and/or disease related to ApoC3 expanded repeats an oligonucleotide or composition of any one of the preceding embodiments.

EXEMPLIFICATION

Certain examples of provided technologies (compounds (oligonucleotides, reagents, etc.), compositions, methods (methods of preparation, use, assessment, etc.)) were presented below.

Various technologies for preparing oligonucleotides and oligonucleotide compositions (both stereorandom and chirally controlled) are known and can be utilized in accordance with the present disclosure, including, for example, those in WO/2010/064146, WO/2011/005761, WO/2013/012758, WO/2014/010250, US2013/0178612, WO/2014/012081, WO/2015/107425, WO/2017/015555, and WO/2017/062862, the methods and reagents of each of which are incorporated herein by reference.

Example 1

Conjugation of Oligonucleotides

In some embodiments, the present disclosure provides methods for conjugation of oligonucleotides, for example, for better delivery to CNS. Examples 1 and 2 show conjugation of oligonucleotides for CNS delivery.

In some embodiments, provided oligonucleotides comprise chemical moieties connected to the 5'-end optionally through linker moieties. In some embodiments, provided oligonucleotides comprises chemical moieties connected to the 5'-end —OH optionally through a linker. In some embodiments, the present disclosure provides the following 5' cConjugation strategies:

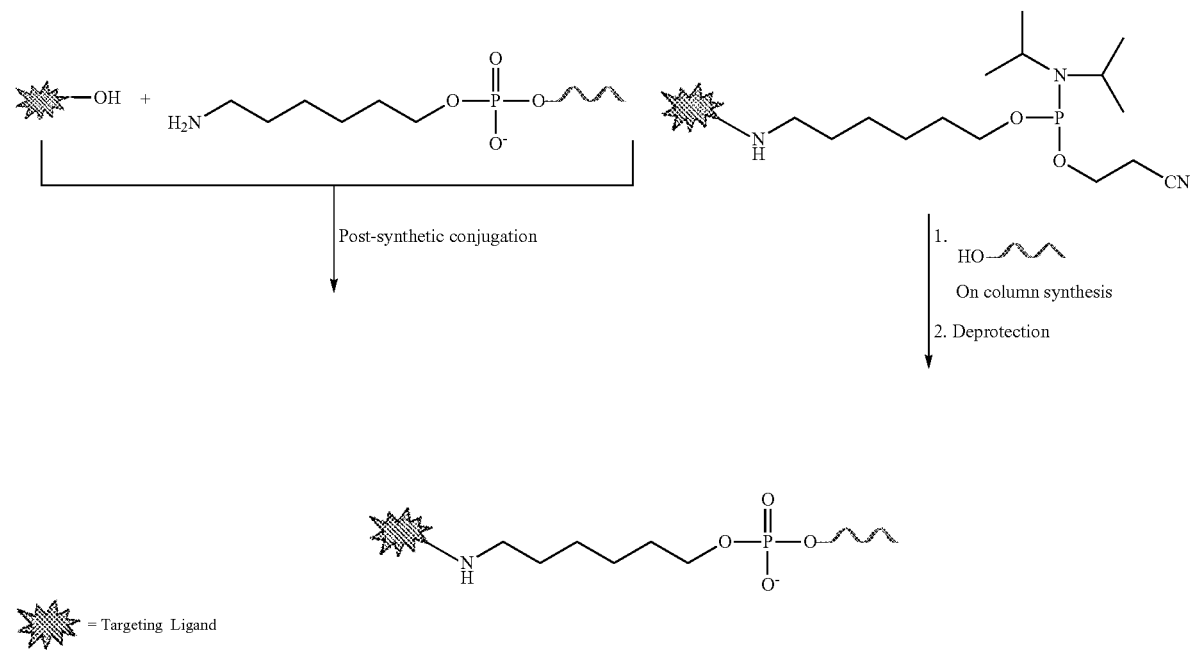

In some embodiments, provided oligonucleotides comprise chemical moieties connected to the 5'-end optionally through linker moieties. In some embodiments, the present disclosure provides the following 3' cConjugation strategies:

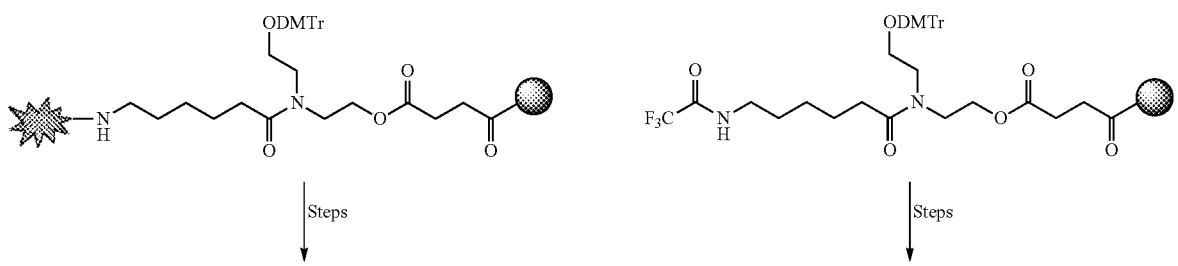

447 448
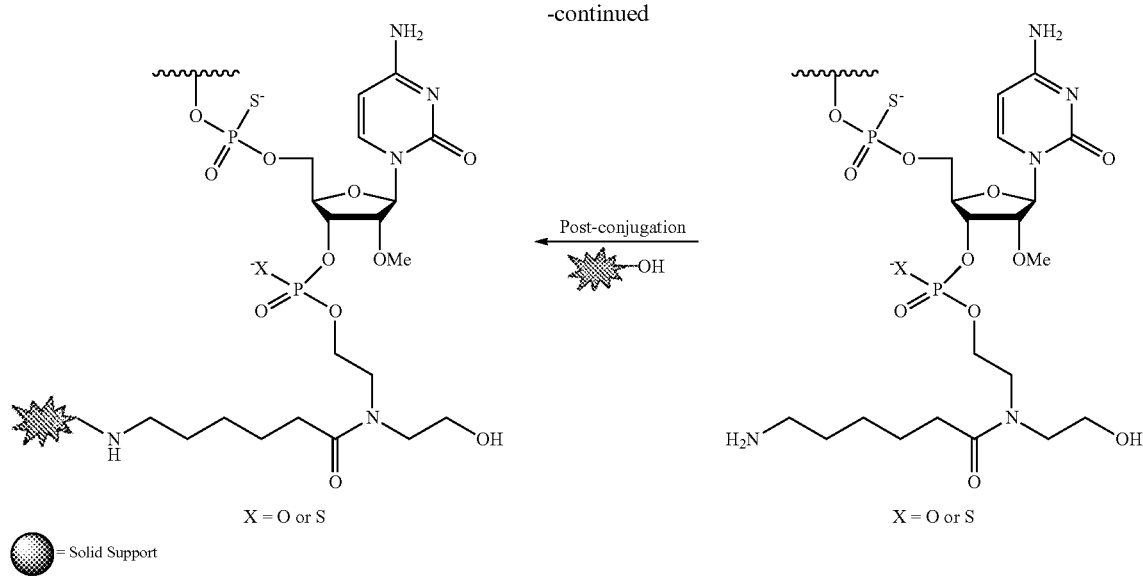
Various chemical moieties, e.g., ligand for cell receptors, can be utilized in accordance with the present disclosure, for example, those described in Juliano et al., J. Am. Chem. Soc. 2010, 132, 8848; Banerjee R et al., Int J Cancer. 2004, 112, 693; J. Med. Chem., 2017, 60 (10), pp 4161-4172; etc. In some embodiments, a chemical moiety is selected from:
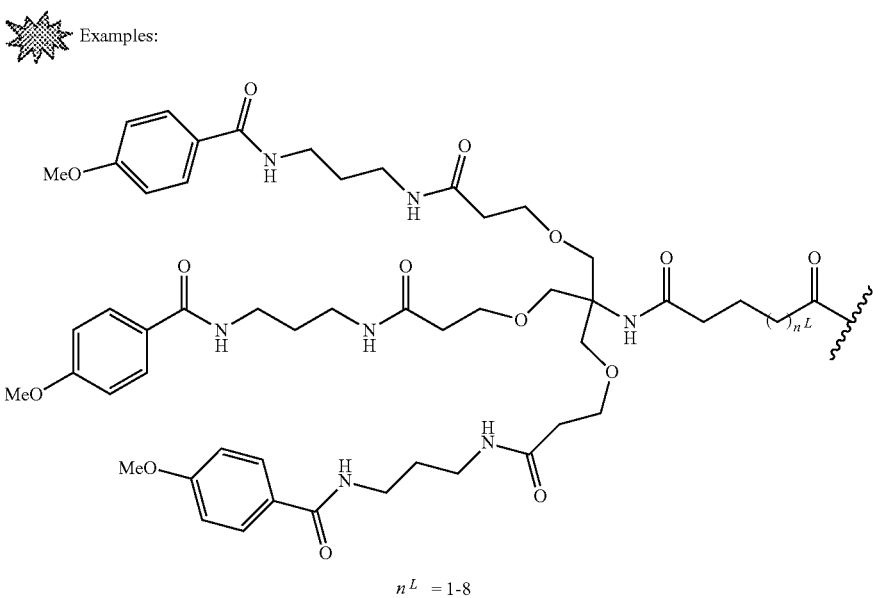
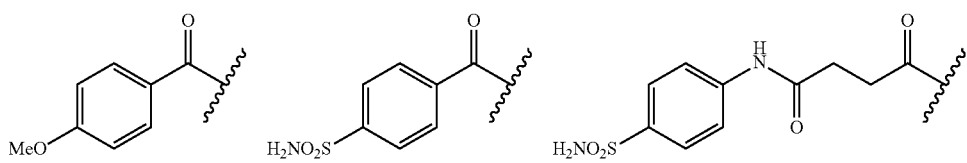

-continued
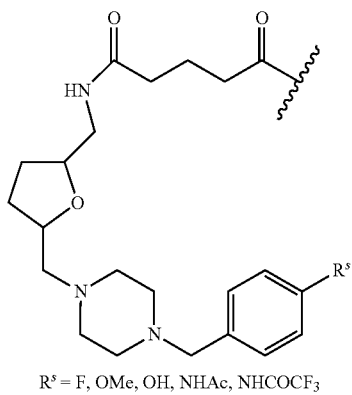
$R^s$ = F, OMe, OH, NHAc, NHCOCF$_3$
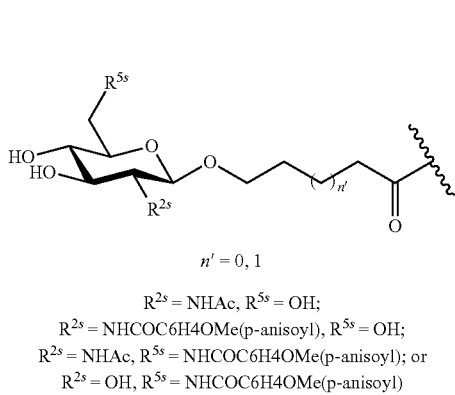
$n^t$ = 0, 1
$R^{2s}$ = NHAc, $R^{5s}$ = OH;
$R^{2s}$ = NHCOC6H4OMe(p-anisoyl), $R^{5s}$ = OH;
$R^{2s}$ = NHAc, $R^{5s}$ = NHCOC6H4OMe(p-anisoyl); or
$R^{2s}$ = OH, $R^{5s}$ = NHCOC6H4OMe(p-anisoyl)
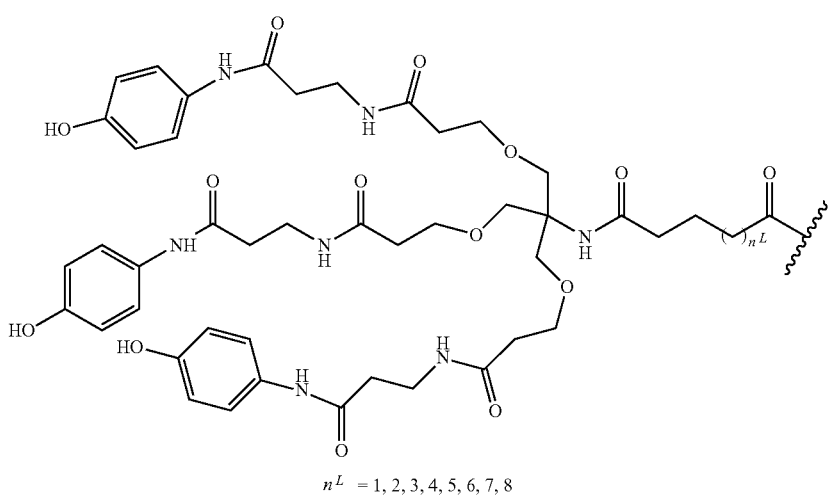
$n^L$ = 1, 2, 3, 4, 5, 6, 7, 8
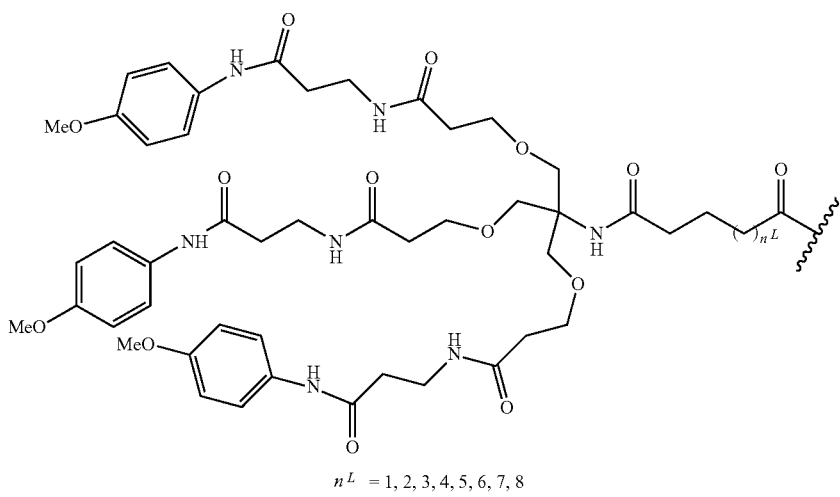
$n^L$ = 1, 2, 3, 4, 5, 6, 7, 8

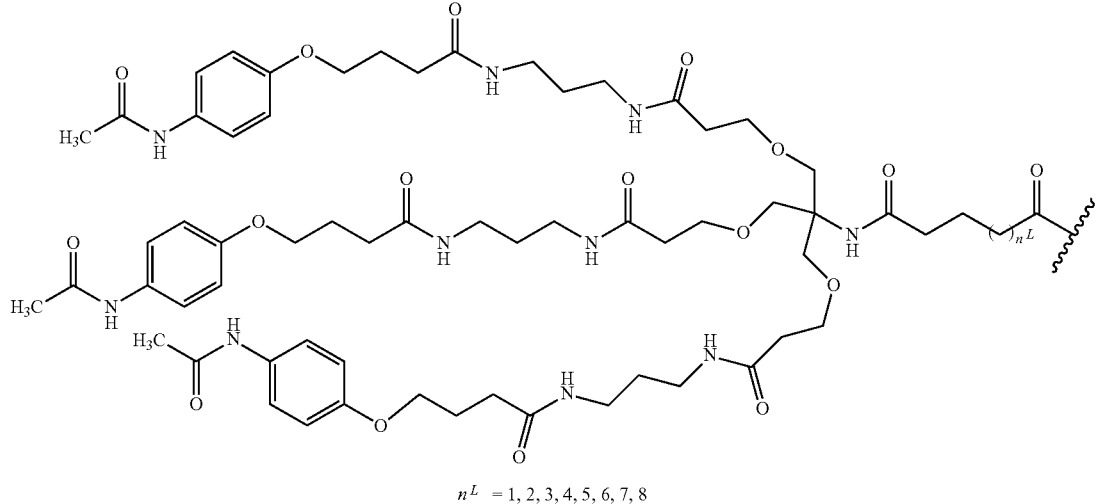
$n^L$ = 1, 2, 3, 4, 5, 6, 7, 8
Conjugates of Various Oligonucleotides
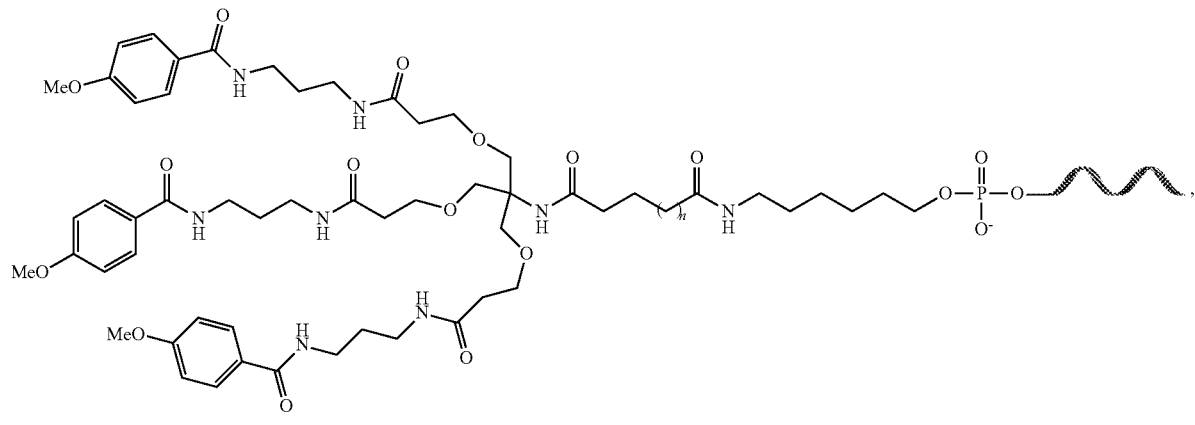
n = 1-8
WV-9063 (C9orf72, intron), WV-9381 (C9orf72, intron), WV-7560 (Malat1), WV-8447 (exon 1a),
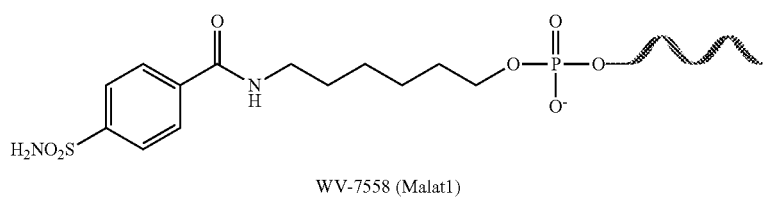
WV-7558 (Malat1)
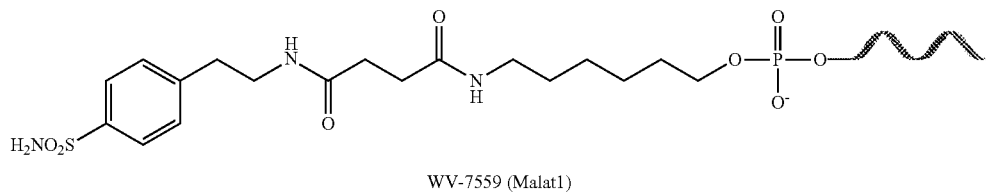
WV-7559 (Malat1)

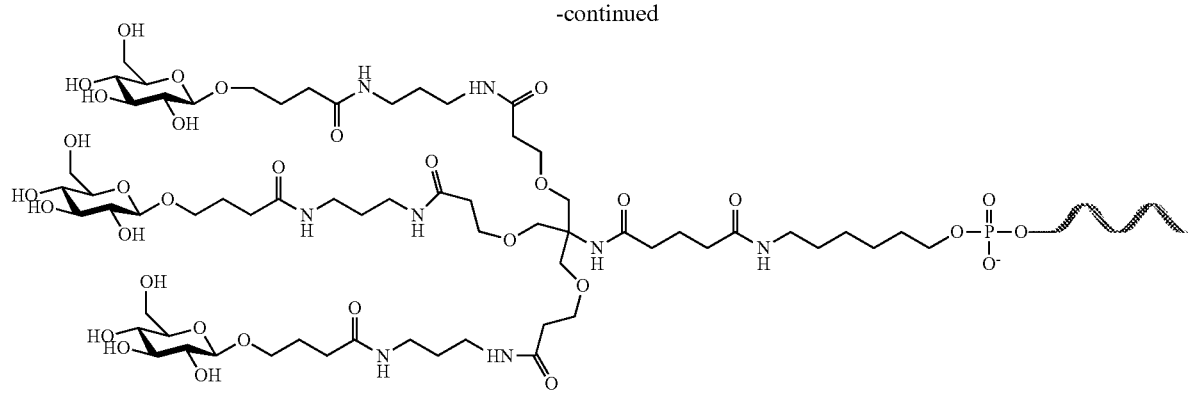
WV-8448 (Malat1), WV-8446 (exon 1a)
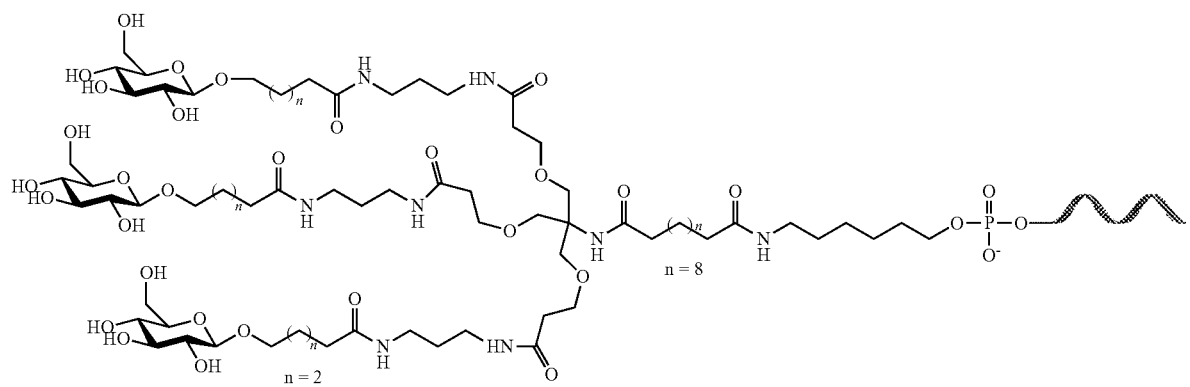
WV-8896 (Malat1), WV-8445 (exon 1a)
Synthesis of 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic acid
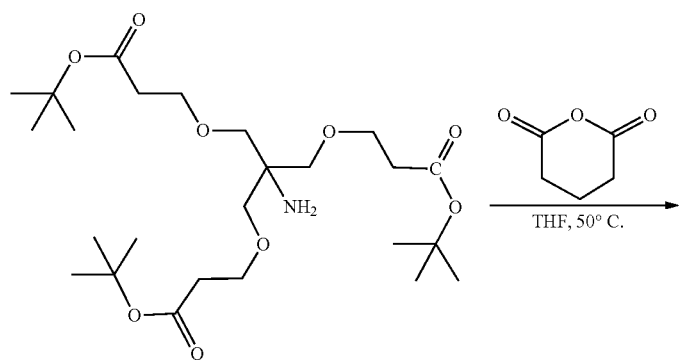

-continued
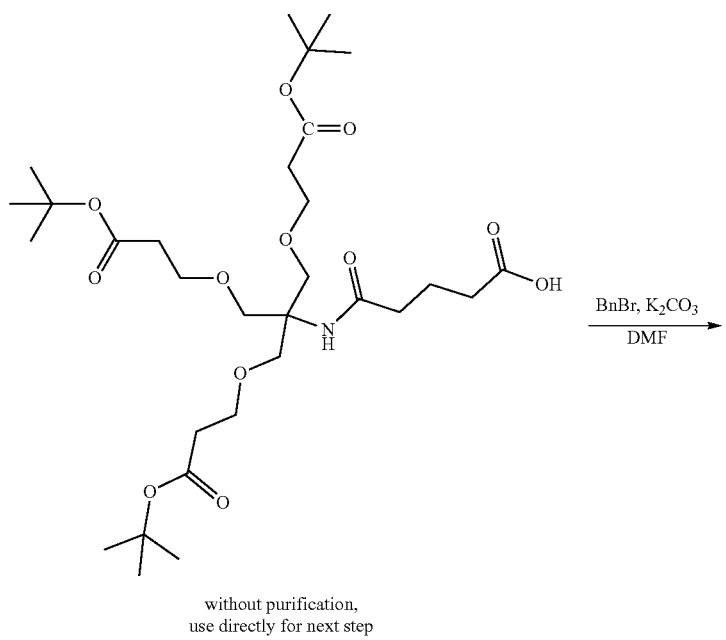
without purification,
use directly for next step
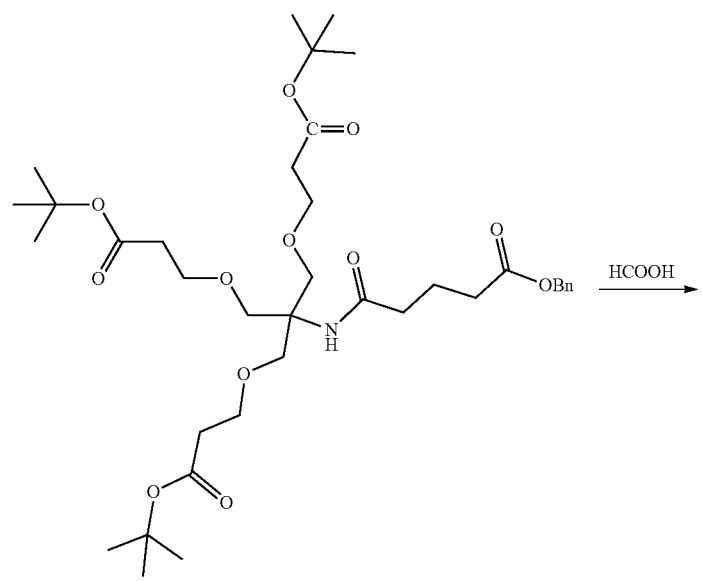
97% over 2 steps
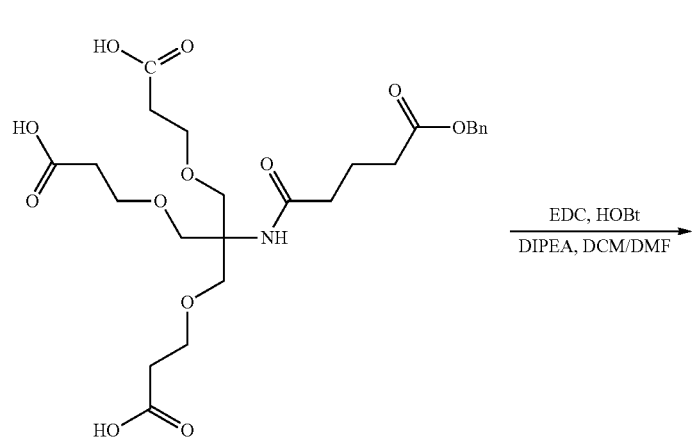

457
-continued
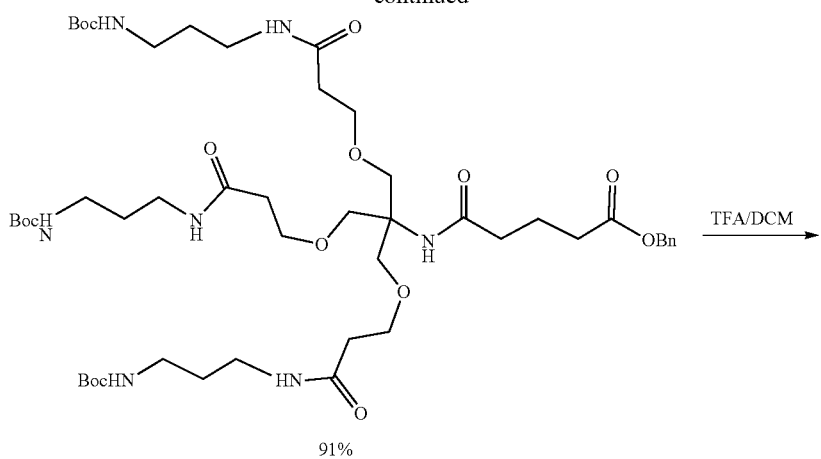
91%
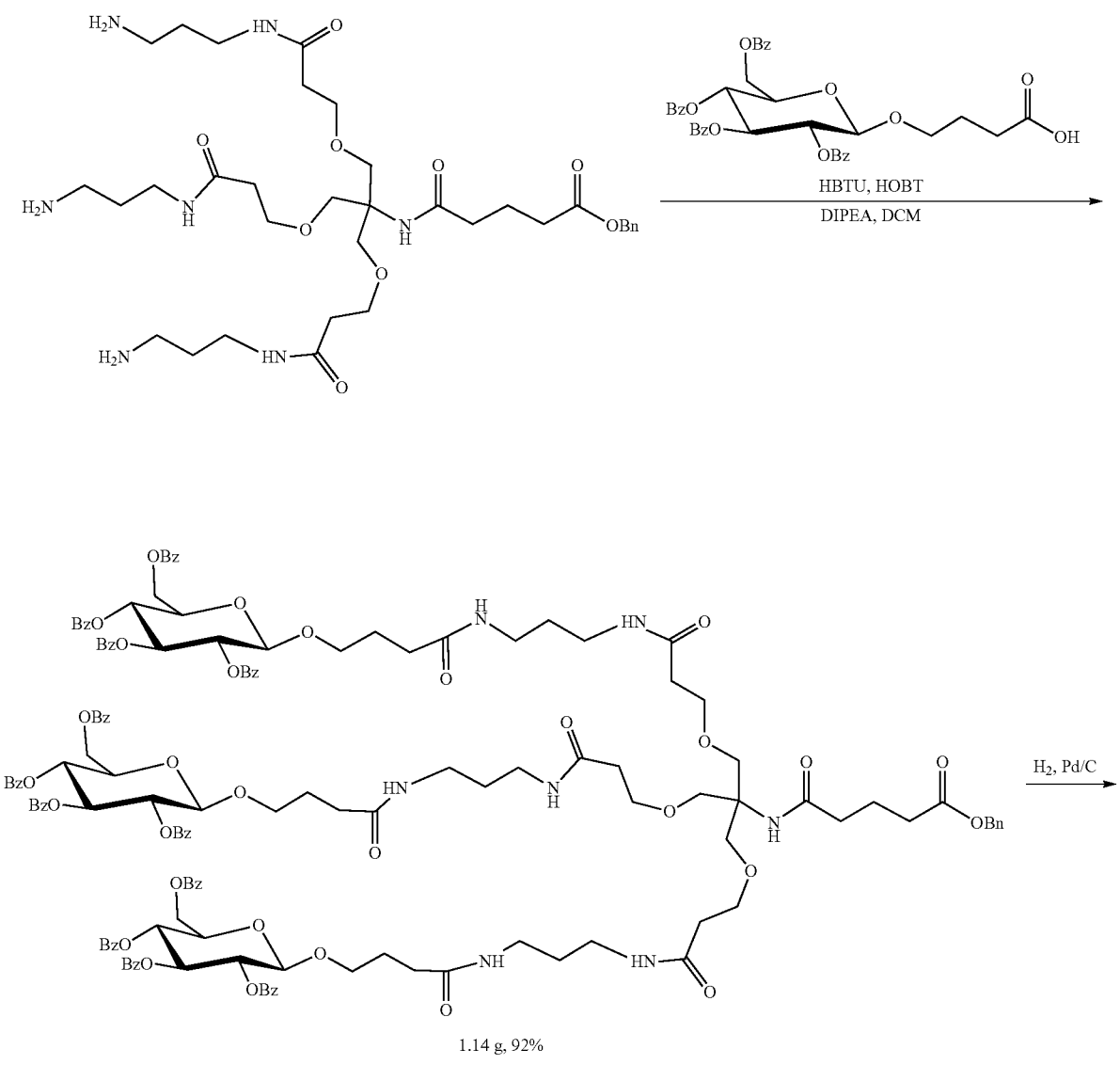
1.14 g, 92%

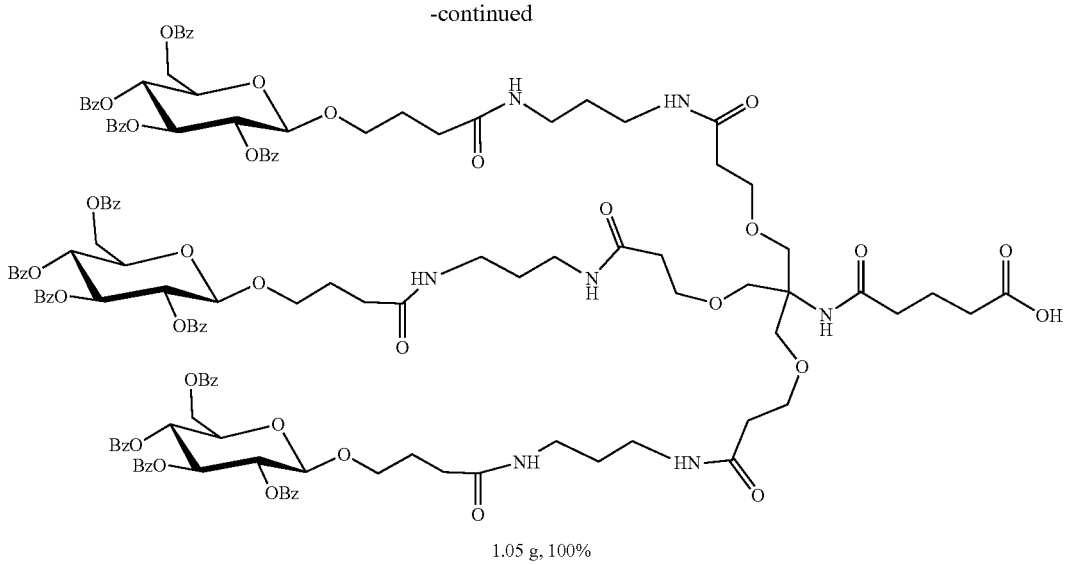

1.05 g, 100%

Step 1: A solution of di-tert-butyl 3,3'-((2-amino-2-((3-(tert-butoxy)-3-oxopropoxy)methyl)propane-1,3-diyl)bis(oxy))dipropanoate 1 (4.0 g, 7.91 mmol) and dihydro-2H-pyran-2,6(3H)-dione (0.903 g, 7.91 mmol) in THF (40 mL) was stirred at 50° C. for 3 hrs and at rt for 3 hrs. LC-MS showed desired product. Solvent was evaporated to give acid 2, which was directly used for next step without purification.

Step 2: To a solution of 5-((9-((3-(tert-butoxy)-3-oxopropoxy)methyl)-2,2,16,16-tetramethyl-4,14-dioxo-3,7,11,15-tetraoxaheptadecan-9-yl)amino)-5-oxopentanoic acid 2 (4.90 g, 7.91 mmol) and (bromomethyl)benzene (1.623 g, 9.49 mmol) in DMF was added anhydrous $K_2CO_3$ (3.27 g, 23.73 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO eluting with 10% EtOAc in hexane to 50% EtOAc in hexane to give di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate 3 (5.43 g, 7.65 mmol, 97% yield) as a colorless oil. $^1$H NMR (400 MHz, Chloroform-d) δ 7.36-7.28 (m, 5H), 6.10 (s, 1H), 5.12 (s, 2H), 3.70 (s, 6H), 3.64 (t, J=8.0 Hz, 6H), 2.50-2.38 (m, 8H), 2.22 (t, J=7.3 Hz, 2H), 1.95 (p, J=7.4 Hz, 2H), 1.45 (s, 27H); MS, 710.5 (M+H)$^+$.

Step 3: A solution of di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate 3 (5.43 g, 7.65 mmol) in formic acid (50 mL) was stirred at room temperature for 48 hrs. LC-MS showed the reaction was not complete. Solvent was evaporated under reduced pressure. The crude product was re-dissolved in formic acid (50 mL) and was stirred at room temperature for 6 hrs. LC-MS showed the reaction was complete. Solvent was evaporated under reduced pressure, co-evaporated with toluene (3×) under reduced pressure, and dried under vacuum to give 3,3'-((2-(5-(benzyloxy)-5-oxopentanamido)-2-((2-carboxyethoxy)methyl)propane-1,3-diyl)bis(oxy))dipropanoic acid 4 (4.22 g, 7.79 mmol, 102% yield) as a white solid. $^1$H NMR (500 MHz, DMSO-d$_6$) δ 12.11 (s, 3H), 7.41-7.27 (m, 5H), 6.97 (s, 1H), 5.07 (s, 2H), 3.55 (t, J=6.4 Hz, 6H), 3.53 (s, 6H), 2.40 (t, J=6.3 Hz, 6H), 2.37-2.26 (m, 2H), 2.08 (t, J=7.3 Hz, 2H), 1.70 (p, J=7.4 Hz, 2H); MS, 542.3 (M+H)$^+$.

Step 4: A solution of 3,3'-((2-(5-(benzyloxy)-5-oxopentanamido)-2-((2-carboxyethoxy)methyl)propane-1,3-diyl)bis(oxy))dipropanoic acid 4 (4.10 g, 7.57 mmol) and HOBt (4.60 g, 34.1 mmol) in DCM (60 mL) and DMF (15 mL) at 0° C. was added tert-butyl (3-aminopropyl)carbamate (5.94 g, 34.1 mmol), EDAC HCl salt (6.53 g, 34.1 mmol) and DIPEA (10.55 ml, 60.6 mmol). The reaction mixture was stirred at 0° C. for 15 minutes and at room temperature for 20 hrs. LC-MS showed the reaction was not complete. EDAC HCl salt (2.0 g) and tert-butyl (3-aminopropyl)carbamate (1.0 g) was added into the reaction mixture. The reaction mixture was stirred at room temperature for 4 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate 5 (6.99 g, 6.92 mmol, 91% yield) as a white solid. $^1$H NMR (500 MHz, Chloroform-d) δ 7.38-7.33 (m, 5H), 6.89 (brs, 3H), 6.44 (s, 1H), 5.23 (brs, 3H), 5.12 (s, 2H), 3.71-3.62 (m, 12H), 3.29 (q, J=6.2 Hz, 6H), 3.14 (q, J=6.5 Hz, 6H), 2.43 (dt, J=27.0, 6.7 Hz, 8H), 2.24 (t, J=7.2 Hz, 2H), 1.96 (p, J=7.5 Hz, 2H), 1.64-1.59 (m, 6H), 1.43 (d, J=5.8 Hz, 27H); MS (ESI): 1011.5 (M+H)+.

Step 5: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (0.326 g, 0.46 mmol) in DCM (5 mL) was added TFA (2 mL). The reaction mixture was stirred at room temperature for 4 hrs. LC-MS showed the reaction was completed. Solvent was evaporated under reduced pressure to give benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. Directly use for next step without purification.

Step 6: To a solution of 5-(((2R,3R,4R,5R,6R)-3-acetamido-4,5-diacetoxy-6-(acetoxymethyl)tetrahydro-2H-pyran-2-yl)oxy)pentanoic acid (1.10 g, 1.61 mmol), HBTU (0.558 g, 1.47 mmol), HOBT (0.062 g, 0.46 mmol) and DIPEA (1.2 mL, 6.9 mmol) in DCM (6 mL) followed by benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate in acetonitrile (5 mL). The mixture was stirred at room temperature for 3 hrs. Solvent was evaporated under reduced pressure to give a residue, which was purified by ISCO (40 g gold column) eluting with DCM to 20% MeOH in DCM to give 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic benzyl ester (1.14 g, 92% yield) as a white solid. MS (ESI): 1353.7 (M/2+H)+.

Step 7: To a solution of 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic benzyl ester (1.09 g, 0.400 mmol) in EtOAc (50 mL) was added 10% Pd—C (200 mg) and methanol (2 mL). The reaction mixture was stirred at room temperature for 3 hrs. LC-MS showed the reaction was complete, diluted with EtOAc, and filtered through celite, washed with 20% MeOH in EtOAc, concentrated under reduced pressure to give 4,10,17-trioxo-15,15-bis((3-oxo-3-((3-(4-(((2R,3R,4S,5R,6R)-3,4,5-tris(benzoyloxy)-6-((benzoyloxy)methyl)tetrahydro-2H-pyran-2-yl)oxy)butanamido)propyl)amino)propoxy)methyl)-1-(((2R,3R,4S,5R,6R)-3,4,5-tris(benzoyloxy)-6-((benzoyloxy)methyl)tetrahydro-2H-pyran-2-yl)oxy)-13-oxa-5,9,16-triazahenicosan-21-oic acid (1.06 g, 100%) as a white solid. MS (ESI): 1308.1 (M+H)+.

Example 2

Synthesis of 4-oxo-4-((4-sulfamoylphenethyl)amino)butanoic acid

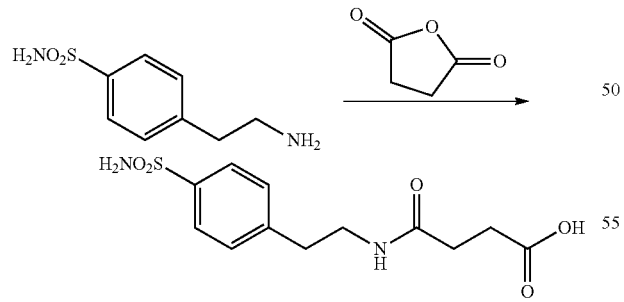

To solid reagents 4-(2-aminoethyl)benzenesulfonamide (2.00 g, 9.99 mmol) and dihydrofuran-2,5-dione (0.999 g, 9.99 mmol) was added THF (30 mL). The reaction mixture was stirred at 60° C. for 7 hrs. Solvent was evaporated under reduced pressure to give 4-oxo-4-((4-sulfamoylphenethyl)amino)butanoic acid (3.00 g, 9.99 mmol, 100% yield) as a white solid. $^1$H NMR (400 MHz, DMSO-d6) δ 12.09 (s, 1H), 7.96 (t, J=5.6 Hz, 1H), 7.72 (d, J=8.1 Hz, 2H), 7.38 (d, J=8.1 Hz, 2H), 7.29 (s, 2H), 3.26 (q, J=6.8 Hz, 2H), 2.76 (t, J=7.2 Hz, 2H), 2.40 (t, J=6.9 Hz, 2H), 2.27 (t, J=6.9 Hz, 2H); MS (ESI), 301.1 (M+H)+.

General Procedure for Conjugation of Sulfonamides with WV-7557 (Synthesis of WV-7558 and 7559)

Procedure: Synthesis of WV-7558 and WV-7559 follows same procedure as described below. To a solution of sulfonamide (5 equivalents), in 2 ml DMF was added HATU (4.5 equivalents) and DIPEA (25 equivalents). This mixture was stirred well for 2 minutes (Scheme 1 and 2).

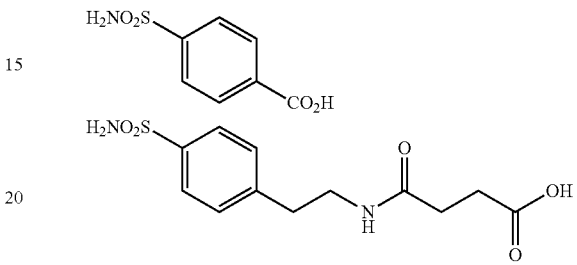

To this solution was added, a solution of WV-7557 (1 equivalent) in water and shaken well for 60 minutes. The solvent was removed under vacuum and crude product was purified by RP column (C18) chromatography to obtain the product. The purified product was desalted over a C-18 cartridge using sodium acetate solution.

Synthesis of WV-7558: Following the general procedure outlined above, 4-sulfamoyl benzoic acid (11 mg, 54.5 μmol), HATU (18.6 mg, 49 μmol) and DIPEA (35 mg, 272 μmol) were stirred for 2 minutes in 2 ml DMF (Scheme 1). This activated HATU intermediate was added into a solution of WV-7557 (75 mg, 10.9 μmol) in 0.75 ml water. The reaction vial was shaken for 60 minutes. Solvent was removed under reduced pressure, purification and desalting was performed as described above. Amount of product obtained is 20 mg. Molecular weight of the product calculated: 7063; Deconvoluted mass obtained: 7065

Scheme 1

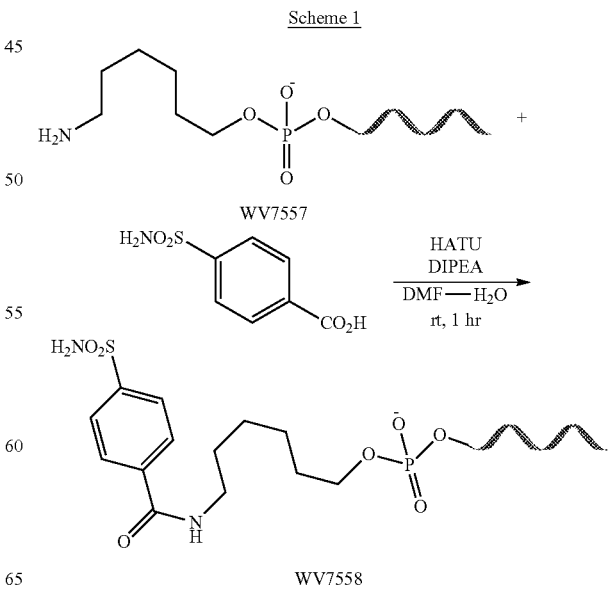

Synthesis of WV-7559: Following the general procedure outlined above, 4-sulfamoyl benzoic acid (16.3 mg, 54.5 µmol), HATU (18.6 mg, 49 µmol) and DIPEA (35 mg, 272 µmol) were stirred for 2 minutes in 2 ml DMF (Scheme 2). This activated HATU intermediate was added into a solution of WV-7557 (75 mg, 10.9 µmol) in 0.75 ml water. The reaction vial was shaken for 60 minutes. Solvent was removed under reduced pressure, purification and desalting was performed as described above. Amount of product obtained is 13 mg. Molecular weight of the product calculated: 7162; Deconvoluted mass obtained: 7165.

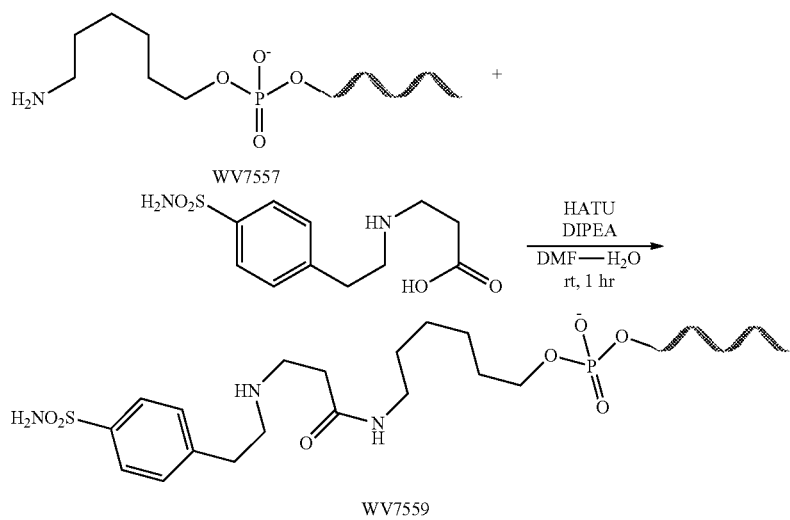

General Procedure for Conjugation of Tri Antennary Anisamide with WV-7557 and WV 8444: Synthesis of WV-7560 and WV 8447

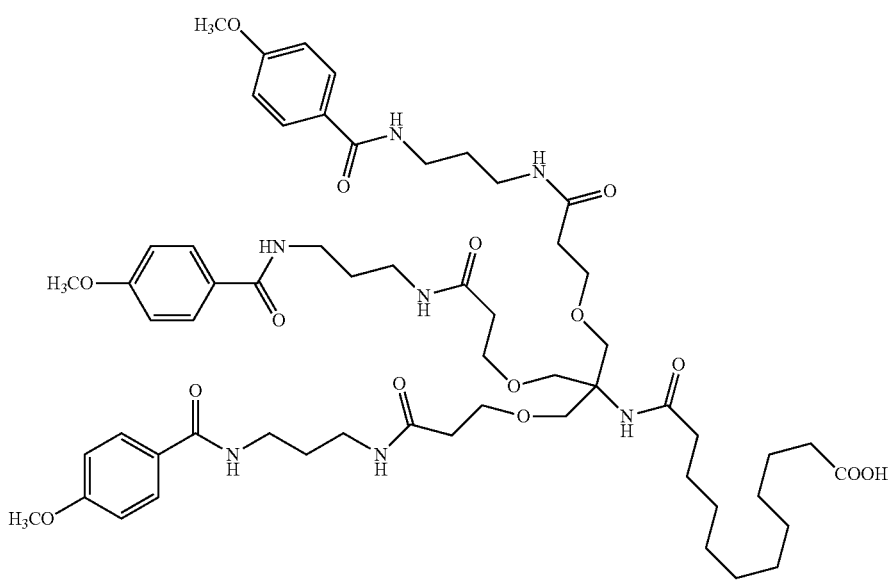 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCCCCCCCCC(=O)O)cc1]

General Procedure: To a solution of triantennary anisamide (2 equivalents), in 2 ml DMF was added HATU (1.8 equivalents) and DIPEA (10 equivalents). This mixture was stirred well for 2 minutes. To this solution was added a solution of WV-7557 (1 equivalent) in water and shaken well for 60 minutes. The solvent was removed under vacuum and crude product was purified by RP column (C8) chromatography to obtain the product. The purified product was desalted over a C-18 cartridge using sodium acetate solution.

Synthesis of WV-7560: To a solution of triantennary anisamide (11 mg, 9.8 μmol), in 2 ml DMF was added HATU (3.34 mg, 8.82 μmol) and DIPEA (6.3 mg, 9 μl, 49 μmol). This mixture was stirred well for 2 minutes (Scheme 3). To this solution was added a solution of WV-7557 (33.7 mg, 4.9 mol) in 0.88 ml water and shaken well for 60 minutes. The solvent was removed under vacuum and crude product was purified by RP column (C8) chromatography to obtain the product WV-7560 (25 mg). The purified product was desalted over a C-18 cartridge using sodium acetate solution. Molecular weight of product calculated: 7982; De-convoluted mass obtained: 7987.

Scheme 3

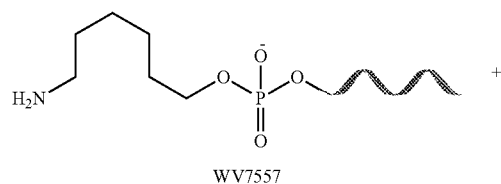

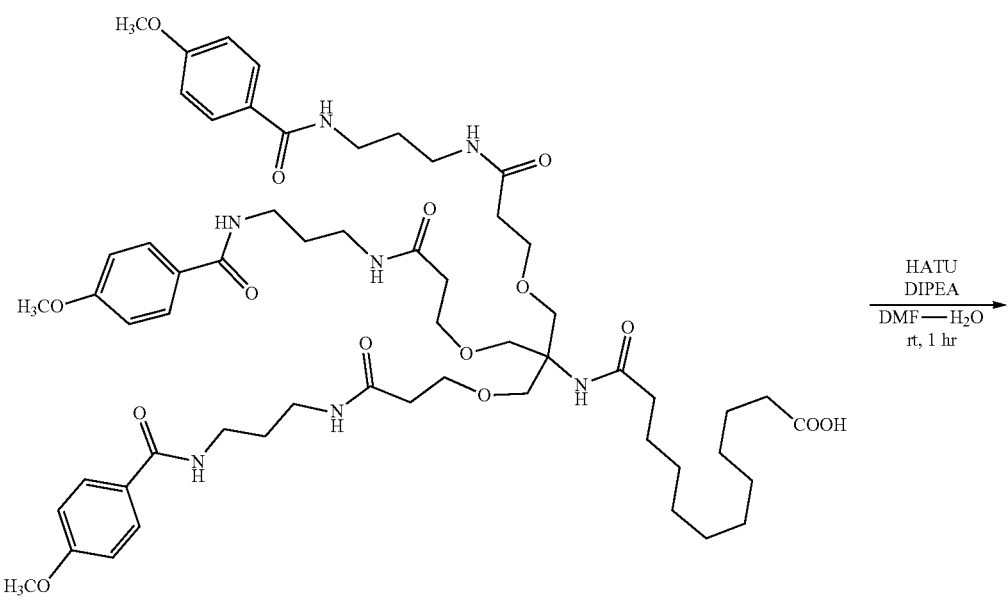

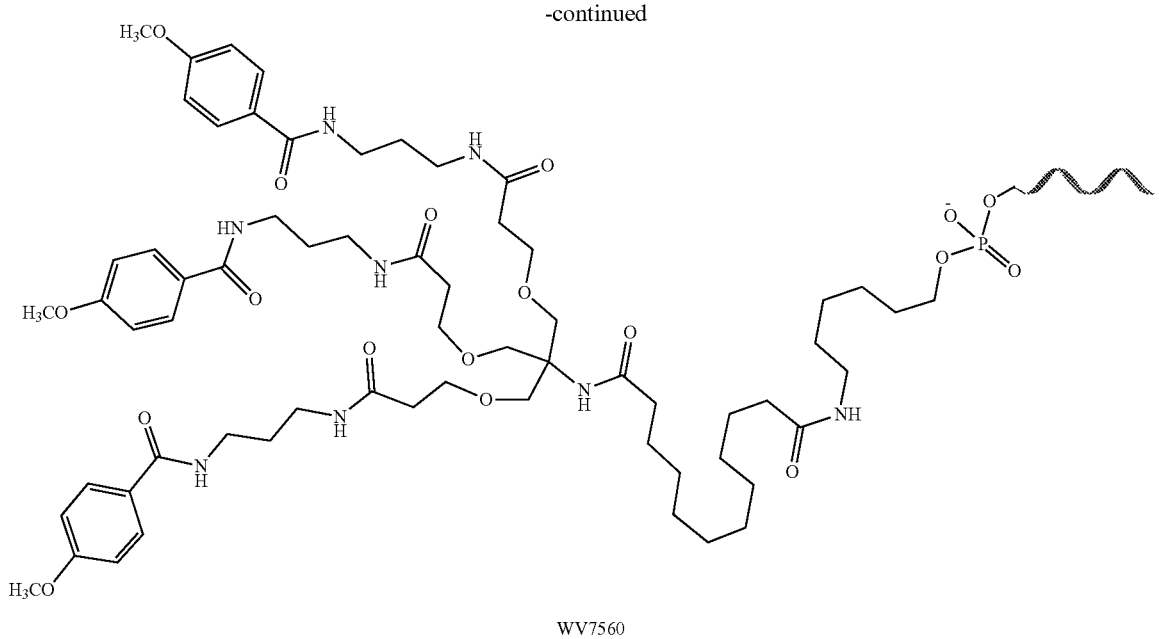

WV7560

Synthesis of WV-8447: To a solution of triantennary anisamide (13 mg, 11.6 μmol), in 2 ml DMF was added HATU (4 mg, 10.4 μmol) and DIPEA (7.5 mg, 10.3 μl, 58 μmol). This mixture was stirred well for 2 minutes (Scheme 4). To this solution was added a solution of WV-8444 (40 mg, 5.8 mol) in 1 ml water and shaken well for 60 minutes. The solvent was removed under vacuum and the crude product was purified by RP column (C8) chromatography to obtain the product WV-8447. The purified product was desalted over a C-18 cartridge using sodium acetate solution. Molecular weight of product calculated: 7970; Deconvoluted mass obtained: 7975.

Scheme 4

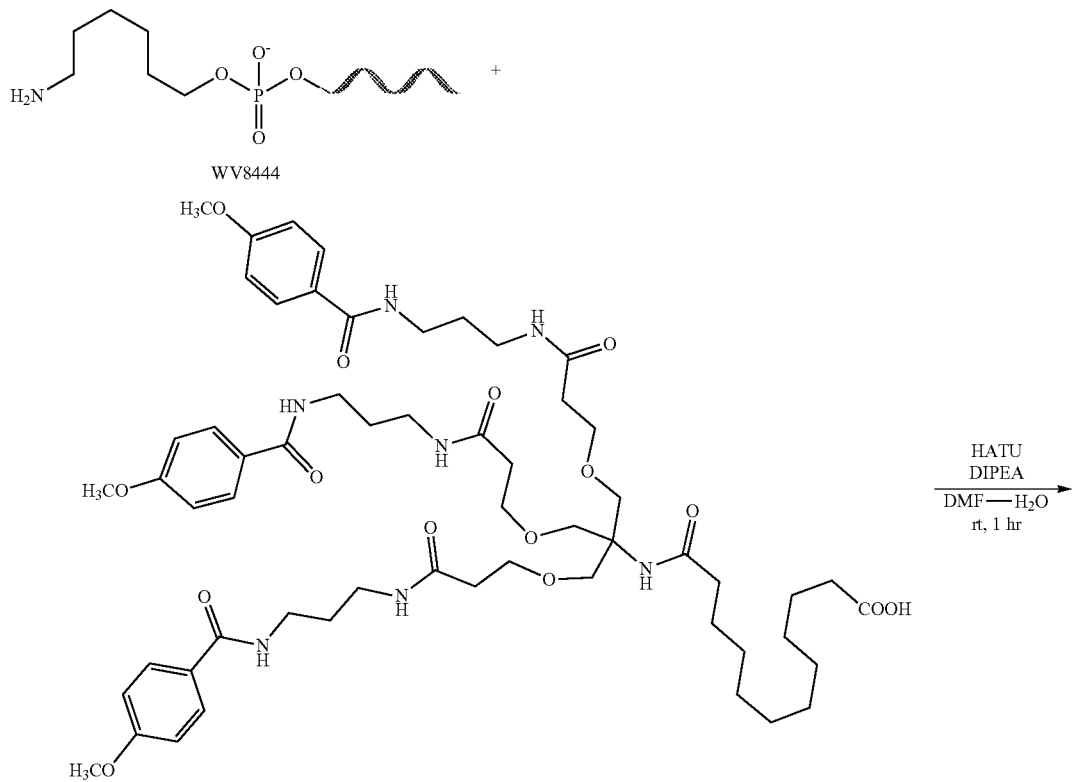

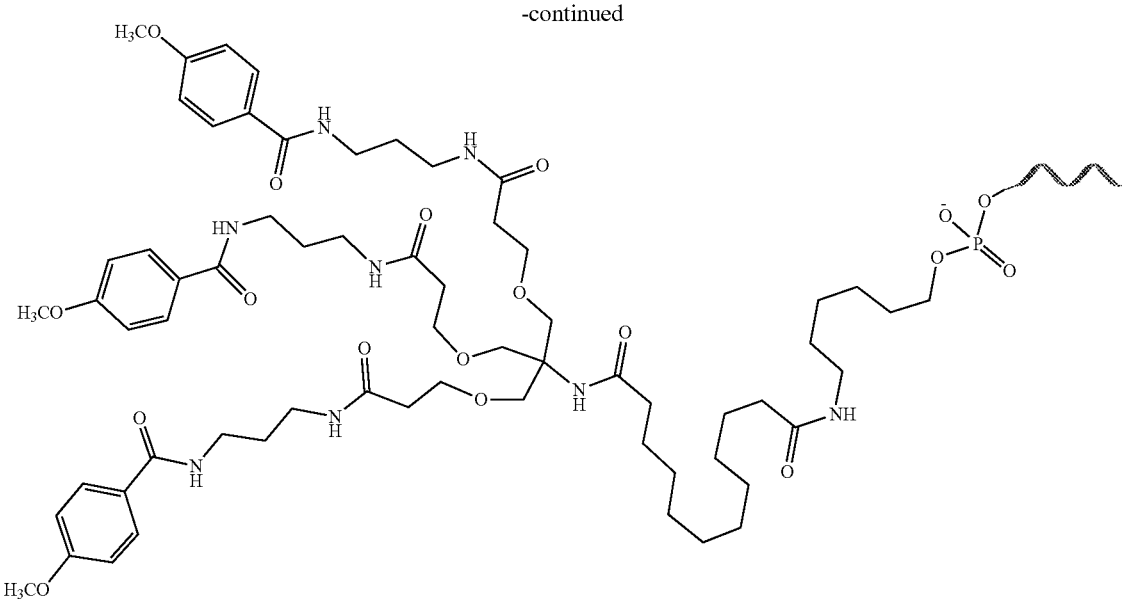

WV8447

General Procedure for Conjugation of Triantennary Glucosamine/Glucose Derivative with WV-7557 or WV-8444

To a solution of triantennary glucosamine or glucose derivative (2 equivalents), in 2 ml DMF was added HATU (1.8 equivalents) and DIPEA (10 equivalents). This mixture was stirred well for 2 minutes. To this solution was added a solution of WV-7557 or WV-8444 (1 equivalent) in water and shaken well for 60 minutes. The solvent was removed under vacuum and crude product was treated with 30% NH₄OH solution at room temperature for 24 hours. The solvent was removed under vacuum and the crude product was purified by RP column (C8) chromatography to obtain the product. The purified product was desalted over a C-18 cartridge using sodium acetate solution.

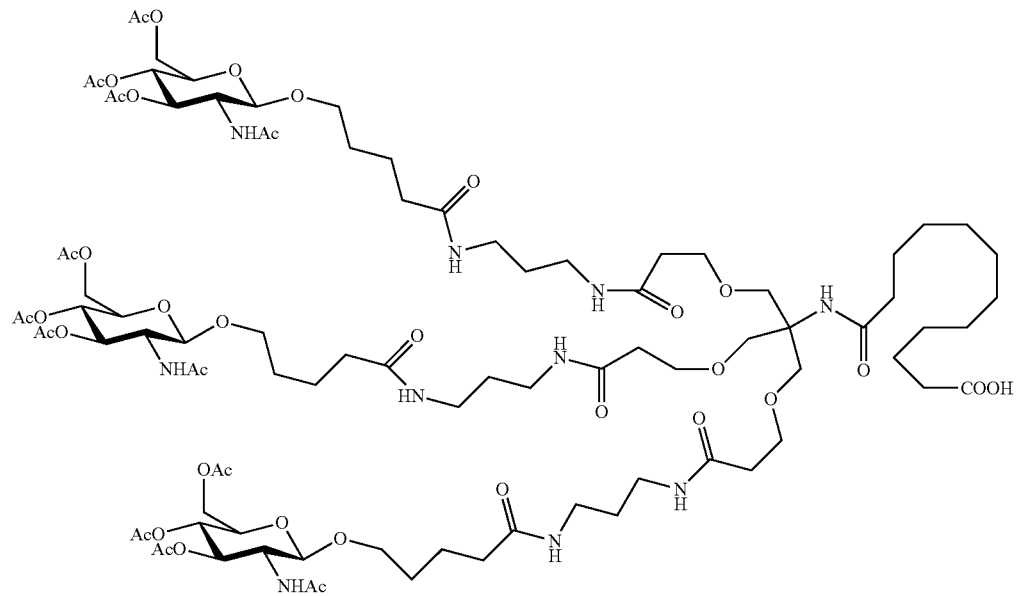

Triantennary Glucosamine Linker

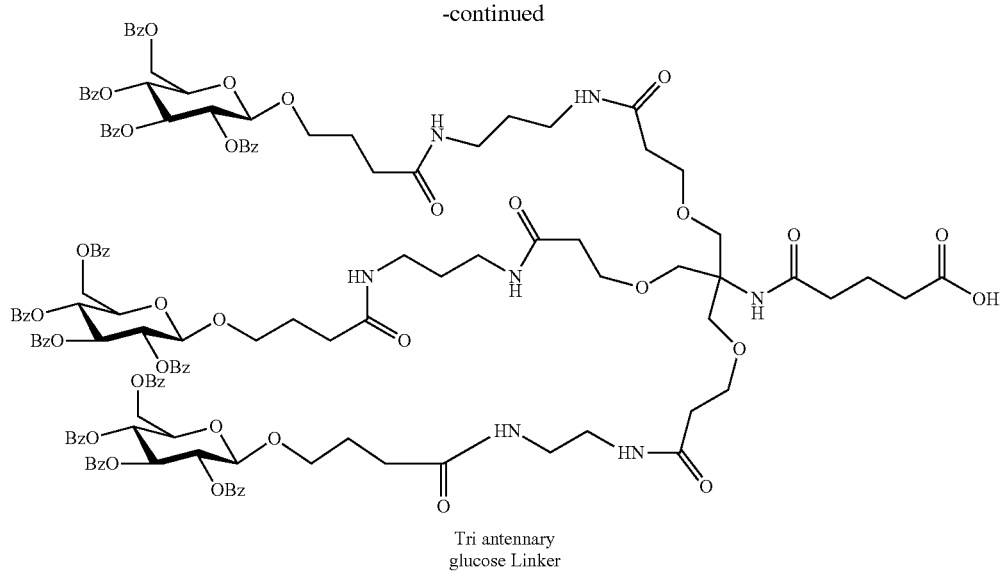

Tri antennary glucose Linker

Synthesis of WV-8896: Following the general procedure shown above, Glucosamine derivative (23.3 mg, 11.6 μmol), HATU (4 mg, 10.44 μmol) and DIPEA (7.5 mg, 58 μmol) was stirred in 2 ml DMF (Scheme 5). To this solution was added 40 mg (5.8 μmol) of WV-7557 in 1 ml water. Reaction mixture was stirred for 60 minutes to obtain the desired product. This product was treated with $NH_4OH$ as described above. Amount of product obtained is 20 mg. Molecular weight calculated: 8496; Deconvoluted mass obtained: 8494

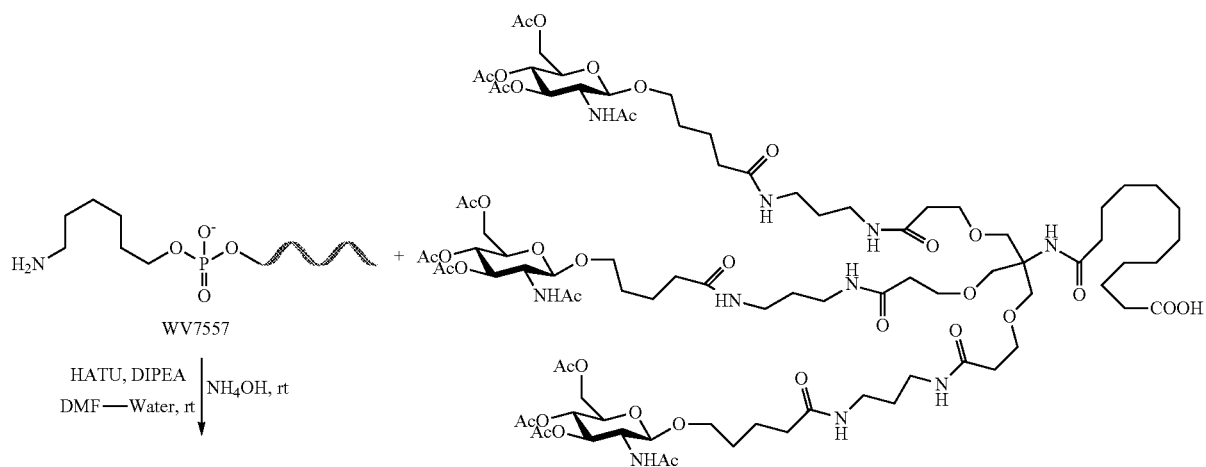

Scheme 5

-continued

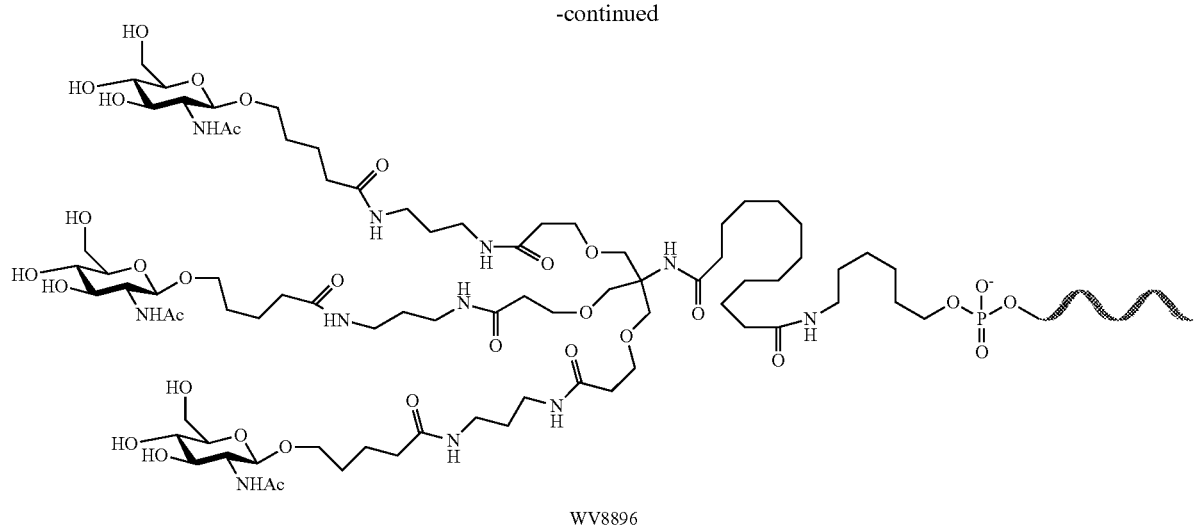

WV8896

Synthesis of WV-8448: Following the general procedure shown above, Glucose derivative (57 mg, 21.8 μmol), HATU (7.5 mg, 19.6 μmol) and DIPEA (14.6 mg, 109 μmol) was stirred in 2 ml DMF (Scheme 6). To this solution was added 75 mg (10.9 μmol) of WV-7557 in 1 ml water. Reaction mixture was stirred for 60 minutes to obtain the desired product. This product was heated at 40° C. with NH₄OH as described above to obtain the product. Molecular weight calculated: 8227; Deconvoluted mass obtained: 8233.

Scheme 6

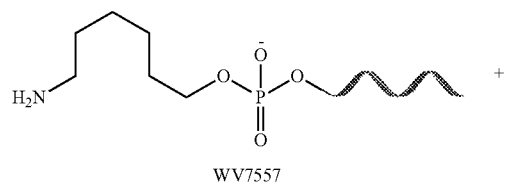

WV7557

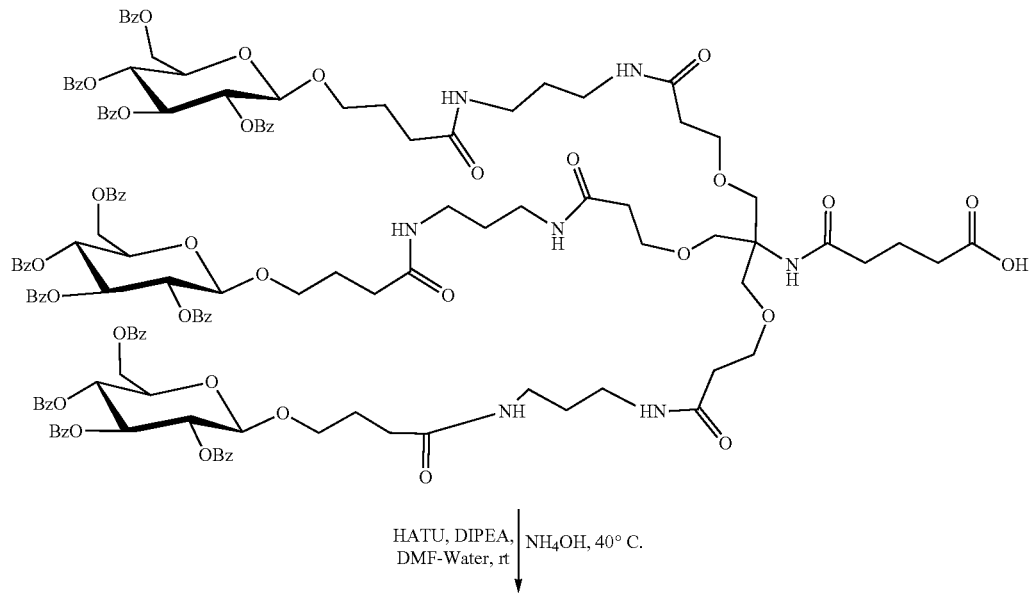

HATU, DIPEA, DMF-Water, rt | NH₄OH, 40° C.

-continued

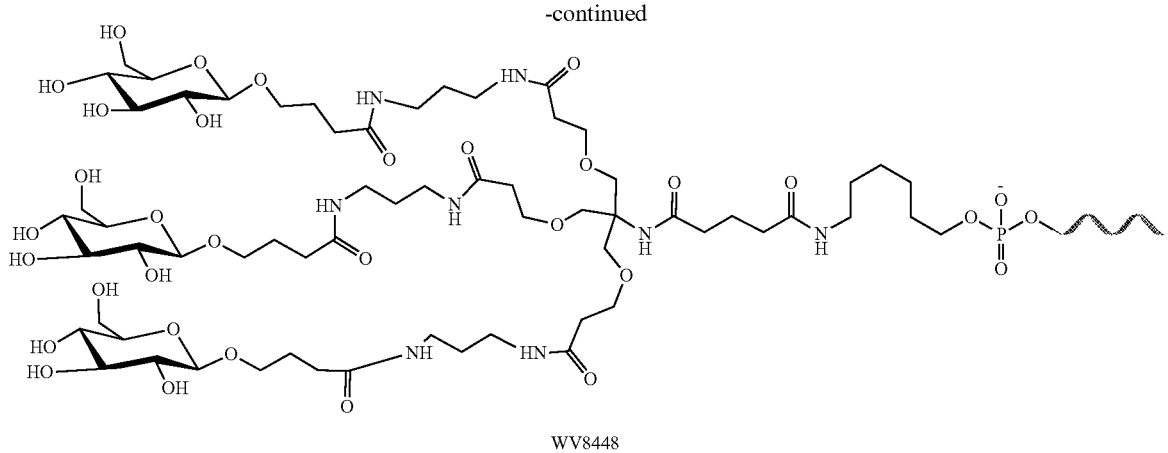

WV8448

Synthesis of WV-8446: Following the general procedure shown above, Glucose derivative (30 mg, 11.6 μmol), HATU (4 mg, 10.4 μmol) and DIPEA (7.5 mg, 58 μmol) was stirred in 2 ml DMF (Scheme 7). To this solution was added 40 mg (5.8 μmol) of WV-8444 in 1 ml water. Reaction mixture was stirred for 60 minutes to obtain the desired product. This product was heated at 40° C. with NH$_4$OH as described above to obtain the product. Molecular weight calculated: 8214; Deconvoluted mass obtained: 8218.

Scheme 7

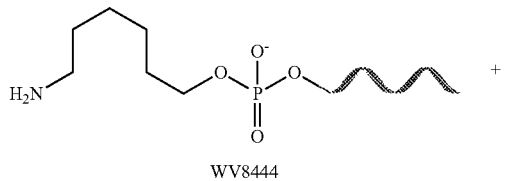

WV8444

+

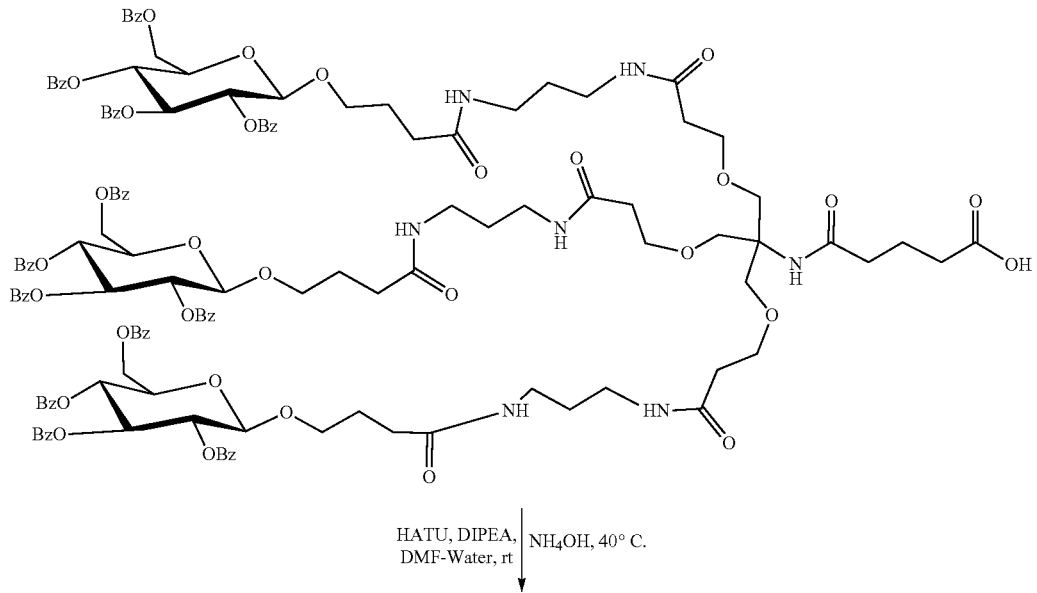

HATU, DIPEA, DMF-Water, rt | NH$_4$OH, 40° C.

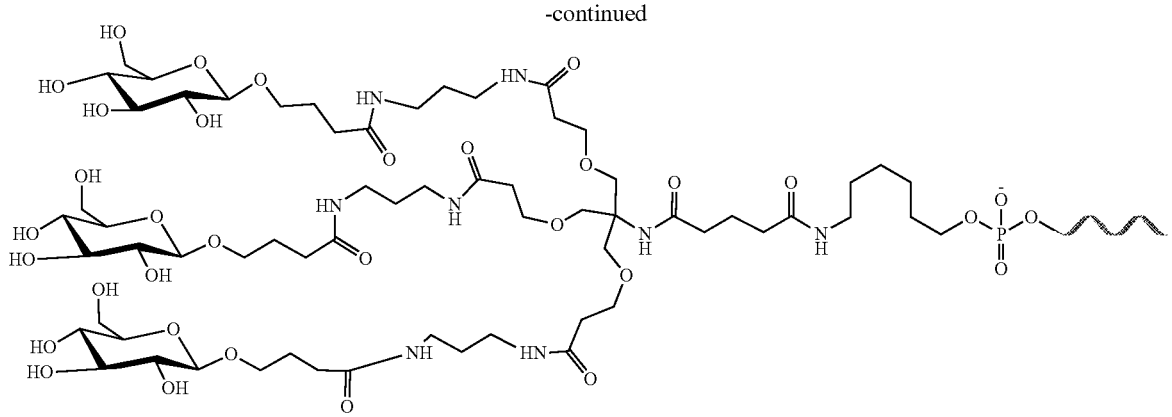

WV8446

Synthesis of WV-8445: Following the general procedure shown above, Glucosamine derivative (24 mg, 12 μmol), HATU (4 mg, 10.4 μmol) and DIPEA (7.5 mg, 58 μmol) was stirred in 2 ml DMF (Scheme 8). To this solution was added 40 mg (5.8 mol) of WV 8444 in 1 ml water. Reaction mixture was stirred for 60 minutes to obtain the desired product. This product was heated at 40° C. with $NH_4OH$ as described above to obtain the product. Molecular weight calculated: 8477; Deconvoluted mass obtained: 8484.

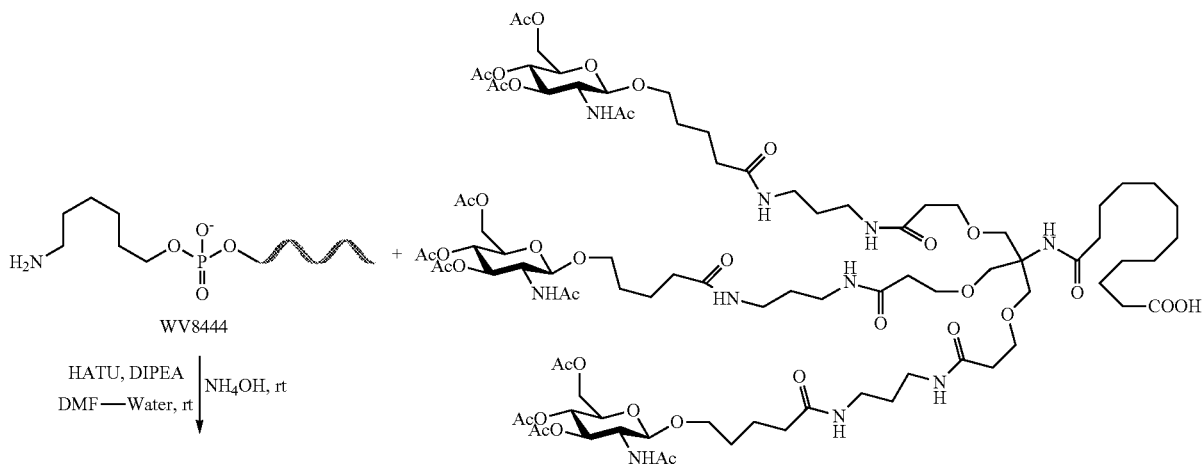

Scheme 8

-continued
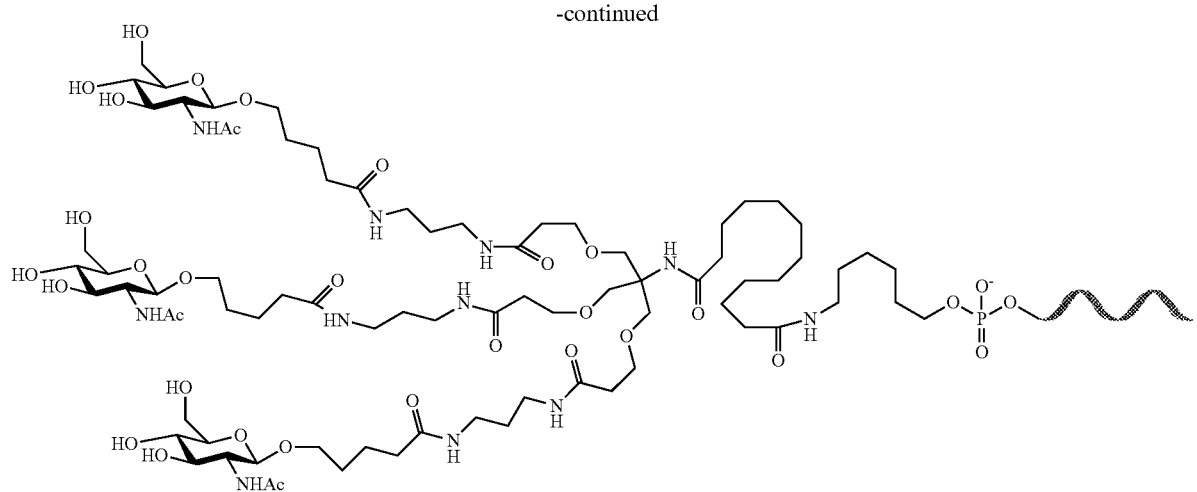
WV8445
Synthesis of GlucNAc Linker
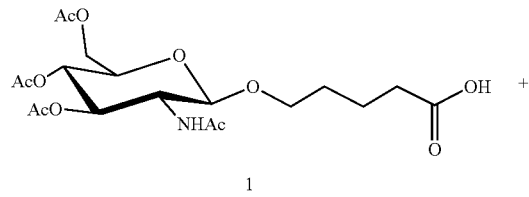
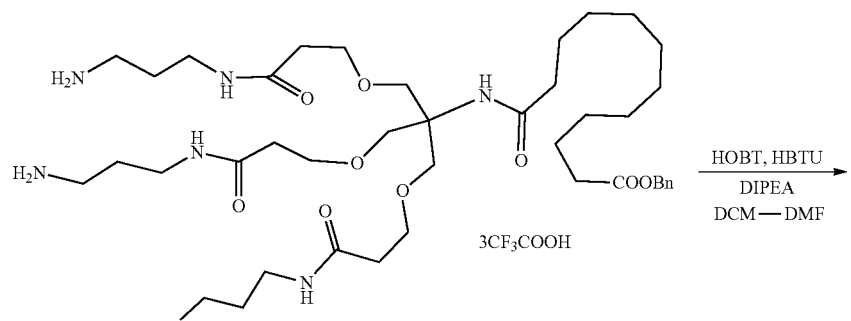

-continued

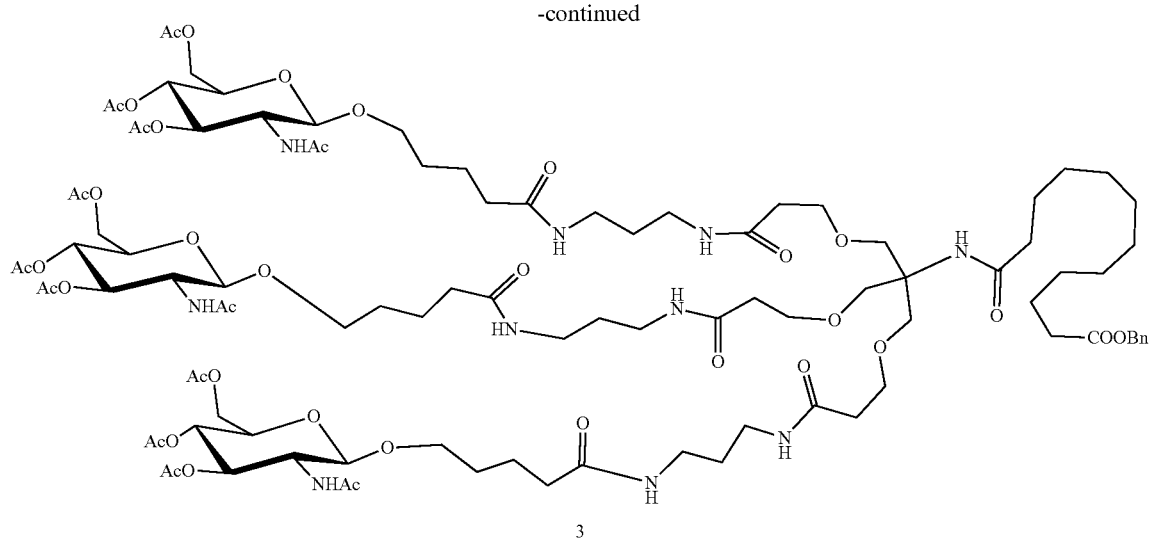

3

GlucNAc acid[1] 1 (1.88 g, 4.2 mmol) and HOBT (0.73 g, 5.4 mmol) was stirred in anhydrous DMF-DCM mixture (11+15 ml) under nitrogen at room temperature for 10 minutes. HBTU (2.05 g, 5.4 mmol) was added followed by DIPEA (2.17 g, 16.8 mmol) at 10° C. To this solution was added tri-amine salt[2] 2 (1.38 g, 1.2 mmol) and stirred overnight. Solvent was removed under vacuum and the residue was dissolved in ethyl acetate (200 ml). To this solution was added 100 ml of a mixture of sat. ammonium chloride, sat. sodium chloride, sat. sodium bicarbonate and water (1:1:1:1). The ethyl acetate layer was turbid initially. After thoroughly shaking the layers got separated. Aqueous layer was extracted with ethyl acetate (×2). Combined organic fractions were washed with brine and dried over anhydrous sodium sulfate. Solvent removal under reduced pressure afforded 490 mg of crude product. This product was purified by CC on an ISCO machine. The eluent was DCM-Methanol (0-20% methanol in DCM). Amount of product obtained was 1.26 g (50%). LC-MS (+mode): 1768 (M-1GlucNAc), 1438 (M-2 GlucNAc), 1108 (M-3 GlucNAc), 1049 (M/2+1).

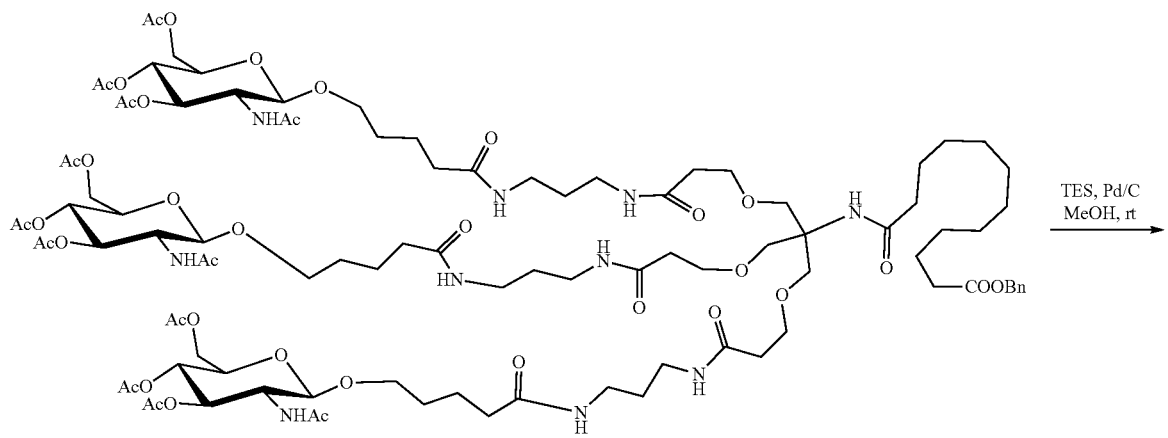

4

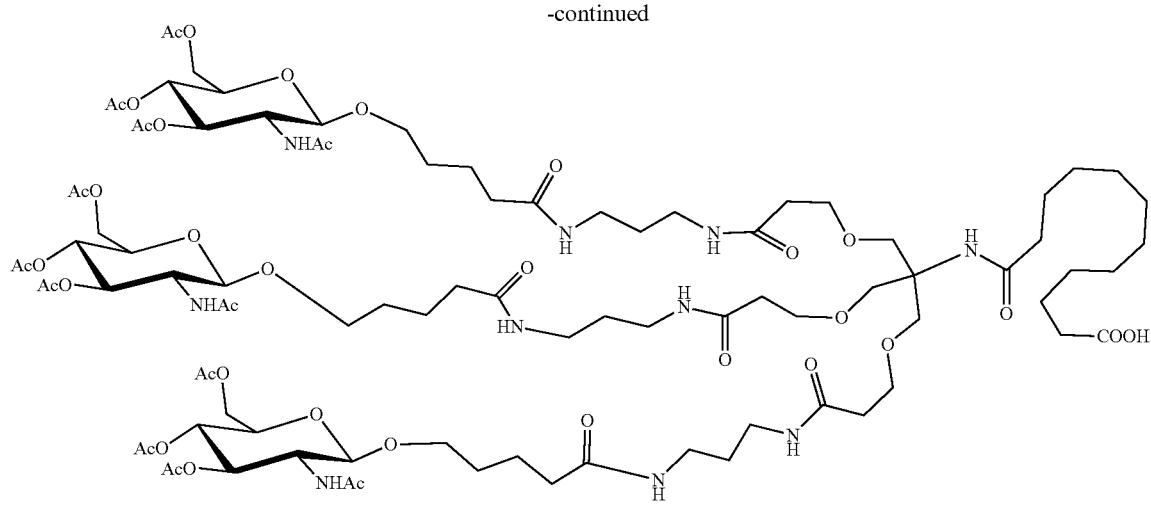

5

Procedure: To a solution of benzyl ester 4 (0.25 g, 0.119 mmol) in 7 ml dry methanol, under an atmosphere of argon, was added 1.5 ml (9.4 mmol) Triethylsilane (TES) drop wise. A vigorous reaction sets in and the RM was stirred for 3 hours. LC-MS analysis of the product indicates completion of reaction. The RM was filtered over celite and solvent was removed under vacuum. The crude product was triturated (×3) with ether-methanol (3:1) mixture and dried under vacuum. This product 5 was used for next reaction without further purification. 1H NMR (500 MHz, DMSO-D6): δ 7.90 (3H, d, J=10 Hz), 7.80 (t, 3H), 7.70 (t, 3H), 5.03 (t, 3H), 4.77 (t, 3H), 4.54 (3H, d, J=10 Hz), 4.14 (3H, dd, $J_1$=9 Hz, $J_2$=5 Hz), 3.97-3.93 (m, 3H), 3.79-3.74 (m, 3H), 3.69-3.61 (m, 6H), 3.51-3.47 (m, 3H), 3.40-3.35 (m, 3H), 3.31 (d, 3H, J9 Hz), 2.98 (m, 12H), 2.23 (t, 3H), 2.13 (t, 3H), 2.01-1.99 (m, 3H), 1.97 (s, 9H), 1.92 (s, 9H), 1.86 (s, 9H), 1.71 (s, 9H), 1.49-1.32 (m, 22H), 1.18 (br s, 12H). Ref 1 and 2: US Patent WO 2014/025805 A1; dated 13 Feb. 2014. References: Juliano et al. *J. Am. Chem. Soc.* 2010, 132, 8848; Banerjee R et al. *Int. J. Cancer.* 2004, 112, 693; He et al. *J. Med. Chem.*, 2017, 60 (10), pp 4161-4172.

General Procedure for the Deprotection of Amine:

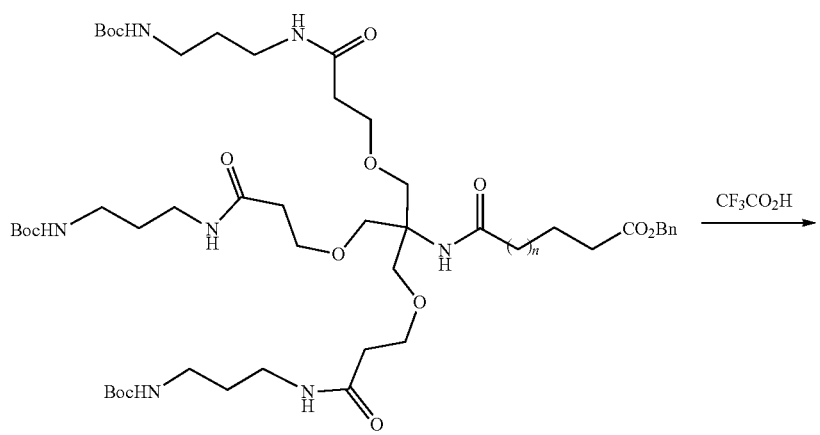

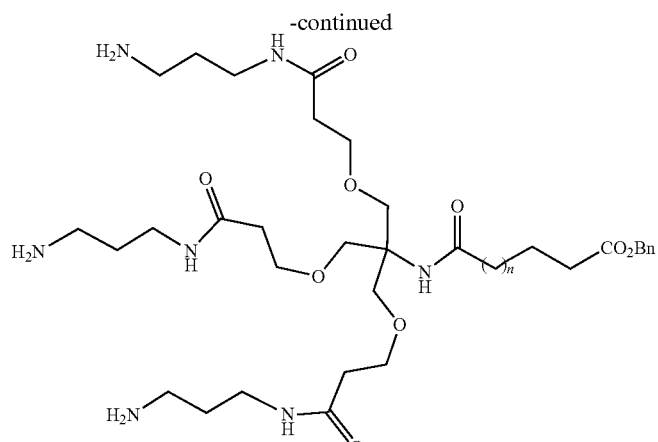

n = 1,8

15.2 g of NHBoc amine was dissolved in dry DCM (100 ml) then TFA (50 ml) was added dropwise at RT. Reaction mixture was stirred at RT overnight. Solvents were removed under reduced pressure then co-evaporated with toluene (2×50 mL) then used for the next step without any further purification. NMR in $CD_3OD$ confirmed the NHBoc deprotection.

General Procedure for the Anisamide Formation:

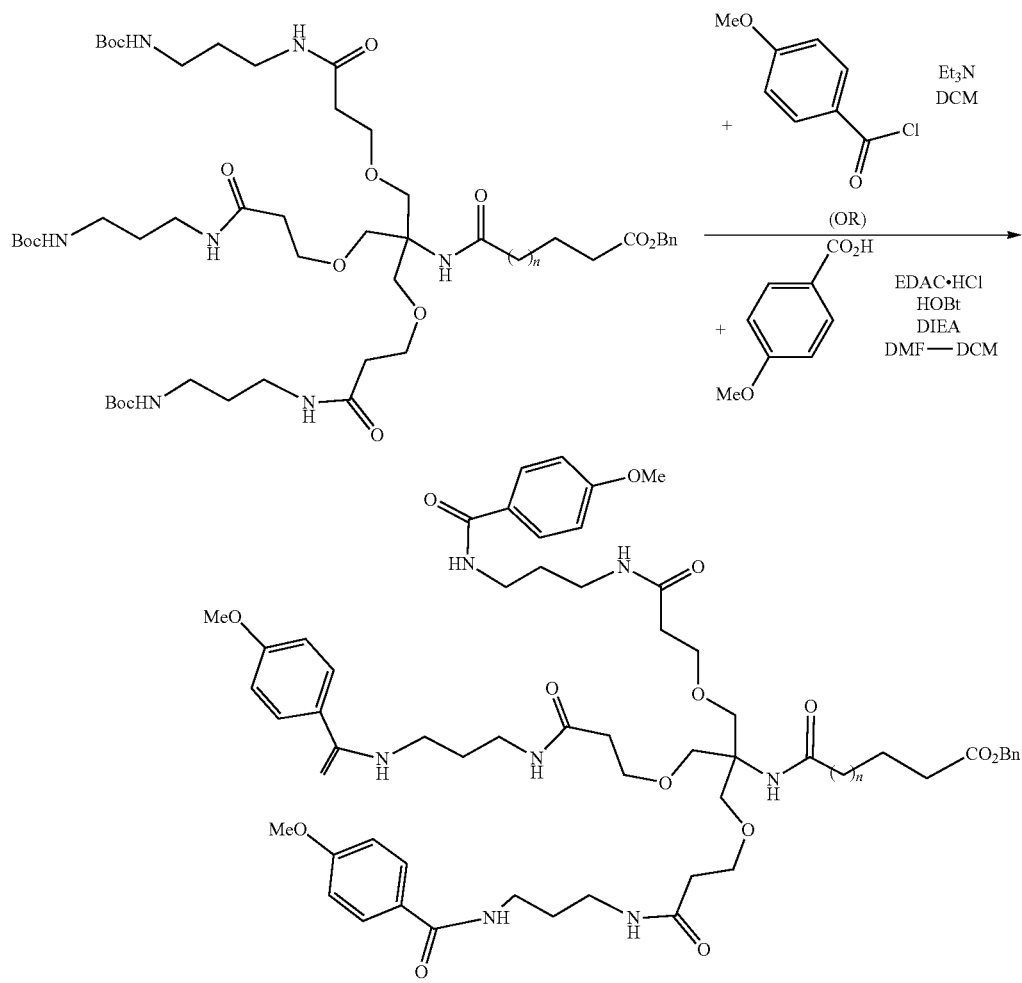

n = 1,8

Procedure-A: The crude amine from the previous step was dissolved in a mixture of DCM (100 ml) and Et$_3$N (10 equ.) at RT. During this process, the reaction mixture was cooled with a water bath. Then 4-Methoxybenzoyl chloride (4 equ) was added dropwise to the reaction mixture under argon atmosphere at RT, stirring continued for 3 h. Reaction mixture was diluted with water and extracted with DCM. Organic layer was extracted with aq. NaHCO$_3$, 1N HCl, brine then dried with magnesium sulfate evaporated to dryness. The crude product was purified by silica column chromatography using DCM-MeOH as eluent.

Procedure-B: The crude amine (0.27 equ), acid and HOBt (1 equ) were dissolved in a mixture of DCM and DMF (2:1) in an appropriate sized RBF under argon. EDAC.HCl (1.25 equ) was added portion wise to the reaction mixture under constant stirring. After 15 mins, the reaction mixture was cooled to ~10° C. then DIEA (2.7 equ) was added over a period of 5 mins. Slowly warmed the reaction mixture to ambient temperature and stirred under argon for overnight. TLC indicated completion of the reaction TLC condition, DCM:MeOH (9.5:0.5). Solvents were removed under reduced pressure, then water was added to the residue, and a gummy solid separated out. The clear solution was decanted, and the solid residue was dissolved in EtOAc and washed successively with water, 10% aqueous citric acid, aq. NaHCO$_3$, followed by saturated brine. The organic layer was separated and dried over magnesium sulfate. Solvent was removed under reduced pressure then the crude product was purified with silica column to get the pure product.

Anisamide:

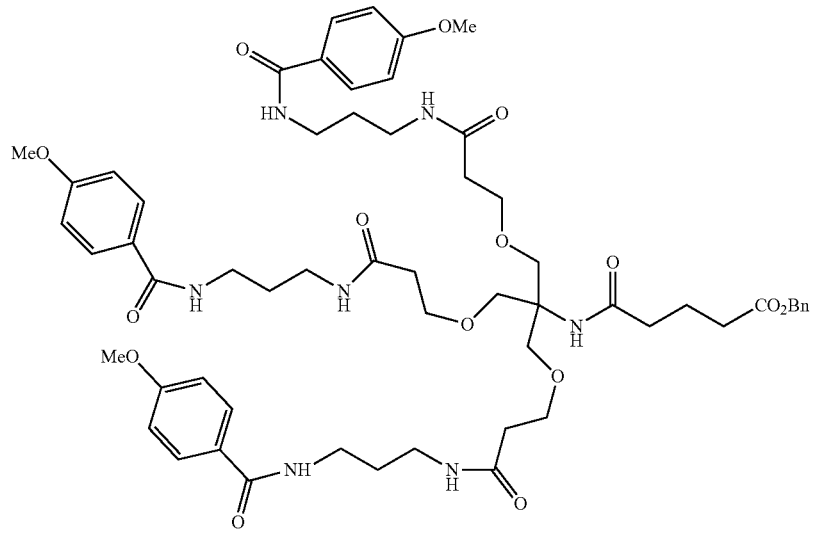

Anisamide was obtained from the amine in 32% yield over 2 steps using the above procedure-B: 1H NMR (CDCl$_3$): δ=7.74 (d, 6H), 7.44 (t, 2H), 7.34 (t, 1H), 7.26 (m, 5H), 7.05 (m, 3H), 6.83 (d, 6H), 6.46 (s, 1H), 5.01 (s, 2H), 3.75 (s, 9H), 3.57 (m, 12H), 3.37 (m, 6H), 3.25 (m, 6H), 2.31 (m, 8H), 2.11 (m, 2H), 1.84 (m, 2H), 1.62 (m, 6H) ppm.

Anisamide:

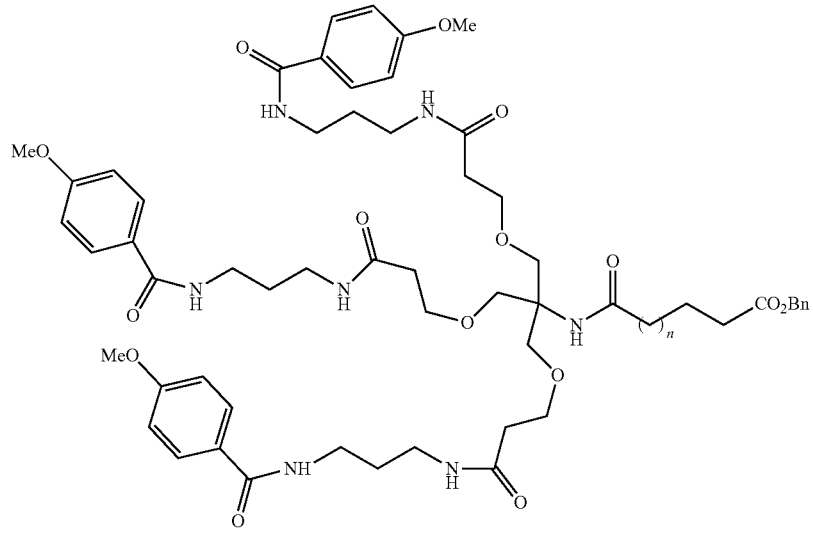 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCC(=O)OCc2ccccc2)cc1]

n = 8

Anisamide was obtained from the amine in 57% yield over 2 steps using the above procedure-A: 1H NMR (CDCl$_3$): δ=7.75 (m, 3H), 7.73 (d, 6H), 7.43 (t, 3H), 7.25 (m, 5H), 6.80 (d, 6H), 6.51 (brs, 1H), 5.01 (s, 2H), 3.72 (s, 9H), 3.58 (m, 6H), 3.21 (m, 12H), 2.33 (t, 3H), 2.25 (t, 2H), 2.02 (t, 2H), 1.64 (q, 6H), 1.52 (p, 2H), 1.41 (q, 2H), 1.12 (m, 12H) ppm.

General Procedure for the Debenzylation:

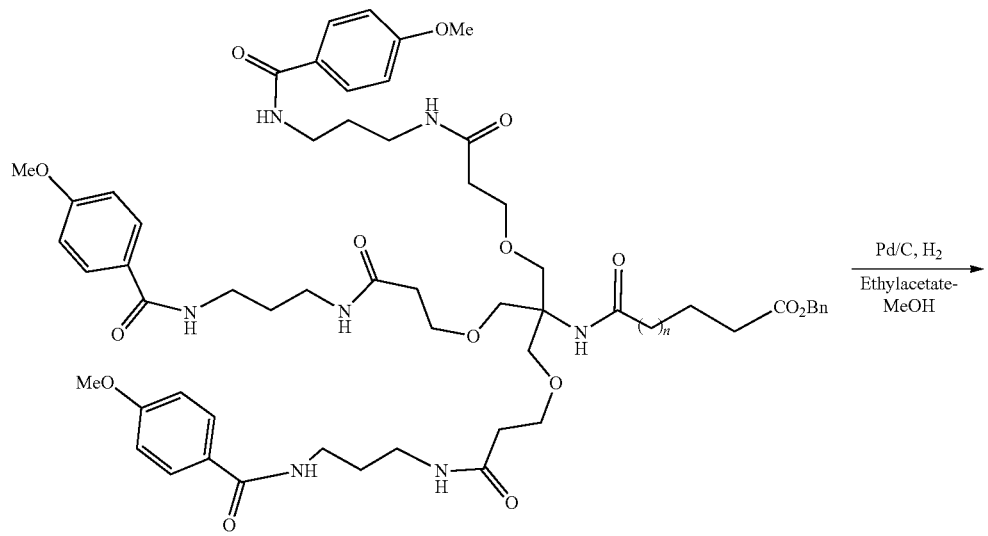

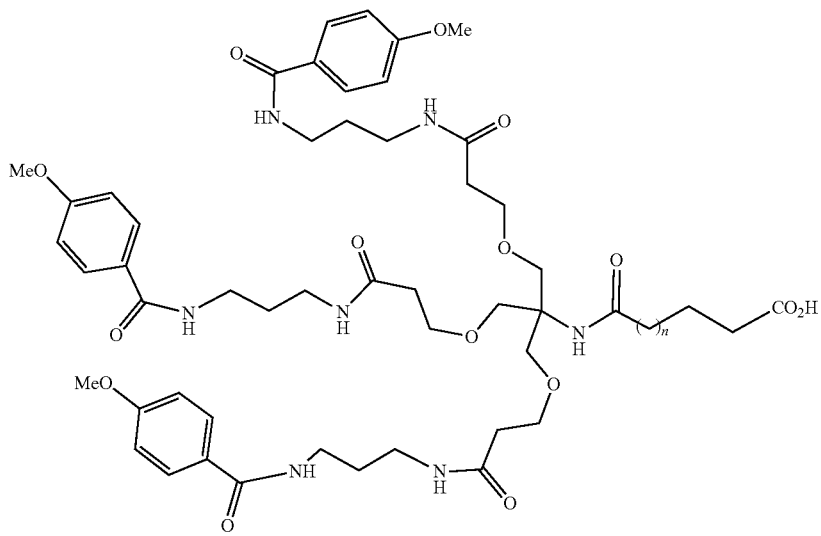

n = 1,8

The benzyl ester (10 g) was dissolved in a mixture of ethyl acetate (100 ml) and methanol (25 ml) then Pd/C, 1 g (10% palladium content) was added under argon atmosphere then the reaction mixture was vacuumed and flushed with hydrogen and stirred at RT under H2 atmosphere for 3 h. TLC indicated completion of the reaction, filtered through pad of celite and washed with methanol, evaporated to dryness to yield a foamy white solid.

Acid:
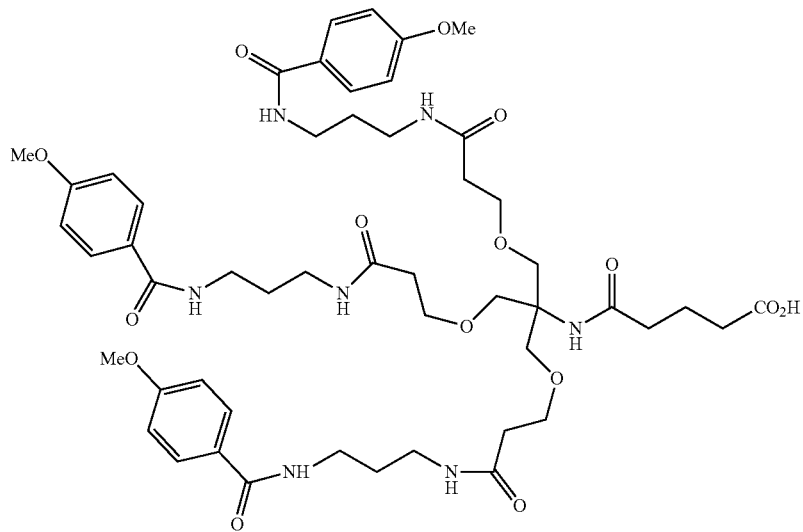 [SMILES: COc1ccc(C(=O)NCCCNC(=O)CCOCC(COCCC(=O)NCCCNC(=O)c2ccc(OC)cc2)(COCCC(=O)NCCCNC(=O)c2ccc(OC)cc2)NC(=O)CCCC(=O)O)cc1]
Yield 98%, 1H NMR (CD$_3$OD): δ=8.35 (t, 1H), 8.01 (t, 1H), 7.82 (d, 6H), 7.27 (d, 1H), 6.99 (d, 6H), 3.85 (s, 9H), 3.68 (m, 12H), 3.41 (m, 6H), 3.29 (m, 6H), 2.42 (m, 6H), 2.31 (q, 2H), 2.21 (td, 2H), 1.80 (m, 8H) ppm.
Acid:
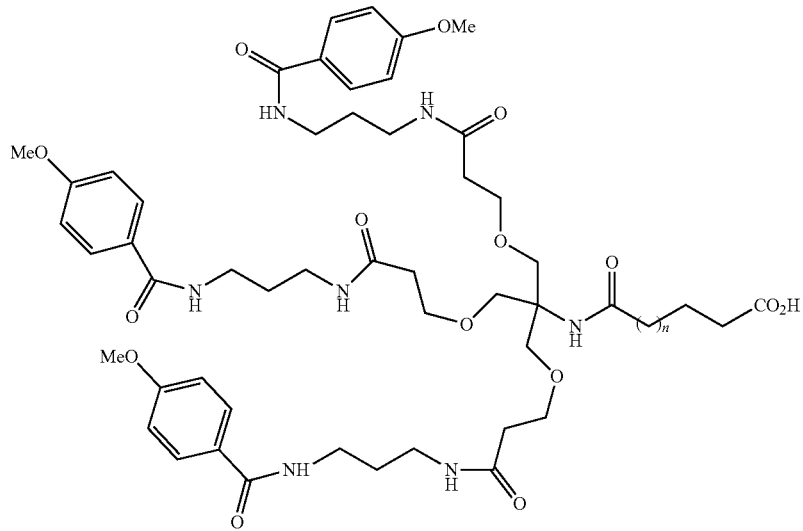
n = 8
Yield 94%, 1H NMR (CD$_3$OD): δ=8.36 (t, 2H), 8.02 (t, 2H), 7.82 (d, 6H), 7.23 (d, 1H), 6.98 (d, 6H), 3.85 (s, 9H), 3.70 (s, 6H), 3.67 (t, 6H), 3.41 (q, 4H), 3.28 (m, 8H), 2.42 (t, 6H), 2.27 (t, 2H), 2.13 (t, 2H), 1.79 (p, 6H), 1.54 (dp, 4H), 1.25 (m, 12H) ppm.
Additional compositions, including oligonucleotides comprising analogues of anisamide, are presented below:

493
494
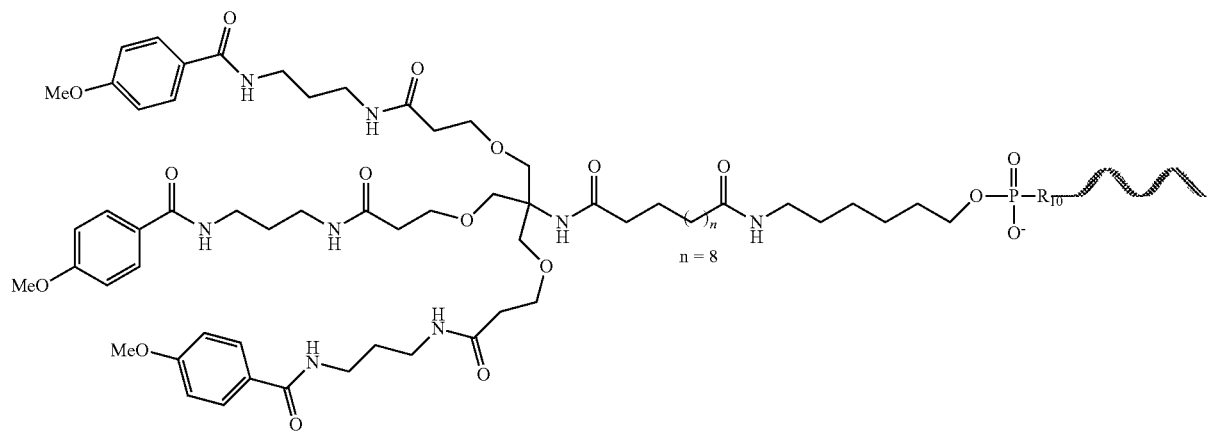
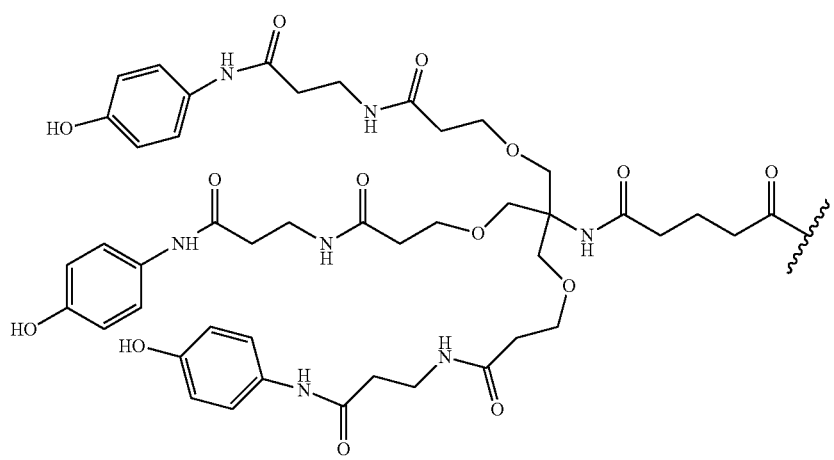
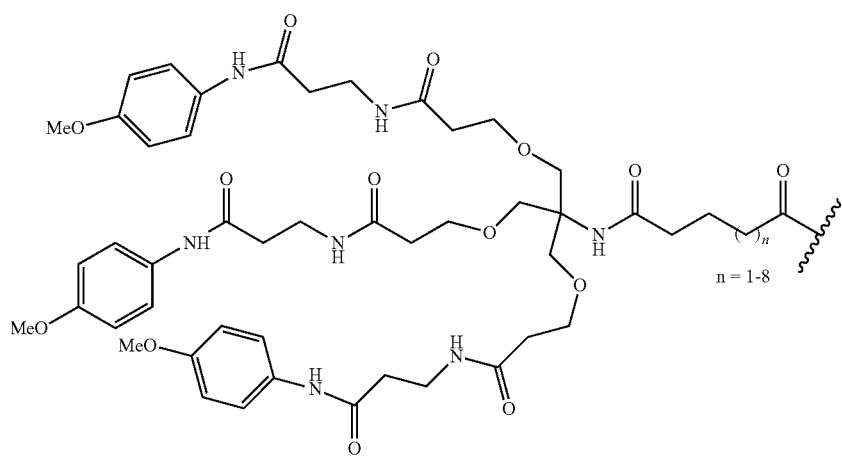

-continued

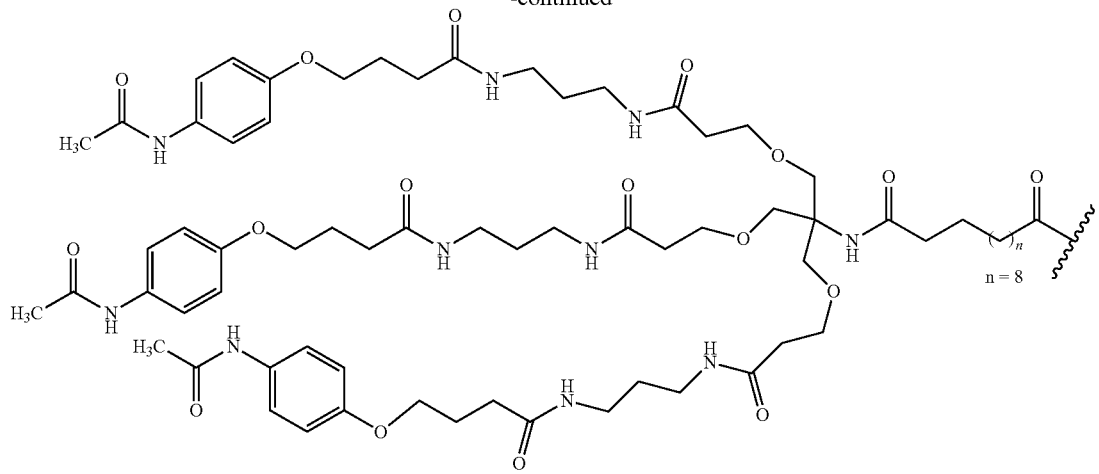

Example 3

Activities of Various Malat1 Oligonucleotides

Non-limiting examples of oligonucleotides which were designed, constructed and/or tested include oligonucleotides to Malat1, as listed herein and described in, for example, Table 1B.

Several Malat1 oligonucleotides, including several which have an asymmetrical format, were tested for their ability to knockdown Malat1 expression in iCell Neurons. The results, shown in the Tables below, show the residual hMalat1 mRNA level relative to hSFRS9. Numbers represent percentage of Malat1 remaining, wherein 100.0 would represent 100% Malat1 remaining (0.00% knockdown) and 0.0 would represent 0.0% Malat1 remaining (100.0% knockdown). Mock represents a negative control.

TABLE 2A

Activity of certan Malat1 oligocnuleotides.

|  | 0.1 nM |  | 1 nM |  |
|---|---|---|---|---|
| Mock | 100 | 100 | 100 | 100 |
| WV-3174 | 87 | 71.6 | 37.5 | 32.2 |
| WV-8109 | 48.9 | 65.4 | 43.3 | 40.3 |
| WV-8097 | 76 | 85.3 | 60.6 | 47.4 |
| WV-8098 | 54.2 | 61.4 | 38.6 | 44.1 |
| WV-8099 | 61.5 | 69.3 | 42.7 | 43.5 |
| WV-8100 | 66.8 | 66.6 | 48.6 | 30.2 |
| WV-8101 | 45.4 | 66.9 | 49.3 | 36.3 |
| WV-8102 | 35.3 | 48.3 | 23.6 | 20.7 |

TABLE 2B

Activity of certan Malat1 oligocnuleotides.

|  | 0.1 nM |  | 1 nM |  |
|---|---|---|---|---|
| Mock | 100 | 100 | 100 | 100 |
| WV-3174 | 87 | 71.6 | 37.5 | 32.2 |
| WV-8110 | 57.5 | 50.2 | 42 | 34.8 |
| WV-8103 | 86.6 | 85.6 | 58.9 | 41.9 |
| WV-8104 | 50.6 | 68.7 | 54.9 | 66.6 |

TABLE 2B-continued

Activity of certan Malat1 oligocnuleotides.

|  | 0.1 nM |  | 1 nM |  |
|---|---|---|---|---|
| WV-8105 | 70.1 | 83.2 | 62 | 45.8 |
| WV-8106 | 93.7 | 90.6 | 46.4 | 68.1 |
| WV-8107 | 72 | 99.7 | 44.1 | 56.1 |
| WV-8108 | 57.8 | 48 | 30.5 | 34.3 |

Several Malat1 oligonucleotides, including several which have an asymmetrical format, were tested for their ability to knockdown Malat1 expression in iCell Neurons. Oligonucleotides were tested at 10 nM, 30 nM, 100 nM, 300 nM, 1000 nM and 3000 nM, and $IC_{50}$ was calculated, and presented below. WV-2431 is a negative control and WV-3174 is a positive control.

TABLE 3A

Activity of certain Malat1 oligonucleotides.

| Oligonucleotide | $IC_{50}$ (nM) |
|---|---|
| WV-2431 | NA |
| WV-3174 | 250 |
| WV-8556 | 2864 |
| WV-8557 | 6874 |
| WV-9060 | 1419 |
| WV-8582 | 2566 |
| WV-8583 | NA |
| WV-8584 | 3945 |
| WV-8585 | 1478 |
| WV-8586 | 1029 |
| WV-8587 | 120 |
| WV-8593 | 275.7 |
| WV-9058 | 273.7 |

Various Malat1 oligonucleotides were designed, constructed and tested which comprise a non-negatively charged internucleotidic linkage. Various Malat1 oligonucleotides comprise 1 or more non-negatively charged internucleotidic linkages.

TABLE 3B

Activity of certain Malat1 oligonucleotides.
Numbers represent knockdown of Malat1 mRNA relative to HPRT1, wherein
1.000 would represent no (0.0%) knockdown and 0.000 represents 100.0%
knockdown; results from replicate experiments are shown.

|  | 0.004 uM | | | 0.02 uM | | | 0.1 uM | | |
|---|---|---|---|---|---|---|---|---|---|
| WV-11533 | 0.74 | 0.75 | 0.87 | 0.40 | 0.37 | 0.41 | 0.14 | 0.14 | 0.09 |
| WV-14556 | 0.81 | 0.84 | 0.91 | 0.46 | 0.42 | 0.58 | 0.15 | 0.23 | 0.17 |
| WV-14557 | 0.75 | 1.10 | 0.96 | 0.46 | 0.40 | 0.54 | 0.19 | 0.19 | 0.21 |
| WV-14558 | 0.96 | 1.11 | 0.90 | 0.77 | 1.08 | 0.78 | 1.27 | 0.40 | 0.45 |
| WV-14559 | 0.80 | 0.62 | 0.75 | 0.35 | 0.36 | 0.37 | 0.12 | 0.17 | 0.13 |
| WV-14560 | 1.11 | 0.99 | 1.03 | 0.44 | 0.48 | 0.60 | 0.29 | 0.31 | 0.15 |
| WV-14561 | 0.71 | 0.73 | 1.04 | 0.47 | 0.41 | 0.48 | 0.22 | 0.24 | 0.16 |
| WV-14562 | 0.79 | 0.60 | 0.60 | 0.53 | 0.45 | 0.64 | 0.22 | 0.33 | 0.24 |
| WV-14563 | 0.76 | 0.96 | 0.79 | 0.57 | 0.51 | 0.53 | 0.23 | 0.23 | 0.24 |
| WV-14564 | 0.72 | 0.65 | 0.70 | 0.58 | 0.47 | 0.50 | 0.17 | 0.20 | 0.21 |
| WV-9491 | 1.02 | 0.96 | 1.28 | 0.82 | 0.93 | 1.27 | 0.88 | 0.91 | 1.06 |

Various Malat1 oligonucleotides were designed, constructed and tested which comprise a non-negatively charged internucleotidic linkage. Various Malat1 oligonucleotides comprise 1, 2 or 3 non-negatively charged internucleotidic linkages in a wing and/or a core.

TABLE 3C

Data of Malat1 oligonucleotides
Numbers represent knockdown of Malat1 mRNA relative to HPRT1, wherein
1.000 would represent no (0.0%) knockdown and 0.000 represents 100.0%
knockdown; results from replicate experiments are shown. WV-9491 is a
negative control that is not designed to target Malat1.

|  | 0.004 uM | | | 0.02 uM | | | 0.1 uM | | |
|---|---|---|---|---|---|---|---|---|---|
| WV-8587 | 1.23 | 1.21 | 0.94 | 0.95 | 0.84 | 0.81 | 0.54 | 0.53 | 0.61 |
| WV-14733 | 1.81 | 1.06 | 1.36 | 1.47 | 1.12 | 1.17 | 0.98 | 0.97 | 0.72 |
| WV-15351 | 1.27 | 0.92 | 1.00 | 0.89 | 0.95 | 0.92 | 0.74 | 0.66 | 0.71 |
| WV-15352 | 1.49 | 1.78 | 1.52 | 0.88 | 0.83 | 0.91 | 0.50 | 0.52 | 0.73 |
| WV-15353 | 0.85 | 0.91 | 1.10 | 0.65 | 0.59 | 0.68 | 0.44 | 0.42 | 0.40 |
| WV-15354 | 1.31 | 1.00 | 0.90 | 0.69 | 0.94 | 0.79 | 0.56 | 0.87 | 0.74 |
| WV-15356 | 0.77 | 0.87 | 0.68 | 0.49 | 0.67 | 0.63 | 0.30 | 0.35 | 0.31 |
| WV-15357 | 0.91 | 1.02 | 1.13 | 0.66 | 0.75 | 0.79 | 0.37 | 0.32 | 0.36 |
| WV-15358 | 0.80 | 0.82 | 0.90 | 0.83 | 0.85 | 0.85 | 0.36 | 0.45 | 0.43 |
| WV-8582 | 1.11 | 1.06 | 1.15 | 1.30 | 1.15 | 1.14 | 0.67 | 0.85 | 1.06 |
| WV-15359 | 1.16 | 1.26 | 1.02 | 0.92 | 0.83 | 0.83 | 0.85 |  | 0.90 |
| WV-15360 | 1.57 | 1.38 | 1.31 | 1.05 | 0.99 | 0.83 | 1.03 | 0.91 | 0.80 |
| WV-15361 | 0.92 | 1.11 | 1.00 | 0.71 | 0.63 | 0.68 | 0.74 | 1.09 | 0.73 |
| WV-15362 | 1.23 | 1.22 | 1.07 | 0.90 | 0.83 | 0.82 | 0.99 | 0.97 | 0.80 |
| WV-15363 | 1.16 | 1.03 | 0.85 | 0.89 | 0.87 | 0.90 | 1.10 | 1.18 | 1.01 |
| WV-14556 | 0.81 | 0.84 | 0.91 | 0.46 | 0.42 | 0.58 | 0.15 | 0.23 | 0.17 |
| WV-14557 | 0.75 | 1.10 | 0.96 | 0.46 | 0.40 | 0.54 | 0.19 | 0.19 | 0.21 |
| WV-14558 | 0.96 | 1.11 | 0.90 | 0.77 | 1.08 | 0.78 | 1.27 | 0.40 | 0.45 |
| WV-14559 | 0.80 | 0.62 | 0.75 | 0.35 | 0.36 | 0.37 | 0.12 | 0.17 | 0.13 |
| WV-14560 | 1.11 | 0.99 | 1.03 | 0.44 | 0.48 | 0.60 | 0.29 | 0.31 | 0.15 |
| WV-14561 | 0.71 | 0.73 | 1.04 | 0.47 | 0.41 | 0.48 | 0.22 | 0.24 | 0.16 |
| WV-11533 | 0.74 | 0.75 | 0.87 | 0.40 | 0.37 | 0.41 | 0.14 | 0.14 | 0.09 |
| WV-14562 | 0.79 | 0.60 | 0.60 | 0.53 | 0.45 | 0.64 | 0.22 | 0.33 | 0.24 |
| WV-14563 | 0.76 | 0.96 | 0.79 | 0.57 | 0.51 | 0.53 | 0.23 | 0.23 | 0.24 |
| WV-14564 | 0.72 | 0.65 | 0.70 | 0.58 | 0.47 | 0.50 | 0.17 | 0.20 | 0.21 |
| WV-9491 | 1.02 | 0.96 | 1.28 | 0.82 | 0.93 | 1.27 | 0.88 | 0.91 | 1.06 |
| WV-14349 | 1.07 | 1.34 | 1.03 | 0.86 | 0.77 | 1.11 | 0.63 | 0.60 | 0.79 |

Various Malat1 oligonucleotides were designed, constructed and tested which comprise one or more non-negatively charged internucleotidic linkages in a core. In various embodiments of a Malat1 oligonucleotide, a phosphorothioate in the Rp configuration is replaced by a non-negatively charged internucleotidic linkage.

TABLE 3D

Data of Malat1 oligonucleotides
Numbers represent knockdown of Malat1 mRNA relative to HPRT1, wherein 1.000 would represent no (0.0%) knockdown and 0.000 represents 100.0% knockdown; results from replicate experiments are shown.

|          | WV-8587 | WV-15351 | WV-15352 | WV-15353 | WV-15354 | WV-9491 |
|----------|---------|----------|----------|----------|----------|---------|
| 0.004 uM | 1.23    | 1.27     | 1.49     | 0.85     | 1.31     | 1.02    |
|          | 1.21    | 0.92     | 1.78     | 0.91     | 1.00     | 0.96    |
|          | 0.94    | 1.00     | 1.52     | 1.10     | 0.90     | 1.28    |
| 0.02 uM  | 0.95    | 0.89     | 0.88     | 0.65     | 0.69     | 0.82    |
|          | 0.84    | 0.95     | 0.83     | 0.59     | 0.94     | 0.93    |
|          | 0.81    | 0.92     | 0.91     | 0.68     | 0.79     | 1.27    |
| 0.1 uM   | 0.54    | 0.74     | 0.50     | 0.44     | 0.56     | 0.88    |
|          | 0.53    | 0.66     | 0.52     | 0.42     | 0.87     | 0.91    |
|          | 0.61    | 0.71     | 0.73     | 0.40     | 0.74     | 1.06    |

Various Malat1 oligonucleotides were designed, constructed and tested which comprise a non-negatively charged internucleotidic linkage. Various Malat1 oligonucleotides comprise 1 or more non-negatively charged internucleotidic linkages.

TABLE 3E

Data of certain oligonucleotides.
Numbers represent knockdown of Malat1 mRNA relative to HPRT1, wherein 1.000 would represent no (0.0%) knockdown and 0.000 represents 100.0% knockdown; results from replicate experiments are shown.

|          | WV-8587 | WV-15356 | WV-15357 | WV-15358 | WV-9491 |
|----------|---------|----------|----------|----------|---------|
| 0.004 uM | 1.23    | 0.77     | 0.91     | 0.80     | 1.02    |
|          | 1.21    | 0.87     | 1.02     | 0.82     | 0.96    |
|          | 0.94    | 0.68     | 1.13     | 0.90     | 1.28    |
| 0.02 uM  | 0.95    | 0.49     | 0.66     | 0.83     | 0.82    |
|          | 0.84    | 0.67     | 0.75     | 0.85     | 0.93    |
|          | 0.81    | 0.63     | 0.79     | 0.85     | 1.27    |
| 0.1 uM   | 0.54    | 0.30     | 0.37     | 0.36     | 0.88    |
|          | 0.53    | 0.35     | 0.32     | 0.45     | 0.91    |
|          | 0.61    | 0.31     | 0.36     | 0.43     | 1.06    |

Various Malat1 oligonucleotides were designed, constructed and tested which comprise a non-negatively charged internucleotidic linkage. Various Malat1 oligonucleotides comprise 1 or more non-negatively charged internucleotidic linkages.

TABLE 3F

Data of certain oligonucleotides.
Numbers represent knockdown of Malat1 mRNA relative to HPRT1, wherein 1.000 would represent no (0.0%) knockdown and 0.000 represents 100.0% knockdown; results from replicate experiments are shown.

|          | WV-8582 | WV-15359 | WV-15360 | WV-15361 | WV-15362 | WV-15363 | WV-9491 |
|----------|---------|----------|----------|----------|----------|----------|---------|
| 0.004 uM | 1.11    | 1.16     | 1.57     | 0.92     | 1.23     | 1.16     | 1.02    |
|          | 1.06    | 1.26     | 1.38     | 1.11     | 1.22     | 1.03     | 0.96    |
|          | 1.15    | 1.02     | 1.31     | 1.00     | 1.07     | 0.85     | 1.28    |
| 0.02 uM  | 1.30    | 0.92     | 1.05     | 0.71     | 0.90     | 0.89     | 0.82    |
|          | 1.15    | 0.83     | 0.99     | 0.63     | 0.83     | 0.87     | 0.93    |
|          | 1.14    | 0.83     | 0.83     | 0.68     | 0.82     | 0.90     | 1.27    |
| 0.1 uM   | 0.67    | 0.85     | 1.03     | 0.74     | 0.99     | 1.10     | 0.88    |
|          | 0.85    |          | 0.91     | 1.09     | 0.97     | 1.18     | 0.91    |
|          | 1.06    | 0.90     | 0.80     | 0.73     | 0.80     | 1.01     | 1.06    |

Various Malat1 oligonucleotides were designed, constructed and tested which comprise a non-negatively charged internucleotidic linkage. Various Malat1 oligonucleotides comprise 1 or more non-negatively charged internucleotidic linkages.

TABLE 3G

Data of certain oligonucleotides.
Numbers represent knockdown of Malat1 mRNA relative to HPRT1, wherein 1.000 would represent no (0.0%) knockdown and 0.000 represents 100.0% knockdown; results from replicate experiments are shown.

|  | 0.004 uM | | | 0.02 uM | | |
| --- | --- | --- | --- | --- | --- | --- |
| WV-11533 | 0.74 | 0.75 | 0.87 | 0.40 | 0.37 | 0.41 |
| WV-14556 | 0.81 | 0.84 | 0.91 | 0.46 | 0.42 | 0.58 |
| WV-14557 | 0.75 | 1.10 | 0.96 | 0.46 | 0.40 | 0.54 |
| WV-14558 | 0.96 | 1.11 | 0.90 | 0.77 | 1.08 | 0.78 |
| WV-14559 | 0.80 | 0.62 | 0.75 | 0.35 | 0.36 | 0.37 |
| WV-14560 | 1.11 | 0.99 | 1.03 | 0.44 | 0.48 | 0.60 |
| WV-14561 | 0.71 | 0.73 | 1.04 | 0.47 | 0.41 | 0.48 |
| WV-14562 | 0.79 | 0.60 | 0.60 | 0.53 | 0.45 | 0.64 |
| WV-14563 | 0.76 | 0.96 | 0.79 | 0.57 | 0.51 | 0.53 |
| WV-14564 | 0.72 | 0.65 | 0.70 | 0.58 | 0.47 | 0.50 |
| WV-9491 | 1.02 | 0.96 | 1.28 | 0.82 | 0.93 | 1.27 |

Example 4

Activities of Various C9orf72 Oligonucleotides

Non-limiting examples of oligonucleotides which were designed, constructed and/or tested include oligonucleotides to C9orf72, as listed herein and described in, for example, Table 1A.

Tables 4A to D show activity of oligonucleotides in knocking down transcripts (Table 4A, all transcripts; Table 4B3, only V3 transcripts; Table 4C, Intron/AS transcripts; and Table 4D, only Exon 1a transcripts) in vitro in iPSC neurons. Table 4C shows knockdown of Intron/AS transcripts (with probes targeting a region 3' to the repeat transcript expansion, the detected area includes both sense and antisense transcripts of the intronic region). Relative-fold change in/HPRT1 is shown. Three replicate experiments are shown for the various oligonucleotides, at a concentration of 1 μM (Column A) or 10 μM (Column B). Numbers represent residual transcript level (all transcripts). For example, with WV-7601, three replicates were done at a concentration of 1 μM (Group A), showing 82.6%, 86.8% and 77.6% residual transcript level (all transcripts), corresponding to 17.4%, 13.2% and 22.3% knockdown, respectively. For WV-7601, three replicates were also performed at a concentration of 10 μM (Group B), showing 76.0%, 68.5%, and 75.0% residual transcript level (all transcripts), corresponding to 24.0%, 31.5%, and 25.0% knockdown, respectively. Delivery of oligonucleotides was gymnotic and cells were tested after 1 week. Controls used included WV-5302 and WV-6493, which target Malat1. Malat1 and oligonucleotides were also tested against Malat1; Malat1 oligonucleotides were efficacious in knocking down Malat1, but oligonucleotides were not efficacious in knocking down Malat1 (data not shown). Controls also include WV-2549 and WV-6028, which target a gene target which is not C9orf72.

TABLE 4A

Activity of C9orf72 oligonucleotides (residual level of all C9orf72 transcripts)

| | A (1 μM) | B (10 μM) |
| --- | --- | --- |
| WV-7601 | 0.826 | 0.760 |
| | 0.868 | 0.685 |
| | 0.776 | 0.750 |
| WV-7657 | 0.832 | 0.622 |
| | 0.844 | 0.676 |
| | 0.886 | 0.719 |
| WV-7658 | 0.917 | 0.798 |
| | 0.850 | 0.676 |
| | 0.880 | 0.704 |
| WV-7659 | 0.882 | 0.740 |
| | 0.946 | 0.631 |
| | 0.852 | 0.626 |
| WV-8005 | 0.795 | 0.622 |
| | 0.768 | 0.568 |
| | 0.763 | 0.609 |
| WV-8006 | 0.952 | 0.681 |
| | 0.835 | 0.662 |
| | 0.774 | 0.700 |
| WV-8007 | 0.727 | 0.605 |
| | 0.697 | 0.568 |
| | 0.702 | 0.545 |
| WV-8008 | 0.747 | 0.502 |
| | 0.637 | 0.601 |
| | 0.717 | 0.584 |
| WV-8009 | 0.722 | 0.593 |
| | 0.732 | 0.605 |
| | 0.779 | 0.553 |
| WV-8010 | 0.688 | 0.572 |
| | 0.742 | 0.626 |
| | 0.835 | 0.622 |
| WV-8011 | 0.650 | 0.486 |
| | 0.702 | 0.486 |
| | 0.655 | 0.483 |
| WV-8012 | 0.707 | 0.489 |
| | 0.687 | 0.496 |
| | 0.655 | 0.496 |
| WV-2549 | 0.939 | 0.900 |
| | 0.920 | 0.888 |
| | 0.907 | |
| WV-6028 | 0.972 | 1.006 |
| | 0.992 | 0.932 |
| | 0.972 | 0.985 |
| WV-3688 | 0.852 | 0.731 |
| | 0.840 | 0.711 |
| | 0.876 | 0.806 |
| WV-6408 | 0.773 | 0.624 |
| | 0.835 | 0.641 |
| | 0.945 | 0.558 |
| WV-3662 | 0.423 | |
| | 0.429 | 0.109 |
| | | 0.086 |
| WV-7118 | 0.405 | 0.240 |
| | 0.380 | 0.240 |
| | 0.380 | 0.237 |
| WV-6936 | 0.937 | 1.044 |
| | 0.862 | 0.974 |
| | 0.924 | 0.915 |
| WV-7027 | 0.963 | 0.928 |
| | 0.868 | 0.981 |
| | 0.937 | 0.994 |
| WV-5302 | 0.880 | 0.947 |
| | 0.874 | 1.029 |
| | 0.937 | 1.022 |
| WV-6493 | 0.990 | 0.981 |
| | 0.833 | 1.001 |
| | 0.990 | 1.044 |
| WV-2376 | 1.018 | 0.987 |
| | 0.911 | 0.693 |
| | 0.970 | 0.764 |
| WV-3542 | 0.892 | 0.994 |
| | 0.892 | 0.967 |
| | 1.004 | 1.022 |

TABLE 4B

Activity of oligonucleotides (residual level of V3 transcripts)

|  | A (1 μM) | B (10 μM) |
|---|---|---|
| WV-7603 | 0.631 | 0.455 |
|  | 0.725 | 0.442 |
|  | 0.740 | 0.445 |
| WV-7604 | 0.572 | 0.436 |
|  | 0.622 | 0.407 |
|  | 0.601 | 0.362 |
| WV-7605 | 0.667 | 0.340 |
|  | 0.695 | 0.354 |
|  | 0.648 | 0.374 |
| WV-7606 | 0.676 | 0.298 |
|  | 0.495 | 0.286 |
|  | 0.576 | 0.247 |
| WV-7601 | 0.475 | 0.286 |
|  | 0.557 | 0.278 |
|  | 0.530 | 0.247 |
| WV-7657 | 0.618 | 0.424 |
|  | 0.676 | 0.364 |
|  | 0.549 | 0.407 |
| WV-7658 | 0.568 | 0.326 |
|  | 0.542 | 0.321 |
|  | 0.572 | 0.304 |
| WV-7659 | 0.558 | 0.333 |
|  | 0.539 | 0.315 |
|  | 0.582 | 0.296 |
| WV-8005 | 0.366 | 0.123 |
|  | 0.327 | 0.124 |
|  | 0.392 | 0.147 |
| WV-8006 | 0.409 | 0.158 |
|  | 0.438 | 0.171 |
|  | 0.473 | 0.157 |
| WV-8007 | 0.182 | 0.056 |
|  | 0.196 | 0.056 |
|  | 0.238 | 0.050 |
| WV-8008 | 0.197 | 0.048 |
|  | 0.183 | 0.045 |
|  | 0.172 | 0.043 |
| WV-8009 | 0.412 | 0.150 |
|  | 0.379 | 0.129 |
|  | 0.406 | 0.110 |
| WV-8010 | 0.339 | 0.137 |
|  | 0.344 | 0.138 |
|  | 0.368 | 0.128 |
| WV-8011 | 0.229 | 0.059 |
|  | 0.244 | 0.067 |
|  | 0.263 | 0.055 |
| WV-8012 | 0.212 | 0.046 |
|  | 0.244 | 0.050 |
|  | 0.217 | 0.057 |
| WV-2549 | 0.827 | 0.821 |
|  | 0.936 | 0.905 |
|  | 0.983 |  |
| WV-6028 | 0.943 | 1.018 |
|  | 0.990 | 0.983 |
|  | 0.905 | 1.011 |
| WV-3688 | 0.735 | 0.502 |
|  | 0.730 | 0.472 |
|  | 0.715 | 0.538 |
| WV-6408 | 0.505 | 0.341 |
|  | 0.557 | 0.343 |
|  | 0.644 | 0.343 |
| WV-3662 | 0.357 |  |
|  | 0.408 | 0.071 |
|  |  | 0.028 |
| WV-7118 | 0.369 | 0.153 |
|  | 0.404 | 0.159 |
|  | 0.352 | 0.148 |
| WV-6936 | 0.843 | 0.562 |
|  | 0.792 | 0.649 |
|  | 0.808 | 0.589 |
| WV-7027 | 0.792 | 0.602 |
|  | 0.819 | 0.731 |
|  | 0.941 | 0.778 |
| WV-5302 | 1.066 | 1.062 |
|  | 1.059 | 1.055 |
|  | 1.066 | 1.077 |

TABLE 4B-continued

Activity of oligonucleotides (residual level of V3 transcripts)

|  | A (1 μM) | B (10 μM) |
|---|---|---|
| WV-6493 | 1.044 | 1.026 |
|  | 1.030 | 1.085 |
|  | 0.995 | 1.115 |
| WV-2376 | 0.981 | 1.108 |
|  | 0.968 | 0.887 |
|  | 0.995 | 0.828 |
| WV-3542 | 1.030 | 1.041 |
|  | 1.009 | 0.991 |
|  | 1.016 | 1.070 |

TABLE 4C

Activity of C9orf72 oligonucleotides (residual level of Intron/AS C9orf72 transcripts)

|  | A (1 μM) | B (10 μM) |
|---|---|---|
| WV-7603 | 0.557 | 0.654 |
|  | 0.767 | 0.705 |
|  | 0.799 | 0.654 |
| WV-7604 | 0.386 | 0.375 |
|  | 0.538 | 0.329 |
|  | 0.535 | 0.299 |
| WV-7605 | 0.851 | 0.585 |
|  | 0.845 | 0.561 |
|  | 0.663 | 0.610 |
| WV-7606 | 0.783 | 0.408 |
|  | 0.178 | 0.623 |
|  | 0.343 | 0.520 |
| WV-7601 | 0.303 | 0.260 |
|  | 0.260 | 0.271 |
|  | 0.265 | 0.311 |
| WV-7657 | 0.715 | 0.606 |
|  | 0.756 | 0.513 |
|  | 0.405 | 0.434 |
| WV-7658 | 0.520 | 0.345 |
|  | 0.502 | 0.277 |
|  | 0.677 | 0.370 |
| WV-7659 | 0.372 | 0.417 |
|  | 0.458 | 0.397 |
|  | 0.359 | 0.479 |
| WV-8005 | 0.471 | 0.346 |
|  | 0.613 | 0.425 |
|  | 0.626 | 0.654 |
| WV-8006 | 0.410 | 0.355 |
|  | 0.474 | 0.663 |
|  | 0.471 | 0.411 |
| WV-8007 | 0.621 | 0.531 |
|  | 0.512 | 0.475 |
|  | 0.548 | 0.307 |
| WV-8008 | 0.439 | 0.645 |
|  | 0.311 | 0.485 |
|  | 0.564 | 0.495 |
| WV-8009 | 0.580 | 0.593 |
|  | 0.685 | 0.479 |
|  | 0.592 | 0.706 |
| WV-8010 | 0.461 | 0.394 |
|  | 0.252 | 0.431 |
|  | 0.407 | 0.341 |
| WV-8011 | 0.514 | 0.415 |
|  | 0.594 | 0.774 |
|  | 0.972 | 0.774 |
| WV-8012 | 0.594 | 1.050 |
|  | 0.650 | 0.633 |
|  | 0.606 | 0.651 |
| WV-2549 | 0.435 | 1.198 |
|  | 1.282 | 1.174 |
|  | 1.318 |  |
| WV-6028 | 1.715 | 2.001 |
|  | 1.049 | 2.604 |
|  | 0.846 | 1.058 |
| WV-3688 | 0.795 | 0.703 |
|  | 0.687 | 0.836 |
|  | 0.554 | 0.764 |

TABLE 4C-continued

Activity of C9orf72 oligonucleotides (residual level of Intron/AS C9orf72 transcripts)

| | A (1 μM) | B (10 μM) |
|---|---|---|
| WV-6408 | 1.071 | 1.029 |
| | 0.741 | 1.036 |
| | 0.789 | 0.940 |
| WV-3662 | 1.273 | |
| | 1.180 | 0.802 |
| | | 1.376 |
| WV-7118 | 1.356 | 1.094 |
| | 0.712 | 1.248 |
| | 1.156 | 0.876 |
| WV-6936 | 1.291 | 1.375 |
| | 1.064 | 1.310 |
| | 1.443 | 1.944 |
| WV-7027 | 0.507 | 0.727 |
| | 0.992 | 1.494 |
| | 0.768 | 1.777 |
| WV-5302 | 1.230 | 2.157 |
| | 0.737 | 0.795 |
| | 1.101 | 0.840 |
| WV-6493 | 0.562 | 1.463 |
| | 0.586 | 0.727 |
| | 0.536 | 0.784 |
| WV-2376 | 0.784 | 1.985 |
| | 1.579 | 0.387 |
| | 0.594 | 0.426 |
| WV-3542 | 1.494 | 1.515 |
| | 1.283 | 1.944 |
| | 1.704 | 2.361 |

TABLE 4D

Activity of C9orf72 oligonucleotides (residual level of Exon 1a C9orf72 transcripts)

| | A (1 μM) | B (10 μM) |
|---|---|---|
| WV-7603 | 1.006 | 1.127 |
| | 1.042 | 1.051 |
| | 0.965 | 0.981 |
| WV-7604 | 0.823 | 1.059 |
| | 0.823 | 0.848 |
| | 0.737 | 0.738 |
| WV-7605 | 1.282 | 1.059 |
| | 1.205 | 1.023 |
| | 1.049 | 1.096 |
| WV-7606 | 0.907 | 0.995 |
| | 0.524 | 1.008 |
| | 0.687 | 1.044 |
| WV-7601 | 0.707 | 1.044 |
| | 0.795 | 0.909 |
| | 0.726 | 0.848 |
| WV-7657 | 0.985 | 0.854 |
| | 0.888 | 0.728 |
| | 0.551 | 0.733 |
| WV-7658 | 0.979 | 1.104 |
| | 0.829 | 0.786 |
| | 1.124 | 1.183 |
| WV-7659 | 1.160 | 1.582 |
| | 1.090 | 1.119 |
| | 0.904 | 1.088 |
| WV-8005 | 0.923 | 1.199 |
| | 0.996 | 1.119 |
| | 0.936 | 1.330 |
| WV-8006 | 1.121 | 1.088 |
| | 1.010 | 1.216 |
| | 0.792 | 0.981 |
| WV-8007 | 1.168 | 1.582 |
| | 0.904 | 1.358 |
| | 0.873 | 1.058 |
| WV-8008 | 1.090 | 1.755 |
| | 0.820 | 1.560 |
| | 1.136 | 1.684 |

TABLE 4D-continued

Activity of C9orf72 oligonucleotides (residual level of Exon 1a C9orf72 transcripts)

| | A (1 μM) | B (10 μM) |
|---|---|---|
| WV-8009 | 0.892 | 1.233 |
| | 0.917 | 1.001 |
| | 0.843 | 0.884 |
| WV-8010 | 0.755 | 0.896 |
| | 0.666 | 1.111 |
| | 1.010 | 1.037 |
| WV-8011 | 1.028 | 1.084 |
| | 1.049 | 1.153 |
| | 1.086 | 1.138 |
| WV-8012 | 0.986 | 1.298 |
| | 0.933 | 1.138 |
| | 0.926 | 1.254 |
| WV-2549 | 0.946 | 1.084 |
| | 1.132 | 1.047 |
| | 1.071 | |
| WV-6028 | 1.197 | 1.194 |
| | 0.959 | 1.334 |
| | 1.086 | 1.054 |
| WV-3688 | 1.013 | 1.122 |
| | 0.852 | 0.977 |
| | 0.795 | 0.943 |
| WV-6408 | 1.101 | 1.254 |
| | 1.049 | 1.316 |
| | 1.172 | 1.245 |
| WV-3662 | 0.939 | |
| | 1.028 | 0.886 |
| | | 1.271 |
| WV-7118 | 1.070 | 1.171 |
| | 1.026 | 1.020 |
| | 1.077 | 1.013 |
| WV-6936 | 1.077 | 0.408 |
| | 0.945 | 0.773 |
| | 1.115 | 0.677 |
| WV-7027 | 1.123 | 0.978 |
| | 1.221 | 1.204 |
| | 1.246 | 1.171 |
| WV-5302 | 1.281 | 1.524 |
| | 1.026 | 1.116 |
| | 1.034 | 0.965 |
| WV-6493 | 1.100 | 1.255 |
| | 0.971 | 1.282 |
| | 0.912 | 1.238 |
| WV-2376 | 1.171 | 1.462 |
| | 1.255 | 0.747 |
| | 0.951 | 0.817 |
| WV-3542 | 1.383 | 1.657 |
| | 1.412 | 1.680 |
| | 1.588 | 2.011 |

Tables 5A to D show activity of various C9orf72 oligonucleotides in knocking down C9orf72 transcripts (Table 5A, all transcripts; Table 5B, only V3 transcripts; Table 5C, Intron/AS; and Table 5D, only Exon 1a transcripts). Relative-fold change in C9orf72/HPRT1 is shown. Three replicate experiments are shown for the various C9orf72 oligonucleotides, at a concentration of 1 μM (Column A) or 10 μM (Column B). As with Tables 5A to D, numbers represent residual transcript level. Delivery of oligonucleotides was gymnotic and cells were tested after 1 week.

TABLE 5A

Activity of C9orf72 oligonucleotides (residual level of all C9orf72 transcripts)

| | A (1 μM) | B (10 μM) |
|---|---|---|
| WV-8122 | 1.031 | 0.928 |
| | 0.975 | 0.802 |
| | 0.942 | 0.718 |

TABLE 5A-continued

Activity of C9orf72 oligonucleotides (residual level of all C9orf72 transcripts)

|         | A (1 μM) | B (10 μM) |
|---------|----------|-----------|
| WV-8311 | 1.090    | 0.915     |
|         | 0.948    | 0.744     |
|         | 0.962    | 0.819     |
| WV-8315 | 0.923    | 0.600     |
|         | 0.935    | 0.596     |
|         | 1.097    | 0.471     |
| WV-8312 | 1.164    | 1.210     |
|         | 1.034    | 1.003     |
|         | 1.006    | 0.969     |
| WV-8313 | 1.201    | 1.550     |
|         | 1.082    | 1.277     |
|         | 1.024    | 1.268     |
| WV-8314 | 1.105    | 1.044     |
|         | 1.176    | 1.052     |
|         | 1.351    | 1.044     |
| WV-8316 | 0.926    | 0.930     |
|         | 0.789    | 0.873     |
|         | 0.846    | 0.898     |
| WV-8317 | 1.013    | 0.996     |
|         | 0.882    | 0.886     |
|         | 0.876    | 0.861     |
| WV-8318 | 1.078    | 1.136     |
|         | 0.919    | 0.969     |
|         | 0.972    | 1.010     |
| WV-2549 | 0.885    | 0.903     |
|         | 0.897    | 0.915     |
|         | 0.989    | 0.922     |
| WV-6028 | 0.840    | 0.855     |
|         | 0.876    | 0.879     |
|         | 1.006    | 0.976     |
| WV-6936 | 0.958    | 0.969     |
|         | 0.999    | 0.892     |
|         | 1.140    | 1.046     |
| WV-7027 | 0.752    | 0.873     |

TABLE 5B

Activity of C9orf72 oligonucleotides (residual level of V3 C9orf72 transcripts)

|         | A (1 μM) | B (10 μM) |
|---------|----------|-----------|
| WV-8114 | 0.880    | 0.372     |
|         | 0.904    | 0.608     |
|         | 0.826    | 0.704     |
| WV-8122 | 0.936    | 0.708     |
|         | 1.003    | 0.689     |
|         | 0.936    | 0.596     |
| WV-8311 | 0.917    | 0.377     |
|         | 0.898    | 0.364     |
|         | 0.930    | 0.377     |
| WV-8315 | 1.018    | 0.552     |
|         | 1.039    | 0.508     |
|         | 0.997    | 0.313     |
| WV-8312 | 0.803    | 0.655     |
|         | 0.803    | 0.683     |
|         | 0.855    | 0.651     |
| WV-8313 | 0.793    | 0.501     |
|         | 0.862    | 0.544     |
|         | 0.832    | 0.511     |
| WV-8314 | 0.593    | 0.335     |
|         | 0.564    | 0.364     |
|         | 0.576    | 0.313     |
| WV-8316 | 0.891    | 0.801     |
|         | 0.843    | 0.707     |
|         | 0.787    | 0.818     |
| WV-8317 | 0.648    | 0.497     |
|         | 0.671    | 0.467     |
|         | 0.699    | 0.518     |
| WV-8318 | 0.360    | 0.235     |
|         | 0.372    | 0.283     |
|         | 0.388    | 0.276     |

TABLE 5B-continued

Activity of C9orf72 oligonucleotides (residual level of V3 C9orf72 transcripts)

|         | A (1 μM) | B (10 μM) |
|---------|----------|-----------|
| WV-2549 | 1.076    | 1.052     |
|         | 1.076    | 1.002     |
|         | 1.053    | 1.044     |
| WV-6028 | 0.955    | 1.065     |
|         | 0.975    | 1.133     |
|         | 0.996    | 1.133     |
| WV-6936 | 0.891    | 0.722     |
|         | 0.873    | 0.665     |
|         | 0.982    | 0.717     |
| WV-7027 | 0.680    | 0.655     |
|         | 0.719    | 0.624     |
|         | 0.676    | 0.587     |

TABLE 5C

Activity of C9orf72 oligonucleotides (residual level of Intron/AS C9orf72 transcripts)

|         | A (1 μM) | B (10 μM) |
|---------|----------|-----------|
| WV-8114 | 1.960    | 0.449     |
|         | 1.906    | 1.090     |
|         | 1.742    | 1.399     |
| WV-8122 | 1.284    | 0.734     |
|         | 1.517    | 0.416     |
|         | 1.008    | 0.317     |
| WV-8311 | 1.987    | 1.193     |
|         | 1.485    | 1.306     |
|         | 1.766    | 1.500     |
| WV-8315 | 1.396    | 0.370     |
|         | 0.934    | 0.298     |
|         | 1.126    | 0.294     |
| WV-8312 | 2.898    | 2.346     |
|         | 3.305    | 1.602     |
|         | 1.965    | 0.940     |
| WV-8313 | 2.072    | 5.115     |
|         | 1.302    | 3.282     |
|         | 1.506    | 3.305     |
| WV-8314 | 2.464    | 1.664     |
|         | 2.696    | 1.585     |
|         | 2.380    | 1.333     |
| WV-8316 | 1.965    | 2.028     |
|         | 1.630    | 0.835     |
|         | 1.279    | 1.879     |
| WV-8317 | 1.687    |           |
|         | 2.337    | 1.028     |
|         | 1.872    | 1.117     |
| WV-8318 | 2.354    |           |
|         | 1.898    | 1.569     |
|         | 1.500    | 2.000     |
| WV-2549 | 1.718    | 1.185     |
|         | 1.455    | 1.046     |
|         | 1.581    | 1.244     |
| WV-6028 | 2.063    | 1.214     |
|         | 1.821    | 1.248     |
|         | 2.437    | 2.099     |
| WV-6936 | 2.593    | 1.454     |
|         | 2.471    | 1.050     |
|         | 3.398    | 2.144     |
| WV-7027 | 1.270    | 1.705     |
|         | 1.075    | 0.742     |
|         | 1.024    | 0.521     |

TABLE 5D

Activity of oligonucleotides (residual level of Exon 1a transcripts)

|  | A (1 µM) | B (10 µM) |
|---|---|---|
| WV-8114 | 1.422 | 0.339 |
|  | 1.462 | 0.713 |
|  | 1.402 | 0.974 |
| WV-8122 | 1.212 | 0.665 |
|  | 1.163 | 0.480 |
|  | 1.063 | 0.401 |
| WV-8311 | 1.392 | 0.222 |
|  | 1.123 | 0.194 |
|  | 1.229 | 0.157 |
| WV-8315 | 1.070 | 0.377 |
|  | 0.919 | 0.347 |
|  | 0.365 | 0.119 |
| WV-8312 | 1.407 | 1.605 |
|  | 1.304 | 1.081 |
|  | 1.030 | 0.713 |
| WV-8313 | 1.667 | 1.103 |
|  | 1.255 | 0.819 |
|  | 1.308 | 0.796 |
| WV-8314 | 1.373 | 1.043 |
|  | 1.392 | 0.980 |
|  | 1.611 | 0.994 |
| WV-8316 | 0.948 | 1.200 |
|  | 0.797 | 0.744 |
|  | 0.797 | 1.096 |
| WV-8317 | 0.941 |  |
|  | 0.941 | 0.837 |
|  | 0.808 | 0.872 |
| WV-8318 | 0.903 |  |
|  | 0.866 | 0.948 |
|  | 0.825 | 1.002 |
| WV-2549 | 1.255 | 0.954 |
|  | 0.971 | 0.859 |
|  | 1.432 | 0.974 |
| WV-6028 | 0.872 | 0.961 |
|  | 0.819 | 0.954 |
|  | 0.941 | 1.388 |
| WV-6936 | 1.059 | 0.749 |
|  | 1.216 | 0.878 |
|  | 1.216 | 0.890 |
| WV-7027 | 0.713 | 1.089 |
|  | 0.770 | 0.770 |
|  | 0.791 | 0.872 |

Tables 6A and B show activity of various C9orf72 oligonucleotides in knocking down C9orf72 transcripts (Table 6A, all transcripts; and Table 61B, only V3 transcripts). Relative-fold change in C9orf72/HPRT1 is shown. Three replicate experiments are shown for the various C9orf72 oligonucleotides, at a concentration of 10 µM. As with Tables 3A to D, numbers represent residual transcript level relative to HPRT1. Delivery of oligonucleotides was gymnotic and cells were tested after 1 week. As a control, C9orf72 oligonucleotides were tested and found not to be efficacious in knocking down Malat1 (data not shown). C9orf72 oligonucleotides were also found not to be efficacious against another target, PFN 1 (data not shown).

TABLE 6A

Activity of C9orf72 oligonucleotides (residual level of all C9orf72 transcripts)

| | Replicate experiments (10 µM) | | |
|---|---|---|---|
| WV-8008 | 0.592 | 0.564 | 0.608 |
| WV-8548 | 0.625 | 0.634 | 0.630 |
| WV-8010 | 0.639 | 0.497 | 0.579 |
| WV-8549 | 0.680 | 0.643 | 0.621 |

TABLE 6A-continued

Activity of C9orf72 oligonucleotides (residual level of all C9orf72 transcripts)

| | Replicate experiments (10 µM) | | |
|---|---|---|---|
| WV-8012 | 0.579 | 0.445 | 0.617 |
| WV-8550 | 0.634 | 0.580 | 0.608 |
| WV-8454 | 0.527 | 0.405 | 0.489 |
| WV-8455 | 0.440 | 0.381 | 0.437 |
| WV-8551 | 0.640 | 0.649 | 0.691 |
| WV-6408 | 0.687 | 0.687 | 0.762 |
| WV-3662 | 0.148 | 0.153 | 0.157 |
| WV-6936 | 0.951 | 0.875 | 1.255 |
| WV-5302 | 0.979 | 0.945 | |
| WV-2376 | 0.926 | 0.972 | |
| Water (negative control) | 1.013 | 0.932 | 1.056 |

TABLE 6B

Activity of C9orf72 oligonucleotides (residual level of V3 C9orf72 transcripts)

| | Replicate experiments (10 µM) | | |
|---|---|---|---|
| WV-8008 | 0.104 | 0.100 | 0.121 |
| WV-8548 | 0.313 | 0.318 | 0.294 |
| WV-8010 | 0.222 | 0.229 | 0.229 |
| WV-8549 | 0.347 | 0.367 | 0.280 |
| WV-8012 | 0.135 | 0.107 | 0.117 |
| WV-8550 | 0.313 | 0.302 | 0.290 |
| WV-8454 | 0.161 | 0.131 | 0.137 |
| WV-8455 | 0.087 | 0.082 | 0.109 |
| WV-8551 | 0.316 | 0.308 | 0.293 |
| WV-6408 | 0.546 | 0.499 | 0.562 |
| WV-3662 | 0.121 | 0.121 | 0.132 |
| WV-6936 | 0.845 | 0.554 | |
| WV-5302 | 0.926 | 0.907 | |
| WV-2376 | 0.876 | 0.907 | |
| Water (negative control) | 1.055 | 0.945 | |

Table 6C, below, shows the IC50 of various C9orf72 oligonucleotides tested in a full dose-response assay in ALS MN (motor neurons), delivered gymnotically and evaluated after 1 week. 10, 2.5, 0.625, 0.16, 0.04 and 0.001 µM concentrations were tested.

TABLE 6C

IC50 of some C9orf72 oligonucleotides

| | IC50 (µM) |
|---|---|
| WV-8011 | 0.9119 |
| WV-8012 | 0.5319 |
| WV-8454 | 0.5982 |
| WV-8455 | 0.5803 |
| WV-8551 | 1.47 |
| WV-8550 | 0.7681 |

TABLE 7A

Activity of various oligonucleotides.

| Assay | Endpoints | WV-6408 | WV-3688 | WV-8005 | WV-8006 | WV-8007 | WV-8008 | WV-8009 | WV-8010 | WV-8011 | WV-8012 |
|---|---|---|---|---|---|---|---|---|---|---|---|
| Reporter ALS neurons | $IC_{50}$ (nM) V3/intron | 1.32/2.63 66/0 | 5.56/8.65 50/23 | 0.5 87/53 | 0.5 84/52 | 0.4 94/52 | 0.3 95/46 | 0.5 87/41 | 0.4 87/61 | 0.4 94/35 | 0.2 95/22 |
| Stability TLR9 | Ms brain Human | 100 clean | 63.2 clean | 72 clean | 88 clean | 77 clean | 77 clean | 93 clean | 92 clean | 22? clean | 77 clean |
| PD (C9-BAC, icv) | V3/intron | 20/30 | Trends in HP, Str. and SC | | | | | 38/39 | 28/43 | 61/77 | 59/73 |
| Efficacy (C9-BAC) | foci DPR | TBD 25% | | | | | | TBD 37% | TBD 11% | TBD 56% | TBD 69% |

TBD, to be determined.

TABLE 7B

Activity of various oligonucleotides.

| Assay | Endpoints | WV-6408 | WV-3688 | WV-8321 | WV-8322 |
|---|---|---|---|---|---|
| Reporter ALS neurons | $IC_{50}$ (nM) V3/intron | 1.32/2.63 66/0 | 5.56/8.65 50/23 | | |
| Stability TLR9 | Ms brain Human | 100 clean | 63.2 clean | 100 | 100 |
| PD (C9-BAC, icv) | V3/intron | KD in HP, Str and SC | Trends in HP, Str. and SC | | |

Table 8. Activity of Various Oligonucleotides.

In Table 8A to 8X, various oligonucleotides were tested at 10 µM in ALS motor neurons (MN). The oligonucleotides differ, inter alia, in base sequence, chemistry pattern (e.g., pattern of 2' sugar modifications), backbone internucleotidic linkage pattern and/or pattern of stereochemistry. In Tables 8A to 8X, shown are residual levels of various transcripts (e.g., all transcripts, or only V3, V1, intron 1, etc.) relative to HPRT1, after treatment with oligonucleotides, wherein 1.000 would represent 10000 relative transcript level (no knockdown) and 0.000 would represent 000 relative transcript level (e.g., 100% knockdown). In Tables 8A to 8X, results from replicate experiments are shown.

TABLE 8A

Activity of various oligonucleotides (residual level of V3 transcripts)

| | | | |
|---|---|---|---|
| WV-3688 | 0.619 | 0.817 | 0.806 |
| WV-7124 | 0.800 | 0.641 | 0.711 |
| WV-6408 | 0.646 | 0.574 | 0.582 |
| WV-7130 | 0.344 | 0.321 | 1.070 |
| WV-8550 | 0.310 | 0.253 | 0.316 |
| WV-8011 | 0.113 | 0.144 | 0.111 |
| WV-8012 | 0.157 | 0.185 | 0.153 |
| WV-2376 | 1.188 | 1.108 | 1.180 |
| WV-9491 | 1.034 | 1.027 | 1.108 |
| WV-5302 | 1.140 | 1.101 | 1.078 |
| WV-6493 | 1.056 | 1.049 | 1.063 |
| WV-8552 | 1.300 | 1.140 | 0.932 |
| water | 0.834 | 1.041 | 0.985 |

TABLE 8B

Activity of various oligonucleotides (residual level of all V transcripts)

| | | | |
|---|---|---|---|
| WV-3688 | 0.845 | 0.881 | 0.862 |
| WV-7124 | 0.799 | 0.845 | 0.893 |
| WV-6408 | 0.810 | 0.751 | 0.767 |
| WV-7130 | 0.788 | 0.542 | |
| WV-8550 | 0.686 | 0.538 | 0.667 |
| WV-8011 | 0.440 | 0.446 | 0.495 |
| WV-8012 | 0.597 | 0.509 | 0.565 |
| WV-2376 | 1.092 | 1.012 | 0.944 |
| WV-9491 | 1.245 | 1.146 | 1.069 |
| WV-5302 | 1.170 | 0.839 | 1.077 |
| WV-6493 | 1.115 | 0.868 | 0.991 |
| WV-8552 | 1.092 | 0.875 | 1.122 |
| water | 1.122 | 0.950 | 1.122 |

TABLE 8C

Activity of various oligonucleotides (residual level of V1 transcripts)

| | | | |
|---|---|---|---|
| WV-3688 | 0.901 | 0.829 | 0.655 |
| WV-7124 | 0.594 | 0.829 | 0.702 |
| WV-6408 | 0.784 | 0.732 | 0.888 |
| WV-7130 | 0.476 | 0.539 | 0.972 |
| WV-8550 | 0.379 | 0.341 | 0.466 |
| WV-8011 | 0.207 | 0.279 | 0.216 |
| WV-8012 | 0.250 | 0.241 | 0.291 |
| WV-2376 | 0.993 | 0.864 | 0.920 |
| WV-9491 | 1.156 | 0.946 | 1.049 |
| WV-5302 | 0.920 | 1.101 | 0.933 |
| WV-6493 | 1.056 | 0.858 | 1.071 |
| WV-8552 | 0.901 | 1.148 | 1.140 |
| Water | 1.197 | 0.846 | 0.999 |

TABLE 8D

Activity of various oligonucleotides (residual level of intron 1 transcripts)

| | | | |
|---|---|---|---|
| WV-3688 | | 0.538 | 0.685 |
| WV-7124 | | 0.681 | 0.538 |
| WV-6408 | 0.516 | 0.408 | 0.509 |
| WV-7130 | 0.399 | 0.523 | |
| WV-8550 | 0.443 | 0.350 | 0.298 |
| WV-8011 | 0.336 | 0.378 | 0.434 |
| WV-8012 | 0.446 | 0.446 | 0.475 |
| WV-2376 | 0.685 | 0.681 | 0.714 |
| WV-9491 | 0.880 | 0.923 | 1.261 |

TABLE 8D-continued

Activity of various oligonucleotides (residual level of intron 1 transcripts)

| | | | |
|---|---|---|---|
| WV-5302 | 0.745 | 1.510 | 1.091 |
| WV-6493 | 0.826 | 0.997 | 1.017 |
| WV-8552 | 1.210 | 0.963 | 1.010 |
| Water | 1.315 | 1.193 | 0.990 |

TABLE 8E

Activity of various oligonucleotides (residual level of V3 transcripts)

| | | | |
|---|---|---|---|
| WV-3688 | 0.619 | 0.817 | 0.806 |
| WV-6408 | 0.646 | 0.574 | 0.582 |
| WV-8550 | 0.310 | 0.253 | 0.316 |
| WV-3662 | 0.105 | 0.121 | 0.119 |
| WV-7188 | 0.065 | 0.074 | 0.062 |
| WV-9494 | 0.009 | 0.006 | 0.009 |
| WV-6936 | 0.795 | 0.972 | 0.800 |
| WV-7027 | 0.741 | 0.882 | 0.900 |
| WV-8595 | 0.926 | 0.741 | 0.919 |
| WV-2376 | 1.188 | 1.108 | 1.180 |
| WV-9491 | 1.034 | 1.027 | 1.108 |
| WV-5302 | 1.140 | 1.101 | 1.078 |
| Water | 0.834 | 1.041 | 0.985 |

TABLE 8F

Activity of various oligonucleotides (residual level of all V transcripts)

| | | | |
|---|---|---|---|
| WV-3688 | 0.845 | 0.881 | 0.862 |
| WV-6408 | 0.810 | 0.751 | 0.767 |
| WV-8550 | 0.686 | 0.538 | 0.667 |
| WV-3662 | 0.160 | 0.155 | 0.145 |
| WV-7188 | 0.116 | 0.116 | 0.108 |
| WV-9494 | 0.013 | 0.010 | 0.012 |
| WV-6936 | 1.099 | 1.084 | 0.957 |
| WV-7027 | 1.040 | 0.991 | 0.931 |
| WV-8595 | 1.280 | 1.005 | 1.186 |
| WV-2376 | 1.092 | 1.012 | 0.944 |
| WV-9491 | 1.245 | 1.146 | 1.069 |
| WV-5302 | 1.170 | 0.839 | 1.077 |
| water | 1.122 | 0.950 | 1.122 |

TABLE 8G

Activity of various oligonucleotides (residual level of V1 transcripts)

| | | | |
|---|---|---|---|
| WV-3688 | 0.901 | 0.829 | 0.655 |
| WV-6408 | 0.784 | 0.732 | 0.888 |
| WV-8550 | 0.379 | 0.341 | 0.466 |
| WV-3662 | 0.185 | 0.099 | 0.182 |
| WV-7188 | 0.114 | 0.128 | 0.106 |
| WV-9494 | 0.023 | 0.018 | 0.026 |
| WV-6936 | 0.913 | 0.939 | 0.907 |
| WV-7027 | 0.702 | 0.757 | 0.926 |
| WV-8595 | 0.952 | 0.959 | 0.959 |
| WV-2376 | 0.993 | 0.864 | 0.920 |
| WV-9491 | 1.156 | 0.946 | 1.049 |
| WV-5302 | 0.920 | 1.101 | 0.933 |
| Water | 1.197 | 0.846 | 0.999 |

TABLE 8H

Activity of various oligonucleotides (residual level of intron 1 transcripts)

| | | | |
|---|---|---|---|
| WV-3688 | | 0.538 | 0.685 |
| WV-6408 | 0.516 | 0.408 | 0.509 |
| WV-8550 | 0.443 | 0.350 | 0.298 |
| WV-3662 | | 0.700 | 0.576 |
| WV-7188 | 0.787 | 0.455 | 0.527 |
| WV-9494 | 0.534 | 0.302 | 0.512 |
| WV-6936 | 0.676 | 0.815 | 0.930 |
| WV-7027 | 1.500 | 0.936 | 0.976 |
| WV-8595 | 0.983 | 1.361 | 0.930 |
| WV-2376 | 0.685 | 0.681 | 0.714 |
| WV-9491 | 0.880 | 0.923 | 1.261 |
| WV-5302 | 0.745 | 1.510 | 1.091 |
| Water | 1.315 | 1.193 | 0.990 |

TABLE 8I

Activity of various oligonucleotides (residual level of V3 transcripts)

| | | | |
|---|---|---|---|
| WV-8550 | 0.310 | 0.253 | 0.316 |
| WV-8011 | 0.113 | 0.144 | 0.111 |
| WV-8012 | 0.157 | 0.185 | 0.153 |
| WV-9493 | 1.013 | 0.978 | 1.034 |
| WV-9492 | 0.784 | 0.811 | 0.741 |
| WV-3536 | 0.789 | 0.510 | 0.678 |
| WV-2376 | 1.188 | 1.108 | 1.180 |
| Water | 0.834 | 1.041 | 0.985 |

TABLE 8J

Activity of various oligonucleotides (residual level of all V transcripts)

| | | | |
|---|---|---|---|
| WV-8550 | 0.686 | 0.538 | 0.667 |
| WV-8011 | 0.440 | 0.446 | 0.495 |
| WV-8012 | 0.597 | 0.509 | 0.565 |
| WV-9493 | 1.122 | 1.084 | 1.069 |
| WV-9492 | 1.107 | 0.816 | 0.924 |
| WV-3536 | 0.991 | 0.783 | 0.977 |
| WV-2376 | 1.092 | 1.012 | 0.944 |
| water | 1.122 | 0.950 | 1.122 |

TABLE 8K

Activity of various oligonucleotides (residual level of V1 transcripts)

| | | | |
|---|---|---|---|
| WV-8550 | 0.379 | 0.341 | 0.466 |
| WV-8011 | 0.207 | 0.279 | 0.216 |
| WV-8012 | 0.250 | 0.241 | 0.291 |
| WV-9493 | 0.933 | 0.979 | 0.952 |
| WV-9492 | 0.712 | 0.737 | 0.858 |
| WV-3536 | 0.687 | 0.493 | 0.598 |
| WV-2376 | 0.993 | 0.864 | 0.920 |
| Water | 1.197 | 0.846 | 0.999 |

TABLE 8L

Activity of various oligonucleotides (residual level of intron 1 transcripts)

| | | | |
|---|---|---|---|
| WV-8550 | 0.443 | 0.350 | 0.298 |
| WV-8011 | 0.336 | 0.378 | 0.434 |
| WV-8012 | 0.446 | 0.446 | 0.475 |

TABLE 8L-continued

Activity of various oligonucleotides (residual level of intron 1 transcripts)

| | | | |
|---|---|---|---|
| WV-9493 | 0.917 | 0.838 | 0.917 |
| WV-9492 | 1.075 | 0.714 | |
| WV-3536 | 0.710 | 0.969 | 1.061 |
| WV-2376 | 0.685 | 0.681 | 0.714 |
| Water | 1.315 | 1.193 | 0.990 |

TABLE 8M

Activity of various oligonucleotides (residual level of V3 transcripts)

| | | | |
|---|---|---|---|
| WV-3688 | 0.751 | 0.677 | 0.573 |
| WV-7124 | 0.546 | 0.482 | 0.799 |
| WV-6408 | 0.649 | 0.593 | 0.573 |
| WV-7130 | 0.365 | 0.343 | 0.389 |
| WV-8550 | 0.297 | 0.286 | 0.260 |
| WV-8011 | 0.135 | 0.123 | 0.097 |
| WV-8012 | 0.111 | 0.162 | 0.106 |
| WV-2376 | 0.833 | 1.033 | 1.092 |
| WV-3542 | 0.977 | 1.069 | 0.970 |
| WV-9491 | 1.047 | 0.899 | 1.011 |
| WV-5302 | 1.011 | 0.944 | 1.162 |
| WV-6493 | 0.984 | 1.099 | 1.502 |
| WV-8552 | 1.146 | 1.077 | 0.991 |
| water | 0.899 | 1.122 | 1.122 |

TABLE 8N

Activity of various oligonucleotides (residual level of all V transcripts)

| | | | |
|---|---|---|---|
| WV-3688 | 0.940 | 0.847 | 0.813 |
| WV-7124 | 0.737 | 0.764 | 1.022 |
| WV-6408 | 0.774 | 0.717 | 0.646 |
| WV-7130 | 0.591 | 0.559 | 0.525 |
| WV-8550 | 0.567 | 0.536 | 0.555 |
| WV-8011 | 0.451 | 0.421 | 0.421 |
| WV-8012 | 0.451 | 0.429 | 0.470 |
| WV-2376 | 1.182 | 1.029 | 1.058 |
| WV-3542 | 0.966 | 0.902 | 0.871 |
| WV-9491 | 1.087 | 0.973 | 0.933 |
| WV-5302 | 0.902 | 0.966 | 0.980 |
| WV-6493 | 1.043 | 0.966 | 0.947 |
| WV-8552 | 1.149 | 1.087 | 0.947 |
| water | 0.895 | 1.029 | 0.987 |

TABLE 8O

Activity of various oligonucleotides (residual level of V1 transcripts)

| | | | |
|---|---|---|---|
| WV-3688 | 0.846 | 0.920 | 0.858 |
| WV-7124 | 0.829 | 0.779 | 1.064 |
| WV-6408 | 0.946 | 0.801 | 0.790 |
| WV-7130 | 0.758 | 0.664 | 0.582 |
| WV-8550 | 0.562 | 0.426 | 0.384 |
| WV-8011 | 0.213 | 0.235 | 0.272 |
| WV-8012 | 0.368 | 0.283 | 0.351 |
| WV-2376 | 1.086 | 0.835 | 0.858 |
| WV-3542 | 0.846 | 1.101 | 0.972 |
| WV-9491 | 0.939 | 1.140 | 0.779 |
| WV-5302 | 0.979 | 1.035 | 1.274 |
| WV-6493 | 1.181 | 1.035 | 0.993 |
| WV-8552 | 1.214 | 0.966 | 0.926 |
| water | 1.079 | 0.870 | 0.889 |

TABLE 8P

Activity of various oligonucleotides (residual level of intron 1 transcripts)

| | | | |
|---|---|---|---|
| WV-3688 | 0.324 | 0.481 | 0.626 |
| WV-7124 | 0.734 | 0.354 | 0.181 |
| WV-6408 | 0.261 | 0.340 | 0.548 |
| WV-7130 | 0.452 | 0.288 | 0.449 |
| WV-8550 | 0.484 | 0.382 | 0.424 |
| WV-8011 | 0.391 | 0.296 | |
| WV-8012 | 0.461 | 0.508 | 0.375 |
| WV-2376 | | 1.038 | 1.269 |
| WV-3542 | 1.184 | 0.879 | 0.600 |
| WV-9491 | 1.060 | 1.023 | 1.674 |
| WV-5302 | 1.217 | 1.295 | 1.097 |
| WV-6493 | 1.136 | 1.418 | |
| WV-8552 | 1.128 | 1.332 | 0.776 |
| water | 0.968 | 0.903 | 0.685 |

TABLE 8Q

Activity of various oligonucleotides (residual level of V3 transcripts)

| | | | |
|---|---|---|---|
| WV-3688 | 0.751 | 0.677 | 0.573 |
| WV-6408 | 0.649 | 0.593 | 0.573 |
| WV-8550 | 0.297 | 0.286 | 0.260 |
| WV-3662 | 0.267 | 0.216 | 0.248 |
| WV-7118 | 0.311 | 0.219 | 0.249 |
| WV-9494 | 0.031 | 0.043 | 0.042 |
| WV-6936 | 0.827 | 0.874 | 0.667 |
| WV-7027 | 0.868 | 0.788 | 0.874 |
| WV-8595 | 0.725 | 0.681 | 0.822 |
| WV-2376 | 0.833 | 1.033 | 1.092 |
| WV-3542 | 0.977 | 1.069 | 0.970 |
| WV-9491 | 1.047 | 0.899 | 1.011 |
| water | 0.899 | 1.122 | 1.122 |

TABLE 8R

Activity of various oligonucleotides (residual level of all V transcripts)

| | | | |
|---|---|---|---|
| WV-3688 | 0.940 | 0.847 | 0.813 |
| WV-6408 | 0.774 | 0.717 | 0.646 |
| WV-8550 | 0.567 | 0.536 | 0.555 |
| WV-3662 | 0.261 | 0.235 | 0.238 |
| WV-7118 | 0.276 | 0.263 | 0.291 |
| WV-9494 | 0.046 | 0.043 | 0.047 |
| WV-6936 | 1.014 | 1.007 | 1.007 |
| WV-7027 | 1.065 | 0.966 | 0.947 |
| WV-8595 | 0.994 | 0.818 | 0.830 |
| WV-2376 | 1.182 | 1.029 | 1.058 |
| WV-3542 | 0.966 | 0.902 | 0.871 |
| WV-9491 | 1.087 | 0.973 | 0.933 |
| water | 0.895 | 1.029 | 0.987 |

TABLE 8S

Activity of various oligonucleotides (residual level of V1 transcripts)

| | | | |
|---|---|---|---|
| WV-3688 | 0.846 | 0.920 | 0.858 |
| WV-6408 | 0.946 | 0.801 | 0.790 |
| WV-8550 | 0.562 | 0.426 | 0.384 |
| WV-3662 | 0.299 | 0.272 | 0.381 |
| WV-7118 | 0.387 | 0.358 | 0.325 |
| WV-9494 | 0.065 | 0.050 | 0.063 |
| WV-6936 | 0.712 | 0.966 | 1.035 |
| WV-7027 | 0.959 | 0.952 | 1.049 |

TABLE 8S-continued

Activity of various oligonucleotides (residual level of V1 transcripts)

| | | | |
|---|---|---|---|
| WV-8595 | 0.742 | 0.790 | 0.841 |
| WV-2376 | 1.086 | 0.835 | 0.858 |
| WV-3542 | 0.846 | 1.101 | 0.972 |
| WV-9491 | 0.939 | 1.140 | 0.779 |
| water | 1.079 | 0.870 | 0.889 |

TABLE 8T

Activity of various oligonucleotides (residual level of intron 1 transcripts)

| | | | |
|---|---|---|---|
| WV-3688 | 0.324 | 0.481 | 0.626 |
| WV-6408 | 0.261 | 0.340 | 0.548 |
| WV-8550 | 0.484 | 0.382 | 0.424 |
| WV-3662 | 0.995 | 0.831 | 0.891 |
| WV-7118 | 0.596 | 0.724 | 0.584 |
| WV-9494 | 0.699 | 0.455 | 0.556 |
| WV-6936 | | 1.144 | 0.948 |
| WV-7027 | 0.729 | 1.176 | 1.260 |
| WV-8595 | 1.045 | 0.837 | 1.209 |
| WV-2376 | | 1.038 | 1.269 |
| WV-3542 | 1.184 | 0.879 | 0.600 |
| WV-9491 | 1.060 | 1.023 | |
| water | 0.968 | 0.903 | 0.685 |

TABLE 8U

Activity of various oligonucleotides (residual level of V3 transcripts)

| | | | |
|---|---|---|---|
| WV-8550 | 0.297 | 0.286 | 0.260 |
| WV-8011 | 0.135 | 0.123 | 0.097 |
| WV-8012 | 0.111 | 0.162 | 0.106 |
| WV-9493 | 0.761 | 0.705 | 0.649 |
| WV-9492 | 0.506 | 0.520 | 0.478 |
| WV-3536 | 0.663 | 0.606 | 0.805 |
| WV-2376 | 0.833 | 1.033 | 1.092 |
| water | 0.899 | 1.122 | 1.122 |

TABLE 8V

Activity of various oligonucleotides (residual level of all V transcripts)

| | | | |
|---|---|---|---|
| WV-8550 | 0.567 | 0.536 | 0.555 |
| WV-8011 | 0.451 | 0.421 | 0.421 |
| WV-8012 | 0.451 | 0.429 | 0.470 |
| WV-9493 | 1.014 | 0.824 | 0.807 |
| WV-9492 | 0.859 | 0.818 | 0.801 |
| WV-3536 | 0.830 | 0.790 | 1.126 |
| WV-2376 | 1.182 | 1.029 | 1.058 |
| water | 0.895 | 1.029 | 0.987 |

TABLE 8W

Activity of various oligonucleotides (residual level of V1 transcripts)

| | | | |
|---|---|---|---|
| WV-8550 | 0.562 | 0.426 | 0.384 |
| WV-8011 | 0.213 | 0.235 | 0.272 |
| WV-8012 | 0.368 | 0.283 | 0.351 |
| WV-9493 | 1.049 | 0.870 | 0.586 |
| WV-9492 | 0.993 | 0.795 | 0.758 |
| WV-3536 | 0.683 | 0.697 | 1.021 |
| WV-2376 | 1.086 | 0.835 | 0.858 |
| water | 1.079 | 0.870 | 0.889 |

TABLE 8X

Activity of various oligonucleotides (residual level of intron 1 transcripts)

| | | | |
|---|---|---|---|
| WV-8550 | 0.484 | 0.382 | 0.424 |
| WV-8011 | 0.391 | 0.296 | 0.781 |
| WV-8012 | 0.461 | 0.508 | 0.375 |
| WV-9493 | 0.391 | 0.942 | 0.724 |
| WV-9492 | 0.481 | 0.989 | 0.942 |
| WV-3536 | 0.729 | 0.948 | 0.580 |
| WV-2376 | | 1.038 | 1.269 |
| water | 0.968 | 0.903 | 0.685 |

Table 9. Activity of Various Oligonucleotides.

In Tables 9A to 9D, various oligonucleotides were tested at 1 μM in ALS motor neurons (MN). The oligonucleotides differ, inter alia, in base sequence, chemistry pattern (e.g., pattern of 2' sugar modifications), backbone internucleotidic linkage pattern and/or pattern of stereochemistry. In Tables 9A to 9D, shown are residual levels of various transcripts (e.g., all transcripts, or only V3, V1, intron 1, etc.) relative to HPRT1, after treatment with oligonucleotides, wherein 1.000 would represent 100% relative transcript level (no knockdown) and 0.000 would represent 0% relative transcript level (e.g., 100% knockdown). In Tables 9A to 9D, results from replicate experiments are shown.

TABLE 9A

Activity of various oligonucleotides (residual level of V3 transcripts)

| | | |
|---|---|---|
| WV-8550 | 0.557 | 0.672 |
| WV-8011 | 0.389 | 0.417 |
| WV-9505 | 0.370 | 0.378 |
| WV-9506 | 0.465 | 0.446 |
| WV-9507 | 0.799 | 0.822 |
| WV-9508 | 0.502 | 0.478 |
| WV-9509 | 0.428 | 0.397 |
| WV-9510 | 0.589 | 0.478 |
| WV-2376 | 1.047 | 1.018 |
| water | 0.899 | 1.122 |

TABLE 9B

Activity of various oligonucleotides (residual level of all V transcripts)

| | | |
|---|---|---|
| WV-8550 | 0.683 | 0.790 |
| WV-8011 | 0.571 | 0.567 |
| WV-9505 | 0.651 | 0.651 |
| WV-9506 | 0.824 | 0.743 |
| WV-9507 | 0.835 | 0.847 |
| WV-9508 | 0.717 | 0.679 |
| WV-9509 | 0.703 | 0.688 |
| WV-9510 | 0.801 | 0.830 |
| WV-2376 | 1.198 | 1.149 |
| water | 0.895 | 1.029 |

TABLE 9C

Activity of various oligonucleotides (residual level of V1 transcripts)

| | | |
|---|---|---|
| WV-8550 | 0.758 | 0.979 |
| WV-8011 | 1.000 | 0.818 |
| WV-9505 | 0.702 | 0.603 |
| WV-9506 | 0.476 | 0.972 |
| WV-9507 | 0.993 | 1.265 |

TABLE 9C-continued

Activity of various oligonucleotides
(residual level of V1 transcripts)

| | | |
|---|---|---|
| WV-9508 | 0.870 | 0.926 |
| WV-9509 | 0.907 | 0.806 |
| WV-9510 | 1.109 | 1.049 |
| WV-2376 | 1.301 | 1.310 |
| water | 1.079 | 0.870 |

TABLE 9D

Activity of various oligonucleotides (residual level of intron 1 transcripts)

| | | |
|---|---|---|
| WV-8550 | 0.781 | 0.533 |
| WV-8011 | 1.002 | 0.600 |
| WV-9505 | 1.009 | 0.916 |
| WV-9506 | 0.910 | 0.765 |
| WV-9507 | 0.634 | 0.843 |
| WV-9508 | 0.724 | 0.657 |
| WV-9509 | 0.512 | 0.873 |
| WV-9510 | 0.245 | 1.045 |
| WV-2376 | 1.128 | 1.226 |
| water | 0.968 | 0.903 |

Table 10. Activity of Various Oligonucleotides.

In Tables 10A to 10B, various oligonucleotides were tested at various concentrations from 0.01 to 10 μM in ALS motor neurons (MN). The oligonucleotides differ, inter alia, in backbone internucleotidic linkage pattern and/or pattern of stereochemistry. In the DNA core, various oligonucleotides comprise one or two SSO [5'-PS (Phosphorothioate) in the Sp configuration, PS in the Sp configuration, PO (Phosphodiester)-3'] or one or two SSR [5'-PS (Phosphorothioate) in the Sp configuration, PS in the Sp configuration, PS in the Rp configuration-3']. In Tables 10A to 10B, shown are residual levels of various transcripts (e.g., all transcripts, or only V3), relative to HPRT1, after treatment with oligonucleotides, wherein 1.000 would represent 100% relative transcript level (no knockdown) and 0.000 would represent 0% relative transcript level (e.g., 100% knockdown). In Tables 10A to 10B, results from replicate experiments are shown.

TABLE 10A

Activity of various oligonucleotides
(residual level of all V transcripts)

| | WV-8011 | WV-9394 | WV-8012 | WV-9395 |
|---|---|---|---|---|
| 10 uM | 0.617 | 0.621 | 0.639 | 0.680 |
| | 0.613 | 0.643 | 0.617 | 0.760 |
| 2.5 uM | 0.724 | 0.724 | 0.739 | 0.754 |
| | 0.699 | 0.704 | 0.680 | 0.849 |
| 0.625 uM | 0.843 | 0.855 | 0.814 | 0.897 |
| | 0.792 | 0.855 | 0.831 | 0.897 |
| 0.16 uM | 0.891 | 0.897 | 0.849 | 0.948 |
| | 0.982 | 0.968 | 0.922 | 0.879 |
| 0.04 uM | 1.038 | 1.097 | 1.009 | 0.962 |
| | 1.082 | 0.975 | 0.942 | 1.082 |
| 0.01 uM | 1.002 | 1.024 | 1.009 | 1.002 |
| | 0.935 | 0.948 | 0.922 | 0.955 |

TABLE 10B

Activity of various oligonucleotides
(residual level of V3 transcripts)

| | WV-8011 | WV-9394 | WV-8012 | WV-9395 |
|---|---|---|---|---|
| 10 uM | 0.023 | 0.042 | 0.026 | 0.026 |
| | 0.033 | 0.032 | 0.023 | 0.025 |
| 2.5 uM | 0.061 | 0.072 | 0.049 | 0.061 |
| | 0.050 | 0.055 | 0.060 | |
| 0.625 uM | 0.125 | 0.147 | 0.133 | 0.130 |
| | 0.152 | 0.146 | 0.139 | 0.169 |
| 0.16 uM | 0.266 | 0.318 | 0.227 | 0.291 |
| | 0.236 | 0.310 | 0.277 | 0.332 |
| 0.04 uM | 0.726 | 0.668 | 0.578 | 0.687 |
| | 0.711 | 0.628 | 0.444 | 0.906 |
| 0.01 uM | 0.992 | 0.932 | 0.817 | 0.992 |
| | 0.888 | 0.978 | 0.932 | 0.900 |

In Tables 11A and 11B, various oligonucleotides were tested at 10 μM in ALS motor neurons (MN). The oligonucleotides differ, inter alia, in base sequence, pattern of internucleotidic linkages, and pattern of chemistry (e.g., pattern of 2'-modifications of sugars), wherein some oligonucleotides have a symmetric (e.g., Table 11B) and some have an asymmetric format (e.g., Table 11A). In Tables 11A and 11B, shown are residual levels of V3 transcript relative to HPRT1, after treatment with oligonucleotides, wherein 1.000 would represent 10000 relative transcript level (no knockdown) and 0.000 would represent 000 relative transcript level (e.g., 100% knockdown). In Tables 11A and 11B, results from replicate experiments are shown. In this and other Tables, all positive and negative controls performed in various experiments are not necessarily shown.

TABLE 11A

Activity of various oligonucleotides
(residual level of V3 transcripts)

| | | | |
|---|---|---|---|
| WV-10406 | 0.250 | 0.267 | 0.264 |
| WV-10407 | 0.301 | 0.314 | 0.297 |
| WV-10408 | 0.201 | 0.211 | 0.228 |
| WV-10409 | 0.301 | 0.314 | 0.279 |
| WV-10410 | 0.301 | 0.363 | 0.287 |
| WV-10411 | 0.381 | 0.332 | 0.325 |
| WV-10412 | 0.368 | 0.414 | 0.400 |
| WV-10413 | 0.492 | 0.428 | 0.459 |
| WV-10414 | 0.341 | 0.358 | 0.437 |
| WV-10415 | 0.160 | 0.239 | 0.231 |
| WV-10416 | 0.239 | 0.239 | 0.214 |
| WV-8550 | 0.173 | 0.184 | 0.200 |
| WV-10417 | 0.309 | 0.479 | 0.411 |
| WV-10418 | 0.198 | 0.279 | 0.244 |
| WV-10419 | 0.314 | 0.420 | 0.332 |
| WV-10420 | 0.453 | 0.517 | 0.546 |
| WV-10421 | 0.447 | 0.658 | 0.539 |
| WV-10422 | 0.485 | 0.444 | 0.577 |
| WV-10423 | 0.573 | 0.602 | 0.479 |
| WV-10424 | 0.711 | 0.741 | 0.811 |
| WV-10425 | 0.558 | 0.341 | 0.403 |
| WV-9491 | 0.984 | 1.107 | 1.317 |
| WV-3662 | 0.047 | 0.051 | 0.058 |
| WV-10426 | 0.531 | | 1.005 |

TABLE 11B

Activity of various oligonucleotides
(residual level of V3 transcripts)

| | | | |
|---|---|---|---|
| WV-6936 | 0.517 | 0.420 | 0.502 |
| WV-6989 | 0.746 | 0.828 | 0.767 |
| WV-7002 | 0.691 | 0.726 | 0.598 |

TABLE 11B-continued

Activity of various oligonucleotides
(residual level of V3 transcripts)

| | | | |
|---|---|---|---|
| WV-6474 | 0.649 | 0.778 | 0.716 |
| WV-3688 | 0.581 | 0.606 | 0.593 |
| WV-6969 | | 0.677 | 0.558 |
| WV-6951 | 0.672 | 0.636 | 0.731 |
| WV-3690 | 0.767 | 0.736 | 0.677 |
| WV-6952 | 0.857 | 0.799 | 0.731 |
| WV-6976 | 0.658 | 0.558 | 0.645 |
| WV-6981 | 0.686 | 0.731 | 0.663 |
| WV-6982 | 0.863 | 0.751 | 0.658 |
| WV-9694 | 0.610 | 0.663 | 0.645 |
| WV-9695 | 0.663 | 0.636 | 0.585 |
| WV-3662 | 0.043 | 0.038 | 0.029 |
| WV-2376 | 0.899 | 1.040 | 0.822 |

Table 12. Activity of Various Oligonucleotides.

In Tables 12A and 12B, various oligonucleotides were tested at 2.5 or 10 µM in ALS motor neurons (MN). The oligonucleotides differ, inter alia, in base sequence, pattern of internucleotidic linkages, and pattern of chemistry (e.g., pattern of 2'-modifications of sugars), wherein some oligonucleotides have a symmetric and some have an asymmetric format. In Tables 12A and 12B, shown are residual levels of V3 or all V transcript relative to HPRT1, after treatment with oligonucleotides, wherein 1.000 would represent 1000 relative transcript level (no knockdown) and 0.000 would represent 0% relative transcript level (e.g., 100% knockdown). In Tables 12A and 12B, results from replicate experiments are shown. In this and other Tables, all positive and negative controls performed in various experiments are not necessarily shown.

TABLE 12A

Activity of various oligonucleotides
(residual level of V3 transcripts)

| | | | |
|---|---|---|---|
| WV-6408 (10 uM) | 0.564 | 0.740 | 0.714 |
| WV-6408 (2.5 uM) | 0.700 | 0.745 | 0.657 |
| WV-12480 (10 uM) | 0.936 | 1.024 | 0.880 |
| WV-12480 (2.5 uM) | 0.956 | 0.873 | 0.798 |
| WV-12481 (10 uM) | 0.541 | 0.667 | 0.657 |
| WV-12481 (2.5 uM) | 0.676 | 0.626 | 0.676 |
| WV-12482 (10 uM) | 0.378 | 0.407 | 0.357 |
| WV-12482 (2.5 uM) | 0.431 | 0.462 | 0.475 |
| WV-12483 (10 uM) | 0.446 | 0.458 | 0.458 |
| WV-12483 (2.5 uM) | 0.530 | 0.478 | 0.505 |
| WV-12484 (10 uM) | 0.580 | 0.667 | 0.705 |
| WV-12484 (2.5 uM) | 0.530 | 0.662 | 0.714 |
| WV-12486 (10 uM) | 0.527 | 0.597 | 0.657 |
| WV-12486 (2.5 uM) | 0.538 | 0.719 | 0.667 |
| WV-8548 (10 uM) | 0.372 | 0.383 | 0.367 |
| WV-8548 (2.5 uM) | 0.523 | 0.509 | 0.516 |
| WV-12439 (10 uM) | 0.419 | 0.549 | 0.446 |
| WV-12439 (2.5 uM) | 0.755 | 0.609 | 0.478 |
| WV-12440 (10 uM) | 0.352 | 0.485 | 0.462 |
| WV-12440 (2.5 uM) | 0.635 | 0.485 | 0.588 |
| WV-12441 (10 uM) | | 0.246 | 0.261 |
| WV-12441 (2.5 uM) | 0.434 | 0.360 | 0.357 |
| WV-12442 (10 uM) | 0.861 | | 0.505 |
| WV-12442 (2.5 uM) | 0.671 | 0.553 | |
| WV-12443 (10 uM) | | | |
| WV-12443 (2.5 uM) | 0.481 | 0.613 | 0.315 |
| WV-12444 (10 uM) | 0.251 | 0.391 | 0.367 |
| WV-12444 (2.5 uM) | | 0.471 | 0.561 |
| WV-12446 (10 uM) | 0.481 | 0.495 | 0.564 |
| WV-12446 (2.5 uM) | | 0.644 | 0.850 |
| WV-12445 (10 uM) | 0.657 | 0.605 | 0.588 |
| WV-12445 (2.5 uM) | | 0.662 | 0.880 |
| WV-12447 (10 uM) | 0.286 | 0.491 | 0.329 |
| WV-12447 (2.5 uM) | | 0.618 | 0.564 |
| WV-12448 (10 uM) | 0.191 | 0.320 | 0.214 |

TABLE 12A-continued

Activity of various oligonucleotides
(residual level of V3 transcripts)

| | | | |
|---|---|---|---|
| WV-12448 (2.5 uM) | | 0.468 | 0.440 |
| WV-12449 (10 uM) | 0.505 | 0.465 | |
| WV-12449 (2.5 uM) | | 0.597 | 0.478 |
| WV-12450 (10 uM) | | | |
| WV-12450 (2.5 uM) | 0.491 | 0.534 | 0.553 |
| WV-12451 (10 uM) | 0.443 | 0.458 | 0.462 |
| WV-12451 (2.5 uM) | 0.545 | 0.452 | 0.502 |
| WV-8550 (10 uM) | 0.273 | 0.298 | 0.278 |
| WV-8550 (2.5 uM) | 0.478 | 0.488 | 0.440 |
| WV-9491 (10 uM) | 0.635 | 1.053 | 1.010 |
| WV-9491 (2.5 uM) | 1.106 | 0.815 | 0.850 |
| WV-3542 (10 uM) | 0.962 | 1.053 | 1.061 |
| WV-3542 (2.5 uM) | 1.113 | 0.983 | 1.039 |

TABLE 12B

Activity of various oligonucleotides
(residual level of all V transcripts)

| | | | |
|---|---|---|---|
| WV-6408 (10 uM) | 0.861 | 0.843 | 0.861 |
| WV-6408 (2.5 uM) | 0.861 | 0.949 | 0.861 |
| WV-12480 (10 uM) | 0.982 | 0.982 | 0.969 |
| WV-12480 (2.5 uM) | 0.923 | 0.910 | 0.956 |
| WV-12481 (10 uM) | 0.838 | 0.832 | 0.809 |
| WV-12481 (2.5 uM) | 0.838 | 0.820 | 0.867 |
| WV-12482 (10 uM) | 0.714 | 0.714 | 0.653 |
| WV-12482 (2.5 uM) | 0.699 | 0.744 | 0.734 |
| WV-12483 (10 uM) | 0.976 | 0.936 | 0.936 |
| WV-12483 (2.5 uM) | 0.820 | 0.861 | 0.917 |
| WV-12484 (10 uM) | 0.996 | 0.969 | 0.976 |
| WV-12484 (2.5 uM) | 0.929 | 0.923 | 0.982 |
| WV-12486 (10 uM) | 0.760 | 0.820 | 0.724 |
| WV-12486 (2.5 uM) | 0.782 | 0.843 | 0.832 |
| WV-8548 (10 uM) | 0.729 | 0.760 | 0.771 |
| WV-8548 (2.5 uM) | 0.771 | 0.826 | 0.798 |
| WV-12439 (10 uM) | 0.898 | 0.873 | 0.855 |
| WV-12439 (2.5 uM) | 0.949 | 0.873 | 0.820 |
| WV-12440 (10 uM) | 0.803 | 0.809 | 0.771 |
| WV-12440 (2.5 uM) | 0.849 | 0.792 | 0.771 |
| WV-12441 (10 uM) | 0.431 | 0.657 | 0.685 |
| WV-12441 (2.5 uM) | 0.657 | 0.719 | 0.695 |
| WV-12442 (10 uM) | 0.976 | 0.861 | 0.996 |
| WV-12442 (2.5 uM) | 0.929 | 0.461 | 0.495 |
| WV-12443 (10 uM) | 0.923 | 0.798 | 0.996 |
| WV-12443 (2.5 uM) | 0.484 | 0.879 | 0.601 |
| WV-12444 (10 uM) | 0.653 | 0.680 | 0.666 |
| WV-12444 (2.5 uM) | | 0.734 | 0.792 |
| WV-12446 (10 uM) | 0.820 | 0.849 | 0.849 |
| WV-12446 (2.5 uM) | | 0.838 | 0.898 |
| WV-12445 (10 uM) | 0.861 | 0.849 | 0.855 |
| WV-12445 (2.5 uM) | | 0.898 | 0.898 |
| WV-12447 (10 uM) | 0.744 | 0.755 | 0.739 |
| WV-12447 (2.5 uM) | | 0.782 | 0.798 |
| WV-12448 (10 uM) | 0.704 | 0.699 | 0.662 |
| WV-12448 (2.5 uM) | | 0.792 | 0.776 |
| WV-12449 (10 uM) | 1.098 | 0.676 | 0.443 |
| WV-12449 (2.5 uM) | | 0.873 | 0.861 |
| WV-12450 (10 uM) | 0.580 | 0.695 | 0.704 |
| WV-12450 (2.5 uM) | 0.917 | 0.923 | 0.996 |
| WV-12451 (10 uM) | 0.832 | 0.885 | 0.820 |
| WV-12451 (2.5 uM) | 0.861 | 0.792 | 0.867 |
| WV-8550 (10 uM) | 0.724 | 0.739 | 0.771 |
| WV-8550 (2.5 uM) | 0.803 | 0.815 | 0.873 |
| WV-9491 (10 uM) | 0.982 | 0.969 | 1.060 |
| WV-9491 (2.5 uM) | 0.962 | 0.996 | 1.053 |
| WV-3542 (10 uM) | 1.017 | 1.038 | 1.024 |
| WV-3542 (2.5 uM) | 1.031 | 0.879 | 0.949 |

Table 13. Activity of Various Oligonucleotides.

In Tables 13A to 13F, various oligonucleotides were tested in c9 BAC mice; mice were administered oligonucleotides ICV in two doses, each 50 µg, one week apart, and tissue was collected a week after the second dose. The oligonucleotides differ, inter alia, in base sequence, pattern of internucleotidic linkages, and pattern of chemistry (e.g., pattern of 2'-modifications of sugars), wherein some oligonucleotides have a symmetric and some have an asymmetric format. In Tables 13A to 13F, shown are residual levels of transcriptions [e.g., all transcripts (all V) or only V3] relative to HPRT1, after treatment with oligonucleotides, wherein 1.000 would represent 10000 relative transcript level (no knockdown) and 0.000 would represent 0% relative transcript level (e.g., 100% knockdown). Results from replicate experiments are shown. Tissues evaluated: SC, spinal cord; and CX, cerebral cortex.

TABLE 13A

Activity of various oligonucleotides (residual level of all V transcripts in CX)

| PBS | WV-8548 | WV-12482 | WV-12483 | WV-12444 | WV-12448 |
|---|---|---|---|---|---|
| 1.011 | 0.798 | 0.676 | 0.735 | 0.705 | 0.523 |
| 0.862 | 1.011 | 0.553 | 0.787 | 0.963 | 0.530 |
| 1.032 | 0.969 | 0.745 | 0.725 | 0.950 | 0.549 |
| 1.091 | 0.976 | 0.720 | 0.777 | 0.997 | 0.827 |
| 1.039 | 0.950 | 0.750 | 0.844 | 0.844 | 0.715 |
| 0.997 | 0.838 | 0.868 | 0.740 | 0.917 | 0.976 |
| 0.856 | 0.771 | 0.333 | 0.761 | 0.844 | 0.662 |
| 1.114 | 0.850 | 0.750 | 0.671 | 0.705 | 0.690 |

TABLE 13B

Activity of various oligonucleotides (residual level of V3 transcripts in CX)

| PBS | WV-8548 | WV-12482 | WV-12483 | WV-12444 | WV-12448 |
|---|---|---|---|---|---|
| 0.935 | 0.754 | 0.708 | 0.684 | 0.739 | 0.439 |
| 0.897 | 1.089 | 0.537 | 0.643 | 0.968 | 0.556 |
| 1.002 | 0.891 | 0.666 | 0.670 | 1.059 | 0.413 |
| 1.009 | 0.928 | 0.704 | 0.781 | 1.009 | 0.775 |
| 0.968 | 0.981 | 0.792 | 0.497 | 0.837 | 0.643 |
| 1.167 | 0.749 | 0.928 | 0.568 | 0.848 | 1.030 |
| 0.872 | 0.533 | 0.229 | 0.814 | 0.803 | 0.759 |
| 1.151 | 0.968 | 0.968 | 0.694 | 0.575 | 0.808 |

TABLE 13C

Activity of various oligonucleotides (residual level of intron 1/AS transcripts in CX)

| PBS | WV-8548 | WV-12482 | WV-12483 | WV-12444 | WV-12448 |
|---|---|---|---|---|---|
| 0.426 | 1.124 | 1.248 | 0.619 | 2.712 | 1.256 |
| 0.441 | 0.840 | 1.944 | 2.113 | 2.344 | 2.280 |
| 0.852 | 0.846 |  | 3.072 | 0.993 | 2.377 |
| 1.213 | 0.646 |  | 3.137 | 0.888 |  |
| 1.433 | 0.325 |  | 3.704 | 1.109 | 2.693 |
| 1.230 |  | 1.453 | 3.247 |  | 1.568 |
|  | 1.180 | 0.673 |  |  | 1.740 |
| 1.404 | 1.827 | 0.301 | 1.931 | 2.218 | 0.864 |

TABLE 13D

Activity of various oligonucleotides (residual level of all V transcripts in SC)

| PBS | WV-8548 | WV-12482 | WV-12483 | WV-12444 | WV-12448 |
|---|---|---|---|---|---|
| 1.635 | 0.747 | 0.692 | 0.603 | 0.528 | 0.747 |
| 0.999 | 1.042 | 0.747 | 1.504 | 0.673 | 0.507 |
| 1.525 | 0.768 | 0.692 | 0.536 | 0.779 | 0.659 |
| 0.742 | 0.835 | 0.721 | 0.598 | 0.806 | 0.727 |
| 0.779 | 0.717 | 0.603 | 0.632 | 0.551 | 0.712 |
| 0.678 | 1.172 | 0.615 | 1.515 | 0.574 | 0.517 |
| 0.697 | 0.727 | 0.795 | 0.558 | 0.574 | 0.586 |
| 0.945 | 0.939 | 0.578 | 0.582 | 0.795 | 0.558 |

TABLE 13E

Activity of various oligonucleotides (residual level of V3 transcripts in SC)

| PBS | WV-8548 | WV-12482 | WV-12483 | WV-12444 | WV-12448 |
|---|---|---|---|---|---|
| 1.325 | 0.681 | 0.686 | 0.465 | 0.513 | 0.805 |
| 1.122 | 1.307 | 0.735 | 0.816 | 0.746 | 0.355 |
| 1.382 | 0.725 | 0.827 | 0.408 | 0.905 | 0.725 |
| 0.788 | 0.772 | 0.799 | 0.389 | 0.856 | 0.475 |
| 0.874 | 0.499 | 0.672 | 0.416 | 0.557 | 0.833 |
| 0.761 | 0.887 | 0.527 | 0.931 | 0.550 | 0.309 |
| 0.777 | 0.715 | 1.069 | 0.443 | 0.557 | 0.301 |
| 0.970 | 0.950 | 0.431 | 0.482 | 0.816 | 0.499 |

TABLE 13F

Activity of various oligonucleotides (residual level of intron 1/AS transcripts in SC)

| PBS | WV-8548 | WV-12482 | WV-12483 | WV-12444 | WV-12448 |
|---|---|---|---|---|---|
| 1.812 | 0.054 | 1.070 | 0.065 | 0.070 | 0.869 |
| 1.942 | 1.545 | 0.998 |  | 0.241 | 0.074 |
|  | 0.055 | 1.163 | 0.258 | 0.131 | 0.438 |
| 0.528 | 0.075 | 1.503 | 0.281 | 0.072 | 0.721 |
| 0.789 | 0.149 | 0.124 | 0.381 | 0.099 | 0.091 |
| 0.701 | 2.293 | 0.015 |  | 0.057 | 0.058 |
| 0.757 | 0.450 | 0.206 | 0.129 | 0.358 | 0.016 |
| 0.472 |  | 0.027 | 0.287 |  | 0.021 |

Table 14. Activity of Various Oligonucleotides.
In Tables 14A to 14B, various oligonucleotides were tested in motor neurons, with oligonucleotides delivered gymnotically at concentrations from 0.003 to 10 µM (Concentrations are provided as exp10). Tested oligonucleotide WV-11532 comprises three neutral internucleotidic linkages. In Tables 14A and 14B, shown are residual levels of transcriptions [e.g., all transcripts (all V) or only V3] relative to HPRT1, after treatment with oligonucleotides, wherein 1.000 would represent 100% relative transcript level (no knockdown) and 0.000 would represent 0% relative transcript level (e.g., 100% knockdown). Results from replicate experiments are shown.

TABLE 14A

Activity of various oligonucleotides (residual level of all V transcripts)

| Conc. | WV-8008 | | | WV-11532 | | |
|---|---|---|---|---|---|---|
| −2.495 | 0.999 | 0.958 | 0.913 | 1.006 | 0.894 | 0.900 |
| −1.796 | 0.965 | 0.864 | 0.882 | 0.972 | 0.829 | 0.858 |

TABLE 14A-continued

Activity of various oligonucleotides
(residual level of all V transcripts)

| Conc. | WV-8008 | | | WV-11532 | | |
|---|---|---|---|---|---|---|
| −1.097 | 1.006 | 0.900 | 0.932 | 0.907 | 0.888 | 0.858 |
| −0.398 | 0.800 | 0.742 | 0.806 | 0.795 | 0.747 | 0.742 |
| 0.301 | 0.624 | 0.611 | 0.687 | 0.562 | 0.554 | 0.554 |
| 1 | 0.524 | 0.500 | 0.521 | 0.409 | 0.411 | 0.387 |

TABLE 14B

Activity of various oligonucleotides
(residual level of V3 transcripts)

| Conc. | WV-8008 | | | WV-11532 | | |
|---|---|---|---|---|---|---|
| −2.495 | 0.947 | 0.871 | 1.014 | 0.927 | 0.853 | 0.908 |
| −1.796 | 0.877 | 0.841 | 0.908 | 0.836 | 0.769 | 0.841 |
| −1.097 | 0.665 | 0.743 | 0.871 | 0.620 | 0.633 | 0.717 |
| −0.398 | 0.555 | 0.427 | 0.707 | 0.421 | 0.415 | 0.427 |
| 0.301 | 0.210 | 0.178 | 0.304 | 0.096 | 0.105 | 0.094 |
| 1 | 0.056 | 0.071 | 0.083 | 0.012 | 0.015 | 0.015 |

A pharmacodynamics study was performed to compare the effects of oligonucleotides on knockdown of transcripts in C9-BAC mice.

C9orf72 oligonucleotides tested were: WV-6408, WV-8009, WV-8010, WV-8011, and WV-8012. Negative controls were PBS (phosphate-buffered saline) and WV-2376, which does not target.

Animals used: Male and Female C9-BAC mice, 12 week-old, 7 groups, 50 mice.

ICV cannulation was performed. ICV injection of PBS or 50 μg of oligonucleotide on Day 1 in awake animals. 2nd dose of PBS or 50 μg of oligonucleotide on Day 8. Dose volume, 2.5 l. Necropsy 2 weeks after first injection.

Necropsy: whole body perfusion with PBS. Dissect lumbar spinal cord (PD) and place thoracic/cervical spinal cord in formalin (histology); dissect one hemibrain (cortex, hippocampus, striatum, cerebellum), flash freeze (exposures/transcripts). Second hemibrain post fixed in formalin, cryoprotected and flash frozen (RNA foci/oligonucleotide visualization).

Transcripts were analyzed from the cerebral cortex and spinal cord. Transcripts analyzed were: All transcripts; V3; V3 (exon 1a); and Intron1/AS (data not shown).

Several oligonucleotides were shown to be capable of knocking down transcripts, including V3, in the cortex and spinal cord of C9-BAC mice.

A pharmacokinetics study was performed to examine the distribution of oligonucleotides in vivo in spinal cord and cerebral cortex of C9-BAC mice.

C9orf72 oligonucleotides tested were: WV-6408, WV-8009, WV-8010, WV-8011, and WV-8012. Negative controls were PBS (phosphate-buffered saline) and WV-2376, which does not target.

Several oligonucleotides showed significant accumulation in spinal cord and cortex (data not shown).

A study was performed to evaluate the effect of oligonucleotides in vivo on polyGP (a dipeptide repeat protein) levels in hippocampus of C9-BAC mice.

C9orf72 oligonucleotides tested were: WV-6408, WV-8009, WV-8010, WV-8011, and WV-8012, several of which are oligonucleotides having an asymmetric format. Negative controls were PBS (phosphate-buffered saline) and WV-2376, which does not target. WT is a control. The data show that the oligonucleotides were capable of decreasing the level of polyGP (a dipeptide repeat protein) in hippocampus in C9-BAC mice (data not shown).

Example 5

Activities of Various PNPLA3 Oligonucleotides

The efficacy of various oligonucleotides which target PNPLA3 were tested. As shown in this Example, various oligonucleotides were designed, constructed and tested for their ability to mediate knockdown of PNPLA3, including in vitro.

Various PNPLA3 oligonucleotides were designed which are complementary to a wild-type PNPLA3 sequence or a mutant, I148M. Various oligonucleotides were tested in Hep3B (I/I) cells, with is homozygous wild-type (I/I aa in PNPLA3); and in Huh7 cells, which is homozygous mutant (M/M aa in PNPLA3, corresponding to I148M). Various oligonucleotides were also tested in primary cynomolgus hepatocytes, which have one mismatch to rs738408 and a perfect match to rs738409.

In various tables, 1.00 would represent 100% PNPLA3 mRNA level (0.0% knockdown) and 0.00 would represent 000 PNPLA3 mRNA (100.0% knockdown) after treatment with oligonucleotides.

TABLE 15

Activity of oligonucleotides.
Primary cyno hepatocytes.

| Conc. (nM) | WV-9893 | | WV-3421 | | WV-12101 | |
|---|---|---|---|---|---|---|
| 1.079181 | 116.7 | 90.2 | 13.6 | 6.5 | 20.1 | 27.6 |
| 0.681241 | 135.5 | 98.9 | 13.9 | 5.4 | 20.1 | |
| 0.283301 | 86.5 | 126.1 | 32.9 | 23.7 | 11.0 | 37.7 |
| −0.11464 | 105.3 | 108.9 | 70.7 | 46.7 | 40.7 | |
| −0.51258 | 121.9 | 114.1 | 89.3 | 81.5 | 70.0 | 97.1 |
| −0.91052 | 112.7 | 137.8 | 124.2 | 113.7 | 81.7 | 114.1 |
| −1.30846 | 116.0 | 110.1 | 134.7 | 80.5 | 81.0 | 72.6 |
| −1.7064 | 120.5 | 106.7 | 105.7 | 140.0 | 82.5 | 77.1 |
| −2.10434 | 120.5 | 108.0 | 131.0 | 95.2 | 98.4 | 88.2 |
| −2.50228 | 94.8 | 99.6 | 89.2 | 85.4 | 106.7 | 89.7 |

TABLE 16

Activity of oligonucleotides.
Oligonucleotides were tested in Huh7 cells.

| Conc. (nM) | 1 | 0.52288 | 0.04576 | −0.4314 | −0.9085 | −1.3856 | −1.8627 |
|---|---|---|---|---|---|---|---|
| WV-7805 | 7.0 | 23.5 | 64.7 | 80.4 | 88.2 | 92.5 | 99.5 |
| | 5.1 | 24.7 | 78.9 | 74.1 | 86.7 | | |
| WV-9890 | 1.6 | 35.0 | | 90.4 | 90.3 | 92.6 | 104.6 |
| | 13.1 | 29.2 | 73.7 | 88.5 | 87.1 | 95.8 | 105.5 |
| WV-12100 | 12.4 | 33.8 | 63.6 | 90.6 | | 102.3 | 101.5 |
| | 10.2 | 27.6 | 76.6 | 80.0 | 83.6 | 80.7 | 85.0 |

TABLE 16-continued

Activity of oligonucleotides.
Oligonucleotides were tested in Huh7 cells.

| Conc. (nM) | 1 | 0.52288 | 0.04576 | −0.4314 | −0.9085 | −1.3856 | −1.8627 |
|---|---|---|---|---|---|---|---|
| WV-9893 | 10.4 | 28.7 | 74.3 | 86.3 | 87.7 | 116.1 | 93.8 |
|  | 4.3 | 36.4 | 80.4 | 91.5 | 110.3 | 108.6 | 106.5 |
| WV-12101 |  | 4.6 | 19.8 | 60.3 | 85.8 | 92.0 | 108.3 |
|  |  | 6.8 | 19.2 | 60.0 | 81.1 | 81.0 | 85.6 |

WV-12101, an oligonucleotide having an asymmetrical format, demonstrated allele-specific dose response and potency in cynomolgus cells despite having one mismatch in the DNA core.

TABLE 17

Activity of oligonucleotides.
Data is shown for 25 nM; oligonucleotides were also tested at 0, 1.6, and 6.2 nM (data not shown). Oligonucleotides were tested in vitro in primary cynomolgus hepatocytes.

| Oligonucleotide | 25 nM |
|---|---|
| WV-3421 | 13 |
| WV-9434 | 63 |
| WV-9439 | 55 |
| WV-9444 | 37 |
| WV-3421 | 12 |
| WV-9435 | 62 |
| WV-9440 | 37 |
| WV-9445 | 34 |
| WV-3421 | 17 |
| WV-9431 | 92 |
| WV-9436 | 70 |
| WV-9441 | 73 |
| WV-9432 | 53 |
| WV-9437 | 36 |
| WV-9442 | 54 |
| WV-9433 | 77 |
| WV-9438 | 44 |
| WV-9443 | 69 |

TABLE 18

Activity of oligonucleotides.
Primary cynomolgus hepatocytes. Data is shown for 4 nM. Oligonucleotides were also tested at 0, 0.1, 0.25, 0.66, 1.6, and 10 nM (data not shown). Numbers represent residual PNPLA3 mRNA level (PNPLA3/HPRT1) and numbers are approximate.

|  | Hep3B (wt) | Huh7 (mutant) |
|---|---|---|
| WV-9890 | 88 | 37 |
| WV-12100 | 103 | 27 |
| WV-9893 | 67 | 10 |
| WV-12101 | 69 | 8 |

WV-9893 and WV-12101 have an asymmetrical format. Additional oligonucleotides which have an asymmetrical format, but which are stereorandom, were tested, which have the double mutation at P9/P12 (positions 9 and 12). WV-8609, WV-8847, WV-8848, WV-8849 all had an IC50 of around 4 to 5 nM.

TABLE 19

Activity of oligonucleotides.
Several PNPLA3 oligonucleotides, some of which have an asymmetric format, were tested for stability in rat liver homogenate at 2 days. Numbers represent % of full-length oligonucleotide remaining; numbers are approximate.

| WV-7805 | 58 |
|---|---|
| WV-8603 | 46 |
| WV-8608 | 73 |
| WV-9889 | 69 |
| WV-9890 | 76 |
| WV-8609 | 26 |
| WV-8601 | 61 |
| WV-8605 | 65 |
| WV-8606 | 105 |
| WV-9891 | 43 |
| WV-9892 | 52 |
| WV-9893 | 115 |

Various PNPLA3 oligonucleotides were also tested for efficacy with an additional component which is a tri-antennary GalNAc conjugate (including, but not limited to WV-7805, WV-8132, WV-8566, WV-8599, WV-9859, and WV-9670). Oligonucleotides were tested in vitro on Huh7-148 OE cells (which comprise the mutant allele of PNPLA3) at 10 nM. Numbers represent PNPLA3 mRNA levels (PNPLA3/HPRT1), and numbers are approximate. In many cases, the oligonucleotides did not demonstrate significant knockdown of wild-type PNPLA3 in cynomolgus (non-human primate or NHP) hepatocytes. For example, WV-8132, WV-8600, WV-9868 and WV-9860 did not demonstrate significant knockdown of wild-type PNPLA3 in cynomolgus (non-human primate or NHP) hepatocytes when tested at up to 10 nM (data not shown).

TABLE 20

Activity of oligonucleotides.
Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

| Negative control | 100 | Negative control | 100 |
|---|---|---|---|
| WV-993 | 117 | WV-993 | 117 |
| WV-7805 | 20 | WV-8600 | 47 |
| WV-8132 | 54 | WV-8564 | 47 |
| WV-8566 | 67 | WV-8596 | 62 |
| WV-8599 | 82 | WV-8597 | 38 |
| WV-9859 | 56 | WV-993 | 117 |
| WV-9670 | 57 | WV-9860 | 65 |
| WV-993 | 117 | WV-9861 | 58 |
| WV-9868 | 48 | WV-9862 | 62 |
| WV-9869 | 50 |  |  |
| WV-9870 | 53 |  |  |

TABLE 21

Activity of oligonucleotides.
Various PNPLA3 oligonucleotides were tested in vitro in an RNase H assay.
PNPLA3 oligonucleotides were incubated in the presence of target RNA
which was the wt allele (WV-8808) or the 148 allele (WV-8807). Numbers
represent the percentage of target RNA (WV-8808 or WV-8807) remaining.
In this table, 100.00 would represent 100% PNPLA3 mRNA level and 0.00
would represent 0% PNPLA3 mRNA after treatment with oligonucleotides.

| Time (mins) | 0 | 5 | 10 | 15 | 20 | 30 | 45 | 60 |
|---|---|---|---|---|---|---|---|---|
| WV-7805 + WV-8807 | 100.0 | 94.1 | 93.4 | 88.6 | 90.6 | 82.8 | 74.5 | 73.4 |
| WV-8603 + WV-8807 | 100.0 | 93.1 | 89.7 | 84.4 | 91.0 | 82.4 | 73.0 | 66.4 |
| WV-8608 + WV-8807 | 100.0 | 95.4 | 92.2 | 89.8 | 87.4 | 81.4 | 79.7 | 72.1 |
| WV-9889 + WV-8807 | 100.0 | 90.9 | 87.7 | 81.9 | 85.7 | 74.4 | 72.9 | 66.4 |
| WV-9890 + WV-8807 | 100.0 | 92.7 | 89.6 | 85.4 | 88.7 | 77.0 | 75.8 | 66.8 |
| WV-7805 + WV-8808 | 100.0 | 99.5 | 97.7 | 98.1 | 96.9 | 96.2 | 95.6 | 93.4 |
| WV-8603 + WV-8808 | 100.0 | 102.2 | 99.4 | 100.3 | 99.1 | 98.5 | 99.2 | 95.6 |
| WV-8608 + WV-8808 | 100.0 | 98.8 | 97.5 | 96.9 | 95.9 | 96.9 | 95.5 | 94.1 |
| WV-9889 + WV-8808 | 100.0 | 99.9 | 99.2 | 99.5 | 98.6 | 97.8 | 97.2 | 96.3 |
| WV-9890 + WV-8808 | 100.0 | 107.5 | 100.7 | 100.8 | 99.1 | 104.2 | 98.3 | 97.5 |
| WV-8601 + WV-8807 | 100.0 | 93.1 | 90.9 | 90.4 | 91.4 | 88.2 | 85.6 | 80.1 |
| WV-8605 + WV-8807 | 100.0 | 98.3 | 96.0 | 96.4 | 96.0 | 96.0 | 87.1 | 86.7 |
| WV-8606 + WV-8807 | 100.0 | 90.1 | 91.6 | 90.7 | 90.9 | 86.6 | 82.4 | 79.1 |
| WV-8609 + WV-8807 | 100.0 | 92.1 | 89.0 | 83.8 | 85.5 | 75.6 | 75.7 | 69.0 |
| WV-8601 + WV-8808 | 100.0 | 99.0 | 100.2 | 100.2 | 97.8 | 97.6 | 97.2 | 94.1 |
| WV-8605 + WV-8808 | 100.0 | 100.7 | 99.7 | 100.9 | 98.4 | 99.1 | 98.5 | 94.6 |
| WV-8606 + WV-8808 | 100.0 | 101.2 | 97.6 | 98.1 | 96.3 | 97.0 | 96.5 | 93.9 |
| WV-8609 + WV-8808 | 100.0 | 96.7 | 93.7 | 98.6 | 96.8 | 95.6 | 96.2 | 94.5 |
| WV-9891 + WV-8807 | 100.0 | 91.6 | 88.3 | 86.1 | 87.9 | 79.8 | 75.6 | 75.2 |
| WV-9892 + WV-8807 | 100.0 | 93.2 | 86.9 | 83.5 | 84.3 | 74.2 | 64.2 | 58.6 |
| WV-9893 + WV-8807 | 100.0 | 94.6 | 88.6 | 86.6 | 88.6 | 77.4 | 69.0 | 65.6 |
| WV-9891 + WV-8808 | 100.0 | 98.3 | 98.6 | 96.9 | 95.0 | 94.2 | 92.8 | 89.8 |
| WV-9892 + WV-8808 | 100.0 | 100.7 | 101.8 | 100.7 | 99.3 | 97.9 | 97.4 | 95.7 |
| WV-9893 + WV-8808 | 100.0 | 100.1 | 100.3 | 100.2 | 99.3 | 96.3 | 96.1 | 93.5 |
| WV-9894 + WV-8807 | 100.0 | 96.2 | 90.1 | 85.1 | 84.7 | 79.5 | 76.8 | 74.9 |
| WV-9895 + WV-8807 | 100.0 | 97.0 | 92.5 | 87.1 | 84.3 | 77.0 | 71.8 | 70.7 |
| WV-9896 + WV-8807 | 100.0 | 98.2 | 93.2 | 86.0 | 81.8 | 74.8 | 69.2 | 70.0 |
| WV-9894 + WV-8808 | 100.0 | 98.8 | 97.1 | 97.4 | 96.1 | 94.0 | 95.4 | 91.4 |
| WV-9895 + WV-8808 | 100.0 | 99.9 | 97.1 | 98.5 | 99.3 | 96.1 | 96.4 | 93.6 |
| WV-9896 + WV-8808 | 100.0 | 99.2 | 99.0 | 98.3 | 96.4 | 95.6 | 93.8 | 90.6 |

The PNPLA3 oligonucleotides WV-980, WV-9893, WV-8606 and WV-7805 also significantly reduced PNPLA3 148 mutant mRNA levels in Huh7 cells with PNLA3 148 mutation (to between about 25 to 5500 residual mutant PNPLA3, relative to HPRT1, at 12.5 nM), but these oligonucleotides did not significantly reduce wt PNPLA3 levels in Huh7 cells with wt PNPLA3 (about 90% or more residual wt PNPLA3 level at 12.5 nM).

Example 6

In Vitro Screening Protocol

Various technologies are available for assessing provided oligonucleotides and compositions and can be utilized in accordance with the present disclosure. This example describes an in vitro screening protocol for certain oligonucleotides. Oligonucleotides were delivered gymnotically to ALS neurons for 48 hours in 24-well plates. Those skilled in the art appreciate that various conditions and/or parameters may be adjusted, and the described protocols may be applied to various suitable oligonucleotides.

RNA Extraction

RNA extraction with RNeasy Plus 96 kit (Qiagen, Waltham, Mass.) following protocol: Purification of Total RNA from Cells Using Vacuum/Spin Technology. (gDNA removal is critical.)

For each well, total RNA was eluted in 60 ul of RNase-free water.

Reverse Transcription

Reverse transcription with High-Capacity RNA-to-cDNA™ Kit (Applied Biosystems; available from ThermoFisher, Waltham, Mass.)

| 2X RT Buffer Mix | 9 ul |
|---|---|
| RNA sample | 13.5 ul |

Heat denaturation at 72° C. for 5 mins, Cool down the plate on ice for at least 2 mins.

To each well of heat denatured RNA, add:

| 2X RT Buffer Mix | 6 |
|---|---|
| 20X RT Enzyme Mix | 1.5 ul |

The final volume of the cDNA is 30 ul.
Real-Time PCR
Taqman Probes:
C9orf72 all variants: Hs00376619_m1 (FAM), Catalog #4351368 (ThermoFisher, Waltham, Mass.)
C9orf72 V3: Hs00948764_m1(FAM), Catalog #4351368 (ThermoFisher, Waltham, Mass.)
C9orf72 Exon 1a:

| | |
|---|---|
| Forward primer | AGATGACGCTTGGTGTGTC |
| Reverse primer | TAAACCCACACCTGCTCTTG |
| probe | CTGCTGCCCGGTTGCTTCTCTTT |

C9orf72 antisense RNA/intron:

| | |
|---|---|
| Forward primer | GGTCAGAGAAATGAGAGGGAAAG |
| Reverse primer | CGAGTGGGTGAGTGAGGA |
| probe | AAATGCGTCGAGCTCTGAGGAGAG |

Internal control: Human HPRT1 (VIC) Hs02800695_m1, Catalog #4448486 (ThermoFisher, Waltham, Mass.)
PCR Reaction:

| | |
|---|---|
| Lightcycler 480 master mix | 10 ul |
| C9 probe (FAM) | 0.5 ul |
| HPRT 1 (VIC) | 0.5 ul |
| cDNA * | up to 9 ul |
| Nuclease-free H2O | to 20 ul |

* 2 ul of cDNA for all variants probe. 9 ul of cDNA for other C9 probes.

Real-time PCR using Bio-rad CFX96 Touch
Run Information:
1 95.0 C for 3:00
2 95.0 C for 0:10
3 60.0 C for 0:30
 +Plate Read
4 GOTO 2, 39 more times
 END Example 7

Example Assays

Example assays useful for assessing provided oligonucleotides and compositions are described. As readily appreciated by those skilled in the art, conditions and/or parameters of the described assays may be readily adjusted for assessing various oligonucleotides, including oligonucleotides having various targets.

Brief Description of Various Assays Performed:
Reporter:
Luciferase assay, as described herein. For some oligonucleotides, two numbers are given (e.g., 1.32/2.63 for WV-6408); these indicate replicate experiments.

ALS Neurons:
Neuronal differentiation of iPSCs: iPSCs derived from fibroblasts from a C9orf72-associated ALS patient (female, 64 years old) were obtained from RUCDR Infinite Biologics. iPSCs were maintained as colonies on Corning Matrigel matrix (Sigma-Aldrich, St. Louis, Mo.) in mTeSR1 medium (STEMCELL Technologies, Vancouver, BC). Neural progenitors were produced using the STEMdiff Neural System (STEMCELL Technologies, Vancouver, BC). iPSCs were suspended in an AggreWell800 plate and grown as embryoid bodies in STEMdiff Neural Induction Medium for 5 days, with daily 75% medium changes. Embryoid bodies were harvested with a 37 μm cell strainer and plated onto Matrigel-coated plates in STEMdiff Neural Induction Medium. Medium was changed daily for 7 days, with 85-95% of embryoid bodies exhibiting neural rosettes 2 days post-plating. Rosettes were picked manually and transferred to plates coated with poly-L-ornithine and laminin in STEMdiff Neural Induction Medium (STEMCELL Technologies, Vancouver, BC). Medium was changed daily for 7 days, until cells reached 90% confluence and were considered neural progenitor cells (NPCs). NPCs were dissociated with TrypLE (Gibco, available through ThermoFisher, Waltham, Mass.) and passaged at a ratio of 1:2 or 1:3 on poly-L-ornithine/laminin plates in a neural maintenance medium (NMM, 70% DMEM, 30% Ham's F12, 1× B27 supplement) supplemented with growth factors (20 ng/ml FGF2, 20 ng/ml EGF, 5 μg/ml heparin). For maturation into neurons, NPCs were maintained and expanded for fewer than five passages, and at >90% confluence were passaged 1:4 onto poly-L-ornithine/laminin-coated plates in NMM supplemented with growth factors. The next day, Day 0 of differentiation, medium was changed to fresh NMM without growth factors. Differentiating neurons were maintained in NMM for 4 or more weeks, with twice weekly 50% medium changes. Cells were re-plated with TrypLE at a density of 125,000 cells/cm$^2$ as needed.

Figure 4:
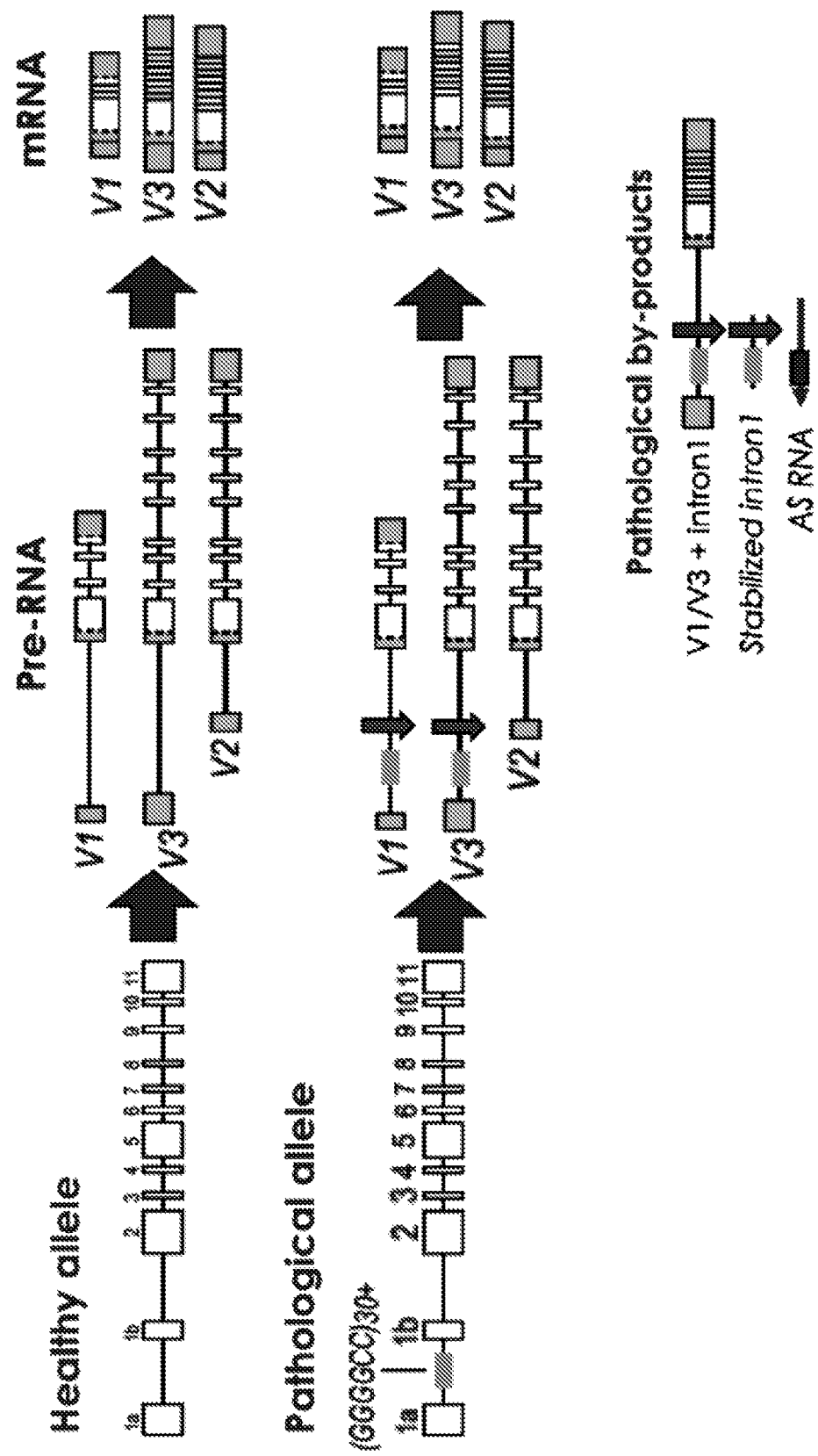
FIG. 4. Example C9orf72 transcripts. V3, V2 and V1 transcripts produced from a healthy and a pathological C9orf72 allele are illustrated, wherein the pathological allele contains a hexanucleotide repeat expansion [horizontal bar, indicated by $(GGGGCC)_{30+}$ (SEQ ID NO: 1)]. The downward-pointing arrow indicates the position of some example C9orf72 oligonucleotides.

V3/intron: Knockdown (KD) of V3 RNA transcript and intron RNA transcript were measured in ALS neurons (FIG. 4). V3 transcripts knocked down are both wild-type and repeat-containing. Note, however, that, while the present disclosure is not bound by any particular theory, the repeat-containing transcript may have a longer retention time in the nucleus and thus may be preferentially knocked down. For WV-6408, V3 was knocked down by 59% and intron by 65%.

Stability:
Stability was assayed in vitro using Mouse (Ms) brain homogenates.

TLR9:
TLR9 Reporter Assay Protocol: Induction of NF-κB (NF-κB inducible SEAP) activity was analyzed using a human TLR9 or mouse TLR9 reporter assay (HEK-Blue™ TLR9 cells, InvivoGen, San Diego, Calif.). Oligonucleotides at a concentration of 50 μM (330 μg/mL) and 2-fold serial dilution were plated into 96-well-plates in the final volume of 20 μL in water. HEK-Blue™ TLR9 cells were added to each well at a density of 7.2×10$^4$ cells in a volume of 180 μL of HEK Blue™ detection medium. Final working concentration of oligonucleotides in the wells was 5, 2.5, 1.25, 0.625, 0.312, 0.156, 0.078, and 0.0375 μM. HEK-Blue™ TLR9 cells were incubated with oligonucleotides for 16 hours at 37° C. and 5% CO$_2$. At the end of the incubation, absorbance at 655 nM was measured by Spectramax. Water was a negative control. Positive controls were WV-2021 and ODN 2359, a CpG oligonucleotide. The results are expressed as fold change in NF-κB activation over vehicle control-treated cells. Reference: Human TLR9 Agonist Kit (InvivoGen, San Diego, Calif.). In this assay, an oligonucleotide is considered "Clean" if no or essential no activity was detected. In some experiments, WV-8005, WV-8006, WV-8007, WV-8008, WV-8009, WV-8010, WV-8011, WV-8012 and WV-8321 showed no appreciable hTLR9 activity, though some showed small activity in mTRL9.

Complement

In some embodiments, complement is assessed in a cynomolgus monkey serum complement activation ex vivo assay. The effects of oligonucleotides on complement activation were measured in cynomolgus monkey serum ex vivo. Serum samples from 3 individual male cynomolgus monkeys were pooled and the pool was used for the studies.

The time course of C3a production was measured by incubating oligonucleotides at a final concentration of 330 μg/mL or the water control at 37° C. in freshly thawed cynomolgus monkey serum (1:30 ratio, v/v). Specifically, 9.24 μL of 10 mg/mL stock of oligonucleotide in vehicle or vehicle alone was added to 270.76 μL of pooled serum, and the resulting mixtures were incubated at 37° C. At 0, 5, 10, and 30 minutes, 20-μL aliquots were collected and the reaction was terminated immediately by addition of 2.2 μL of 18 mg/mL EDTA.

C3a concentrations were measured using MicroVue C3a Plus Enzyme Immunoassays at a 1:3000 dilution. The results were presented as the complement split product concentration increase upon the treatment of pooled serum with oligonucleotides compared with the treatment with the vehicle control.

PD (Pharmacodynamics) (C9-BAC, Icv or Intracerebroventricular Injection):

PD and Efficacy were Tested in: C9orf72-BAC (C9-BAC) Mouse Model:

The transgenic mice used for in vivo pharmacological studies have been described in O'Rourke et al. 2015 Neuron. 88(5): 892-901. Briefly, the transgenic construct was designed using a bacterial artificial chromosome (BAC) clone derived from fibroblasts of a patient with amyotrophic lateral sclerosis (ALS), carrying the human chromosome 9 open reading frame 72 gene (C9orf72) with a hexanucleotide repeat expansion (GGGGCC) in the intron between the alternatively-spliced non-coding first exons 1a and 1b (variant 3). The BAC isolated a ~166 kbp sequence (~36 kbp human C9orf72 genomic sequence, with ~110 kbp upstream and ~20 kbp downstream sequences). Upon amplification of different BAC subclones, one subclone with a limited contraction to 100-1000 GGGGCC repeats (SEQ ID NO: 608) was used. The Tg(C9orf72_3) line 112 mice (JAX Stock No. 023099, Jackson Laboratories, Bar Harbor, Me.) have several tandem copies of the C9orf72_3 transgene, with each copy having between 100-1000 repeats ([GGGGCC]100-1000) (SEQ ID NO: 608). However, only mice expressing 500 or more repeats were selected for in vivo studies used herein.

In Vivo Procedures:

For injections of oligonucleotides into the lateral ventricle, mice were anesthetized and placed on a rodent stereotaxic apparatus; they were then implanted with a stainless-steel guide cannula in one of their lateral ventricles (coordinates: −0.3 mm posterior, +1.0 mm lateral and −2.2 mm vertically from bregma), which was secured in place using dental cement. Mice were allowed a one-week recovery period prior to the injection of compounds. Typical pharmacological studies involved the injection of up to 50 μg oligonucleotide in a volume of 2.5 μl on day 1, which was followed by another injection of the same amount and volume on day 8. Euthanasia was performed on day 15; the mice were deeply anesthetized with avertin and transcardiacally perfused with saline. Brains were rapidly removed from the skull, one hemisphere was processed for histological analyses, the other hemisphere dissected and frozen on dry ice for biochemical analyses. Similarly, spinal cord was dissected and frozen on dry ice (lumbar) or processed for histological analyses (cervical/thoracic).

Efficacy (C9-BAC): Foci:

Tissue Preparation and Histological Analyses

Hemibrains and spinal cord were drop-fixed in 4% paraformaldehyde for 24 hours, then transferred to 30% sucrose for 24-48 hours and frozen in liquid nitrogen. Serial sagittal 20-μm thick sections were cut at −18° C. in a cryostat and placed on Superfrost slides.

Efficacy (C9-BAC): PolyGP (DPR Assay):

Tissue Preparation for Protein and PolyGP Quantification:

Brain and spinal cord samples were processed using a 2-step extraction procedure; each step was followed by centrifugation at 10,000 rpm for 10 minutes at 4° C. The first step consisted of homogenizing samples in RIPA (50 mM Tris, 150 mM NaCl, 0.5% DOC, 1% NP40, 0.1% SDS and Complete™, pH 8.0). The second step consisted of resuspension of the pellet in 5M guanidine-HCl.

PolyGP's were quantified in each pool using a Mesoscale-based assay. Briefly, the polyclonal antibody AB1358 (Millipore, available from Millipore Sigma, Billerica, Ma.) was used as both capture and detection antibody. MULTI-ARRAY 96 Sm Spot Plate Pack, SECTOR Plate was coated with 1 μl of 10 ug/ml purified anti-polyGP antibody (Millipore, AB1358, available from Millipore Sigma, Billerica, Ma.) in PBS directly on small spot overnight at 4 C. After washing 3 times with PBST (0.05% Tween-20 in PBS), the plates were blocked with MSD Blocker A Kit (R93AA-2) or 10% FBS/PBS, at room temperature for 1 hour. Poly-GP purified from HEK-293 cells (by anti-FLAG affinity purification after plasmids transfection, Genescript custom made) were serial diluted with 10% FBS/PBS and used as standard. 25 μl of standard poly-GP and samples (diluted or non-diluted) were added to each well, incubated at room temperature for 1-2 hours. After 3 washes with PBST, sulfo-tagged anti-GP (AB1358) were added 25 μl per well, and incubated at room temperature for another hour. The plates were then washed 3 times, 150 l/well of MSD Read Buffer T (lx) (R92TC-2, MSD) was added to each well and read by MSD (MESO QUICKPLEX SQ 120) according to manufacturer's default setting.

Expression of C9orf72 protein was determined by western blotting. Briefly, proteins from RIPA extracts were size fractionated by 4-12% SDS-PAGE (Criterion gel, Bio-Rad) and transferred onto PVDF membrane. To detect C9orf72, the membrane was immunoblotted using the mouse monoclonal anti-C9orf72 antibody GT779 (1:2000; GeneTex, Irvine, Calif.), followed by secondary DyLight conjugated antibody. Visualization was conducted using the Odyssey/Li-Cor imaging system.

Some Additional Abbreviations:

Cx: Cortex
HP: Hippocampus
KD: knockdown
SC: Spinal Cord
Str: Striatum

Additional protocols for experiments are presented below.

A non-limiting example of a hybridization assay for detecting a target nucleic acid is described herein. Such an assay can be used for detecting and/or quantifying a C9orf72 oligonucleotide, or any other nucleic acid or oligonucleotide to any target, including targets which are not C9orf72.

Pharmacokinetics Studies:

Tissue Preparation for Oligonucleotide Quantification and Transcript Quantification:

Tissues were dissected and fresh-frozen in the pre-weighted Eppendorf tubes. Tissue weight were calculated by re-weight the tubes. 4 volume of Trizol or lysis buffer (4 M Guanidine; 0.33% N-Lauryl Sarcosine; 25 mM Sodium Citrate; 10 mM DTT) were added to one unit weight (4 µl of buffer for 1 mg tissue). Tissue lysis were done by Precellys Evolution tissue homogenizer (Bertin Technologies, Montigny-le-Bretonneux, France) until all the tissue pieces were dissolved at 4 C. 30-50 µl of tissue lysates were saved in 96 well plate for PK measurement, and rest of lysates were stored at −80 C (if it is in lysis buffer) or continue with RNA extraction (if it is in Trizol buffer).

Transcript Quantification:
Hybridization probes (IDT-DNA)
Capture probe: "C9-Intron-Cap"/5AmMC12/TGGCGAGTGG (SEQ ID NO: 609)
Detection probe: "C9-Intron-Det": GTGAGTGAGG/3BioTEG/(SEQ ID NO: 610)
5AmC12 is a 5'-amine with $C_{12}$ linker.
3BioTEG is a Biotinylated probe.

Maleic anhydride activated 96 well plate (Pierce 15110) was coated with 50 µl of capture probe at 500 nM in 2.5% NaHCO$_3$(Gibco, 25080-094) for 2 hours at 37 C. The plate then washed 3 times with PBST (PBS+0.1% Tween-20), blocked with 5% fat free milk-PBST at 37 C for 1 hour. Payload oligonucleotide was serial diluted into matrix. This standard together with original samples were diluted with lysis buffer (4 M Guanidine; 0.33% N-Lauryl Sarcosine; 25 mM Sodium Citrate; 10 mM DTT) so that oligonucleotide amount in all samples is less than 50 ng/ml. 20 µl of diluted samples were mixed with 180 µl of 333 nM detection probe diluted in PBST, then denatured in PCR machine (65 C, 10 min, 95 C, 15 min, 4 C ∞). 50 µl of denatured samples were distributed in blocked ELISA plate in triplicates, and incubated overnight at 4 C. After 3 washes of PBST, 1:2000 streptavidin-AP (SouthernBiotech, 7100-04) in PBST was added, 50 µl per well and incubated at room temperature for 1 hour. After extensive wash with PBST, 100 µl of AttoPhos (Promega S1000) was added, incubated at room temperature in dark for 10 min and read on plate reader (Molecular Device, M5) fluorescence channel: Ex435 nm, Em555 nm. The oligonucleotide in samples were calculated according to standard curve by 4-parameter regression.

FISH Protocol for GGGGCC and GGCCCC RNA Foci
Fixation:
The slides were dried at room temperature for 30 mins then fixed in 4% PFA for 20 mins. After fixation, the slides were washed for 3 times in PBS then stored at 4° C. in 70% prechilled ethanol for at least 30 min.

Pre-Hybridization:
The slides were rehydrated in FISH washing buffer (40% formamide, 2×SSC in DEPC water) for 10 min. Hybridization buffer (40% Formamide, 2×SSC, 0.1 mg/ml BSA, 0.1 g/ml dextran sulfate, 1% Vanadyl sulfate complex, 0.25 mg/ml tRNA in DEPC water) was added on slides and incubated at 55° C. for 30 min.

Preparation of the Probe:
Cy3-(GGCCCC)3 (SEQ ID NO: 611) (detecting sense repeat expansion) and Cy3-(GGGGCC)3 (SEQ ID NO: 612) (detecting antisense repeat expansion) probes were denatured at 95° C. for 10 mins. After cooling down on ice, the probes were diluted to 200 ng/ml with cold hybridization buffer.

Hybridization:
The slides were briefly washed with FISH washing buffer and diluted probes were added on the slides. The slides were incubated at 55° C. for 3 hours in a hybridization oven. After hybridization, slides were washed 3 times at 55° C. with FISH washing buffer, 15 min per wash. Then slides were briefly washed once with 1×PBS.

Neuronal Nuclei Immunofluorescence Staining:
The slides were blocked with blocking solution (2% normal goat serum in PBS) for 1 hour. Anti-NeuN antibody (MAB377, Millipore) was diluted 1:500 in blocking solution and applied to the slides at 4° C. over night. The slides were then washed 3 times with PBS and incubate with 1:500 diluted goat anti-mouse secondary antibody with Alexa Fluor 488(Life technology) at room temperature for 1 hour. Then the slides were washed 3 times with PBS. Finally, the sides were mounted with DAPI for imaging.

Imaging and Foci Quantification:
The images were taken with RPI spinning disk confocal microscope (Zeiss) at 40× magnification. 488, CY3 and DAPI channels were collected. RNA foci were quantified with ImageJ software (NIH).

In Vitro RNase HC Activity
Oligonucleotide-RNA duplexes were incubated with human RNase HC at 37° C. Duplexes were prepared by mixing equimolar solutions of oligonucleotide and RNA (20 µM each), heating to a suitable temperature, e.g., 90° C. for a period of time, e.g., 2 minutes, and cooling slowly over several hours. Each RNase HC reaction contained 5.56 µM oligonucleotide-RNA duplex in RNase H buffer (75 mM KCl, 50 mM Tris-HCl, 3 mM MgCl$_2$, 10 mM dithiothreitol, pH=8.3) in a reaction volume of 90 µL. The mixture was pre-incubated at 37° C. for 10 minutes prior to the addition of 10 µL of enzyme solution (0.025 µM) with final concentrations of 5.0 µM substrate and 0.0025 µM RNase HC (2000:1 ratio). The reactions were quenched at 5, 10, 15, 30, 45, 60 min using 7.0 µL of 500 mM EDTA disodium solution in water. For the 0 min time point, EDTA was added to the reaction mixture before the addition of enzyme. Controls ensured that EDTA inhibited the enzyme activity completely. After all the reactions were quenched, analyses were performed using, e.g., HPLC. For example, 10 µL of each was injected onto an Agilent Poroshell 120 EC-C18 column (2.7 µm, 2.1×50 mm) at 70° C. using Buffer A (200 mM HFIP and 8 mM triethylamine) and Buffer B (A+methanol, 50:50, v/v) as eluents using the gradient in the chart below.

| Time (min) | Flow (ml/min) | % A | % B | Curve |
|---|---|---|---|---|
| 1 | 0.0 | 0.20 | 90.0 | 10.0 | |
| 2 | 15.00 | 0.20 | 70.0 | 30.0 | 6 |
| 3 | 22.00 | 0.20 | 40.0 | 60.0 | 6 |
| 4 | 25.00 | 0.20 | 5.0 | 95.0 | 6 |
| 5 | 25.50 | 0.20 | 90.0 | 10.0 | 6 |
| 6 | 30.0 | 0.20 | 90.0 | 10.0 | 1 |

UV absorbance was recorded at suitable wave lengths, e.g., 254 nm and 280 nm. Peak areas from the chromatograms, corresponding to full-length RNA oligomer, were integrated and normalized against the antisense strand. The amount of RNA remaining against the data at 0 min time point as 100% was plotted against time to show relative rates of RNA cleavage. RNA cleavage products were identified by LC/MS. Example data were presented in FIG. 2 and FIG. 3. As confirmed, provided chirally controlled oligonucleotide compositions of oligonucleotides whose pattern of backbone chiral centers comprising OpSpSp can provide particularly useful and advantageous cleavage of target nucleic acids.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, within the scope of the appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. An oligonucleotide composition comprising oligonucleotides of a particular oligonucleotide type characterized by:
   a) a common base sequence;
   b) a common pattern of backbone linkages;
   c) a common pattern of backbone chiral centers;
   wherein the composition is enriched, relative to a substantially racemic preparation of oligonucleotides having the same common base sequence, for oligonucleotides of the particular oligonucleotide type; and
   wherein each oligonucleotide of the particular oligonucleotide type is independently an oligonucleotide comprising a first wing, a second wing and a core in a format of first wing-core-second wing or second wing-core-first wing, wherein:
   (i) the first wing and the second wing comprise different sugar modifications; and
   (ii) oligonucleotides of the particular oligonucleotide type comprise (Op)n(Sp)m in the core, wherein:
   Sp indicates the S configuration of a chiral linkage phosphorus of a chiral modified internucleotidic linkage;
   Op indicates an achiral linkage phosphorus of a natural phosphate linkage, wherein the nucleotidic unit comprising Op comprises a 5'-modification on its sugar; and
   each of n and m is independently 1-20.

2. The composition of claim 1, wherein n is 1.

3. The composition of claim 1, wherein the core does not comprise a 2'-OMe modified sugar; the first wing comprises a 2'-OMe modified sugar; and the second wing comprises a 2'-sugar modification which is not 2'-OMe and which is not present in the core.

4. The composition of claim 1, wherein the core does not comprise a 2'-MOE modified sugar; the first wing comprises a 2'-MOE modified sugar; and the second wing comprises a 2'-sugar modification which is not 2'-MOE and which is not present in the core.

5. The composition of claim 1, wherein the oligonucleotide is capable of decreasing the level, expression and/or activity of a target gene or a gene product thereof.

6. The composition of claim 1, wherein m is 2 or greater.

7. The composition of claim 6, wherein each sugar in the oligonucleotide is independently a 2'-deoxyribose, a bicyclic sugar, or a modified sugar wherein the modification is 2'-MOE, 2'-OMe, or 2'-F.

8. The composition of claim 1, wherein each internucleotidic linkage in the oligonucleotides is independently a phosphodiester linkage, a phosphorothioate, or a non-negatively-charged internucleotidic linkage.

9. The composition of claim 8, wherein the oligonucleotides comprise five or more chirally controlled internucleotidic linkages.

10. The composition of claim 1, wherein the first wing and second wing comprise a different sugar modification.

11. The composition of claim 1, wherein the first wing and second wing comprise a different internucleotidic linkage(s) or pattern of internucleotidic linkages thereof.

12. The composition of claim 1, wherein the first wing and second wing comprise a different stereochemistry of internucleotidic linkage(s) or pattern thereof.

13. The composition of claim 1, wherein the first wing comprises a sugar or sugar modification not present in the core, and wherein the second wing comprises a sugar or sugar modification not present in the first wing or core.

14. The composition of claim 2, wherein the first wing comprises a first sugar or sugar modification not present in the core, and wherein the second wing comprises a first sugar or sugar modification not present in the first wing or core, and wherein the second wing further comprises a second sugar or sugar modification not present in the first wing or core.

15. The composition of claim 1, wherein the core does not comprise a 2'-OMe, 2'-MOE or 2'-F modified sugar; the first wing comprises a 2'-F and not a 2'-MOE or a 2'-OMe modified sugar; and the second wing comprises a 2'-MOE and does not comprise a 2'-OMe or a 2'-F sugar.

16. The composition of claim 1, wherein at least 0.1%, 0.5%, 1%, 5%, 10%, 15%, 20%, 25%, 30%, 35%, 40%, 45%, 50%, 55%, 60%, 65%, 70%, 75%, 80%, 85%, 90%, or 95% of all oligonucleotides in the composition that have the common base sequence are oligonucleotides of the type.

17. The composition of claim 1, wherein oligonucleotides of the composition comprise a non-negatively charged internucleotidic linkage.

18. A method for selective suppression of a transcript from a target nucleic acid sequence for which one or more similar sequences exist within a population, each of which contains a specific nucleotide characteristic sequence element that defines the target nucleic acid sequence relative to the similar sequences, the method comprising steps of:
   contacting a sample comprising transcripts of the target nucleic acid sequence with a chirally controlled oligonucleotide composition of claim 1;
   wherein the common base sequence for the oligonucleotides of the particular oligonucleotide type is or comprises a sequence that is complementary to the characteristic sequence element that defines the target nucleic acid sequence.

19. The method of claim 18, wherein a characteristic sequence element is or comprises one or more nucleobases that differentiate the target nucleic acid sequence from similar sequence(s) in a genome and/or products encoded thereby; optionally wherein a characteristic sequence element is a nucleobase that differentiates the target nucleic acid sequence from similar sequence(s) in a genome and/or products encoded thereby.

20. A method for allele-specific suppression of a transcript from a target nucleic acid sequence for which a plurality of alleles exist within a population, each of which contains a specific nucleotide characteristic sequence element that defines the allele relative to other alleles of the same target nucleic acid sequence, the method comprising steps of:
   contacting a sample comprising transcripts of the target nucleic acid sequence with a chirally controlled oligonucleotide composition of claim 1;
   wherein the common base sequence for the oligonucleotides of the particular oligonucleotide type is or comprises a sequence that is complementary to the characteristic sequence element that defines a particular allele.

21. The method of claim 20, wherein the composition provides suppression of the transcript at a level that is greater than a level of suppression observed for another allele or a similar sequence.

22. The method of claim 20, wherein each oligonucleotide of the particular oligonucleotide type independently comprises a first wing, a second wing and a core in a format of first wing-core-second wing or second wing-core-first wing, wherein:
   the nucleobase complementary to the characteristic sequence element is located at position 1, 2, 3, 4, 5, 6, 7, 8, 9, 10, 11, 12, 13, 14, 15, 16, 17, 18, 19, or 20 or further from the 5'-end of an oligonucleotide; or the nucleobase complementary to the characteristic sequence element is located at position 1, 2, 3, 4, 5, 6, 7, 8, 9, 10, 11, 12, 13, 14, 15, 16, 17, 18, 19, or 20 or further from the 5'-end of a core.

23. A method for reducing a level of a transcript or a protein encoded thereby in a system, comprising administering a composition of claim 1.

* * * * *

SEQUENCE LISTING

```
<160> NUMBER OF SEQ ID NOS: 613

<210> SEQ ID NO 1
<211> LENGTH: 180
<212> TYPE: DNA
<213> ORGANISM: Homo sapiens
<220> FEATURE:
<223> OTHER INFORMATION: See specification as filed for detailed
      description of substitutions and preferred embodiments

<400> SEQUENCE: 1
ggggccgggg ccggggccgg ggccggggcc ggggccgggg ccggggccgg ggccggggcc      60
ggggccgggg ccggggccgg ggccggggcc ggggccgggg ccggggccgg ggccggggcc     120
ggggccgggg ccggggccgg ggccggggcc ggggccgggg ccggggccgg ggccggggcc     180

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
gcauagcgag cgagggaaaa c                                                21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
guuuucccuc gcucgcuaug c                                                21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tacaggctgc ggttgtttcc                                                  20

<210> SEQ ID NO 5
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 5
ccttccctga aggttcctcc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gugcugcgat ccccauucca                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ccucactcac ccactcgcca                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
gccaggatgc cgcctccuca                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cctcactcac ccactcgcca                                                  20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
```
gccgcctcct cactcaccca                                          20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
accgggcagc agggacggcu                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
guucaccctc agcgaguacu                                          20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
cuugutcacc ctcagcgagu                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
gagcutgcta caggcugcgg                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
gcgcgactcc tgagtuccag                                          20

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
caggatgccg cctccucacu                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
ccaggatgcc gcctccucac                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gccacccgcc aggatgccgc                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
cgccucttcc cggcagccga                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accgggcagc agggacggct                                                     20

<210> SEQ ID NO 21
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 21
gtgctgcgat ccccattcca                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
ccucactcac ccactcgcca                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cctcactcac ccactcgcca                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cctcactcac ccactcgcca                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ccucactcac ccactcgcca                                                    20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
```
ccucactcac ccactcgcca                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ccucactcac ccactcgcca                                            20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
ccucactcac ccactcgcca                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cctcactcac ccactcgcca                                            20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cctcactcac ccactcgcca                                            20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cctcactcac ccactcgcca                                            20

<210> SEQ ID NO 32
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 32
cctcactcac ccactcgcca                                                  20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cctcactcac ccactcgcca                                                  20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cctcactcac ccactcgcca                                                  20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
cctcactcac ccactcgcca                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cctcactcac ccactcgcca                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctcactcac ccactcgcca                                                  20

<210> SEQ ID NO 38
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 38
cctcactcac ccactcgcca                                                      20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cctcactcac ccactcgcca                                                      20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
accgggcagc agggacggcu                                                      20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
accgggcagc agggacggcu                                                      20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
accgggcagc agggacggcu                                                      20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
accgggcagc agggacggcu                                                      20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 44
accgggcagc agggacggcu                                          20

<210> SEQ ID NO 45
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
accgggcagc agggacggcu                                          20

<210> SEQ ID NO 46
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
accgggcagc agggacggcu                                          20

<210> SEQ ID NO 47
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
accgggcagc agggacggcu                                          20

<210> SEQ ID NO 48
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
accgggcagc agggacggcu                                          20

<210> SEQ ID NO 49
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
accgggcagc agggacggcu                                          20

<210> SEQ ID NO 50
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 50
accgggcagc agggacggcu                                              20

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
accgggcagc agggacggcu                                              20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
accgggcagc agggacggcu                                              20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
accgggcagc agggacggcu                                              20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
accgggcagc agggacggcu                                              20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
accgggcagc agggacggcu                                              20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 56
accgggcagc agggacggcu                                                20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
accgggcagc agggacggct                                                20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
accgggcagc agggacggct                                                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
accgggcagc agggacggct                                                20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
accgggcagc agggacggcu                                                20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
accgggcagc agggacggct                                                20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
```
accgggcagc agggacggct                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
accgggcagc agggacggct                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctcactcac ccactcgcca                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cctcactcac ccactcgcca                                                    20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctcactcac ccactcgcca                                                    20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cctcactcac ccactcgcca                                                    20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cctcactcac ccactcgcca        20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cctcactcac ccactcgcca        20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cctcactcac ccactcgcca        20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cctcactcac ccactcgcca        20

<210> SEQ ID NO 72
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
accgggcagc agggacggcu        20

<210> SEQ ID NO 73
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
accgggcagc agggacggcu        20

<210> SEQ ID NO 74
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
accgggcagc agggacggcu        20

```
<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
accgggcagc agggacggcu                                                   20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
accgggcagc agggacggcu                                                   20

<210> SEQ ID NO 77
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
accgggcagc agggacggcu                                                   20

<210> SEQ ID NO 78
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
accgggcagc agggacggcu                                                   20

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
accgggcagc agggacggcu                                                   20

<210> SEQ ID NO 80
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
accgggcagc agggacggcu                                                   20
```

```
<210> SEQ ID NO 81
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
accgggcagc agggacggcu                                                    20

<210> SEQ ID NO 82
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
accgggcagc agggacggcu                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
cctcactcac ccactcgcca                                                    20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cctcactcac ccactcgcca                                                    20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cctcactcac ccactcgcca                                                    20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cctcactcac ccactcgcca                                                    20
```

```
<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cctcactcac ccactcgcca                                           20

<210> SEQ ID NO 88
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
accgggcagc agggacggcu                                           20

<210> SEQ ID NO 89
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
accgggcagc agggacggcu                                           20

<210> SEQ ID NO 90
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
accgggcagc agggacggcu                                           20

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
accgggcagc agggacggcu                                           20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
accgggcagc agggacggcu                                           20

<210> SEQ ID NO 93
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
accgggcagc agggacggcu                                              20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
accgggcagc agggacggcu                                              20

<210> SEQ ID NO 95
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
accgggcagc agggacggcu                                              20

<210> SEQ ID NO 96
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
accgggcagc agggacggcu                                              20

<210> SEQ ID NO 97
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
accgggcagc agggacggcu                                              20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cctcactcac ccactcgcca                                              20

<210> SEQ ID NO 99
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cctcactcac ccactcgcca                                                 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cctcactcac ccactcgcca                                                 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cctcactcac ccactcgcca                                                 20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cctcactcac ccactcgcca                                                 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cctcactcac ccactcgcca                                                 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cctcactcac ccactcgcca                                                 20

<210> SEQ ID NO 105
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 105
cctcactcac ccactcgcca                                                 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
cctcactcac ccactcgcca                                                 20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cctcactcac ccactcgcca                                                 20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
cctcactcac ccactcgcca                                                 20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cctcactcac ccactcgcca                                                 20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cctcactcac ccactcgcca                                                 20

<210> SEQ ID NO 111
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
uacccgcgcc tcttcccggc                                                 20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ctacccgcgc ctcttcccgg                                                 20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
gggcuctcct cagagcucga                                                 20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
gggtgtcggg ctttcgccuc                                                 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gcatccgggc cccgggcuuc                                                 20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 116
ccttccctga aggttccucc                                                    20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cccggcccct agcgcgcgac                                                    20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
cccggcccct agcgcgcgac                                                    20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
gtgcugcgat ccccauucca                                                    20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cctcactcac ccactcgcca                                                    20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
cctcactcac ccactcgcca                                                    20

<210> SEQ ID NO 122

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cctcactcac ccactcgcca                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cctcactcac ccactcgcca                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cctcactcac ccactcgcca                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
cctcactcac ccactcgcca                                              20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cccggcccct agcgcgcgac                                              20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
uacaggctgc ggttguuucc                                              20
```

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
gatgccgcct cctcacucac                                               20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
atgccgcctc ctcacucacc                                               20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
ugccgcctcc tcactcaccc                                               20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gccgcctcct cactcaccca                                               20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccgcctcctc actcacccac                                               20

<210> SEQ ID NO 133
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
cgccucctca ctcacccacu                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
gcctcctcac tcacccacuc                                              20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
cctcctcact cacccacucg                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
ctccucactc acccacucgc                                              20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
uccucactca cccacucgcc                                              20

<210> SEQ ID NO 138
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 138
ctcactcacc cactcgccac                                                    20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cactcaccca ctcgccaccg                                                    20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
actcacccac tcgccaccgc                                                    20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ctcacccact cgccaccgcc                                                    20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
ucacccactc gccaccgccu                                                    20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
cacccactcg ccaccgccug                                                    20
```

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
acccactcgc caccgccugc                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
cccactcgcc accgccugcg                                              20

<210> SEQ ID NO 146
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
ccacucgcca ccgccugcgc                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
ucacucaccc actcgccacc                                              20

<210> SEQ ID NO 148
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ccucacucac ccacucgcca                                              20

<210> SEQ ID NO 149
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 149
cccggcccct agcgcgcgac                                                   20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
cctcactcac ccactcgcca                                                   20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
ccucactcac ccactcgcca                                                   20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
cctcactcac ccactcgcca                                                   20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
cctcactcac ccactcgcca                                                   20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
cctcactcac ccactcgcca                                                   20

<210> SEQ ID NO 155
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cctcactcac ccactcgcca                                                     20

<210> SEQ ID NO 156
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
uggcgagugg gugagugagg                                                     20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ctcactcacc cactcgccac                                                     20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
tcctcactca cccacucgcc                                                     20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgccgcctcc tcactcaccc                                                     20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
```

```
gcgcgactcc tgagtuccag                                                   20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
gagcttgcta caggcugcgg                                                   20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
caggatgccg cctccucacu                                                   20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
cucactcacc cactcgccac                                                   20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
ccucactcac ccactcgcca                                                   20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 165
uccucactca cccactcgcc                                               20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
ugccgcctcc tcactcaccc                                               20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcgcgactcc tgagttccag                                               20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
gagcutgcta caggctgcgg                                               20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
caggatgccg cctcctcact                                               20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ctcactcacc cactcgccac                                               20

<210> SEQ ID NO 171
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 171
tcctcactca cccactcgcc                                                    20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
tgccgcctcc tcactcaccc                                                    20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gcgcgactcc tgagttccag                                                    20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gagcttgcta caggctgcgg                                                    20

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
caggaatgcc gcctcctcac t                                                  21

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
caggatgccg cctcctcact                                                    20

<210> SEQ ID NO 177
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
cctcacucac ccacucgcca                                               20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
cctcacucac ccacucgcca                                               20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
cctcacucac ccacucgcca                                               20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cctcactcac ccactcgcca                                               20

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cctcactcac ccactcgcca                                               20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cctcactcac ccactcgcca                                              20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cctcactcac ccactcgcca                                              20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cctcactcac ccactcgcca                                              20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cctcactcac ccactcgcca                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cctcactcac ccactcgcca                                              20

<210> SEQ ID NO 187
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
cctcactcac ccactcgcca                                              20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cctcactcac ccactcgcca                                            20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cctcactcac ccactcgcca                                            20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tgccgcctcc tcactcaccc                                            20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgccgcctcc tcactcaccc                                            20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tgccgcctcc tcactcaccc                                            20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cctcactcac ccactcgcca                                            20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
cctcactcac ccactcgcca                                            20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
cctcactcac ccactcgcca                                                    20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cctcactcac ccactcgcca                                                    20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cctcactcac ccactcgcca                                                    20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cctcactcac ccactcgcca                                                    20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
uctcactcac ccactuguua                                                    20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 200
uctcactcac ccactgacuc                                              20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cctcaggctg gttatcgcca                                              20

<210> SEQ ID NO 202
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
accgggcagc agggacggcu                                              20

<210> SEQ ID NO 203
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
accgggcagc agggacggcu                                              20

<210> SEQ ID NO 204
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
accgggcagc agggacggcu                                              20

<210> SEQ ID NO 205
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
accgggcagc agggacggcu                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 206
ugccaggctg gttatgacuc                                                    20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
ugccaggctg gttatgacuc                                                    20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
ugccaggctg gttatgacuc                                                    20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
ugccaggctg gttatgacuc                                                    20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
ugccaggctg gttatgacuc                                                    20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
       oligonucleotide
<220> FEATURE:
<223> OTHER INFORMATION: Description of Combined DNA/RNA Molecule:
      Synthetic oligonucleotide

<400> SEQUENCE: 211
ugccaggctg gttatgacuc                                              20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
ugccaggctg gttatgacuc                                              20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
ugccaggctg gttatgacuc                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
ugccaggctg gttatgacuc                                              20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
ugccaggctg gttatgacuc                                              20

<210> SEQ ID NO 216
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
ugccaggctg gttatgacuc                                               20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
ugccaggctg gttatgacuc                                               20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
ugccaggctg gttatgacuc                                               20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
ugccaggctg gttatgacuc                                               20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
ugccaggctg gttatgacuc                                               20

<210> SEQ ID NO 221
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
ugccaggctg gttatgacuc                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
tgccaggctg gttatgacuc                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
ugccaggctg gttatgacuc                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
tgccaggctg gttatgacuc                                              20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
ugccaggctg gttatgacuc                                              20

<210> SEQ ID NO 226
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
ugccaggctg gttatgacuc                                              20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
ugccaggctg gttatgacuc                                              20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
tgccaggctg gttatgacuc                                              20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
tgccaggctg gttatgacuc                                              20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
tgccaggctg gttatgacuc                                              20

<210> SEQ ID NO 231
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
tgccaggctg gttatgacuc                                                    20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
tgccaggctg gttatgacuc                                                    20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
tgccaggctg gttatgacuc                                                    20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
tgccaggctg gttatgacuc                                                    20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
tgccaggctg gttatgacuc                                                    20

<210> SEQ ID NO 236
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
tgccaggctg gttatgacuc                                            20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
tgccaggctg gttatgacuc                                            20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
tgccaggctg gttatgacuc                                            20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
tgccaggctg gttatgacuc                                            20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
ugccaggctg gttatgacuc                                            20
```

```
<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
ugccaggctg gttatgacuc                                                       20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
ugccaggctg gttatgacuc                                                       20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
ugccaggctg gttatgacuc                                                       20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
ugccaggctg gttatgacuc                                                       20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
ugccaggctg gttatgacuc                                                       20
```

```
<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
ugccaggctg gttatgacuc                                                     20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
ugccaggctg gttatgacuc                                                     20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
ugccaggctg gttatgacuc                                                     20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
ugccaggctg gttatgacuc                                                     20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
ugccaggctg gttatgacuc                                                     20
```

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
ugccaggctg gttatgacuc                                                   20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gggtcagctg ccaatgctag                                                   20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gggtcagctg ccaatgctag                                                   20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
ugccaggctg gttatgacuc                                                   20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
ugccaggctg gttatgacuc                                                   20

<210> SEQ ID NO 256
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
ugccaggctg gttatgacuc                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
ugccaggctg gttatgacuc                                              20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
ugccaggctg gttatgacuc                                              20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
ugccaggctg gttatgacuc                                              20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
ugccaggctg gttatgacuc                                              20

<210> SEQ ID NO 261
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
ugccaggctg gttatgacuc                                              20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
ugccaggctg gttatgacuc                                              20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
ugccaggctg gttatgacuc                                              20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
ugccaggctg gttatgacuc                                              20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
ugccaggctg gttatgacuc                                              20

<210> SEQ ID NO 266
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
ugccaggctg gttatgacuc                                              20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
ugccaggctg gttatgacuc                                              20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
ugccaggctg gttatgacuc                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
ugccaggctg gttatgacuc                                              20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
ugccaggctg gttatgacuc                                              20
```

```
<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
ugccaggctg gttatgacuc                                                   20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
ugccaggctg gttatgacuc                                                   20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
ugccaggctg gttatgacuc                                                   20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
ugccaggctg gttatgacuc                                                   20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
ugccaggctg gttatgacuc                                                   20
```

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
ugccaggctg gttatgacuc                                              20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
ugccaggctg gttatgacuc                                              20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
ugccaggctg gttatgacuc                                              20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
ugccaggctg gttatgacuc                                              20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
ugccaggctg gttatgacuc                                              20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
ugccaggctg gttatgacuc                                              20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
ugccaggctg gttatgacuc                                              20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
ugccaggctg gttatgacuc                                              20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
ugccaggctg gttatgacuc                                              20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
ugccaggctg gttatgacuc                                               20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
ugccaggctg gttatgacuc                                               20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
ugccaggctg gttatgacuc                                               20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
ugccaggctg gttatgacuc                                               20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
ugccaggctg gttatgacuc                                               20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ugccaggctg gttatgacuc                                           20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
ugccaggctg gttatgacuc                                           20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
ugccaggctg gttatgacuc                                           20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
ugccaggctg gttatgacuc                                           20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
ugccaggctg gttatgacuc                                           20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 295
ugccaggctg gttatgacuc                                               20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 296
ugccaggctg gttatgacuc                                               20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
ugccaggctg gttatgacuc                                               20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
ugccaggctg gttatgacuc                                               20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
ugccaggctg gttatgacuc                                               20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 300
ugccaggctg gttatgacuc                                              20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
ugccaggctg gttatgacuc                                              20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
ugccaggctg gttatgacuc                                              20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
ugccaggctg gttatgacuc                                              20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
ugccaggctg gttatgacuc                                              20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 305
ugccaggctg gttatgacuc                                          20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
ugccaggctg gttatgacuc                                          20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
ugccaggctg gttatgacuc                                          20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
ugccaggctg gttatgacuc                                          20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 309
ugccaggctg gttatgacuc                                          20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
    Synthetic oligonucleotide

<400> SEQUENCE: 310
ugccaggctg gttatgacuc                                               20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 311
ugccaggctg gttatgacuc                                               20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 312
ugccaggctg gttatgacuc                                               20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 313
ugccaggctg gttatgacuc                                               20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 314
ugccaggctg gttatgacuc                                               20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide

<400> SEQUENCE: 315
ugccaggctg gttatgacuc                                                    20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
ugccaggctg gttatgacuc                                                    20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
ugccaggctg gttatgacuc                                                    20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
ugccaggctg gttatgacuc                                                    20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
ugccaggctg gttatgacuc                                                    20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 320
ugccaggctg gttatgacuc                                             20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
ugccaggctg gttatgacuc                                             20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 322
ugccaggctg gttatgacuc                                             20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
ugccaggctg gttatgacuc                                             20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
ugccaggctg gttatgacuc                                             20

<210> SEQ ID NO 325
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
ugccaggctg gttatgacuc                                              20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
ugccaggctg gttatgacuc                                              20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
ugccaggctg gttatgacuc                                              20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
ugccaggctg gttatgacuc                                              20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
ugccaggctg gttatgacuc                                              20

<210> SEQ ID NO 330
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
ugccaggctg gttatgacuc                                              20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
ugccaggctg gttatgacuc                                              20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
ugccaggctg gttatgacuc                                              20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
ugccaggctg gttatgacuc                                              20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
ugccaggctg gttatgacuc                                              20

<210> SEQ ID NO 335
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
ugccaggctg gttatgacuc                                                    20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
ugccaggctg gttatgacuc                                                    20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
ugccaggctg gttatgacuc                                                    20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
ugccaggctg gttatgacuc                                                    20

<210> SEQ ID NO 339
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
ugccaggctg gttatgacuc                                                    20

<210> SEQ ID NO 340
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
ugccaggctg gttatgacuc                                               20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
ugccaggctg gttatgacuc                                               20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
ugccaggctg gttatgacuc                                               20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 343
ugccaggctg gttatgacuc                                               20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
ugccaggctg gttatgacuc                                               20

<210> SEQ ID NO 345
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
ugccaggctg gttatgacuc                                              20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
ugccaggctg gttatgacuc                                              20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
ugccaggctg gttatgacuc                                              20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
ugccaggctg gttatgacuc                                              20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
ugccaggctg gttatgacuc                                              20
```

```
<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
ugccaggctg gttatgacuc                                                     20

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
ugccaggctg gttatgacuc                                                     20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
ugccaggctg gttatgacuc                                                     20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
ugccaggctg gttatgacuc                                                     20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
uguagaaagg catgaagcag                                                     20
```

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
uguagaaagg catgaagcag                                                   20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
ugtagaaagg gatgaagcag                                                   20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
tgtagaaagg gatgaagcag                                                   20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tgtagaaagg gatgaagcag                                                   20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
tgtagaaagg catgaagcag                                                   20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
ggacctgagg atggaccgcg                    20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ggacctgagg atggaccgcg                    20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
ggacctgagg atggaccgcg                    20

<210> SEQ ID NO 363
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ggacctgagg atggaccgcg                    20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ggacctgagg atggaccgcg                    20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
ggacctgagg atggaccgcg                    20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 366
ggacctgagg atggaccgcg                                              20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
ggacctgagg atggaccgcg                                              20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ggacctgagg atggaccgcg                                              20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
cuguagaaag gcatgaagca                                              20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
cuguagaaag gcatgaagca                                              20

<210> SEQ ID NO 371
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
cugcuucaug ccuuucuaca gugg                                         24

<210> SEQ ID NO 372
<211> LENGTH: 24
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 372
cugcuucauc cccuucuaca gugg                                          24

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 373
ctgtagaaag ggatgaagca                                               20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 374
ctgtagaaag ggatgaagca                                               20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 375
ctgtagaaag ggatgaagca                                               20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 376
ctgtagaaag gcatgaagca                                               20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 377
ctgtagaaag gcatgaagca                                               20

<210> SEQ ID NO 378
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 378
ctgtagaaag gcatgaagca                                                    20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
ctgtagaaag gcatgaagca                                                    20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
ctgtagaaag gcatgaagca                                                    20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ctgtagaaag gcatgaagca                                                    20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
ctgtagaaag gcatgaagca                                                    20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ctgtagaaag gcatgaagca                                                    20

<210> SEQ ID NO 384
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 384
ctgtagaaag gcatgaagca                                                      20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
ctgtagaaag gcatgaagca                                                      20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
ctgtagaaag gcatgaagca                                                      20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
ctgtagaaag gcatgaagca                                                      20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
ctgtagaaag gcatgaagca                                                      20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
ctgtagaaag gcatgaagca                                                      20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
oligonucleotide

<400> SEQUENCE: 390
ctgtagaaag gcatgaagca                                                20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
ctgtagaaag gcatgaagca                                                20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
ctgtagaaag gcatgaagca                                                20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
ctgtagaaag gcatgaagca                                                20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
ctgtagaaag gcatgaagca                                                20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ctgtagaaag gcatgaagca                                                20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 396
ctgtagaaag gcatgaagca                                                    20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
ctgtagaaag gcatgaagca                                                    20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
ctgtagaaag gcatgaagca                                                    20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
ctgtagaaag gcatgaagca                                                    20

<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ctgtagaaag gcatgaagca                                                    20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
ctgtagaaag gcatgaagca                                                    20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 402
ctgtagaaag gcatgaagca                                                  20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
ctgtagaaag gcatgaagca                                                  20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ctgtagaaag gcatgaagca                                                  20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ctgtagaaag gcatgaagca                                                  20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ctgtagaaag gcatgaagca                                                  20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
ctgtagaaag gcatgaagca                                                  20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
```
ctgtagaaag gcatgaagca                                                20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
ctgtagaaag gcatgaagca                                                20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
ctgtagaaag gcatgaagca                                                20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
ctgtagaaag gcatgaagca                                                20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ctgtagaaag gcatgaagca                                                20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
ctgtagaaag gcatgaagca                                                20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414

```
ctgtagaaag gcatgaagca                                              20
```

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415

```
ctgtagaaag gcatgaagca                                              20
```

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416

```
ctgtagaaag gcatgaagca                                              20
```

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417

```
ctgtagaaag gcatgaagca                                              20
```

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418

```
ctgtagaaag gcatgaagca                                              20
```

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419

```
ctgtagaaag gcatgaagca                                              20
```

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420

```
ctgtagaaag gcatgaagca                                              20
```

```
<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
ctgtagaaag gcatgaagca                                            20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
ctgtagaaag gcatgaagca                                            20

<210> SEQ ID NO 423
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cgaacatgac ctccgcac                                              18

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
ccacugtaga aaggaugaa                                             20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
ccacugtaga aaggcaugaa                                            20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 426
ccacugtaga aaggcaugaa                                            20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 427
ccacugtaga aaggcaugaa                                            20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
ccacugtaga aaggcaugaa                                            20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
ccacugtaga aaggcaugaa                                            20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
ccacugtaga aaggcaugaa                                            20

<210> SEQ ID NO 431
<211> LENGTH: 20
<212> TYPE: DNA
<213> ORGANISM: Artificial Sequence
<220> FEATURE:

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 431
ccacugtaga aaggcatgaa                                                   20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 432
ccacugtaga aaggcatgaa                                                   20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 433
ccacugtaga aaggcatgaa                                                   20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 434
ccacugtaga aaggcatgaa                                                   20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 435
ccacugtaga aaggcatgaa                                                   20

<210> SEQ ID NO 436
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 436
ccactgtaga aagggatgaa                                                      20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
ccactgtaga aagggatgaa                                                      20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
ccactgtaga aaggcaugaa                                                      20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
ccactgtaga aaggcatgaa                                                      20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
cacugtagaa aggcaugaag                                                      20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
```
cacugtagaa aggcatgaag                                                20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
cactgtagaa agggaugaag                                                20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
cactgtagaa agggatgaag                                                20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
cactgtagaa agggatgaag                                                20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
cactgtagaa aggcaugaag                                                20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
cactgtagaa aggcaugaag                                                20

<210> SEQ ID NO 447

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
cactgtagaa aggcatgaag cagg                                            24

<210> SEQ ID NO 448
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
cactgtagaa aggcatgaag cagg                                            24

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
cactgtagaa aggcatgaag cagg                                            24

<210> SEQ ID NO 450
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
cactgtagaa aggcatgaag cagg                                            24

<210> SEQ ID NO 451
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
cactgtagaa aggcatgaag cagg                                            24

<210> SEQ ID NO 452
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
cactgtagaa aggcatgaag cagg                                            24

<210> SEQ ID NO 453
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
cactgtagaa aggcatgaag cagg                                              24

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
aggcugggat cctccacguc                                                   20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
acuguagaaa ggcatgaagc                                                   20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
acuguagaaa ggcatgaagc                                                   20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
actguagaaa gggatgaagc                                                   20

<210> SEQ ID NO 458
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
actguagaaa ggcatgaagc                                              20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
actgtagaaa gggatgaagc                                              20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
actgtagaaa gggatgaagc                                              20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
actgtagaaa ggcatgaagc                                              20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
agctucttgt ccagcuuuau                                              20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
```
agctucttgt ccagcuuuau                                            20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
agctucttgt ccagcuuuau                                            20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
agctucttgt ccagcuuuau                                            20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
agctucttgt ccagcuuuau                                            20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 467
agctucttgt ccagcuuuau                                            20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 468
agctucttgt ccagcuuuau                                               20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 469
agctucttgt ccagcuuuau                                               20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
agctucttgt ccagcuuuau                                               20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 471
agctucttgt ccagcuuuau                                               20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 472
agctucttgt ccagcuuuau                                               20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 473
agctucttgt ccagcuuuau                                               20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
cttgtccagc tttatuggga                                               20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 475
cttgtccagc tttatuggga                                               20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 476
cttgtccagc tttatuggga                                               20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 477
cttgtccagc tttatuggga                                               20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
atagcagctt cttgtccagc                                            20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
atagcagctt cttgtccagc                                            20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
atagcagctt cttgtccagc                                            20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
atagcagctt cttgtccagc                                            20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 482
cttgtccagc tttatuggga                                            20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 483
cttgtccagc tttatuggga                                            20

<210> SEQ ID NO 484
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
cttgtccagc tttatuggga                                              20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
cttgtccagc tttatuggga                                              20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
atagcagctt cttgtccagc                                              20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
atagcagctt cttgtccagc                                              20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
atagcagctt cttgtccagc                                              20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
atagcagctt cttgtccagc                                              20
```

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
atagcagctt cttgtccagc                                                   20

<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
atagcagctt cttgtccagc                                                   20

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
atagcagctt cttgtccagc                                                   20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
atagcagctt cttgtccagc                                                   20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
atagcagctt cttgtccagc                                                   20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
atagcagctt cttgtccagc                                                   20

```
<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
atagcagctt cttgtccagc                                               20

<210> SEQ ID NO 497
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
atagcagctt cttgtccagc                                               20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 498
cttguccagc tttatuggga                                               20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
cttguccagc tttatuggga                                               20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
cttguccagc tttatuggga                                               20

<210> SEQ ID NO 501
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
cttguccagc tttatuggga                                              20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
atagcagctt cttgtccagc                                              20

<210> SEQ ID NO 503
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
atagcagctt cttgtccagc                                              20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
atagcagctt cttgtccagc                                              20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
atagcagctt cttgtccagc                                              20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
cttguccagc tttatuggga                                              20
```

```
<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
cttguccagc tttatuggga                                              20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
cttguccagc tttatuggga                                              20

<210> SEQ ID NO 509
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
cttguccagc tttatuggga                                              20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
atagcagctt cttgtccagc                                              20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
atagcagctt cttgtccagc                                              20

<210> SEQ ID NO 512
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 512
atagcagctt cttgtccagc                                              20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
atagcagctt cttgtccagc                                              20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 514
agctucttgt ccagcuuuau                                              20

<210> SEQ ID NO 515
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 515
agctucttgt ccagcuuuau                                              20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 516
agctucttgt ccagcuuuau                                              20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 517
agctucttgt ccagcuuuau                                              20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
agctucttgt ccagcuuuau                                              20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
agctucttgt ccagcuuuau                                              20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
agctucttgt ccagcuuuau                                              20

<210> SEQ ID NO 521
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
agctucttgt ccagcuuuau                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 522
agctucttgt ccagcuuuau                                          20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
agctucttgt ccagcuuuau                                          20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
agctucttgt ccagcuuuau                                          20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
agctucttgt ccagcuuuau                                          20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
agcttcttgt ccagcuuuau                                          20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 527
agcttcttgt ccagcuuuau                                                   20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
agcttcttgt ccagctuuau                                                   20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
agcttcttgt ccagctuuau                                                   20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
agcttcttgt ccagcuuuau                                                   20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
agcttcttgt ccagcuuuau                                                   20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 532
agcttcttgt ccagctuuau                                                  20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 533
agcttcttgt ccagctuuau                                                  20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 534
agcttcttgt ccagcuuuau                                                  20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 535
agcttcttgt ccagcuuuau                                                  20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 536
agcttcttgt ccagctuuau                                                  20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 537
agcttcttgt ccagctuuau                                               20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 538
gcactgagaa tactgucccu                                               20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
cactgagaat actgtcccuu                                               20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
actgagaata ctgtcccuuu                                               20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
ctgagaatac tgtcccuuuu                                               20

<210> SEQ ID NO 542
<211> LENGTH: 20
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
tgagaatact gtcccuuuua                                              20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 543
gagaatactg tccctuuuaa                                              20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 544
agaatactgt cccttuuaag                                              20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
gaatactgtc cctttuaagc                                              20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
aatactgtcc cttttaagca                                              20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
atactgtccc ttttaagcaa                                           20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
tactgtccct tttaagcaac                                           20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
actgtccctt ttaagcaacc                                           20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550 ctgtccctttt taagcaaccu                                          20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551 tgtcccttttt aagcaaccua                                          20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
gtccctttta agcaaccuac                                           20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 553
tcccttttaa gcaaccuaca                                           20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 554
cccttttaag caaccuacag                                           20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 555
ccttttaagc aacctacagg                                           20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 556
cttttaagca acctacaggg                                           20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 557
ttttaagcaa cctacagggg                                           20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 558
tttaagcaac ctacaggggc                                          20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
ttaagcaacc tacaggggca                                          20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
taagcaacct acaggggcag                                          20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
aagcaaccta cagggggcagc                                         20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
agcaacctac aggggcagcc                                          20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
gcaaccacta ggggcagccc                                          20

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 564
caacctacag gggcagcccu                                              20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
aacctacagg ggcagcccug                                              20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
acctacaggg gcagcccugg                                              20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
agcttcttgt ccagcuuuau                                              20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
gcacugagaa tactgtccct                                              20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 569
cacugagaat actgtccctt                                                      20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 570
acugagaata ctgtcccttt                                                      20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 571
cugagaatac tgtccctttt                                                      20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
ugagaatact gtccctttta                                                      20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
gagaatactg tcccttttaa                                                      20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 574
agaauactgt ccctttaag                                              20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 575
gaauactgtc cctttaagc                                              20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 576
aauactgtcc cttttaagca                                             20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
auacugtccc ttttaagcaa                                             20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
uacugtccct tttaagcaac                                             20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 579
acugucccuu uuaagcaacc                                                  20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 580
cugucccuuu uaagcaacct                                                  20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
ugucccuuuu aagcaaccta                                                  20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 582
guccctttta agcaacctac                                                  20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
ucccutuuaa gcaacctaca                                                  20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 584
cccuuttaag caacctacag                                              20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 585
ccuuutaagc aacctacagg                                              20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 586
cuuuuaagca acctacaggg                                              20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 587
uuuuaagcaa cctacagggg                                              20

<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 588
uuuaagcaac ctacaggggc                                              20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
        Synthetic oligonucleotide

<400> SEQUENCE: 589
uuaagcaacc tacaggggca                                               20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide
<220> FEATURE:
<223> OTHER INFORMATION: Description of Combined DNA/RNA Molecule:
        Synthetic oligonucleotide

<400> SEQUENCE: 590
uaagcaacct acaggggcag                                               20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 591
aagcaaccta cagggggcagc                                              20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 592
agcaacctac aggggcagcc                                               20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 593
gcaacctaca ggggcagccc                                               20

<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
        oligonucleotide

<400> SEQUENCE: 594
caacctacag gggcagccct                                               20

<210> SEQ ID NO 595
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 595
aaccuacagg ggcagccctg                                                   20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 596
accuacaggg gcagccctgg                                                   20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 597
cuuguccagc tttattggga                                                   20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 598
agcuucttgt ccagctttat                                                   20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 599
auagcagctt cttgtccagc                                                   20
```

```
<210> SEQ ID NO 600
<211> LENGTH: 6000
<212> TYPE: DNA
<213> ORGANISM: Homo sapiens
<220> FEATURE:
<221> NAME/KEY: misc_feature
<222> LOCATION: (1)..(6000)
<223> OTHER INFORMATION: This sequence may encompass at least 30, 50,
      100, 150, 200, 300, 400, 500, 600, 700, 800, 900, or 1000 "ggggcc"
      repeats
<220> FEATURE:
<223> OTHER INFORMATION: See specification as filed for detailed
      description of substitutions and preferred embodiments

<400> SEQUENCE: 600
ggggccgggg ccggggccgg ggccggggcc ggggccgggg ccggggccgg ggccggggcc        60
ggggccgggg ccggggccgg ggccggggcc ggggccgggg ccggggccgg ggccggggcc       120
ggggccgggg ccggggccgg ggccggggcc ggggccgggg ccggggccgg ggccggggcc       180
ggggccgggg ccggggccgg ggccggggcc ggggccgggg ccggggccgg ggccggggcc       240
ggggccgggg ccggggccgg ggccggggcc ggggccgggg ccggggccgg ggccggggcc       300
ggggccgggg ccggggccgg ggccggggcc ggggccgggg ccggggccgg ggccggggcc       360
ggggccgggg ccggggccgg ggccggggcc ggggccgggg ccggggccgg ggccggggcc       420
ggggccgggg ccggggccgg ggccggggcc ggggccgggg ccggggccgg ggccggggcc       480
ggggccgggg ccggggccgg ggccggggcc ggggccgggg ccggggccgg ggccggggcc       540
ggggccgggg ccggggccgg ggccggggcc ggggccgggg ccggggccgg ggccggggcc       600
ggggccgggg ccggggccgg ggccggggcc ggggccgggg ccggggccgg ggccggggcc       660
ggggccgggg ccggggccgg ggccggggcc ggggccgggg ccggggccgg ggccggggcc       720
ggggccgggg ccggggccgg ggccggggcc ggggccgggg ccggggccgg ggccggggcc       780
ggggccgggg ccggggccgg ggccggggcc ggggccgggg ccggggccgg ggccggggcc       840
ggggccgggg ccggggccgg ggccggggcc ggggccgggg ccggggccgg ggccggggcc       900
ggggccgggg ccggggccgg ggccggggcc ggggccgggg ccggggccgg ggccggggcc       960
ggggccgggg ccggggccgg ggccggggcc ggggccgggg ccggggccgg ggccggggcc      1020
ggggccgggg ccggggccgg ggccggggcc ggggccgggg ccggggccgg ggccggggcc      1080
ggggccgggg ccggggccgg ggccggggcc ggggccgggg ccggggccgg ggccggggcc      1140
ggggccgggg ccggggccgg ggccggggcc ggggccgggg ccggggccgg ggccggggcc      1200
ggggccgggg ccggggccgg ggccggggcc ggggccgggg ccggggccgg ggccggggcc      1260
ggggccgggg ccggggccgg ggccggggcc ggggccgggg ccggggccgg ggccggggcc      1320
ggggccgggg ccggggccgg ggccggggcc ggggccgggg ccggggccgg ggccggggcc      1380
ggggccgggg ccggggccgg ggccggggcc ggggccgggg ccggggccgg ggccggggcc      1440
ggggccgggg ccggggccgg ggccggggcc ggggccgggg ccggggccgg ggccggggcc      1500
ggggccgggg ccggggccgg ggccggggcc ggggccgggg ccggggccgg ggccggggcc      1560
ggggccgggg ccggggccgg ggccggggcc ggggccgggg ccggggccgg ggccggggcc      1620
ggggccgggg ccggggccgg ggccggggcc ggggccgggg ccggggccgg ggccggggcc      1680
ggggccgggg ccggggccgg ggccggggcc ggggccgggg ccggggccgg ggccggggcc      1740
ggggccgggg ccggggccgg ggccggggcc ggggccgggg ccggggccgg ggccggggcc      1800
ggggccgggg ccggggccgg ggccggggcc ggggccgggg ccggggccgg ggccggggcc      1860
ggggccgggg ccggggccgg ggccggggcc ggggccgggg ccggggccgg ggccggggcc      1920
```

-continued

```
ggggccgggg ccggggccgg ggccggggcc ggggccgggg ccggggccgg ggccggggcc    1980
ggggccgggg ccggggccgg ggccggggcc ggggccgggg ccggggccgg ggccggggcc    2040
ggggccgggg ccggggccgg ggccggggcc ggggccgggg ccggggccgg ggccggggcc    2100
ggggccgggg ccggggccgg ggccggggcc ggggccgggg ccggggccgg ggccggggcc    2160
ggggccgggg ccggggccgg ggccggggcc ggggccgggg ccggggccgg ggccggggcc    2220
ggggccgggg ccggggccgg ggccggggcc ggggccgggg ccggggccgg ggccggggcc    2280
ggggccgggg ccggggccgg ggccggggcc ggggccgggg ccggggccgg ggccggggcc    2340
ggggccgggg ccggggccgg ggccggggcc ggggccgggg ccggggccgg ggccggggcc    2400
ggggccgggg ccggggccgg ggccggggcc ggggccgggg ccggggccgg ggccggggcc    2460
ggggccgggg ccggggccgg ggccggggcc ggggccgggg ccggggccgg ggccggggcc    2520
ggggccgggg ccggggccgg ggccggggcc ggggccgggg ccggggccgg ggccggggcc    2580
ggggccgggg ccggggccgg ggccggggcc ggggccgggg ccggggccgg ggccggggcc    2640
ggggccgggg ccggggccgg ggccggggcc ggggccgggg ccggggccgg ggccggggcc    2700
ggggccgggg ccggggccgg ggccggggcc ggggccgggg ccggggccgg ggccggggcc    2760
ggggccgggg ccggggccgg ggccggggcc ggggccgggg ccggggccgg ggccggggcc    2820
ggggccgggg ccggggccgg ggccggggcc ggggccgggg ccggggccgg ggccggggcc    2880
ggggccgggg ccggggccgg ggccggggcc ggggccgggg ccggggccgg ggccggggcc    2940
ggggccgggg ccggggccgg ggccggggcc ggggccgggg ccggggccgg ggccggggcc    3000
ggggccgggg ccggggccgg ggccggggcc ggggccgggg ccggggccgg ggccggggcc    3060
ggggccgggg ccggggccgg ggccggggcc ggggccgggg ccggggccgg ggccggggcc    3120
ggggccgggg ccggggccgg ggccggggcc ggggccgggg ccggggccgg ggccggggcc    3180
ggggccgggg ccggggccgg ggccggggcc ggggccgggg ccggggccgg ggccggggcc    3240
ggggccgggg ccggggccgg ggccggggcc ggggccgggg ccggggccgg ggccggggcc    3300
ggggccgggg ccggggccgg ggccggggcc ggggccgggg ccggggccgg ggccggggcc    3360
ggggccgggg ccggggccgg ggccggggcc ggggccgggg ccggggccgg ggccggggcc    3420
ggggccgggg ccggggccgg ggccggggcc ggggccgggg ccggggccgg ggccggggcc    3480
ggggccgggg ccggggccgg ggccggggcc ggggccgggg ccggggccgg ggccggggcc    3540
ggggccgggg ccggggccgg ggccggggcc ggggccgggg ccggggccgg ggccggggcc    3600
ggggccgggg ccggggccgg ggccggggcc ggggccgggg ccggggccgg ggccggggcc    3660
ggggccgggg ccggggccgg ggccggggcc ggggccgggg ccggggccgg ggccggggcc    3720
ggggccgggg ccggggccgg ggccggggcc ggggccgggg ccggggccgg ggccggggcc    3780
ggggccgggg ccggggccgg ggccggggcc ggggccgggg ccggggccgg ggccggggcc    3840
ggggccgggg ccggggccgg ggccggggcc ggggccgggg ccggggccgg ggccggggcc    3900
ggggccgggg ccggggccgg ggccggggcc ggggccgggg ccggggccgg ggccggggcc    3960
ggggccgggg ccggggccgg ggccggggcc ggggccgggg ccggggccgg ggccggggcc    4020
ggggccgggg ccggggccgg ggccggggcc ggggccgggg ccggggccgg ggccggggcc    4080
ggggccgggg ccggggccgg ggccggggcc ggggccgggg ccggggccgg ggccggggcc    4140
ggggccgggg ccggggccgg ggccggggcc ggggccgggg ccggggccgg ggccggggcc    4200
ggggccgggg ccggggccgg ggccggggcc ggggccgggg ccggggccgg ggccggggcc    4260
```

-continued

| | |
|---|---|
| ggggccgggg ccggggccgg ggccggggcc ggggccgggg ccggggccgg ggccggggcc | 4320 |
| ggggccgggg ccggggccgg ggccggggcc ggggccgggg ccggggccgg ggccggggcc | 4380 |
| ggggccgggg ccggggccgg ggccggggcc ggggccgggg ccggggccgg ggccggggcc | 4440 |
| ggggccgggg ccggggccgg ggccggggcc ggggccgggg ccggggccgg ggccggggcc | 4500 |
| ggggccgggg ccggggccgg ggccggggcc ggggccgggg ccggggccgg ggccggggcc | 4560 |
| ggggccgggg ccggggccgg ggccggggcc ggggccgggg ccggggccgg ggccggggcc | 4620 |
| ggggccgggg ccggggccgg ggccggggcc ggggccgggg ccggggccgg ggccggggcc | 4680 |
| ggggccgggg ccggggccgg ggccggggcc ggggccgggg ccggggccgg ggccggggcc | 4740 |
| ggggccgggg ccggggccgg ggccggggcc ggggccgggg ccggggccgg ggccggggcc | 4800 |
| ggggccgggg ccggggccgg ggccggggcc ggggccgggg ccggggccgg ggccggggcc | 4860 |
| ggggccgggg ccggggccgg ggccggggcc ggggccgggg ccggggccgg ggccggggcc | 4920 |
| ggggccgggg ccggggccgg ggccggggcc ggggccgggg ccggggccgg ggccggggcc | 4980 |
| ggggccgggg ccggggccgg ggccggggcc ggggccgggg ccggggccgg ggccggggcc | 5040 |
| ggggccgggg ccggggccgg ggccggggcc ggggccgggg ccggggccgg ggccggggcc | 5100 |
| ggggccgggg ccggggccgg ggccggggcc ggggccgggg ccggggccgg ggccggggcc | 5160 |
| ggggccgggg ccggggccgg ggccggggcc ggggccgggg ccggggccgg ggccggggcc | 5220 |
| ggggccgggg ccggggccgg ggccggggcc ggggccgggg ccggggccgg ggccggggcc | 5280 |
| ggggccgggg ccggggccgg ggccggggcc ggggccgggg ccggggccgg ggccggggcc | 5340 |
| ggggccgggg ccggggccgg ggccggggcc ggggccgggg ccggggccgg ggccggggcc | 5400 |
| ggggccgggg ccggggccgg ggccggggcc ggggccgggg ccggggccgg ggccggggcc | 5460 |
| ggggccgggg ccggggccgg ggccggggcc ggggccgggg ccggggccgg ggccggggcc | 5520 |
| ggggccgggg ccggggccgg ggccggggcc ggggccgggg ccggggccgg ggccggggcc | 5580 |
| ggggccgggg ccggggccgg ggccggggcc ggggccgggg ccggggccgg ggccggggcc | 5640 |
| ggggccgggg ccggggccgg ggccggggcc ggggccgggg ccggggccgg ggccggggcc | 5700 |
| ggggccgggg ccggggccgg ggccggggcc ggggccgggg ccggggccgg ggccggggcc | 5760 |
| ggggccgggg ccggggccgg ggccggggcc ggggccgggg ccggggccgg ggccggggcc | 5820 |
| ggggccgggg ccggggccgg ggccggggcc ggggccgggg ccggggccgg ggccggggcc | 5880 |
| ggggccgggg ccggggccgg ggccggggcc ggggccgggg ccggggccgg ggccggggcc | 5940 |
| ggggccgggg ccggggccgg ggccggggcc ggggccgggg ccggggccgg ggccggggcc | 6000 |

<210> SEQ ID NO 601
<211> LENGTH: 3000
<212> TYPE: DNA
<213> ORGANISM: Homo sapiens
<220> FEATURE:
<221> NAME/KEY: misc_feature
<222> LOCATION: (1)..(3000)
<223> OTHER INFORMATION: This sequence may encompass at least 30, 50, 100, 200, 300, 400, or 500 "ggggcc" repeats
<220> FEATURE:
<223> OTHER INFORMATION: See specification as filed for detailed description of substitutions and preferred embodiments

<400> SEQUENCE: 601

| | |
|---|---|
| ggggccgggg ccggggccgg ggccggggcc ggggccgggg ccggggccgg ggccggggcc | 60 |
| ggggccgggg ccggggccgg ggccggggcc ggggccgggg ccggggccgg ggccggggcc | 120 |
| ggggccgggg ccggggccgg ggccggggcc ggggccgggg ccggggccgg ggccggggcc | 180 |

-continued

| | |
|---|---|
| ggggccgggg ccggggccgg ggccggggcc ggggccgggg ccggggccgg ggccggggcc | 240 |
| ggggccgggg ccggggccgg ggccggggcc ggggccgggg ccggggccgg ggccggggcc | 300 |
| ggggccgggg ccggggccgg ggccggggcc ggggccgggg ccggggccgg ggccggggcc | 360 |
| ggggccgggg ccggggccgg ggccggggcc ggggccgggg ccggggccgg ggccggggcc | 420 |
| ggggccgggg ccggggccgg ggccggggcc ggggccgggg ccggggccgg ggccggggcc | 480 |
| ggggccgggg ccggggccgg ggccggggcc ggggccgggg ccggggccgg ggccggggcc | 540 |
| ggggccgggg ccggggccgg ggccggggcc ggggccgggg ccggggccgg ggccggggcc | 600 |
| ggggccgggg ccggggccgg ggccggggcc ggggccgggg ccggggccgg ggccggggcc | 660 |
| ggggccgggg ccggggccgg ggccggggcc ggggccgggg ccggggccgg ggccggggcc | 720 |
| ggggccgggg ccggggccgg ggccggggcc ggggccgggg ccggggccgg ggccggggcc | 780 |
| ggggccgggg ccggggccgg ggccggggcc ggggccgggg ccggggccgg ggccggggcc | 840 |
| ggggccgggg ccggggccgg ggccggggcc ggggccgggg ccggggccgg ggccggggcc | 900 |
| ggggccgggg ccggggccgg ggccggggcc ggggccgggg ccggggccgg ggccggggcc | 960 |
| ggggccgggg ccggggccgg ggccggggcc ggggccgggg ccggggccgg ggccggggcc | 1020 |
| ggggccgggg ccggggccgg ggccggggcc ggggccgggg ccggggccgg ggccggggcc | 1080 |
| ggggccgggg ccggggccgg ggccggggcc ggggccgggg ccggggccgg ggccggggcc | 1140 |
| ggggccgggg ccggggccgg ggccggggcc ggggccgggg ccggggccgg ggccggggcc | 1200 |
| ggggccgggg ccggggccgg ggccggggcc ggggccgggg ccggggccgg ggccggggcc | 1260 |
| ggggccgggg ccggggccgg ggccggggcc ggggccgggg ccggggccgg ggccggggcc | 1320 |
| ggggccgggg ccggggccgg ggccggggcc ggggccgggg ccggggccgg ggccggggcc | 1380 |
| ggggccgggg ccggggccgg ggccggggcc ggggccgggg ccggggccgg ggccggggcc | 1440 |
| ggggccgggg ccggggccgg ggccggggcc ggggccgggg ccggggccgg ggccggggcc | 1500 |
| ggggccgggg ccggggccgg ggccggggcc ggggccgggg ccggggccgg ggccggggcc | 1560 |
| ggggccgggg ccggggccgg ggccggggcc ggggccgggg ccggggccgg ggccggggcc | 1620 |
| ggggccgggg ccggggccgg ggccggggcc ggggccgggg ccggggccgg ggccggggcc | 1680 |
| ggggccgggg ccggggccgg ggccggggcc ggggccgggg ccggggccgg ggccggggcc | 1740 |
| ggggccgggg ccggggccgg ggccggggcc ggggccgggg ccggggccgg ggccggggcc | 1800 |
| ggggccgggg ccggggccgg ggccggggcc ggggccgggg ccggggccgg ggccggggcc | 1860 |
| ggggccgggg ccggggccgg ggccggggcc ggggccgggg ccggggccgg ggccggggcc | 1920 |
| ggggccgggg ccggggccgg ggccggggcc ggggccgggg ccggggccgg ggccggggcc | 1980 |
| ggggccgggg ccggggccgg ggccggggcc ggggccgggg ccggggccgg ggccggggcc | 2040 |
| ggggccgggg ccggggccgg ggccggggcc ggggccgggg ccggggccgg ggccggggcc | 2100 |
| ggggccgggg ccggggccgg ggccggggcc ggggccgggg ccggggccgg ggccggggcc | 2160 |
| ggggccgggg ccggggccgg ggccggggcc ggggccgggg ccggggccgg ggccggggcc | 2220 |
| ggggccgggg ccggggccgg ggccggggcc ggggccgggg ccggggccgg ggccggggcc | 2280 |
| ggggccgggg ccggggccgg ggccggggcc ggggccgggg ccggggccgg ggccggggcc | 2340 |
| ggggccgggg ccggggccgg ggccggggcc ggggccgggg ccggggccgg ggccggggcc | 2400 |
| ggggccgggg ccggggccgg ggccggggcc ggggccgggg ccggggccgg ggccggggcc | 2460 |
| ggggccgggg ccggggccgg ggccggggcc ggggccgggg ccggggccgg ggccggggcc | 2520 |

| | | | | |
|---|---|---|---|---|
| ggggccgggg | ccggggccgg | ggccggggcc | ggggccgggg | ccggggccgg ggccggggcc | 2580 |
| ggggccgggg | ccggggccgg | ggccggggcc | ggggccgggg | ccggggccgg ggccggggcc | 2640 |
| ggggccgggg | ccggggccgg | ggccggggcc | ggggccgggg | ccggggccgg ggccggggcc | 2700 |
| ggggccgggg | ccggggccgg | ggccggggcc | ggggccgggg | ccggggccgg ggccggggcc | 2760 |
| ggggccgggg | ccggggccgg | ggccggggcc | ggggccgggg | ccggggccgg ggccggggcc | 2820 |
| ggggccgggg | ccggggccgg | ggccggggcc | ggggccgggg | ccggggccgg ggccggggcc | 2880 |
| ggggccgggg | ccggggccgg | ggccggggcc | ggggccgggg | ccggggccgg ggccggggcc | 2940 |
| ggggccgggg | ccggggccgg | ggccggggcc | ggggccgggg | ccggggccgg ggccggggcc | 3000 |

<210> SEQ ID NO 602
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 602
agatgacgct tggtgtgtc                                                19

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 603
taaacccaca cctgctcttg                                               20

<210> SEQ ID NO 604
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 604
ctgctgcccg gttgcttctc ttt                                           23

<210> SEQ ID NO 605
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 605
ggtcagagaa atgagaggga aag                                           23

<210> SEQ ID NO 606
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 606
cgagtgggtg agtgagga                                              18

<210> SEQ ID NO 607
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 607
aaatgcgtcg agctctgagg agag                                       24

<210> SEQ ID NO 608
<211> LENGTH: 6000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(6000)
<223> OTHER INFORMATION: This sequence may encompass 100-1000 "ggggcc"
      repeating units

<400> SEQUENCE: 608
ggggccgggg ccggggccgg ggccggggcc ggggccgggg ccggggccgg ggccggggcc    60
ggggccgggg ccggggccgg ggccggggcc ggggccgggg ccggggccgg ggccggggcc   120
ggggccgggg ccggggccgg ggccggggcc ggggccgggg ccggggccgg ggccggggcc   180
ggggccgggg ccggggccgg ggccggggcc ggggccgggg ccggggccgg ggccggggcc   240
ggggccgggg ccggggccgg ggccggggcc ggggccgggg ccggggccgg ggccggggcc   300
ggggccgggg ccggggccgg ggccggggcc ggggccgggg ccggggccgg ggccggggcc   360
ggggccgggg ccggggccgg ggccggggcc ggggccgggg ccggggccgg ggccggggcc   420
ggggccgggg ccggggccgg ggccggggcc ggggccgggg ccggggccgg ggccggggcc   480
ggggccgggg ccggggccgg ggccggggcc ggggccgggg ccggggccgg ggccggggcc   540
ggggccgggg ccggggccgg ggccggggcc ggggccgggg ccggggccgg ggccggggcc   600
ggggccgggg ccggggccgg ggccggggcc ggggccgggg ccggggccgg ggccggggcc   660
ggggccgggg ccggggccgg ggccggggcc ggggccgggg ccggggccgg ggccggggcc   720
ggggccgggg ccggggccgg ggccggggcc ggggccgggg ccggggccgg ggccggggcc   780
ggggccgggg ccggggccgg ggccggggcc ggggccgggg ccggggccgg ggccggggcc   840
ggggccgggg ccggggccgg ggccggggcc ggggccgggg ccggggccgg ggccggggcc   900
ggggccgggg ccggggccgg ggccggggcc ggggccgggg ccggggccgg ggccggggcc   960
ggggccgggg ccggggccgg ggccggggcc ggggccgggg ccggggccgg ggccggggcc  1020
ggggccgggg ccggggccgg ggccggggcc ggggccgggg ccggggccgg ggccggggcc  1080
ggggccgggg ccggggccgg ggccggggcc ggggccgggg ccggggccgg ggccggggcc  1140
ggggccgggg ccggggccgg ggccggggcc ggggccgggg ccggggccgg ggccggggcc  1200
ggggccgggg ccggggccgg ggccggggcc ggggccgggg ccggggccgg ggccggggcc  1260
ggggccgggg ccggggccgg ggccggggcc ggggccgggg ccggggccgg ggccggggcc  1320
ggggccgggg ccggggccgg ggccggggcc ggggccgggg ccggggccgg ggccggggcc  1380
ggggccgggg ccggggccgg ggccggggcc ggggccgggg ccggggccgg ggccggggcc  1440

-continued

| | |
|---|---|
| ggggccgggg ccggggccgg ggccggggcc ggggccgggg ccggggccgg ggccggggcc | 1500 |
| ggggccgggg ccggggccgg ggccggggcc ggggccgggg ccggggccgg ggccggggcc | 1560 |
| ggggccgggg ccggggccgg ggccggggcc ggggccgggg ccggggccgg ggccggggcc | 1620 |
| ggggccgggg ccggggccgg ggccggggcc ggggccgggg ccggggccgg ggccggggcc | 1680 |
| ggggccgggg ccggggccgg ggccggggcc ggggccgggg ccggggccgg ggccggggcc | 1740 |
| ggggccgggg ccggggccgg ggccggggcc ggggccgggg ccggggccgg ggccggggcc | 1800 |
| ggggccgggg ccggggccgg ggccggggcc ggggccgggg ccggggccgg ggccggggcc | 1860 |
| ggggccgggg ccggggccgg ggccggggcc ggggccgggg ccggggccgg ggccggggcc | 1920 |
| ggggccgggg ccggggccgg ggccggggcc ggggccgggg ccggggccgg ggccggggcc | 1980 |
| ggggccgggg ccggggccgg ggccggggcc ggggccgggg ccggggccgg ggccggggcc | 2040 |
| ggggccgggg ccggggccgg ggccggggcc ggggccgggg ccggggccgg ggccggggcc | 2100 |
| ggggccgggg ccggggccgg ggccggggcc ggggccgggg ccggggccgg ggccggggcc | 2160 |
| ggggccgggg ccggggccgg ggccggggcc ggggccgggg ccggggccgg ggccggggcc | 2220 |
| ggggccgggg ccggggccgg ggccggggcc ggggccgggg ccggggccgg ggccggggcc | 2280 |
| ggggccgggg ccggggccgg ggccggggcc ggggccgggg ccggggccgg ggccggggcc | 2340 |
| ggggccgggg ccggggccgg ggccggggcc ggggccgggg ccggggccgg ggccggggcc | 2400 |
| ggggccgggg ccggggccgg ggccggggcc ggggccgggg ccggggccgg ggccggggcc | 2460 |
| ggggccgggg ccggggccgg ggccggggcc ggggccgggg ccggggccgg ggccggggcc | 2520 |
| ggggccgggg ccggggccgg ggccggggcc ggggccgggg ccggggccgg ggccggggcc | 2580 |
| ggggccgggg ccggggccgg ggccggggcc ggggccgggg ccggggccgg ggccggggcc | 2640 |
| ggggccgggg ccggggccgg ggccggggcc ggggccgggg ccggggccgg ggccggggcc | 2700 |
| ggggccgggg ccggggccgg ggccggggcc ggggccgggg ccggggccgg ggccggggcc | 2760 |
| ggggccgggg ccggggccgg ggccggggcc ggggccgggg ccggggccgg ggccggggcc | 2820 |
| ggggccgggg ccggggccgg ggccggggcc ggggccgggg ccggggccgg ggccggggcc | 2880 |
| ggggccgggg ccggggccgg ggccggggcc ggggccgggg ccggggccgg ggccggggcc | 2940 |
| ggggccgggg ccggggccgg ggccggggcc ggggccgggg ccggggccgg ggccggggcc | 3000 |
| ggggccgggg ccggggccgg ggccggggcc ggggccgggg ccggggccgg ggccggggcc | 3060 |
| ggggccgggg ccggggccgg ggccggggcc ggggccgggg ccggggccgg ggccggggcc | 3120 |
| ggggccgggg ccggggccgg ggccggggcc ggggccgggg ccggggccgg ggccggggcc | 3180 |
| ggggccgggg ccggggccgg ggccggggcc ggggccgggg ccggggccgg ggccggggcc | 3240 |
| ggggccgggg ccggggccgg ggccggggcc ggggccgggg ccggggccgg ggccggggcc | 3300 |
| ggggccgggg ccggggccgg ggccggggcc ggggccgggg ccggggccgg ggccggggcc | 3360 |
| ggggccgggg ccggggccgg ggccggggcc ggggccgggg ccggggccgg ggccggggcc | 3420 |
| ggggccgggg ccggggccgg ggccggggcc ggggccgggg ccggggccgg ggccggggcc | 3480 |
| ggggccgggg ccggggccgg ggccggggcc ggggccgggg ccggggccgg ggccggggcc | 3540 |
| ggggccgggg ccggggccgg ggccggggcc ggggccgggg ccggggccgg ggccggggcc | 3600 |
| ggggccgggg ccggggccgg ggccggggcc ggggccgggg ccggggccgg ggccggggcc | 3660 |
| ggggccgggg ccggggccgg ggccggggcc ggggccgggg ccggggccgg ggccggggcc | 3720 |
| ggggccgggg ccggggccgg ggccggggcc ggggccgggg ccggggccgg ggccggggcc | 3780 |
| ggggccgggg ccggggccgg ggccggggcc ggggccgggg ccggggccgg ggccggggcc | 3840 |

-continued

| | |
|---|---|
| ggggccgggg ccggggccgg ggccggggcc ggggccgggg ccggggccgg ggccggggcc | 3900 |
| ggggccgggg ccggggccgg ggccggggcc ggggccgggg ccggggccgg ggccggggcc | 3960 |
| ggggccgggg ccggggccgg ggccggggcc ggggccgggg ccggggccgg ggccggggcc | 4020 |
| ggggccgggg ccggggccgg ggccggggcc ggggccgggg ccggggccgg ggccggggcc | 4080 |
| ggggccgggg ccggggccgg ggccggggcc ggggccgggg ccggggccgg ggccggggcc | 4140 |
| ggggccgggg ccggggccgg ggccggggcc ggggccgggg ccggggccgg ggccggggcc | 4200 |
| ggggccgggg ccggggccgg ggccggggcc ggggccgggg ccggggccgg ggccggggcc | 4260 |
| ggggccgggg ccggggccgg ggccggggcc ggggccgggg ccggggccgg ggccggggcc | 4320 |
| ggggccgggg ccggggccgg ggccggggcc ggggccgggg ccggggccgg ggccggggcc | 4380 |
| ggggccgggg ccggggccgg ggccggggcc ggggccgggg ccggggccgg ggccggggcc | 4440 |
| ggggccgggg ccggggccgg ggccggggcc ggggccgggg ccggggccgg ggccggggcc | 4500 |
| ggggccgggg ccggggccgg ggccggggcc ggggccgggg ccggggccgg ggccggggcc | 4560 |
| ggggccgggg ccggggccgg ggccggggcc ggggccgggg ccggggccgg ggccggggcc | 4620 |
| ggggccgggg ccggggccgg ggccggggcc ggggccgggg ccggggccgg ggccggggcc | 4680 |
| ggggccgggg ccggggccgg ggccggggcc ggggccgggg ccggggccgg ggccggggcc | 4740 |
| ggggccgggg ccggggccgg ggccggggcc ggggccgggg ccggggccgg ggccggggcc | 4800 |
| ggggccgggg ccggggccgg ggccggggcc ggggccgggg ccggggccgg ggccggggcc | 4860 |
| ggggccgggg ccggggccgg ggccggggcc ggggccgggg ccggggccgg ggccggggcc | 4920 |
| ggggccgggg ccggggccgg ggccggggcc ggggccgggg ccggggccgg ggccggggcc | 4980 |
| ggggccgggg ccggggccgg ggccggggcc ggggccgggg ccggggccgg ggccggggcc | 5040 |
| ggggccgggg ccggggccgg ggccggggcc ggggccgggg ccggggccgg ggccggggcc | 5100 |
| ggggccgggg ccggggccgg ggccggggcc ggggccgggg ccggggccgg ggccggggcc | 5160 |
| ggggccgggg ccggggccgg ggccggggcc ggggccgggg ccggggccgg ggccggggcc | 5220 |
| ggggccgggg ccggggccgg ggccggggcc ggggccgggg ccggggccgg ggccggggcc | 5280 |
| ggggccgggg ccggggccgg ggccggggcc ggggccgggg ccggggccgg ggccggggcc | 5340 |
| ggggccgggg ccggggccgg ggccggggcc ggggccgggg ccggggccgg ggccggggcc | 5400 |
| ggggccgggg ccggggccgg ggccggggcc ggggccgggg ccggggccgg ggccggggcc | 5460 |
| ggggccgggg ccggggccgg ggccggggcc ggggccgggg ccggggccgg ggccggggcc | 5520 |
| ggggccgggg ccggggccgg ggccggggcc ggggccgggg ccggggccgg ggccggggcc | 5580 |
| ggggccgggg ccggggccgg ggccggggcc ggggccgggg ccggggccgg ggccggggcc | 5640 |
| ggggccgggg ccggggccgg ggccggggcc ggggccgggg ccggggccgg ggccggggcc | 5700 |
| ggggccgggg ccggggccgg ggccggggcc ggggccgggg ccggggccgg ggccggggcc | 5760 |
| ggggccgggg ccggggccgg ggccggggcc ggggccgggg ccggggccgg ggccggggcc | 5820 |
| ggggccgggg ccggggccgg ggccggggcc ggggccgggg ccggggccgg ggccggggcc | 5880 |
| ggggccgggg ccggggccgg ggccggggcc ggggccgggg ccggggccgg ggccggggcc | 5940 |
| ggggccgggg ccggggccgg ggccggggcc ggggccgggg ccggggccgg ggccggggcc | 6000 |

<210> SEQ ID NO 609
<211> LENGTH: 10
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 609
tggcgagtgg                                                          10

<210> SEQ ID NO 610
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 610
gtgagtgagg                                                          10

<210> SEQ ID NO 611
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 611
ggccccggcc ccggcccc                                                 18

<210> SEQ ID NO 612
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 612
ggggccgggg ccggggcc                                                 18

<210> SEQ ID NO 613
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
gguggcgagu gggugaguga ggag                                          24